US012637461B2

(12) United States Patent
Aspnes et al.

(10) Patent No.: US 12,637,461 B2
(45) Date of Patent: May 26, 2026

(54) COMPOUNDS FOR THE ACTIVATION OF AMPK

(71) Applicant: PFIZER INC., New York, NY (US)

(72) Inventors: Gary Erik Aspnes, Biberach an der Riss (DE); Christopher Ryan Butler, Canton, MA (US); Matthew Frank Paul Calabrese, Old Lyme, CT (US); Kimberly O'keefe Cameron, Niantic, CT (US); John Marion Curto, Mystic, CT (US); Michael Eric Green, Medford, MA (US); Xinjun Hou, Winchester, MA (US); Shenping Liu, Waterford, CT (US); Christopher Lee Mcclendon, Newton, MA (US); John Charles Murray, Oakdale, CT (US); Advaita Panchagnula, Mystic, CT (US); Colin Richard Rose, Quaker Hill, CT (US); Kyle Thomas Tarantino, Killingsworth, CT (US); Meihua Mike Tu, Acton, MA (US); Rayomand Jal Unwalla, Bedford, MA (US); Joseph Scott Warmus, Ledyard, CT (US); Jun Xiao, Lyme, CT (US); Qingyi Yang, Lexington, MA (US); Lei Zhang, Auburndale, MA (US)

(73) Assignee: Pfizer Inc., New York, NY (US)

( * ) Notice: Subject to any disclaimer, the term of this patent is extended or adjusted under 35 U.S.C. 154(b) by 401 days.

(21) Appl. No.: 18/484,527

(22) Filed: Oct. 11, 2023

(65) Prior Publication Data

US 2024/0182468 A1 Jun. 6, 2024

Related U.S. Application Data

(60) Provisional application No. 63/520,197, filed on Aug. 17, 2023, provisional application No. 63/379,985, filed on Oct. 18, 2022.

(51) Int. Cl.

| | |
|---|---|
| ***C07D 471/04*** | (2006.01) |
| ***A61K 31/444*** | (2006.01) |
| ***A61K 31/4545*** | (2006.01) |
| ***A61K 31/4725*** | (2006.01) |
| ***A61K 31/4985*** | (2006.01) |
| ***A61K 31/501*** | (2006.01) |
| ***A61K 31/519*** | (2006.01) |
| ***A61K 31/5377*** | (2006.01) |
| ***A61K 45/06*** | (2006.01) |
| ***C07D 401/14*** | (2006.01) |
| ***C07D 519/00*** | (2006.01) |

(52) U.S. Cl.

CPC .......... *C07D 471/04* (2013.01); *A61K 31/444* (2013.01); *A61K 31/4545* (2013.01); *A61K 31/4725* (2013.01); *A61K 31/4985* (2013.01); *A61K 31/501* (2013.01); *A61K 31/519* (2013.01); *A61K 31/5377* (2013.01); *A61K 45/06* (2013.01); *C07D 401/14* (2013.01); *C07D 519/00* (2013.01)

(58) Field of Classification Search

CPC .. C07D 471/04; C07D 401/14; C07D 519/00; A61K 31/444; A61K 31/4545; A61K 31/4725; A61K 31/4985; A61K 31/501; A61K 31/519; A61K 31/5377; A61K 45/06

See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Davis et al. |
| 4,673,564 | A | 6/1987 | Sonobe et al. |

(Continued)

FOREIGN PATENT DOCUMENTS

| | | |
|---|---|---|
| CN | 112079830 | 12/2020 |
| EP | 0901786 | 3/1999 |

(Continued)

OTHER PUBLICATIONS

S. Wu, et al. (International Journal of Molecular Sciences. 2020; 21(14):4987). (Year: 2020).*

(Continued)

*Primary Examiner* — James H Alstrum-Acevedo
*Assistant Examiner* — Manahil Mirghani Ali Abdalhameed

(57) ABSTRACT

Described herein are compounds of Formula I,

Formula I

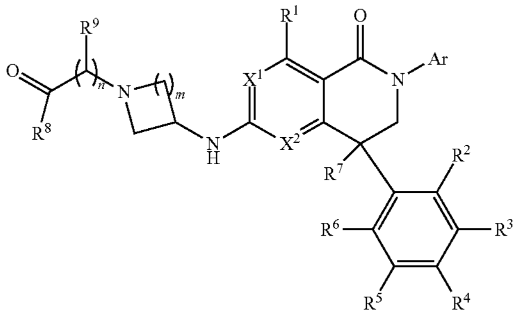

wherein the variables are defined herein, their use as activators from AMPK, pharmaceutical compositions containing such compounds and their use to treat, for example, heart failure or peripheral vascular disease.

23 Claims, 4 Drawing Sheets

(56) References Cited

U.S. PATENT DOCUMENTS

| | | | |
|---|---|---|---|
| 4,894,235 A | 1/1990 | Schmersahl et al. | |
| 5,013,556 A | 5/1991 | Yau et al. | |
| 5,340,591 A | 8/1994 | Nakata et al. | |
| 5,456,923 A | 10/1995 | Nakamichi et al. | |
| 5,612,359 A | 3/1997 | Murugesan | |
| 5,707,646 A | 1/1998 | Hayashi et al. | |
| 5,939,099 A | 8/1999 | Sanner et al. | |
| 6,043,265 A | 3/2000 | Morrison et al. | |
| 7,601,736 B2 | 10/2009 | Kim et al. | |
| 10,329,282 B2 | 6/2019 | Zhao et al. | |
| 2012/0046242 A1 | 2/2012 | Moon et al. | |
| 2021/0198213 A1 | 7/2021 | Zhou et al. | |
| 2023/0023140 A1* | 1/2023 | Shin ..................... | C07D 471/08 |

FOREIGN PATENT DOCUMENTS

| | | |
|---|---|---|
| EP | 0901789 | 3/1999 |
| WO | 00/01389 | 1/2000 |
| WO | 2005/063768 A1 | 7/2005 |
| WO | 2008123755 | 10/2008 |
| WO | 2010/075286 A1 | 7/2010 |
| WO | 12/0001020 | 1/2012 |
| WO | 12/101068 | 8/2012 |
| WO | 2022178420 | 8/2022 |

OTHER PUBLICATIONS

K. Baltgalvis, et al. (American Journal of Physiology-Heart and Circulatory Physiology, 2014, 306:8, H1128-H1145. (Year: 2014).*
S. Marek-Iannucci et al. (JCI Insight. Sep. 2, 20212;6(18): e15198. (Year: 2021).*
Q. Zhao Q, et al. (2021) Front. Cell Dev. Biol. 9:691585. (Year: 2021).*
Alberti, K. G., et al., "The Metabolic Syndrome—A New Worldwide Definition," Lancet, 366, 1059-62 (2005).
Almarsson et al., "Crystal engineering of the composition of pharmaceutical phases. Do pharmaceutical co-crystals represent a new path to improved medicines?", Chem Commun, 17, 1889-1896 (2004).
Benjamin, E.J. et al., "Heart Disease and Stroke Statistics—2019 Update A Report From the American Heart Association.", Circulation 139, E56-E528 (2019).
Birk, J.B. et al., "Predominant alpha2/beta2/gamma3 AMPK activation during exercise in human skeletal muscle", J Physiol 577(3), 1021-1032 (2006).
Bragazzi, N.L. et al., "Burden of heart failure and underlying causes in 195 countries and territories from 1990 to 2017", Eur J Prev Cardiol 28, 1682-1690 (2021).
Chen, H. et al., "Exercise training maintains cardiovascular health: signaling pathways involved and potential therapeutics", Signal Transduct Target Ther 7, 306 (2022).
Costford, S.R. et al., "Gain-of-function R225W mutation in human AMPKgamma(3) causing increased glycogen and decreased triglyceride in skeletal muscle", PLoS One 2, e903 (2007).
Crawford, S.A. et al., "Naturally occurring R225W mutation of the gene encoding AMP-activated protein kinase (AMPK)gamma(3) results in increased oxidative capacity and glucose uptake in human primary myotubes", Diabetologia 53, 1986-1997 (2010).
Criqui, M.H. et al., "Lower Extremity Peripheral Artery Disease: Contemporary Epidemiology, Management Gaps, and Future Directions: A Scientific Statement From the American Heart Association", Circulation 144(9), e171-e191 (2021).
Dunlay, S.M., et al., "Epidemiology of heart failure with preserved ejection fraction", Nat Rev Cardiol 14, 591-602 (2017).
Haleblian, "Characterization of Habits and Crystalline Modificaiton of Solids and Their Pharmaceutical Applications", J Pharm Sci, 64 (8), 1269-1288, (Aug. 1975).
Kjobsted, R. et al., "AMPK in skeletal muscle function and metabolism", FASEB J 32(4), 1741-1777 (2018).
Mahlapuu, M. et al., "Expression profiling of the gamma-subunit isoforms of AMP-activated protein kinase suggests a major role for gamma3 in white skeletal muscle", Am J Physiol Endocrinol Metab 286(2), E194-200 (2004).
Liu, et al. "Discovery and Optimization of Glucose Uptake Inhibitors", J. Med Chem, vol. 63(10), pp. 5201-5211 (2020).
Nayor, M. et al., "Impaired Exercise Tolerance in Heart Failure With Preserved Ejection Fraction: Quantification of Multiorgan System Reserve Capacity", JACC Heart Fail 8(8), 605-617 (2020).
Paulekuhn, G. S. et al., "Trends in Active Pharmaceutical Ingredient Salt Selection Based on Analysis of the Orange Book Database", J. Med. Chem. 50(26), 6665-6672 (2007).
Pedersen, et al., "Exercise as medicine—evidence for prescribing exercise as therapy in 26 different chronic diseases", Scand J Med Sci Sports 25 Suppl 3, 1-72 (2015).
Salaun et al., "Optically Active 2-Vinylcyclobutanones", Tetrahedron, 45(10), 3151-3162 (1989).
Shah, S.J. et al., "Phenotype-Specific Treatment of Heart Failure With Preserved Ejection Fraction: A Multiorgan Roadmap", Circulation 134(1), 73-90 (2016).
Timmis, A. et al., "European Society of Cardiology: Cardiovascular Disease Statistics 2017", Eur Heart J 39(7), 508-579 (2018).
Treat-Jacobson, D. et al., "Implementation of Supervised Exercise Therapy for Patients With Symptomatic Peripheral Artery Disease: A Science Advisory From the American Heart Association", Circulation 140(13), e700-e710 (2019).
Tucker, W.J. et al., "Impact of Exercise Training on Peak Oxygen Uptake and its Determinants in Heart Failure with Preserved Ejection Fraction", Card Fail Rev 2, 95-101 (2016).
Wojtaszewski, J.F. et al., "5'AMP activated protein kinase expression in human skeletal muscle: effects of strength training and type 2 diabetes", J Physiol 564(2), 563-573 (2005).
Zimmet, P. Z., et al., "The Metabolic Syndrome: Perhaps an Etiologic Mystery but Far From a Myth—Where Does the International Diabetes Federation Stand?," Diabetes & Endocrinology, 7(2), (2005).
PCT/IB2023/060470 International Search Report and Written Opinion mailed Dec. 12, 2023.

* cited by examiner

COMPOUNDS FOR THE ACTIVATION OF AMPK

CROSS-REFERENCE TO RELATED APPLICATIONS

This application claims the benefit of U.S. Provisional Patent Application No. 63/520,197, filed on Aug. 17, 2023 and U.S. Provisional Patent Application No. 63/379,985, filed on Oct. 18, 2022, both of which are incorporated herein by reference in their entireties.

BACKGROUND OF THE DISCLOSURE

The present disclosure relates to novel compounds for the activation of adenosine monophosphate-activated protein kinase (AMPK), pharmaceutical compositions containing the compounds, and the use of these compounds for treating or preventing diseases, conditions, or disorders ameliorated by activation of AMPK.

Human skeletal muscle (vastus lateralis) contains three AMPK heterotrimeric complexes, α2β2γ1, α1β2γ1, and α2β2γ3 each contributing to ~65%, ~15%, and ~20% of the total AMPK complex protein pool in this tissue, respectively. (Wojtaszewski, J. F. et al. 5'AMP activated protein kinase expression in human skeletal muscle: effects of strength training and type 2 diabetes. *J Physiol* 564, 563-573 (2005); Kjobsted, R. et al. AMPK in skeletal muscle function and metabolism. *FASEB J* 32, 1741-1777 (2018)). The γ3 subunit is exclusively expressed in skeletal muscle and the α2β2γ3 complex represents the major complex in skeletal muscle activated during exercise. (Kjobsted; Mahlapuu, M. et al. Expression profiling of the gamma-subunit isoforms of AMP-activated protein kinase suggests a major role for gamma3 in white skeletal muscle. *Am J Physiol Endocrinol Metab* 286, E194-200 (2004)) Additionally, in human vastus lateralis muscle, α2β2γ3 is the only AMPK complex activated during short (up to 20 minute) and intense exercise. (Birk, J. B. & Wojtaszewski, J. F. Predominant alpha2/beta2/gamma3 AMPK activation during exercise in human skeletal muscle. *J Physiol* 577, 1021-1032 (2006)). Typically exercise intensity at a minimum of 60% peak $VO_2$ is required to activate AMPK, however, low intensity exercise performed until exhaustion at 30-40% peak $VO_2$ has also been reported to activate AMPK in skeletal muscle. (Wojtaszewski; Kjobsted). Muscle satellite cells obtained from the vastus lateralis muscle of carriers for the rare γ3 gain of function variant, R225W, exhibit a ~90% increase in glycogen content and a ~30% decrease in intramuscular triglycerides. (Costford, S. R. et al. Gain-of-function R225W mutation in human AMPKgamma(3) causing increased glycogen and decreased triglyceride in skeletal muscle. *PLoS One* 2, e903 (2007)). Further phenotyping of these individuals confirmed these initial findings and also demonstrated that myotubes from carriers had threefold higher mitochondrial content and oxidative capacity together with greater basal glucose uptake and glycogen synthesis rates versus control myotubes. (Crawford, S. A. et al. Naturally occurring R225W mutation of the gene encoding AMP-activated protein kinase (AMPK)gamma(3) results in increased oxidative capacity and glucose uptake in human primary myotubes. Diabetologia 53, 1986-1997 (2010)). Additionally, upon exercise, R225W carriers displayed a remarkable resistance to muscular fatigue and a trend towards increased glucose uptake. (Crawford). As such, AMPKγ3 is considered a key molecular driver of the beneficial effects of exercise.

Exercise ameliorates a host of diseases including obesity, metabolic syndrome, diabetes, heart failure, peripheral artery disease, cachexia, frailty, and some musculo-skeletal disorders. (Pedersen, B. K. & Saltin, B. Exercise as medicine—evidence for prescribing exercise as therapy in 26 different chronic diseases. *Scand J Med Sci Sports* 25 Suppl 3, 1-72 (2015)). Conversely, inactivity is considered a risk factor for a multitude of cardiometabolic diseases. Patients who exercise have reduced cardiovascular morbidity and mortality, including lower blood pressure, improved insulin sensitivity, and reduced plasma lipoprotein levels. (Chen, H. et al. Exercise training maintains cardiovascular health: signaling pathways involved and potential therapeutics. *Signal Transduct Target Ther* 7, 306 (2022)).

Heart failure represents a global health challenge with an estimated prevalence of 30 million individuals affected worldwide that incudes >6 million patients in the United States, contributing in 2017 to 1 in 8 deaths. (Timmis, A. et al. European Society of Cardiology: Cardiovascular Disease Statistics 2017. *Eur Heart J* 39, 508-+(2018); Bragazzi, N. L. et al. Y Burden of heart failure and underlying causes in 195 countries and territories from 1990 to 2017. *Eur J Prev Cardiol* 28, 1682-1690 (2021); Benjamin, E. J. et al. Heart Disease and Stroke Statistics-2019 Update A Report From the American Heart Association. *Circulation* 139, E56-E528 (2019)). Heart failure with preserved ejection fraction (HFpEF) accounts for at least half of heart failure cases and is recognized as not a single disease but one with a complex heterogenous pathophysiology due to the presence of multiple comorbidities. (Dunlay, S. M., Roger, V. L. & Redfield, M. M. Epidemiology of heart failure with preserved ejection fraction. *Nat Rev Cardiol* 14, 591-602 (2017); Shah, S. J. et al. Phenotype-Specific Treatment of Heart Failure With Preserved Ejection Fraction: A Multiorgan Roadmap. *Circulation* 134, 73-90 (2016)). Exercise intolerance is a key feature of HFpEF as measured by a reduction in peak oxygen consumption (peak $VO_2$) and is a major source of morbidity for these patients. The peak $VO_2$ for HFpEF patients is often below established thresholds to support independent living, and this decrease in $VO_2$ peak is secondary to central and peripheral abnormalities that result in reduced oxygen delivery to and/or utilization by exercising skeletal muscle. (Tucker, W. J. et al. Impact of Exercise Training on Peak Oxygen Uptake and its Determinants in Heart Failure with Preserved Ejection Fraction. *Card Fail Rev* 2, 95-101 (2016); Nayor, M. et al. Impaired Exercise Tolerance in Heart Failure With Preserved Ejection Fraction: Quantification of Multiorgan System Reserve Capacity. *JACC Heart Fail* 8, 605-617 (2020)). A recent review of randomized control exercise interval trials in subjects with HFpEF demonstrated that endurance training alone or when combined with resistance training is an effective approach to increase peak $VO_2$. (Tucker). These findings suggest that therapeutic strategies to enhance skeletal muscle function may have benefit for treating HFpEF.

Peripheral artery disease (PAD) is an atherosclerotic disease of the lower limb arteries that is present in as many as 230 million individuals worldwide. PAD patients have reduced physical activity as PAD impairs the ability of patients to perform daily tasks such as walking without pain. Consistent with this, PAD patients have poorer walking endurance, slower walking velocity, and poor balance. PAD is the third leading cause of atherosclerotic morbidity and mortality after coronary heart disease and stroke and can progress to critical limb ischemia or eventually amputation. PAD is exacerbated by smoking and additionally metabolic comorbidities such as diabetes and can contribute to diabetic complications such as foot ulcers. PAD is also associated with microvascular disease. Evidence-based therapies for PAD include anticoagulant therapy, lipid lowering therapies such as statins, antihypertensives, improved glycemic control, and cessation of smoking. In addition to this, supervised exercise is considered first line therapy to improve walking impairment in these patients and has demonstrated improvement in treadmill walking distance and pain free walking distance. However, supervised exercise, though most efficacious, is often not feasible for these patients due to treatment barriers such as access. (Treat-Jacobson, D. et al. Implementation of Supervised Exercise Therapy for Patients With Symptomatic Peripheral Artery Disease: A Science Advisory From the American Heart Association. *Circulation* 140, e700-e710 (2019); Criqui, M. H. et al. Lower Extremity Peripheral Artery Disease: Contemporary Epidemiology, Management Gaps, and Future Directions: A Scientific Statement From the American Heart Association. *Circulation* 144, e171-e191 (2021)).

Accordingly, there remains a need for selective small molecule AMPKγ3 activators.

SUMMARY OF THE DISCLOSURE

The present disclosure provides, in part, compounds of Formula I and pharmaceutically acceptable salts thereof. Such compounds may increase the activity of AMPKγ3 and may be useful in treating heart failure and other diseases. Also provided are pharmaceutical compositions and medicaments, comprising the disclosed compounds or salts, alone or in combination with additional therapeutic agents. The present disclosure also provides, in part, methods for preparing such compounds, pharmaceutically acceptable salts and compositions, and methods of using the foregoing. This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

According to an embodiment of the disclosure there is provided a compound of Formula Formula I

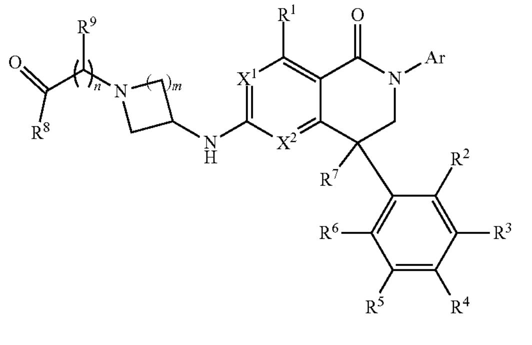

wherein:

Ar is $(C_2\text{-}C_9)$heteroaryl or phenyl; wherein Ar is optionally substituted with 1, 2, or 3 substituents selected from the group consisting of halogen, —$N(R^{10})(R^{11})$, —$CH_2$—$(NR^{10}R^{11})$, —$(C_1\text{-}C_6)$alkyl, —$(C_1\text{-}C_6)$hydroxyalkyl, —$(C_1\text{-}C_6)$haloalkyl, —$(C_1\text{-}C_6)$haloalkoxy, —$(C_1\text{-}C_6)$alkoxy, —$OR^{10}$, —$(C_3\text{-}C_6)$cycloalkyl, and —$(C_3\text{-}C_6)$heterocycloalkyl;

$X^1$ is CH or nitrogen;

$X^2$ is $CR^{12}$ or nitrogen;

$R^1$ is hydrogen, —O—$(C_1\text{-}C_6)$alkyl, —O—$(C_1\text{-}C_6)$cycloalkyl, or —$N(R^{10})(R^{10})$;

$R^2$, $R^3$, $R^4$, $R^5$ and $R^6$ are each independently hydrogen, halogen, —$(C_1\text{-}C_3)$alkyl, or —$N(R^{10})(R^{11})$;

$R^7$ is —H, —$(C_1\text{-}C_6)$alkyl, —$(C_3\text{-}C_6)$cycloalkyl, —OH, or —$CH_2OH$;

$R^8$ is —$(C_1\text{-}C_6)$alkyl, —$(C_0\text{-}C_2)$alkyl-$(C_3\text{-}C_8)$cycloalkyl, —$(C_0\text{-}C_2)$alkyl-$N(R^{10}R^{11})$, —$(C_0\text{-}C_2)$alkyl-$(C_3\text{-}C_9)$heterocycloalkyl, —$(C_1\text{-}C_6)$haloalkoxy, —$(C_1\text{-}C_6)$alkyl-$(C_1\text{-}C_6)$alkoxy, or —$(C_0\text{-}C_2)$alkyl-$(C_2\text{-}C_6)$heteroaryl; wherein $R^8$ is optionally substituted with 1, 2, 3, or 4 substituents selected from the group consisting of halogen, hydroxy, —$(C_1\text{-}C_6)$alkyl, —$(C_1\text{-}C_6)$haloalkyl, —$(C_1\text{-}C_6)$alkoxy, —$(C_1\text{-}C_6)$hydroxyalkyl, —$(C_1\text{-}C_6)$haloalkoxy, —$(C_1\text{-}C_6)$hydroxyalkoxy, and —$(C_3\text{-}C_6)$cycloalkyl;

$R^9$ is hydrogen or —$(C_1\text{-}C_3)$alkyl; or $R^8$ and $R^9$ taken together form a $(C_4\text{-}C_9)$heterocycloalkyl, wherein the $(C_4\text{-}C_9)$heterocycloalkyl is optionally substituted with 1 or 2 substituents selected from the group consisting of oxo, halogen, and —$(C_1\text{-}C_6)$alkyl; and $R^{10}$ and $R^{11}$ are each independently hydrogen, —$(C_1\text{-}C_6)$alkyl, —$(C_1\text{-}C_6)$haloalkyl, —$(C_0\text{-}C_2)$alkyl-$(C_3\text{-}C_6)$cycloalkyl, —$(C_1\text{-}C_6)$alkyl-$(C_1\text{-}C_6)$alkoxy, or —$(C_3\text{-}C_8)$heterocycloalkyl; or wherein $R^{10}$ and $R^{11}$ form a $(C_3\text{-}C_8)$heterocycloalkyl; wherein $R^{10}$ and $R^{11}$ independently are optionally substituted with 1 or 2 substituents selected from the group consisting of hydroxy, oxo, halogen, and cyclopropyl;

$R^{12}$ is hydrogen, methyl, —$CH_2OH$, or halogen;

m is 1, 2, or 3;

n is 0 or 1, wherein, when n is 0, $R^9$ is absent;

or a pharmaceutically acceptable salt of said compound.

According to an embodiment of the disclosure, a method of treating or reducing the risk of hospitalization for heart failure, cardiovascular death, congestive heart failure, heart failure with New York Heart Association Class I-IV symptoms, heart failure with reduced left ventricular function (HF-rEF), heart failure with preserved left ventricular function (HF-pEF), heart failure with midrange ejection fraction (HF-mrEF), cardiovascular death, heart failure in patients with Type II diabetes mellitus, coronary heart disease, unstable angina, peripheral vascular disease (for example, peripheral artery disease), renovascular disease, pulmonary hypertension, vasculitis, acute coronary syndromes and modification of cardiovascular risk comprising administering to a human in need of such treatment the compound of Formula I or a pharmaceutically acceptable salt of said compound.

In another embodiment, a pharmaceutical composition comprises the compound of Formula I or a pharmaceutically acceptable salt of said compound; and a pharmaceutically acceptable carrier, vehicle, or diluent.

In still another embodiment, a pharmaceutical combination composition comprises a first compound, the first compound being the compound of Formula I or a pharmaceutically acceptable salt of said compound; a second compound, said second compound being an anti-heart failure treatment agent; and a pharmaceutical carrier, vehicle, or diluent.

It is to be understood that both the foregoing general description and the following detailed description are exemplary and explanatory only and are not restrictive of the disclosure, as claimed.

DETAILED DESCRIPTION OF THE DISCLOSURE

Figure 1:
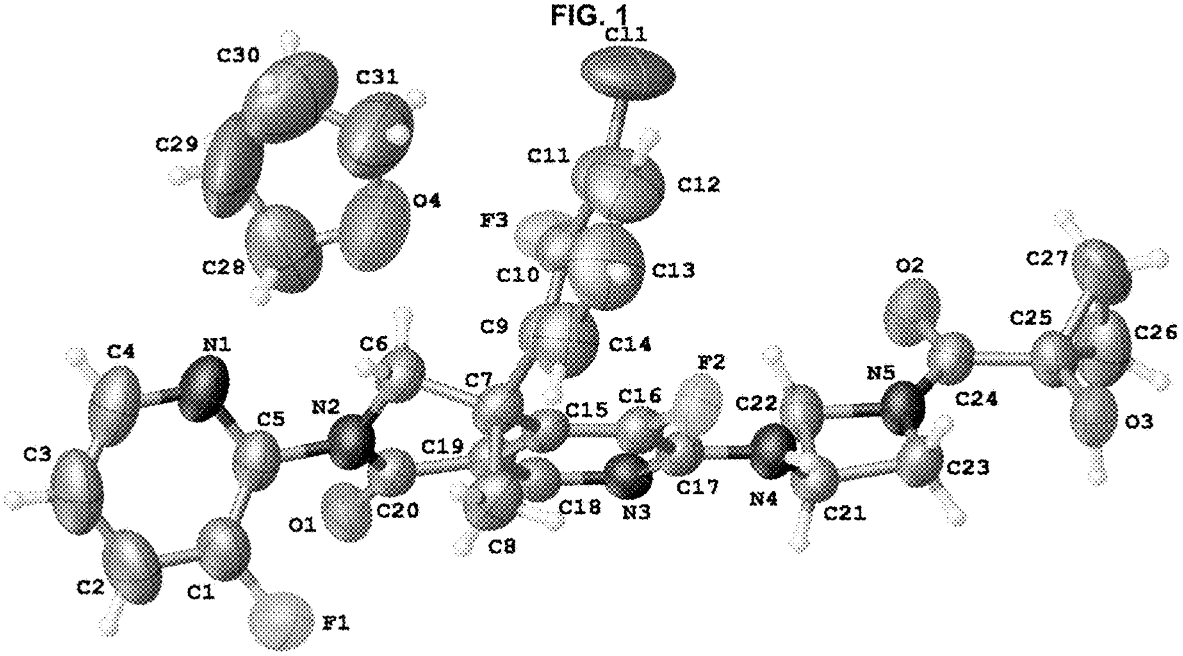
FIG. 1 is an illustration of a small molecule crystal structure of the compound of Example 1.

The present disclosure may be understood more readily by reference to the following detailed description of the aspects of the disclosure and the Examples included herein. It is to be understood that this disclosure is not limited to specific synthetic methods of making that may of course vary. It is to be also understood that the terminology used herein is for the purpose of describing specific aspects and embodiments only and is not intended to be limiting.

In an aspect, a compound has the Formula I:

Formula I

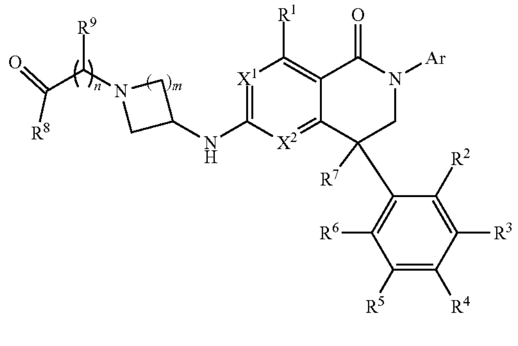

wherein:

Ar is $(C_2\text{-}C_9)$heteroaryl or phenyl; wherein Ar is optionally substituted with 1, 2, or 3 substituents selected from the group consisting of halogen, $—N(R^{10})(R^{11})$, $—CH_2—(NR^{10})R^{11})$, $—(C_1\text{-}C_6)$alkyl, $—(C_1\text{-}C_6)$hydroxyalkyl, $—(C_1\text{-}C_6)$haloalkyl, $—(C_1\text{-}C_6)$haloalkoxy, $—(C_1\text{-}C_6)$alkoxy, $—OR^{10}$, $—(C_3\text{-}C_6)$cycloalkyl, and $—(C_3\text{-}C_6)$heterocycloalkyl;

$X^1$ is CH or nitrogen;

$X^2$ is $CR^{12}$ or nitrogen;

$R^1$ is hydrogen, $—O—(C_1\text{-}C_6)$alkyl, $—O—(C_1\text{-}C_6)$cycloalkyl, or $—N(R^{10})(R^{11})$;

$R^2$, $R^3$, $R^4$, $R^5$ and $R^6$ are each independently hydrogen, halogen, $—(C_1\text{-}C_3)$alkyl, or $—N(R^{10})(R^{11})$;

$R^7$ is —H, $—(C_1\text{-}C_6)$alkyl, $—(C_3\text{-}C_6)$cycloalkyl, —OH, or $—CH_2OH$;

$R^8$ is $—(C_1\text{-}C_6)$alkyl, $—(C_0\text{-}C_2)$alkyl-$(C_3\text{-}C_8)$cycloalkyl, $—(C_0\text{-}C_2)$alkyl-$N(R^{10}R^{11})$, $—(C_0\text{-}C_2)$alkyl-$(C_3\text{-}C_9)$heterocycloalkyl, $—(C_1\text{-}C_6)$haloalkoxy, $—(C_1\text{-}C_6)$alkyl-$(C_1\text{-}C_6)$alkoxy, or $—(C_0\text{-}C_2)$alkyl-$(C_2\text{-}C_6)$heteroaryl; wherein $R^8$ is optionally substituted with 1, 2, 3, or 4 substituents selected from the group consisting of halogen, hydroxy, $—(C_1\text{-}C_6)$alkyl, $—(C_1\text{-}C_6)$haloalkyl, $—(C_1\text{-}C_6)$alkoxy, $—(C_1\text{-}C_6)$hydroxyalkyl, $—(C_1\text{-}C_6)$haloalkoxy, $—(C_1\text{-}C_6)$hydroxyalkoxy, and $—(C_3\text{-}C_6)$cycloalkyl;

$R^9$ is hydrogen or $—(C_1\text{-}C_3)$alkyl; or $R^8$ and $R^9$ taken together form a $(C_4\text{-}C_9)$heterocycloalkyl, wherein the $(C_4\text{-}C_9)$heterocycloalkyl is optionally substituted with 1 or 2 substituents selected from the group consisting of oxo, halogen, and $—(C_1\text{-}C_6)$alkyl; and $R^{10}$ and $R^{11}$ are each independently hydrogen, $—(C_1\text{-}C_6)$alkyl, $—(C_1\text{-}C_6)$haloalkyl, $—(C_0\text{-}C_2)$alkyl-$(C_3\text{-}C_6)$cycloalkyl, $—(C_1\text{-}C_6)$alkyl-$(C_1\text{-}C_6)$alkoxy, or $—(C_3\text{-}C_8)$heterocycloalkyl; or wherein $R^{10}$ and $R^{11}$ taken together form a $(C_3\text{-}C_8)$heterocycloalkyl; wherein $R^{10}$ and $R^{11}$ or the $(C_3\text{-}C_8)$heterocycloalkyl formed by $R^{10}$ and $R^{11}$ taken together are independently optionally substituted with 1 or 2 substituents selected from the group consisting of hydroxy, oxo, halogen, and cyclopropyl;

$R^{12}$ is hydrogen, methyl, $—CH_2OH$, or halogen;

m is 1, 2, or 3;

n is 0 or 1, wherein, when n is 0 $R^9$ is absent;

or a pharmaceutically acceptable salt of said compound.

In the various aspects of the disclosure, the compound can be a compound of the formula Ia or a pharmaceutically acceptable salt of said compound.

Formula Ia

Ia

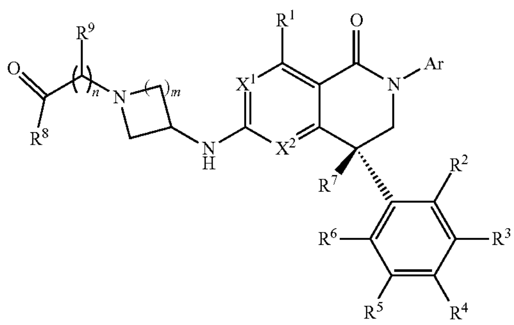

In the various aspects of the disclosure, Ar is $(C_2\text{-}C_9)$heteroaryl or phenyl; wherein Ar is optionally substituted with 1, 2, or 3 substituents selected from the group consisting of halogen, $—N(R^{10})(R^{11})$, $—CH_2—(NR^{10}R^{11})$, $—(C_1\text{-}C_6)$alkyl, $—(C_1\text{-}C_6)$hydroxyalkyl, $—(C_1\text{-}C_6)$haloalkyl, $—(C_1\text{-}C_6)$haloalkoxy, $—OR^{10}$, $—(C_3\text{-}C_6)$cycloalkyl, and $—(C_3\text{-}C_6)$heterocycloalkyl.

In the various aspects of the disclosure, Ar is $(C_2\text{-}C_6)$heteroaryl that is substituted with 1 or 2 substituents selected from the group consisting of F, $—(C_1\text{-}C_3)$alkyl, $—(C_1\text{-}C_3)$hydroxyalkyl, $—NH_2$, and morpholino; or a pharmaceutically acceptable salt thereof.

In the various aspects of the disclosure, Ar can be pyrazolyl, imidazolyl, pyridinyl, or imidazopyridinyl and wherein Ar is optionally substituted with 1 or 2 substituents selected from the group consisting of F, $—(C_1\text{-}C_3)$alkyl, $—(C_1\text{-}C_2)$hydroxyalkyl, $—NH_2$, and

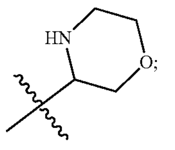 [SMILES: *C1COCCN1]

or a pharmaceutically acceptable salt thereof.

In the various aspects of the disclosure, Ar can be pyrazolyl substituted with F and methyl; or a pharmaceutically acceptable salt thereof.

In the various aspects of the disclosure, $X^1$ can be nitrogen and $X^2$ can be nitrogen or CF; or a pharmaceutically acceptable salt thereof.

In the various aspects of the disclosure, m can be 1; or a pharmaceutically acceptable salt thereof.

In the various aspects of the disclosure, n can be 0; or a pharmaceutically acceptable salt thereof.

In the various aspects of the disclosure, $R^8$ can be —($C_1$-$C_3$)alkyl, —($C_0$-$C_2$)alkyl-cyclopropyl, —($C_0$-$C_2$)alkyl-NH($R^{11}$), ($C_3$-$C_6$)heterocycloalkyl, or —($C_0$-$C_2$)alkyl-($C_2$-$C_6$)heteroaryl; wherein Re is optionally substituted with 1 or 2 substituents selected from the group consisting of F, hydroxy, —($C_1$-$C_3$)alkyl, —($C_1$-$C_2$)fluoroalkyl, —($C_1$-$C_3$)alkoxy, —($C_1$-$C_3$)hydroxyalkyl, and cyclopropyl; or a pharmaceutically acceptable salt thereof.

In the various aspects of the disclosure, $R^8$ can be —($C_0$-$C_2$)alkyl-cyclopropyl substituted with 1 or 2 substituents selected from the group consisting of F, hydroxy, or —($C_1$-$C_3$)alkyl; or a pharmaceutically acceptable salt thereof.

In the various aspects of the disclosure, $R^1$ can be hydrogen; or a pharmaceutically acceptable salt thereof.

In the various aspects of the disclosure, $R^2$ can be F; $R^3$ can be $C_1$, methyl, or F; $R^4$ can be hydrogen or F; and $R^5$ and $R^6$ can be H; or a pharmaceutically acceptable salt thereof.

In the various aspects of the disclosure, $R^7$ can be methyl; or a pharmaceutically acceptable salt thereof.

In the various aspects of the disclosure, the compound can be (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one; (4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one; (4R)-4-(3-chloro-2-fluorophenyl)-5-fluoro-6-({1-[(1S,2S)-2-fluorocyclopropane-1-carbonyl]azetidin-3-yl}amino)-2-(3-fluoropyridin-2-yl)-4-methyl-3,4-dihydro-2,7-naphthyridin-1(2H)-one; (4R)-4-(3-chloro-2-fluorophenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one; (4R)-4-(3-chloro-2-fluorophenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one; (4R)-2-(5-aminopyridin-2-yl)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one; or (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one; or a pharmaceutically acceptable salt thereof.

In the various aspects of the disclosure, the compound can be (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one; (4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one; (4R)-2-(5-aminopyridin-2-yl)-4-(3-chloro-2-fluorophenyl)-5-fluoro-6-({1-[(1 S,2S)-2-fluorocyclopropane-1-carbonyl]azetidin-3-yl}amino)-4-methyl-3,4-dihydro-2,7-naphthyridin-1(2H)-one; or a pharmaceutically acceptable salt thereof.

In the various aspects of the disclosure, the compound can be (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one; or a pharmaceutically acceptable salt thereof.

In the various aspects of the disclosure, the compound can be (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one.

In the various aspects of the disclosure, the compound can be

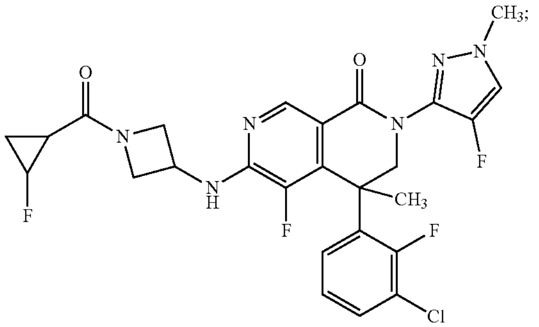 [SMILES: Cn1cc(F)c(N2CC(C)(c3cccc(Cl)c3F)c3c(cnc(NC4CN(C(=O)C5CC5F)C4)c3F)C2=O)n1]

or a pharmaceutically acceptable salt thereof.

In the various aspects of the disclosure, the compound can be

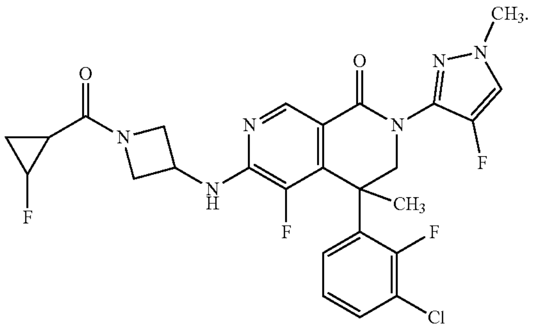 [SMILES: Cn1cc(F)c(N2CC(C)(c3cccc(Cl)c3F)c3c(cnc(NC4CN(C(=O)C5CC5F)C4)c3F)C2=O)n1]

In the various aspects of the disclosure, at least one hydrogen (H) in the compound is deuterium (D).

In the various aspects of the disclosure, the compound is of formula 3D, 6D, 22D, or 23D:

3D

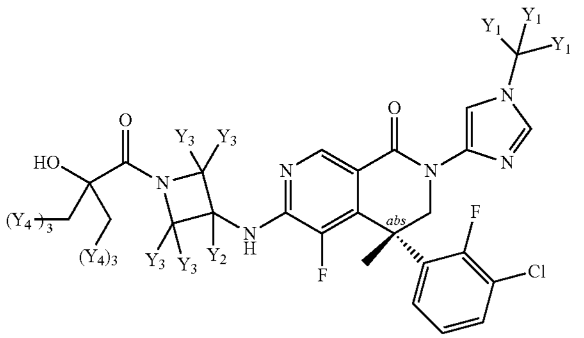

6D

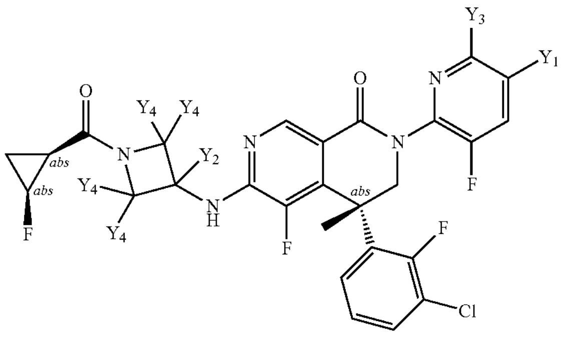

22D

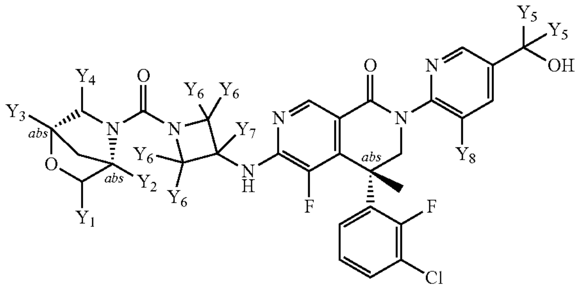

23D

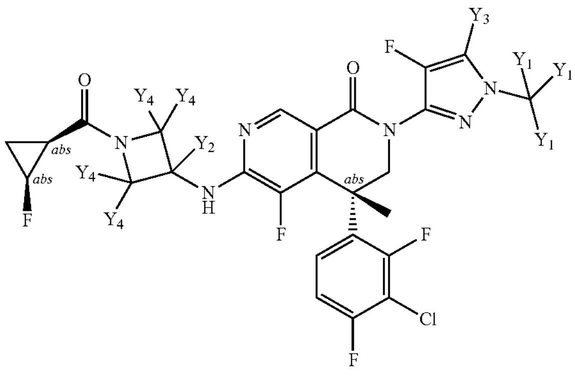

or a pharmaceutically acceptable salt thereof; wherein $Y_1$, $Y_2$, $Y_3$, $Y_4$, $Y_5$, $Y_6$, and $Y_7$ are each independently H or D; wherein when the compound is of the formula 3D, at least one of $Y_1$, $Y_2$, $Y_3$, and $Y_4$ in formula 3D is D; when the compound is of the formula 6D, at least one of $Y_1$, $Y_2$, $Y_3$, and $Y_4$ in formula 6D is D; when the compound is of the formula 22D, at least one of $Y_1$, $Y_2$, $Y_3$, $Y_4$, $Y_5$, $Y_6$, and $Y_7$ in formula 22D is D; and when the compound is of the formula 23D, at least one of $Y_1$, $Y_2$, $Y_3$, and $Y_4$ in formula 23D is D.

In the various aspects of the disclosure, the compound is of the formula 2D-I or 2D-II:

2D-I

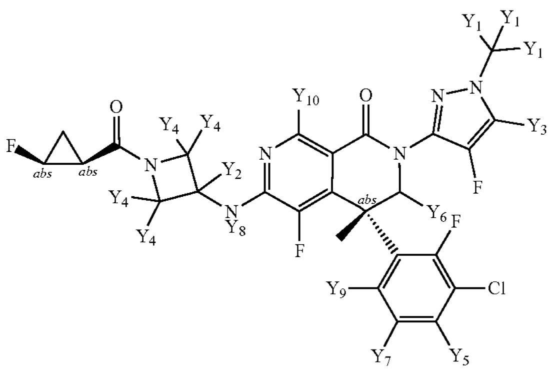

2D-II

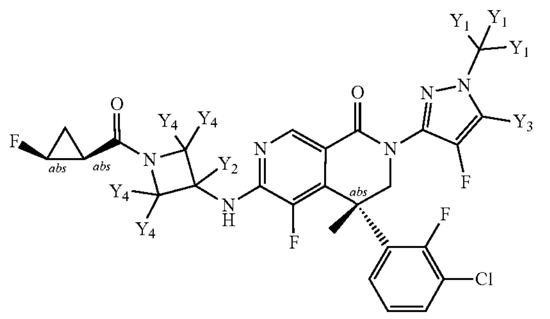

or a pharmaceutically acceptable salt thereof; wherein $Y_1$, $Y_2$, $Y_3$, $Y_4$, $Y_5$, $Y_6$, $Y_7$, $Y_8$, $Y_9$, and $Y_{10}$ are each independently H or D; wherein when the compound is of the formula 2D-1, at least one of $Y_1$, $Y_2$, $Y_3$, $Y_4$, $Y_5$, $Y_6$, $Y_7$, $Y_8$, $Y_9$, and $Y_{10}$ in formula 2D-I is D; and when the compound is of the formula 2D-II, then at least one of $Y_1$, $Y_2$, $Y_3$, or $Y_4$ in formula 2D-II is D.

In the various aspects of the disclosure, a method of treating or reducing the risk of hospitalization for heart failure, cardiovascular death, congestive heart failure, heart failure with New York Heart Association Class I-IV symptoms, heart failure with reduced left ventricular function (HF-rEF), heart failure with preserved left ventricular function (HF-pEF), heart failure with midrange ejection fraction (HF-mrEF), cardiovascular death, heart failure in patients with Type II diabetes mellitus, coronary heart disease, unstable angina, peripheral vascular disease (for example, peripheral artery disease), renovascular disease, pulmonary hypertension, vasculitis, acute coronary syndromes and modification of cardiovascular risk can comprise administering to a human in need of such treatment the compound of the disclosure or a pharmaceutically acceptable salt of said compound.

In the various aspects of the disclosure, the method can comprise treating heart failure or peripheral artery disease.

In the various aspects of the disclosure, a pharmaceutical composition can comprise the compound of the present disclosure or a pharmaceutically acceptable salt of said compound; and a pharmaceutically acceptable carrier, vehicle, or diluent.

In the various aspects of the disclosure, pharmaceutical combination composition can comprise a first compound, the first compound being the compound of the present disclosure or a pharmaceutically acceptable salt of said compound; a second compound, said second compound being an anti-heart failure treatment agent; and a pharmaceutical carrier, vehicle, or diluent.

In the various aspects of the disclosure, said anti-heart failure treatment agent can be an ACE inhibitor, an SGLT-2 inhibitor, an angiotensin receptor blocker, an angiotensin-receptor neprilysin inhibitor, a beta-adrenergic receptor blocker, a calcium channel blocker, or a vasodilator.

In the various aspects of the disclosure, said anti-heart failure agent can be valsartan, sacubitril, dapagliflozin, empagliflozin, canagliflozin, or ertuglifozin.

In the various aspects of the disclosure, a crystal comprises a compound of the formula (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one.

In the various aspects of the disclosure, a powder of the compound of the disclosure can have a powder x-ray diffraction pattern comprising 2-theta values of (CuKα radiation, wavelength of 1.54056 Å) 9.8±0.2, 17±0.2, and 19.8±0.2.

In the various aspects of the disclosure, a powder of the compound of the disclosure can have a powder x-ray diffraction pattern comprising 2-theta values of (CuKα radiation, wavelength of 1.54056 Å) 6.1±0.2, 7.2±0.2, 12.2±0.2, and 13.2±0.2.

Each of the aspects described above can be combined with any other aspect described herein not inconsistent with the aspect with which it is combined. In addition, any of the compounds described in the Examples, or pharmaceutically acceptable salts thereof, may be claimed individually or grouped together with one or more other compounds of the Examples, or pharmaceutically acceptable salts thereof, for any of the aspects described herein.

Furthermore, each of the aspects described herein envisions within its scope pharmaceutically acceptable salts of the compounds described herein. Accordingly, the phrase "or a pharmaceutically acceptable salt thereof" is implicit in the description of all compounds described herein where appropriate.

Unless otherwise defined herein, scientific and technical terms used in connection with the present disclosure have the meanings that are commonly understood by those of ordinary skill in the art.

The disclosure described herein suitably may be practiced in the absence of any element(s) not specifically disclosed herein.

"Compounds of the disclosure" include compounds of Formula I and the novel intermediates used in the preparation thereof. One of ordinary skill in the art will appreciate that compounds of the disclosure include conformational isomers (e.g., cis and trans isomers) and all optical isomers (e.g., enantiomers and diastereomers), racemic, diastereomeric and other mixtures of such isomers and tautomers thereof, where they may exist. One of ordinary skill in the art will also appreciate that compounds of the disclosure include solvates, hydrates, isomorphs, polymorphs, esters, salt forms, prodrugs, and isotopically labelled versions thereof, where they may be formed.

As used herein, the singular form "a", "an", and "the" include plural references unless indicated otherwise. For example, "a" substituent includes one or more substituents. As used herein "or" means "and/or" unless clearly indicated otherwise.

As used herein, the term "about" when used to modify a numerically defined parameter means that the parameter may vary by an acceptable range of deviation for the particular value as determined by one of skill in the art considering the measurement in question and the error associated therewith. For example, "about" can mean as much as 10% below or above the stated numerical value for that parameter. For example, a dose of about 5 mg means 5±10%, i.e., it can vary between 4.5 mg and 5.5 mg.

If substituents are described as being "independently selected" from a group, each substituent is selected independent of the other. Each substituent therefore may be identical to or different from the other substituent(s).

"Optional" or "optionally" means that the subsequently described event or circumstance may, but need not occur, and the description includes instances where the event or circumstance occurs and instances in which it does not.

The terms "optionally substituted" and "substituted or unsubstituted" are used interchangeably to indicate that the particular group being described may have no non-hydrogen substituents (i.e., unsubstituted), or the group may have one or more non-hydrogen substituents (i.e., substituted). If not otherwise specified, the total number of substituents that may be present is equal to the number of H atoms present on the unsubstituted form of the group being described. Where an optional substituent is attached via a double bond, such as an oxo (=O) substituent, the group occupies two available valences, so the total number of other substituents that are included is reduced by two. In the case where optional substituents are selected independently from a list of alternatives, the selected groups may be the same or different. Throughout the disclosure, it will be understood that the number and nature of optional substituent groups will be limited to the extent that such substitutions make chemical sense to one of ordinary skill in the art.

"Halogen" or "halo" refers to fluoro, chloro, bromo and iodo (F, Cl, Br, I). The halogen can refer to F or Cl.

"Cyano" refers to a substituent having a carbon atom joined to a nitrogen atom by a triple bond, i.e., —C≡N.

"Hydroxy" refers to an —OH group.

"Oxo" refers to a double bonded oxygen (=O).

"Alkyl" refers to a saturated, monovalent aliphatic hydrocarbon radical that has a specified number of carbon atoms, including straight chain or branched chain groups. Alkyl groups may contain, but are not limited to, 1 to 12 carbon atoms ("$C_1$-$C_{12}$ alkyl"), 1 to 8 carbon atoms ("$C_1$-$C_8$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), or 1 to 2 carbon atoms ("$C_1$-$C_2$ alkyl"). Examples include, but are not limited to, methyl, ethyl, n-propyl, isopropyl, n-butyl, sec-butyl, isobutyl, tert-butyl, n-pentyl, isopentyl, neopentyl, n-hexyl, n-heptyl, n-octyl, and the like. Alkyl groups may be optionally substituted, unsubstituted or substituted, as further defined herein. "Alkyl" can also refer to a saturated, divalent aliphatic hydrocarbon radical that has a specified number of carbon atoms, including straight chain or branched chain groups, where such a saturated, divalent aliphatic hydrocarbon radical can also be referred to as "alkylene". For example, a —($C_0$-$C_2$)alkyl-($C_3$-$C_8$)cycloalkyl can be referred to as a —($C_0$-$C_2$)alkylene-($C_3$-$C_8$)cycloalkyl; a —($C_0$-$C_2$)alkyl-N($R^{10}R^{11}$) can also be referred to as a —($C_0$-$C_2$)alkylene-N($R^{10}R^{11}$); a —($C_0$-$C_2$)alkyl-($C_3$-$C_9$) heterocycloalkyl can also be referred to as a —($C_0$-$C_2$)

alkylene-$(C_3-C_9)$heterocycloalkyl; a —$(C_1-C_6)$alkyl-$(C_1-C_6)$alkoxy can also be referred to as a —$(C_1-C_6)$alkylene-$(C_1-C_6)$alkoxy; a —$(C_0-C_2)$alkyl-$(C_2-C_6)$heteroaryl can also be referred to as a —$(C_0-C_2)$alkylene-$(C_2-C_6)$heteroaryl; etc.

"Fluoroalkyl" refers to an alkyl group, as defined herein, wherein from one to all of the hydrogen atoms of the alkyl group are replaced by fluoro atoms. Examples include, but are not limited to, fluoromethyl, difluoromethyl, fluoroethyl, difluoroethyl, trifluoroethyl, and tetrafluoroethyl. Examples of fully substituted fluoroalkyl groups (also referred to as perfluoroalkyl groups) include trifluoromethyl (—$CF_3$) and pentafluoroethyl (—$C_2F_5$).

"Alkoxy" refers to an alkyl group, as defined herein, that is single bonded to an oxygen atom. The attachment point of an alkoxy radical to a molecule is through the oxygen atom. An alkoxy radical may be depicted as alkyl-O—. Alkoxy groups may contain, but are not limited to, 1 to 8 carbon atoms ("$C_1$-$C_8$ alkoxy"), 1 to 6 carbon atoms ("$C_1$-$C_6$ alkoxy"), 1 to 4 carbon atoms ("$C_1$-$C_4$ alkoxy"), or 1 to 3 carbon atoms ("$C_1$-$C_3$ alkoxy"). Alkoxy groups include, but are not limited to, methoxy, ethoxy, n-propoxy, isobutoxy, and the like.

"Alkyl-alkoxy" refers to an alkyl group, as defined herein, that is substituted by an alkoxy group, as defined herein. Examples include, but are not limited to, $CH_3OCH_2$—, $CH_3OCH_2CH_2$—, and $CH_3CH_2OCH_2$—.

"Alkenyl" means a straight or branched hydrocarbon chain that comprises at least one carbon-carbon double bond. Examples include, but are not limited to, ethenyl, 1-propenyl, 2-propenyl, 1-, 2-, or 3-butenyl, and the like.

"Alkynyl" means a straight or branched chain hydrocarbon that has one or more unsaturated carbon-carbon bonds, at least one of which is a triple bond. Examples include, but are not limited to, ethynyl, 1-propynyl, 2-propynyl, 1-, 2-, or 3-butynyl, and the like.

"Cycloalkyl" refers to a non-aromatic, saturated and/or partially saturated carbocyclic ring system that has the specified number of carbon atoms that can be a monocyclic, bridged, spiro, or fused bicyclic or polycyclic ring system that is connected to the base molecule through at least one carbon atom of the cycloalkyl ring. The "cycloalkyl" can refer to a non-aromatic, saturated carbocyclic ring system. When the number of carbon atoms is specified (e.g., $(C_3-C_{12})$cycloalkyl), the number means the number of ring members present in the one or more rings. Cycloalkyl groups may contain, but are not limited to, 3 to 12 carbon atoms ("$C_3$-$C_{12}$ cycloalkyl"), 3 to 8 carbon atoms ("$(C_3-C_8)$ cycloalkyl"), 3 to 6 carbon atoms ("$(C_3-C_6)$cycloalkyl"), 3 to 5 carbon atoms ("$(C_3-C_5)$cycloalkyl") or 3 to 4 carbon atoms ("$(C_3-C_4)$cycloalkyl"). Examples include, but are not limited to, cyclopropyl, cyclobutyl, cyclopentyl, cyclohexyl, cycloheptyl, adamantanyl, and the like. Cycloalkyl groups may be optionally substituted or unsubstituted.

"Heterocycloalkyl" refers to a non-aromatic, saturated ring system containing the specified number of ring atoms and containing at least one heteroatom selected from N, O, and S as a ring member or selected from N and O, where ring S atoms are optionally substituted by one or two oxo groups (i.e., $S(O)_q$, where q is 0, 1 or 2) and where the heterocycloalkyl ring is connected to the base molecule via a ring atom, which may be C or N. When the number of carbon atoms is specified, the number means the number of carbon atoms present in the one or more rings where at least one additional heteroatom is present in the one or more rings (e.g., $(C_3-C_{12})$heterocycloalkyl includes 3 to 12 carbon atoms and at least one heteroatom in the one or more rings). Heterocycloalkyl rings include rings which are spirocyclic, bridged, or fused to one or more other heterocycloalkyl or carbocyclic rings, where such spirocyclic, bridged, or fused rings may themselves be saturated, partially unsaturated or aromatic to the extent unsaturation or aromaticity makes chemical sense, provided the point of attachment to the base molecule is an atom of the heterocycloalkyl portion of the ring system. Heterocycloalkyl rings may contain 1 to 4 heteroatoms selected from N, O, and $S(O)_q$ as ring members, or 1 to 2 ring heteroatoms, provided that such heterocycloalkyl rings do not contain two contiguous oxygen or sulfur atoms.

Heterocycloalkyl rings may be optionally substituted, unsubstituted or substituted, as further defined herein. Such substituents may be present on the heterocyclic ring attached to the base molecule, or on a spirocyclic, bridged or fused ring attached thereto.

Heterocycloalkyl rings may include, but are not limited to, 3- to 8-membered heterocyclyl groups (i.e., $C_3$-$C_8$ heterocyclyl groups), for example, 4- to 7- or 4- to 6-membered heterocycloalkyl groups, in accordance with the definition herein. Illustrative examples of heterocycloalkyl rings include, but are not limited to monovalent radicals of oxirane, oxetane, azetidine, tetrahydrofuran, pyrrolidine, tetrahydropyrane, piperidine, morpholine, and piperazine. Illustrative examples of bridged and fused heterocycloalkyl groups include, but are not limited to, monovalent radicals of 2-oxa-5-azabicyclo[2.2.1]heptane 3-oxa-8-azabicyclo[3.2.1]octane, 3-azabicyclo[3.1.0]hexane, and 2-azabicyclo[3.1.0]hexane.

"Aryl" or "aromatic" refers to a monocyclic, biaryl, or fused bicyclic or polycyclic ring system that contains the specified number of ring atoms, in which all atoms in the ring are of $sp^2$ hybridization and in which the pi electrons are in conjugation. Aryl groups may contain, but are not limited to, 6 to 20 carbon atoms ("$C_6$-$C_{20}$ aryl"), 6 to 14 carbon atoms ("$C_6$-$C_{14}$ aryl"), 6 to 12 carbon atoms ("$C_6$-$C_{12}$ aryl"), or 6 to 10 carbon atoms ("$C_6$-$C_{10}$ aryl"). Fused aryl groups may include an aryl ring (e.g., a phenyl ring) fused to another aryl ring. Examples include, but are not limited to, phenyl, biphenyl, naphthyl, anthracenyl, phenanthrenyl, and indenyl. Aryl groups may be fused to non-aromatic rings, for example, the aryl ring can include indanyl. Aryl groups may be optionally substituted, unsubstituted or substituted, as further defined herein.

Similarly, "heteroaryl" refers to monocyclic or heterobiaryl, or fused bicyclic or polycyclic ring systems that contain the specified number of ring atoms and include at least one heteroatom selected from N, O, and S as a ring member in a ring in which all carbon atoms in the ring are of $sp^2$ hybridization and in which the pi electrons are in conjugation. Heteroaryl groups may contain, but are not limited to, 5 to 20 ring atoms ("5- to 20-membered heteroaryl"), 5 to 14 ring atoms ("5- to 14-membered heteroaryl"), 5 to 12 ring atoms ("5- to 12-membered heteroaryl"), 5 to 10 ring atoms ("5- to 10-membered heteroaryl"), 5 to 9 ring atoms ("5- to 9-membered heteroaryl"), or 5 to 6 ring atoms ("5- to 6-membered heteroaryl"). When the number of carbon atoms is specified, the number means the number of carbon atoms present in the one or more rings where at least one additional heteroatom is present in the one or more rings (e.g., $(C_2-C_9)$heteroaryl includes 2 to 9 carbon atoms and at least one heteroatom in the one or more rings). Heteroaryl rings are attached to the base molecule via a ring atom of the heteroaromatic ring. Thus, either 5- or 6-membered heteroaryl rings, alone or in a fused structure, may be attached to the base molecule via a ring C or N atom. Examples of heteroaryl groups include, but are not limited to, pyrrolyl, furanyl, thiophenyl, pyrazolyl, imidazolyl, isoxazolyl, oxazolyl, isothiazolyl, thiazolyl, triazolyl, oxadiazolyl, thiadiazolyl, tetrazolyl, pyridinyl, pyridizinyl, pyrimidinyl, pyrazinyl, benzofuranyl, benzothiophenyl, indolyl, benzamidazolyl, indazolyl, quinolinyl, isoquinolinyl, purinyl, triazinyl, naphthyridinyl, cinnolinyl, quinazolinyl, quinoxalinyl, imidazopyridinyl, pyrazolopyidinyl, pyridopyimidinyl, and carbazolyl. Examples of 5- or 6-membered heteroaryl groups include, but are not limited to, pyrrolyl, furanyl, thiophenyl, pyrazolyl, imidazolyl, isoxazolyl, oxazolyl, isothiazolyl, thiazolyl, triazolyl, pyridinyl, pyrimidinyl, pyrazinyl, and pyridazinyl rings. Heteroaryl groups may be optionally substituted, unsubstituted or substituted, as further defined herein.

"Amino" refers to a group —$NH_2$, which is unsubstituted. Where the amino is described as substituted or optionally substituted, the term includes groups of the form —$NR^{10}R^{11}$, where each of $R^{10}$ and $R^{11}$ is defined as further described herein. For example, "alkylamino" refers to a group —$NR^{10}R^{11}$, wherein one of $R^{10}$ and $R^{11}$ is an alkyl moiety and the other is hydrogen, and "dialkylamino" refers to —$NR^{10}R^{11}$ wherein both of $R^{10}$ and $R^{11}$ are alkyl moieties, where the alkyl moieties have the specified number of carbon atoms (e.g., —$NH(C_1$-$C_4$ alkyl) or —$N(C_1$-$C_4$ alkyl$)_2$).

"Aminoalkyl" refers to an alkyl group, as defined above, that is substituted by 1, 2, or 3 amino groups, as defined herein.

The term "pharmaceutically acceptable" means the substance (e.g., the compounds described herein) and any salt thereof, or composition containing the substance or salt of the disclosure is suitable for administration to a subject or patient.

"Deuterium enrichment factor" as used herein means the ratio between the deuterium abundance and the natural abundance of deuterium, each relative to hydrogen abundance. An atomic position designated as having deuterium typically has a deuterium enrichment factor of, in particular aspects, at least 1000 (15% deuterium incorporation), at least 2000 (30% deuterium incorporation), at least 3000 (45% deuterium incorporation), at least 3500 (52.5% deuterium incorporation), at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

As used herein and unless clearly indicated otherwise, percentages are weight percent based on the total weight of the composition.

The compound has the Formula I or a pharmaceutically acceptable salt thereof.

Formula I

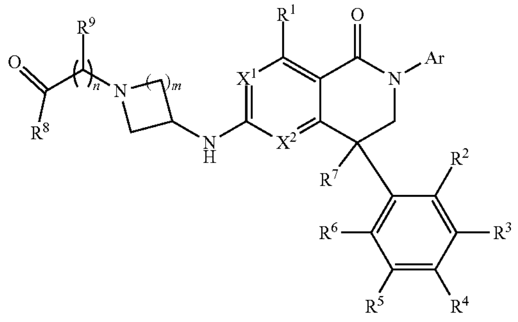

The compound can have the Formula Ia or a pharmaceutically acceptable salt thereof.

Formula Ia

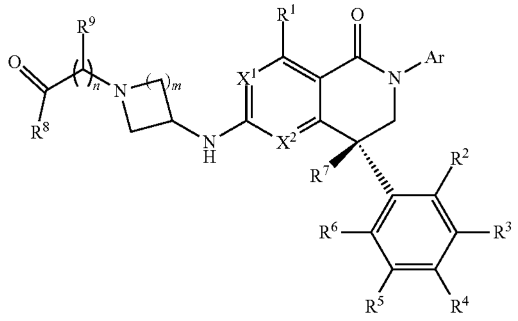

Ar is ($C_2$-$C_9$)heteroaryl or phenyl. Ar can be ($C_3$-$C_6$)heteroaryl. The heteroatom in the ($C_2$-$C_9$)heteroaryl can be at least one of N or O. Ar can be pyrazolyl, imidazolyl, pyridinyl, or imidazopyridinyl. Ar can be ($C_2$-$C_6$)heteroaryl. Ar can be imidazolyl, phenyl, pyridinyl, pyrazolyl, or imidazo[1,2-a]pyridinyl.

Ar can be substituted with 1, 2, or 3 substituents selected from the group consisting of halogen, —$N(R^{10})(R^{11})$, —$CH_2$—($NR^{10}R^{11}$), —($C_1$-$C_6$)alkyl, —($C_1$-$C_6$)hydroxyalkyl, —($C_1$-$C_6$)haloalkyl, —($C_1$-$C_6$)haloalkoxy, —($C_1$-$C_6$)alkoxy, —$OR^{10}$, —($C_3$-$C_6$)cycloalkyl, and —($C_3$-$C_6$)heterocycloalkyl. Ar can be substituted with 1, 2, or 3 substituents selected from the group consisting of halogen, —$N(R^{10})(R^{11})$, —$CH_2$—($NR^{10}R^{11}$), —($C_1$-$C_6$)alkyl, —($C_1$-$C_6$)hydroxyalkyl, —($C_1$-$C_6$)haloalkyl, —($C_1$-$C_6$)haloalkoxy, —$OR^{10}$, —($C_3$-$C_6$)cycloalkyl, and —($C_3$-$C_6$)heterocycloalkyl. Ar can be substituted with 1, 2, or 3 substituents selected from the group consisting of halogen, —$N(R^{10})(R^{11})$, —$CH_2$—($NR^{10}R^{11}$), —($C_1$-$C_3$)alkyl, —($C_1$-$C_3$)hydroxyalkyl, —($C_1$-$C_3$)haloalkyl, —($C_1$-$C_3$)haloalkoxy, —($C_1$-$C_6$)alkoxy, and —($C_3$-$C_6$)heterocycloalkyl. Ar can be substituted with 1 or 2 substituents selected from the group consisting of F, —($C_1$-$C_3$)hydroxyalkyl, —$NH_2$, and morpholino. Ar can be substituted with at least one of halogen (for example, F) or methyl. Ar can be substituted with 1 or 2 substituents selected from the group consisting of F, —($C_1$-$C_2$)hydroxyalkyl, —$NH_2$, and

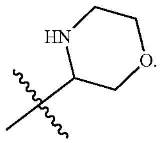 [SMILES: *C1COCCN1]

Ar can be pyrazolyl substituted with F and methyl.

$X^1$ is CH or nitrogen. $X^2$ is $CR^{12}$ or nitrogen, wherein $X^2$ can be CF. $X^1$ and $X^2$ can be nitrogen. $X^1$ can be CH and $X^2$ can be CF. $X^1$ can be nitrogen and $X^2$ can be CF.

$R^1$ is hydrogen, —O—$(C_1-C_6)$alkyl, —O—$(C_1-C_6)$cycloalkyl, or —$N(R^{10})(R^{11})$. $R^1$ can be hydrogen.

$R^2$, $R^3$, $R^4$, $R^5$ and $R^6$ are each independently hydrogen, halogen, or —$(C_1-C_3)$alkyl. Two or three of $R^2$, $R^3$, $R^4$, $R^5$ and $R^6$ can be halogen, wherein each halogen independently can be F or Cl. $R^2$ can be F. $R^3$ can be Cl or F or methyl. $R^4$ can be hydrogen or F. $R^5$ and $R^6$ can be hydrogen. $R^2$ can be F, $R^3$ can be Cl, $R^4$ can be F, and both of $R^5$ and $R^6$ can be hydrogen. $R^2$ can be F, $R^3$ can be F or Cl, and all of $R^4$, $R^5$, and $R^6$ can be hydrogen.

$R^7$ is —H, —$(C_1-C_6)$alkyl, —$(C_3-C_6)$cycloalkyl, —OH, or —$CH_2OH$. $R^7$ can be —$(C_1-C_3)$alkyl, —$(C_3-C_6)$cycloalkyl, —OH, or —$CH_2OH$. $R^7$ can be methyl.

$R^8$ can be —$(C_1-C_6)$alkyl, —$(C_0-C_2)$alkyl-$(C_3-C_8)$cycloalkyl, —$(C_0-C_2)$alkyl-$N(R^{10}R^{11})$, —$(C_0-C_2)$alkyl-$(C_3-C_9)$heterocycloalkyl, —$(C_1-C_6)$haloalkoxy, —$(C_1-C_6)$alkyl-$(C_1-C_6)$alkoxy, or —$(C_0-C_2)$alkyl-$(C_2-C_6)$heteroaryl. $R^8$ can be —$(C_1-C_4)$alkyl, —$(C_0-C_2)$alkyl-$(C_3-C_8)$cycloalkyl, —$(C_0-C_2)$alkyl-$N(R^{10}R^{11})$, —$(C_0-C_2)$alkyl-$(C_3-C_9)$heterocycloalkyl, —$(C_1-C_6)$alkyl-alkoxy, or —$(C_0-C_2)$alkyl-$(C_2-C_6)$heteroaryl. $R^8$ can be —$(C_1-C_3)$alkyl, —$(C_0-C_2)$alkyl-cyclopropyl, —$(C_0-C_2)$alkyl-$NH(R^{11})$, —$(C_4-C_6)$heterocycloalkyl, or —$(C_0-C_2)$alkyl-$(C_2-C_6)$heteroaryl. The heteroatom in the —$(C_0-C_2)$alkyl-$(C_4-C_6)$heterocycloalkyl or the —$(C_0-C_2)$alkyl-$(C_2-C_6)$heteroaryl can be at least one of N or O. $R^8$ can be —$(C_0-C_2)$alkyl-cyclopropyl. $R^8$ can be azetidinyl, —$CH_2$-cyclopropyl, cyclobutyl, ethyl, methoxyethyl, imidazolyl, morpholinyl, piperidinyl, pyrimidinyl, pyridazinyl (optionally fused to pyrrolidinyl), pyrrolidinyl, trifluoroethyl, trifluoropropyl, triazolyl, a monovalent radical of 5-azabicyclo[2.2.1]heptane, a monovalent radical of 2-oxa-5-azabicyclo[2.2.1]heptane, a monovalent radical of 2-azabicyclo[2.1.1]hexane, or a monovalent radical of 6-oxaspiro[2.5]octane.

$R^8$ can be substituted with 1, 2, 3, or 4 substituents selected from the group consisting of halogen, hydroxy, —$(C_1-C_6)$alkyl, —$(C_1-C_6)$haloalkyl, —$(C_1-C_6)$alkoxy, —$(C_1-C_6)$hydroxyalkyl, —$(C_1-C_6)$haloalkoxy, —$(C_1-C_6)$hydroxyalkoxy, and —$(C_3-C_6)$cycloalkyl. $R^8$ can be substituted with 1, 2, or 3 substituents selected from the group consisting of halogen, hydroxy, —$(C_1-C_3)$alkyl, —$(C_1-C_3)$haloalkyl, —$(C_1-C_3)$alkoxy, —$(C_1-C_3)$hydroxyalkyl, and cyclopropyl. $R^8$ can be substituted with 1 or 2 substituents selected from the group consisting of F, hydroxy, —$(C_1-C_3)$alkyl, —$(C_1-C_2)$fluoroalkyl, —$(C_1-C_3)$alkoxy, —$(C_1-C_3)$hydroxyalkyl, and cyclopropyl. $R^8$ can be substituted with at least one of hydroxy, cyclopropyl, methyl, F, trifluoromethyl; —$CH_2$—$(C_4-C_6)$heterocycloalkyl, —$(CH_2)$—$N(R^{10})(R^{11})$, —$CH_2OH$, or a monovalent t-butyl alcohol. $R^8$ can be substituted with 1 or 2 substituents selected from the group consisting of F, methyl, or methyl alcohol. $R^8$ can be cyclopropyl substituted with at least one F.

$R^9$ can be hydrogen or —$(C_1-C_3)$alkyl.

$R^8$ and $R^9$ can form $(C_4-C_9)$heterocycloalkyl. The heteroatom of the $(C_4-C_9)$heterocycloalkyl can be at least one of N or O. The $(C_4-C_9)$heterocycloalkyl can be substituted with 1 or 2 substituents selected from the group consisting of oxo, halogen, and —$(C_1-C_6)$alkyl, for example, $(C_1-C_3)$alkyl or methyl. The $(C_4-C_9)$heterocycloalkyl can be fused to a $(C_2-C_6)$heteroaryl. The $(C_4-C_9)$heterocycloalkyl can form a monovalent piperidinyl group, a monovalent morpholinyl group, or monovalent pyrrolidinyl group.

Each $R^{10}$ and $R^{11}$ independently are each independently hydrogen, —$(C_1-C_6)$alkyl, —$(C_1-C_6)$haloalkyl, —$(C_0-C_2)$alkyl-$(C_3-C_6)$cycloalkyl, —$(C_1-C_6)$alkyl-$(C_1-C_6)$alkoxy, or —$(C_3-C_8)$heterocycloalkyl. Each $R^{10}$ and $R^{11}$ independently can be hydrogen, —$(C_1-C_4)$alkyl, —$(C_2-C_3)$haloalkyl, —$(C_0-C_2)$alkyl-$(C_3-C_5)$cycloalkyl, —$(C_1-C_6)$alkyl-alkoxy, or —$(C_3-C_6)$heterocycloalkyl, or $R^{10}$ and $R^{11}$ form a $(C_3-C_8)$heterocycloalkyl. $R^{10}$ and $R^{11}$ taken together can form a $(C_3-C_8)$heterocycloalkyl; wherein the $(C_3-C_8)$heterocycloalkyl formed by $R^{10}$ and $R^{11}$ taken together can optionally be substituted with 1 or 2 substituents selected from the group consisting of hydroxy, oxo, halogen, and cyclopropyl.

Each $R^{10}$ or $R^{11}$ independently can be substituted with 1 or 2 substituents selected from the group consisting of hydroxy, oxo, halogen, and cyclopropyl. The heteroatom of each $R^{10}$ or $R^{11}$ independently can include at least one of N or O.

$R^{12}$ is hydrogen, methyl, —$CH_2OH$, or halogen. $R^{12}$ can be H or halogen.

The variable m is 1, 2, or 3. The variable m can be 1. The variable n is 0 or 1, when n is 0 $R^9$ is absent. The variable m can be 1 and the variable n can be 0.

The compound can include at least one of (4R)-4-(3-chloro-2-fluorophenyl)-5-fluoro-6-({1-[(1 S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one; (4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one; (4R)-4-(3-chloro-2-fluorophenyl)-5-fluoro-6-({1-[(1S,2S)-2-fluorocyclopropane-1-carbonyl]azetidin-3-yl}amino)-2-(3-fluoropyridin-2-yl)-4-methyl-3,4-dihydro-2,7-naphthyridin-1(2H)-one; or (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one; or a pharmaceutically acceptable salt thereof.

Salts encompassed within the term "pharmaceutically acceptable salts" refer to the compounds of this disclosure which are generally prepared by reacting the free base or free acid with a suitable organic or inorganic acid, or a suitable organic or inorganic base, respectively, to provide a salt of the compound of the disclosure that is suitable for administration to a subject or patient.

In addition, the compounds of Formula I may also include other salts of such compounds that are not necessarily pharmaceutically acceptable salts, which may be useful as intermediates for one or more of the following: 1) preparing compounds of Formula I; 2) purifying compounds of Formula I; 3) separating enantiomers of compounds of Formula I; or 4) separating diastereomers of compounds of Formula I.

Suitable acid addition salts are formed from acids that form non-toxic salts. Examples include, but are not limited to, acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate, 1,5-naphathalenedisulfonic acid and xinofoate salts.

Suitable base salts are formed from bases that form non-toxic salts. Examples include, but are not limited to lithium, aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see Paulekun, G. S. et al., Trends in Active Pharmaceutical Ingredient Salt Selection Based on Analysis of the Orange Book Database, J. Med. Chem. 2007; 50(26), 6665-6672.

Pharmaceutically acceptable salts of compounds of the disclosure may be prepared by methods well known to one skilled in the art, including but not limited to the following procedures (i) by reacting a compound of the disclosure with the desired acid or base;

(ii) by removing an acid- or base-labile protecting group from a suitable precursor of a compound of the disclosure or by ring-opening a suitable cyclic precursor, for example, a lactone or lactam, using the desired acid or base; or (iii) by converting one salt of a compound of the disclosure to another. This may be accomplished by reaction with an appropriate acid or base or by means of a suitable ion exchange procedure.

These procedures are typically carried out in solution. The resulting salt may precipitate out and be collected by filtration or may be recovered by evaporation of the solvent.

The compounds of the disclosure, and pharmaceutically acceptable salts thereof, may exist in unsolvated and solvated forms. The term 'solvate' is used herein to describe a molecular complex comprising the compound of the disclosure, or a pharmaceutically acceptable salt thereof, and one or more pharmaceutically acceptable solvent molecules, for example, ethanol. The term 'hydrate' is employed when said solvent is water.

In addition, the compounds of Formula I may also include other solvates of such compounds that are not necessarily pharmaceutically acceptable solvates, which may be useful as intermediates for one or more of the following: 1) preparing compounds of Formula I; 2) purifying compounds of Formula I; 3) separating enantiomers of compounds of Formula I; or 4) separating diastereomers of compounds of Formula I.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex may have a well-defined stoichiometry independent of humidity. When, however, the solvent or water is weakly bound, as in channel solvates and hygroscopic compounds, the water/solvent content may be dependent on humidity and drying conditions. In such cases, non-stoichiometry will be the norm.

The compound includes all pharmaceutically acceptable isotopically-labeled compounds of the disclosure, wherein one or more atoms are replaced by atoms having the same atomic number, but an atomic mass or mass number different from the atomic mass or mass number which predominates in nature.

Examples of isotopes suitable for inclusion in the compound may include isotopes of hydrogen, such as $^{2}H$ and $^{3}H$, carbon, such as $^{11}C$, $^{13}C$ and $^{14}C$, chlorine, such as $^{36}C_1$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of the disclosure, for example, those incorporating a radioactive isotope, are useful in one or both of drug or substrate tissue distribution studies. The radioactive isotopes tritium, i.e., $^{3}H$, and carbon-14, i.e., $^{14}C$, are particularly useful for this purpose in view of their ease of incorporation and ready means of detection.

Substitution with deuterium, i.e., $^{2}H$, may afford certain therapeutic advantages resulting from greater metabolic stability.

Substitution with positron emitting isotopes, such as $^{11}C$, $^{18}F$, $^{15}O$ and $^{13}N$, may be useful in Positron Emission Topography (PET) studies for examining substrate receptor occupancy.

This disclosure can provide deuterium-labeled (or deuterated) compounds and salts, where the formula and variables of such compounds and salts are each and independently as described herein. "Deuterated" means that at least one of the atoms in the compound is deuterium in an abundance that is greater than the natural abundance of deuterium (typically approximately 0.015%). A skilled artisan recognized that in chemical compounds with a hydrogen atom, the hydrogen atom actually represents a mixture of H and D, with about 0.015% being D. The concentration of the deuterium incorporated into the deuterium-labeled compounds and salt of the disclosure may be defined by the deuterium enrichment factor. It is understood that one or more deuterium may exchange with hydrogen under physiological conditions.

The deuterium compound can be selected from any one of the compounds set forth in Tables 3 and 4 shown in the Examples section in Examples 1 to 112.

One or more hydrogen atoms on certain metabolic sites on the compounds of the disclosure can be deuterated.

Isotopically-labeled compounds of the disclosure may generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the disclosure include those wherein the solvent of crystallization may be isotopically substituted, e.g., $D_2O$, $d_6$-acetone, $d_6$-DMSO.

Also included within the scope of the disclosure are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, for example, hydrogen bonded complex (cocrystal) may be formed with either a neutral molecule or with a salt. Co-crystals may be prepared by melt crystallization, by recrystallization from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the disclosure may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically, such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

The compounds of the disclosure may also exist in a mesomorphic state (mesophase or liquid crystal) when subjected to suitable conditions. The mesomorphic state is intermediate between the true crystalline state and the true liquid state (either melt or solution) and consists of two-dimensional order on the molecular level. Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^{-}Na^{+}$, $—COO^{-}K^{+}$, or $—SO_3^{-}Na^{+}$) or non-ionic (such as $—N^{-}N^{+}(CH_3)_3$) polar head group. For more information, see Crystals and the Polarizing Microscope by N. H. Hartshorne and A. Stuart, $4^{th}$ Edition (Edward Arnold, 1970).

In general, the compounds of this disclosure can be made by processes which include processes analogous to those known in the chemical arts, particularly in light of the description contained herein. Certain processes for the manufacture of the compounds of this disclosure are provided as further features of the disclosure and are illustrated by the following reaction schemes. Other processes may be described in the experimental section. Specific synthetic schemes for preparation of the compounds of Formula I are outlined below.

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, certain compounds contain primary amines or carboxylic acid functionalities that may interfere with reactions at other sites of the molecule if left unprotected. Accordingly, such functionalities may be protected by an appropriate protecting group that may be removed in a subsequent step. Suitable protecting groups for amine and carboxylic acid protection include those protecting groups commonly used in peptide synthesis (such as N-tert-butoxycarbonyl, benzyloxycarbonyl, and 9-fluorenylmethylenoxycarbonyl for amines and lower alkyl or benzyl esters for carboxylic acids), which are generally not chemically reactive under the reaction conditions described and can typically be removed without chemically altering other functionality in the Formula I compound.

The scope of the disclosure includes all crystal forms of the compounds of the disclosure, including racemates and racemic mixtures (conglomerates) thereof. Also within the scope of the disclosure are intermediate compounds as hereinafter defined, all salts, solvates and complexes thereof, and all solvates and complexes of salts thereof as defined hereinbefore for compounds of Formula I. The disclosure includes all polymorphs of the aforementioned species and crystal habits thereof.

The compounds of Formula I and intermediates may contain asymmetric or chiral centers, and, therefore, exist in different stereoisomeric forms. Unless specified otherwise, it is intended that all stereoisomeric forms of the compounds as well as mixtures thereof, including racemic mixtures are included herein. In addition, all geometric and positional isomers are included within the scope of the compounds. For example, if a compound incorporates a double bond or a fused ring, both the cis- and trans-forms, as well as mixtures, are embraced within the scope of the disclosure.

In addition, the compounds of Formula I and intermediates embrace all atropisomers and stereoisomeric mixtures thereof, including racemic mixtures. Atropisomers include those that can be isolated as separate stereoisomers and retain their stereoisomeric purity for various lengths of time including moderate and long times. Atropisomers also include those isomers that cannot be readily separated as separate stereoisomers due to interconversion over some time period including short to moderate times.

Chiral compounds of the disclosure (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts, or solvents, or by converting one stereoisomer into the other by asymmetric transformation.

Where the compounds possess two or more stereogenic centers and the absolute or relative stereochemistry is given in the name, the designations R and S refer respectively to each stereogenic center in ascending numerical order (1, 2, 3, etc.) according to the conventional IUPAC number schemes for each molecule. Where the compounds possess one or more stereogenic centers and no stereochemistry is given in the name or structure, it is understood that the name or structure is intended to encompass all forms of the compound, including the racemic form.

The compounds of this disclosure may contain olefin-like double bonds. When such bonds are present, the compounds of the disclosure exist as cis and trans configurations and as mixtures thereof. The term "cis," when used for substituents on a ring, refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

It is also possible that the intermediates and compounds of Formula I may exist in different tautomeric forms, and all such forms are embraced within the scope of the disclosure. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the tetrazole moiety where the proton may migrate between the four ring nitrogens as follows.

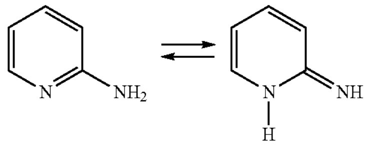 [SMILES: Nc1ccccn1 ; N=c1cccc[nH]1]

Valence tautomers include interconversions by reorganization of some of the bonding electrons.

Included within the scope of the claimed compounds of the present disclosure are all stereoisomers, geometric isomers, and tautomeric forms of the compounds of Formula I, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

The compounds of the disclosure, or their pharmaceutically acceptable salts, may be prepared by a variety of methods that are analogously known in the art. The reaction schemes described below, together with synthetic methods known in the art of organic chemistry, or modifications and derivatizations that are familiar to those of ordinary skill in the art, illustrate methods for preparing the compounds. It will be appreciated that it may be necessary or desirable to carry out the transformations in a different order from that described in the schemes, or to modify one or more of the transformations, to provide the desired compound of the disclosure.

The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences, it may be necessary and/or desirable to protect sensitive or reactive groups on any of the molecules concerned. This can be achieved by means of conventional protecting groups (-PG), such as those described in T. W. Greene and P. G. M. Wuts, Protective Groups In Organic Chemistry, John Wiley & Sons, 2007, which are hereby incorporated by reference. Due to the multitude of protection and deprotection possibilities, and the multitude of sequential changes that could occur to accommodate them, only one of these possible manipulations will generally be described.

Compounds of the present disclosure, or the pharmaceutically acceptable salts of said compounds, or their tautomers and radioisotopes, can be prepared according to the reaction schemes discussed herein below. Examples of isotopes suitable for inclusion in the compounds of the disclosure include isotopes of: hydrogen, such as $^{2}H$ and $^{3}H$; carbon, such as $^{11}C$, $^{13}C$, and $^{14}C$; fluorine, such as $^{18}F$; chlorine, such as $^{36}Cl$; nitrogen, such as $^{13}N$ and $^{15}N$; oxygen, such as $^{15}O$, $^{17}O$, and $^{18}O$. Substitution with heavier isotopes such as deuterium (D), i.e., $^{2}H$, may afford certain therapeutic advantages resulting from greater metabolic stability, for example, increased in vivo half-life or reduced dosage requirements, and hence may be preferred in some circumstances.

Isolation and purification of the products is accomplished by standard procedures, which are known to a chemist of ordinary skill.

One skilled in the art will recognize that, in some cases, the compounds will be generated as a mixture of diastereomers and/or enantiomers; these may be separated at various stages of the synthetic scheme using conventional techniques or a combination of such techniques, such as, but not limited to, crystallization, normal-phase chromatography, reversed-phase chromatography and chiral chromatography, to afford the single enantiomers of the disclosure; for example, see "Stereochemistry of Organic Compounds" by E. L. Eliel and S. H. Wilen (Wiley, New York, 1994).

Unless otherwise indicated, the substituents in the schemes are defined as above. It will be understood by one skilled in the art that the various symbols, superscripts, and subscripts used in the schemes, methods and examples are used for convenience of representation and/or to reflect the order in which they are introduced in the schemes and are not intended to necessarily correspond to the symbols, superscripts, or subscripts in the appended claims. The schemes are representative of methods useful in synthesizing the compounds of the present disclosure. They are not to constrain the scope of the disclosure in any way.

The pyridine ring substructure of Formula C may be prepared as discussed in Scheme 1. 4,6-Dihalogen-substituted pyridine-3-carboxylic acids of Formula A, where LG=leaving group, synthesized by literature methods or purchased commercially, can be reacted with sodium thioalkoxide and an appropriate base, such as 1,8-diazabicyclo [5.4.0]undec-7-ene or potassium carbonate, in a polar solvent such as ethanol or dimethyl sulfoxide to afford Formula B. Protection of the carboxylic acid of Formula B can be performed with a suitable alkyl halide and appropriate base such as potassium carbonate, in a polar solvent such as dimethyl sulfoxide, to afford Formula C. Alternatively, the carboxylic acid can be converted to an acyl chloride and treated with an alkyl alcohol. This can be achieved by a number of methods, including, but not limited to, the use of oxalyl chloride and catalytic N,N-dimethylformamide in an aprotic solvent such as dichloromethane, followed by treatment with an alkyl alcohol and a base such as triethylamine or N,N-diisopropylethylamine.

Scheme 1

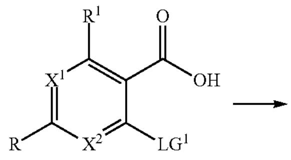

A $X^1 = N$; $X^2 = C—F$;

$R^1 = H$ $LG^1 = F, Cl, Br$

-continued

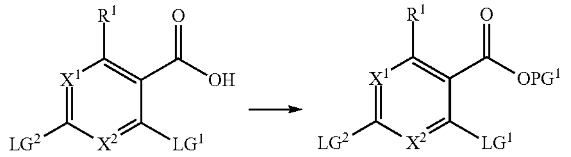

B $LG^2 = SMe$

C

2-Arylalkylnitriles of Formula F can be prepared by a variety of methods, including, but not limited to, those outlined in Scheme 2, or may be purchased from commercial sources. Reaction of Formula D1 (X=Br or I) with tert-butyl cyanoacetate, in the presence of a palladium catalyst and a strong base such as sodium tert-butoxide, will afford 2-(tert-butoxy)-1-cyano-2-oxo-1-arylethyl-1-ide, which can undergo alkylation with the desired primary or secondary alkyl halide (Cl, Br, I) to afford Formula E, as shown in Scheme 2a. Loss of the tert-butoxycarbonyl group of Formula E can be achieved by use of sodium chloride in water and a polar solvent such as dimethyl sulfoxide at elevated temperature (100° C.) to provide general Formula F (*Org. Lett.* 2013, 15, 6190). Schemes 2b and 2c detail alternative methods to access Formula F in one step; these include reaction with potassium 2-cyanopropanoate via palladium-catalyzed decarboxylation (*Angew. Chem., Int. Ed.* 2011, 50, 4470), and reaction of an acetophenone derivative such as Formula D2 with 1-(isocyanomethanesulfonyl)-4-methylbenzene (TosMIC) in the presence of a strong base such as potassium tert-butoxide.

Scheme 2

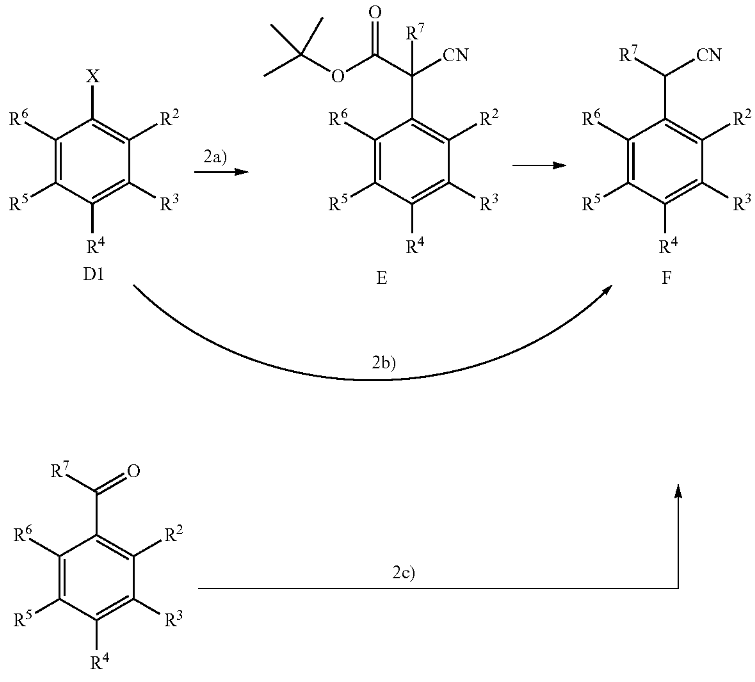

D1 E F D2

Formula C and Formula F can be combined to provide general Formula G with the use of a strong base such as lithium bis(trimethylsilyl)amide or sodium bis(trimethylsilyl)amide in an aprotic solvent such as toluene or tetrahydrofuran at −10 to 25° C. for 2-24 hours, as shown in Scheme 3. When $LG^2$ is halide (F, Cl), Formula G may be converted directly to Formula J via an $S_NAr$ reaction with a nitrogen nucleophile in the presence of a base such as N,N-diisopropylethylamine in an aprotic solvent such as, but not limited to, toluene or dimethyl sulfoxide. When $LG^2$ is thiomethyl, Formula G is oxidized to exclusively sulfoxide or sulfone, or a mixture of both, through many known methods in the literature including meta-chloroperoxybenzoic acid in dichloromethane. The resulting Formula H is converted to Formula J in analogous manner as Formula G when $LG^2$ is halide (F, Cl). Reduction of the nitrile to the corresponding amine by a number of methods is well known to those skilled in the art. One such approach is conversion of Formula J to Formula K with the use of Raney nickel in the presence of 15-50 psi hydrogen atmosphere in solvents such as toluene, tetrahydrofuran, methanol, ethanol and/or propan-2-ol at 25 to 90° C. for 5-36 hours. The addition of a Brønsted acid such as acetic acid can limit protodehalogenation. When $X^2$=C—H in Formula K, it can be transformed to C—F by treatment with a fluorination reagent such as 1-(chloromethyl)-4-fluoro-1,4-diazoniabicyclo[2.2.2]octane bis(tetrafluoroborate) (Selectfluor™) in a mixture of solvents such as methyl tert-butyl ether and N,N-dimethylformamide at 40° C. for 7 hours. C—N coupling of amines and aryl halides is routinely done by the Ullmann-Goldberg reaction. Application of this transformation to the piperidin-2-one of Formula K can be utilized to provide Formula L. For optimal results, the corresponding halide of X—Ar is Br or I, stoichiometric Cu(I) catalysts are used with an appropriate diamine ligand such as $N^1$,$N^2$-dimethylethane-1,2-diamine or $N^1$,$N^2$-dimethylcyclohexane-1,2-diamine, and a base such as tripotassium phosphate, potassium carbonate or cesium carbonate is employed, in such solvents as 1,4-dioxane, tetrahydrofuran, toluene, 2-methyltetrahydrofuran, n-butanol and/or N-methyl-2-pyrrolidone.

Scheme 3

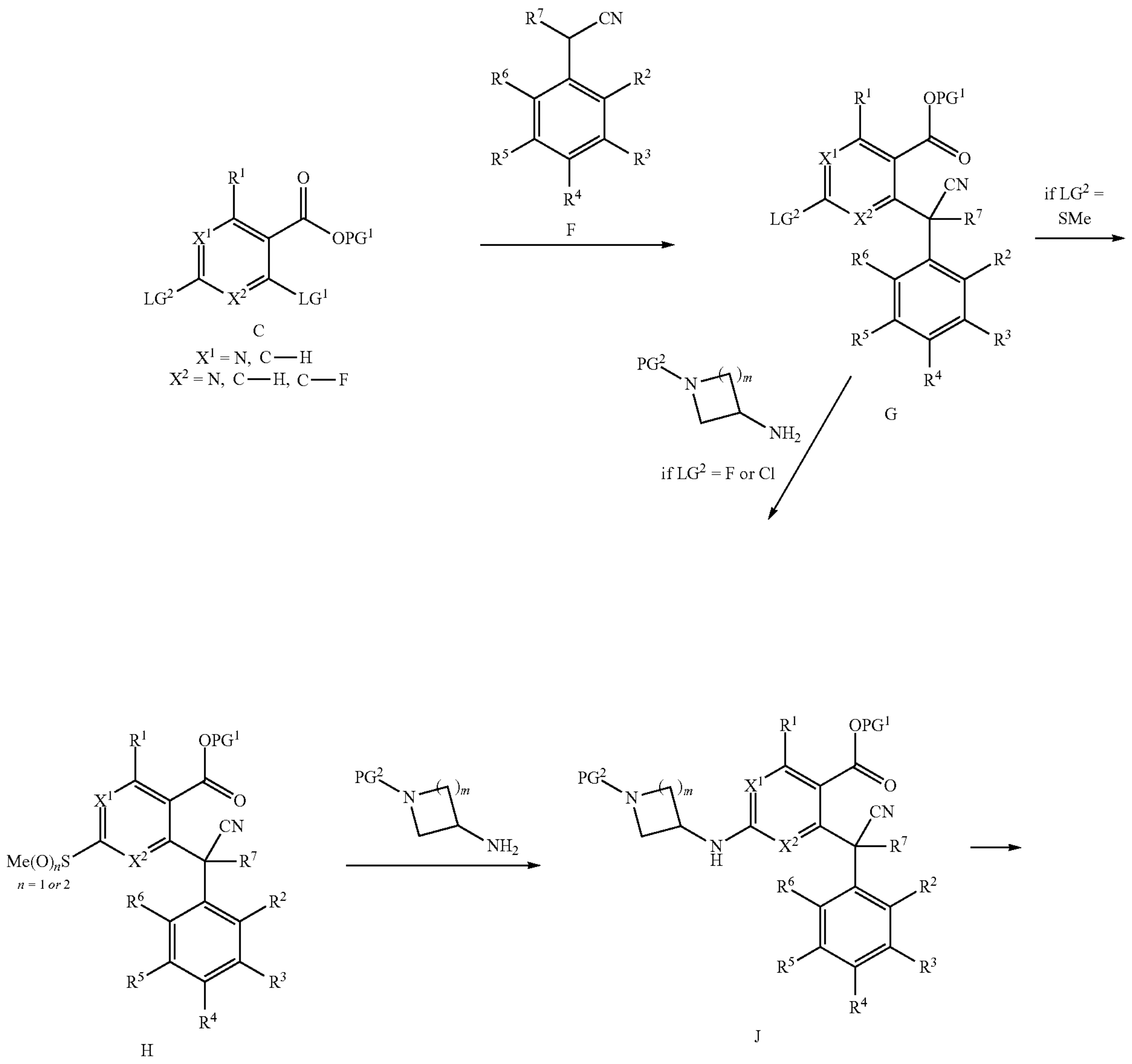

-continued

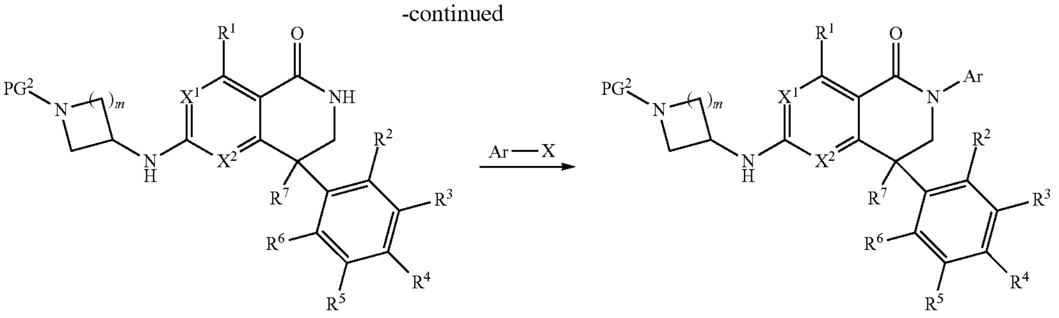

K L

An alternative approach to Formula L is detailed in Scheme 4. The synthesis of 1,1-diarylstyrenes from tosylhydrazones and aryl halides is well known (*Angew. Chem., Int. Ed.* 2011, 50, 7486). Formula M can be prepared from a tosylhydrazone of the corresponding acetophenone derivative and an aryl halide such as Formula C in the presence of a palladium catalyst, a strong base such as lithium tert-butoxide, and an aprotic solvent such as cyclopentyl methyl ether at 100° C. for 2-16 hours. Utilization of catalytic tosylhydrazide (4-methylbenzene-1-sulfonohydrazide) may be employed to improve product formation. Formula C wherein $R^1 \neq H$ is readily prepared from reaction of an aliphatic amine or alcohol with an alkyl 4,6-dichloro-2-(methylsulfanyl)pyrimidine-5-carboxylate (*Heterocycles* 2009, 78, 2263). Transamidation of an alkyl ester such as Formula M with a primary amine nucleophile can be accomplished through the use of trimethylaluminum or 1,3,4,6,7,8-hexahydro-2H-pyrimido[1,2-a]pyrimidine in an aprotic solvent such as tetrahydrofuran. The resultant amide can undergo in situ cyclization to provide Formula N. General Formula O can be furnished by treatment with a strong base such as lithium bis(trimethylsilyl)amide or sodium bis(trimethylsilyl)amide in an aprotic solvent like tetrahydrofuran, followed by reaction with a primary or secondary alkyl halide (Cl, Br, I). An acid-labile protecting group such as (2,4-dimethoxyphenyl)methyl can be removed in neat trifluoroacetic acid. The resultant piperidin-2-one of Formula P can undergo C—N arylation, oxidation of the $LG^2$ thioether, and $S_NAr$ displacement with a nucleophilic amine in a similar manner as that detailed in Scheme 3, furnishing Formula L.

Scheme 4

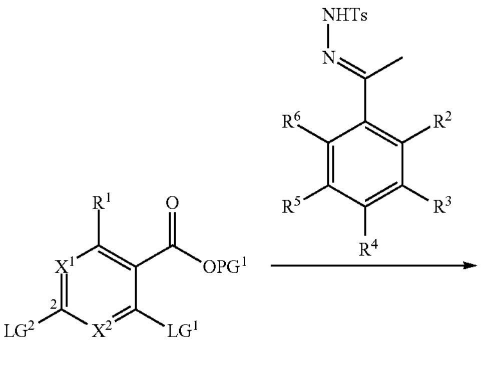

C $X^1, X^2 = N$ $LG^1 = Cl, Br, I$; $LG^2 = SMe$

-continued

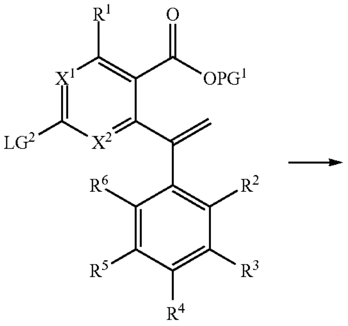

M

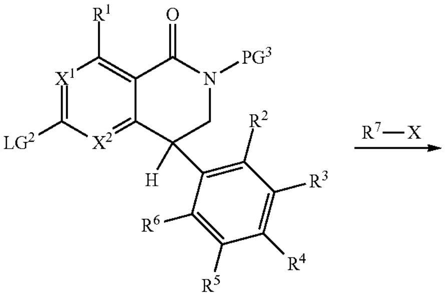

N

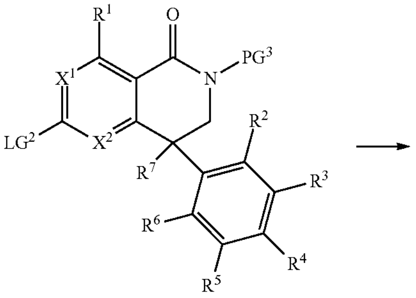

O

-continued

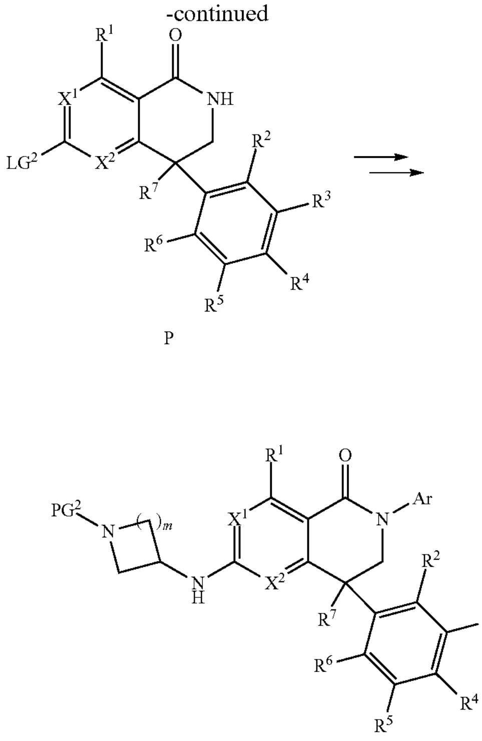

P

L

An alternative approach to Formula L wherein $X^1$ and $X^2$ are N is detailed in Scheme 5. Formula Q can be converted to a suitable substrate for palladium-catalyzed $sp^2$-$sp^2$ cross-coupling by reaction with trifluoromethanesulfonic anhydride in a basic solvent such as pyridine. Formula R can be reacted with a substituted boronic acid or boronate ester in the presence of a palladium catalyst and ligand complex, in the manner of a Suzuki reaction, to provide compounds of general Formula S. Acid-catalyzed conversion of pyranone to pyridone can be achieved by use of hydrochloric acid and an aniline at elevated temperature (100° C.) for prolonged reaction times (24-48 hours). Reduction of the pyridone of Formula T to afford Formula U can be achieved by use of a hydride source such as lithium tri-sec-butylborohydride (L-Selectride) at −78° C. to room temperature in an aprotic solvent such as tetrahydrofuran. Formula V can be furnished from Formula U by treatment with a strong base such as sodium hydride, lithium bis(trimethylsilyl)amide, or sodium bis(trimethylsilyl)amide in an aprotic solvent like tetrahydrofuran, followed by reaction with a primary or secondary alkyl halide (Cl, Br, I). Synthesis of the pyrimidine core of Formula X is achieved in two steps. First, the piperidone is activated by generation of homologated carbonyl Formula W; one method when $R^1$=H employs 1-tert-butoxy-N,N,N,N'-tetramethylmethanediamine (Bredereck's reagent) in an aprotic solvent such as toluene, at an elevated temperature of 110° C.; other methods will be known to one skilled in the art. Formula X is then furnished by reacting Formula W with a commercially available, or readily prepared, substituted guanidine in a polar solvent such as ethanol, with a base such as potassium carbonate, at elevated temperature (75° C.) and prolonged reaction time (24 hours). Oxidation of the activated benzylic carbon in Formula X can be achieved to provide Formula L by reaction with one of many known oxidants, such as potassium permanganate in acetonitrile.

Scheme 5

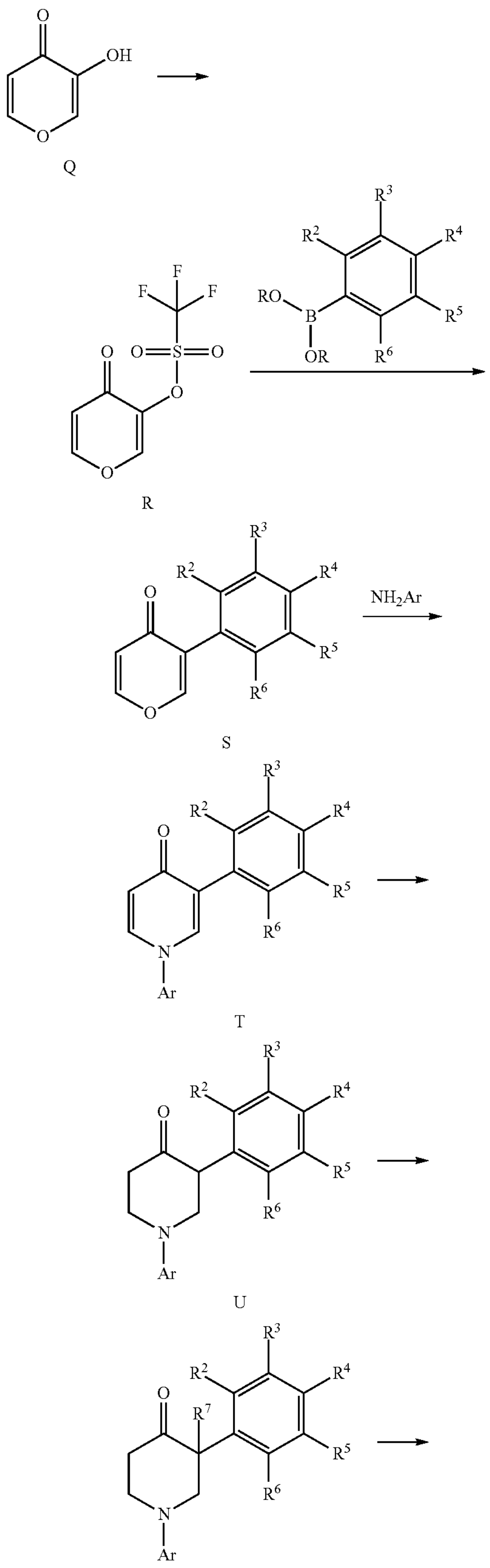

Q

R

S

T

U

V

-continued

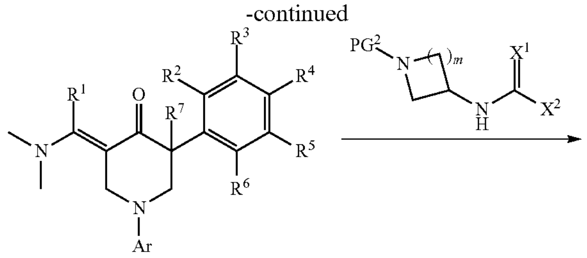

W

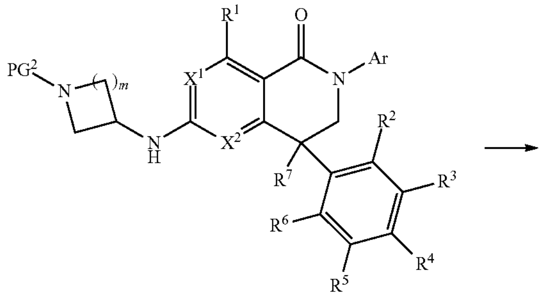

X

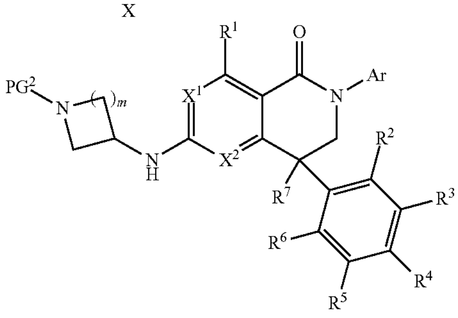

L $X^1, X^2 = N$

General compounds of Formula I can be synthesized from Formula L as detailed in Scheme 6. Removal of an appropriate protecting group such as tert-butyl carbamate is achieved with strong acid such as trifluoroacetic acid or methanesulfonic acid in a single solvent or a mixed solvent system selected from those such as dichloromethane, 1,2-dichloroethane, chloroform, 2,2,2-trifluoroethanol, and 1,1,1,3,3,3-hexafluoropropan-2-ol. Functionalization of the resultant nucleophilic secondary amine of Formula Y in its neutral or salt form can be accomplished via many well-known transformations in the literature such as, but not limited to, those shown in Schemes 6a-6c. Alkylation of secondary amines (Scheme 6a) is commonly achieved by reaction with primary or secondary alkyl halides (Cl, Br, I) in the presence of a moderate base such as potassium carbonate, potassium bicarbonate, or N,N-diisopropylethylamine, in an aprotic solvent such as acetonitrile or N,N-dimethylformamide. The addition of potassium iodide is routinely used to improve product formation. Amide formation from secondary amines (Scheme 6b1) is typically accomplished by use of a readily available carboxylic acid and an amide-coupling reagent such as, but not limited to, propylphosphonic anhydride (2,4,6-tripropyl-1,3,5,2,4,6-trioxatriphosphinane 2,4,6-trioxide; T3P), or 1-[3-(dimethylamino)propyl]-3-ethylcarbodiimide hydrochloride (EDCI) and 2-hydroxypyridine 1-oxide (HOPO), or O-(7-azabenzotriazol-1-yl)-N,N,N'N'-tetramethyluronium hexafluorophosphate (HATU), in the presence of a base such as triethylamine or 4-methylmorpholine and an aprotic solvent such as dichloromethane, N,N-dimethylacetamide, or N,N-dimethylformamide. Alternatively, the carboxylic acid can be activated in a separate step, such as conversion to the acid chloride by use of oxalyl chloride and catalytic N,N-dimethylformamide in dichloromethane, or via the ester derived from treatment with 1-hydroxypyrrolidine-2,5-dione (NHS) and 1,3-dicyclohexylcarbodiimide (DCC), followed by reaction with the secondary amine nucleophile (Scheme 6b2). Chloroacetyl chloride is a versatile reagent to first react with Formula Y followed by the addition of nucleophilic amines (Scheme 6b3). Urea formation from secondary amines can be carried out using readily available reagents such as isocyanato(trimethyl)silane or N-alkyl-1H-imidazole-1-carboxamide and their more reactive salts (Org. Process Res. Dev. 2021, 25, 500) in the presence of triethylamine and an aprotic solvent such as acetonitrile, dichloromethane, or tetrahydrofuran (Scheme 6c1). Alternatively, the secondary amine of Formula Y can be activated by conversion to an electron-poor carbamate, which is highly reactive to displacement with primary and secondary amines, in the presence of triethylamine and dimethyl sulfoxide (*Chem. Eur. J.* 2006, 12, 8056) (Scheme 6c2). In many cases, $R^8$ of the general Formula I may contain a functional group that is incompatible with the various methods described in Schemes 6a-6c, which will require use of a protecting group. Examples of such protecting groups include, but are not limited to, acid-labile tert-butyl carbamate on amines and lactams; base-labile acetyl on alcohols; aryl nitrile that can undergo reduction to a requisite amine. Schemes 6a-6c may introduce additional stereocenters resulting in new diastereomers of Formula I, which may require separation through methods well known to one skilled in the art.

Scheme 6

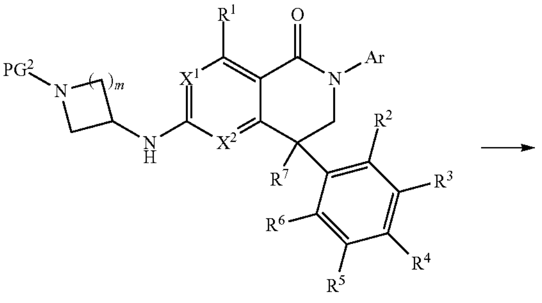

L

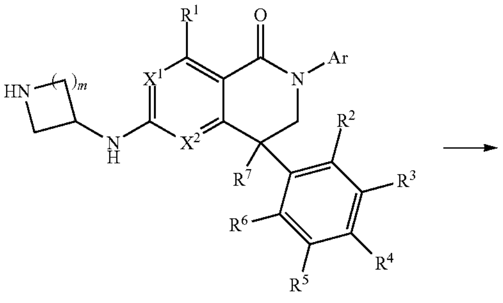

Y

-continued

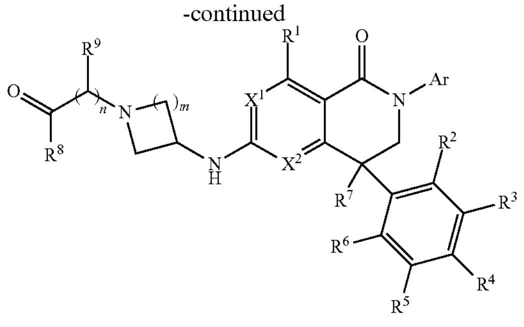

Formula I a. Alkylation

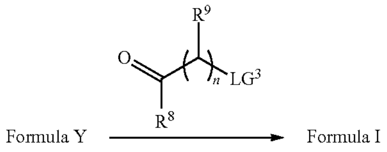

b. Amide Formation

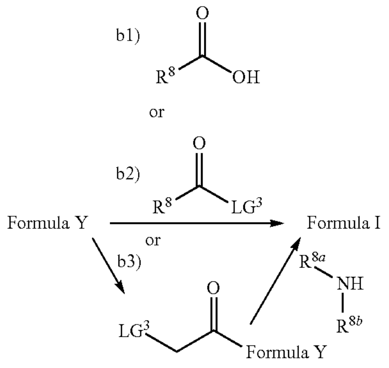

c. Urea Formation

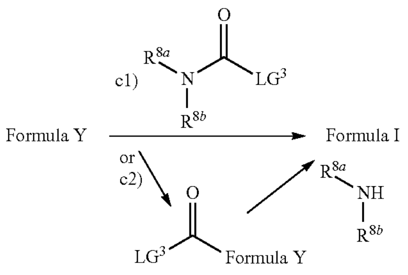

An alternative approach to general Formula I is depicted in Scheme 7. Formula K can be subjected to removal of $PG^2$ and functionalization of the resulting secondary amine in a manner analogous to that depicted in Scheme 6. The penultimate piperidin-2-one can undergo C—N arylation with aryl halides in a similar manner as that detailed in Scheme 3, to furnish general Formula I.

Scheme 7

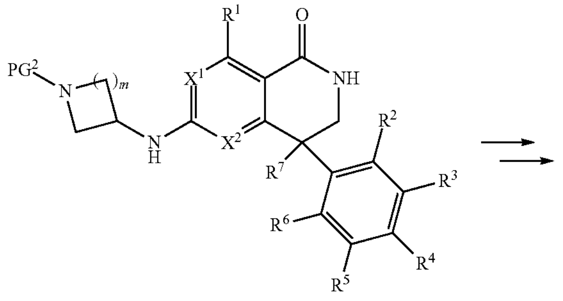

K

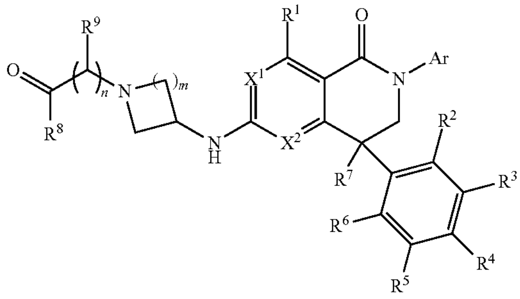

Formula I

Reactants X—Ar (X=Br, I), as utilized in Schemes 3, 4 and 7, are widely available from commercial vendors. In some instances, X—Ar may require synthesis by methods well known to one skilled in the art. One non-limiting example of the formation of X—Ar is depicted in Scheme 8. Formula Z can be converted to Formula AA by imine formation with 2-[(tributylstannyl)methoxy]ethan-1-amine, followed by copper-catalyzed cyclization (*Org. Lett.* 2014, 16, 1236).

Scheme 8

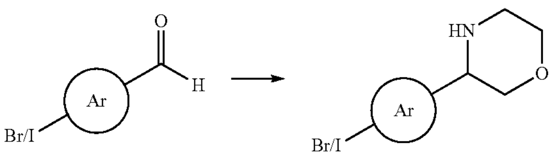

Z

AA

An alternative approach to general Formula I is depicted in Scheme 9. Formula DD is prepared from Formula P and is a competent electrophile for $S_N$Ar substitution as shown in Scheme 4. Reaction of Formula DD with primary amine nucleophiles, such as those shown in Formula CC, in the presence of mild base such as sodium bicarbonate or triethylamine, in a polar solvent such as dimethyl sulfoxide from 45 to 60° C. over 3-16 hours, can produce compounds of general Formula I. Formula CC may be utilized in its neutral or salt form. Formula CC is routinely provided in two steps from commercially available or widely known compounds of Formula BB in a manner analogous to that depicted in Scheme 6a-c.

Scheme 9

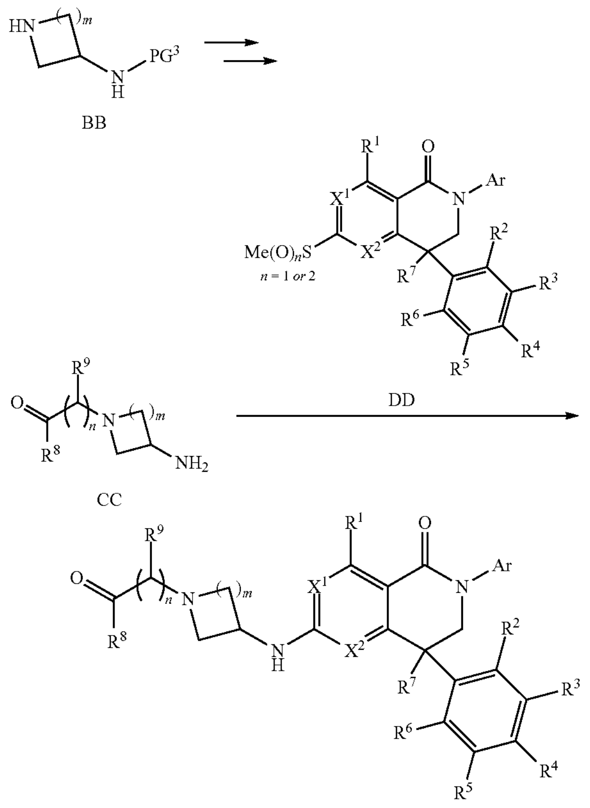

Formula I

The starting materials and reagents for the above-described Formula I compounds are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

This disclosure is also directed at pharmaceutical compositions having a therapeutically effective amount of a compound of Formula I or a pharmaceutically acceptable salt of said compound and a pharmaceutically acceptable carrier, vehicle, or diluent.

The compounds of this disclosure may also be used in conjunction with other pharmaceutical agents (e.g., anti-heart failure agents) for the treatment of the disease/conditions described herein. This disclosure is also directed at pharmaceutical combination compositions that include: a therapeutically effective amount of a composition having:

a first compound, said first compound being a compound of any of Formula I or a pharmaceutically acceptable salt of said compound;

a second compound, said second compound being a treatment agent for kidney disease, an anti-diabetic agent; a non-alcoholic steatohepatitis treatment agent, a non-alcoholic fatty liver disease treatment agent, an anti-heart failure treatment agent, or a peripheral artery disease treatment agent; and a pharmaceutical carrier, vehicle, or diluent.

The anti-heart failure agent can be an ACE inhibitor, an angiotensin receptor blocker, an angiotensin-receptor neprilysin inhibitor, a beta-adrenergic receptor blocker, a calcium channel blocker, an SGLT2 inhibitor, or a vasodilator.

The compounds can be administered alone or in combination with one or more additional therapeutic agents. By “administered in combination” or “combination therapy” it is meant that a compound and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect. The phrases “concurrent administration,” “co-administration,” “simultaneous administration,” and “administered simultaneously” mean that the compounds are administered in combination. Thus, the methods of prevention and treatment described herein include use of combination agents.

The combination agents are administered to a mammal in a therapeutically effective amount. By “therapeutically effective amount” it is meant an amount of a compound of Formula I that, when administered alone or in combination with an additional therapeutic agent to a mammal, is effective to treat the desired disease/condition (e.g., peripheral artery disease, heart failure, or diabetes).

Given the anti-heart failure activity of the compounds of this disclosure, they may be co-administered with other anti-heart failure agents such as ACE inhibitors (e.g. captopril, enalapril, fosinopril, Lisinopril, perindopril, quinapril, Ramipril, trandolapril), Angiotensin II receptor blockers (e.g., Candesartan, Losartan, Valsartan), Angiotensin-receptor neprilysin inhibitors (sacubitril/valsartan), $I_f$ channel blocker Ivabradine, Beta-Adrenergic blocking agents (e.g., bisoprolol, metoprolol succinate, carvedilol), SGLT2 inhibitors, Aldosterone antagonists (e.g., spironolactone, eplerenone), cardiac myosin activator (e.g. omecamtiv mecarbil), guanylate cyclase stimulator (e.g. vericiguat), cardiac myosin inhibitor (e.g. mavacamten), SERCA2a activator (e.g. istaroxime), hydralazine and isosorbide dinitrate, diuretics (e.g., furosemide, bumetanide, torsemide, chlorothiazide, amiloride, hydrochlorothiazide, Indapamide, Metolazone, Triamterene), or digoxin.

The compounds of Formula I can also be used in combination with antihypertensive agents and such antihypertensive activity is readily determined by those skilled in the art according to standard assays (e.g., blood pressure measurements). Examples of suitable anti-hypertensive agents include: alpha adrenergic blockers; beta adrenergic blockers; calcium channel blockers (e.g., diltiazem, verapamil, nifedipine, and amlodipine); vasodilators (e.g., hydralazine), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, torsemide, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., gemopatrilat and nitrates). An exemplary antianginal agent is ivabradine.

Examples of suitable calcium channel blockers (L-type or T-type) include diltiazem, verapamil, nifedipine and amlodipine and mybefradil.

Examples of suitable cardiac glycosides include digitalis and ouabain.

The compound of Formula I can be co-administered with one or more diuretics. Examples of diuretics include (a) loop diuretics such as furosemide (such as LASIX™) torsemide (such as DEMADEX™), bemetanide (such as BUMEX™), and ethacrynic acid (such as EDECRIN™); (b) thiazide-type diuretics such as chlorothiazide (such as DIURIL™ ESIDRIX™ or HYDRODIURIL™), hydrochlorothiazide (such as MICROZIDE™ or ORETIC™) benzthiazide, hydroflumethiazide (such as SALURON™), bendroflumethiazide, methychlorthiazide, polythiazide, trichlormethiazide, and indapamide (such as LOZOL™); (c) phthalimidine-type diuretics such as chlorthalidone (such as HYGROTON™), and metolazone (such as ZAROXOLYN™); (d) quinazoline-type diuretics such as quinethazone; and (e) potassium-sparing diuretics such as triamterene (such as DYRENIUM™), and amiloride (such as MIDAMOR™ or MODURETIC™) The compound of Formula I can be co-administered with a loop diuretic. The loop diuretic can be selected from furosemide and torsemide. The compound of Formula I can be co-administered with furosemide. The compound of Formula I can be co-administered with torsemide, which can optionally be a controlled or modified release form of torsemide.

The compound of Formula I can be co-administered with a thiazide-type diuretic. The thiazide-type diuretic can be selected from the group consisting of chlorothiazide and hydrochlorothiazide. The compound of Formula I can be co-administered with chlorothiazide. The compound of Formula I can be co-administered with hydrochlorothiazide.

The compound of Formula I can be co-administered with a phthalimidine-type diuretic. The phthalimidine-type diuretic can be chlorthalidone.

Those skilled in the art will recognize that the compounds of this disclosure may also be used in conjunction with other cardiovascular or cerebrovascular treatments including PCI, stenting, drug-eluting stents, stem cell therapy, and medical devices such as implanted pacemakers, defibrillators, or cardiac resynchronization therapy.

The compounds of Formula I can be used in combination with drugs such as anti-hypertensives, diuretics, or SGLT2 inhibitors (e.g., dapagliflozin, empagliflozin, or other SGLT2 inhibitors recited herein).

The compounds of Formula I can be used in combination with drugs used in the management of peripheral artery disease. This includes many of the agents used in the management of cardiovascular disease (mentioned above) as well as anti-platelet medications (e.g., clopidogrel, ticagrelor) and phosphodiesterase inhibitors (e.g., cilostazol).

The compounds in Formula I can be used in combination with drugs used in management of type 2 diabetes, the metabolic syndrome and/or obesity including metformin, glucagon-like peptide 1 (GLP-1) receptor agonists (e.g., liraglutide, semaglutide, dulaglutide), dipeptidyl peptidase 4 (DPP-4) inhibitors (e.g., linagliptin), SGLT2 inhibitors (e.g., empagliflozin, canagliflozin, dapagliflozin), sulfonylureas (e.g., glipizide, glimepiride), meglitinides (e.g., repaglinide, nateglinide), thiazolidinediones (e.g., rosiglitazone, pioglitazone), and insulin (e.g., neutral protamine Hagedorn (NPH), detemir, glargine, degludec, lispro, aspart, glulisine, regular).

Particularly when provided as a single dosage unit, the potential exists for a chemical interaction between the combined active ingredients. For this reason, when a Formula I compound and a second therapeutic agent are combined in a single dosage unit they may be formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that effects a sustained release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products, whether administered in a single dosage form or administered in separate forms but at the same time by the same manner, will be readily apparent to those skilled in the art, once armed with the present disclosure.

In combination therapy treatment, both the compounds of this disclosure and the other drug therapies are administered to mammals (e.g., humans, male or female) by conventional methods.

The present compound can be administered in order to treat diseases, conditions, and/or disorders activated by the activation of AMPK in an animal, particularly a human, that includes administering to the animal or human in need of such treatment a therapeutically effective amount of a compound of the present disclosure or a pharmaceutical composition comprising an effective amount of a compound of the present disclosure and a pharmaceutically acceptable excipient, diluent, or carrier. The compound is particularly useful for treating diseases, conditions, and/or disorders that benefit from the activation of AMPK.

As AMPKγ3 is a key molecular driver of the beneficial effects of exercise the compound is useful for treating disease, conditions and/or disorders that benefit from exercise.

Exercise ameliorates a host of diseases including obesity, metabolic syndrome, diabetes, heart failure, peripheral artery disease, cachexia, frailty, and some musculo-skeletal disorders. (Pedersen, B. K. & Saltin, B. Exercise as medicine—evidence for prescribing exercise as therapy in 26 different chronic diseases. *Scand J Med Sci Sports* 25 Suppl 3, 1-72 (2015)). Conversely, inactivity is considered a risk factor for a multitude of cardiometabolic diseases. Patients who exercise have reduced cardiovascular morbidity and mortality, including lower blood pressure, improved insulin sensitivity, and reduced plasma lipoprotein levels. (Chen, H. et al. Exercise training maintains cardiovascular health:

signaling pathways involved and potential therapeutics. *Signal Transduct Target Ther*7, 306 (2022)).

The compound of the present disclosure can be administered for the treatment of or to reduce the risks of hospitalization for heart failure, cardiovascular death, congestive heart failure, heart failure with New York Heart Association Class I-IV symptoms, heart failure with reduced left ventricular function (HF-rEF), heart failure with preserved left ventricular function (HF-pEF), heart failure with midrange ejection fraction (HF-mrEF), cardiovascular death, heart failure in patients with Type II diabetes mellitus, coronary heart disease, unstable angina, peripheral vascular disease (for example, peripheral artery disease), renovascular disease, pulmonary hypertension, vasculitis, acute coronary syndromes and modification of cardiovascular risk.

The compound of the present disclosure can be administered for the treatment of peripheral artery disease.

The compound can be administered for the treatment of obesity, and obesity-related disorders (e.g., overweight, weight gain, or weight maintenance). Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25 to 29.9 kilograms per meter squared ($kg/m^2$), and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

The compound can be administered for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology,* 7(2), (2005); and Alberti, K. G., et al., "The Metabolic Syndrome—A New Worldwide Definition," *Lancet,* 366, 1059-62 (2005).

The compound can be administered for the treatment (e.g., delaying the progression or onset) of diabetes or diabetes-related disorders including Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy.

The administration of the compounds of the present disclosure can provide a statistically significant ($p<0.05$) reduction in at least one cardiovascular disease risk factor, such as lowering of plasma leptin, C-reactive protein (CRP) and/or cholesterol, as compared to a vehicle control containing no drug. The administration of compounds of the present disclosure may also provide a statistically significant ($p<0.05$) reduction in glucose serum levels.

Administration of the compounds of this disclosure can be via any method which delivers a compound of this disclosure systemically and/or locally. These methods include oral routes, parenteral, intraduodenal routes, buccal, intranasal etc. Generally, the compounds of this disclosure are administered orally, but parenteral administration (e.g., intravenous, intramuscular, subcutaneous, or intramedullary) may be utilized, for example, where oral administration is inappropriate for the target or where the patient is unable to ingest the drug.

The dosage regimen for the compounds of the disclosure or compositions containing said compounds is based on a variety of factors, including the type, age, weight, sex, and medical condition of the patient; the severity of the condition; the route of administration; and the activity of the particular compound employed. Thus, the dosage regimen may vary widely. For example, the total daily dose of a compound of the disclosure can be about 0.01 to about 100 mg/kg (i.e., mg compound of the disclosure per kg body weight) for the treatment of the indicated conditions discussed herein. In another example, total daily dose of the compound of the can be about 0.1 to about 50 mg/kg, or about 0.5 to about 30 mg/kg. It is not uncommon that the administration of the compound will be repeated a plurality of times in a day (typically no greater than 4 times). Multiple doses per day typically may be used to increase the total daily dose, if desired.

For administration to human patients, an oral daily dose of the compounds herein may be in the range 1 milligrams (mg) to 5000 mg depending, of course, on the mode of and frequency of administration, the disease state, and the age and condition of the patient, etc. An oral daily dose is in the range of 3 mg to 3000 mg may be used. A further oral daily dose is in the range of 5 mg to 1000 mg. For convenience, the compounds of Formula I can be administered in a unit dosage form. If desired, multiple doses per day of the unit dosage form can be used to increase the total daily dose. The unit dosage form, for example, may be a tablet or capsule containing about 0.1, 0.5, 1, 5, 10, 15, 20, 25, 30, 35, 40, 45, 50, 55, 60, 65, 70, 75, 80, 85, 90, 95, 100, 125, 150, 175, 200, 250, 500, or 1000 mg of the compound. The total daily dose may be administered in single or divided doses and may, at the physician's discretion, fall outside of the typical ranges given herein.

For administration to human patients, an infusion daily dose of the compounds herein may be in the range 1 mg to 2000 mg depending, of course, on the mode of and frequency of administration, the disease state, and the age and condition of the patient, etc. A further infusion daily dose is in the range of 5 mg to 1000 mg. The total daily dose may be administered in single or divided doses and may, at the physician's discretion, fall outside of the typical ranges given herein.

These compounds may also be administered to animals other than humans, for example, for the indications detailed above. The precise dosage administered of each active ingredient will vary depending upon any number of factors, including but not limited to, the type of animal and type of disease state being treated, the age of the animal, and the route(s) of administration.

A dosage of the combination pharmaceutical agents to be used in conjunction with the Formula I compound is used that is effective for the indication being treated. Such dosages can be determined by standard assays such as those referenced above and provided herein. The combination agents may be administered simultaneously or sequentially in any order.

These dosages are based on an average human subject having a weight of about 60 kg to 70 kg. The physician will readily be able to determine doses for subjects whose weight falls outside this range, such as infants and the elderly.

Dosage regimens may be adjusted to provide the optimum desired response. For example, a single bolus may be administered, several divided doses may be administered over time, or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure is dictated by and directly dependent on (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, intra-patient dose-escalation may be used as determined by the skilled artisan. Determining appropriate dosages and regiments for administration of the chemotherapeutic agent are well-known in the relevant art and would be understood to be encompassed by the skilled artisan once provided the teachings disclosed herein.

Sustained-release preparations may be used. Suitable examples of sustained-release preparations include semipermeable matrices of solid hydrophobic polymers containing the compound of the disclosure, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

This disclosure further comprises use of a compound of Formula I for use as a medicament (such as a unit dosage tablet or unit dosage capsule). This disclosure comprises the use of a compound of Formula I for the manufacture of a medicament (such as a unit dosage tablet or unit dosage capsule) to treat one or more of the conditions previously identified in the above sections discussing methods of treatment. This disclosure further comprises a compound of formula I, or a pharmaceutically acceptable salt thereof, for use as a medicament and a compound of formula I, or a pharmaceutically acceptable salt therefore, for use in any method of treatment herein disclosed.

A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The compounds of the disclosure or combinations can be administered alone but will generally be administered in an admixture with one or more suitable pharmaceutical excipients, adjuvants, diluents, or carriers known in the art and selected with regard to the intended route of administration and standard pharmaceutical practice. The compound of the disclosure or combination may be formulated to provide immediate-, delayed-, modified-, sustained-, pulsed- or controlled-release dosage forms depending on the desired route of administration and the specificity of release profile, commensurate with therapeutic needs.

The pharmaceutical composition comprises a compound of the disclosure or a combination in an amount generally in the range of from about 1% to about 75%, 80%, 85%, 90% or even 95% (by weight) of the composition, usually in the range of about 1%, 2% or 3% to about 50%, 60% or 70%, more frequently in the range of about 1%, 2% or 3% to less than 50% such as about 25%, 30% or 35%.

Methods of preparing various pharmaceutical compositions with a specific amount of active compound are known to those skilled in this art. For examples, see Remington: The Practice of Pharmacy, Lippincott Williams and Wilkins, Baltimore Md. 20.sup.th ed. 2000.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Examples of suitable aqueous and nonaqueous carriers or diluents (including solvents and vehicles) include water, ethanol, polyols (propylene glycol, polyethylene glycol, glycerol, and the like), suitable mixtures thereof, triglycerides including vegetable oils such as olive oil, and injectable organic esters such as ethyl oleate. A preferred carrier is Miglyol™ brand caprylic/capric acid ester with glycerin or propylene glycol (e.g., Miglyol™ 812, Miglyol™ 829, Miglyol™ 840) available from Condea Vista Co., Cranford, N.J. Proper fluidity can be maintained, for example, by the use of a coating such as lecithin, by the maintenance of the required particle size in the case of dispersions, and by the use of surfactants.

These compositions for parenteral injection may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, chews, lozenges, pills, powders, and multi-particulate preparations (granules). In such solid dosage forms, a compound of Formula I or a combination is admixed with at least one inert excipient, diluent, or carrier. Suitable excipients, diluents or carriers include materials such as sodium citrate or dicalcium phosphate and/or (a) one or more fillers or extenders (e.g., microcrystalline cellulose (available as Avicel™ from FMC Corp.) starches, lactose, sucrose, mannitol, silicic acid, xylitol, sorbitol, dextrose, calcium hydrogen phosphate, dextrin, alpha-cyclodextrin, beta-cyclodextrin, polyethylene glycol, medium chain fatty acids, titanium oxide, magnesium oxide, aluminum oxide, and the like); (b) one or more binders (e.g., carboxymethylcellulose, methylcellulose, hydroxypropylcellulose, hydroxypropylmethylcellulose, gelatin, gum arabic, ethyl cellulose, polyvinyl alcohol, pullulan, pregelatinized starch, agar, tragacanth, alginates, gelatin, polyvinylpyrrolidone, sucrose, acacia, and the like); (c) one or more humectants (e.g., glycerol and the like); (d) one or more disintegrating agents (e.g., agar-agar, calcium carbonate, potato or tapioca starch, alginic acid, certain complex silicates, sodium carbonate, sodium lauryl sulphate, sodium starch glycolate (available as Explotab™ from Edward Mendell Co.), cross-linked polyvinyl pyrrolidone, croscarmellose sodium A-type (available as Ac-di-sol™), polyacrilin potassium (an ion exchange resin), and the like); (e) one or more solution retarders (e.g., paraffin and the like); (f) one or more absorption accelerators (e.g., quaternary ammonium compounds and the like); (g) one or more wetting agents (e.g., cetyl alcohol, glycerol monostearate, and the like); (h) one or more adsorbents (e.g., kaolin, bentonite, and the like); and/or (i) one or more lubricants (e.g., talc, calcium stearate, magnesium stearate, stearic acid, polyoxyl stearate, cetanol, talc, hydrogenated castor oil, sucrose esters of fatty acid, dimethylpolysiloxane, microcrystalline wax, yellow beeswax, white beeswax, solid polyethylene glycols, sodium lauryl sulfate, and the like). In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules may be prepared with coatings and shells, such as enteric coatings and others well known in the art. They may also contain opacifying agents, and can also be of such composition that they release the compound of Formula I and/or the additional pharmaceutical agent in a delayed manner. Examples of embedding compositions that can be used are polymeric substances and waxes. The drug may also be in micro-encapsulated form, if appropriate, with one or more of the above-mentioned excipients.

For tablets, the active agent will typically comprise less than 50% (by weight) of the formulation, for example, less than about 10% such as 5% or 2.5% by weight. The predominant portion of the formulation comprises fillers, diluents, disintegrants, lubricants and optionally, flavors. The composition of these excipients is well known in the art. Frequently, the fillers/diluents will comprise mixtures of two or more of the following components: microcrystalline cellulose, mannitol, lactose (all types), starch, and di-calcium phosphate. The filler/diluent mixtures typically comprise less than 98% by weight of the formulation and preferably less than 95%, for example 93.5%. Preferred disintegrants include Ac-di-sol™, Explotab™, starch and sodium lauryl sulphate. When present, a disintegrant will usually comprise less than 10% by weight of the formulation or less than 5%, for example about 3%. A preferred lubricant is magnesium stearate. When present a lubricant will usually comprise less than 5% by weight of the formulation or less than 3%, for example about 1%.

Tablets may be manufactured by standard tableting processes, for example, direct compression or a wet, dry or melt granulation, melt congealing process and extrusion. The tablet cores may be mono or multi-layer(s) and can be coated with appropriate overcoats known in the art.

Liquid dosage forms for oral administration include pharmaceutically acceptable emulsions, solutions, suspensions, syrups, and elixirs. In addition to the compound of Formula I or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), Miglyol™ (available from CONDEA Vista Co., Cranford, N.J.), glycerol, tetrahydrofurfuryl alcohol, polyethylene glycols and fatty acid esters of sorbitan, or mixtures of these substances, and the like.

Besides such inert diluents, the composition may also include excipients, such as wetting agents, emulsifying and suspending agents, sweetening, flavoring, and perfuming agents.

Oral liquid forms of the compounds of the disclosure or combinations include solutions, wherein the active compound is fully dissolved. Examples of solvents include all pharmaceutically precedented solvents suitable for oral administration, particularly those in which the compounds of the disclosure show good solubility, e.g., polyethylene glycol, polypropylene glycol, edible oils, and glyceryl- and glyceride-based systems. Glyceryl- and glyceride-based systems may include, for example, the following branded products (and corresponding generic products): Captex™ 355 EP (glyceryl tricaprylate/caprate, from Abitec, Columbus Ohio), Crodamol™ GTC/C (medium chain triglyceride, from Croda, Cowick Hall, UK) or Labrafac™ CC (medium chain triglycerides, from Gattefosse), Captex™ 500P (glyceryl triacetate i.e. triacetin, from Abitec), Capmul™ MCM (medium chain mono- and diglycerides, from Abitec), Miglyol™ 812 (caprylic/capric triglyceride, from Condea, Cranford N.J.), Migyol™ 829 (caprylic/capric/succinic triglyceride, from Condea), Migyol™ 840 (propylene glycol dicaprylate/dicaprate, from Condea), Labrafil™ M1944CS (oleoyl macrogol-6 glycerides, from Gattefosse), Peceol™ (glyceryl monooleate, from Gattefosse) and Maisine™ 35-1 (glyceryl monooleate, from Gattefosse). Of particular interest are the medium chain (about $C_8$ to $C_{10}$) triglyceride oils. These solvents frequently make up the predominant portion of the composition, i.e., greater than about 50%, usually greater than about 80%, for example about 95% or 99%. Adjuvants and additives may also be included with the solvents principally as taste-mask agents, palatability and flavoring agents, antioxidants, stabilizers, texture, and viscosity modifiers and solubilizers.

Suspensions, in addition to the compound of Formula I or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of Formula I or a combination with suitable non-irritating excipients or carriers, such as cocoa butter, polyethylene glycol or a suppository wax which are solid at ordinary room temperature, but liquid at body temperature, and therefore, melt in the rectum or vaginal cavity thereby releasing the active component(s).

Dosage forms for topical administration of the compounds of Formula I or combinations include ointments, creams, lotions, powders, and sprays. The drugs are admixed with a pharmaceutically acceptable excipient, diluent or carrier, and any preservatives, buffers, or propellants that may be required.

Many of the present compounds are poorly soluble in water, e.g., less than about 1 microgram per milliliter (μg/mL). Therefore, liquid compositions in solubilizing, non-aqueous solvents such as the medium chain triglyceride oils discussed above are a preferred dosage form for these compounds.

Solid amorphous dispersions, including dispersions formed by a spray-drying process, are also a preferred dosage form for the poorly soluble compounds of the disclosure. By "solid amorphous dispersion" is meant a solid material in which at least a portion of the poorly soluble compound is in the amorphous form and dispersed in a water-soluble polymer. By "amorphous" is meant that the poorly soluble compound is not crystalline. By "crystalline" is meant that the compound exhibits long-range order in three dimensions of at least 100 repeat units in each dimension. Thus, the term amorphous is intended to include not only material that has essentially no order, but also material that may have some small degree of order, but the order is in less than three dimensions and/or is only over short distances. Amorphous material may be characterized by techniques known in the art such as powder x-ray diffraction (PXRD) crystallography, solid state NMR, or thermal techniques such as differential scanning calorimetry (DSC).

Preferably, at least a major portion (i.e., at least about 60 wt %) of the poorly soluble compound in the solid amorphous dispersion is amorphous. The compound can exist within the solid amorphous dispersion in relatively pure amorphous domains or regions, as a solid solution of the compound homogeneously distributed throughout the polymer or any combination of these states or those states that lie intermediate between them. Preferably, the solid amorphous dispersion is substantially homogeneous so that the amorphous compound is dispersed as homogeneously as possible throughout the polymer. As used herein, "substantially homogeneous" means that the fraction of the compound that is present in relatively pure amorphous domains or regions within the solid amorphous dispersion is relatively small, on the order of less than 20 wt %, and preferably less than 10 wt % of the total amount of drug.

Water-soluble polymers suitable for use in the solid amorphous dispersions should be inert, in the sense that they do not chemically react with the poorly soluble compound in an adverse manner, are pharmaceutically acceptable, and have at least some solubility in aqueous solution at physiologically relevant pHs (e.g., 1-8). The polymer can be neutral or ionizable, and should have an aqueous-solubility of at least 0.1 milligrams per milliliter (mg/mL) over at least a portion of the pH range of 1-8.

Water-soluble polymers suitable for use with the compounds of Formula I may be cellulosic or non-cellulosic. The polymers may be neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate (HPMCAS), hydroxypropyl methyl cellulose (HPMC), hydroxypropyl methyl cellulose phthalate (HPMCP), carboxy methyl ethyl cellulose (CMEC), cellulose acetate phthalate (CAP), cellulose acetate trimellitate (CAT), polyvinylpyrrolidone (PVP), hydroxypropyl cellulose (HPC), methyl cellulose (MC), block copolymers of ethylene oxide and propylene oxide (PEO/PPO, also known as poloxamers), and mixtures thereof. Especially preferred polymers include HPMCAS, HPMC, HPMCP, CMEC, CAP, CAT, PVP, poloxamers, and mixtures thereof. Most preferred is HPMCAS. See European Patent Application Publication No. 0 901 786 A2, the disclosure of which is incorporated herein by reference.

The solid amorphous dispersions may be prepared according to any process for forming solid amorphous dispersions that results in at least a major portion (at least 60% by weight) of the poorly soluble compound being in the amorphous state. Such processes include mechanical, thermal, and solvent processes. Exemplary mechanical processes include milling and extrusion; melt processes including high temperature fusion, solvent-modified fusion, and melt-congeal processes; and solvent processes including non-solvent precipitation, spray coating and spray drying. See, for example, the following U.S. Patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In a preferred process, the solid amorphous dispersion is formed by spray drying, as disclosed in European Patent Application Publication No. 0 901 786 A2. In this process, the compound and polymer are dissolved in a solvent, such as acetone or methanol, and the solvent is then rapidly removed from the solution by spray drying to form the solid amorphous dispersion. The solid amorphous dispersions may be prepared to contain up to about 99 wt % of the compound, e.g., 1 wt %, 5 wt %, 10 wt %, 25 wt %, 50 wt %, 75 wt %, 95 wt %, or 98 wt % as desired.

The solid dispersion may be used as the dosage form itself or it may serve as a manufacturing-use-product (MUP) in the preparation of other dosage forms such as capsules, tablets, solutions, or suspensions. An example of an aqueous suspension is an aqueous suspension of a 1:1 (w/w) compound/HPMCAS-HF spray-dried dispersion containing 2.5 mg/mL of compound in 2% polysorbate-80. Solid dispersions for use in a tablet or capsule will generally be mixed with other excipients or adjuvants typically found in such dosage forms. For example, an exemplary filler for capsules contains a 2:1 (w/w) compound/HPMCAS-MF spray-dried dispersion (60%), lactose (fast flow) (15%), microcrystalline cellulose (e.g., Avicel.sup.(R0-102) (15.8%), sodium starch (7%), sodium lauryl sulfate (2%) and magnesium stearate (1%).

The HPMCAS polymers are available in low, medium, and high grades as Aqoat.sup.(R)-LF, Aqoat.sup.(R)-MF and Aqoat.sup.(R)-HF respectively from Shin-Etsu Chemical Co., LTD, Tokyo, Japan. The higher MF and HF grades are generally preferred.

Liposomes containing these agents and/or compounds of the disclosure are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the disclosure may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

The formulations to be used for intravenous administration must be sterile. This is readily accomplished by, for example, filtration through sterile filtration membranes. Compounds of the disclosure are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™, and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 micrometers (μm), particularly 0.1 and 0.5 μm, and have a pH in the range of 5.5 to 8.0.

The emulsion compositions can be those prepared by mixing a compound of the disclosure with Intralipid™ or the components thereof (soybean oil, egg phospholipids, glycerol, and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. The compositions can be administered by the oral or nasal respiratory route for local or systemic effect. Compositions in preferably sterile pharmaceutically acceptable solvents may be nebulized by use of gases. Nebulized solutions may be breathed directly from the nebulizing device or the nebulizing device may be attached to a face mask, tent, or intermittent positive pressure breathing machine. Solution, suspension, or powder compositions may be administered, preferably orally or nasally, from devices which deliver the formulation in an appropriate manner.

The compounds herein may be formulated for oral, buccal, intranasal, parenteral (e.g., intravenous, intramuscular, or subcutaneous), or rectal administration or in a form suitable for administration by inhalation. The compounds of the disclosure may also be formulated for sustained delivery.

Methods of preparing various pharmaceutical compositions with a certain amount of active ingredient are known, or will be apparent in light of this disclosure, to those skilled in this art. For examples of methods of preparing pharmaceutical compositions see *Remington's Pharmaceutical Sciences,* 20th Edition (Lippincott Williams & Wilkins, 2000).

Pharmaceutical compositions according to the disclosure may contain 0.1%-95% of the compound(s) of this disclosure, preferably 1%-70%. In any event, the composition to be administered will contain a quantity of a compound(s) according to the disclosure in an amount effective to treat the disease/condition of the subject being treated.

Since this disclosure has an aspect that relates to the treatment of the disease/conditions described herein with a combination of active ingredients which may be administered separately, the disclosure also relates to combining separate pharmaceutical compositions in kit form. The kit comprises two separate pharmaceutical compositions: a compound of Formula I, a prodrug thereof or a salt of such compound or prodrug and a second compound as described above. The kit comprises a means for containing the separate compositions such as a container, a divided bottle, or a divided foil packet. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

A dispenser can be designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Also, as this disclosure has an aspect that relates to the treatment of the disease/conditions described herein with a combination of active ingredients which may be administered jointly, the disclosure also relates to combining separate pharmaceutical compositions in a single dosage form, such as (but not limited to) a single tablet or capsule, a bilayer or multilayer tablet or capsule, or through the use of segregated components or compartments within a tablet or capsule.

The active ingredient may be delivered as a solution in an aqueous or non-aqueous vehicle, with or without additional solvents, co-solvents, excipients, or complexation agents selected from pharmaceutically acceptable diluents, excipients, vehicles, or carriers.

The active ingredient may be formulated as a solid dispersion or as a self-emulsified drug delivery system (SEDDS) with pharmaceutically acceptable excipients.

The active ingredient may be formulated as an immediate release or modified release tablet or capsule. Alternatively, the active ingredient may be delivered as the active ingredient alone within a capsule shell, without additional excipients.

An amount of a compound of Formula I or combination of a compound of Formula I can be administered to a non-human animal such that an effective dose is received. Generally, a daily dose that is administered orally to an animal is between about 0.01 and about 1,000 milligrams per kilogram (mg/kg) of body weight, e.g., between about 0.01 and about 300 mg/kg or between about 0.01 and about 100 mg/kg or between about 0.01 and about 50 mg/kg of body weight, or between about 0.01 and about 25 mg/kg, or about 0.01 and about 10 mg/kg or about 0.01 and about 5 mg/kg.

Conveniently, a compound of Formula I (or combination) can be carried in the drinking water so that a therapeutic dosage of the compound is ingested by the non-human animal with the daily water supply. The compound can be directly metered into drinking water, preferably in the form of a liquid, water-soluble concentrate (such as an aqueous solution of a water-soluble salt).

Conveniently, a compound of Formula I (or combination) can also be added directly to the feed of the non-human animal, as such, or in the form of an animal feed supplement, also referred to as a premix or concentrate. A premix or concentrate of the compound in an excipient, diluent or carrier is more commonly employed for the inclusion of the agent in the feed. Suitable excipients, diluents or carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective excipient, diluent or carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to non-human animals. In such instances, the animals are permitted to consume the usual diet. Alternatively, such concentrated supplements may be added directly to the feed to produce a nutritionally balanced, finished feed containing a therapeutically effective level of a compound. The mixtures are thoroughly blended by standard procedures, such as in a twin shell blender, to ensure homogeneity.

If the supplement is used as a top dressing for the feed for the non-human animal, it likewise helps to ensure uniformity of distribution of the compound across the top of the dressed feed.

Drinking water and feed effective for increasing lean meat deposition and for improving lean meat to fat ratio are generally prepared by mixing a compound of Formula I with a sufficient amount of non-human animal feed to provide from about 0.001 to about 500 parts per million by weight (ppm) of the compound in the feed or water.

The preferred medicated swine, cattle, sheep, and goat feed generally contain from about 1 to about 400 grams of a compound of Formula I (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound (or combination) per ton of feed.

For parenteral administration in non-human animals, the compounds of Formula I (or combination) may be prepared in the form of a paste or a pellet and administered as an implant, usually under the skin of the head or ear of the animal in which increase in lean meat deposition and improvement in lean meat to fat ratio is sought. Paste Formulations may be prepared by dispersing the drug in a pharmaceutically acceptable oil such as peanut oil, sesame oil, corn oil or the like. Pellets containing an effective amount of a compound of Formula I, pharmaceutical composition, or combination may be prepared by admixing a compound of Formula I or combination with a diluent such as carbowax, carnauba wax, and the like, and a lubricant, such as magnesium or calcium stearate, may be added to improve the pelleting process. It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

Experimental Procedures

The following illustrate the synthesis of various compounds of the present disclosure. Additional compounds within the scope of this disclosure may be prepared using the methods illustrated in these Examples, either alone or in combination with techniques generally known in the art. All starting materials in these Preparations and Examples are either commercially available or can be prepared by methods known in the art or as described herein.

Reactions were performed in air or, when oxygen- or moisture-sensitive reagents or intermediates were employed, under an inert atmosphere (nitrogen or argon). When appropriate, reaction apparatuses were dried under dynamic vacuum using a heat gun, and anhydrous solvents (Sure-Seal™ products from Aldrich Chemical Company, Milwaukee, Wisconsin or DriSolv™ products from EMD Chemicals, Gibbstown, NJ) were employed. In some cases, commercial solvents were passed through columns packed with 4 Å molecular sieves, until the following QC standards for water were attained: a) <100 ppm for dichloromethane, toluene, N,N-dimethylformamide, and tetrahydrofuran; b) <180 ppm for methanol, ethanol, 1,4-dioxane, and diisopropylamine. For very sensitive reactions, solvents were further treated with metallic sodium, calcium hydride, or molecular sieves, and distilled just prior to use. Other commercial solvents and reagents were used without further purification. For syntheses referencing procedures in other Examples or Methods, reaction conditions (reaction time and temperature) may vary. Products were generally dried under vacuum before being carried on to further reactions or submitted for biological testing.

When indicated, reactions were heated by microwave irradiation using Biotage Initiator or Personal Chemistry Emrys Optimizer microwave instruments. Reaction progress was monitored using thin-layer chromatography (TLC), liquid chromatography-mass spectrometry (LCMS), high-performance liquid chromatography (HPLC), and/or gas chromatography-mass spectrometry (GCMS) analyses. TLC was performed on pre-coated silica gel plates with a fluorescence indicator (254 nm excitation wavelength) and visualized under UV light and/or with $I_2$, $KMnO_4$, $CoCl_2$, phosphomolybdic acid, or ceric ammonium molybdate stains. LCMS data were acquired on an Agilent 1100 Series instrument with a Leap Technologies autosampler, Gemini C18 columns, acetonitrile/water gradients, and either trifluoroacetic acid, formic acid, or ammonium hydroxide modifiers. The column eluent was analyzed using a Waters ZQ mass spectrometer scanning in both positive and negative ion modes from 100 to 1200 Da. Other similar instruments were also used. HPLC data were generally acquired on an Agilent 1100 Series instrument using Gemini or XBridge C18 columns, acetonitrile/water gradients, and either trifluoroacetic acid or ammonium hydroxide modifiers. GCMS data were acquired using a Hewlett Packard 6890 oven with an HP 6890 injector, HP-1 column (12 m×0.2 mm×0.33 μm), and helium carrier gas. Samples were analyzed on an HP 5973 mass selective detector, scanning from 50 to 550 Da using electron ionization. Purifications were performed by medium performance liquid chromatography (MPLC) using Isco CombiFlash Companion, AnaLogix IntelliFlash 280, Biotage SP1, or Biotage Isolera One instruments and pre-packed Isco RediSep or Biotage Snap silica cartridges. Chiral purifications were generally performed by chiral supercritical fluid chromatography (SFC) using Berger or Thar instruments; ChiralPAK-AD, -AS, -IC, Chiralcel-OD, or -OJ columns; and $CO_2$ mixtures with methanol, ethanol, propan-2-ol, or acetonitrile, alone or modified using trifluoroacetic acid or propan-2-amine. UV detection was used to trigger fraction collection. For syntheses referencing procedures in other Examples or Methods, purifications may vary; in general, solvents and the solvent ratios used for eluents/gradients were chosen to provide appropriate $R_f$s or retention times.

Mass spectrometry data are reported from LCMS analyses. Mass spectrometry (MS) was performed via atmospheric pressure chemical ionization (APCI), electrospray ionization (ESI), electron impact ionization (E1) or electron scatter (ES) ionization sources. Proton nuclear magnetic spectroscopy ($^1H$ NMR) chemical shifts are given in parts per million downfield from tetramethylsilane and were recorded on 300, 400, 500, or 600 MHz Varian, Bruker, or Jeol spectrometers. Chemical shifts are expressed in parts per million (ppm, 6) referenced to the residual peaks of the deuterated solvent (chloroform, 7.26 ppm; $CD_2HOD$, 3.31 ppm; acetonitrile-$d_2$, 1.94 ppm; dimethyl sulfoxide-$d_5$, 2.50 ppm; DHO, 4.79 ppm). The peak shapes are described as follows: s, singlet; d, doublet; t, triplet; q, quartet; quin, quintet; m, multiplet; br s, broad singlet; app, apparent. Analytical SFC data were acquired on a Berger analytical instrument as described above. Optical rotation data were acquired on a PerkinElmer model 343 polarimeter using a 1 dm cell. Silica gel chromatography was performed primarily using medium-pressure Biotage or ISCO systems using columns pre-packaged by various commercial vendors including Biotage and ISCO. Microanalyses were performed by Quantitative Technologies Inc. and were within 0.4% of the calculated values.

Unless otherwise noted, chemical reactions were performed at room temperature (about 23 degrees Celsius).

Unless noted otherwise, all reactants were obtained commercially and used without further purification, or were prepared using methods known in the literature.

The terms "concentrated," "evaporated," and "concentrated in vacuo" refer to the removal of solvent at reduced pressure on a rotary evaporator with a bath temperature less than 60° C. The abbreviation "min" and "h" stand for "minutes" and "hours" respectively. The term "TLC" refers to thin-layer chromatography, "room temperature or ambient temperature" means a temperature between 18 and 25° C., "GCMS" refers to gas chromatography-mass spectrometry, "LCMS" refers to liquid chromatography-mass spectrometry, "UPLC" refers to ultra-performance liquid chromatography and "HPLC" refers to high-performance liquid chromatography, "SFC" refers to supercritical fluid chromatography.

Hydrogenation may be performed in a Parr Shaker under pressurized hydrogen gas, or in a Thales-nano H-Cube flow hydrogenation apparatus at full hydrogen and a flow rate between 1 and 2 mL/minute at the specified temperature.

HPLC, UPLC, LCMS, GCMS, and SFC retention times were measured using the methods noted in the procedures.

In some examples, chiral separations were carried out to separate enantiomers or diastereomers of certain compounds of the disclosure (in some examples, the separated enantiomers are designated as ENANT-1 and ENANT-2, according to their order of elution; similarly, separated diastereomers are designated as DIAST-1 and DIAST-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated either by the absence of drawn or described stereochemistry, or by the presence of (+/−) adjacent to the structure; in this latter case, the indicated stereochemistry represents just one of the two enantiomers that make up the racemic mixture.

The compounds and intermediates described below were named using the naming convention provided with ACD/

ChemSketch 2017.2.1, File Version C40H41, Build 99535 (Advanced Chemistry Development, Inc., Toronto, Ontario, Canada). The naming convention provided with ACD/ChemSketch 2017.2.1 is well known by those skilled in the art and it is believed that the naming convention provided with ACD/ChemSketch 2017.2.1 generally comports with the IUPAC (International Union for Pure and Applied Chemistry) recommendations on Nomenclature of Organic Chemistry and the CAS Index rules.

Preparation P1 tert-Butyl 3-{[(5R)-5-(3-chloro-2-fluorophenyl)-4-fluoro-5-methyl-8-oxo-5,6,7,8-tetrahydro-2,7-naphthyridin-3-yl]amino}azetidine-1-carboxylate (P1)

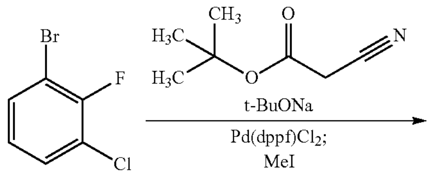

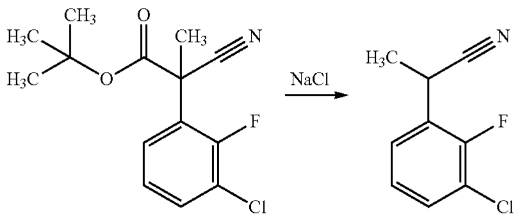

C1 C2

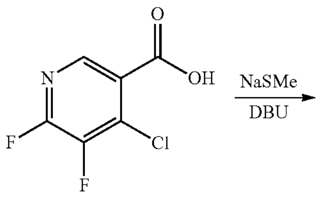

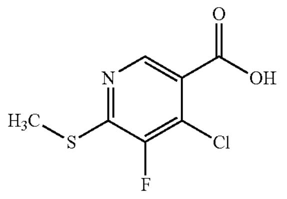

C3

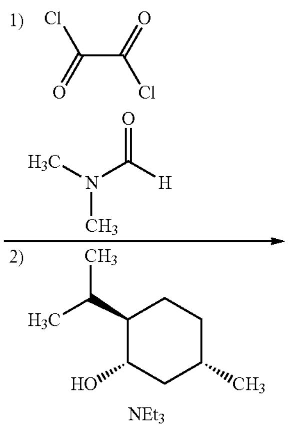

-continued

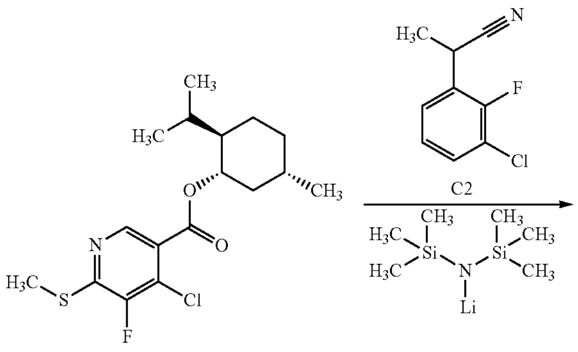

C4

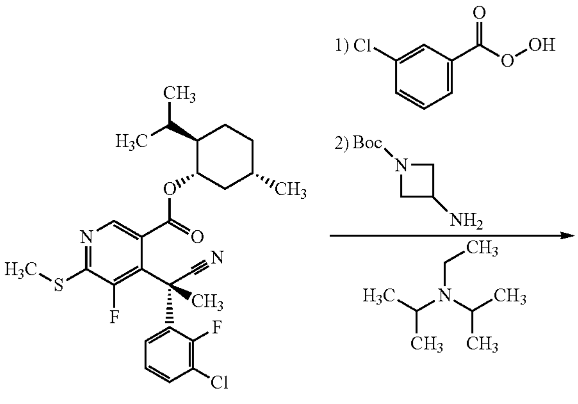

C5

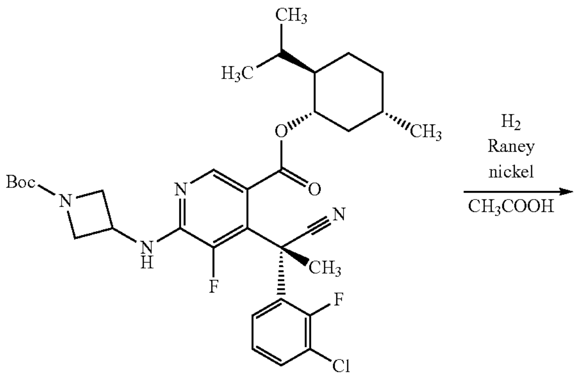

C6

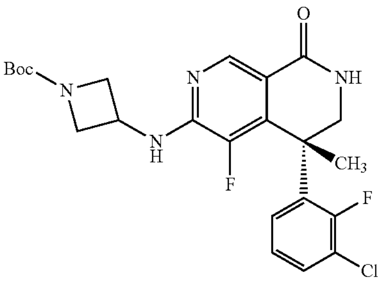

P1

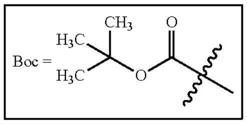

Step 1. Synthesis of tert-butyl 2-(3-chloro-2-fluorophenyl)-2-cyanopropanoate ($C_1$)

A mixture of 1-bromo-3-chloro-2-fluorobenzene (125 g, 597 mmol), tert-butyl cyanoacetate (88.5 g, 627 mmol), sodium tert-butoxide (143 g, 1.49 mol), and [1,1'-bis(diphenylphosphino)ferrocene]dichloropalladium(II), dichloromethane complex [Pd(dppf)$Cl_2$; 14.6 g, 17.9 mmol] in 1,4-dioxane (1.5 L) was stirred for 4 hours at 80° C. The resulting mixture, containing tert-butyl (3-chloro-2-fluorophenyl)(cyano)acetate, was cooled to 25° C., whereupon it was treated drop-wise with iodomethane (74.3 mL, 1.19 mol) and then stirred for 4 hours at 40° C. The reaction mixture was filtered, the filter cake was washed with ethyl acetate (3×500 mL), and the combined filtrates were concentrated under reduced pressure. The resulting material was diluted with ethyl acetate (1 L); L-cysteine (15.0 g, 124 mmol) was added, and the mixture was stirred at 20° C. for 16 hours. After dilution with water (1 L), the mixture was filtered through a pad of diatomaceous earth; the filter cake was washed with ethyl acetate (300 mL), and the aqueous layer of the filtrate was extracted with ethyl acetate (3×300 mL). The combined organic layers were washed with saturated aqueous sodium chloride solution (300 mL), dried over sodium sulfate, filtered, and concentrated in vacuo. The resulting solid was diluted with ethanol (200 mL), warmed to 50° C. to effect complete dissolution, cooled down to 20° C. and allowed to stand for 16 hours. Collection of the precipitate afforded C1 as a pale-yellow solid. Yield: 123 g, 434 mmol, 73%. $^1$H NMR (400 MHz, chloroform-d) δ 7.48-7.39 (m, 2H), 7.16 (ddd, J=8.0, 8.0, 1.3 Hz, 1H), 1.95 (s, 3H), 1.48 (s, 9H).

Step 2. Synthesis of 2-(3-chloro-2-fluorophenyl)propanenitrile (C2)

A solution of C1 (123 g, 434 mmol) and sodium chloride (25.3 g, 433 mmol) in a mixture of water (780 mL) and 1-methylpyrrolidin-2-one (390 mL) was stirred at 100° C. for 40 hours. The reaction mixture was extracted with methyl tert-butyl ether (3×500 mL), and the combined organic layers were washed with saturated aqueous sodium chloride solution (3×500 mL), dried over sodium sulfate, filtered, and concentrated in vacuo at approximately 35° C., affording C2 as a pale-brown oil. Yield: 78.0 g, 425 mmol, 98%. $^1$H NMR (400 MHz, chloroform-d) d 7.42-7.32 (m, 2H), 7.13 (br dd, J=8, 8, 1H), 4.18 (q, J=7.2 Hz, 1H), 1.63 (d, J=7.3 Hz, 3H).

Step 3. Synthesis of 4-chloro-5-fluoro-6-(methylsulfanyl)pyridine-3-carboxylic acid (C3)

Sodium methanethiolate (78.9 g, 1.13 mol) was added over approximately 20 minutes to a 0° C. solution of 4-chloro-5,6-difluoropyridine-3-carboxylic acid (204 g, 1.05 mol) and 1,8-diazabicyclo[5.4.0]undec-7-ene (DBU; 321 mL, 2.11 mol) in ethanol (1.5 L). After the reaction mixture had been stirred at 15° C. for 16 hours, it was concentrated in vacuo, whereupon it was diluted with water (1 L), and the pH was adjusted to approximately 4 by addition of hydrochloric acid (4 M; 1 L, 4 mol). The resulting mixture was extracted with ethyl acetate (3×2 L); the combined organic layers were washed with saturated aqueous sodium chloride solution (1 L), dried over sodium sulfate, filtered, and concentrated in vacuo. The residue was diluted with ethyl acetate (600 mL) and stirred for 16 hours at 15° C. The resulting solid was collected via filtration, providing C3 as an off-white solid. Yield: 189 g, 853 mmol, 81%. LCMS m/z 221.8 (chlorine isotope pattern observed) $[M+H]^+$. $^1$H NMR (400 MHz, chloroform-d) δ 8.91 (s, 1H), 2.64 (s, 3H).

Step 4. Synthesis of (1S,2R,5S)-5-methyl-2-(propan-2-γ1)cyclohexyl 4-chloro-5-fluoro-6-(methylsulfanyl)pyridine-3-carboxylate (C4)

Oxalyl chloride (108 g, 851 mmol) was added drop-wise, over approximately 20 minutes, to a 0° C. solution of C3 (63.0 g, 284 mmol) and N,N-dimethylformamide (2.19 mL, 28.3 mmol) in dichloromethane (1.5 L). After the reaction mixture had been stirred at 15° C. for 3 hours, concentration under reduced pressure afforded 4-chloro-5-fluoro-6-(methylsulfanyl)pyridine-3-carbonyl chloride. This material was dissolved in dichloromethane (1.5 L), cooled to 15° C., and treated with triethylamine (59.2 mL, 426 mmol) and (1 S,2R,5S)-5-methyl-2-(propan-2-γ1)cyclohexan-1-ol [(+)-menthol; 79.9 g, 511 mmol]. This reaction mixture was stirred for 16 hours, whereupon it was concentrated in vacuo; silica gel chromatography (Gradient: 0% to 3% ethyl acetate in petroleum ether) afforded C4 as a colorless gum. Yield: 76.0 g, 211 mmol, 74%. LCMS m/z 360.0 (chlorine isotope pattern observed) $[M+H]^+$. $^1$H NMR (400 MHz, chloroform-d) δ 8.75 (s, 1H), 4.96 (td, J=10.9, 4.4 Hz, 1H), 2.61 (s, 3H), 2.21-2.09 (m, 1H), 2.02-1.91 (m, 1H), 1.79-1.69 (m, 2H), 1.62-1.48 (m, 3H), 1.19-1.06 (m, 2H), 0.94 (d, J=6.5 Hz, 3H), 0.92 (d, J=7.0 Hz, 3H), 0.80 (d, J=6.9 Hz, 3H).

Step 5. Synthesis of (1S,2R,5S)-5-methyl-2-(propan-2-γ1)cyclohexyl 4-[(1R)-1-(3-chloro-2-fluorophenyl)-1-cyanoethyl]-5-fluoro-6-(methylsulfanyl)pyridine-3-carboxylate (C5)

This reaction was carried out in 2 batches. A solution of lithium bis(trimethylsilyl)amide in tetrahydrofuran (1 M; 119 mL, 119 mmol) was added to a 0° C. solution of C4 (39.0 g, 108 mmol) and C2 (24.3 g, 132 mmol) in toluene (800 mL). After 2 hours, saturated aqueous ammonium chloride solution (500 mL) was added; the two reaction batches were combined at this point and extracted with ethyl acetate (3×500 mL). The combined organic layers were washed with saturated aqueous sodium chloride solution (500 mL), dried over sodium sulfate, filtered, and concentrated in vacuo. The residue was diluted with heptane (750 mL), stirred at 40° C. for 2 hours, and then allowed to cool to 15° C. After stirring for 30 minutes, the resulting solid was collected via filtration, affording C5 as an off-white solid. Combined yield: 41.0 g, 80.9 mmol, 37%. $^1$H NMR (400 MHz, chloroform-d) δ 8.54 (s, 1H), 7.48-7.34 (m, 2H), 7.16 (td, J=8.0, 1.3 Hz, 1H), 4.70 (td, J=10.9, 4.4 Hz, 1H), 2.59 (s, 3H), 2.35 (d, J=3.2 Hz, 3H), 1.99-1.90 (m, 1H), 1.89-1.79 (m, 1H), 1.73-1.63 (m, 2H), 1.50-1.35 (m, 2H), 1.35-1.20 (m, 1H), 1.09-0.82 (m, 2H), 0.90 (d, J=6.9 Hz, 3H), 0.88 (d, J=6.5 Hz, 3H), 0.72 (d, J=6.9 Hz, 3H).

Step 6. Synthesis of (1S,2R,5S)-5-methyl-2-(propan-2-γ1)cyclohexyl 6-{[1-(tert-butoxycarbonyl)azetidin-3-yl]amino}-4-[(1R)-1-(3-chloro-2-fluorophenyl)-1-cyanoethyl]-5-fluoropyridine-3-carboxylate (C6)

3-Chloroperoxybenzoic acid (85%, 18.1 g, 89.2 mmol) was added to a 0° C. solution of C5 (41.0 g, 80.9 mmol) in dichloromethane (600 mL). The reaction mixture was stirred at 15° C. for 16 hours, whereupon LCMS analysis indicated conversion to a mixture of the corresponding sulfoxide and sulfone: LCMS m/z 523.1 and 539.0 (chlorine isotope pattern observed for both) $[M+H]^+$. The reaction mixture was diluted with a mixture of saturated aqueous sodium thiosulfate solution (700 mL) and saturated aqueous sodium bicarbonate solution (500 mL). The organic layer was washed sequentially with saturated aqueous sodium bicarbonate solution (800 mL) and saturated aqueous sodium chloride solution (500 mL), dried over sodium sulfate, filtered, and concentrated in vacuo. This material was dissolved in dimethyl sulfoxide (135 mL), treated with N,N-diisopropylethylamine (35.3 mL, 202 mmol) and tert-butyl 3-aminoazetidine-1-carboxylate (20.9 g, 121 mmol), and heated at 80° C. for 3 hours, whereupon it was cooled and partitioned between water (300 mL) and petroleum ether (150 mL). After 1 hour, the resulting precipitate was collected via filtration, washed with water (2×150 mL) and washed with petroleum ether (100 mL). The filter cake was layered with a mixture of methyl tert-butyl ether (30 mL) and petroleum ether (150 mL), stirred at 15° C. for 16 hours, and filtered; this filter cake was washed with petroleum ether (3×50 mL) to provide C6 as a white solid. Yield: 41.5 g, 65.8 mmol, 81%. LCMS m/z 631.3 $[M+H]^+$. $^1$H NMR (400 MHz, chloroform-d) δ 8.28 (s, 1H), 7.44 (br t, J=7.5 Hz, 1H), 7.38 (br t, J=7.4 Hz, 1H), 7.14 (br t, J=8.0 Hz, 1H), 5.43-5.35 (m, 1H), 4.81-4.67 (m, 1H), 4.55 (td, J=10.9, 4.4 Hz, 1H), 4.34 (t, J=8.4 Hz, 2H), 3.90-3.76 (m, 2H), 2.35 (d, J=3.0 Hz, 3H), 1.87-1.79 (m, 1H), 1.79-1.70 (m, 1H), 1.70-1.58 (m, 3H), 1.45 (s, 9H), 1.45-1.30 (m, 2H), 1.08-0.79 (m, 8H), 0.66 (d, J=6.9 Hz, 3H).

Step 7 Synthesis of tert-butyl 3-{[(5R)-5-(3-chloro-2-fluorophenyl)-4-fluoro-5-methyl-8-oxo-5,6,7,8-tetrahydro-2,7-naphthyridin-3-yl]amino}azetidine-1-carboxylate (P1)

To a solution of C6 (21.5 g, 34.1 mmol) in a mixture of tetrahydrofuran (220 mL) and methanol (220 mL) were added acetic acid (19.5 mL, 341 mmol) and Raney nickel (63 g, 1.1 mol), whereupon the reaction mixture was heated to 50° C. under hydrogen (50 psi). After 5 hours, the reaction mixture was allowed to cool to 15° C. and was combined with a similar reaction carried out using C6 (20.0 g, 31.7 mmol). The reaction supernatant was decanted away from the solids, which were then stirred in a solution of dichloromethane in methanol (10%, 1 L) at 50° C. for 30 minutes and decanted, this process was repeated three times. The combined supernatants were concentrated in vacuo, diluted with ethyl acetate (1 L) and washed with saturated aqueous potassium carbonate solution (1 L) followed by saturated aqueous sodium chloride solution (2×500 mL). The organic layer was then dried over sodium sulfate, filtered, and concentrated under reduced pressure. The crude mixture was diluted with a mixture of ethyl acetate in heptane (25%, 300 mL), stirred at 15° C. for 1 hour, and filtered, affording P1 as a white solid. Combined yield: 25.0 g, 52.2 mmol, 79%. LCMS m/z 479.3 $[M+H]^+$. $^1$H NMR (400 MHz, methanol-$d_4$) δ 8.52 (s, 1H), 7.45 (br t, J=7.5 Hz, 1H), 7.29 (br t, J=7.6 Hz, 1H), 7.18 (br t, J=8.0 Hz, 1H), 4.82-4.73 (m, 1H), 4.34-4.19 (m, 2H), 3.96-3.79 (m, 3H), 3.27 (d, J=13.0 Hz, 1H), 1.86 (s, 3H), 1.44 (s, 9H). Specific rotation of a sample of P1 synthesized by the same procedure: $[\alpha]^{22}_D$=+249.5° (MeOH, c=0.2 g/100 mL).

The absolute stereochemistry at the quaternary center of P1 and its precursors was established via single-crystal X-ray structural determination of Example 1 (see below), which was synthesized from P1.

Preparations P2 and P3 tert-Butyl 3-{[5-(3-chloro-2,4-difluorophenyl)-4-fluoro-5-methyl-8-oxo-5,6,7,8-tetrahydro-2,7-naphthyridin-3-yl]amino}azetidine-1-carboxylate, ENANT-1 (P2) and tert-Butyl 3-{[5-(3-chloro-2,4-difluorophenyl)-4-fluoro-5-methyl-8-oxo-5,6,7,8-tetrahydro-2,7-naphthyridin-3-yl]amino}azetidine-1-carboxylate, ENANT-2 (P3)

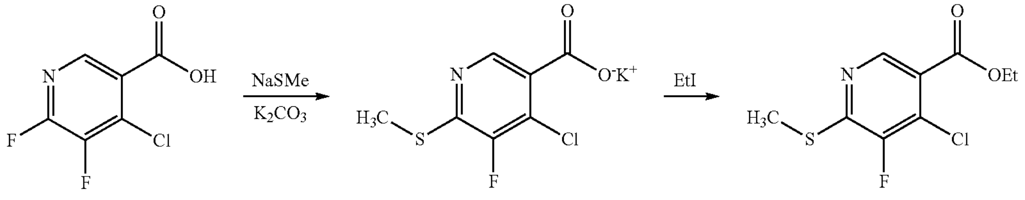

C7

C8

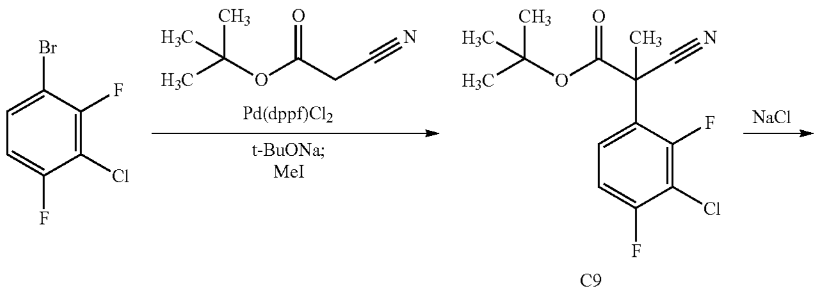

C9

-continued
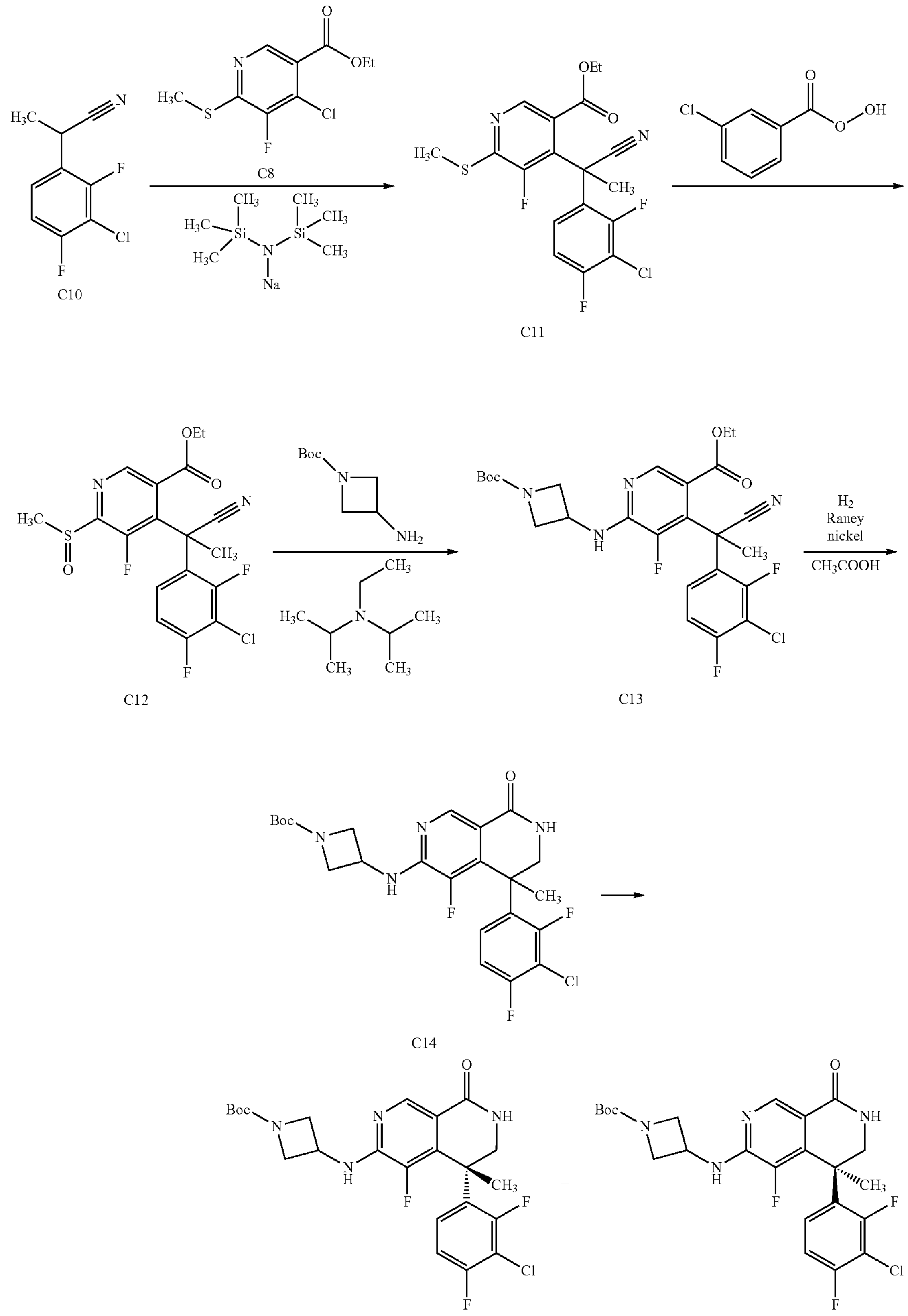
P2 (ENANT-1) and P3 (ENANT-2)

Step 1. Synthesis of potassium 4-chloro-5-fluoro-6-(methylsulfanyl)pyridine-3-carboxylate (C7)

A solution of sodium methanethiolate (20.3 g, 290 mmol) in ethanol (500 mL) was added in a drop-wise manner over 1 hour to a 0° C. solution of potassium carbonate (71.4 g, 517 mmol) and 4-chloro-5,6-difluoropyridine-3-carboxylic acid (50.0 g, 258 mmol) in ethanol (1 L). After the reaction mixture had been stirred at 15° C. for 16 hours, additional sodium methanethiolate (5.06 g, 72.2 mmol) was added, and stirring was continued for 4 hours at 15° C. LCMS analysis indicated conversion to C7: LCMS m/z 222.0 (chlorine isotope pattern observed) $[M+H]^+$; removal of solvent in vacuo afforded C7 as a white solid, which was used directly in the next step.

Step 2. Synthesis of ethyl 4-chloro-5-fluoro-6-(methylsulfanyl)pyridine-3-carboxylate (C8)

Iodoethane (52.3 g, 335 mmol) was slowly added to a 15° C. solution of C7 (from the previous step; 5258 mmol) in dimethyl sulfoxide (1.5 L). After 6 hours, LCMS analysis indicated conversion to C8: LCMS m/z 249.8 (chlorine isotope pattern observed) $[M+H]^+$, and the reaction mixture was combined with a similar reaction carried out using C7 (5258 mmol) and diluted with water (3 L). The resulting solid was collected via filtration and stirred in ethanol (100 mL) at 15° C. for 1 hour; filtration afforded C8 as a white solid. Combined yield: 78.9 g, 316 mmol, 61% over 2 steps. $^1$H NMR (400 MHz, chloroform-d) δ 8.76 (s, 1H), 4.41 (q, J=7.1 Hz, 2H), 2.62 (s, 3H), 1.41 (t, J=7.1 Hz, 3H).

Step 3. Synthesis of tert-butyl 2-(3-chloro-2,4-difluorophenyl)-2-cyanopropanoate (C9)

A solution of 1-bromo-3-chloro-2,4-difluorobenzene (16.0 g, 70.4 mmol), tert-butyl cyanoacetate (9.93 g, 70.3 mmol), [1,1'-bis(diphenylphosphino)ferrocene]dichloropalladium(II), dichloromethane complex (1.44 g, 1.76 mmol), and sodium tert-butoxide (16.9 g, 176 mmol) in 1,4-dioxane (300 mL) was heated to 85° C. After 16 hours, the mixture was allowed to cool to 20° C. and iodomethane (6.49 mL, 104 mmol) was added. After 16 hours, the mixture was filtered and washed with methyl tert-butyl ether (3×300 mL). The filtrate was concentrated in vacuo; silica gel chromatography (Gradient: 0% to 5% ethyl acetate in petroleum ether) afforded C9 as a white solid. Yield: 19.2 g, 63.6 mmol, 90%. $^1$H NMR (400 MHz, chloroform-d) δ 7.41 (ddd, J=8.9, 8.1, 5.5 Hz, 1H), 7.05 (ddd, J=8.9, 7.9, 1.9 Hz, 1H), 1.95 (s, 3H), 1.49 (s, 9H).

Step 4. Synthesis of 2-(3-chloro-2,4-difluorophenyl)propanenitrile (C10)

A solution of C9 (19.2 g, 63.6 mmol) and sodium chloride (2.98 g, 51.0 mmol) in a mixture of water (150 mL) and dimethyl sulfoxide (150 mL) was heated to 100° C. After 20 hours, the reaction mixture was allowed to cool to 15° C. and was extracted with methyl tert-butyl ether (2×200 mL); the combined organic layers were washed with saturated aqueous sodium chloride solution (2×300 mL), dried over sodium sulfate, filtered, and concentrated in vacuo to afford C10 as a yellow oil (10.2 g), which was used directly in the next step. $^1$H NMR (400 MHz, chloroform-d), product peaks only: δ 7.39 (ddd, J=8.5, 8.5, 5.5 Hz, 1H), 7.05 (ddd, J=8.8, 7.9, 1.9 Hz, 1H), 4.16 (q, J=7.2 Hz, 1H), 1.64 (d, J=7.3 Hz, 3H).

Step 5. Synthesis of ethyl 4-[1-(3-chloro-2,4-difluorophenyl)-1-cyanoethyl]-5-fluoro-6-(methylsulfanyl)pyridine-3-carboxylate (C11)

A solution of sodium bis(trimethylsilyl)amide in tetrahydrofuran (1 M; 38.4 mL, 38.4 mmol) was added in a drop-wise manner over 30 minutes to a 0° C. solution of C8 (8.00 g, 32.0 mmol) and C10 (from the previous step; 9.1 g, 545.1 mmol) in toluene (300 mL). After 30 minutes, LCMS analysis indicated conversion to C11: LCMS m/z 415.1 (chlorine isotope pattern observed) $[M+H]^+$; the reaction mixture was allowed to warm to 15° C. and combined with a similar reaction carried out using C8 (1.0 g, 4.0 mmol). The mixture was diluted with saturated aqueous ammonium chloride solution (300 mL) and extracted with ethyl acetate (3×300 mL). The combined organic layers were washed with saturated aqueous sodium chloride solution (500 mL), dried over sodium sulfate, filtered, concentrated in vacuo, and purified via silica gel chromatography (Gradient: 0% to 30% ethyl acetate in petroleum ether), providing C11 as a yellow solid. Combined yield: 8.80 g, 21.2 mmol, 59%. $^1$H NMR (400 MHz, chloroform-d) δ 8.43 (s, 1H), 7.38 (ddd, J=8.6, 8.6, 5.6 Hz, 1H), 7.11-7.03 (m, 1H), 4.24-4.06 (m, 2H), 2.59 (s, 3H), 2.32 (d, J=2.1 Hz, 3H), 1.26 (t, J=7.1 Hz, 3H).

Step 6. Synthesis of ethyl 4-[1-(3-chloro-2,4-difluorophenyl)-1-cyanoethyl]-5-fluoro-6-(methanesulfinyl)pyridine-3-carboxylate (C12)

3-Chloroperoxybenzoic acid (80%, 5.03 g, 23.3 mmol) was added to a 0° C. solution of C11 (8.80 g, 21.2 mmol) in dichloromethane (120 mL), whereupon the reaction mixture was stirred at 15° C. After 1 hour, LCMS analysis indicated conversion to C12: LCMS m/z 430.9 (chlorine isotope pattern observed) $[M+H]^+$. The reaction mixture was diluted with saturated aqueous sodium thiosulfate solution (50 mL) and saturated aqueous sodium bicarbonate solution (100 mL), then extracted with dichloromethane (3×100 mL). The combined organic layers were washed with saturated aqueous sodium chloride solution (300 mL), dried over sodium sulfate, filtered, and concentrated in vacuo to provide C12 as a yellow solid, which was used directly in the following step.

Step 7. Synthesis of ethyl 6-{[1-(tert-butoxycarbonyl)azetidin-3-yl]amino}-4-[1-(3-chloro-2,4-difluorophenyl)-1-cyanoethyl]-5-fluoropyridine-3-carboxylate (C13)

To a solution of C12 (from the previous step; 521.2 mmol) in dimethyl sulfoxide (120 mL) were added N,N-diisopropylethylamine (8.19 g, 63.4 mmol) and tert-butyl 3-aminoazetidine-1-carboxylate (5.46 g, 31.7 mmol), and the reaction mixture was heated to 80° C. After 16 hours, LCMS analysis indicated conversion to C13: LCMS m/z 539.1 (chlorine isotope pattern observed) $[M+H]^+$; the reaction mixture was allowed to cool to 15° C., diluted with saturated aqueous sodium chloride solution (200 mL), and extracted with ethyl acetate (2×200 mL). The combined organic layers were washed with saturated aqueous sodium chloride solution (4×200 mL), dried over sodium sulfate, filtered, and concentrated in vacuo. Silica gel chromatography (Gradient: 0% to 40% ethyl acetate in petroleum ether) afforded C13 as a yellow solid. Yield: 10.1 g, 18.7 mmol, 88% over 2 steps. $^1$H NMR (400 MHz, methanol-$d_4$) δ 8.10 (s, 1H), 7.57 (td, J=8.9, 5.7 Hz, 1H), 7.25 (td, J=8.7, 1.9 Hz, 1H), 4.76 (tt, J=7.7, 5.5 Hz, 1H), 4.32-4.21 (m, 2H), 4.10-3.98 (m, 2H), 3.95-3.85 (m, 2H), 2.35 (d, J=1.9 Hz, 3H), 1.45 (s, 9H), 1.19 (t, J=7.1 Hz, 3H).

Step 8. Synthesis of tert-butyl 3-{[5-(3-chloro-2,4-difluorophenyl)-4-fluoro-5-methyl-8-oxo-5,6,7,8-tetrahydro-2,7-naphthyridin-3-yl]amino}azetidine-1-carboxylate (C14)

To a solution of C13 (10.1 g, 18.7 mmol) in a mixture of methanol (60 mL) and tetrahydrofuran (60 mL) were added acetic acid (5.63 g, 93.8 mmol) and Raney nickel (5.0 g, 85 mmol). The reaction mixture was heated at 50° C. under hydrogen (15 psi) for 16 hours, whereupon it was allowed to cool to 15° C., filtered, and concentrated in vacuo. The residue was treated with methyl tert-butyl ether (20 mL) and stirred for 1 hour before being filtered. The collected solids were washed with methyl tert-butyl ether (3×10 mL) to afford C14 as a white solid. Yield: 7.89 g, 15.9 mmol, 85%. LCMS m/z 497.3 (chlorine isotope pattern observed) $[M+H]^+$. $^1$H NMR (400 MHz, methanol-$d_4$) δ 8.53 (s, 1H), 7.35 (td, J=8.9, 5.9 Hz, 1H), 7.14 (td, J=8.7, 1.8 Hz, 1H), 4.82-4.73 (m, 1H), 4.34-4.19 (m, 2H), 3.96-3.78 (m, 3H), 3.27 (d, J=13.1 Hz, 1H), 1.86 (s, 3H), 1.45 (s, 9H).

Step 9. Isolation of tert-butyl 3-{[5-(3-chloro-2,4-difluorophenyl)-4-fluoro-5-methyl-8-oxo-5,6,7,8-tetrahydro-2,7-naphthyridin-3-yl]amino}azetidine-1-carboxylate, ENANT-1 (P2) and tert-butyl 3-{[5-(3-chloro-2,4-difluorophenyl)-4-fluoro-5-methyl-8-oxo-5,6,7,8-tetrahydro-2,7-naphthyridin-3-yl]amino}azetidine-1-carboxylate, ENANT-2 (P3)

Separation of C14 (6.90 g, 13.9 mmol) into its component enantiomers was carried out via supercritical fluid chromatography [Column: Chiral Technologies Chiralcel OJ-H, 30×250 mm, 5 μm; Mobile phase: 7:3 carbon dioxide/(1:1 acetonitrile/methanol); Backpressure: 100 bar; Flow rate: 80 mL/minute]. The first-eluting enantiomer, a tan solid that exhibited a negative (−) rotation, was designated as P2 and the second-eluting enantiomer, a yellow-orange solid that exhibited a positive (+) rotation, as P3.

P2 (ENANT-1)—Yield: 3.51 g, 7.06 mmol, 51%. Retention time: 1.61 minutes (Analytical conditions. Column: Chiral Technologies Chiralcel OJ-H, 4.6×250 mm, 5 μm; Mobile phase A: carbon dioxide; Mobile phase B: 1:1 acetonitrile/methanol; Gradient: 5% B for 0.25 minutes, then 5% to 70% B over 2.25 minutes, then 70% B for 0.75 minutes; Back pressure: 100 bar; Flow rate: 3.0 mL/minute).

P3 (ENANT-2)—Yield: 2.72 g, 5.47 mmol, 39%. Retention time: 2.05 minutes (Analytical conditions identical to those used for P2).

Preparations P4 and P5 tert-Butyl 3-{[5-(2,4-difluoro-3-methylphenyl)-4-fluoro-5-methyl-8-oxo-5,6,7,8-tetrahydro-2,7-naphthyridin-3-yl]amino}azetidine-1-carboxylate, ENANT-1 (P4) and tert-Butyl 3-{[5-(2,4-difluoro-3-methylphenyl)-4-fluoro-5-methyl-8-oxo-5,6,7,8-tetrahydro-2,7-naphthyridin-3-yl]amino}azetidine-1-carboxylate ENANT-2 (P5)

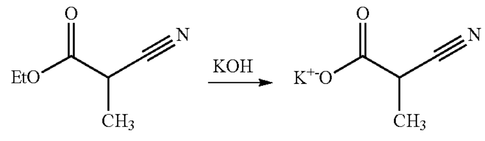

C15

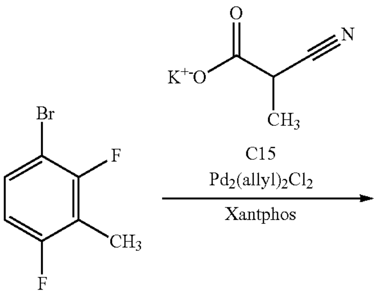

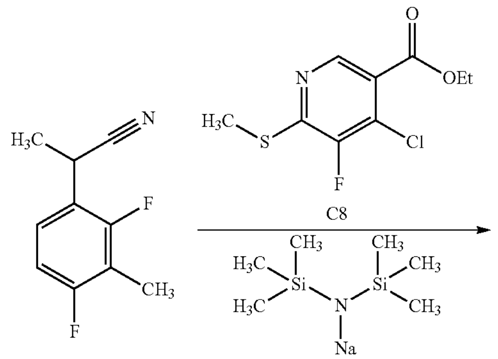

C16

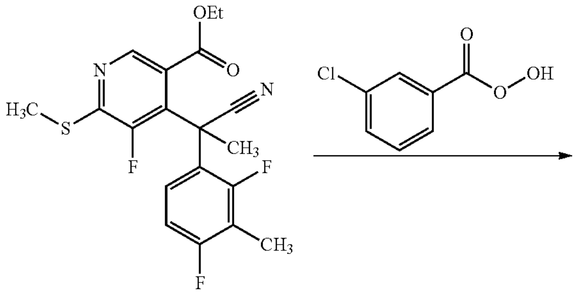

C17

-continued

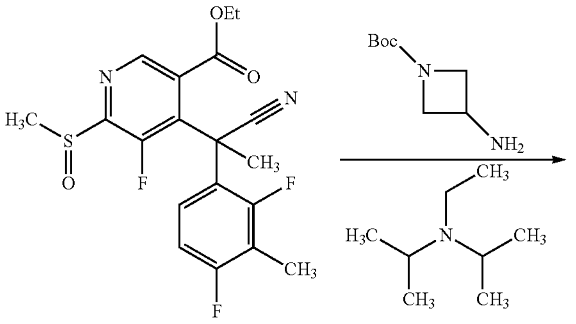

C18

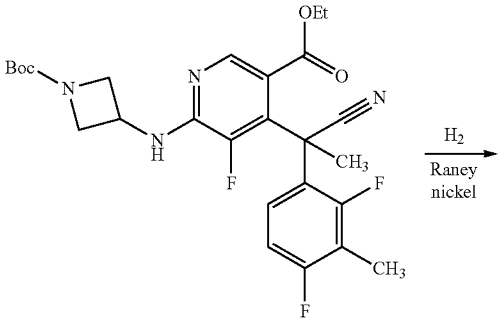

C19

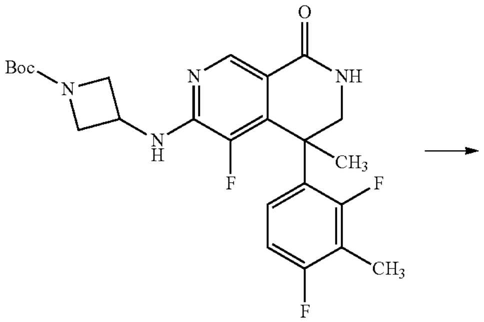

C20

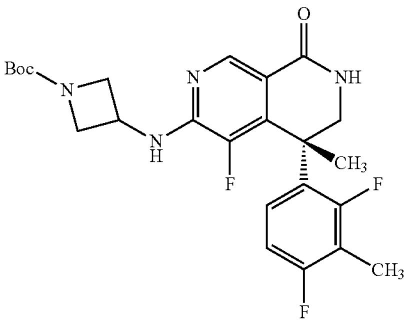

+

-continued

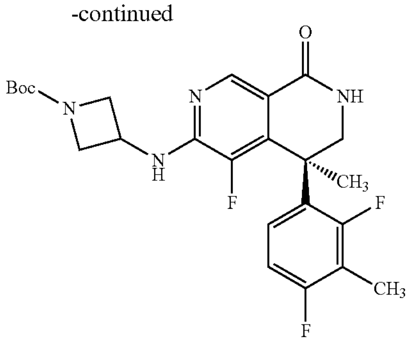

P4 (ENANT-1) and P5 (ENANT-2)

Step 1. Synthesis of Potassium 2-cyanopropanoate (C15)

Ethyl 2-cyanopropanoate (100 g, 787 mmol) was slowly added to a 0° C. solution of potassium hydroxide (43.2 g, 770 mmol) in a mixture of methanol (1.0 L) and water (28.3 mL, 1.57 mol). After the reaction mixture had been stirred at 30° C. for 14 hours, it was concentrated under reduced pressure, treated with toluene (100 mL), and concentrated a second time. The residue was taken up in a mixture of methyl tert-butyl ether (150 mL) and tetrahydrofuran (50 mL), stirred for 3 hours at 15° C., and filtered, affording C15 as a white solid. Yield: 101 g, 736 mmol, 94%. $^{1}H$ NMR (400 MHz, DMSO-$d_6$) δ 3.04 (q, J=7.4 Hz, 1H), 1.24 (d, J=7.5 Hz, 3H).

Step 2. Synthesis of 2-(2,4-difluoro-3-methylphenyl)propanenitrile (C16)

A solution of 1-bromo-2,4-difluoro-3-methylbenzene (17.5 g, 84.5 mmol), C15 (23.2 g, 169 mmol), 4,5-bis (diphenylphosphino)-9,9-dimethylxanthene (Xantphos; 1.47 g, 2.54 mmol), and allylpalladium(II) chloride dimer (0.93 g, 2.54 mmol) in xylene (150 mL) was heated at 120° C. for 16 hours, whereupon the reaction mixture was allowed to cool to 25° C. It was then filtered, and the filtrate was concentrated in vacuo; silica gel chromatography (Gradient: 0% to 2% ethyl acetate in petroleum ether) afforded C16 as a yellow oil. Yield: 11.2 g, 61.8 mmol, 73%. $^{1}H$ NMR (400 MHz, chloroform-d) δ 7.26 (td, J=8.5, 6.1 Hz, 1H), 6.89 (td, J=8.6, 1.7 Hz, 1H), 4.12 (q, J=7.2 Hz, 1H), 2.21 (t, J=1.9 Hz, 3H), 1.62 (d, J=7.3 Hz, 3H).

Step 3. Synthesis of ethyl 4-[1-cyano-1-(2,4-difluoro-3-methylphenyl)ethyl]-5-fluoro-6-(methylsulfanyl)pyridine-3-carboxylate (C17)

A solution of sodium bis(trimethylsilyl)amide in tetrahydrofuran (1 M; 55.9 mL, 55.9 mmol) was added to a 0° C. solution of C8 (12.7 g, 50.9 mmol) and C16 (10.1 g, 55.7 mmol) in toluene (300 mL). The reaction mixture was allowed to warm to 15° C. and stir for 2 hours, whereupon it was diluted with water (100 mL) and saturated aqueous ammonium chloride solution (300 mL). The resulting mixture was extracted with ethyl acetate (3×300 mL), and the combined organic layers were washed with saturated aqueous sodium chloride solution (300 mL), dried over sodium sulfate, filtered, and concentrated in vacuo; silica gel chromatography (Gradient: 0% to 10% ethyl acetate in petroleum ether) provided C17 as a yellow gum. Yield: 10.2 g, 25.9 mmol, 51%. $^1$H NMR (400 MHz, chloroform-d) δ 8.37 (s, 1H), 7.26 (td, J=8.7, 6.0 Hz, 1H), 6.92 (td, J=8.6, 1.7 Hz, 1H), 4.19-4.00 (m, 2H), 2.58 (s, 3H), 2.29 (d, J=1.8 Hz, 3H), 2.14 (t, J=2.0 Hz, 3H), 1.24 (t, J=7.2 Hz, 3H).

Step 4. Synthesis of ethyl 4-[1-cyano-1-(2,4-difluoro-3-methylphenyl)ethyl]-5-fluoro-6-(methanesulfinyl)pyridine-3-carboxylate (C18)

3-Chloroperoxybenzoic acid (80%, 5.83 g, 27.0 mmol) was added to a 0° C. solution of C17 (11.1 g, 28.1 mmol) in dichloromethane (150 mL). After the reaction mixture had been stirred at 20° C. for 2 hours, additional 3-chloroperoxybenzoic acid (80%, 0.50 g, 2.3 mmol) was added. Stirring was continued for 1 hour, whereupon saturated aqueous sodium thiosulfate solution (150 mL) and saturated aqueous sodium bicarbonate solution (150 mL) were added, and the resulting mixture was extracted with dichloromethane (3×150 mL). The combined organic layers were washed with saturated aqueous sodium chloride solution (150 mL), dried over sodium sulfate, filtered, and concentrated in vacuo, affording C18 as a pale-yellow solid, which was used directly in the following step.

Step 5. Synthesis of ethyl 6-{[1-(tert-butoxycarbonyl)azetidin-3-yl]amino}-4-[1-cyano-1-(2,4-difluoro-3-methylphenyl)ethyl]-5-fluoropyridine-3-carboxylate (C19)

To a solution of C18 (from the previous step; 528.1 mmol) in dimethyl sulfoxide (150 mL) were added N,N-diisopropylethylamine (14.0 mL, 80.4 mmol) and tert-butyl 3-aminoazetidine-1-carboxylate (7.27 g, 42.2 mmol). After the reaction mixture had been heated at 80° C. for 16 hours, LCMS analysis indicated conversion to C19: LCMS m/z 519.1 [M+H]$^+$, and the mixture was allowed to cool to 15° C., diluted with water (1 L), and extracted with ethyl acetate (3×150 mL). The combined organic layers were washed with saturated aqueous sodium chloride solution (150 mL), dried over sodium sulfate, filtered, and concentrated in vacuo. Silica gel chromatography (Gradient: 0% to 30% ethyl acetate in petroleum ether) afforded C19 as a white solid. Yield: 11.6 g, 22.4 mmol, 80% over 2 steps. $^1$H NMR (400 MHz, chloroform-d) δ 8.09 (s, 1H), 7.30-7.19 (m, 1H, assumed; partially obstructed by solvent peak), 6.90 (td, J=8.6, 1.6 Hz, 1H), 5.38-5.30 (m, 1H), 4.80-4.69 (m, 1H), 4.38-4.28 (m, 2H), 4.08-3.92 (m, 2H), 3.86-3.78 (m, 2H), 2.30 (d, J=1.9 Hz, 3H), 2.14 (br s, 3H), 1.44 (s, 9H), 1.17 (t, J=7.1 Hz, 3H).

Step 6. Synthesis of tert-butyl 3-{[5-(2,4-difluoro-3-methylphenyl)-4-fluoro-5-methyl-8-oxo-5,6,7,8-tetrahydro-2,7-naphthyridin-3-yl]amino}azetidine-1-carboxylate (C20)

To a solution of C19 (11.6 g, 22.4 mmol) in a mixture of methanol (200 mL) and tetrahydrofuran (200 mL) was added Raney nickel (5.0 g, 85 mmol), whereupon the reaction mixture was heated at 50° C. under hydrogen (15 psi) for 16 hours. It was then allowed to cool to 15° C. and filtered; the filtrate was concentrated in vacuo. The residue was treated with ethyl acetate (50 mL) and methyl tert-butyl ether (50 mL), stirred for 1 hour, and the solid was collected via filtration. This material was taken up in ethanol (80 mL) and tetrahydrofuran (10 mL), heated to 90° C. for 5 minutes, cooled to 15° C. and treated with methyl tert-butyl ether (50 mL). Three-quarters of the volatiles were removed via concentration, and the resulting solid was collected via filtration to provide C20 as a white solid (6.00 g). The filtrate was concentrated in vacuo and purified via silica gel chromatography (Gradient: 0% to 8% 2-methyltetrahydrofuran in dichloromethane) to afford additional C20 as a white solid (2.00 g). Combined yield: 8.00 g, 16.8 mmol, 75%. LCMS m/z 477.1 [M+H]$^+$. $^1$H NMR (400 MHz, methanol-$d_4$) δ 8.50 (s, 1H), 7.23-7.12 (m, 1H), 6.92 (br t, J=8.7 Hz, 1H), 4.83-4.71 (m, 1H), 4.31-4.21 (m, 2H), 3.94-3.80 (m, 3H), 3.21 (d, J=12.9 Hz, 1H), 2.14 (br s, 3H), 1.82 (br s, 3H), 1.44 (s, 9H).

Step 7. Isolation of tert-butyl 3-{[5-(2,4-difluoro-3-methylphenyl)-4-fluoro-5-methyl-8-oxo-5,6,7,8-tetrahydro-2,7-naphthyridin-3-yl]amino}azetidine-1-carboxylate, ENANT-1 (P4) and tert-butyl 3-{[5-(2,4-difluoro-3-methylphenyl)-4-fluoro-5-methyl-8-oxo-5,6,7,8-tetrahydro-2,7-naphthyridin-3-yl]amino}azetidine-1-carboxylate ENANT-2 (P5)

Separation of C20 (7.00 g, 14.7 mmol) into its component enantiomers was carried out via supercritical fluid chromatography (Column: Chiral Technologies Chiralpak AS-H, 30×250 mm, 5 μm; Mobile phase: 7:3 carbon dioxide/methanol; Back pressure: 100 bar; Flow rate: 250 mL/minute). The first-eluting enantiomer, which exhibited a negative (−) rotation, was designated as P4 and the second-eluting enantiomer, which exhibited a positive (+) rotation, as P5. Both were obtained as yellow foams.

P4 (ENANT-1)—Yield: 3.37 g, 7.07 mmol, 48%. Retention time: 3.62 minutes (Analytical conditions. Column: Chiral Technologies Chiralpak AS-H, 4.6×250 mm, 5 μm; Mobile phase A: carbon dioxide; Mobile phase B: methanol; Gradient: 5% B for 0.50 minutes, then 5% to 100% B over 5.50 minutes; Back pressure: 100 bar; Flow rate: 3.0 mL/minute).

P5 (ENANT-2)—Yield: 3.37 g, 7.07 mmol, 48%. Retention time: 4.18 minutes (Analytical conditions identical to those used for P4).

Preparations P6 and P7
tert-Butyl 3-{[5-(2,3-difluorophenyl)-4-fluoro-5-methyl-8-oxo-5,6,7,8-tetrahydro-2,7-naphthyridin-3-yl]amino}azetidine-1-carboxylate, ENANT-1 (P6) and tert-Butyl 3-{[5-(2,3-difluorophenyl)-4-fluoro-5-methyl-8-oxo-5,6,7,8-tetrahydro-2,7-naphthyridin-3-yl]amino}azetidine-1-carboxylate
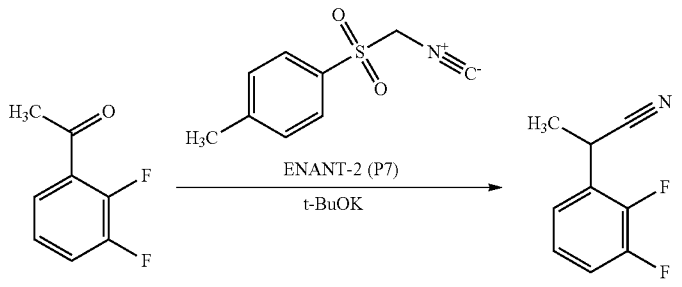
C21
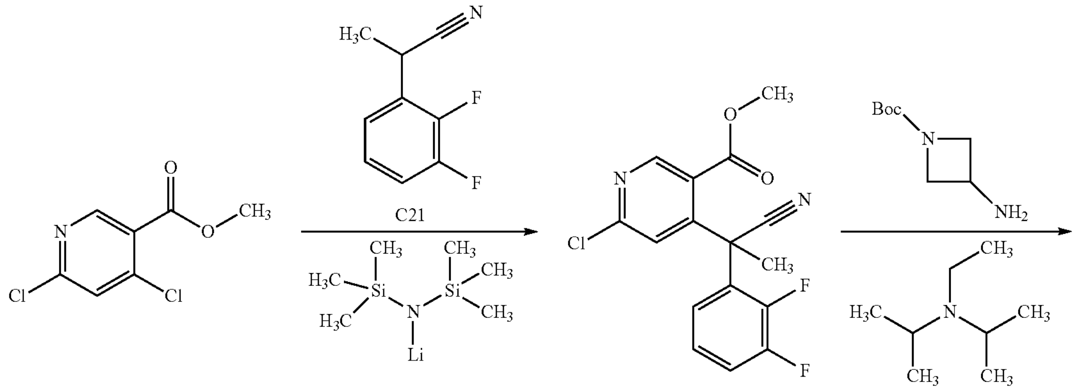
C22
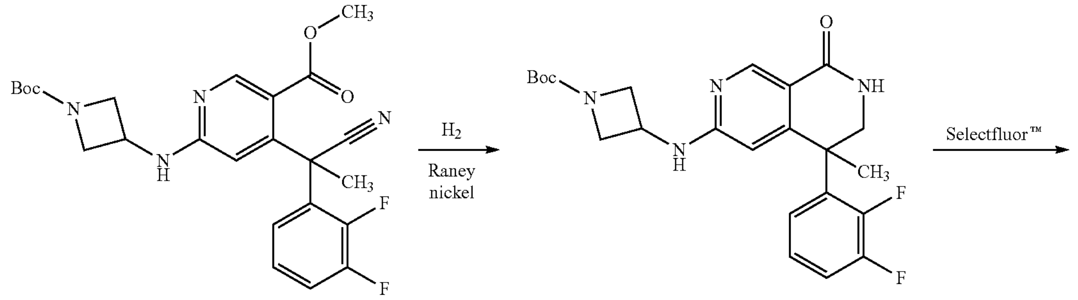
C23
C24
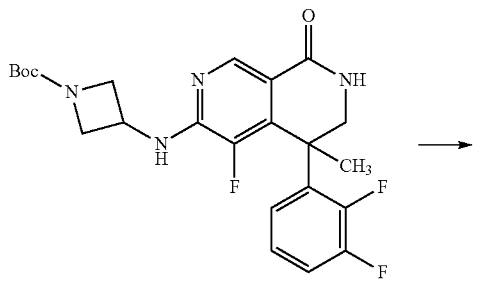
C25

-continued

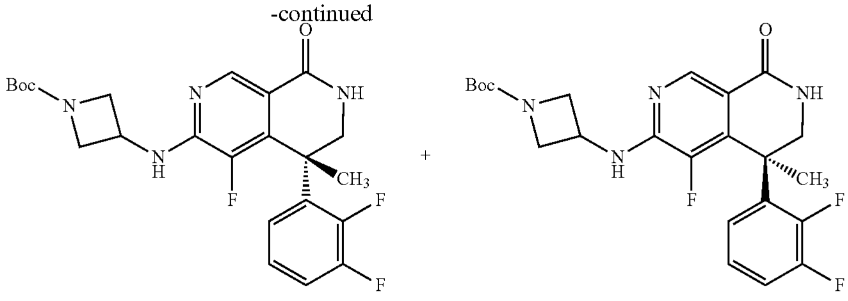

P6 (ENANT-1) and P7 (ENANT-2)

Step 1. Synthesis of 2-(2,3-difluorophenyl)propanenitrile (C21)

A solution of potassium tert-butoxide (31.6 g, 282 mmol) in 1,2-dimethoxyethane (200 mL) was slowly added to a 0° C. solution of 1-(2,3-difluorophenyl)ethan-1-one (22.0 g, 141 mmol) and 1-(isocyanomethanesulfonyl)-4-methylbenzene (TosMIC; 30.3 g, 155 mmol) in 1,2-dimethoxyethane (300 mL), at a rate that maintained the reaction temperature below 5° C. The reaction mixture was stirred at 0° C. for 2 hours, then at room temperature (10° C. to 15° C.) for an additional 2 hours. Chilled water (1 L) was added, and the resulting mixture was extracted with ethyl acetate (3×500 mL); the combined organic layers were washed with saturated aqueous sodium chloride solution, dried over sodium sulfate, filtered, and concentrated in vacuo. Chromatography on silica gel (Gradient: 0% to 3% ethyl acetate in petroleum ether) afforded C21 as a yellow oil. Yield: 17.0 g; corrected for residual solvent: 13.0 g, 77.8 mmol, 55%. $^1$H NMR (400 MHz, chloroform-d), product peaks only: δ 7.30-7.23 (m, 1H, assumed; partially obscured by solvent peak), 7.21-7.11 (m, 2H), 4.21 (q, J=7.3 Hz, 1H), 1.66 (d, J=7.3 Hz, 3H).

Step 2. Synthesis of methyl 6-chloro-4-[1-cyano-1-(2,3-difluorophenyl)ethyl]pyridine-3-carboxylate (C22)

A solution of lithium bis(trimethylsilyl)amide in tetrahydrofuran (1 M; 53.4 mL, 53.4 mmol) was added drop-wise over 30 minutes to a −20° C. solution of methyl 4,6-dichloropyridine-3-carboxylate (10.0 g, 48.5 mmol) and C21 (from the previous step; 80%, 10.4 g, 49.8 mmol) in toluene (200 mL). After 30 minutes at −20° C., LCMS analysis of the reaction mixture indicated the presence of C22: LCMS m/z 337.1 (chlorine isotope pattern observed) [M+H]$^+$. The reaction mixture was diluted with saturated aqueous ammonium chloride solution (200 mL) and extracted with methyl tert-butyl ether (3×100 mL). The combined organic layers were washed with saturated aqueous sodium chloride solution (100 mL), dried over sodium sulfate, filtered, and concentrated in vacuo; silica gel chromatography (Gradient: 0% to 20% ethyl acetate in petroleum ether) afforded 22 as a white solid. Yield: 7.05 g, 20.9 mmol, 43%. $^1$H NMR (400 MHz, chloroform-d) δ 8.63 (s, 1H), 7.66 (s, 1H), 7.30-7.15 (m, 3H, assumed; partially obscured by solvent peak), 3.60 (s, 3H), 2.28 (s, 3H).

Step 3. Synthesis of methyl 6-{[1-(tert-butoxycarbonyl)azetidin-3-yl]amino}-4-[1-cyano-1-(2,3-difluorophenyl)ethyl]pyridine-3-carboxylate (C23)

To a solution of C22 (7.05 g, 20.9 mmol) in dimethyl sulfoxide (100 mL) were added N,N-diisopropylethylamine (8.12 g, 62.8 mmol) and tert-butyl 3-aminoazetidine-1-carboxylate (4.69 g, 27.2 mmol). The reaction mixture was heated to 100° C. for 16 hours, whereupon LCMS analysis indicated conversion to C23: LCMS m/z 473.1 [M+H]$^+$. After the reaction mixture had cooled to 15° C., it was combined with a similar reaction carried out using C22 (7.64 g, 22.7 mmol), diluted with water (300 mL), and extracted with ethyl acetate (3×200 mL). The combined organic layers were washed with saturated aqueous sodium chloride solution (200 mL), dried over sodium sulfate, filtered, and concentrated in vacuo. Silica gel chromatography (Gradient: 0% to 40% ethyl acetate in petroleum ether) provided C23 as a yellow solid. Combined yield: 16.5 g, 34.9 mmol, 80%. $^1$H NMR (400 MHz, chloroform-d) δ 8.57 (s, 1H), 7.20-7.06 (m, 3H), 6.68 (s, 1H), 5.35 (br d, J=6.4 Hz, 1H), 4.75-4.62 (m, 1H), 4.39-4.30 (m, 2H), 3.86-3.77 (m, 2H), 3.55 (s, 3H), 2.24 (s, 3H), 1.45 (s, 9H).

Step 4. Synthesis of tert-butyl 3-{[5-(2,3-difluorophenyl)-5-methyl-8-oxo-5,6,7,8-tetrahydro-2,7-naphthyridin-3-yl]amino}azetidine-1-carboxylate (C24)

To a solution of C23 (5.49 g, 11.6 mmol) in methanol (150 mL) was added Raney nickel (5.0 g, 85 mmol), and the reaction mixture was heated at 45° C. under hydrogen (15 psi). After 16 hours, it was cooled to 15° C., combined with similar reactions carried out using C23 (5.50 g, 5.50 g, and 2.40 g; total 28.4 mmol), filtered, and concentrated in vacuo. The residue was treated with methanol (10 mL), ethyl acetate (10 mL), and methyl tert-butyl ether (50 mL) and stirred for 4 hours, whereupon the suspension was filtered to afford C24 as a white solid.

Combined yield: 13.8 g, 31.0 mmol, 78%. LCMS m/z 445.0 [M+H]$^+$. $^1$H NMR (400 MHz, chloroform-d) δ 8.83 (s, 1H), 7.20-7.10 (m, 1H), 7.06-6.98 (m, 1H), 6.80-6.72 (m, 1H), 5.92 (s, 1H), 5.79 (br s, 1H), 5.29-5.18 (m, 1H), 4.64-4.52 (m, 1H), 4.34-4.21 (m, 2H), 4.06 (dd, J=12.6, 3.0 Hz, 1H), 3.81-3.68 (m, 2H), 3.33 (dd, J=12.7, 3.0 Hz, 1H), 1.76 (s, 3H), 1.43 (s, 9H).

Step 5. Synthesis of tert-butyl 3-{[5-(2,3-difluorophenyl)-4-fluoro-5-methyl-8-oxo-5,6,7,8-tetrahydro-2,7-naphthyridin-3-yl]amino}azetidine-1-carboxylate (C25)

A solution of 1-(chloromethyl)-4-fluoro-1,4-diazoniabicyclo[2.2.2]octane bis(tetrafluoroborate) (Selectfluor™) in N,N-dimethylformamide (0.22 M; 163 mL, 35.9 mmol) was added to a 40° C. solution of C24 (13.3 g, 29.9 mmol) in a mixture of methyl tert-butyl ether (300 mL) and N,N-dimethylformamide (150 mL). After 7 hours, the mixture was allowed to cool to 15° C., diluted with water (1 L), and extracted with ethyl acetate (3×500 mL). The combined organic layers were washed with saturated aqueous sodium chloride solution (500 mL), dried over sodium sulfate, and filtered; silica gel chromatography (Gradient: 0% to 3% methanol in dichloromethane) afforded a solid. This was treated with a solution of methanol (4 mL), ethyl acetate (20 mL), and methyl tert-butyl ether (50 mL), and after 1 hour, the suspension was filtered. Purification via reversed-phase HPLC (Column: YMC-Actus Triart C18, 50×250 mm, 7 μm; Mobile phase A: water containing 0.05% ammonium hydroxide; Mobile phase B: acetonitrile; Gradient: 30% to 70% B; Flow rate: 60 mL/minute), afforded C25 as a white solid. Yield: 3.50 g, 7.57 mmol, 25%. LCMS m/z 463.4 $[M+H]^+$. $^1H$ NMR (400 MHz, methanol-$d_4$) δ 8.52 (s, 1H), 7.29-7.20 (m, 1H), 7.20-7.07 (m, 2H), 4.79 (tt, J=7.7, 5.4 Hz, 1H), 4.27 (t, J=8.1 Hz, 2H), 3.95-3.82 (m, 3H), 3.32-3.26 (m, 1H, assumed; partially obscured by solvent peak), 1.87 (br s, 3H), 1.44 (s, 9H).

Step 6. Isolation of tert-butyl 3-{[5-(2,3-difluorophenyl)-4-fluoro-5-methyl-8-oxo-5,6,7,8-tetrahydro-2,7-naphthyridin-3-yl]amino}azetidine-1-carboxylate, ENANT-1 (P6) and tert-butyl 3-{[5-(2,3-difluorophenyl)-4-fluoro-5-methyl-8-oxo-5,6,7,8-tetrahydro-2,7-naphthyridin-3-yl]amino}azetidine-1-carboxylate, ENANT-2 (P7)

Separation of C25 (2.50 g, 5.41 mmol) into its component enantiomers was carried out via supercritical fluid chromatography (Column: Chiral Technologies Chiralpak IJ, 30×250 mm, 5 μm; Mobile phase: 7:3 carbon dioxide/methanol; Back pressure: 100 bar; flow rate: 80 mL/minute). The first-eluting enantiomer, which exhibited a negative (−) rotation, was designated as P6 and the second-eluting diastereomer, which exhibited a positive (+) rotation as P7; both were obtained as white solids.

P6 (ENANT-1)—Yield: 1.12 g, 2.42 mmol, 45%. Retention time: 3.35 minutes (Analytical conditions. (Column: Chiral Technologies Chiralpak IJ, 4.6×250 mm, 5 μm; Mobile phase A: carbon dioxide; Mobile phase B: methanol; Gradient: 5% B for 0.50 minutes, then 5% to 100% B over 5.50 minutes; Back pressure: 100 bar; Flow rate: 3.0 mL/minute)

P7 (ENANT-2)—Yield: 1.08 g, 2.34 mmol, 43%. Retention time: 3.61 minutes (Analytical conditions identical to those used for P6).

Preparations P8 and P9 tert-Butyl (3R)-3-{[5-(3-chloro-2-fluorophenyl)-4-fluoro-5-methyl-8-oxo-5,6,7,8-tetrahydro-2,7-naphthyridin-3-yl]amino}pyrrolidine-1-carboxylate, DIAST-1 (P8) and tert-Butyl (3R)-3-{[5-(3-chloro-2-fluorophenyl)-4-fluoro-5-methyl-8-oxo-5,6,7,8-tetrahydro-2,7-naphthyridin-3-yl]amino}pyrrolidine-1-carboxylate, DIAST-2 (P9)

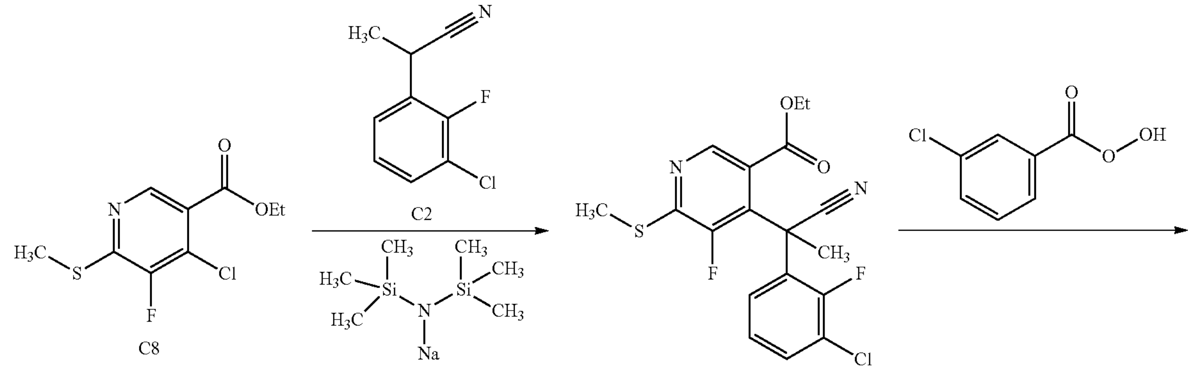

C8 C2 C26

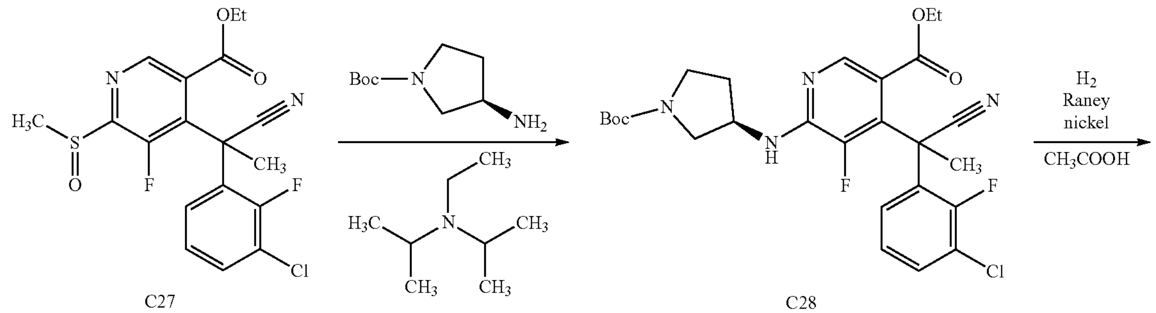

C27 C28

-continued

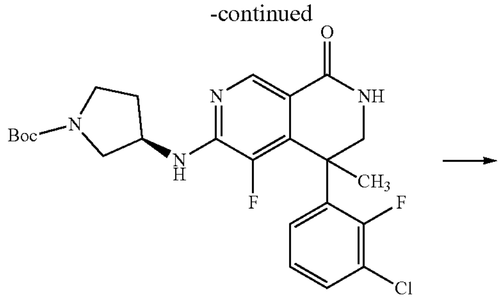

C29

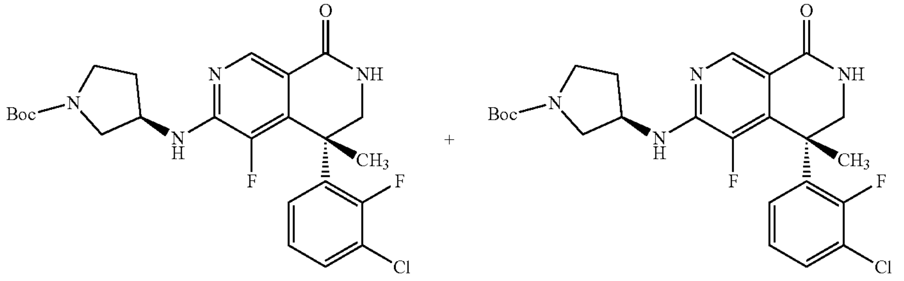

P8 (DIAST-1) and P9 (DIAST-2)

Step 1. Synthesis of ethyl 4-[1-(3-chloro-2-fluorophenyl)-1-cyanoethyl]-5-fluoro-6-(methylsulfanyl)pyridine-3-carboxylate (C26)

A solution of sodium bis(trimethylsilyl)amide in tetrahydrofuran (1 M; 64.8 mL, 64.8 mmol) was added to a 0° C. solution of C8 (14.7 g, 58.9 mmol) and C2 (85%, 14.0 g, 64.8 mmol) in toluene (300 mL). After the reaction mixture had been warmed to 25° C. and stirred for 2 hours, it was diluted with water (150 mL) and with saturated aqueous ammonium chloride solution (150 mL). The resulting mixture was extracted with ethyl acetate (3×300 mL), and the combined organic layers were washed with saturated aqueous sodium chloride solution (300 mL), dried over sodium sulfate, filtered, and concentrated in vacuo. Silica gel chromatography (Gradient: 0% to 10% ethyl acetate in petroleum ether) afforded C26 as a yellow solid. Yield: 18.4 g, 46.4 mmol, 79%. LCMS m/z 397.0 (chlorine isotope pattern observed) $[M+H]^+$. NMR data was obtained from a similar reaction carried out on smaller scale: $^1H$ NMR (400 MHz, chloroform-d) δ 8.42 (s, 1H), 7.45 (ddd, J=8.3, 6.9, 1.6 Hz, 1H), 7.39 (ddd, J=8.3, 6.8, 1.6 Hz, 1H), 7.18 (td, J=8.1, 1.3 Hz, 1H), 4.19-4.00 (m, 2H), 2.59 (s, 3H), 2.32 (d, J=2.2 Hz, 3H), 1.24 (t, J=7.2 Hz, 3H).

Step 2. Synthesis of ethyl 4-[1-(3-chloro-2-fluorophenyl)-1-cyanoethyl]-5-fluoro-6-(methanesulfinyl)pyridine-3-carboxylate (C27)

3-Chloroperoxybenzoic acid (6.22 g, 36.0 mmol) was added to a 0° C. solution of C26 (11.0 g, 27.7 mmol) in dichloromethane (150 mL), and the reaction mixture was stirred at 20° C. After 2 hours, additional 3-chloroperoxybenzoic acid (1.00 g, 5.79 mmol) was added, and after 1 more hour, LCMS analysis indicated conversion to C27: LCMS m/z 413.1 (chlorine isotope pattern observed) $[M+H]^+$. The reaction mixture was diluted with saturated aqueous sodium thiosulfate solution (150 mL) and saturated aqueous sodium bicarbonate solution (150 mL) and extracted with dichloromethane (3×150 mL). The combined organic layers were washed with saturated aqueous sodium chloride solution (200 mL), dried over sodium sulfate, filtered, and concentrated in vacuo, affording C27 as a white solid (11.4 g); this material was used directly in the following step.

Step 3. Synthesis of ethyl 6-{[(3R)-1-(tert-butoxycarbonyl)pyrrolidin-3-yl]amino}-4-[1-(3-chloro-2-fluorophenyl)-1-cyanoethyl]-5-fluoropyridine-3-carboxylate (C28)

To a solution of C27 (from the previous step; 11.2 g, 527.2 mmol) in dimethyl sulfoxide (300 mL) were added N,N-diisopropylethylamine (10.6 g, 82.0 mmol) and tert-butyl (3R)-3-aminopyrrolidine-1-carboxylate (7.61 g, 40.9 mmol), whereupon the reaction mixture was heated to 80° C. After 16 hours, it was allowed to cool to 25° C., diluted with water (1 L), and extracted with ethyl acetate (3×200 mL). The combined organic layers were washed with saturated aqueous sodium chloride solution (1 L), dried over sodium sulfate, filtered, concentrated in vacuo, and purified via silica gel chromatography (Gradient: 0% to 25% ethyl acetate in petroleum ether), providing C28 as a yellow solid. This material was a mixture of diastereomers. Yield: 13.0 g, 24.3 mmol, 89% over 2 steps. LCMS m/z 557.1 (chlorine isotope pattern observed) $[M+Na^+]$. $^1H$ NMR (400 MHz, methanol-$d_4$) δ [8.13 (s) and 8.12 (s), total 1H], 7.57-7.47 (m, 2H), 7.27 (br t, J=8.1 Hz, 1H), 4.66-4.55 (m, 1H), 4.08-3.93 (m, 1H), 3.76-3.67 (m, 1H), 3.57-3.46 (m, 1H), 3.46-3.35 (m, 1H), 3.31-3.24 (m, 2H, assumed; partially obscured by solvent peak), 2.34 (d, J=2.0 Hz, 3H), 2.31-2.19 (m, 1H), 2.07-1.93 (m, 1H), 1.46 (br s, 9H), 1.23-1.15 (m, 3H).

Step 4. Synthesis of tert-butyl (3R)-3-{[5-(3-chloro-2-fluorophenyl)-4-fluoro-5-methyl-8-oxo-5,6,7,8-tetrahydro-2,7-naphthyridin-3-yl]amino}pyrrolidine-1-carboxylate (C29)

To a solution of C28 (12.0 g, 22.4 mmol) in a mixture of methanol (150 mL) and tetrahydrofuran (150 mL) were added acetic acid (6.4 mL, 112 mmol) and Raney nickel (5.0 g, 85 mmol). The reaction mixture was heated at 50° C. under hydrogen (15 psi) for 16 hours, whereupon it was allowed to cool to 25° C., combined with a similar reaction carried out using C28 (1.00 g, 1.87 mmol), filtered, and concentrated in vacuo. Silica gel chromatography (Gradient: 0% to 10% 2-methyltetrahydrofuran in dichloromethane), followed by a second purification using silica gel chromatography (Gradient: 0% to 2% methanol in dichloromethane), afforded C29 as a white solid, a mixture of diastereomers. Combined yield: 8.70 g, 17.6 mmol, 73%. LCMS m/z 493.4 (chlorine isotope pattern observed) $[M+H]^+$. $^1H$ NMR (400 MHz, methanol-$d_4$) δ 8.55 (s, 1H), 7.44 (br t, J=7.3 Hz, 1H), 7.33-7.23 (m, 1H), 7.22 (br t, J=8.0 Hz, 1H), 4.67-4.58 (m, 1H), 3.87 (d, J=12.9 Hz, 1H), 3.77-3.67 (m, 1H), 3.55-3.45 (m, 1H), 3.45-3.34 (m, 1H), 3.31-3.19 (m, 2H), 2.32-2.17 (m, 1H), 2.06-1.90 (m, 1H), 1.89 (br s, 3H), 1.45 (br s, 9H).

Step 5. Isolation of tert-butyl (3R)-3-{[5-(3-chloro-2-fluorophenyl)-4-fluoro-5-methyl-8-oxo-5,6,7,8-tetrahydro-2,7-naphthyridin-3-yl]amino}pyrrolidine-1-carboxylate, DIAST-1 (P8) and tert-butyl (3R)-3-{[5-(3-chloro-2-fluorophenyl)-4-fluoro-5-methyl-8-oxo-5,6,7,8-tetrahydro-2,7-naphthyridin-3-yl]amino}pyrrolidine-1-carboxylate, DIAST-2 (P9)

Separation of C29 (7.70 g, 15.6 mmol) into its component diastereomers was carried out via supercritical fluid chromatography (Column: Chiral Technologies Chiralpak AD-H, 30×250 mm, 5 μm; Mobile phase: 7:3 carbon dioxide/methanol; Back pressure: 100 bar; Flow rate: 80 mL/minute). The first-eluting diastereomer, which exhibited a negative (−) rotation, was designated as P8, and the second-eluting diastereomer, which exhibited a positive (+) rotation, as P9; both were obtained as yellow foams.

P8 (DIAST-1)—Yield: 3.47 g, 7.04 mmol, 45%. Retention time: 4.13 minutes (Analytical conditions. Column: Chiral Technologies Chiralpak AD-H, 4.6×250 mm, 5 μm; Mobile phase A: carbon dioxide; Mobile phase B: methanol; Gradient: 5% B for 0.50 minutes, then 5% to 100% B over 5.50 minutes; Back pressure: 100 bar; Flow rate: 3.0 mL/minute).

P9 (DIAST-2)—Yield: 3.76 g, 7.63 mmol, 49%. Retention time: 4.36 minutes (Analytical conditions identical to those used for P8).

Preparations P10 and P11 tert-Butyl 3-{[8-(3-chloro-2-fluorophenyl)-8-methyl-5-oxo-5,6,7,8-tetrahydropyrido[4,3-d]pyrimidin-2-yl]amino}azetidine-1-carboxylate, ENANT-1 (P10) and tert-Butyl 3-{[8-(3-chloro-2-fluorophenyl)-8-methyl-5-oxo-5,6,7,8-tetrahydropyrido[4,3-d]pyrimidin-2-yl]amino}azetidine-1-carboxylate, ENANT-2 (P11)

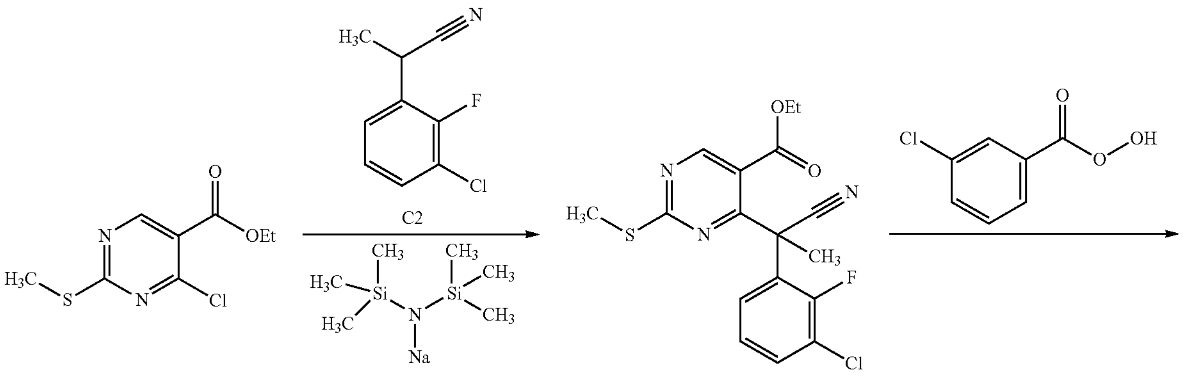

C2

C30

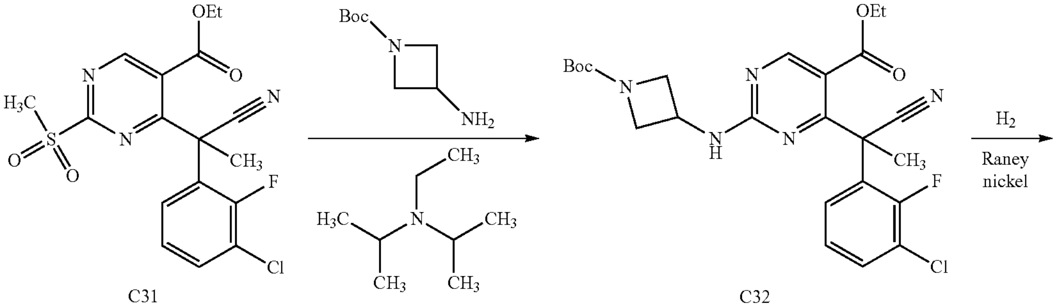

C31

C32

-continued

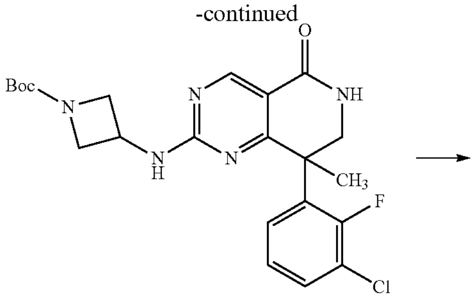

C33

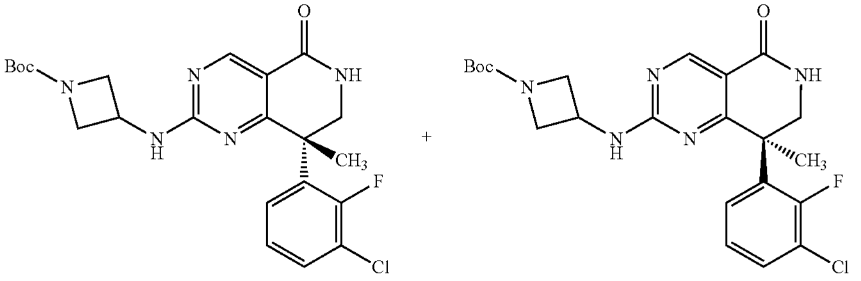

P10 (ENANT-1) and P11 (ENANT-2)

Step 1. Synthesis of ethyl 4-[1-(3-chloro-2-fluorophenyl)-1-cyanoethyl]-2-(methylsulfanyl)pyrimidine-5-carboxylate (C30)

A solution of sodium bis(trimethylsilyl)amide in tetrahydrofuran (1 M; 98.9 mL, 98.9 mmol) was added in a drop-wise manner over 10 minutes to a 0° C. solution of ethyl 4-chloro-2-(methylsulfanyl)pyrimidine-5-carboxylate (24.9 g, 107 mmol) and C2 (15.2 g, 82.8 mmol) in tetrahydrofuran (100 mL). After 30 minutes, the reaction mixture was warmed to 25° C. for 1 hour, whereupon it was diluted with saturated aqueous ammonium chloride solution (150 mL) and extracted with ethyl acetate (3×150 mL). The combined organic layers were washed with saturated aqueous sodium chloride solution (150 mL), dried over sodium sulfate, filtered, and concentrated in vacuo; silica gel chromatography (Gradient: 0% to 20% ethyl acetate in petroleum ether) afforded C30 as a yellow oil. Yield: 21.0 g, 55.3 mmol, 67%. LCMS m/z 380.0 (chlorine isotope pattern observed) $[M+H]^+$. $^1H$ NMR (400 MHz, chloroform-d) δ 8.87 (s, 1H), 7.45 (ddd, J=8.3, 7.0, 1.6 Hz, 1H), 7.40 (ddd, J=8.3, 6.8, 1.6 Hz, 1H), 7.16 (td, J=8.0, 1.3 Hz, 1H), 4.17-4.00 (m, 2H), 2.62 (s, 3H), 2.25 (s, 3H), 1.15 (t, J=7.1 Hz, 3H).

Step 2. Synthesis of ethyl 4-[1-(3-chloro-2-fluorophenyl)-1-cyanoethyl]-2-(methanesulfonyl)pyrimidine-5-carboxylate (C31)

3-Chloroperoxybenzoic acid (80%, 29.8 g, 138 mmol) was added to a 0° C. solution of C30 (21.0 g, 55.3 mmol) in dichloromethane (300 mL). After the reaction mixture had been stirred at 25° C. for 2 hours, LCMS analysis indicated conversion to C31: LCMS m/z 412.0 (chlorine isotope pattern observed) $[M+H]^+$. The reaction mixture was diluted with saturated aqueous sodium thiosulfate solution (200 mL) and extracted with dichloromethane (3×150 mL); the combined organic layers were washed sequentially with saturated aqueous sodium bicarbonate solution (200 mL) and saturated aqueous sodium chloride solution (200 mL), dried over sodium sulfate, filtered, and concentrated in vacuo to provide C31 as a white solid. This material was used directly in the following step.

Step 3. Synthesis of ethyl 2-{[1-(tert-butoxycarbonyl)azetidin-3-yl]amino}-4-[1-(3-chloro-2-fluorophenyl)-1-cyanoethyl]pyrimidine-5-carboxylate (C32)

To a solution of C31 (from the previous step; 555.3 mmol) in toluene (400 mL) were added N,N-diisopropylethylamine (35.8 g, 277 mmol) and tert-butyl 3-aminoazetidine-1-carboxylate (14.3 g, 83.0 mmol). After the reaction mixture had been heated at 50° C. for 2 hours, LCMS analysis indicated conversion to C32: LCMS m/z 526.2 $[M+Na^+]$. The reaction mixture was concentrated in vacuo; silica gel chromatography (Gradient: 0% to 50% ethyl acetate in petroleum ether) afforded C32 as a yellow solid. Yield: 21.0 g, 41.7 mmol, 75% over 2 steps. $^1H$ NMR (400 MHz, chloroform-d) δ 8.78 (s, 1H), 7.48-7.39 (m, 1H), 7.39-7.32 (m, 1H), 7.14 (t, J=8.0 Hz, 1H), 6.22-5.98 (m, 1H), 4.86-4.58 (m, 1H), 4.41-4.17 (m, 2H), 4.15-3.95 (m, 2H), 3.94-3.79 (m, 2H), 2.17 (s, 3H), 1.44 (s, 9H), 1.20-1.05 (m, 3H).

Step 4. Synthesis of tert-butyl 3-{[8-(3-chloro-2-fluorophenyl)-8-methyl-5-oxo-5,6,7,8-tetrahydropyrido[4,3-d]pyrimidin-2-yl]amino}azetidine-1-carboxylate (C33)

To a solution of C32 (21.0 g, 41.7 mmol) in methanol (400 mL) was added Raney nickel (10 g, 170 mmol). The reaction mixture was heated at 45° C. under hydrogen (15 psi) for 32 hours, whereupon it was allowed to cool to 25° C., filtered, and the filter cake was rinsed with methanol (3×100 mL). The combined filtrates were concentrated in vacuo; silica gel chromatography (Gradient: 0% to 100% ethyl acetate in petroleum ether) afforded C33 as a white solid. Yield: 16.0 g, 34.6 mmol, 83%. LCMS m/z 462.0 (chlorine isotope pattern observed) $[M+H]^+$. $^1H$ NMR (400 MHz, methanol-$d_4$), characteristic peaks, integrations are approximate: δ

8.78 (s, 1H), 7.53-7.36 (m, 1H), 7.31-7.07 (m, 2H), [4.77-4.63 (m) and 4.36-4.15 (m), total 2H], 3.96 (d, J=13.0 Hz, 1H), 1.76 (s, 3H), 1.42 (s, 9H).

Step 5. Isolation of tert-butyl 3-{[8-(3-chloro-2-fluorophenyl)-8-methyl-5-oxo-5,6,7,8-tetrahydropyrido[4,3-d]pyrimidin-2-yl]amino}azetidine-1-carboxylate, ENANT-1 (P10) and tert-butyl 3-{[8-(3-chloro-2-fluorophenyl)-8-methyl-5-oxo-5,6,7,8-tetrahydropyrido[4,3-d]pyrimidin-2-yl]amino}azetidine-1-carboxylate, ENANT-2 (P11)

Separation of C33 (61.5 g, 133 mmol) into its component enantiomers was carried out via supercritical fluid chromatography {Column: Phenomenex Lux Cellulose-3, 50×250 mm, 5 μm; Mobile phase: 3:1 carbon dioxide/[methanol containing 0.2% (7 M ammonia in methanol)]; Back pressure: 120 bar; Flow rate: 200 mL/minute}. The first-eluting enantiomer, which exhibited a negative (−) rotation, was designated as P10, and the second-eluting enantiomer, which exhibited a positive (+) rotation, as P11; both were obtained as white solids.

P10 (ENANT-1)—Yield: 28.6 g, 61.9 mmol, 47%. Retention time: 4.21 minutes. [Analytical conditions. Column: Phenomenex Lux Cellulose-3, 4.6×250 mm, 5 μm; Mobile phase A: carbon dioxide; Mobile phase B: methanol containing 0.2% (7 M ammonia in methanol); Gradient: 5% B for 1.00 minute, then 5% to 60% B over 8.00 minutes; Back pressure: 120 bar; Flow rate: 3.0 mL/minute].

P11 (ENANT-2)—Yield: 27.0 g, 58.5 mmol, 44%. Retention time: 5.41 minutes (Analytical conditions identical to those used for P10).

Preparations P12 and P13

8-(3-Chloro-2-fluorophenyl)-6-[(2,4-dimethoxyphenyl)methyl]-8-methyl-2-(methylsulfanyl)-7,8-dihydropyrido[4,3-d]pyrimidin-5(6H)-one, ENANT-1 (P12) and 8-(3-Chloro-2-fluorophenyl)-6-[(2,4-dimethoxyphenyl)methyl]-8-methyl-2-(methylsulfanyl)-7,8-dihydropyrido[4,3-d]pyrimidin-5(6H)-one, ENANT-2 (P13)

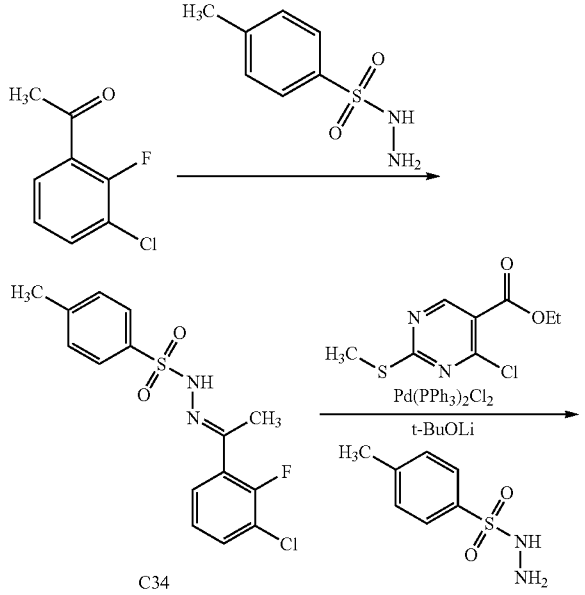

C34

-continued

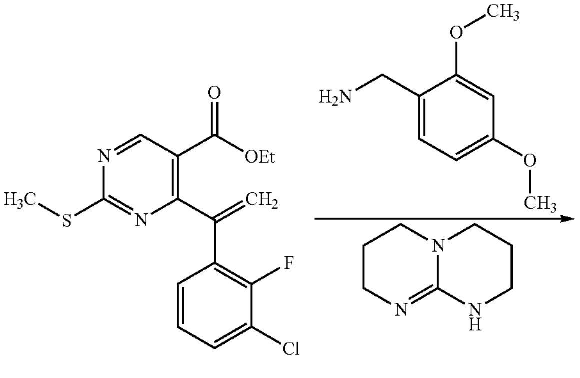

C35

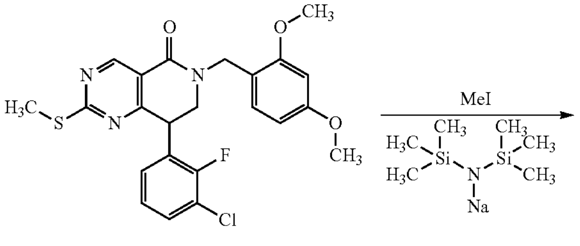

C36

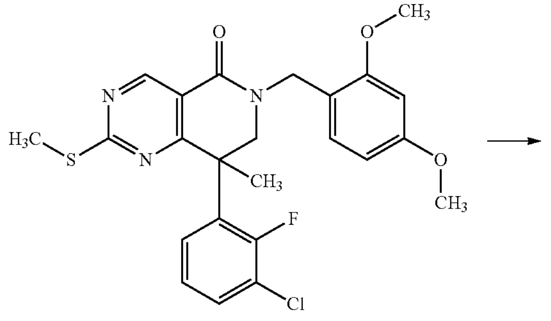

C37

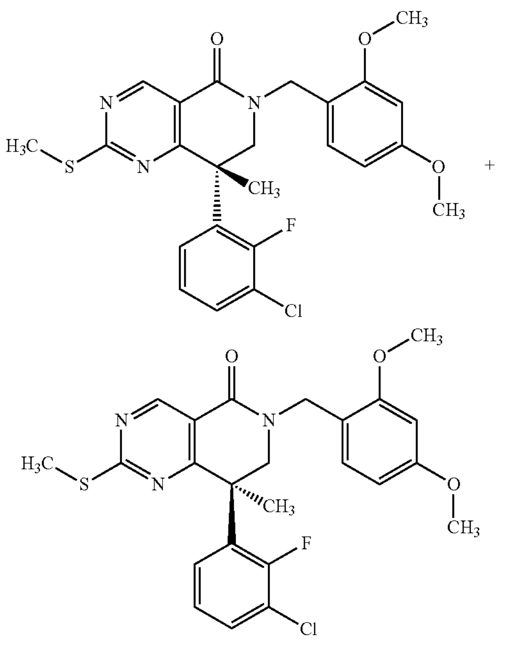

P12 (ENANT-1) and P13 (ENANT-2)

Step 1. Synthesis of N'-[1-(3-chloro-2-fluorophenyl) ethylidene]-4-methylbenzene-1-sulfonohydrazide (C34)

A solution of 4-methylbenzene-1-sulfonohydrazide (97.8 g, 525 mmol) and 1-(3-chloro-2-fluorophenyl)ethan-1-one (82.4 g, 477 mmol) in ethanol (1.5 L) was heated to reflux for 16 hours. Solvent was then removed in vacuo and the residue was layered with a mixture of ethyl acetate in petroleum ether (13%, 800 mL). After 1 hour, collection of the solid via filtration provided C34 as a white solid. Yield: 150 g, 440 mmol, 92%. $^1$H NMR (400 MHz, chloroform-d) δ 7.92-7.85 (m, 3H), 7.42-7.30 (m, 4H), 7.06 (td, J=7.9, 1.1 Hz, 1H), 2.43 (s, 3H), 2.17 (d, J=3.1 Hz, 3H).

Step 2. Synthesis of ethyl 4-[1-(3-chloro-2-fluoro-phenyl)ethenyl]-2-(methylsulfanyl)pyrimidine-5-carboxylate (C35)

A solution of ethyl 4-chloro-2-(methylsulfanyl)pyrimidine-5-carboxylate (40.0 g, 172 mmol), C34 (68.0 g, 200 mmol), dichlorobis(triphenylphosphine)palladium(II) (12.1 g, 17.2 mmol), and 4-methylbenzene-1-sulfonohydrazide (6.40 g, 34.4 mmol) in cyclopentyl methyl ether (600 mL) was heated to 100° C., whereupon a solution of lithium tert-butoxide in cyclopentyl methyl ether (0.8 M; 641 mL, 513 mmol) was added in a drop-wise manner over 50 minutes. After 16 hours, the reaction mixture was allowed to cool to 25° C., diluted with methyl tert-butyl ether (500 mL), filtered, and concentrated in vacuo; silica gel chromatography (Gradient: 0% to 10% ethyl acetate in petroleum ether) afforded C35 as a yellow oil. Yield: 42.0 g, 119 mmol, 69%. $^1$H NMR (400 MHz, chloroform-d) δ 8.86 (s, 1H), 7.33 (ddd, J=7.8, 6.8, 1.9 Hz, 1H), 7.12-7.00 (m, 2H), 5.99 (s, 1H), 5.96 (s, 1H), 4.03 (q, J=7.1 Hz, 2H), 2.60 (s, 3H), 1.15 (t, J=7.1 Hz, 3H).

Step 3. Synthesis of 8-(3-chloro-2-fluorophenyl)-6-[(2,4-dimethoxyphenyl)methyl]-2-(methylsulfanyl)-7,8-dihydropyrido[4,3-d]pyrimidin-5(6H)-one (C36)

A solution of 1-(2,4-dimethoxyphenyl)methanamine (23.9 g, 143 mmol) in tetrahydrofuran (100 mL) was added in a drop-wise manner over 15 minutes to a 15° C. solution of C35 (42.0 g, 119 mmol) and 1,3,4,6,7,8-hexahydro-2H-pyrimido[1,2-a]pyrimidine (2.49 g, 17.9 mmol) in tetrahydrofuran (400 mL). After 16 hours, the reaction mixture was concentrated in vacuo; silica gel chromatography (Gradient: 10% to 50% ethyl acetate in heptane) afforded C36 as a yellow solid. Yield: 39.0 g, 82.3 mmol, 69%. $^1$H NMR (400 MHz, chloroform-d) δ 9.16 (s, 1H), 7.27-7.21 (m, 1H, assumed; partially obscured by solvent peak), 7.05 (d, J=9.0 Hz, 1H), 6.84 (br t, J=8.0 Hz, 1H), 6.47 (ddd, J=8.0, 6.5, 1.6 Hz, 1H), 6.32-6.26 (m, 2H), 4.82 (d, J=14.2 Hz, 1H), 4.50 (t, J=5.1 Hz, 1H), 4.35 (d, J=14.2 Hz, 1H), 3.90 (dd, component of ABX system, J=13.1, 5.0 Hz, 1H), 3.78 (dd, component of ABX system, J=13.0, 5.5 Hz, 1H), 3.77 (s, 3H), 3.71 (s, 3H), 2.48 (s, 3H).

Step 4. Synthesis of 8-(3-chloro-2-fluorophenyl)-6-[(2,4-dimethoxyphenyl)methyl]-8-methyl-2-(methylsulfanyl)-7,8-dihydropyrido[4,3-d]pyrimidin-5(6H)-one (C37)

A solution of sodium bis(trimethylsilyl)amide in tetrahydrofuran (1 M; 90.5 mL, 90.5 mmol) was added in a drop-wise manner over 30 minutes to a 0° C. solution of C36 (39.0 g, 82.3 mmol) in tetrahydrofuran (500 mL). After 30 minutes, iodomethane (15.9 g, 112 mmol) was added, and the reaction mixture was allowed to warm to 20° C. After 1 hour, it was diluted with saturated aqueous ammonium chloride solution (300 mL) and extracted with ethyl acetate (3×300 mL). The combined organic layers were dried over sodium sulfate, filtered, concentrated in vacuo, and purified using silica gel chromatography (Gradient 0% to 10% ethyl acetate in dichloromethane). The resulting material was treated with ethanol (300 mL); after 1 hour, the solid was collected via filtration to afford C37 as a white solid. Yield: 20.0 g, 41.0 mmol, 50%. LCMS m/z 488.1 (chlorine isotope pattern observed) $[M+H]^+$. $^1$H NMR (400 MHz, chloroform-d) δ 9.16 (s, 1H), 7.27-7.21 (m, 1H, assumed; partially obscured by solvent peak), 6.95 (d, J=8.4 Hz, 1H), 6.88 (br t, J=8.0 Hz, 1H), 6.48 (ddd, J=8.0, 7.6, 1.6 Hz, 1H), 6.38 (d, J=2.4 Hz, 1H), 6.29 (dd, J=8.3, 2.4 Hz, 1H), 4.75 (d, J=14.2 Hz, 1H), 4.47 (d, J=14.3 Hz, 1H), 4.05 (d, J=13.2 Hz, 1H), 3.80 (s, 3H), 3.73 (s, 3H), 3.44 (d, J=13.2 Hz, 1H), 2.47 (s, 3H), 1.67 (s, 3H).

Step 5. Isolation of 8-(3-chloro-2-fluorophenyl)-6-[(2,4-dimethoxyphenyl)methyl]-8-methyl-2-(methylsulfanyl)-7,8-dihydropyrido[4,3-d]pyrimidin-5(6H)-one, ENANT-1 (P12) and 8-(3-chloro-2-fluorophenyl)-6-[(2,4-dimethoxyphenyl)methyl]-8-methyl-2-(methylsulfanyl)-7,8-dihydropyrido[4,3-d]pyrimidin-5(6H)-one, ENANT-2 (P13)

Separation of C37 (40.2 g, 82.4 mmol) into its component enantiomers was carried out via supercritical fluid chromatography [Column: Chiral Technologies Chiralpak IG, 21.2×250 mm, 5 μm; Mobile phase: 3:2 carbon dioxide/(propan-2-ol containing 0.2% propan-2-amine); Back pressure: 120 bar; Flow rate: 150 mL/minute]. The first-eluting enantiomer, which exhibited a negative (−) rotation, was designated as P12, and the second-eluting enantiomer, which exhibited a positive (+) rotation, as P13; both were obtained as off-white solids.

P12 (ENANT-1)—Yield: 18.6 g, 38.1 mmol, 46%. Retention time: 9.06 minutes (Analytical conditions. Column: Chiral Technologies Chiralpak IG, 4.6×250 mm, 5 μm; Mobile phase A: carbon dioxide; Mobile phase B: propan-2-ol containing 0.2% propan-2-amine; Gradient: 5% B for 1.00 minute, then 5% to 60% B over 8.00 minutes, then 60% B; Back pressure: 120 bar; Flow rate: 3.0 mL/minute).

P13 (ENANT-2)—Yield: 20.5 g, 42.0 mmol, 51%. Retention time: 10.21 minutes (Analytical conditions identical to those used for P12).

Preparation P14

(3-Aminoazetidin-1-yl)[(1S,2S)-2-fluorocyclopropyl]methanone, trifluoroacetate salt (P14)

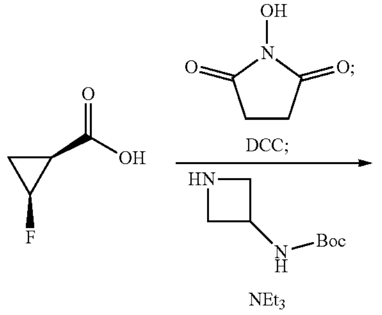

-continued

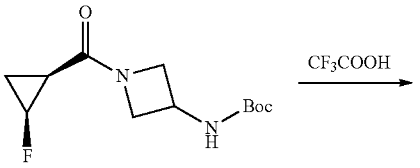

C38

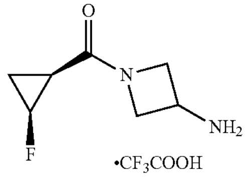

•$CF_3COOH$

P14

Step 1. Synthesis of tert-butyl {1-[(1S,2S)-2-fluorocyclopropane-1-carbonyl]azetidin-3-yl}carbamate (C38)

To a solution of (1S,2S)-2-fluorocyclopropane-1-carboxylic acid (500 mg, 4.80 mmol) in tetrahydrofuran (20 mL) were added 1-hydroxypyrrolidine-2,5-dione (553 mg, 4.80 mmol) and 1,3-dicyclohexylcarbodiimide (DCC; 991 mg, 4.80 mmol). The reaction mixture was stirred at 30° C. for 6 hours, to provide a mixture containing 1-{[(1S,2S)-2-fluorocyclopropane-1-carbonyl]oxy}pyrrolidine-2,5-dione. To this were added tert-butyl azetidin-3-ylcarbamate (910 mg, 5.28 mmol) and triethylamine (2.0 mL, 14 mmol), whereupon stirring was continued for 16 hours at 25° C. The reaction mixture was then concentrated in vacuo and purified using silica gel chromatography (Gradient: 0% to 100% ethyl acetate in petroleum ether) to provide C38 as a white solid. Yield: 770 mg, 2.98 mmol, 62%. LCMS m/z 259.1 $[M+H]^+$. $^1H$ NMR (400 MHz, methanol-$d_4$) δ 4.79 (dtd, J=65.6, 6.2, 3.6 Hz, 1H, assumed; partially obscured by water peak), 4.60-4.49 (m, 1H), 4.49-4.34 (m, 1H), 4.30-4.19 (m, 1H), 4.18-4.06 (m, 1H), 3.85 (dd, J=10.3, 5.4 Hz, 1H), 1.84-1.73 (m, 1H), 1.70-1.57 (m, 1H), 1.45 (s, 9H), 1.13-1.02 (m, 1H).

Step 2. Synthesis of (3-aminoazetidin-1-yl)[(1S,2S)-2-fluorocyclopropyl]methanone, trifluoroacetate salt (P14)

Trifluoroacetic acid (1 mL) was added to a solution of C38 (200 mg, 0.774 mmol) in dichloromethane (4 mL), and the reaction mixture was stirred at 20° C. overnight. Concentration in vacuo provided P14 as a yellow gum (assumed quantitative); this material was used directly in further chemistry. LCMS m/z 159.1 $[M+H]^+$.

Preparations P15 and P16

3-(2,3-Difluorophenyl)-3-methyl-1-phenylpiperidin-4-one, ENANT-1 (P15) and 3-(2,3-Difluorophenyl)-3-methyl-1-phenylpiperidin-4-one, ENANT-2 (P16)

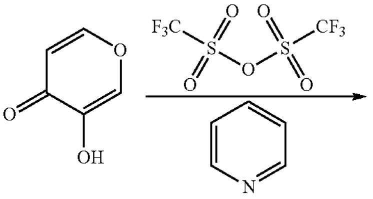

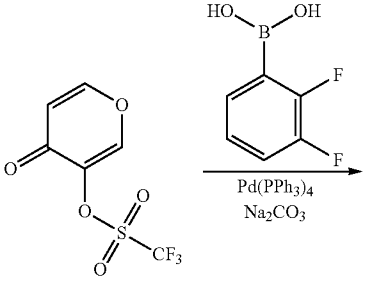

C39

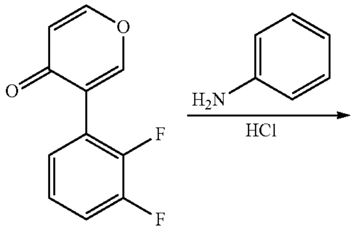

C40

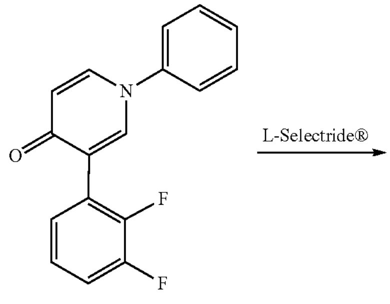

C41

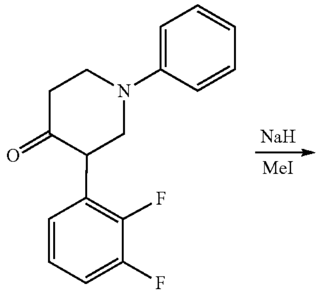

C42

-continued

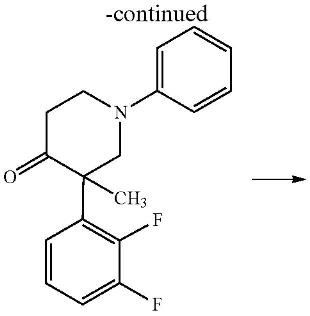

C43

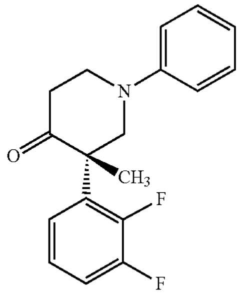

+

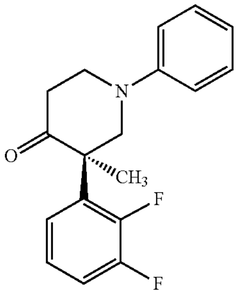

P15 (ENANT-1) and P16 (ENANT-2)

Step 1. Synthesis of 4-oxo-4H-pyran-3-γl trifluoromethanesulfonate (C39)

A 0° C. solution of 3-hydroxy-4H-pyran-4-one (13.0 g, 116 mmol) in pyridine (150 mL) was treated drop-wise with trifluoromethanesulfonic anhydride (50.0 g, 177 mmol) over a period of 1 hour, at a rate that maintained the internal reaction temperature below 10° C. The cooling bath was allowed to warm slowly to room temperature overnight, whereupon the reaction mixture was cooled in an ice bath and slowly quenched with methanol, while keeping the internal reaction temperature below 20° C. Once addition of methanol no longer resulted in an increase in temperature, the reaction mixture was concentrated under reduced pressure (60° C./15 mbar) and then azeotroped with heptane. The residue was dissolved in a mixture of ethyl acetate and heptane (3:1, 60 mL), applied to the top of a silica pad, and eluted with a mixture of ethyl acetate and heptane (4:1, 2 L). After the eluent had been concentrated in vacuo, the resulting solid was dissolved in a minimal amount of ethyl acetate and treated with heptane, providing a slurry that was stirred at room temperature overnight. Collection of the solid via filtration, followed by washing of the filter cake with heptane, afforded C39 as a white solid (21.1 g). The combined filtrates were concentrated under reduced pressure, and the residue was similarly treated with ethyl acetate and heptane, providing a second crop of C39. Combination of the two batches afforded C39 as a white solid. Yield: 26.0 g, 106 mmol, 91%. GCMS m/z 244.0 [M+H$^+$]. $^1$H NMR (400 MHz, chloroform-d) δ 8.09 (s, 1H), 7.80 (d, J=5.8 Hz, 1H), 6.59 (d, J=5.8 Hz, 1H).

Step 2. Synthesis of 3-(2,3-difluorophenyl)-4H-pyran-4-one (C40)

A solution of C39 (11.2 g, 45.9 mmol), (2,3-difluorophenyl)boronic acid (10.1 g, 64.0 mmol), and sodium carbonate (14.6 g, 138 mmol) in a mixture of 1,4-dioxane (240 mL) and water (60 mL) was degassed under high vacuum for 10 minutes, until bubbling ceased, then sparged with nitrogen for 15 minutes. The deoxygenated mixture was then treated with tetrakis(triphenylphosphine)palladium(0) (95%, 8.37 g, 6.88 mmol) and the slurry was heated at reflux in a preheated aluminum block for 2 hours, whereupon the reaction mixture was allowed to cool to room temperature with stirring overnight. It was then concentrated in vacuo and partitioned between ethyl acetate (500 mL) and water (400 mL); the aqueous layer was extracted with ethyl acetate (3×200 mL), and the combined organic layers were washed sequentially with water (150 mL) and saturated aqueous sodium chloride solution (150 mL), dried over magnesium sulfate, filtered, and concentrated under reduced pressure. Chromatography on silica gel (Gradient: 30% to 55% ethyl acetate in heptane) provided C40 as a yellow solid. Yield: 7.00 g, 33.6 mmol, 73%. LCMS m/z 209.1 [M+H]$^+$. $^1$H NMR (400 MHz, chloroform-d) δ 7.93 (br s, 1H), 7.79 (dd, J=5.8, 1.1 Hz, 1H), 7.25-7.10 (m, 3H), 6.51 (d, J=5.8 Hz, 1H).

Step 3. Synthesis of 3-(2,3-difluorophenyl)-1-phenylpyridin-4(1H)-one (C41)

A solution of C40 (7.00 g, 33.6 mmol) and aniline (6.4 mL, 70 mmol) in hydrochloric acid (1 M; 5.0 L) was stirred at reflux overnight. Aniline (4.0 mL, 44 mmol) was again added, and heating was continued for a second night. After the reaction mixture had been allowed to cool slowly to room temperature, the resulting slurry was carefully neutralized by addition of solid sodium bicarbonate and extracted with ethyl acetate (3×350 mL). The combined organic layers were dried over magnesium sulfate, filtered, and concentrated in vacuo; the residue was slurried in a mixture of heptane (400 mL) and ethyl acetate (50 mL) at 50° C. for 1 hour, followed by 30° C. overnight. After cooling to room temperature, the slurry was filtered, and the filter cake was washed with heptane to afford C41 as a beige solid. Yield: 7.93 g, 28.0 mmol, 83%. LCMS m/z 284.1 [M+H]$^+$. $^1$H NMR (400 MHz, chloroform-d) 6 $^1$H NMR (400 MHz, $CDCl_3$) δ 7.84 (br s, 1H), 7.66 (dd, J=7.7, 2.5 Hz, 1H), 7.59-7.51 (m, 2H), 7.51-7.38 (m, 4H), 7.19-7.09 (m, 2H), 6.71 (br d, J=7.7 Hz, 1H).

Step 4. Synthesis of 3-(2,3-difluorophenyl)-1-phenylpiperidin-4-one (C42)

A solution of lithium tri-sec-butylborohydride in tetrahydrofuran (L-Selectride™; 1.0 M; 84 mL, 84 mmol) was added drop-wise over 45 minutes to a −76° C. solution of C41 (9.52 g, 33.6 mmol) in tetrahydrofuran (300 mL). After the reaction mixture had been stirred at −78° C. for 20 minutes, the reaction flask was partially removed from the cooling bath and allowed to warm slowly to room temperature. Stirring was continued for 20 minutes at room temperature, whereupon the reaction mixture was cooled in an ice bath and quenched by slow drop-wise addition of saturated aqueous ammonium chloride solution. When the vigorous bubbling had ceased, additional saturated aqueous ammonium chloride solution (40 mL) was added. The aqueous layer was extracted with tetrahydrofuran (200 mL), and the combined organic layers were cooled to 0° C. and diluted with aqueous sodium hydroxide solution (5 M; 10 mL, 50 mmol). To this stirring mixture was added drop-wise over 35 minutes, very slowly and carefully {Caution: very exothermic), 30% hydrogen peroxide (approximately 33 mL), until vigorous reaction ceased. After the resulting mixture had been stirred at 10° C. for 1 hour, solid sodium bisulfite was cautiously added until no further reaction was observed. Stirring was continued at room temperature for 45 minutes, whereupon the mixture was diluted with water (20 mL) and saturated aqueous sodium chloride solution (30 mL). The aqueous layer was extracted with diethyl ether (2×200 mL), and the combined organic layers were dried over sodium sulfate, filtered, and concentrated in vacuo. The resulting material was combined with the product from a similar reaction carried out using C41 (2.00 g, 7.06 mmol) and purified using silica gel chromatography (Gradient: 0% to 25% ethyl acetate in heptane) to provide C42 as a straw-yellow oil. Yield: 7.28 g, 25.3 mmol, 62%. $^1$H NMR (400 MHz, chloroform-d) δ 7.33 (dd, J=8.6, 7.4 Hz, 2H), 7.18-7.05 (m, 2H), 7.03 (br d, J=8 Hz, 2H), 7.00-6.95 (m, 1H), 6.92 (br t, J=7.3 Hz, 1H), 4.20-4.04 (m, 3H), 3.58-3.38 (m, 2H), 2.79 (ddd, component of ABXY system, J=14.6, 11.9, 6.1 Hz, 1H), 2.62 (ddd, component of ABXY system, J=14.8, 3.0, 3.0 Hz, 1H).

Step 5. Synthesis of 3-(2,3-difluorophenyl)-3-methyl-1-phenylpiperidin-4-one (C43)

Sodium hydride (60% dispersion in mineral oil; 2.01 g, 50.2 mmol) was added in 4 portions to a 0° C. solution of C42 (95%, 14.2 g, 47.0 mmol) in tetrahydrofuran (250 mL), whereupon the ice bath was removed. After the reaction mixture had been stirred for 45 minutes, iodomethane (3.1 mL, 50 mmol) was added drop-wise over 30 minutes. The reaction mixture was allowed to stir at room temperature for 4 hours, then cooled to 0° C. and carefully treated with water (5 mL), followed by saturated aqueous sodium chloride solution (95 mL) and diethyl ether (100 mL). The aqueous layer was extracted with diethyl ether (2×200 mL), and the combined organic layers were dried over sodium sulfate, filtered, and concentrated in vacuo. Chromatography on silica gel (Gradient: 0% to 25% ethyl acetate in heptane) afforded C43 as a straw-yellow oil. Yield: 9.85 g, 32.7 mmol, 70%. LCMS m/z 302.2 [M+H]$^+$. $^1$H NMR (400 MHz, chloroform-d) δ 7.29 (dd, J=8.8, 7.3 Hz, 2H), 7.17-7.05 (m, 3H), 6.96 (br d, J=8.8 Hz, 2H), 6.90 (br t, J=7.2, 1H), 3.93 (d, J=12.8 Hz, 1H), 3.69-3.54 (m, 2H), 3.37 (d, J=12.9, 1H), 2.89-2.73 (m, 2H), 1.58 (s, 3H).

Step 6. Isolation of 3-(2,3-difluorophenyl)-3-methyl-1-phenylpiperidin-4-one, ENANT-1 (P15) and 3-(2,3-difluorophenyl)-3-methyl-1-phenylpiperidin-4-one, ENANT-2 (P16)

Separation of C43 (15.8 g, 52.4 mmol) into its component enantiomers was carried out using supercritical fluid chromatography {Column: Phenomenex Lux Cellulose-2, 21.2×250 mm, 5 μm; Mobile phase: 92.5: 7.5 carbon dioxide/[ethanol containing 0.2% (7 M ammonia in methanol)]; Back pressure: 100 bar; Flow rate: 80 mL/minute}. The first-eluting enantiomer, which exhibited a positive (+) rotation, was designated as P15 and the second-eluting enantiomer, which exhibited a negative (−) rotation, as P16.

P15 (ENANT-1)—Yield: 5.79 g, 19.2 mmol, 37%. Retention time: 3.79 minutes [Analytical conditions. Column: Phenomenex Lux Cellulose-2, 4.6×250 mm, 5 μm; Mobile phase A: carbon dioxide; Mobile phase B: ethanol containing 0.2% (7 M ammonia in methanol); Gradient: 5% B for 1.00 minute, then 5% to 60% B over 8.0 minutes; Back pressure: 120 bar; Flow rate: 3.0 mL/minute].

P16 (ENANT-2)—Yield: 6.09 g, 20.2 mmol, 38%. Retention time: 4.20 minutes (Analytical conditions identical to those used for P15).

Preparations P17 and P18 tert-Butyl 3-{[4-(3-chloro-2-fluorophenyl)-5-fluoro-4-methyl-1-oxo-1,2,3,4-tetrahydroisoquinolin-6-yl]amino}azetidine-1-carboxylate, ENANT-1 (P17) and tert-Butyl 3-{[4-(3-chloro-2-fluorophenyl)-5-fluoro-4-methyl-1-oxo-1,2,3,4-tetrahydroisoquinolin-6-yl]amino}azetidine-1-carboxylate, ENANT-2 (P18)

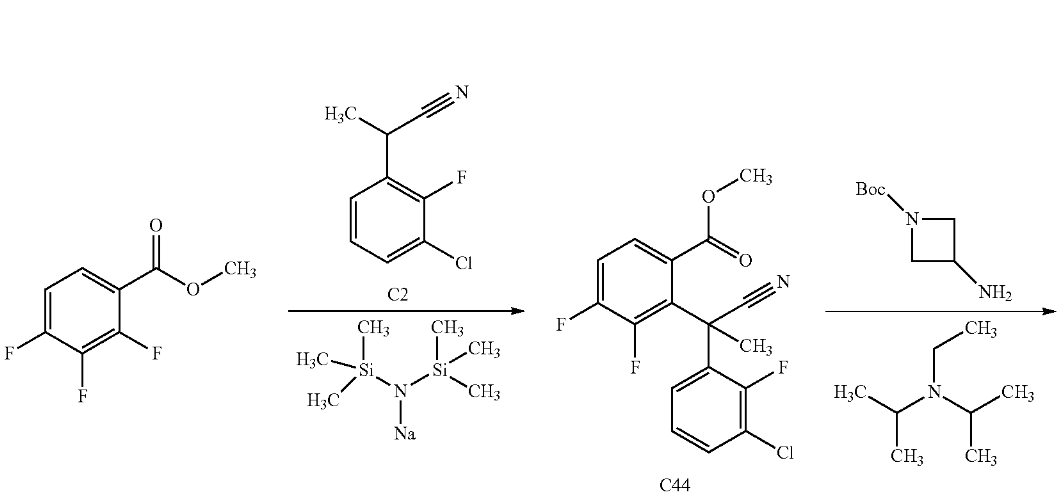

-continued

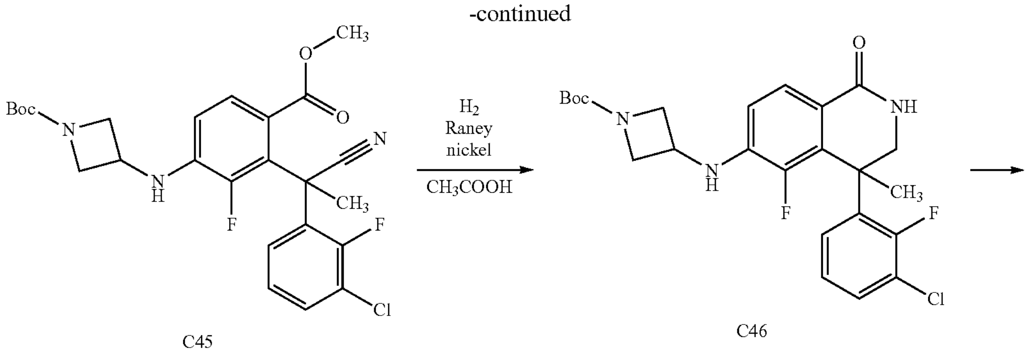

C45 C46

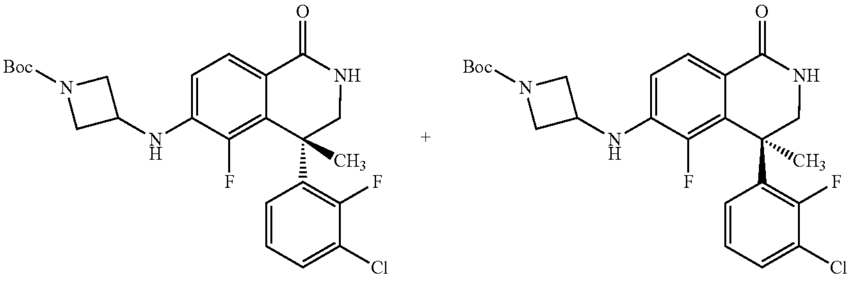

P17 (ENANT-1) and P18 (ENANT-2)

Step 1. Synthesis of methyl 2-[1-(3-chloro-2-fluorophenyl)-1-cyanoethyl]-3,4-difluorobenzoate (C44)

A solution of sodium bis(trimethylsilyl)amide in tetrahydrofuran (1 M; 197 mL, 197 mmol) was added to a 0° C. solution of methyl 2,3,4-trifluorobenzoate (34.0 g, 179 mmol) and C2 (34.5 g, 188 mmol) in toluene (600 mL). After 1 hour, hydrochloric acid (0.5 M; 100 mL) was added; the resulting mixture was stirred for 15 minutes, diluted with water (200 mL), and extracted with ethyl acetate (2×200 mL). The combined organic layers were washed with saturated aqueous sodium chloride solution (3×300 mL), dried over sodium sulfate, filtered, concentrated in vacuo, and subjected to silica gel chromatography (Gradient: 0% to 40% ethyl acetate in petroleum ether), providing C44 as a yellow gum. Yield: 7.95 g, 22.5 mmol, 13% yield. LCMS m/z 354.1 (chlorine isotope pattern observed) $[M+H]^+$. $^1H$ NMR (400 MHz, chloroform-d) δ 7.49-7.39 (m, 2H), 7.32 (ddd, component of ABXY system, J=8.7, 5.2, 1.9 Hz, 1H), 7.26-7.19 (m, 1H), 7.19 (td, J=8.1, 1.4 Hz, 1H), 3.69 (s, 3H), 2.34 (d, J=2.1 Hz, 3H).

Step 2. Synthesis of tert-butyl 3-{3-[1-(3-chloro-2-fluorophenyl)-1-cyanoethyl]-2-fluoro-4-(methoxycarbonyl)anilino}azetidine-1-carboxylate (C45)

To a solution of C44 (7.95 g, 22.5 mmol) in dimethyl sulfoxide (100 mL) were added N,N-diisopropylethylamine (11.6 g, 89.7 mmol) and tert-butyl 3-aminoazetidine-1-carboxylate (5.81 g, 33.7 mmol). The reaction mixture was heated to 90° C.; after 48 hours, LCMS analysis indicated conversion to C45: LCMS m/z 506.2 (chlorine isotope pattern observed) $[M+H]^+$. The reaction mixture was then cooled to 25° C., diluted with water (50 mL), and extracted with ethyl acetate (2×50 mL). The combined organic layers were washed with saturated aqueous sodium chloride solution (3×50 mL), dried over sodium sulfate, filtered, and concentrated in vacuo. Silica gel chromatography (Gradient: 0% to 60% ethyl acetate in petroleum ether) afforded C45 as a yellow solid. Yield: 4.87 g, 9.63 mmol, 43%. $^1H$ NMR (400 MHz, chloroform-d) δ 7.44-7.33 (m, 2H), 7.29-7.25 (m, 1H), 7.14 (td, J=8.0, 1.3 Hz, 1H), 6.40 (t, J=8.1 Hz, 1H), 4.35-4.27 (m, 2H), 4.25-4.17 (m, 1H), 3.82-3.75 (m, 2H), 3.58 (s, 3H), 2.32 (d, J=2.2 Hz, 3H), 1.44 (s, 9H).

Step 3. Synthesis of tert-butyl 3-{[4-(3-chloro-2-fluorophenyl)-5-fluoro-4-methyl-1-oxo-1,2,3,4-tetrahydroisoquinolin-6-yl]amino}azetidine-1-carboxylate (C46)

To a solution of C45 (4.87 g, 9.63 mmol) and acetic acid (2.89 g, 48.1 mmol) in methanol (100 mL) was added Raney nickel (5.0 g, 85 mmol), whereupon the reaction mixture was heated to 30° C. under hydrogen (15 psi). After 6 hours, it was allowed to cool to 25° C., filtered, and concentrated in vacuo. The residue was layered with ethanol (20 mL) and heated to 90° C. for 2 hours; the resultant solid was collected via filtration, combined with the product from a similar reaction carried out using C45 (1.50 g, 2.96 mmol), and subjected to reversed-phase HPLC (Column: Welch Ultisil Diol, 25×150 mm, 5 μm; Mobile phase A: heptane; Mobile phase B: ethanol; Gradient 0% to 50% B; Flow rate: 25 mL/minute) to afford C46 as a white solid. Yield: 4.02 g, 8.41 mmol, 68%. LCMS m/z 500.3 (chlorine isotope pattern observed) $[M+Na^+]$. $^1H$ NMR (400 MHz, chloroform-d) δ 7.89 (d, J=8.4 Hz, 1H), 7.38-7.29 (m, 1H), 7.07-6.94 (m, 2H), 6.45 (t, J=8.2 Hz, 1H), 6.08 (br s, 1H), 4.61-4.52 (m, 1H), 4.38-4.19 (m, 3H), 3.97 (br d, J=12.6 Hz, 1H), 3.84-3.70 (m, 2H), 3.30 (dd, J=12.6, 3.4 Hz, 1H), 1.88 (s, 3H), 1.43 (s, 9H).

Step 4. Isolation of tert-butyl 3-{[4-(3-chloro-2-fluorophenyl)-5-fluoro-4-methyl-1-oxo-1,2,3,4-tetrahydroisoquinolin-6-yl]amino}azetidine-1-carboxylate, ENANT-1 (P17) and tert-butyl 3-{[4-(3-chloro-2-fluorophenyl)-5-fluoro-4-methyl-1-oxo-1,2,3,4-tetrahydroisoquinolin-6-yl]amino}azetidine-1-carboxylate, ENANT-2 (P18)

Separation of C46 (4.02 g, 8.41 mmol) into its component enantiomers was carried out using supercritical fluid chromatography {Column: Chiral Technologies Chiralpak IG, 30×250 mm, 5 μm; Mobile phase: 65:35 carbon dioxide/[methanol containing 0.2% (7 M ammonia in methanol)]; Back pressure: 100 bar; Flow rate: 80 mL/minute}. The first-eluting enantiomer, which exhibited a negative (−) rotation, was designated as P17, and the second-eluting enantiomer, which exhibited a positive (+) rotation, as P18; both were obtained as solids.

P17 (ENANT-1)—Yield: 1.78 g, 3.72 mmol, 44%. Retention time: 2.20 minutes [Analytical conditions. Column: Chiral Technologies Chiralpak IG, 4.6×100 mm, 3 μm; Mobile phase A: carbon dioxide; Mobile phase B: methanol containing 0.2% (7 M ammonia in methanol); Gradient: 5% B for 0.25 minutes, then 5% to 70% B over 2.25 minutes, then 70% B; Back pressure: 100 bar; Flow rate: 2.5 mL/minute].

P18 (ENANT-2)—Yield: 1.78 g, 3.72 mmol, 44%. Retention time: 2.56 minutes (Analytical conditions identical to those used for P17).

Preparation P19

8-(3-Chloro-2-fluorophenyl)-4-(dimethylamino)-6-(3-fluoropyridin-2-yl)-2-(methanesulfinyl)-8-methyl-7,8-dihydropyrido[4,3-d]pyrimidin-5(6H)-one, from C52 (ENANT-1) (P19)

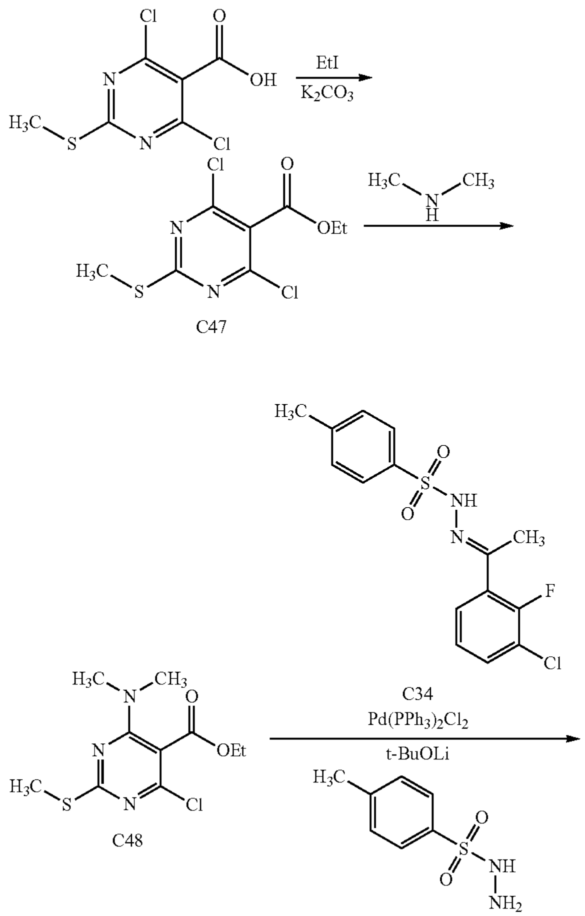

C47

C34

C48

-continued

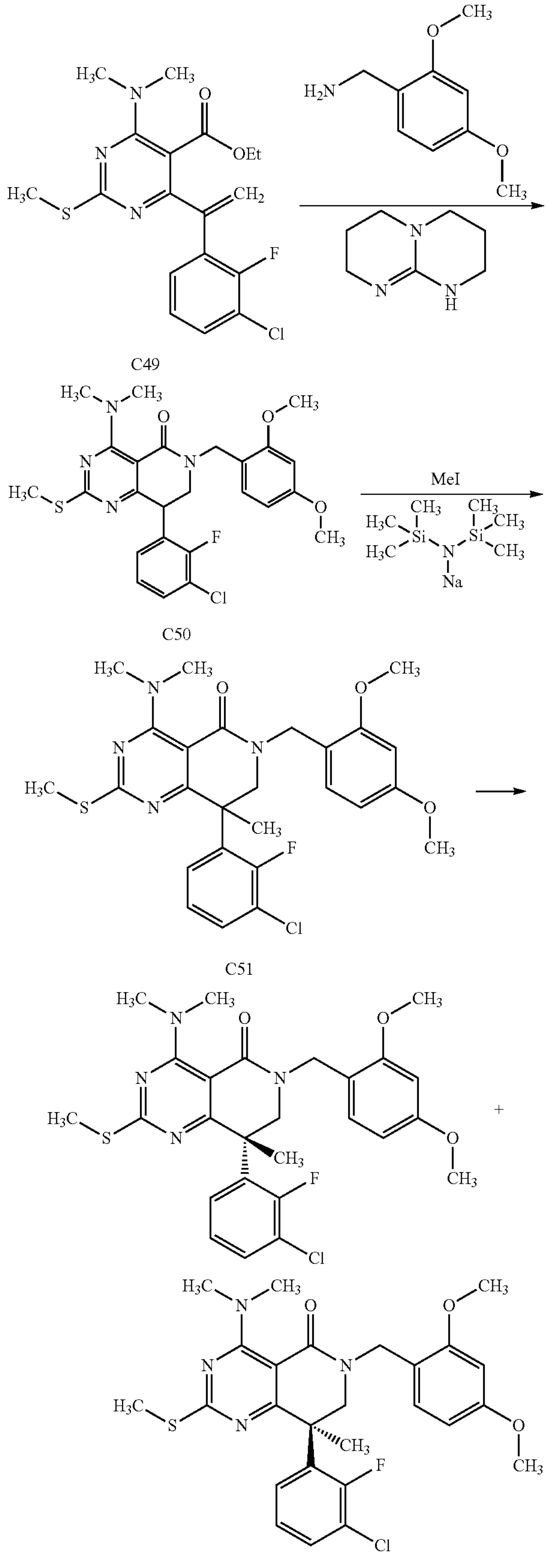

C49

C50

C51

+

C52 (ENANT-1) and C53 (ENANT-2)

-continued

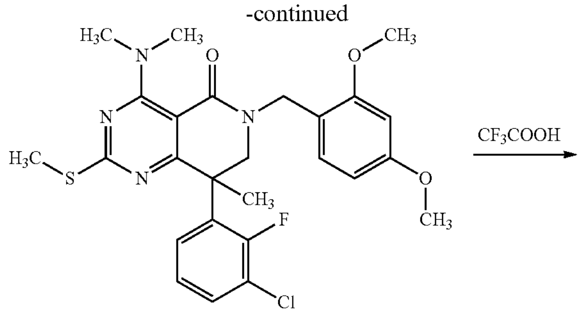

C52 (ENANT-1)

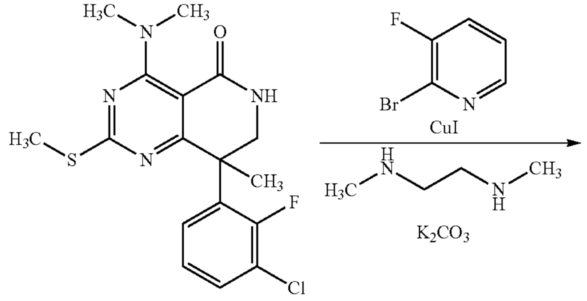

C54 [from C52 (ENANT-1)]

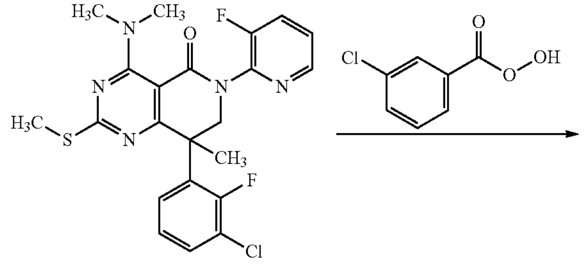

C55 [from C52 (ENANT-1)]

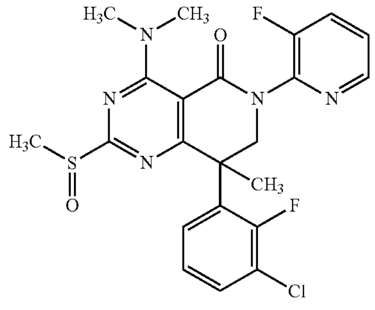

P19 [from C52 (ENANT-1)]

Step 1. Synthesis of ethyl 4,6-dichloro-2-(methylsulfanyl)pyrimidine-5-carboxylate (C47)

Potassium carbonate (4.16 g, 30.1 mmol) was added in one portion to a 0° C. solution of 4,6-dichloro-2-(methylsulfanyl)pyrimidine-5-carboxylic acid (6.00 g, 25.1 mmol) in N,N-dimethylformamide (150 mL). After the reaction mixture had been stirred for 30 minutes, iodoethane (5.09 g, 32.6 mmol) was added drop-wise and stirring was continued at 0° C. for 30 minutes. The reaction mixture was then stirred at 15° C. for 16 hours, whereupon it was quenched by careful addition of hydrochloric acid (0.5 M; 100 mL) and extracted with ethyl acetate (2×150 mL). The combined organic layers were washed with saturated aqueous sodium chloride solution (3×150 mL), dried over magnesium sulfate, filtered, and concentrated in vacuo; silica gel chromatography (Gradient: 0% to 10% ethyl acetate in petroleum ether) afforded C47 as a yellow solid. Yield: 6.15 g, 23.0 mmol, 92%. LCMS m/z 267.1 (chlorine isotope pattern observed) $[M+H]^+$. $^1$H NMR (400 MHz, chloroform-d) δ 4.45 (q, J=7.1 Hz, 2H), 2.58 (s, 3H), 1.41 (t, J=7.1 Hz, 3H).

Step 2. Synthesis of ethyl 4-chloro-6-(dimethylamino)-2-(methylsulfanyl)pyrimidine-5-carboxylate (C48)

A solution of dimethylamine in tetrahydrofuran (2 M; 56.2 mL, 112 mmol) was added drop-wise to a 0° C. solution of C47 (6.00 g, 22.5 mmol) in tetrahydrofuran (150 mL). After the reaction mixture had been stirred at 15° C. for 6 hours, it was concentrated under reduced pressure; the residue was dissolved in ethyl acetate (50 mL), washed with saturated aqueous sodium chloride solution (50 mL), dried over sodium sulfate, filtered, and concentrated in vacuo to provide C48 as a yellow solid (6.50 g). Yield: assumed quantitative. $^1$H NMR (400 MHz, chloroform-d) δ 4.36 (q, J=7.2 Hz, 2H), 3.11 (s, 6H), 2.49 (s, 3H), 1.38 (t, J=7.2 Hz, 3H).

Step 3. Synthesis of ethyl 4-[1-(3-chloro-2-fluorophenyl)ethenyl]-6-(dimethylamino)-2-(methylsulfanyl)pyrimidine-5-carboxylate (C49).

A suspension of lithium tert-butoxide (4.79 g, 59.8 mmol) in methoxycyclopentane (50 mL) was added drop-wise to a 100° C. mixture of C34 (7.82 g, 22.9 mmol), C48 (5.50 g, 19.9 mmol), dichlorobis(triphenylphosphine)palladium(II) (1.40 g, 1.99 mmol), and 4-methylbenzene-1-sulfonohydrazide (743 mg, 3.99 mmol) in methoxycyclopentane (100 mL). After the reaction mixture had been stirred at 100° C. for 2 hours, it was diluted with methyl tert-butyl ether (100 mL) and filtered. The filtrate was concentrated in vacuo and purified using silica gel chromatography (Gradient: 0% to 20% ethyl acetate in petroleum ether) to afford C49 as a yellow solid. Yield: 7.00 g, 17.7 mmol, 89%. $^1$H NMR (400 MHz, chloroform-d) δ 7.30 (ddd, J=8.2, 6.7, 1.7 Hz, 1H), 7.17 (ddd, J=8.3, 6.8, 1.7 Hz, 1H), 7.00 (td, J=7.9, 1.1 Hz, 1H), 5.85 (br s, 1H), 5.68 (br s, 1H), 3.97 (q, J=7.2 Hz, 2H), 3.09 (s, 6H), 2.49 (s, 3H), 1.14 (t, J=7.2 Hz, 3H).

Step 4. Synthesis of 8-(3-chloro-2-fluorophenyl)-6-[(2,4-dimethoxyphenyl)methyl]-4-(dimethylamino)-2-(methylsulfanyl)-7,8-dihydropyrido[4,3-d]pyrimidin-5(6H)-one (C50)

A solution of 1-(2,4-dimethoxyphenyl)methanamine (2.96 g, 17.7 mmol) in tetrahydrofuran (100 mL) was added drop-wise over 15 minutes to a 0° C. to 5° C. solution of C49 (7.00 g, 17.7 mmol) and 1,3,4,6,7,8-hexahydro-2H-pyrimido[1,2-a]pyrimidine (246 mg, 1.77 mmol) in tetrahydrofuran (50 mL). The reaction mixture was stirred below 10° C. for 2 hours, whereupon it was warmed to 25° C. and stirred at 25° C. for 2 days. LCMS analysis at this point indicated conversion to C50, but C49 was still present: LCMS m/z 517.3 and 396.2 (chlorine isotope patterns observed for both) $[M+H]^+$. The reaction temperature was increased to 60° C.; after an additional 2 days, the reaction mixture was concentrated in vacuo and subjected to chromatography on silica gel (Gradient: 0% to 40% ethyl acetate in petroleum ether), providing C50 as a yellow solid. Yield: 5.50 g, 10.6 mmol, 60%. $^1$H NMR (400 MHz, chloroform-d) δ 7.13-7.07 (m, 1H), 7.03 (d, J=8.0 Hz, 1H), 6.66 (t, J=7.9

Hz, 1H), 6.34-6.28 (m, 1H), 6.22-6.16 (m, 2H), 4.69 (d, J=14.1 Hz, 1H), 4.28-4.19 (m, 2H), 3.93 (dd, component of ABX system, J=13.3, 4.2 Hz, 1H), 3.76-3.71 (m, 1H), 3.76 (s, 3H), 3.71 (s, 3H), 3.18 (s, 6H), 2.44 (s, 3H).

Step 5. Synthesis of 8-(3-chloro-2-fluorophenyl)-6-[(2,4-dimethoxyphenyl)methyl]-4-(dimethylamino)-8-methyl-2-(methylsulfanyl)-7,8-dihydropyrido[4,3-d]pyrimidin-5(6H)-one (C51)

A solution of sodium bis(trimethylsilyl)amide in tetrahydrofuran (1 M; 10.6 mL 10.6 mmol) was added drop-wise to a 0° C. solution of C50 (5.00 g, 9.67 mmol) in tetrahydrofuran (100 mL), whereupon the reaction mixture was stirred at 0° C. for 30 minutes. Iodomethane (2.06 g, 14.5 mmol) was added drop-wise, and the reaction mixture was warmed to room temperature (15° C.) and stirred for 1 hour. After drop-wise addition of saturated aqueous ammonium chloride solution (100 mL), the mixture was extracted with ethyl acetate (3×50 mL), dried over sodium sulfate, filtered, and concentrated in vacuo. Silica gel chromatography (Gradient: 0% to 35% ethyl acetate in petroleum ether) afforded C51 as a white solid. Yield: 2.60 g, 4.90 mmol, 51%. LCMS m/z 531.2 (chlorine isotope pattern observed) $[M+H]^+$. $^1H$ NMR (400 MHz, chloroform-d) δ 7.13 (ddd, J=8.3, 6.8, 1.6 Hz, 1H), 6.93 (d, J=8.4 Hz, 1H), 6.78 (td, J=8.0, 1.1 Hz, 1H), 6.49 (td, J=7.6, 1.6 Hz, 1H), 6.35 (d, J=2.4 Hz, 1H), 6.20 (dd, J=8.3, 2.4 Hz, 1H), 4.48 (AB quartet, $J_{AB}$=14.2 Hz, $\Delta\nu_{AB}$=88.3 Hz, 2H), 3.96 (d, J=13.4 Hz, 1H), 3.78 (s, 3H), 3.76 (s, 3H), 3.45 (d, J=13.3 Hz, 1H), 3.16 (s, 6H), 2.45 (s, 3H), 1.60 (br d, J=1.5 Hz, 3H).

Step 6. Isolation of 8-(3-chloro-2-fluorophenyl)-6-[(2,4-dimethoxyphenyl)methyl]-4-(dimethylamino)-8-methyl-2-(methylsulfanyl)-7,8-dihydropyrido[4,3-d]pyrimidin-5(6H)-one, ENANT-1 (C52) and 8-(3-chloro-2-fluorophenyl)-6-[(2,4-dimethoxyphenyl)methyl]-4-(dimethylamino)-8-methyl-2-(methylsulfanyl)-7,8-dihydropyrido[4,3-d]pyrimidin-5(6H)-one, ENANT-2 (C53)

Separation of C51 (2.00 g, 3.77 mmol) into its component enantiomers was carried out via supercritical fluid chromatography {Column: Chiral Technologies Chiralpak AD-H, 30×250 mm, 5 μm; Mobile phase: 7:3 carbon dioxide/[methanol containing 0.2% (7 M ammonia in methanol)]; Back pressure: 200 bar; Flow rate: 80 mL/minute}. The first-eluting enantiomer, which exhibited a positive (+) rotation, was designated as C52 and the second-eluting enantiomer, which exhibited a negative (−) rotation, as C53. Both were isolated as white solids.

C52 (ENANT-1)—Yield: 924 mg, 1.74 mmol, 46%. Retention time: 5.92 minutes [Analytical conditions. Column: Chiral Technologies Chiralpak AD-H, 4.6×250 mm, 5 μm; Mobile phase A: carbon dioxide; Mobile phase B: methanol containing 0.2% (7 M ammonia in methanol); Gradient: 5% B for 1.00 minute, then 5% to 60% B over 8.00 minutes, then 60% B; Back pressure: 120 bar; Flow rate: 3.0 mL/minute].

C53 (ENANT-2)—Yield: 1.05 g, 1.98 mmol, 52%. Retention time: 7.91 minutes (Analytical conditions identical to those used for C52).

Step 7. Synthesis of 8-(3-chloro-2-fluorophenyl)-4-(dimethylamino)-8-methyl-2-(methylsulfanyl)-7,8-dihydropyrido[4,3-d]pyrimidin-5(6H)-one, from C52 (ENANT-1) (C54)

A solution of C52 (ENANT-1) (1.49 g, 2.81 mmol) in trifluoroacetic acid (40 mL) was stirred at 70° C. for 16 hours, whereupon LCMS analysis indicated conversion to C54: LCMS m/z 381.1 (chlorine isotope pattern observed) $[M+H]^+$. The reaction mixture was concentrated in vacuo, diluted with water (60 mL), and adjusted to a pH of approximately 9 by addition of saturated aqueous potassium carbonate solution. After extraction with ethyl acetate (3×50 mL), the combined organic layers were concentrated under reduced pressure to provide C54 [from C52 (ENANT-1)] as a yellow oil. The crude product was used directly in the following step.

Step 8. Synthesis of 8-(3-chloro-2-fluorophenyl)-4-(dimethylamino)-6-(3-fluoropyridin-2-yl)-8-methyl-2-(methylsulfanyl)-7,8-dihydropyrido[4,3-d]pyrimidin-5(6H)-one, from C52 (ENANT-1) (C55)

To a solution of C54 [from C52 (ENANT-1)] [from the previous step, and from a similar reaction carried out using 0.734 mmol of C52 (ENANT-1); 53.54 mmol] in 1,4-dioxane (100 mL) were added 2-bromo-3-fluoropyridine (936 mg, 5.32 mmol), $N^1$,$N^2$-dimethylethane-1,2-diamine (625 mg, 7.09 mmol), potassium carbonate (1.47 g, 10.6 mmol), and copper(I) iodide (676 mg, 3.55 mmol). After the reaction mixture had been stirred at 100° C. for 16 hours, it was cooled to 20° C. and diluted with water (50 mL). The resulting mixture was extracted with ethyl acetate (3×30 mL), and the combined organic layers were washed with saturated aqueous sodium chloride solution (2×30 mL), dried over sodium sulfate, filtered, and concentrated in vacuo. Silica gel chromatography (Gradient: 20 to 80% ethyl acetate in petroleum ether) afforded C55 [from C52 (ENANT-1)] as a pale-brown gum. Yield: 1.67 g, 3.51 mmol, 99% over 2 steps. LCMS m/z 476.2 (chlorine isotope pattern observed) $[M+H]^+$. $^1H$ NMR (400 MHz, chloroform-d) δ 8.23 (d, J=4.7 Hz, 1H), 7.38 (ddd, J=9.6, 8.1, 1.5 Hz, 1H), 7.32-7.25 (m, 1H, assumed; partially obscured by solvent peak), 7.21-7.15 (m, 1H), 7.02-6.93 (m, 2H), 4.58 (d, J=13.0 Hz, 1H), 3.91 (d, J=13.1 Hz, 1H), 3.16 (br s, 6H), 2.46 (s, 3H), 1.82 (s, 3H).

Step 9. Synthesis of 8-(3-chloro-2-fluorophenyl)-4-(dimethylamino)-6-(3-fluoropyridin-2-yl)-2-(methanesulfinyl)-8-methyl-7,8-dihydropyrido[4,3-d]pyrimidin-5(6H)-one, from C52 (ENANT-1) (P19)

To a 0° C. solution of C55 (600 mg, 1.26 mmol) in dichloromethane (10 mL) was added 3-chloroperoxybenzoic acid (85%, 384 mg, 1.89 mmol). After the reaction mixture had been stirred at 20° C. for 1 hour, LCMS analysis indicated conversion to P19 and its sulfone analogue: LCMS m/z 492.0 and 508.0 (chlorine isotope patterns observed for both) $[M+H]^+$. Saturated aqueous sodium thiosulfate solution (30 mL) was added and stirring was continued at 20° C. for 30 minutes, whereupon the mixture was extracted with ethyl acetate (3×30 mL). The combined organic layers were washed sequentially with saturated aqueous sodium bicarbonate solution (2×30 mL) and saturated aqueous sodium chloride solution (30 mL), dried over sodium sulfate, filtered, and concentrated in vacuo to provide P19 [from C52 (ENANT-1)] as a yellow solid. This material was used in further chemistry without additional purification. Yield: 600 mg, 1.22 mmol, 97%.

Example 1
(4R)-4-(3-Chloro-2-fluorophenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one (1)
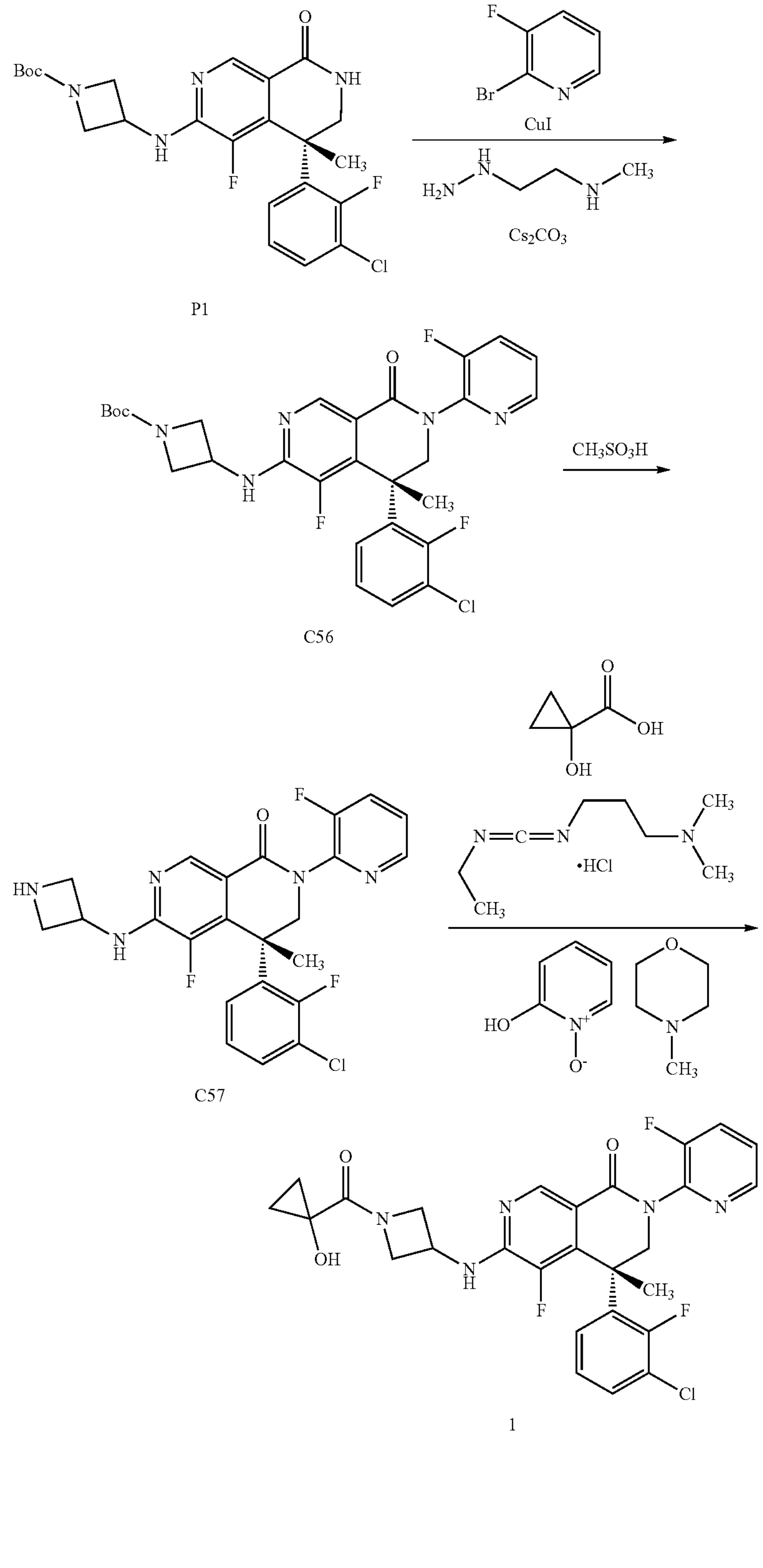
P1
C56
C57
1

Step 1. Synthesis of tert-butyl 3-{[(5R)-5-(3-chloro-2-fluorophenyl)-4-fluoro-7-(3-fluoropyridin-2-yl)-5-methyl-8-oxo-5,6,7,8-tetrahydro-2,7-naphthyridin-3-yl]amino}azetidine-1-carboxylate (C56)

A mixture of P1 (2.06 g, 4.30 mmol), cesium carbonate (4.20 g, 12.9 mmol), and copper(I) iodide (819 mg, 4.30 mmol) in 1,4-dioxane (43 mL) was treated with 2-bromo-3-fluoropyridine (0.481 mL, 4.73 mmol) and $N^1$,$N^2$-dimethylethane-1,2-diamine (0.926 mL, 8.70 mmol). After the reaction mixture had been heated at 95° C. for 18 hours, it was allowed to cool to 25° C. and diluted with water (100 mL). The aqueous layer was extracted with ethyl acetate (3×150 mL), and the combined organic layers were washed with saturated aqueous sodium chloride solution (50 mL), dried over magnesium sulfate, filtered, and concentrated in vacuo. Silica gel chromatography (Gradient: 25% to 100% ethyl acetate in heptane) afforded C56 as a pale-yellow solid. Yield: 1.57 g, 2.74 mmol, 64%. LCMS m/z 574.2 (chlorine isotope pattern observed) $[M+H]^+$. $^1$H NMR (400 MHz, chloroform-d) δ 8.82 (s, 1H), 8.25 (d, J=4.6 Hz, 1H), 7.47 (br t, J=8.9 Hz, 1H), 7.39 (t, J=7.4 Hz, 1H), 7.26-7.19 (m, 2H, assumed; partially obscured by solvent peak), 7.10 (t, J=8.0 Hz, 1H), 5.24-5.16 (m, 1H), 4.87-4.79 (m, 1H), 4.56 (d, J=12.9 Hz, 1H), 4.40-4.31 (m, 2H), 3.85-3.76 (m, 2H), 3.74 (d, J=12.8 Hz, 1H), 1.94 (s, 3H), 1.45 (s, 9H).

Step 2. Synthesis of (4R)-6-[(azetidin-3-γ1)amino]-4-(3-chloro-2-fluorophenyl)-5-fluoro-2-(3-fluoropyridin-2-yl)-4-methyl-3,4-dihydro-2,7-naphthyridin-1(2H)-one (C57)

Methanesulfonic acid (1.77 mL, 27.3 mmol) was added over 1 minute to a solution of C56 (1.57 g, 2.74 mmol) in 1,1,1,3,3,3-hexafluoropropan-2-ol (27 mL). After 20 minutes at room temperature, the pH was adjusted to >7 by addition of saturated aqueous sodium bicarbonate solution (50 mL), whereupon the mixture was concentrated under reduced pressure to remove most of the 1,1,1,3,3,3-hexafluoropropan-2-ol. The aqueous layer was extracted with ethyl acetate (3×75 mL); the combined organic layers were washed with saturated aqueous sodium chloride solution (50 mL), dried over magnesium sulfate, filtered, and concentrated in vacuo to provide C57 as a pale-yellow foam (2 g), which was used directly in the following step. LCMS m/z 474.2 (chlorine isotope pattern observed) $[M+H]^+$. $^1$H NMR (400 MHz, methanol-$d_4$) δ 8.64 (s, 1H), 8.27 (d, J=4.6 Hz, 1H), 7.65 (br t, J=9.0 Hz, 1H), 7.45 (t, J=7.4 Hz, 1H), 7.42-7.33 (m, 2H), 7.19 (t, J=8.0 Hz, 1H), 5.04-4.93 (m, 1H), 4.47 (d, J=12.9 Hz, 1H), 4.00-3.87 (m, 2H), 3.84-3.70 (m, 2H), 3.76 (d, J=13.0 Hz, 1H), 1.93 (s, 3H).

Step 3. Synthesis of (4R)-4-(3-chloro-2-fluorophenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one (1)

1-[3-(Dimethylamino)propyl]-3-ethylcarbodiimide hydrochloride (629 mg, 3.28 mmol), 2-hydroxypyridine 1-oxide (304 mg, 2.74 mmol), and 4-methylmorpholine (0.902 mL 8.20 mmol) were added to a 25° C. solution of C57 (from the previous step; 2 g, 52.74 mmol) and 1-hydroxycyclopropane-1-carboxylic acid (335 mg, 3.28 mmol) in N,N-dimethylacetamide (20 mL). After 16 hours, the reaction mixture was diluted with water (50 mL) and the aqueous layer was extracted with ethyl acetate (4×70 mL). The combined organic layers were dried over magnesium sulfate, filtered, and concentrated in vacuo; silica gel chromatography (Gradient: 5% to 10% methanol in ethyl acetate) afforded a foam, which was treated with ethyl acetate (20 mL), heated to 50° C., and slowly diluted with heptane (40 mL). After 40 hours at 50° C., the resultant solid was collected via filtration at 45° C. and rinsed with warm heptane (3×10 mL) to provide (4R)-4-(3-chloro-2-fluorophenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one (1) as a white solid. Yield: 934 mg, 1.67 mmol, 61% over 2 steps. LCMS m/z 558.2 (chlorine isotope pattern observed) $[M+H]^+$. $^1$H NMR (400 MHz, DMSO-$d_6$) δ 8.56 (s, 1H), 8.30 (br d, J=4.6 Hz, 1H), 8.02 (br d, J=4 Hz, <1H), 7.80 (ddd, J=9.9, 8.2, 1.4 Hz, 1H), 7.63-7.56 (m, 1H), 7.49-7.39 (m, 2H), 7.29 (t, J=8.0 Hz, 1H), 5.98 (s, 1H), 4.81-4.65 (m, 2H), 4.43-4.27 (m, 1H), 4.34 (d, J=13.0 Hz, 1H), 4.22-4.11 (m, 1H), 3.96-3.82 (m, 1H), 3.84 (d, J=12.9 Hz, 1H), 1.88 (br s, 3H), 1.07-0.96 (m, 2H), 0.82-0.73 (m, 2H).

A crystal of 1 suitable for X-ray structural determination was prepared as follows.

A sample of 1 (6 mg) was added to a 1 dram vial equipped with a septum. Tetrahydrofuran (0.75 mL) was added, and the resulting mixture was concentrated to an oil; this material was again treated with tetrahydrofuran (0.75 mL), followed by addition of heptane (0.2 mL). One-quarter of the septum was cut out, and the contents of the vial were allowed to slowly evaporate. After 12 days, a crystal appropriate for X-ray single-crystal structural analysis was obtained.

Single-Crystal X-Ray Structural Determination of Example 1

Single Crystal X-Ray Analysis

Data collection was performed on a Bruker D8 Quest diffractometer at 298 K. Data collection consisted of omega and phi scans.

The structure was solved by intrinsic phasing using SHELX software suite in the orthorhombic space group $P2_12_12_1$. The structure was subsequently refined by the full-matrix least squares method. All non-hydrogen atoms were found and refined using anisotropic displacement parameters.

The hydrogen atoms located on nitrogen and oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

The asymmetric unit is comprised of one molecule of 1 and one molecule of tetrahydrofuran. The structure contains no residual void space.

The absolute stereochemistry was confirmed as (R).

The final R-index was 4.85%. A final difference Fourier revealed no missing or misplaced electron density.

Pertinent crystal, data collection, and refinement information is summarized in Table A. Atomic coordinates, bond lengths, bond angles, and displacement parameters are listed in Tables B-E. FIG. 1 provides an illustration of the crystal structure of the compound of Example 1.

Software and References

SHELXTL, Version 5.1, Bruker AXS, 1997.
PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE A

Crystal data and structure refinement for 1.

| | |
|---|---|
| Empirical formula | $C_{27}H_{23}ClF_3N_5O_3$—$C_4H_8O$ |
| Formula weight | 630.06 |
| Temperature | 298.00K |
| Wavelength | 1.54178 Å |
| Crystal system | Orthorhombic |
| Space group | $P2_12_12_1$ |
| Unit cell dimensions | a = 7.1412(2) Å α = 90° |
| | b = 13.2677(3) Å β = 90° |
| | c = 32.2069(7) Å γ = 90° |
| Volume | 3051.52(13) $Å^3$ |
| Z | 4 |
| $\rho_{calc}$ | 1.371 $g/cm^3$ |
| μ | 1.655 $mm^{-1}$ |
| F(000) | 1312.0 |
| Crystal size | 0.204 × 0.135 × 0.042 $mm^3$ |
| Radiation | CuKα |
| 2Θ range for data collection | 5.488 to 160.53° |
| Index ranges | −8 ≤ h ≤ 9, −16 ≤ k ≤ 16, −41≤ l ≤41 |
| Reflections collected | 100759 |
| Independent reflections | 6599 [$R_{int}$ = 0.0467, $R_{sigma}$ = 0.0157] |
| Data/restraints/parameters | 6599/2/406 |
| Goodness-of-fit on $F^2$ | 1.025 |
| Final R indices [I ≥ 2σ(I)] | $R_1$ = 0.0486, $wR_2$ = 0.1310 |
| R indices (all data) | $R_1$ = 0.0597, $wR_2$ = 0.1434 |
| Largest diff. peak and hole | 0.18 and −0.38 e $Å^{-3}$ |
| Flack parameter | 0.002(6) |

TABLE B

Fractional Atomic coordinates (×$10^4$) and equivalent isotropic displacement parameters ($Å^2$ × $10^3$) for 1. U(eq) is defined as one-third of the trace of the orthogonalized $U^{ij}$ tensor.

| | x | y | z | U(eq) |
|---|---|---|---|---|
| Cl1 | 7162(3) | 8627.1(8) | 5562.5(6) | 139.4(6) |
| F1 | 10245(4) | 2541(2) | 6933.9(9) | 104.5(8) |
| F2 | 8837(3) | 5166.3(16) | 5141.2(5) | 69.9(5) |
| F3 | 6995(3) | 6601.2(15) | 5871.5(8) | 80.1(6) |
| O1 | 6656(4) | 3097(2) | 6709.1(7) | 73.7(7) |
| O2 | −827(4) | 4339(3) | 4302.8(8) | 82.1(7) |
| O3 | 2167(4) | 3960(2) | 3423.7(7) | 70.4(6) |
| N1 | 9280(5) | 4988(3) | 7358.5(9) | 79.6(9) |
| N2 | 8734(4) | 4384(2) | 6686.7(8) | 63.8(6) |
| N3 | 5202(4) | 3464.8(18) | 5472.0(7) | 54.7(6) |
| N4 | 5995(4) | 4072(2) | 4816.6(8) | 60.6(6) |
| N5 | 2177(4) | 3866.0(19) | 4285.6(7) | 55.9(6) |
| C1 | 10069(6) | 3291(4) | 7214.7(13) | 84.6(11) |
| C2 | 10682(8) | 3133(5) | 7615.3(15) | 108.4(16) |
| C3 | 10595(8) | 3943(6) | 7885.8(15) | 115.1(19) |
| C4 | 9922(7) | 4839(5) | 7748.9(13) | 98.2(15) |
| C5 | 9354(5) | 4211(3) | 7099.4(10) | 67.8(8) |
| C6 | 9281(5) | 5328(3) | 6481.0(10) | 64.1(8) |
| C7 | 9812(4) | 5141(3) | 6023.5(10) | 58.8(7) |
| C8 | 11514(5) | 4434(4) | 6001.4(12) | 77.7(10) |
| C9 | 10185(5) | 6174(3) | 5832.4(10) | 64.9(8) |
| C10 | 8762(6) | 6866(3) | 5775.7(12) | 71.2(9) |
| C11 | 9045(8) | 7824(3) | 5615.6(15) | 93.2(13) |
| C12 | 10813(12) | 8102(5) | 5510(2) | 127(2) |
| C13 | 12247(10) | 7448(6) | 5555(2) | 125(2) |
| C14 | 11979(7) | 6486(4) | 5717.1(15) | 95.5(13) |
| C15 | 8186(4) | 4582(2) | 5821.5(9) | 51.3(6) |
| C16 | 7801(4) | 4588(2) | 5405.0(9) | 53.0(6) |

TABLE B-continued

Fractional Atomic coordinates (×$10^4$) and equivalent isotropic displacement parameters ($Å^2$ × $10^3$) for 1. U(eq) is defined as one-third of the trace of the orthogonalized $U^{ij}$ tensor.

| | x | y | z | U(eq) |
|---|---|---|---|---|
| C17 | 6324(4) | 4029(2) | 5232.0(9) | 51.9(6) |
| C18 | 5597(4) | 3429(2) | 5876.1(9) | 53.9(6) |
| C19 | 7042(4) | 3949(2) | 6066.9(9) | 53.4(6) |
| C20 | 7424(5) | 3773(2) | 6510.5(9) | 58.8(7) |
| C21 | 4529(5) | 3463(2) | 4637.6(9) | 58.3(7) |
| C22 | 2502(5) | 3779(2) | 4733.7(9) | 59.4(7) |
| C23 | 4147(5) | 3688(3) | 4175.3(9) | 59.3(7) |
| C24 | 603(5) | 4146(2) | 4100.7(9) | 57.1(7) |
| C25 | 548(5) | 4225(3) | 3637.1(9) | 63.8(8) |
| C26 | −1301(7) | 3997(5) | 3440.1(14) | 102.0(16) |

TABLE C

Bond lengths [Å] for 1.

| Atom | Atom | Length | Atom | Atom | Length |
|---|---|---|---|---|---|
| Cl1 | C11 | 1.725(6) | C7 | C9 | 1.527(5) |
| F1 | C1 | 1.350(5) | C7 | C15 | 1.524(4) |
| F2 | C16 | 1.363(3) | C9 | C10 | 1.381(5) |
| F3 | C10 | 1.346(4) | C9 | C14 | 1.397(6) |
| O1 | C20 | 1.230(4) | C10 | C11 | 1.386(6) |
| O2 | C24 | 1.238(4) | C11 | C12 | 1.359(9) |
| O3 | C25 | 1.391(4) | C12 | C13 | 1.350(10) |
| N1 | C4 | 1.353(5) | C13 | C14 | 1.392(8) |
| N1 | C5 | 1.327(5) | C15 | C16 | 1.369(4) |
| N2 | C5 | 1.420(4) | C15 | C19 | 1.414(4) |
| N2 | C6 | 1.470(5) | C16 | C17 | 1.405(4) |
| N2 | C20 | 1.362(4) | C18 | C19 | 1.384(4) |
| N3 | C17 | 1.341(4) | C19 | C20 | 1.473(4) |
| N3 | C18 | 1.333(4) | C21 | C22 | 1.539(5) |
| N4 | C17 | 1.360(4) | C21 | C23 | 1.543(4) |
| N4 | C21 | 1.443(4) | C24 | C25 | 1.497(4) |
| N5 | C22 | 1.466(4) | C25 | C26 | 1.496(6) |
| N5 | C23 | 1.470(4) | C25 | C27 | 1.471(6) |
| N5 | C24 | 1.325(4) | C26 | C27 | 1.477(8) |
| C1 | C2 | 1.378(6) | O4 | C28 | 1.391(8) |
| C1 | C5 | 1.374(6) | O4 | C31 | 1.386(9) |
| C2 | C3 | 1.385(9) | C28 | C29 | 1.433(13) |
| C3 | C4 | 1.356(9) | C29 | C30 | 1.412(13) |
| C6 | C7 | 1.542(4) | C30 | C31 | 1.353(12) |
| C7 | C8 | 1.536(5) | | | |

TABLE D

Bond angles [°] for 1.

| Atom | Atom | Atom | Angle | Atom | Atom | Atom | Angle |
|---|---|---|---|---|---|---|---|
| C5 | N1 | C4 | 117.2(4) | C16 | C15 | C7 | 124.6(3) |
| C5 | N2 | C6 | 118.5(3) | C16 | C15 | C19 | 115.8(3) |
| C20 | N2 | C5 | 120.5(3) | C19 | C15 | C7 | 119.4(3) |
| C20 | N2 | C6 | 120.2(3) | F2 | C16 | C15 | 120.3(3) |
| C18 | N3 | C17 | 117.1(3) | F2 | C16 | C17 | 117.2(2) |
| C17 | N4 | C21 | 119.7(3) | C15 | C16 | C17 | 122.4(3) |
| C22 | N5 | C23 | 94.2(2) | N3 | C17 | N4 | 119.2(3) |
| C24 | N5 | C22 | 126.8(3) | N3 | C17 | C16 | 121.0(2) |
| C24 | N5 | C23 | 138.4(2) | N4 | C17 | C16 | 119.9(3) |
| F1 | C1 | C2 | 119.0(4) | N3 | C18 | C19 | 125.0(3) |
| F1 | C1 | C5 | 120.5(3) | C15 | C19 | C20 | 122.0(3) |
| C5 | C1 | C2 | 120.4(5) | C18 | C19 | C15 | 118.6(3) |
| C1 | C2 | C3 | 117.2(5) | C18 | C19 | C20 | 119.3(3) |
| C4 | C3 | C2 | 119.4(4) | O1 | C20 | N2 | 121.6(3) |
| N1 | C4 | C3 | 123.4(5) | O1 | C20 | C19 | 122.5(3) |
| N1 | C5 | N2 | 116.8(3) | N2 | C20 | C19 | 115.9(3) |
| N1 | C5 | C1 | 122.3(3) | N4 | C21 | C22 | 116.7(3) |
| C1 | C5 | N2 | 120.8(3) | N4 | C21 | C23 | 113.9(3) |
| N2 | C6 | C7 | 111.0(3) | C22 | C21 | C23 | 88.6(2) |
| C8 | C7 | C6 | 109.7(3) | N5 | C22 | C21 | 88.4(2) |

TABLE D-continued

Bond angles [°] for 1.

| Atom | Atom | Atom | Angle | Atom | Atom | Atom | Angle |
|---|---|---|---|---|---|---|---|
| C9 | C7 | C6 | 106.4(3) | N5 | C23 | C21 | 88.1(2) |
| C9 | C7 | C8 | 113.0(3) | O2 | C24 | N5 | 121.4(3) |
| C15 | C7 | C6 | 107.4(3) | O2 | C24 | C25 | 119.2(3) |
| C15 | C7 | C8 | 106.6(3) | N5 | C24 | C25 | 119.4(3) |
| C15 | C7 | C9 | 113.4(3) | O3 | C25 | C24 | 116.9(3) |
| C10 | C9 | C7 | 121.5(3) | O3 | C25 | C26 | 118.3(3) |
| C10 | C9 | C14 | 116.3(4) | O3 | C25 | C27 | 117.0(3) |
| C14 | C9 | C7 | 122.2(4) | C26 | C25 | C24 | 115.6(3) |
| F3 | C10 | C9 | 119.1(3) | C27 | C25 | C24 | 117.1(3) |
| F3 | C10 | C11 | 117.5(4) | C27 | C25 | C26 | 59.7(4) |
| C9 | C10 | C11 | 123.4(4) | C27 | C26 | C25 | 59.3(3) |
| C10 | C11 | Cl1 | 119.3(4) | C25 | C27 | C26 | 61.0(3) |
| C12 | C11 | Cl1 | 122.1(4) | C31 | O4 | C28 | 108.2(7) |
| C12 | C11 | C10 | 118.6(5) | O4 | C28 | C29 | 104.7(7) |
| C13 | C12 | C11 | 120.2(5) | C30 | C29 | C28 | 109.4(7) |
| C12 | C13 | C14 | 121.7(5) | C31 | C30 | C29 | 105.0(9) |
| C13 | C14 | C9 | 119.8(5) | C30 | C31 | O4 | 111.7(8) |

TABLE E

Anisotropic displacement parameters ($Å^2 \times 10^3$) for 1. The anisotropic displacement factor exponent takes the form: $-2\pi^2[h^2 a^{*2} U^{11} + 2 h k a^* b^* U^{12} + \ldots]$.

| | $U^{11}$ | $U^{22}$ | $U^{33}$ | $U^{23}$ | $U^{13}$ | $U^{12}$ |
|---|---|---|---|---|---|---|
| Cl1 | 162.9(14) | 56.4(5) | 198.8(16) | 18.9(7) | 27.9(13) | 8.8(7) |
| F1 | 120(2) | 94.8(17) | 99.2(17) | −11.4(13) | −19.7(15) | 29.5(16) |
| F2 | 73.2(12) | 82.6(12) | 53.7(9) | −6.1(8) | 7.0(8) | −17.5(10) |
| F3 | 72.9(12) | 59.2(10) | 108.3(15) | 3.9(10) | 19.7(11) | 1.9(9) |
| O1 | 84.8(17) | 75.0(15) | 61.4(12) | 8.9(11) | −8.5(12) | −8.1(13) |
| O2 | 61.8(14) | 116(2) | 68.6(14) | −12.4(14) | 9.7(12) | −0.1(14) |
| O3 | 70.8(14) | 89.2(17) | 51.3(11) | 2.5(11) | 5.7(10) | −1.6(13) |
| N1 | 75.7(18) | 104(2) | 58.5(15) | −17.9(16) | −3.0(14) | −4.5(18) |
| N2 | 69.9(16) | 68.9(15) | 52.6(12) | −5.5(12) | −7.2(12) | −2.7(13) |
| N3 | 55.8(13) | 52.3(12) | 56.1(12) | 0.1(10) | −3.7(10) | 3.7(11) |
| N4 | 61.7(15) | 69.5(16) | 50.5(12) | −4.8(11) | −4.2(11) | −3.8(13) |
| N5 | 56.9(14) | 65.5(14) | 45.2(11) | 1.5(10) | 1.8(10) | −4.6(12) |
| C1 | 81(2) | 104(3) | 68(2) | 0(2) | −13.2(18) | 14(2) |
| C2 | 104(3) | 136(4) | 85(3) | 21(3) | −29(3) | 13(3) |
| C3 | 103(4) | 175(6) | 68(2) | 8(3) | −22(3) | −3(4) |
| C4 | 84(3) | 149(5) | 61(2) | −20(3) | −5.9(19) | −17(3) |
| C5 | 61.9(18) | 90(2) | 52.1(16) | −5.2(16) | −4.2(14) | −0.6(17) |
| C6 | 69.9(19) | 65.7(18) | 56.7(15) | −8.8(14) | −3.2(14) | −6.5(16) |
| C7 | 51.7(15) | 65.7(17) | 59.1(15) | −12.4(13) | 1.1(13) | −0.7(13) |
| C8 | 53.5(18) | 99(3) | 80(2) | −19(2) | −8.7(16) | 12.5(18) |
| C9 | 64.2(18) | 69.6(19) | 61.0(16) | −9.3(14) | 5.5(14) | −13.0(16) |
| C10 | 79(2) | 57.3(17) | 77(2) | −6.4(15) | 10.4(18) | −9.7(16) |
| C11 | 117(4) | 60(2) | 103(3) | −2(2) | 15(3) | −21(2) |
| C12 | 148(6) | 85(3) | 146(5) | 14(3) | 16(5) | −47(4) |
| C13 | 104(4) | 136(5) | 135(5) | 14(4) | 17(4) | −59(4) |
| C14 | 70(2) | 118(4) | 99(3) | 2(3) | 7(2) | −26(2) |
| C15 | 51.8(14) | 49.0(14) | 53.1(14) | −8.2(11) | 0.0(12) | 5.0(11) |
| C16 | 54.0(15) | 53.2(14) | 51.9(14) | −3.3(11) | 4.4(12) | −0.1(12) |
| C17 | 52.7(14) | 51.1(14) | 51.7(14) | −5.8(11) | −1.4(11) | 5.9(12) |
| C18 | 56.4(15) | 49.2(14) | 56.3(14) | 1.3(12) | −0.3(12) | 3.2(12) |
| C19 | 56.2(15) | 50.8(14) | 53.2(14) | −3.5(11) | −2.6(12) | 5.2(13) |
| C20 | 64.5(18) | 57.5(15) | 54.3(15) | −3.2(13) | −2.5(13) | 2.8(14) |
| C21 | 70.3(19) | 50.3(15) | 54.5(15) | −3.4(12) | −10.4(14) | 0.3(14) |
| C22 | 69.5(19) | 63.7(16) | 45.0(13) | 4.6(12) | −0.2(13) | −14.2(15) |
| C23 | 59.9(16) | 67.5(17) | 50.4(14) | −6.5(13) | −0.9(13) | 5.8(14) |
| C24 | 58.5(17) | 61.8(16) | 50.9(14) | −4.3(12) | 0.4(13) | −5.8(13) |
| C25 | 62.7(18) | 76(2) | 52.6(15) | 3.9(14) | −2.1(14) | 3.2(16) |
| C26 | 76(3) | 156(5) | 75(2) | −8(3) | −17(2) | 5(3) |
| C27 | 125(4) | 134(5) | 84(3) | 25(3) | −4(3) | 56(4) |
| O4 | 240(7) | 162(5) | 110(3) | −20(3) | 14(4) | −34(5) |
| C28 | 110(4) | 200(8) | 136(5) | 40(6) | 16(4) | 22(5) |
| C29 | 490(30) | 222(11) | 75(4) | −11(5) | 49(8) | −6(15) |
| C30 | 232(11) | 189(9) | 191(9) | −47(8) | 76(9) | −5(9) |
| C31 | 321(15) | 136(6) | 122(5) | −12(5) | 44(8) | −17(8) |

Example 2
(4R)-4-(3-Chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one (2)
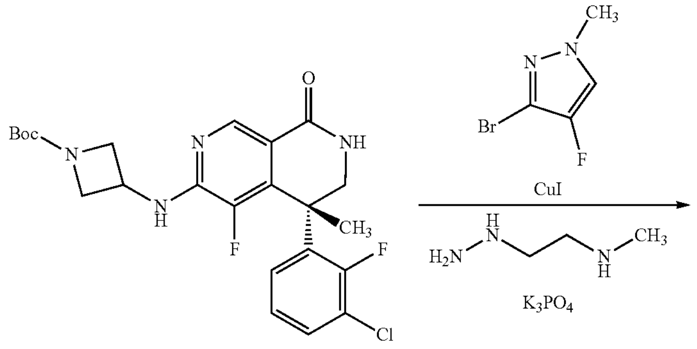
P1
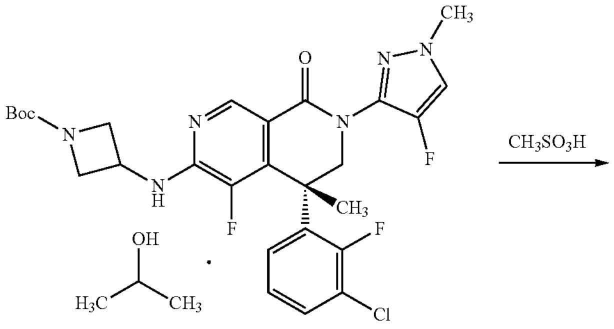
C58
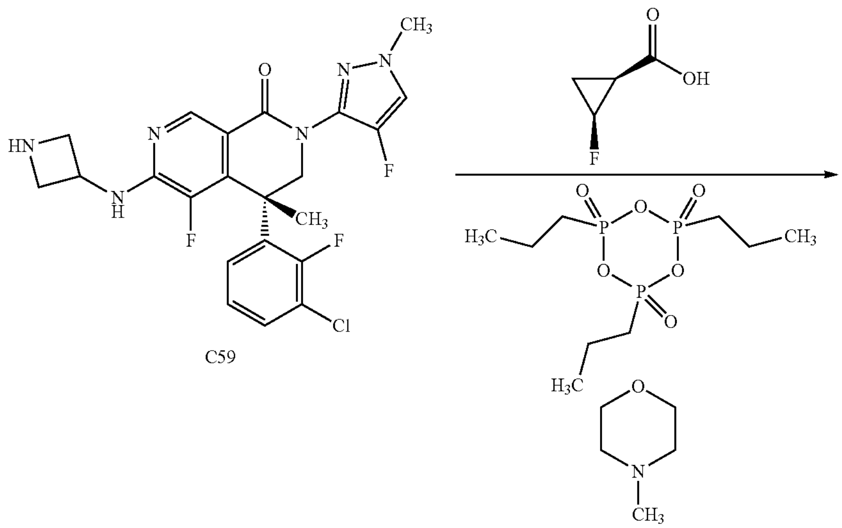
C59

-continued

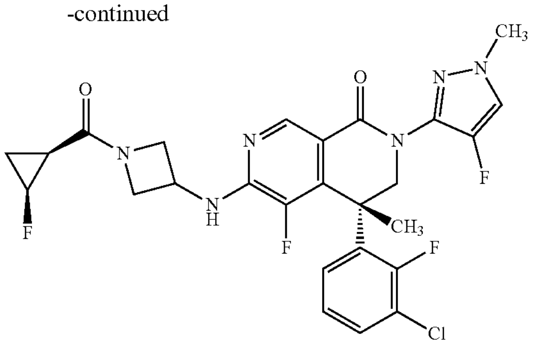

2

Step 1. Synthesis of tert-butyl 3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidine-1-carboxylate, propan-2-ol solvate (C58)

A mixture of P1 (31.9 g, 66.6 mmol), tripotassium phosphate (38.9 g, 183 mmol), and copper(I) iodide (12.7 g, 66.7 mmol) was treated with toluene (500 mL), 3-bromo-4-fluoro-1-methyl-1H-pyrazole (8.60 mL, 75.9 mmol), and $N^1,N^2$-dimethylethane-1,2-diamine (21.5 mL, 202 mmol). After the reaction mixture had been heated at 90° C. for 18 hours, it was allowed to cool to 25° C., whereupon it was partitioned between ethyl acetate (500 mL) and a mixture of saturated aqueous ammonium chloride solution (250 mL) and water (250 mL). The organic layer was washed with a mixture of saturated aqueous ammonium chloride solution (75 mL) and water (75 mL), then with saturated aqueous sodium chloride solution (100 mL); the combined aqueous layers were extracted with ethyl acetate (200 mL), and this organic layer was washed with a solution of saturated aqueous sodium chloride (50 mL). The combined organic layers were dried over magnesium sulfate, filtered through a plug of silica gel (100 g), eluting with ethyl acetate (500 mL), and subsequently concentrated in vacuo. The resulting solid was treated with propan-2-ol (350 mL), heated to 50° C. for 16 hours, and allowed to cool to 25° C. with stirring. After 1 hour, the solid was collected via filtration, and rinsed once with propan-2-ol and twice with heptane, affording C58 as a white solid. Yield: 37.8 g, 59.3 mmol, 89%.

LCMS m/z 577.3 (chlorine isotope pattern observed) $[M+H]^+$. $^1H$ NMR (400 MHz, DMSO-$d_6$), characteristic peaks: δ 8.51 (s, 1H), 7.92 (br d, J=6.2 Hz, 1H), 7.82 (d, J=4.5 Hz, 1H), 7.58 (t, J=7.5 Hz, 1H), 7.39 (t, J=7.6 Hz, 1H), 7.26 (t, J=8.0 Hz, 1H), 4.76-4.64 (m, 1H), 4.21 (d, J=12.9 Hz, 1H), 4.17-4.05 (m, 2H), 3.91-3.83 (m, 1H), 3.71 (s, 3H), 1.85 (br s, 3H), 1.38 (s, 9H).

Step 2. Synthesis of (4R)-6-[(azetidin-3-γ1)amino]-4-(3-chloro-2-fluorophenyl)-5-fluoro-2-(4-fluoro-1-methyl-1H-pyrazol-3-yl)-4-methyl-3,4-dihydro-2,7-naphthyridin-1(2H)-one (C59)

Methanesulfonic acid (2.66 mL, 41.0 mmol) was added to a solution of C58 (11.2 g, 17.6 mmol) in 2,2,2-trifluoroethan-1-ol (48 mL), and the reaction mixture was stirred for 65 minutes, whereupon it was concentrated in vacuo. The residue was diluted with toluene (20 mL) and concentrated once more; the resulting foam was dissolved in dichloromethane (250 mL) and the pH was adjusted to >7 by addition of aqueous potassium carbonate solution (1 M; 160 mL). After 15 minutes of stirring, the mixture was washed with saturated aqueous sodium chloride solution (50 mL), dried over sodium sulfate, filtered, and concentrated under reduced pressure to provide C59 as a light-yellow solid (9.67 g). This material was used directly in the following step. LCMS m/z 477.3 (chlorine isotope pattern observed) $[M+H]^+$. $^1H$ NMR (400 MHz, DMSO-$d_6$), product peaks only, characteristic peaks: δ 8.50 (s, 1H), 7.81 (d, J=4.6 Hz, 1H), 7.78 (br d, J=6.8 Hz, 1H), 7.40 (t, J=7.7 Hz, 1H), 4.87-4.74 (m, 1H), 4.20 (d, J=12.8 Hz, 1H), 3.72-3.65 (m, 1H), 3.71 (s, 3H), 3.64-3.46 (m, 4H), 1.84 (br s, 3H).

Step 3. Synthesis of (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one (2)

2,4,6-Tripropyl-1,3,5,2,4,6-trioxatriphosphinane 2,4,6-trioxide (50% solution in N,N-dimethylformamide; 2.97 g, 4.67 mmol) was added in a drop-wise manner over 5 minutes to a solution of 4-methylmorpholine (1.10 mL, 10.0 mmol), (1S,2S)-2-fluorocyclopropane-1-carboxylic acid (91%, 532 mg, 4.65 mmol) and C59 (from the previous step; 2.01 g, 53.66 mmol) in dichloromethane (33 mL). After 16 hours, the reaction mixture was diluted with a solution of water (15 mL) and saturated aqueous ammonium chloride solution (15 mL). The aqueous layer was extracted with dichloromethane (35 mL), and the combined organic layers were dried over sodium sulfate, filtered, and concentrated under reduced pressure. The residue was diluted with heptane (10 mL) and concentrated in vacuo, whereupon the resulting solid was mixed with ethyl acetate (8 mL), heated to 42° C., and treated with heptane (2 mL) drop-wise over 7 minutes. After an additional 10 minutes, the mixture was allowed to cool to 25° C. and stir for 16 hours. The resultant solid was collected via filtration and rinsed with a mixture of ethyl acetate and heptane (1:1, 10 mL), affording (4R)-4-(3-chloro-2-fluorophenyl)-5-fluoro-6-({1-[(1 S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one (2) as a white solid. This crystal form was designated as Form 1 (see data below). Yield: 1.64 g, 2.91 mmol, 80% over 2 steps. LCMS m/z 563.3 (chlorine isotope pattern observed) $[M+H]^+$. $^1H$ NMR (400 MHz, DMSO-$d_6$) δ 8.52 (s, 1H), 8.05-7.98 (m, 1H), 7.82 (d, J=4.5 Hz, 1H), 7.59 (t, J=7.5 Hz, 1H), 7.45-7.36 (m, 1H), 7.27 (t, J=8.0 Hz, 1H), [4.97-4.89 (m) and 4.84-4.71 (m), total 2H], 4.55 (dt, J=35.7, 8.2 Hz, 1H), 4.27-4.10 (m, 3H), 3.97-3.83

(m, 1H), 3.76-3.70 (m, 1H), 3.71 (s, 3H), 1.86-1.72 (m, 1H), 1.85 (s, 3H), 1.57-1.42 (m, 1H), 1.08-0.94 (m, 1H).

Acquisition of Powder X-ray Diffraction (PXRD Data) for Crystalline Example 2, Form 1

Powder X-ray diffraction analysis was conducted using a Bruker AXS D8 Endeavor diffractometer equipped with a Cu radiation source. The divergence slit was set at 11 mm continuous illumination. Diffracted radiation was detected by a PSD-Lynx Eye detector, with the detector PSD opening set at 4.123 degrees. The X-ray tube voltage and amperage were set to 40 kV and 40 mA respectively. In addition, the energy dispersive detector, a nickel filter was used to screen out unwanted wavelengths. Data was collected in the Theta-Theta goniometer at the Cu wavelength from 3.0 to 40.0 degrees 2-Theta using a step size of 0.016 degrees and a step time of 0.4 second. The antiscatter screen was set to a fixed distance of 1.5 mm. Samples were rotated at 15/min during collection. Samples were prepared by placing them in a silicon low background sample holder and rotated during collection. Data were collected using Bruker DIFFRAC Plus software and analysis was performed by EVA diffract plus software.

The PXRD data file was not processed prior to peak searching. The peak search algorithm in the EVA software was applied to make preliminary peak assignments using a threshold value of 1. To ensure validity, adjustments were manually made; the output of automated assignments was visually checked, and peak positions were adjusted to the peak maximum. Peaks with relative intensity of ≥3% were generally chosen. The peaks which were not resolved or were consistent with noise were not selected. A typical error associated with the peak position from PXRD, stated in USP, is up to +/−0.2° 2-Theta (USP-941).

Figure 2:
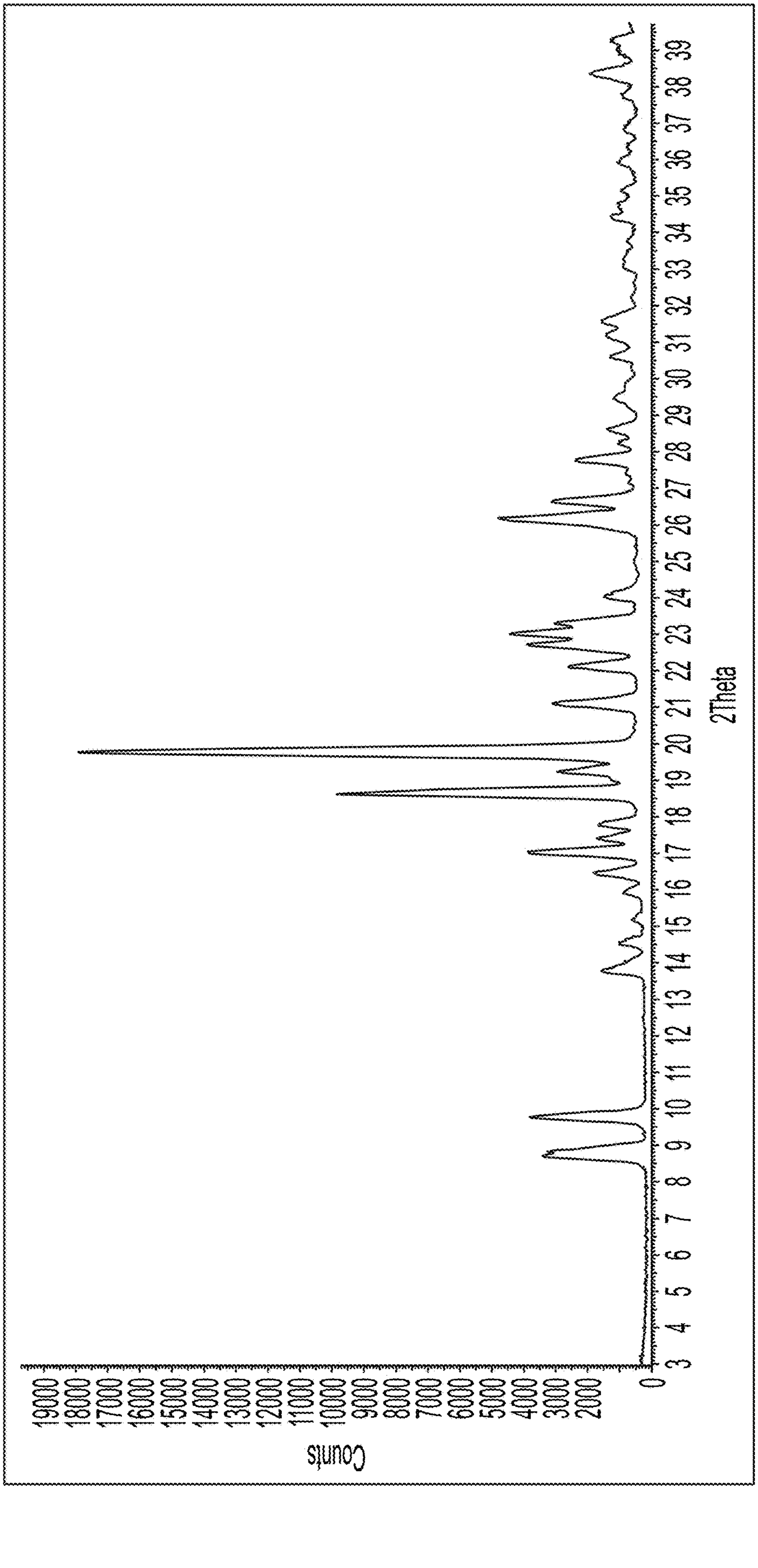
FIG. 2 is a characteristic X-ray powder diffraction pattern showing (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one of Example 2, Form 1 (Vertical Axis: Intensity (CPS); Horizontal Axis: Two theta (degrees)).

A representative diffraction pattern for Form 1 of Example 2 is provided in FIG. 2. A list of diffraction peaks expressed in terms of the degree 28 and relative intensities of a PXRD from a sample of crystalline Example 2, Form 1 is shown in Table 1A (key peaks) and Table 1B below.

TABLE 1A

| Key PXRD peak list for Example 2, Form 1. Angle 2Θ (°) |
|---|
| 9.8, 17, and 19.8 |

TABLE 1B

PXRD peak list for Example 2, Form 1.

| Angle (2-theta) | Rel. Intensity |
|---|---|
| 8.8 | 17% |
| 9.8 | 20% |
| 13.8 | 7% |
| 14.5 | 4% |
| 16.5 | 8% |
| 17.0 | 20% |
| 17.4 | 7% |
| 17.8 | 6% |
| 18.6 | 54% |
| 19.3 | 14% |
| 19.8 | 100% |
| 21.1 | 15% |
| 22.1 | 12% |
| 22.7 | 19% |
| 23.0 | 23% |
| 23.3 | 15% |
| 24.1 | 6% |
| 26.2 | 25% |
| 26.7 | 15% |
| 27.8 | 11% |
| 28.6 | 5% |
| 29.5 | 4% |
| 30.6 | 4% |
| 31.2 | 5% |
| 31.6 | 6% |
| 34.4 | 4% |
| 35.9 | 3% |
| 38.4 | 8% |
| 39.0 | 3% |
| 39.3 | 4% |

Conversion of Example 2, Form 1 to Example 2, Form 2

A sample of 2, crystal form 1 (1.54 g, 2.74 mmol), was mixed with propan-2-yl acetate (31 mL) and heated to 70° C. with stirring. After 1 hour, the slurry was cooled slightly and stirred at 65° C. After 15 hours, the slurry was removed from the heating bath and stirred for 1 hour. The resultant solid was collected via filtration and rinsed with isopropyl acetate (20 mL), affording 2, crystalline Form 2 as a white solid (90% yield; 1.39 g, 2.47 mmol). PXRD data is provided below.

Powder X-ray Diffraction (PXRD Data) for Crystalline Example 2, Form 2

Figure 3:
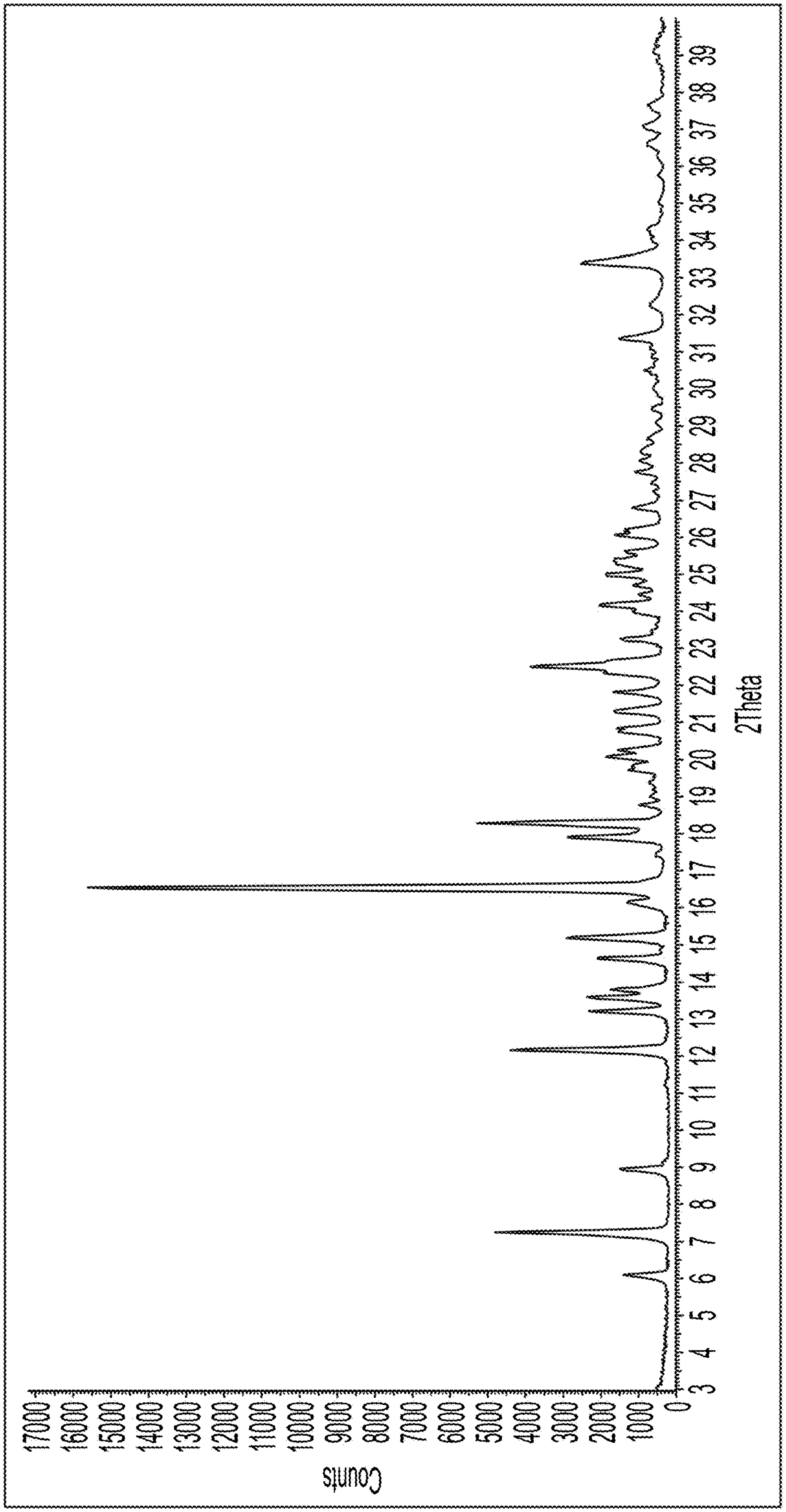
FIG. 3 is a characteristic X-ray powder diffraction pattern showing (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one Example 2, Form 2 (Vertical Axis: Intensity (CPS); Horizontal Axis: Two theta (degrees)).

Using methodology identical to that described above for Example 2, Form 1, a diffraction pattern for Form 2 of Example 2 was obtained, and is provided in FIG. 3. A list of diffraction peaks expressed in terms of the degree 28 and relative intensities of a PXRD from a sample of crystalline Example 2, Form 2 is shown in Table 2A (key peaks) and Table 2B below.

TABLE 2A

| Key PXRD peak list for Example 2, Form 2. Angle 2Θ (°) |
|---|
| 6.1, 7.2, 12.2, and 13.2 |

TABLE 2B

PXRD peak list for Example 2, Form 2.

| Angle (2-theta) | Rel. Intensity |
|---|---|
| 6.1 | 7% |
| 7.2 | 29% |
| 8.9 | 8% |
| 12.2 | 27% |
| 13.2 | 13% |
| 13.6 | 13% |
| 13.8 | 10% |
| 14.6 | 12% |
| 15.2 | 17% |

TABLE 2B-continued

| PXRD peak list for Example 2, Form 2. | |
|---|---|
| Angle (2-theta) | Rel. Intensity |
| 16.1 | 7% |
| 16.5 | 100% |
| 17.9 | 17% |
| 18.3 | 32% |
| 18.8 | 4% |
| 19.8 | 4% |
| 20.1 | 10% |
| 20.3 | 7% |
| 20.8 | 8% |
| 21.3 | 8% |
| 21.8 | 8% |
| 22.3 | 10% |
| 22.5 | 23% |
| 23.2 | 8% |
| 24.0 | 4% |
| 24.2 | 10% |
| 24.4 | 3% |
| 24.7 | 5% |
| 25.0 | 9% |
| 25.3 | 7% |
| 25.6 | 6% |
| 26.1 | 5% |
| 26.8 | 5% |
| 27.7 | 5% |
| 28.0 | 4% |
| 28.3 | 3% |
| 30.5 | 3% |
| 31.3 | 8% |
| 33.4 | 16% |
| 37.1 | 3% |

Example 3

(4R)-4-(3-Chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one (3)

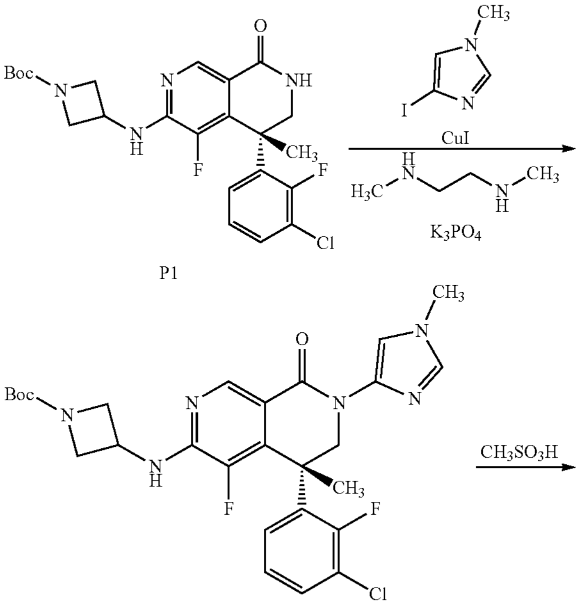

P1

C60

-continued

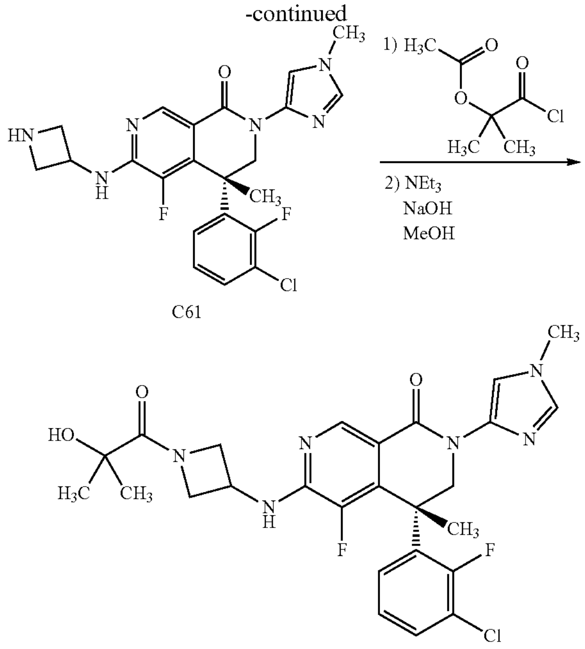

C61

3

Step 1. Synthesis of tert-butyl 3-{[(5R)-5-(3-chloro-2-fluorophenyl)-4-fluoro-5-methyl-7-(1-methyl-1H-imidazol-4-yl)-8-oxo-5,6,7,8-tetrahydro-2,7-naphthyridin-3-yl]amino}azetidine-1-carboxylate (C60)

A mixture of P1 (500 mg, 1.04 mmol), 4-iodo-1-methyl-1H-imidazole (235 mg, 1.13 mmol), tripotassium phosphate (665 mg, 3.13 mmol), and copper(I) iodide (199 mg, 1.04 mmol) was treated with toluene (10.4 mL) and $N^1$,$N^2$-dimethylethane-1,2-diamine (0.337 mL, 3.16 mmol). The reaction mixture was heated to 85° C.; after 2 hours, it was allowed to cool to 25° C. and partitioned between saturated aqueous ammonium chloride solution (20 mL) and ethyl acetate (20 mL). The organic layer was washed sequentially with saturated aqueous ammonium chloride solution (15 mL) and saturated aqueous sodium chloride solution (15 mL), dried over magnesium sulfate, filtered, and concentrated in vacuo. The resulting white solid was combined with the product of similar reactions carried out using P1 (400 mg, 0.835 mmol). Purification via silica gel chromatography (Gradient: 25% to 100% ethyl acetate in heptane) afforded C60 as an off-white solid. Combined yield: 515 mg, 0.921 mmol, 49%. LCMS m/z 559.3 (chlorine isotope pattern observed) $[M+H]^+$. $^1H$ NMR (400 MHz, DMSO-$d_6$) δ 8.52 (s, 1H), 7.84 (br d, J=6.0 Hz, 1H), 7.60-7.53 (m, 1H), 7.47 (br s, 1H), 7.45 (br s, 1H), 7.37-7.30 (m, 1H), 7.24 (t, J=8.0 Hz, 1H), 4.75-4.64 (m, 1H), 4.46 (d, J=13.3 Hz, 1H), 4.25 (d, J=13.3 Hz, 1H), 4.18-4.06 (m, 2H), 3.92-3.76 (m, 2H), 3.63 (s, 3H), 1.80 (s, 3H), 1.38 (s, 9H).

Step 2. Synthesis of (4R)-6-[(azetidin-3-γ1)amino]-4-(3-chloro-2-fluorophenyl)-5-fluoro-4-methyl-2-(1-methyl-1H-imidazol-4-yl)-3,4-dihydro-2,7-naphthyridin-1(2H)-one (C61)

Methanesulfonic acid (0.50 mL, 7.7 mmol) was added to a solution of C60 (500 mg, 0.894 mmol) in 2,2,2-trifluoroethan-1-ol (3 mL). After 20 minutes, volatiles were removed in vacuo, and the residue was diluted with water (5 mL). The pH was adjusted to >7 by addition of an aqueous solution of sodium hydroxide (1 M; 16 mL, 16 mmol); after 30 minutes of stirring, the resulting solid was collected via filtration and rinsed with water (2×5 mL) to afford C61 as a white solid. Yield: 294 mg, 0.641 mmol, 72%. LCMS m/z 459.3 (chlorine isotope pattern observed) $[M+H]^+$. $^1H$ NMR (400 MHz, DMSO-$d_6$) δ 8.50 (s, 1H), 7.70 (br d, J=6.7 Hz, 1H), 7.56 (ddd, J=7.5, 6.9, 1.6 Hz, 1H), 7.46 (br d, half of AB quartet, J=1.6 Hz, 1H), 7.44 (br s, 1H), 7.37-7.31 (m, 1H), 7.24 (t, J=8.0 Hz, 1H), 4.85-4.73 (m, 1H), 4.34 (AB quartet, $J_{AB}$=13.2 Hz, $\Delta\nu_{AB}$=72.1 Hz, 2H), 3.63 (s, 3H), 3.61-3.43 (m, 4H), 1.79 (br s, 3H).

Step 3. Synthesis of (4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one (3)

1-Chloro-2-methyl-1-oxopropan-2-yl acetate (0.101 mL, 0.697 mmol) was added to a solution of C61 (290 mg, 0.632 mmol) and triethylamine (0.30 mL, 2.2 mmol) in dichloromethane (6.3 mL). After 15 minutes, volatiles were removed in vacuo. To the mixture were added methanol (3 mL) and an aqueous solution of sodium hydroxide (2 M; 1.8 mmol, 3.6 mmol). After 16 hours, the pH was adjusted to approximately 4.5 by addition of hydrochloric acid (1 M; 1.8 mL, 1.8 mmol), and the aqueous layer was extracted with dichloromethane (2×30 mL). The combined organic layers were washed with a mixture of saturated aqueous sodium chloride solution (8 mL) and water (22 mL), dried over magnesium sulfate, filtered, and concentrated in vacuo. The resulting solid was combined with the product of a smaller-scale reaction (0.17 mmol), layered with ethyl acetate (10 mL) and ethanol (0.5 mL), and heated to 55° C. for 2 hours. The mixture was allowed to cool to 25° C.; after 1 hour, the resulting solid was collected via filtration and washed with ethyl acetate (3×3 mL), affording (4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one (3) as a white solid. Yield: 360 mg, 0.661 mmol, 82%. LCMS m/z 543.3 (chlorine isotope pattern observed) $[M-H]^-$. $^1H$ NMR (400 MHz, DMSO-$d_6$) δ 8.52 (s, 1H), 7.88 (br d, J=5 Hz, 1H), 7.60-7.53 (m, 1H), 7.47 (br s, 1H), 7.45 (br s, 1H), 7.35 (br t, J=7.7 Hz, 1H), 7.24 (t, J=8.0 Hz, 1H), 5.04 (d, J=6.1 Hz, 1H), 4.73-4.60 (m, 2H), 4.50-4.41 (m, 1H), 4.38-4.21 (m, 2H), 4.13 (t, J=8.5 Hz, 1H), 3.92-3.77 (m, 1H), 3.63 (s, 3H), 1.80 (br s, 3H), 1.29-1.21 (m, 6H).

Example 4

(4R)-4-(3-Chloro-2-fluorophenyl)-5-fluoro-2-[5-(hydroxymethyl)pyridin-2-yl]-4-methyl-6-{[1-(pyridazine-3-carbonyl)azetidin-3-yl]amino}-3,4-dihydro-2,7-naphthyridin-1(2H)-one (4)

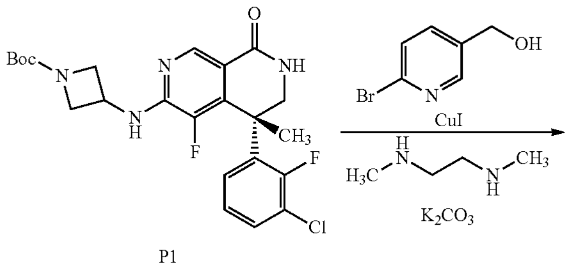

P1

-continued

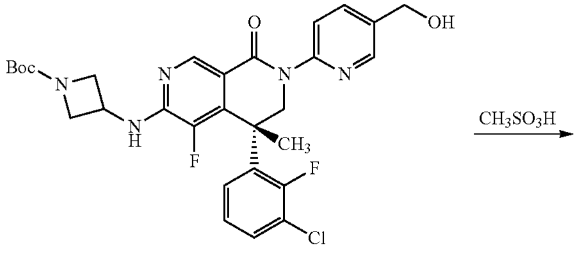

C62

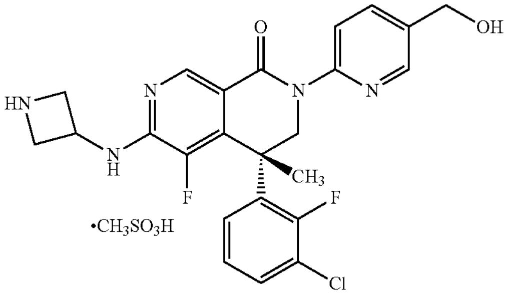

C63

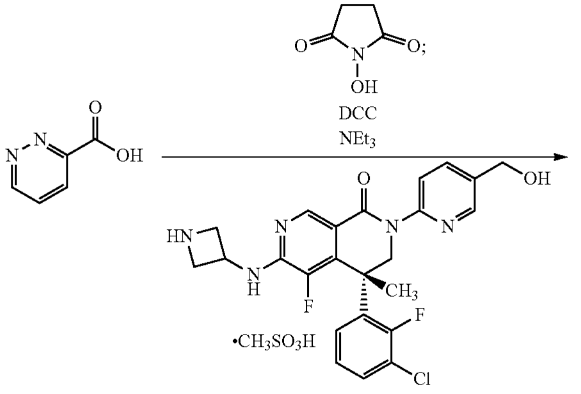

C63

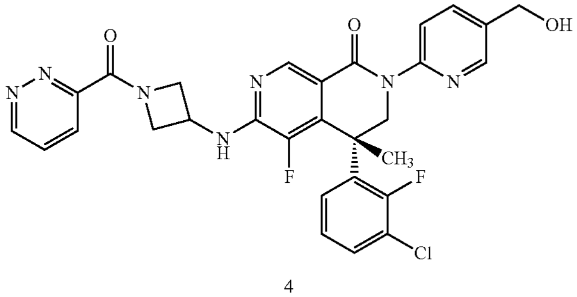

4

Step 1. Synthesis of tert-butyl 3-({(5R)-5-(3-chloro-2-fluorophenyl)-4-fluoro-7-[5-(hydroxymethyl)pyridin-2-yl]-5-methyl-8-oxo-5,6,7,8-tetrahydro-2,7-naphthyridin-3-yl}amino)azetidine-1-carboxylate (C62)

To a solution of P1 (200 mg, 0.418 mmol) in 1,4-dioxane (4 mL) were added (6-bromopyridin-3-γ1)methanol (118 mg, 0.628 mmol), $N^1$,$N^2$-dimethylethane-1,2-diamine (36.8 mg, 0.417 mmol), potassium carbonate (173 mg, 1.25 mmol), and copper(I) iodide (79.5 mg, 0.417 mmol), whereupon the reaction mixture was heated at 100° C. After 12 hours, LCMS analysis indicated conversion to C62: LCMS m/z 586.1 (chlorine isotope pattern observed) $[M+H]^+$. The reaction mixture was diluted with saturated aqueous sodium chloride solution (15 mL) and extracted with ethyl acetate (2×20 mL); the combined organic layers were dried over sodium sulfate, filtered, concentrated in vacuo, and purified using silica gel chromatography (Gradient: 0% to 100% ethyl acetate in petroleum ether), affording C62 as a yellow solid. Yield: 220 mg, 0.375 mmol, 90%.

Step 2. Synthesis of (4R)-6-[(azetidin-3-γ1)amino]-4-(3-chloro-2-fluorophenyl)-5-fluoro-2-[5-(hydroxymethyl)pyridin-2-yl]-4-methyl-3,4-dihydro-2,7-naphthyridin-1(2H)-one, methanesulfonic acid salt (C63)

Methanesulfonic acid (90.2 mg, 0.939 mmol) was added to a 25° C. solution of C62 (110 mg, 0.188 mmol) in 1,1,1,3,3,3-hexafluoropropan-2-ol (2 mL). After 15 minutes, the mixture was diluted with acetonitrile (10 mL) and concentrated in vacuo, providing C63 as a yellow gum (109 mg); half of this material was used in the following step.

Step 3. Synthesis of (4R)-4-(3-chloro-2-fluorophenyl)-5-fluoro-2-[5-(hydroxymethyl)pyridin-2-yl]-4-methyl-6-{[1-(pyridazine-3-carbonyl)azetidin-3-yl]amino}-3,4-dihydro-2,7-naphthyridin-1(2H)-one (4)

1,3-Dicyclohexylcarbodiimide (DCC; 33.3 mg, 0.161 mmol) was added to a 25° C. solution of 1-hydroxypyrrolidine-2,5-dione (20.4 mg, 0.177 mmol) and pyridazine-3-carboxylic acid (20.0 mg, 0.161 mmol) in dimethyl sulfoxide (1.5 mL). After 16 hours, C63 (54 mg, 594 μmol) and triethylamine (0.129 mL, 0.926 mmol) were added. The reaction mixture was then stirred for 1 hour, whereupon it was concentrated in vacuo and purified using reversed-phase HPLC (Column: Welch Xtimate C18, 40×150 mm, 5 μm; Mobile phase A: 10 mM aqueous ammonium bicarbonate solution containing 0.05% ammonium hydroxide; Mobile phase B: acetonitrile; Gradient: 18% to 55% B; Flow rate: 60 mL/minute) to afford (4R)-4-(3-chloro-2-fluorophenyl)-5-fluoro-2-[5-(hydroxymethyl)pyridin-2-yl]-4-methyl-6-{[1-(pyridazine-3-carbonyl)azetidin-3-yl]amino}-3,4-dihydro-2,7-naphthyridin-1(2H)-one (4) as a white solid. Yield: 14.7 mg, 24.8 μmol, 26% over 2 steps. LCMS m/z 592.2 (chlorine isotope pattern observed) $[M+H]^+$. $^1H$ NMR (400 MHz, methanol-$d_4$) δ 9.31-9.23 (m, 1H), 8.69 (s, 1H), 8.38 (d, J=2.2 Hz, 1H), 8.24 (br d, J=8.6 Hz, 1H), 7.88 (dd, J=8.5, 5.1 Hz, 1H), 7.78 (dd, component of ABX system, J=8.5, 2.4 Hz, 1H), 7.70 (d, J=8.4 Hz, half of AB quartet, 1H), 7.44 (ddd, J=8.5, 5.1, 1.7 Hz, 1H), 7.30 (br t, J=7.5 Hz, 1H), 7.18 (t, J=8.0 Hz, 1H), 5.20-5.10 (m, 1H), 5.06-4.57 (m, 3H, assumed; partially obscured by water peak), 4.62 (s, 2H), 4.58 (d, J=13.3 Hz, 1H), 4.29-4.18 (m, 1H), 4.10 (d, J=13.3 Hz, 1H), 1.92 (s, 3H).

Alternate Synthesis of Example 4

(4R)-4-(3-Chloro-2-fluorophenyl)-5-fluoro-2-[5-(hydroxymethyl)pyridin-2-yl]-4-methyl-6-{[1-(pyridazine-3-carbonyl)azetidin-3-yl]amino}-3,4-dihydro-2,7-naphthyridin-1(2H)-one (4)

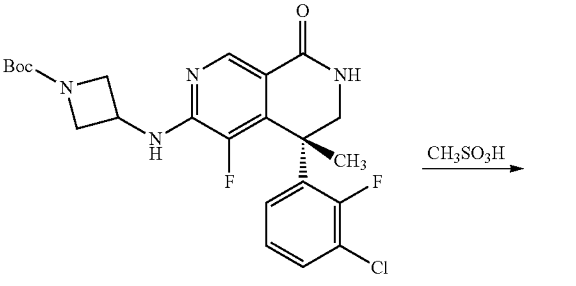

P1

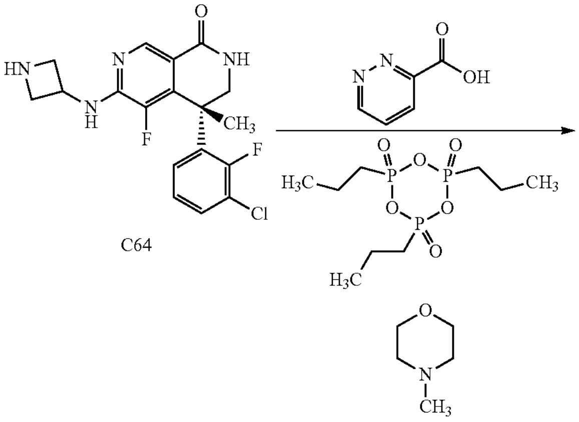

C64

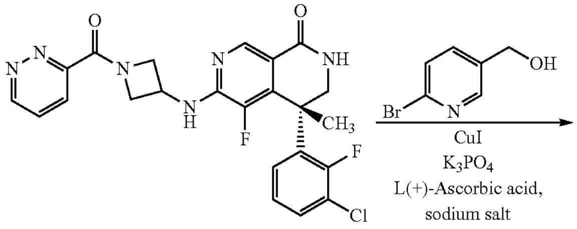

C65

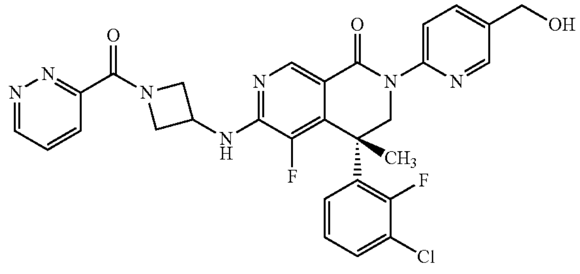

4

Step 1. Synthesis of (4R)-6-[(azetidin-3-γ1)amino]-4-(3-chloro-2-fluorophenyl)-5-fluoro-4-methyl-3,4-dihydro-2,7-naphthyridin-1(2H)-one (C64)

A mixture of P1 (2.40 g, 5.01 mmol) and methanesulfonic acid (976 μL, 15.0 mmol) in 2,2,2-trifluoroethan-1-ol (15 mL) was stirred at room temperature for 45 minutes, whereupon it was concentrated in vacuo. The residue was partitioned between aqueous sodium hydroxide solution (1 M; 30 mL, 30 mmol), saturated aqueous sodium chloride solution (10 mL), and dichloromethane (50 mL), and the aqueous layer was then extracted with dichloromethane (2×50 ml). After the combined organic layers had been dried over sodium sulfate and filtered, the filtrate was concentrated under reduced pressure to afford C64 as a foam (1.98 g). This material was taken directly to the following step. LCMS m/z 379.3 $[M+H]^+$. $^1H$ NMR (400 MHz, DMSO-$d_6$) δ 8.38 (s, 1H), 7.85 (br s, 1H), 7.62-7.52 (m, 2H), 7.34 (t, J=7.6 Hz, 1H), 7.30-7.21 (m, 1H), 4.83-4.71 (m, 1H), 3.68 (d, J=12.8 Hz, 1H), 3.61-3.50 (m, 3H), 3.48 (t, J=7.4 Hz, 1H), 3.22-3.14 (m, 1H), 1.76 (s, 3H).

Step 2. Synthesis of (4R)-4-(3-chloro-2-fluorophenyl)-5-fluoro-4-methyl-6-{[1-(pyridazine-3-carbonyl)azetidin-3-yl]amino}-3,4-dihydro-2,7-naphthyridin-1(2H)-one (C65)

A mixture of C64 (from the previous step; 1.98 g, 55.01 mmol), pyridazine-3-carboxylic acid (744 mg, 6.00 mmol), 4-methylmorpholine (1.52 mL, 13.8 mmol), and 2,4,6-tripropyl-1,3,5,2,4,6-trioxatriphosphinane 2,4,6-trioxide (50% solution by weight in N,N-dimethylformamide; 3.81 g, 5.99 mmol) in dichloromethane (30 mL) was stirred at room temperature overnight. The reaction mixture was then diluted with dichloromethane (25 mL) and extracted with a mixture of water and saturated aqueous ammonium chloride solution (1:1, 20 mL). After the aqueous layer had been extracted with dichloromethane (2×30 mL), the combined organic layers were concentrated in vacuo and purified via silica gel chromatography (Gradient: 0% to 12% methanol in dichloromethane), affording C65 as a white solid. Yield: 1.67 g, 3.44 mmol, 69% over 2 steps. LCMS m/z 485.3 (chlorine isotope pattern observed) $[M+H]^+$. $^1H$ NMR (400 MHz, DMSO-$d_6$), characteristic peaks: δ 9.37-9.31 (m, 1H), 8.12 (d, J=8.4 Hz, 1H), 7.94-7.81 (m, 3H), 7.61-7.52 (m, 1H), 7.39-7.29 (m, 1H), 7.29-7.21 (m, 1H), 4.97-4.87 (m, 1H), 4.87-4.76 (m, 1H), 4.64-4.50 (m, 1H), 4.46 (t, J=9.2 Hz, 1H), 3.70 (d, J=12.8 Hz, 1H), 1.77 (s, 3H).

Step 3. Synthesis of (4R)-4-(3-chloro-2-fluorophenyl)-5-fluoro-2-[5-(hydroxymethyl)pyridin-2-yl]-4-methyl-6-{[1-(pyridazine-3-carbonyl)azetidin-3-yl]amino}-3,4-dihydro-2,7-naphthyridin-1(2H)-one (4)

A mixture of C65 (800 mg, 1.65 mmol), (6-bromopyridin-3-γl)methanol (403 mg, 2.14 mmol), potassium phosphate (963 mg, 4.54 mmol), copper(I) iodide (251 mg, 1.32 mmol), $N^1$,$N^2$-dimethylethane-1,2-diamine (0.532 mL, 5.00 mmol), and L(+)-ascorbic acid, sodium salt (65.4 mg, 0.330 mmol) in toluene (previously sparged with nitrogen for 15 minutes; 14 mL) was sparged with nitrogen for 1 minute, whereupon the reaction vessel was sealed and heated at 85° C. for 16 hours. The reaction mixture was then partitioned between half-saturated aqueous ammonium chloride solution (30 mL) and ethyl acetate (30 mL); the resulting aqueous layer was extracted with ethyl acetate (2×30 mL), whereupon the combined organic layers were dried over sodium sulfate, filtered, and concentrated in vacuo. Silica gel chromatography (Gradient: 0% to 14% methanol in ethyl acetate) provided (4R)-4-(3-chloro-2-fluorophenyl)-5-fluoro-2-[5-(hydroxymethyl)pyridin-2-yl]-4-methyl-6-{[1-(pyridazine-3-carbonyl)azetidin-3-yl]amino}-3,4-dihydro-2,7-naphthyridin-1(2H)-one (4) as a white solid. Yield: 761 mg, 1.28 mmol, 78%. LCMS m/z 592.4 (chlorine isotope pattern observed) $[M+H]^+$. $^1H$ NMR (400 MHz, methanol-$d_4$) δ 9.27 (br d, J=5.0 Hz, 1H), 8.69 (s, 1H), 8.38 (br s, 1H), 8.23 (d, J=8.5 Hz, 1H), 7.91-7.83 (m, 1H), 7.73 (br AB quartet, $J_{AB}$=8.3 Hz, $\Delta\nu_{AB}$=26.3 Hz, 2H), 7.44 (t, J=7.5 Hz, 1H), 7.30 (t, J=7.7 Hz, 1H), 7.17 (t, J=8.1 Hz, 1H), 5.18-5.08 (m, 1H), 5.05-4.94 (m, 1H), 4.81-4.69 (m, 1H), 4.69-4.52 (m, 1H), 4.62 (s, 2H), 4.57 (d, J=13.3 Hz, 1H), 4.29-4.17 (m, 1H), 4.16-4.05 (m, 1H), 1.92 (s, 3H).

Example 5

(4R)-4-(3-Chloro-2-fluorophenyl)-5-fluoro-6-({1-[(1S,2S)-2-fluorocyclopropane-1-carbonyl]azetidin-3-yl}amino)-4-methyl-2-(pyridin-2-yl)-3,4-dihydro-2,7-naphthyridin-1(2H)-one

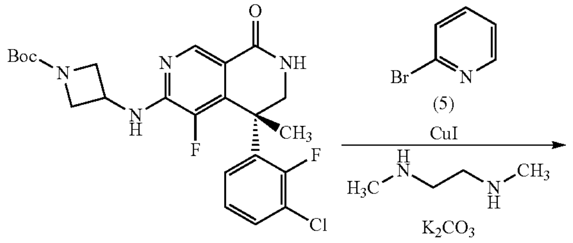

P1

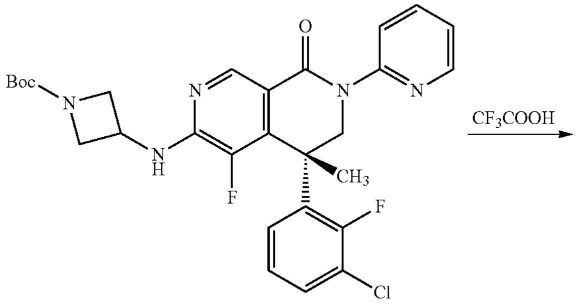

C66

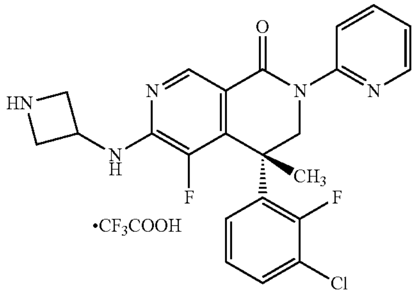

C67

-continued

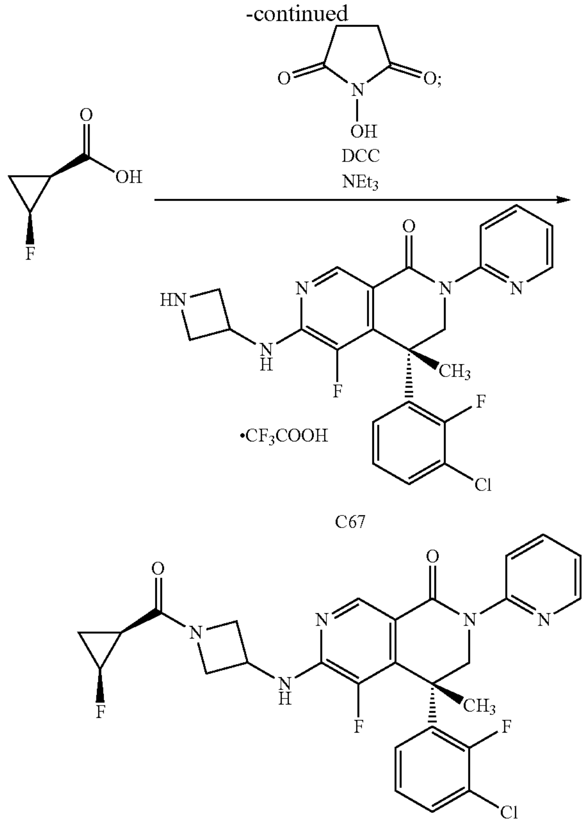

C67

5

Step 1. Synthesis of tert-butyl 3-{[(5R)-5-(3-chloro-2-fluorophenyl)-4-fluoro-5-methyl-8-oxo-7-(pyridin-2-yl)-5,6,7,8-tetrahydro-2,7-naphthyridin-3-yl]amino}azetidine-1-carboxylate (C66)

A mixture of P1 (54.0 mg, 0.113 mmol), 2-bromopyridine (19.6 mg, 0.124 mmol), potassium carbonate (46.7 mg, 0.338 mmol), and copper(I) iodide (64.4 mg, 0.338 mmol) in 1,4-dioxane (2 mL) was treated with $N^1$,$N^2$-dimethylethane-1,2-diamine (4.97 mg, 56.4 μmol), and the reaction mixture was heated at 85° C. After 32 hours, LCMS analysis indicated conversion to C66: LCMS m/z 578.1 (chlorine isotope pattern observed) $[M+Na^+]$. After the reaction mixture had cooled, it was diluted with saturated aqueous sodium chloride solution (2 mL) and extracted with a mixture of ethyl acetate and tetrahydrofuran (1:1, 3x3 mL). The combined organic layers were dried over sodium sulfate, filtered, and concentrated in vacuo; silica gel chromatography (Gradient: 0% to 60% ethyl acetate in petroleum ether) afforded C66 as a colorless gum. Yield: 52.0 mg, 93.5 μmol, 83%.

Step 2. Synthesis of (4R)-6-[(azetidin-3-γ1)amino]-4-(3-chloro-2-fluorophenyl)-5-fluoro-4-methyl-2-(pyridin-2-yl)-3,4-dihydro-2,7-naphthyridin-1(2H)-one, trifluoroacetic acid salt (C67)

Trifluoroacetic acid (1 mL) was added to a 35° C. solution of C66 (52.0 mg, 93.5 μmol) in dichloromethane (4 mL). After 1 hour, the reaction mixture was concentrated in vacuo to afford C67, which was used directly in the following step. LCMS m/z 456.0 (chlorine isotope pattern observed) $[M+H^+]$.

Step 3. Synthesis of (4R)-4-(3-chloro-2-fluorophenyl)-5-fluoro-6-({1-[(1S,2S)-2-fluorocyclopropane-1-carbonyl]azetidin-3-yl}amino)-4-methyl-2-(pyridin-2-yl)-3,4-dihydro-2,7-naphthyridin-1(2H)-one (5)

1,3-Dicyclohexylcarbodiimide (DCC; 23.8 mg, 0.115 mmol) was added to a 35° C. solution of 1-hydroxypyrrolidine-2,5-dione (13.3 mg, 0.116 mmol) and (1S,2S)-2-fluorocyclopropane-1-carboxylic acid (12.0 mg, 0.115 mmol) in tetrahydrofuran (1 mL). After 6 hours, C67 (from the previous step; 593.5 μmol) and triethylamine (39.4 μL, 0.283 mmol) were added. After a further 6 hours, the reaction mixture was concentrated in vacuo and purified using reversed-phase HPLC (Column: Boston Prime C18, 30×150 mm, 5 μm; Mobile phase A: water containing 0.05% ammonium hydroxide; Mobile phase B: acetonitrile; Gradient: 43% to 65% B; Flow rate: 25 mL/minute), providing (4R)-4-(3-chloro-2-fluorophenyl)-5-fluoro-6-({1-[(1S,2S)-2-fluorocyclopropane-1-carbonyl]azetidin-3-yl}amino)-4-methyl-2-(pyridin-2-yl)-3,4-dihydro-2,7-naphthyridin-1(2H)-one (5) as a white solid. Yield: 5.55 mg, 10.2 μmol, 11% over 2 steps. LCMS m/z 542.1 (chlorine isotope pattern observed) $[M+H^+]$. $^1H$ NMR (400 MHz, methanol-$d_4$), integrations are approximate: δ 8.69 (br s, 1H), 8.41 (d, J=4.9 Hz, 1H), 7.83-7.75 (m, 1H), 7.72 (d, half of AB quartet, J=8.3 Hz, 1H), 7.46 (t, J=7.3 Hz, 1H), 7.32 (t, J=7.5 Hz, 1H), 7.23-7.15 (m, 2H), 5.00-4.65 (m, 2H or 3H, assumed; partially obscured by water peak), 4.62-4.52 (m, 1H or 2H), 4.45-4.34 (m, 1H), 4.32-4.22 (m, 1H), 4.11 (d, J=13.2 Hz, 1H), 4.07-3.97 (m, 1H), 1.92 (s, 3H), 1.88-1.76 (m, 1H), 1.74-1.59 (m, 1H), 1.16-1.02 (m, 1H).

Example 6

(4R)-4-(3-Chloro-2-fluorophenyl)-5-fluoro-6-({1-[(1S,2S)-2-fluorocyclopropane-1-carbonyl]azetidin-3-yl}amino)-2-(3-fluoropyridin-2-yl)-4-methyl-3,4-dihydro-2,7-naphthyridin-1(2H)-one (6)

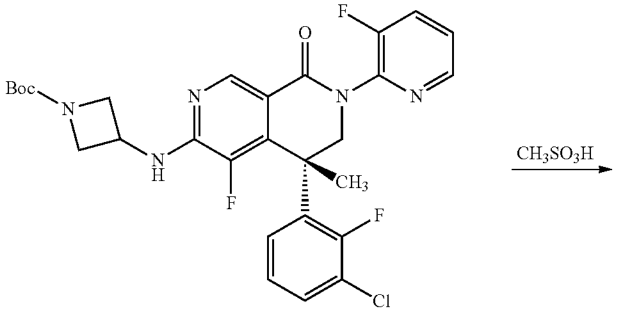

C56

-continued

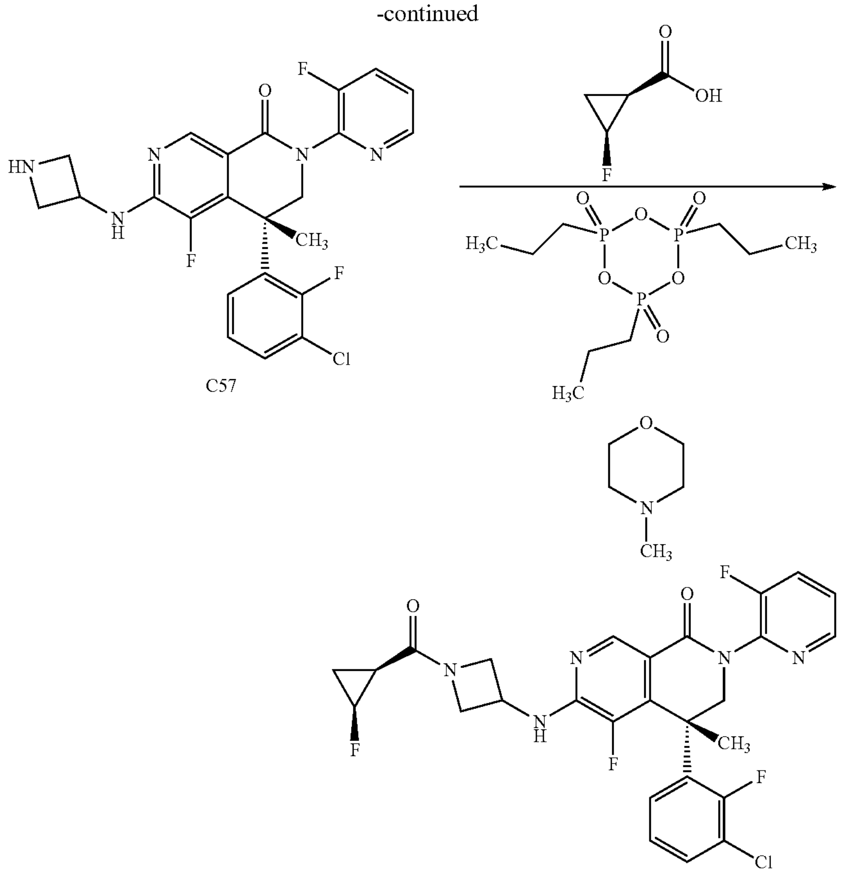

C57

6

Step 1. Synthesis of (4R)-6-[(azetidin-3-γl)amino]-4-(3-chloro-2-fluorophenyl)-5-fluoro-2-(3-fluoropyridin-2-yl)-4-methyl-3,4-dihydro-2,7-naphthyridin-1(2H)-one (C57)

Methanesulfonic acid (0.451 mL, 6.95 mmol) was added in one portion to a solution of C56 (1.14 g, 1.99 mmol) in 2,2,2-trifluoroethan-1-ol (10 mL). After the reaction mixture had been stirred at room temperature for 45 minutes, it was concentrated in vacuo, treated with toluene (5 mL), and concentrated again. The residue was partitioned between aqueous potassium carbonate solution (1 M; 20 mL) and dichloromethane (30 mL); this mixture was stirred for 10 minutes, whereupon saturated aqueous sodium chloride solution (10 mL) was added. The aqueous layer was extracted with dichloromethane (2×30 mL), and the combined organic layers were dried over sodium sulfate, filtered, and concentrated under reduced pressure to afford C57 as a solid (998 mg). This material was progressed directly to the following step. LCMS m/z 474.3 (chlorine isotope pattern observed) $[M+H]^+$.

Step 2. Synthesis of (4R)-4-(3-chloro-2-fluorophenyl)-5-fluoro-6-({1-[(1S,2S)-2-fluorocyclopropane-1-carbonyl]azetidin-3-yl}amino)-2-(3-fluoropyridin-2-yl)-4-methyl-3,4-dihydro-2,7-naphthyridin-1(2H)-one (6)

A mixture of C57 (from the previous step: 998 mg, ≤1.99 mmol), (1S,2S)-2-fluorocyclopropane-1-carboxylic acid (289 mg, 2.78 mmol), 4-methylmorpholine (0.655 mL, 5.96 mmol), and 2,4,6-tripropyl-1,3,5,2,4,6-trioxatriphosphinane 2,4,6-trioxide (50% solution by weight in N,N-dimethylformamide; 1.77 g, 2.78 mmol) in dichloromethane (20 mL) was stirred at room temperature overnight. The reaction mixture was then partitioned between dichloromethane (30 mL) and half-saturated aqueous ammonium chloride solution (30 mL). The aqueous layer was extracted with dichloromethane (2×30 mL), and the combined organic layers were dried over sodium sulfate, filtered, and concentrated in vacuo. After the residue had been repeatedly diluted and concentrated under reduced pressure, using a mixture of dichloromethane and heptane (1:1, 3×10 mL), it was purified using silica gel chromatography (Gradient: 0% to 12% methanol in dichloromethane), affording a white solid (925 mg). Most of this material (900 mg) was dissolved in ethyl acetate (4.5 mL) at 55° C. and treated drop-wise with heptane (1.5 mL); the resulting mixture was maintained at 50° C. for 12 hours, then at room temperature for 4 hours. Collection of the precipitate, followed by washing of the filter cake with a 2:1 mixture of ethyl acetate and heptane, provided (4R)-4-(3-chloro-2-fluorophenyl)-5-fluoro-6-({1-[(1 S,2S)-2-fluorocyclopropane-1-carbonyl]azetidin-3-yl}amino)-2-(3-fluoropyridin-2-yl)-4-methyl-3,4-dihydro-2,7-naphthyridin-1(2H)-one (6) as a white solid. Yield: 650 mg, 1.16 mmol, 60% over 2 steps. LCMS m/z 560.4 (chlorine isotope pattern observed) $[M+H]^+$. $^1H$ NMR (400 MHz, DMSO-$d_6$) δ 8.56 (s, 1H), 8.30 (br d, J=4.7 Hz, 1H), 8.06 (br t, J=7.4 Hz, 1H), 7.80 (t, J=9.1 Hz, 1H), 7.59 (t, J=7.5 Hz, 1H), 7.49-7.39 (m, 2H), 7.29 (t, J=8.0 Hz, 1H),

[4.97-4.89 (m) and 4.85-4.71 (m), total 2H], 4.55 (dt, J=35.3, 8.2 Hz, 1H), 4.35 (d, J=12.9 Hz, 1H), 4.23-4.10 (m, 2H), 3.98-3.84 (m, 1H), 3.84 (d, J=13.2 Hz, 1H), 1.88 (s, 3H), 1.87-1.72 (m, 1H), 1.57-1.42 (m, 1H), 1.08-0.95 (m, 1H).

Example 7

(4R)-4-(3-Chloro-2-fluorophenyl)-5-fluoro-2-(4-fluoro-1-methyl-1H-pyrazol-3-yl)-6-{[1-(1-hydroxycyclobutane-1-carbonyl)azetidin-3-yl]amino}-4-methyl-3,4-dihydro-2,7-naphthyridin-1(2H)-one (7)

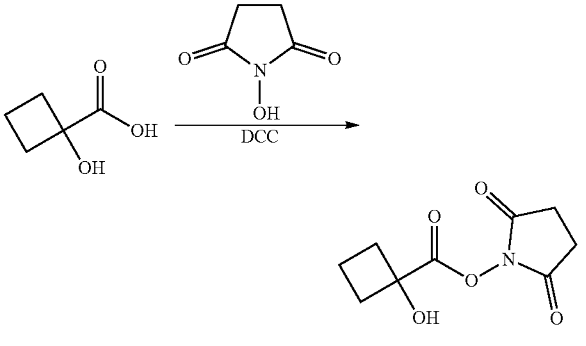

C68

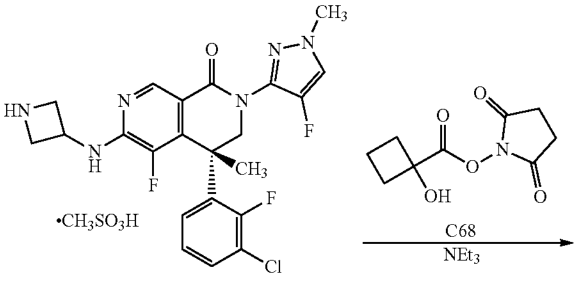

C59, methanesulfonate salt

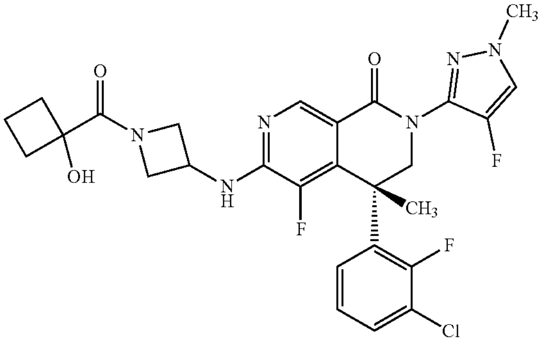

7

Step 1. Synthesis of 1-[(1-hydroxycyclobutane-1-carbonyl)oxy]pyrrolidine-2,5-dione (C68)

To a solution of 1-hydroxycyclobutane-1-carboxylic acid (52.4 mg, 0.451 mmol) in tetrahydrofuran (2.0 mL) were added 1-hydroxypyrrolidine-2,5-dione (57.1 mg, 0.496 mmol) and 1,3-dicyclohexylcarbodiimide (DCC; 102 mg, 0.494 mmol). The reaction mixture was stirred at 25° C. for 8 hours to provide a solution containing C68; this crude reaction mixture was used directly for the following step.

Step 2. Synthesis of (4R)-4-(3-chloro-2-fluorophenyl)-5-fluoro-2-(4-fluoro-1-methyl-1H-pyrazol-3-yl)-6-{[1-(1-hydroxycyclobutane-1-carbonyl)azetidin-3-yl]amino}-4-methyl-3,4-dihydro-2,7-naphthyridin-1(2H)-one (7)

To a 0° C. mixture of C59, methanesulfonate salt (199 mg, 0.347 mmol) in acetonitrile (3.0 mL) were added triethylamine (352 mg, 3.48 mmol) and a solution of C68 in tetrahydrofuran (from the previous step; 50.451 mmol of C68 in 2 mL of tetrahydrofuran). After the reaction mixture had been stirred at room temperature for 16 hours, it was concentrated in vacuo and purified using reversed-phase HPLC (Column: Boston Prime C18, 30×150 mm, 5 µm; Mobile phase A: water containing 0.05% ammonium hydroxide; Mobile phase B: acetonitrile; Gradient: 28% to 58% B; Flow rate: 30 mL/minute) to provide (4R)-4-(3-chloro-2-fluorophenyl)-5-fluoro-2-(4-fluoro-1-methyl-1H-pyrazol-3-yl)-6-{[1-(1-hydroxycyclobutane-1-carbonyl) azetidin-3-yl]amino}-4-methyl-3,4-dihydro-2,7-naphthyridin-1(2H)-one (7) as a white solid. Yield: 118 mg, 0.205 mmol, 59%. LCMS m/z 575.3 (chlorine isotope pattern observed) $[M+H]^+$. $^1H$ NMR (400 MHz, methanol-$d_4$) δ 8.62 (s, 1H), 7.58 (d, J=4.5 Hz, 1H), 7.46 (ddd, J=8.3, 7.0, 1.6 Hz, 1H), 7.34 (br t, J=7.5 Hz, 1H), 7.19 (br t, J=8.0 Hz, 1H), 4.9-4.78 (m, 1H, assumed; partially obscured by water peak), 4.77-4.69 (m, 1H), 4.41-4.24 (m, 2H), 4.35 (d, J=12.7 Hz, 1H), 4.03-3.93 (m, 1H), 3.78 (s, 3H), 3.70 (d, J=12.9 Hz, 1H), 2.65-2.53 (m, 2H), 2.16-2.01 (m, 2H), 1.94 (br s, 3H), 1.91-1.80 (m, 1H), 1.80-1.67 (m, 1H).

Example 8

(4R)-4-(3-Chloro-2-fluorophenyl)-5-fluoro-6-({1-[(1R,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one (8)

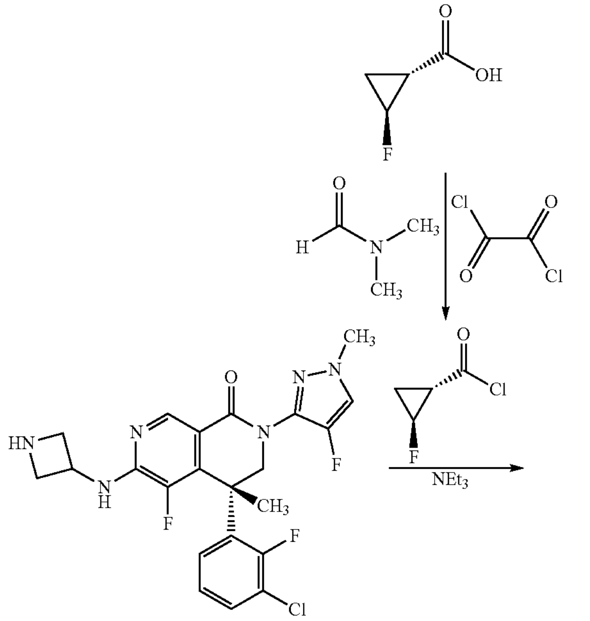

C59

-continued

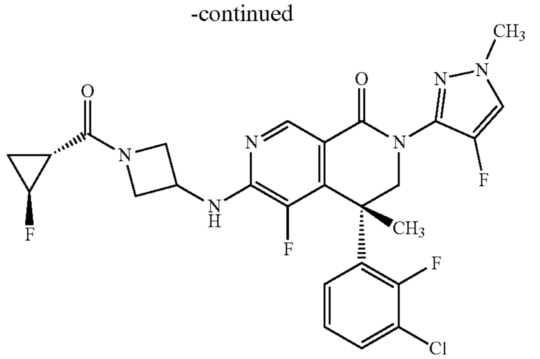

8

Oxalyl chloride (25.4 µL, 0.291 mmol) was added to a 0° C. solution of (1R,2S)-2-fluorocyclopropane-1-carboxylic acid (23.7 mg, 0.228 mmol) and N,N-dimethylformamide (5 mg, 70 µmol) in dichloromethane (1 mL), whereupon the reaction mixture was allowed to warm to 25° C. After 3 hours, triethylamine (31.8 µL, 0.228 mmol) was added, and the resulting mixture was added to a 0° C. solution of C59 (68%, 160 mg, 0.23 mmol) in dichloromethane (1 mL). This reaction mixture was warmed to 25° C., stirred for 16 hours, and then diluted with water. After the aqueous layer had been extracted with dichloromethane (4x2 mL), the combined organic layers were washed with saturated aqueous sodium chloride solution (5 mL) and concentrated in vacuo. Silica gel chromatography (Gradient: 0% to 8% methanol in dichloromethane) followed by reversed-phase HPLC (Column: Waters XBridge C18, 19x100 mm, 5 µm; Mobile phase A: water containing 0.03% ammonium hydroxide; Mobile phase B: acetonitrile containing 0.03% ammonium hydroxide; Gradient: 15% to 55% B; Flow rate: 25 mL/minute) afforded (4R)-4-(3-chloro-2-fluorophenyl)-5-fluoro-6-({1-[(1R,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one (8). Yield: 49.1 mg, 87.2 µmol, 38%. LCMS m/z 563.2 (chlorine isotope pattern observed) [M+H]$^+$. Retention time: 2.61 minutes (Analytical conditions. Column: Waters Atlantis dC18, 4.6x50 mm, 5 µm; Mobile phase A: water containing 0.05% trifluoroacetic acid (v/v); Mobile phase B: acetonitrile containing 0.05% trifluoroacetic acid (v/v); Gradient: 5.0% to 95% B, linear over 4.0 minutes, then 95% B for 1.0 minute; Flow rate: 2 mL/minute.

Examples 9 and 10

(4R)-4-(3-Chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-1 (9) and (4R)-4-(3-Chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-2 (10)

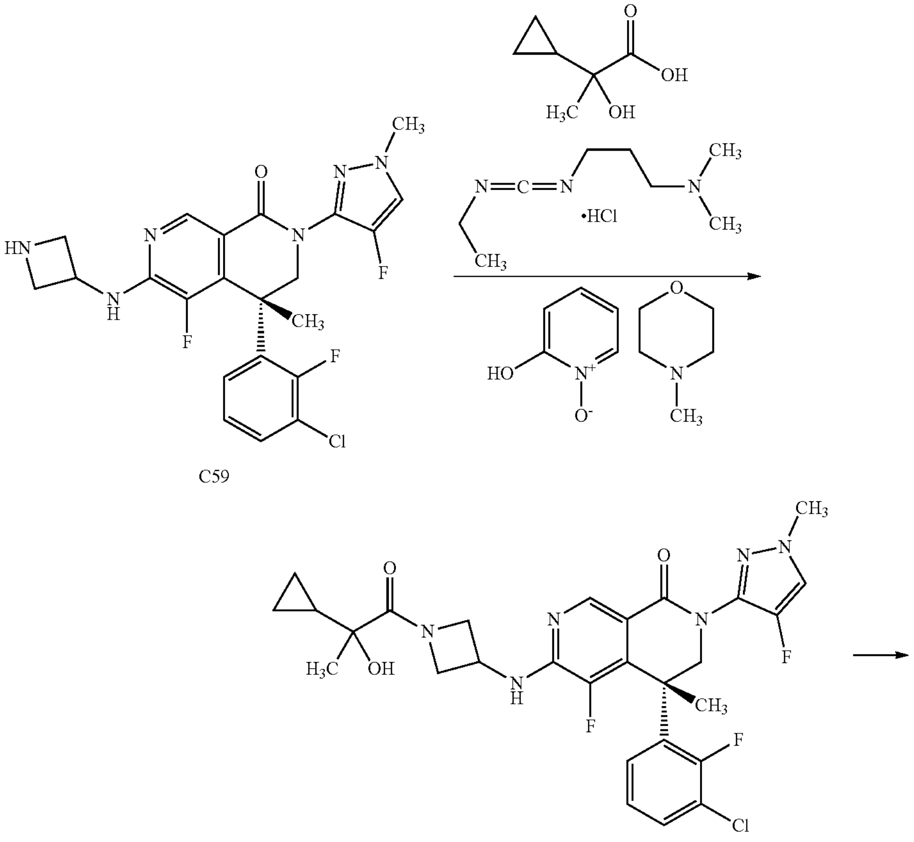

C59

C69

-continued

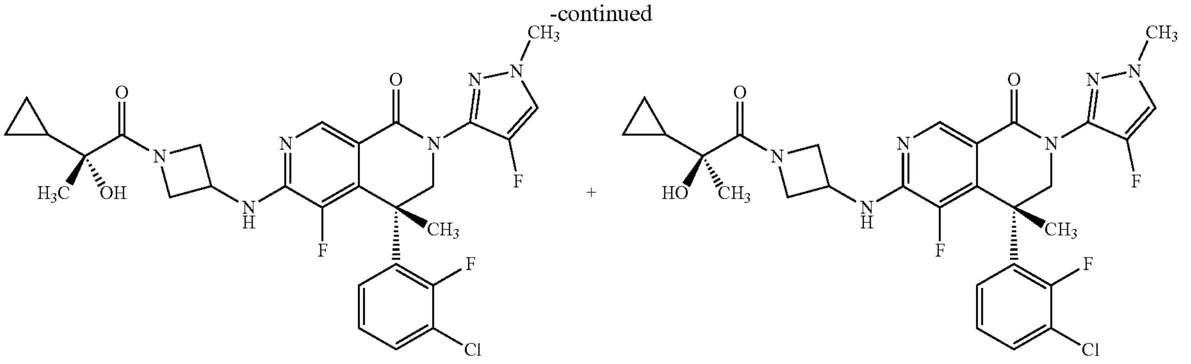

9 (DIAST-1) and 10 (DIAST-2)

Step 1. Synthesis of (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one (C69)

1-[3-(Dimethylamino)propyl]-3-ethylcarbodiimide hydrochloride (140 mg, 0.730 mmol), 2-hydroxypyridine 1-oxide (70 mg, 0.63 mmol) and 4-methylmorpholine (0.200 mL 1.82 mmol) were added to a solution of C59 (90%; 291 mg, 0.549 mmol) in N,N-dimethylacetamide (2.8 mL) at 25° C. After 4 hours, the mixture was diluted with dichloromethane (50 mL), washed with water (3×25 mL), dried over magnesium sulfate, filtered, and concentrated in vacuo; silica gel chromatography (Gradient: 0% to 7% methanol in dichloromethane) afforded C69 as a white foam. Yield: 257 mg, 0.436 mmol, 79%. LCMS m/z 589.4 (chlorine isotope pattern observed) $[M+H]^+$.

Step 2. Isolation of (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-1 (9) and (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-2 (10)

Separation of C69 (1.41 g, 2.39 mmol) into its component diastereomers was carried out via supercritical fluid chromatography {Column: Chiral Technologies Chiralcel OZ, 30×250 mm, 5 μm; Mobile phase: 55:45 carbon dioxide/[methanol containing 0.2% (7 M ammonia in methanol)]; Back pressure: 100 bar, Flow rate: 80 mL/minute}. The first-eluting diastereomer was designated as 9, and the second-eluting diastereomer as 10; both (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-1 (9) and (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-2 (10) were obtained as white solids.

9 (DIAST-1)—Yield: 620 mg, 1.05 mmol, 44%. The isolated material was treated with ethyl acetate (6 mL) and heated to 50° C. After 30 minutes, the solid was collected via filtration and rinsed with ethyl acetate (1×6 mL), affording (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-1 (9) as a white solid. Yield: 339 mg, 0.576 mmol, 24%. LCMS m/z 589.3 (chlorine isotope pattern observed) $[M+H]^+$. $^1H$ NMR (400 MHz, methanol-$d_4$) δ 8.62 (s, 1H), 7.58 (d, J=4.5 Hz, 1H), 7.47 (br t, J=7.4 Hz, 1H), 7.34 (br t, J=7.6 Hz, 1H), 7.20 (br t, J=8.0 Hz, 1H), 4.93-4.76 (m, 2H, assumed; partially obscured by water peak), 4.49-4.30 (m, 2H), 4.36 (d, J=12.9 Hz, 1H), 4.03-3.92 (m, 1H), 3.78 (s, 3H), 3.70 (d, J=12.9 Hz, 1H), 1.94 (s, 3H), 1.36 (d, J=5.6 Hz, 3H), 1.26-1.15 (m, 1H), 0.55-0.46 (m, 1H), 0.46-0.29 (m, 3H). Retention time: 5.70 minutes [Analytical conditions. Column: Chiral Technologies Chiralcel OZ, 4.6×250 mm, 5 μm; Mobile phase A: carbon dioxide; Mobile phase B: methanol containing 0.2% (7 M ammonia in methanol); Gradient: 5% B for 1.00 minute, then 5% to 100% B over 5.00 minutes, then 100% B; Back pressure: 120 bar, Flow rate: 3.0 mL/minute].

10 (DIAST-2)—Yield: 590 mg, 1.00 mmol, 42%. Retention time: 6.03 minutes (Analytical conditions identical to those used for 9).

Example 11

2-(3-{[(5R)-5-(3-Chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-cyclopropyl-N-methylacetamide (11)

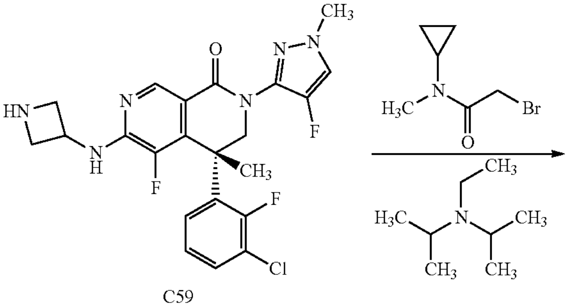

C59

-continued

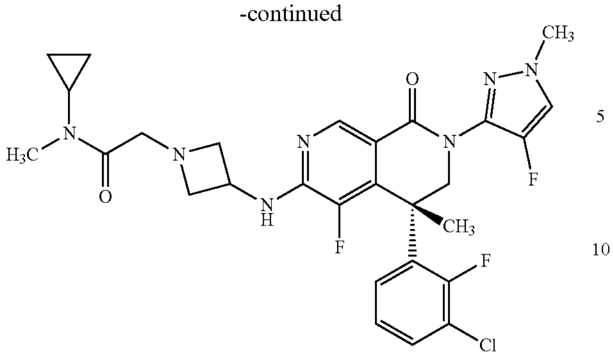

11

2-Bromo-N-cyclopropyl-N-methylacetamide (7.99 mg, 41.6 μmol) was added to a solution of C59 (24.8 mg, 52.0 μmol) and N,N-diisopropylethylamine (10.1 mg, 78.1 μmol) in dichloromethane (2 mL). After 16 hours, the mixture was concentrated in vacuo and purified using reversed-phase HPLC (Column: Boston Prime C18, 30×150 mm, 5 μm; Mobile phase A: water containing 0.05% ammonium hydroxide; Mobile phase B: acetonitrile; Gradient: 23% to 53% B; Flow rate: 30 mL/minute), affording 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-cyclopropyl-N-methylacetamide (11) as a white solid. Yield: 4.27 mg, 7.26 μmol, 17%. LCMS m/z 588.2 (chlorine isotope pattern observed) $[M+H]^+$. $^1H$ NMR (400 MHz, methanol-$d_4$) δ 8.60 (s, 1H), 7.58 (d, J=4.5 Hz, 1H), 7.47 (br t, J=7.8 Hz, 1H), 7.35 (br t, J=7.7 Hz, 1H), 7.20 (br t, J=8.1 Hz, 1H), 4.85-4.71 (m, 1H, assumed; partially obscured by water peak), 4.35 (d, J=12.9 Hz, 1H), 3.98-3.84 (m, 2H), 3.78 (s, 3H), 3.72-3.62 (m, 3H), 3.3-3.21 (m, 2H, assumed; partially obscured by solvent peak), 2.89 (s, 3H), 2.77-2.69 (m, 1H), 1.93 (s, 3H), 0.93-0.85 (m, 2H), 0.82-0.74 (m, 2H).

Example 12

(4R)-4-(3-Chloro-2-fluorophenyl)-5-fluoro-2-(4-fluoro-1-methyl-1H-pyrazol-3-yl)-4-methyl-6-({1-[(pyrrolidin-1-γl)acetyl]azetidin-3-yl}amino)-3,4-dihydro-2,7-naphthyridin-1(2H)-one (12)

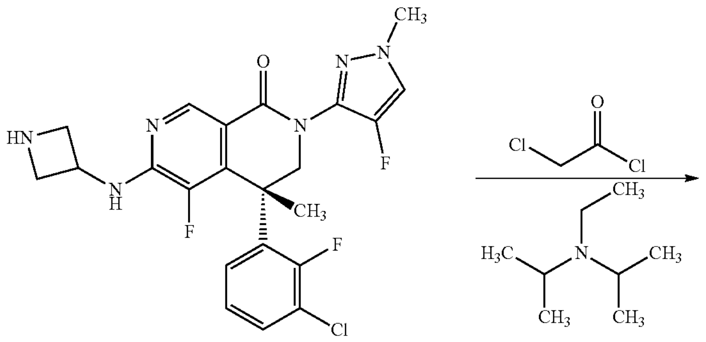

C59

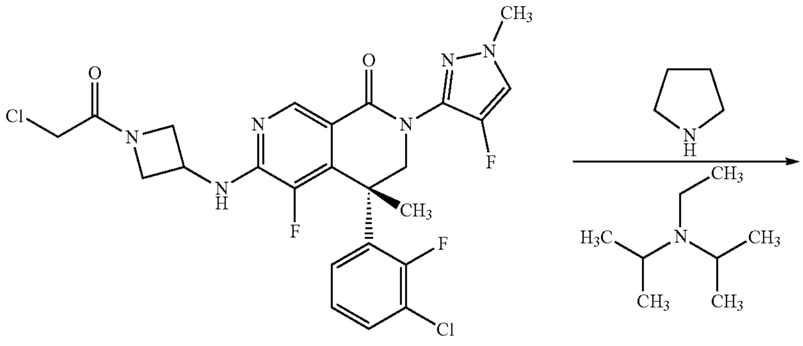

C70

-continued

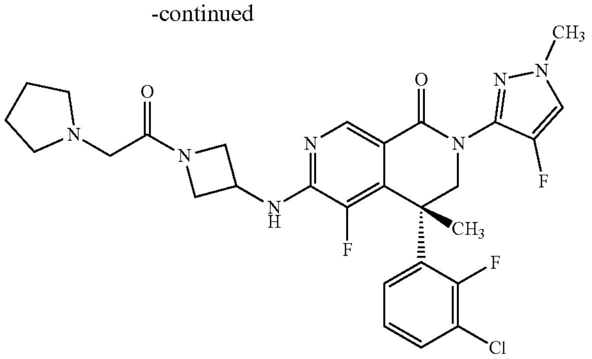

12

Step 1. Synthesis of (4R)-6-{[1-(chloroacetyl)azetidin-3-yl]amino}-4-(3-chloro-2-fluorophenyl)-5-fluoro-2-(4-fluoro-1-methyl-1H-pyrazol-3-yl)-4-methyl-3,4-dihydro-2,7-naphthyridin-1(2H)-one (C70)

Chloroacetyl chloride (0.230 mL, 2.89 mmol) was added to a 0° C. solution of C59 (90%; 1.35 g, 2.55 mmol) and N,N-diisopropylethylamine (1.33 mL, 7.64 mmol) in dichloromethane (26 mL). After 5 minutes, the reaction mixture was allowed to warm to 25° C., and 3 hours later, additional chloroacetyl chloride (70 μL, 0.88 mmol) was added. After 16 hours, the reaction mixture was diluted with water (25 mL) and dichloromethane (25 mL). The organic layer was treated with saturated aqueous ammonium chloride solution (25 mL) and the mixture was passed through a pad of diatomaceous earth; the organic layer was then dried over magnesium sulfate, filtered, and concentrated in vacuo. Purification via silica gel chromatography (Gradient: 2% to 5.5% methanol in dichloromethane) afforded C70 as a tan foam. Yield: 851 mg, 1.54 mmol, 60%. LCMS m/z 553.2 (dichloro isotope pattern observed) $[M+H]^+$. $^1H$ NMR (400 MHz, DMSO-$d_6$) δ 8.51 (s, 1H), 8.00 (br d, J=5.8 Hz, 1H), 7.82 (d, J=4.5 Hz, 1H), 7.59 (t, J=7.4 Hz, 1H), 7.41 (t, J=7.6 Hz, 1H), 7.27 (t, J=8.0 Hz, 1H), 4.81-4.70 (m, 1H), 4.52 (t, J=8.3 Hz, 1H), 4.26-4.18 (m, 2H), 4.17-4.01 (m, 3H), 4.01-3.88 (m, 1H) 3.76-3.67 (m, 4H), 1.85 (s, 3H).

Step 2. Synthesis of (4R)-4-(3-chloro-2-fluorophenyl)-5-fluoro-2-(4-fluoro-1-methyl-1H-pyrazol-3-yl)-4-methyl-6-({1-[(pyrrolidin-1-γl)acetyl]azetidin-3-yl}amino)-3,4-dihydro-2,7-naphthyridin-1(2H)-one (12)

Pyrrolidine (0.162 mL, 1.94 mmol) was added to a solution of C70 (365 mg, 0.660 mmol) and N,N-diisopropylethylamine (0.345 mL, 1.98 mmol) in N,N-dimethylformamide (3.2 mL). After 90 minutes, the reaction mixture was diluted with water (20 mL) and extracted with ethyl acetate (30 mL), whereupon the organic layer was washed with saturated aqueous sodium chloride solution (20 mL), dried over magnesium sulfate, filtered, and concentrated in vacuo. The residue was eluted through a plug of silica gel (3 g) using 7% methanol in dichloromethane (60 mL), providing a beige solid. This solid was layered with ethyl acetate (5 mL), heated to 45° C., and treated with heptane (60 uL). After 2 hours, the resulting solid was collected via filtration and washed with ethyl acetate (3×2 mL), affording (4R)-4-(3-chloro-2-fluorophenyl)-5-fluoro-2-(4-fluoro-1-methyl-1H-pyrazol-3-yl)-4-methyl-6-({1-[(pyrrolidin-1-γl)acetyl]azetidin-3-yl}amino)-3,4-dihydro-2,7-naphthyridin-1(2H)-one (12) as a white solid. Yield: 245 mg, 0.417 mmol, 63%. LCMS m/z 588.4 (chlorine isotope pattern observed) $[M+H]^+$. $^1H$ NMR (400 MHz, methanol-$d_4$) δ 8.62 (s, 1H), 7.58 (d, J=4.4 Hz, 1H), 7.47 (t, J=7.4 Hz, 1H), 7.40-7.31 (m, 1H), 7.20 (t, J=8.0 Hz, 1H), 4.93-4.85 (m, 1H, assumed; partially obscured by water peak), 4.61 (t, J=8.6 Hz, 1H), 4.41-4.32 (m, 2H), 4.23-4.11 (m, 1H), 4.04-3.93 (m, 1H), 3.78 (s, 3H), 3.69 (d, J=12.9 Hz, 1H), 3.24 (s, 2H), 2.70-2.60 (m, 4H), 1.94 (s, 3H), 1.86-1.76 (m, 4H).

Example 13

(4R)-4-(3-Chloro-2-fluorophenyl)-5-fluoro-2-(4-fluoro-1-methyl-1H-pyrazol-3-yl)-4-methyl-6-[(1-{[(propan-2-γl)amino]acetyl}azetidin-3-γl)amino]-3,4-dihydro-2,7-naphthyridin-1(2H)-one (13)

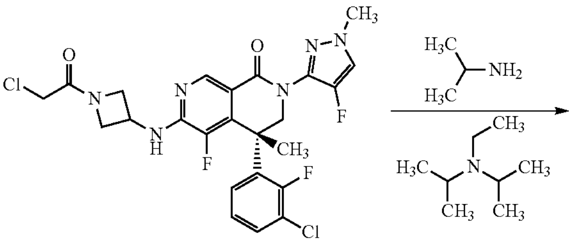

C70

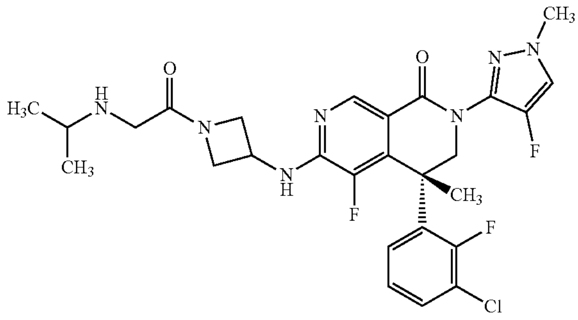

13

Propan-2-amine (0.300 mL, 3.52 mmol) was added to a solution of C70 (634 mg, 1.15 mmol) and N,N-diisopropylethylamine (0.600 mL, 3.44 mmol) in N,N-dimethylformamide (6 mL). After 1 hour, propan-2-amine (0.300 mL, 3.52 mmol) was again added. After 3 hours, the reaction mixture was diluted with water (20 mL) and extracted with ethyl acetate (30 mL); the organic layer was washed with saturated aqueous sodium chloride solution (20 mL), dried over magnesium sulfate, filtered, concentrated in vacuo, diluted with heptane (20 mL) and concentrated again. The residue was passed through a plug of silica gel (4 g), eluting with 10% methanol in dichloromethane (150 mL). The resulting solid was layered with ethanol (4 mL), heated to 45° C. for 8 hours, and allowed to cool to 25° C. After an additional 8 hours, the solid was collected via filtration and washed with ethanol (2×3 mL), providing (4R)-4-(3-chloro-2-fluorophenyl)-5-fluoro-2-(4-fluoro-1-methyl-1H-pyrazol-3-yl)-4-methyl-6-[(1-{[(propan-2-γ1)amino]acetyl}azetidin-3-γ1)amino]-3,4-dihydro-2,7-naphthyridin-1(2H)-one (13) as a beige solid. Yield: 281 mg, 0.488 mmol, 42%. LCMS m/z 576.4 (chlorine isotope pattern observed) $[M+H]^+$. $^1H$ NMR (400 MHz, methanol-$d_4$) δ 8.63 (s, 1H), 7.59 (d, J=4.5 Hz, 1H), 7.47 (t, J=7.4 Hz, 1H), 7.41-7.32 (m, 1H), 7.20 (t, J=8.0 Hz, 1H), 4.98-4.89 (m, 1H), 4.57 (t, J=8.5 Hz, 1H), 4.43-4.32 (m, 2H), 4.20-4.09 (m, 1H), 4.06-3.95 (m, 1H), 3.78 (s, 3H), 3.70 (d, J=12.9 Hz, 1H), 3.27 (s, 2H), 2.87-2.76 (m, 1H), 1.94 (s, 3H), 1.09 (d, J=6.3 Hz, 6H).

Example 14

(4R)-2-[4-(Aminomethyl)-2,5-difluorophenyl]-4-(3-chloro-2-fluorophenyl)-5-fluoro-6-({1-[(1 S,2S)-2-fluorocyclopropane-1-carbonyl]azetidin-3-yl}amino)-4-methyl-3,4-dihydro-2,7-naphthyridin-1(2H)-one, partial formate salt (0.5 equivalents) (14)

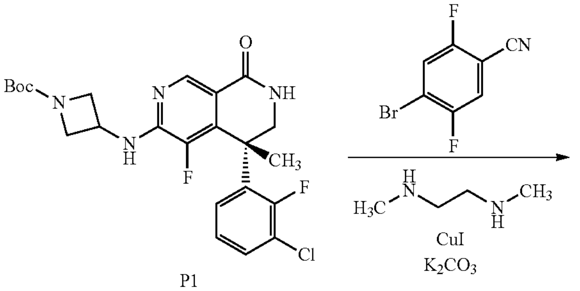

P1

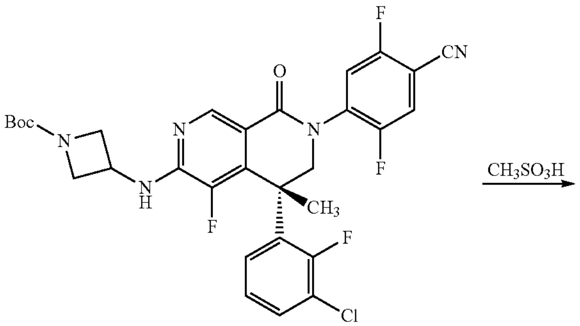

C71

-continued

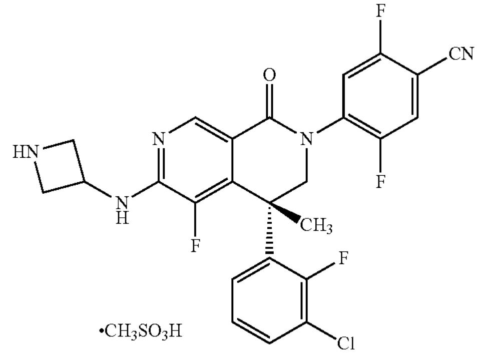

C72

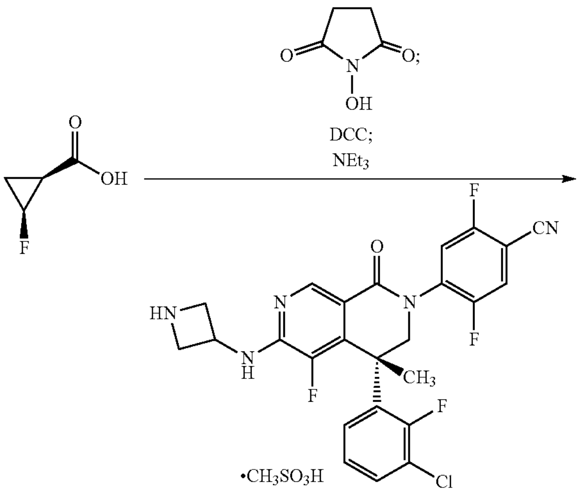

C72

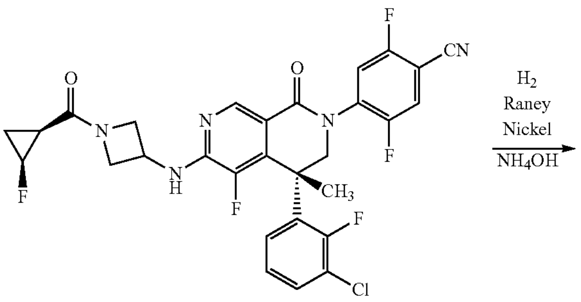

C73

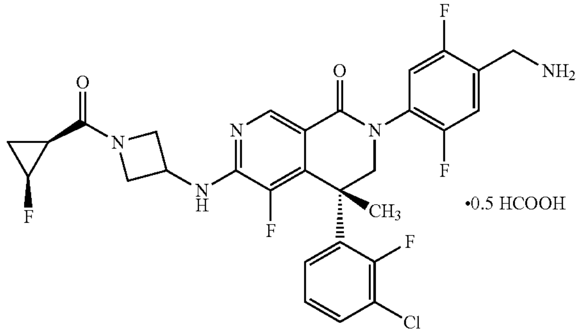

14

Step 1. Synthesis of tert-butyl 3-{[(5R)-5-(3-chloro-2-fluorophenyl)-7-(4-cyano-2,5-difluorophenyl)-4-fluoro-5-methyl-8-oxo-5,6,7,8-tetrahydro-2,7-naphthyridin-3-yl]amino}azetidine-1-carboxylate (C71)

A mixture of P1 (500 mg, 1.04 mmol), potassium carbonate (433 mg, 3.13 mmol), and copper(I) iodide (298 mg, 1.56 mmol) was treated with 1,4-dioxane (10 mL), 4-bromo-2,5-difluorobenzonitrile (455 mg, 2.09 mmol), and $N^1,N^2$-dimethylethane-1,2-diamine (138 mg, 1.57 mmol). After the reaction mixture had been heated at 100° C. for 16 hours, additional 4-bromo-2,5-difluorobenzonitrile (228 mg, 1.05 mmol) was added; stirring was continued at 100° C. for 14 hours, whereupon the reaction mixture was allowed to cool to 25° C. and diluted with water (20 mL). The aqueous layer was extracted with ethyl acetate (3×15 mL), and the combined organic layers were washed with saturated aqueous sodium chloride solution (20 mL), dried over sodium sulfate, filtered, and concentrated in vacuo. Silica gel chromatography (Gradient: 0% to 80% ethyl acetate in heptane) provided C71 as a yellow solid. Yield: 350 mg, 0.568 mmol, 55%. LCMS m/z 616.1 (chlorine isotope pattern observed) $[M+H]^+$.

Step 2. Synthesis of 4-[(4R)-6-[(azetidin-3-γl) amino]-4-(3-chloro-2-fluorophenyl)-5-fluoro-4-methyl-1-oxo-3,4-dihydro-2,7-naphthyridin-2(1H)-yl]-2,5-difluorobenzonitrile, methanesulfonate salt (C72)

Methanesulfonic acid (406 mg, 4.22 mmol) was added to a 15° C. solution of C71 (520 mg, 0.844 mmol) in 1,1,1,3,3,3-hexafluoropropan-2-ol (10 mL). After 15 minutes, the resulting mixture, containing C72, was used in the following step.

Step 3. Synthesis of 4-[(4R)-4-(3-chloro-2-fluorophenyl)-5-fluoro-6-({1-[(1S,2S)-2-fluorocyclopropane-1-carbonyl]azetidin-3-yl}amino)-4-methyl-1-oxo-3,4-dihydro-2,7-naphthyridin-2(1)-yl]-2,5-difluorobenzonitrile (C73)

1,3-Dicyclohexylcarbodiimide (DCC; 317 mg, 1.54 mmol) was added to a 25° C. solution of 1-hydroxypyrrolidine-2,5-dione (195 mg, 1.69 mmol) and (1S,2S)-2-fluorocyclopropane-1-carboxylic acid (160 mg, 1.54 mmol) in tetrahydrofuran (10 mL). After 2 hours, the reaction mixture was cooled to 15° C. and treated with a solution of C72 in 1,1,1,3,3,3-hexafluoropropan-2-ol (10 mL) (from the previous step; 50.844 mmol of C72), followed by triethylamine (1.17 mL, 8.39 mmol), whereupon stirring was continued for 16 hours. The reaction mixture was concentrated in vacuo; silica gel chromatography (Gradient: 0% to 10% methanol in dichloromethane) afforded a yellow solid, LCMS m/z 624.1 (chlorine isotope pattern observed) $[M+Na]^+$. This material was further purified via silica gel chromatography (Gradient: 0% to 100% ethyl acetate in petroleum ether), providing C73 as a yellow solid. Yield: 400 mg, 0.664 mmol, 79% over 2 steps. $^1H$ NMR (400 MHz, methanol-$d_4$), characteristic peaks: δ 8.64 (d, J=1.6 Hz, 1H), 7.72 (dd, J=9.4, 5.7 Hz, 1H), 7.53-7.44 (m, 2H), 7.43-7.35 (m, 1H), 7.22 (t, J=8.0 Hz, 1H), 4.50-4.31 (m, 2H), 4.32-4.20 (m, 1H), 4.06-3.95 (m, 1H), 3.75-3.65 (m, 1H), 1.96 (s, 3H).

Step 4. Synthesis of (4R)-2-[4-(aminomethyl)-2,5-difluorophenyl]-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one, partial formate salt (0.5 equivalents) (14)

Raney nickel (300 mg, 0.51 mmol) was added to a 25° C. solution of C73 (370 mg, 0.615 mmol) and aqueous ammonium hydroxide solution (28%, 1 mL, 7.2 mmol) in a mixture of tetrahydrofuran (10 mL) and methanol (10 mL). After the reaction mixture had been hydrogenated (15 psi) for 2 hours, dichloromethane (10 mL), tetrahydrofuran (10 mL), and methanol (10 mL) were added, and the mixture was allowed to stir for 1 hour. It was then filtered; the filtrate was concentrated in vacuo and purified via reversed-phase HPLC (Column: Phenomenex C18, 30×150 mm, 5 μm; Mobile phase A: water containing 0.05% formic acid; Mobile phase B: acetonitrile; Gradient: 18% to 38% B; Flow rate: 35 mL/minute), affording (4R)-2-[4-(aminomethyl)-2,5-difluorophenyl]-4-(3-chloro-2-fluorophenyl)-5-fluoro-6-({1-[(1 S,2S)-2-fluorocyclopropane-1-carbonyl]azetidin-3-yl}amino)-4-methyl-3,4-dihydro-2,7-naphthyridin-1(2H)-one, partial formate salt (0.5 equivalents) (14) as a white solid. Yield: 194 mg, 0.308 mmol, 50%. LCMS m/z 606.3 (chlorine isotope pattern observed) $[M+H]^+$. $^1H$ NMR (400 MHz, methanol-$d_4$) δ 8.63 (d, J=1.5 Hz, 1H), 8.54 (br s, 0.5H), 7.51-7.46 (m, 1H), 7.39-7.28 (m, 2H), 7.25-7.16 (m, 2H), 5.00-4.88 (m, 2H, assumed; partially obscured by water peak), 4.74-4.64 (m, 1H), 4.48-4.32 (m, 2H), 4.32-4.21 (m, 1H), 4.05 (s, 2H), 4.05-3.96 (m, 1H), 3.72-3.65 (m, 1H), 1.97 (s, 3H), 1.90-1.75 (m, 1H), 1.75-1.57 (m, 1H), 1.16-1.03 (m, 1H).

Example 15

(4R)-2-(5-Aminopyridin-2-yl)-4-(3-chloro-2-fluorophenyl)-5-fluoro-6-({1-[(1 S,2S)-2-fluorocyclopropane-1-carbonyl]azetidin-3-yl}amino)-4-methyl-3,4-dihydro-2,7-naphthyridin-1(2H)-one (15)

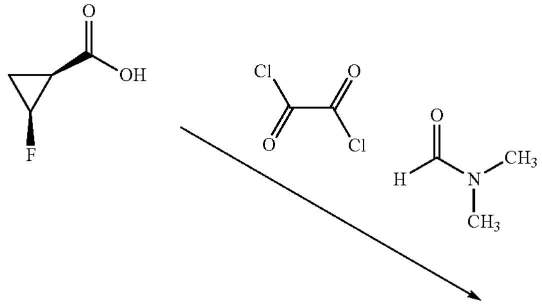

-continued

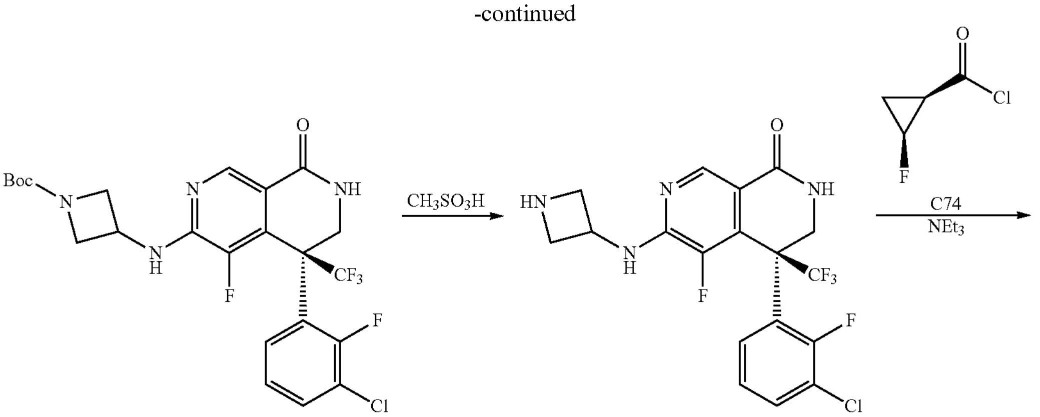

P1 C64

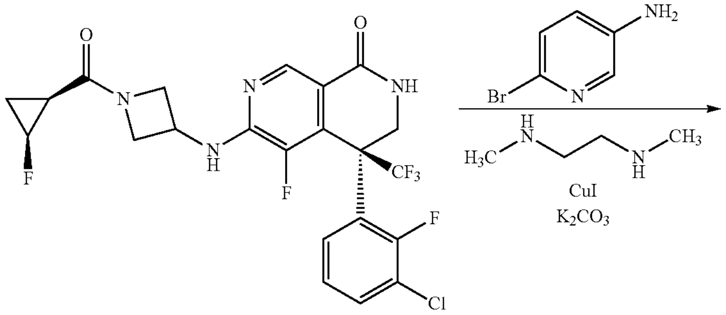

C75

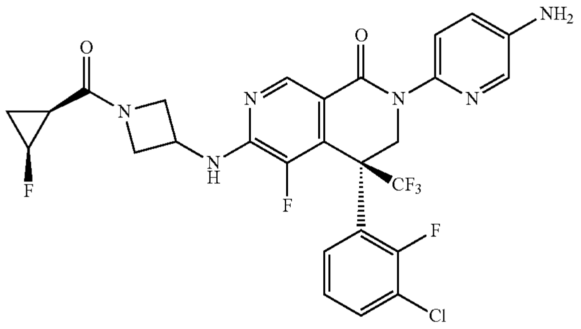

15

Step 1. Synthesis of (4R)-6-[(azetidin-3-γl)amino]-4-(3-chloro-2-fluorophenyl)-5-fluoro-4-methyl-3,4-dihydro-2,7-naphthyridin-1(2H)-one (C64)

Methanesulfonic acid (2.71 mL, 41.8 mmol) was added to a solution of P1 (2.00 g, 4.18 mmol) in 1,1,1,3,3,3-hexafluoropropan-2-ol (40 mL). After 20 minutes, the reaction mixture was concentrated under reduced pressure and diluted with water (20 mL); the pH was then adjusted to >9 by addition of 1 M aqueous sodium hydroxide solution. Dichloromethane (30 mL) was added, and the resulting mixture was filtered through a pad of diatomaceous earth. The aqueous layer of the filtrate was extracted with dichloromethane (3x30 mL), and the combined organic layers were dried over magnesium sulfate, filtered, and concentrated in vacuo to afford C64 as a white foam (2.5 g), which was used directly in the following step. LCMS m/z 379.3 (chlorine isotope pattern observed) $[M+H]^+$.

Step 2. Synthesis of (4R)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one (C75)

Oxalyl chloride (537 μL, 6.16 mmol) was added to a 0° C. solution of (1S,2S)-2-fluorocyclopropane-1-carboxylic acid (565 mg, 5.43 mmol) and N,N-dimethylformamide (40 μL, 0.52 mmol) in dichloromethane (20 mL). After the reaction mixture had been stirred at 15° C. for 1.5 hours, it was cooled to 0° C. and treated with triethylamine (2.35 mL, 16.9 mmol). The resulting mixture, containing (1R,2S)-2-fluorocyclopropane-1-carbonyl chloride (C74), was added to a 0° C. solution of C64 (from the previous step; 54.18 mmol) in dichloromethane (20 mL). The reaction mixture was stirred at 15° C. for 17 hours, whereupon the solid was collected via filtration and washed with dichloromethane (20 mL) to provide C75 as a beige solid. Yield: 1.48 g, 3.18 mmol, 76% over 2 steps. LCMS m/z 465.3 (chlorine isotope pattern observed) $[M+H]^+$. $^1$H NMR (400 MHz, DMSO-$d_6$) δ 8.42 (d, J=1.8 Hz, 1H), 7.90 (br s, 1H), 7.86-7.78 (m, 1H), 7.62-7.53 (m, 1H), 7.40-7.31 (m, 1H), 7.26 (t, J=8.0 Hz, 1H), [4.96-4.89 (m) and 4.81-4.68 (m), total 2H], 4.61-4.45 (m, 1H), 4.21-4.08 (m, 2H), 3.94-3.81 (m, 1H), 3.70 (d, J=12.8 Hz, 1H), 3.20 (br d, J=12.8 Hz, 1H), 1.85-1.72 (m, 1H), 1.77 (s, 3H), 1.56-1.42 (m, 1H), 1.06-0.95 (m, 1H).

Step 3. Synthesis of (4R)-2-(5-aminopyridin-2-yl)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one (15)

A mixture of C75 (79%, 1.24 g, 2.11 mmol), 6-bromopyridin-3-amine (438 mg, 2.53 mmol), potassium carbonate (874 mg, 6.32 mmol), and copper(I) iodide (401 mg, 2.11 mmol) was treated with 1,4-dioxane (22 mL) and butan-1-ol (11 mL). The resulting mixture was sparged with nitrogen for 10 minutes, treated with $N^1$,$N^2$-dimethylethane-1,2-diamine (454 μL, 4.26 mmol), and heated to 85° C. After 18 hours, the reaction mixture was allowed to cool to 25° C. and diluted with saturated aqueous ammonium chloride solution (5 mL) and water (5 mL). Ethyl acetate (20 mL) was added, and the mixture was filtered through a pad of diatomaceous earth. The aqueous layer was extracted with ethyl acetate (2×20 mL), and the combined organic layers were washed sequentially with saturated aqueous ammonium chloride solution (50 mL) and saturated aqueous sodium chloride solution (100 mL), dried over magnesium sulfate, filtered, and concentrated in vacuo. Silica gel chromatography (Gradient: 0% to 10% ethanol in dichloromethane) provided material that was then treated with a solution of 16% heptane in 2-methyltetrahydrofuran (3.1 mL) and heated to 45° C. After 18 hours, filtration and rinsing of the collected solids with a solution of 16% heptane in 2-methyltetrahydrofuran (2×3 mL) provided (4R)-2-(5-aminopyridin-2-yl)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one (15) as a beige solid. Yield: 374 mg, 0.671 mmol, 32%. LCMS m/z 557.4 (chlorine isotope pattern observed) $[M+H]^+$. $^1H$ NMR (400 MHz, DMSO-$d_6$) δ 8.54 (d, J=1.7 Hz, 1H), 7.97-7.90 (m, 1H), 7.72 (d, J=2.9 Hz, 1H), 7.61-7.55 (m, 1H), 7.44-7.37 (m, 1H), 7.34 (br d, J=8.8 Hz, 1H), 7.27 (t, J=8.0 Hz, 1H), 6.96 (dd, J=8.7, 2.9 Hz, 1H), 5.28 (br s, 2H), [4.96-4.90 (m) and 4.82-4.72 (m), total 2H], 4.63-4.47 (m, 1H), 4.31 (d, J=13.2 Hz, 1H), 4.23-4.11 (m, 2H), 3.97-3.84 (m, 2H), 1.86-1.73 (m, 1H), 1.82 (s, 3H), 1.56-1.43 (m, 1H), 1.07-0.96 (m, 1H).

Examples 16 and 17

(4R)-4-(3-Chloro-2-fluorophenyl)-5-fluoro-4-methyl-2-{5-[(3S)-morpholin-3-yl]pyridin-2-yl}-6-{[1-(pyridazine-3-carbonyl)azetidin-3-yl]amino}-3,4-dihydro-2,7-naphthyridin-1(2H)-one [from C79 (DIAST-1)] (16) and (4R)-4-(3-Chloro-2-fluorophenyl)-5-fluoro-4-methyl-2-{5-[(3R)-morpholin-3-yl]pyridin-2-yl}-6-{[1-(pyridazine-3-carbonyl)azetidin-3-yl]amino}-3,4-dihydro-2,7-naphthyridin-1(2H)-one [from C80 (DIAST-2)] (17)

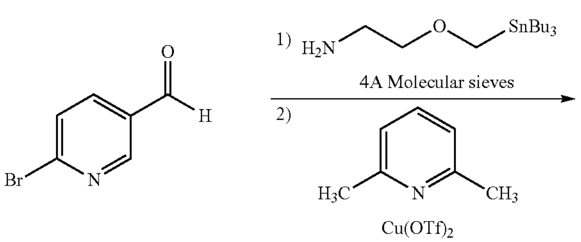

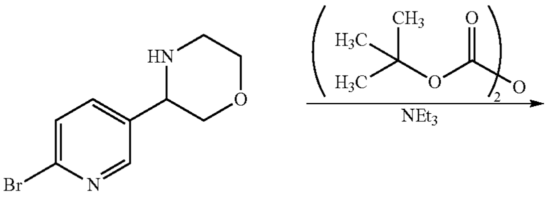

C76

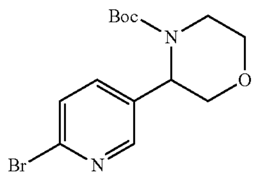

C77

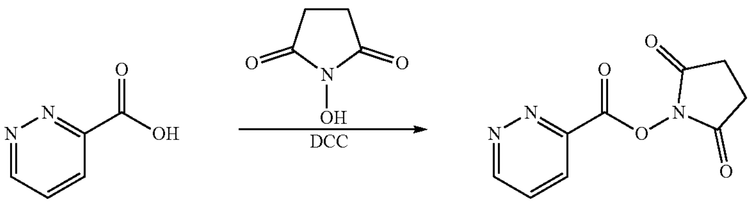

C78

-continued
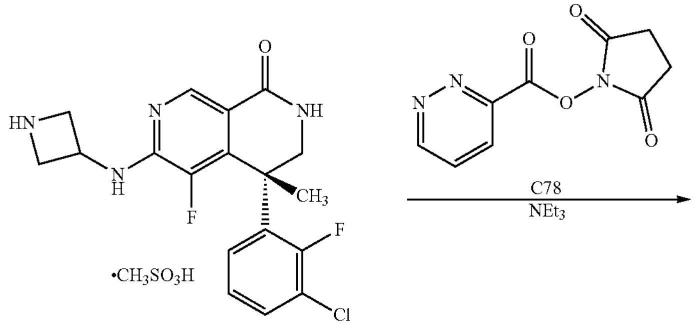
C64, methanesulfonate salt
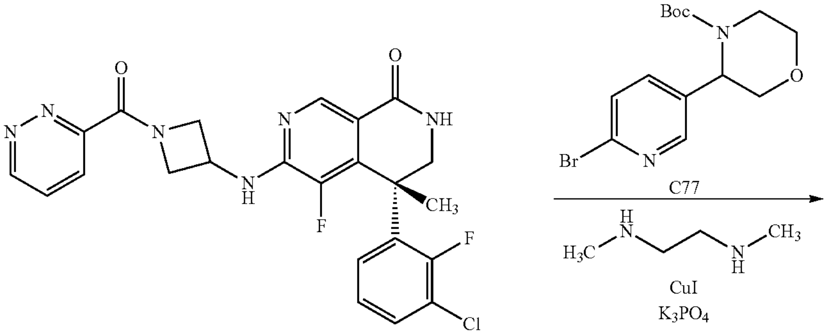
C65
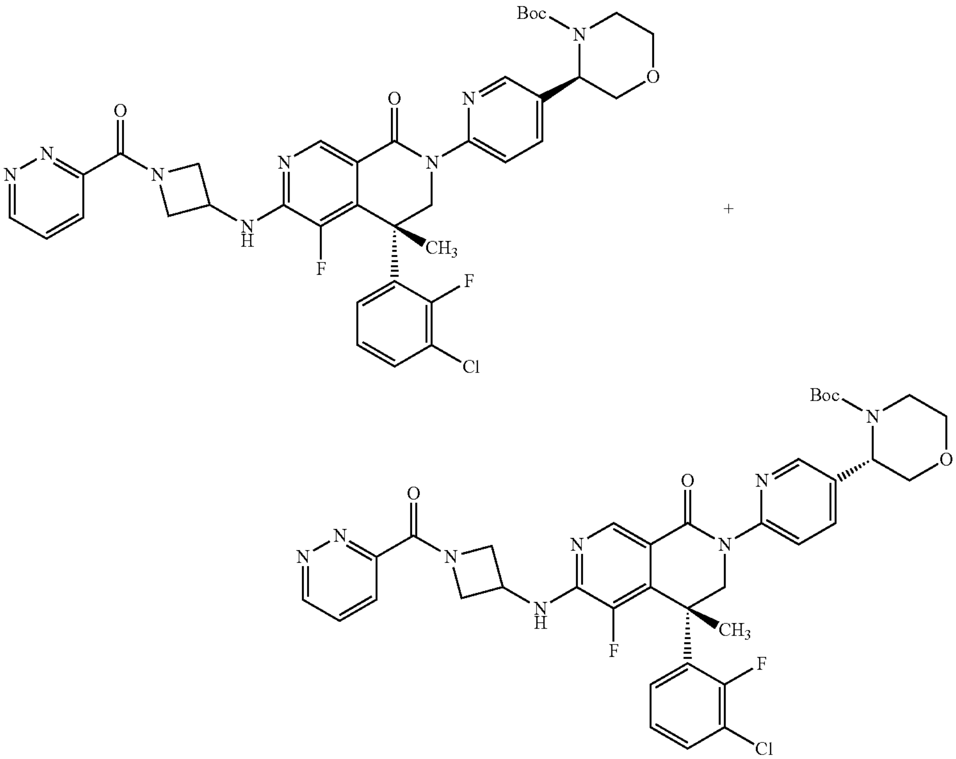
C79 (DIAST-1) and C80 (DIAST-2)

-continued
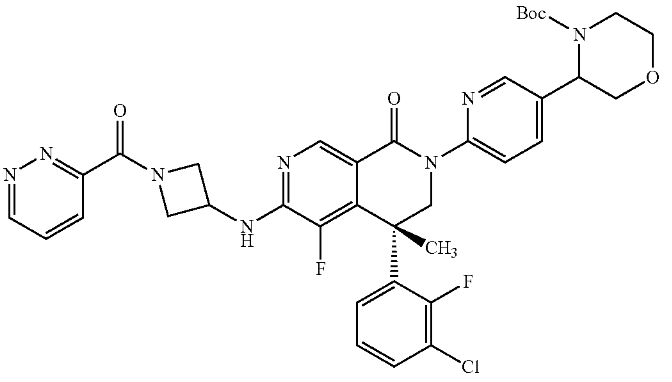
C79 (DIAST-1)
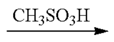
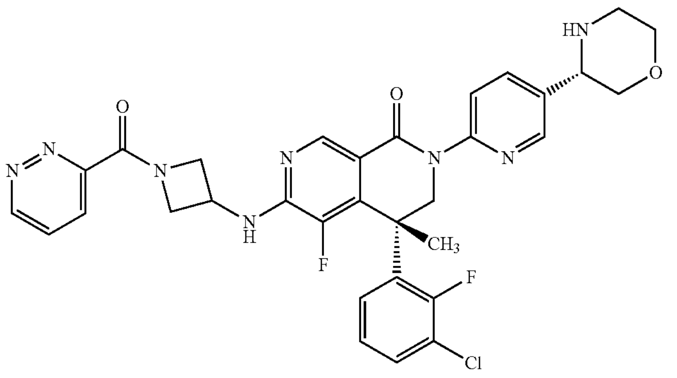
16 [from C79 (DIAST-1)]
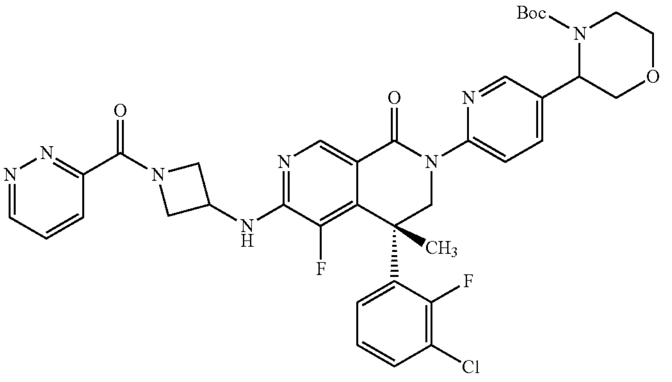
C80 (DIAST-2)
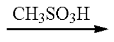
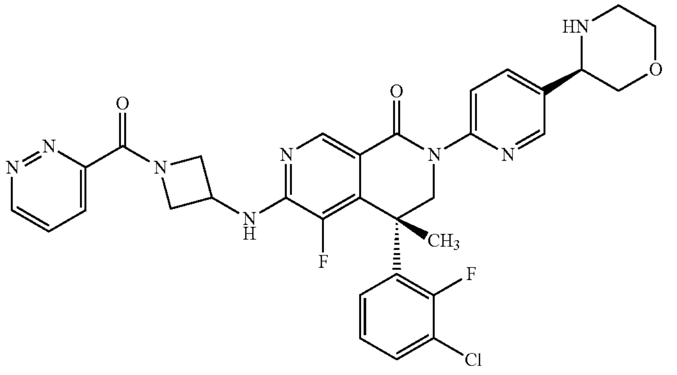
17 [from C80 (DIAST-2)]

Step 1. Synthesis of 3-(6-bromopyridin-3-γ1)morpholine (C76)

To a 15° C. solution of 2-[(tributylstannyl)methoxy] ethan-1-amine (979 mg, 2.69 mmol) in dichloromethane (12.5 mL) were added 6-bromopyridine-3-carbaldehyde (500 mg, 2.69 mmol) and powdered 4 Å molecular sieves (250 mg), whereupon the reaction mixture was stirred at 25° C. for 16 hours. Filtration provided a solution of the intermediate imine.

Copper(II) trifluoromethanesulfonate (972 mg, 2.69 mmol) was dried at 110° C. at 0.1 mbar for 2 hours. 1,1,1,3,3,3-Hexafluoropropan-2-ol (15 mL) was then added, followed by 2,6-dimethylpyridine (288 mg, 2.69 mmol); the resulting suspension was stirred at room temperature for 1 hour, whereupon the imine solution prepared above was added. After the reaction mixture had been stirred at 25° C. for 16 hours, it was combined with a similar reaction carried out using 6-bromopyridine-3-carbaldehyde (93.0 mg, 0.500 mmol), diluted with dichloromethane (20 mL), treated with a mixture of 12.5% ammonium hydroxide solution and saturated aqueous sodium chloride solution (1:1, 30 mL), and stirred vigorously at 15° C. for 15 minutes. The aqueous layer was extracted with dichloromethane (3×20 mL), and the combined organic layers were washed sequentially with water and saturated aqueous sodium chloride solution, dried over sodium sulfate, filtered, and concentrated in vacuo, providing C76 as a dark green mixture. This material was used directly in the following step. LCMS m/z 242.8 (bromine isotope pattern observed) $[M+H]^+$.

Step 2. Synthesis of tert-butyl 3-(6-bromopyridin-3-γ1)morpholine-4-carboxylate (C77)

To a solution of C76 (from the previous step; 53.19 mmol) in dichloromethane (15 mL) were added triethylamine (1.33 mL, 9.54 mmol) and di-tert-butyl dicarbonate (1.04 g, 4.77 mmol). The reaction mixture was stirred at 25° C. for 19 hours, whereupon it was concentrated in vacuo and purified via silica gel chromatography (Gradient: 0% to 20% ethyl acetate in petroleum ether) to afford C77 as an off-white solid. Yield: 500 mg, 1.46 mmol, 46% over 2 steps. LCMS m/z 344.8 (bromine isotope pattern observed) $[M+H]^+$. $^1H$ NMR (400 MHz, chloroform-d) δ 8.52 (br s, 1H), 7.76 (dd, J=8.3, 2.5 Hz, 1H), 7.46 (d, J=8.3 Hz, 1H), 5.06 (br s, 1H), 4.24 (br d, J=12.1 Hz, 1H), 3.92 (br dd, J=11.6, 3.7 Hz, 1H), 3.87 (dd, J=12.1, 3.7 Hz, 1H), 3.79 (br d, J=13.7 Hz, 1H), 3.60 (td, J=11.8, 3.0 Hz, 1H), 3.01 (ddd, J=13.7, 12.1, 3.7 Hz, 1H), 1.47 (s, 9H).

Step 3. Synthesis of 1-[(pyridazine-3-carbonyl)oxy] pyrrolidine-2,5-dione (C78)

To a solution of pyridazine-3-carboxylic acid (40.0 mg, 0.322 mmol) in dimethyl sulfoxide (1.0 mL) were added 1-hydroxypyrrolidine-2,5-dione (40.8 mg, 0.355 mmol) and 1,3-dicyclohexylcarbodiimide (DCC; 66.5 mg, 0.322 mmol). The reaction mixture was stirred at 30° C. for 16 hours to provide a solution of C78 in dimethyl sulfoxide (1.0 mL), which was used directly in the following step.

Step 4. Synthesis of (4R)-4-(3-chloro-2-fluorophenyl)-5-fluoro-4-methyl-6-{[1-(pyridazine-3-carbonyl)azetidin-3-yl]amino}-3,4-dihydro-2,7-naphthyridin-1(2H)-one (C65)

To a 0° C. solution of C78 (from the previous step; 50.322 mmol in 1.0 mL dimethyl sulfoxide) was added triethylamine (0.439 mL, 3.15 mmol), followed by a solution of C64, methanesulfonate salt (150 mg, 0.316 mmol) in acetonitrile (1.0 mL). After the reaction mixture had been stirred at 30° C. for 40 hours, it was cooled to 0° C. and treated once more with a solution of C78 (50.158 mmol) in dimethyl sulfoxide (1 mL). Stirring was continued at 30° C. for 16 hours, whereupon the reaction mixture was concentrated in vacuo and purified via reversed-phase HPLC (Column: Phenomenex C18, 30×80 mm, 5 μm; Mobile phase A: water containing 0.05% ammonium hydroxide; Mobile phase B: acetonitrile; Gradient: 28% to 48% B; Flow rate: 35 mL/minute) to provide C65 as a white solid. Yield: 80.0 mg, 0.165 mmol, 52%. LCMS m/z 485.1 (chlorine isotope pattern observed) $[M+H]^+$.

Step 5. Synthesis of tert-butyl 3-{6-[(4R)-4-(3-chloro-2-fluorophenyl)-5-fluoro-4-methyl-1-oxo-6-{[1-(pyridazine-3-carbonyl)azetidin-3-yl]amino}-3,4-dihydro-2,7-naphthyridin-2(1)-yl]pyridin-3-yl}morpholine-4-carboxylate, DIAST-1 (C79) and tert-butyl 3-{6-[(4R)-4-(3-chloro-2-fluorophenyl)-5-fluoro-4-methyl-1-oxo-6-{[1-(pyridazine-3-carbonyl)azetidin-3-yl]amino}-3,4-dihydro-2,7-naphthyridin-2(1H)-yl]pyridin-3-yl}morpholine-4-carboxylate, DIAST-2 (C80)

To a mixture of C65 (80 mg, 0.16 mmol) and C77 (62.3 mg, 0.182 mmol) in 1-methylpyrrolidin-2-one (2 mL) were added tripotassium phosphate (105 mg, 0.495 mmol), copper(I) iodide (31.4 mg, 0.165 mmol), and $N^1,N^2$-dimethylethane-1,2-diamine (43.6 mg, 0.495 mmol). After the reaction mixture had been stirred at 100° C. for 16 hours, it was diluted with saturated aqueous sodium chloride solution (5 mL) and extracted with 2-methyltetrahydrofuran (3×5 mL). The combined organic layers were dried over sodium sulfate, concentrated in vacuo and subjected to reversed-phase HPLC (Column: Boston Prime C18, 30×150 mm, 5 μm; Mobile phase A: water containing 0.05% ammonium hydroxide (v/v); Mobile phase B: acetonitrile; Gradient: 39% to 69% B; Flow rate: 30 mL/minute). The purified material was separated into its component diastereomers using supercritical fluid chromatography [Column: Chiral Technologies Chiralpak AD, 30×250 mm, 10 μm; Mobile phase: 55:45 carbon dioxide/(propan-2-ol containing 0.1% ammonium hydroxide); Flow rate: 80 mL/minute]. The first-eluting diastereomer was designated as C79 and the second-eluting diastereomer as C80; both tert-butyl 3-{6-[(4R)-4-(3-chloro-2-fluorophenyl)-5-fluoro-4-methyl-1-oxo-6-{[1-(pyridazine-3-carbonyl)azetidin-3-yl]amino}-3,4-dihydro-2,7-naphthyridin-2(1)-yl]pyridin-3-yl}morpholine-4-carboxylate, DIAST-1 (C79) and tert-butyl 3-{6-[(4R)-4-(3-chloro-2-fluorophenyl)-5-fluoro-4-methyl-1-oxo-6-{[1-(pyridazine-3-carbonyl)azetidin-3-yl]amino}-3,4-dihydro-2,7-naphthyridin-2(1M)-yl]pyridin-3-yl}morpholine-4-carboxylate, DIAST-2 (C80) were obtained as white solids.

C79 (DIAST-1)—Yield: 20.0 mg, 26.8 μmol, 17%. LCMS m/z 769.2 (chlorine isotope pattern observed) $[M+Na^+]$. Retention time: 2.08 minutes [Analytical conditions. Column: Chiral Technologies Chiralpak AD-3, 4.6×150 mm, 3 μm; Mobile phase: 1:1 carbon dioxide/(propan-2-ol containing 0.05% diethylamine); Back pressure: 1500 psi; Flow rate: 2.3 mL/minute]. C80 (DIAST-2)—Yield: 28.4 mg, 38.0 μmol, 24%. LCMS m/z 747.2 (chlorine isotope pattern observed) $[M+H]^+$. Retention time: 2.69 minutes (Analytical conditions identical to those used for C79).

Step 6. Synthesis of (4R)-4-(3-chloro-2-fluorophenyl)-5-fluoro-4-methyl-2-{5-[(3S)-morpholin-3-yl]pyridin-2-yl}-6-{[1-(pyridazine-3-carbonyl)azetidin-3-yl]amino}-3,4-dihydro-2,7-naphthyridin-1(2H)-one, from C79 (DIAST-1) (16)

To a 15° C. solution of C79 (DIAST-1) (20.0 mg, 26.8 μmol) in 1,1,1,3,3,3-hexafluoropropan-2-ol (0.5 mL) was added methanesulfonic acid (12.9 mg, 0.134 mmol); after the reaction mixture had been stirred at 15° C. for 15 minutes, it was cooled to 0° C. and treated with triethylamine (37.2 μL, 0.267 mmol). The resulting mixture was concentrated in vacuo and purified using reversed-phase HPLC (Column: Phenomenex C18, 30×80 mm, 5 μm; Mobile phase A: water containing 0.05% ammonium hydroxide; Mobile phase B: acetonitrile; Gradient: 33% to 53% B; Flow rate: 35 mL/minute), affording (4R)-4-(3-chloro-2-fluorophenyl)-5-fluoro-4-methyl-2-{5-[(3S)-morpholin-3-yl]pyridin-2-yl}-6-{[1-(pyridazine-3-carbonyl)azetidin-3-yl]amino}-3,4-dihydro-2,7-naphthyridin-1(2H)-one [16, from C79 (DIAST-1)] as a white solid. Yield: 4.3 mg, 6.6 μmol, 25%. LCMS m/z 647.4 (chlorine isotope pattern observed) $[M+H]^+$. $^1$H NMR (400 MHz, methanol-$d_4$), characteristic peaks: δ 9.30-9.26 (m, 1H), 8.69 (s, 1H), 8.43 (d, J=2.3 Hz, 1H), 8.25 (br d, J=8.6 Hz, 1H), 7.88 (dd, J=8.6, 5.1 Hz, 1H), 7.82 (dd, component of ABX system, J=8.6, 2.4 Hz, 1H), 7.73 (d, half of AB quartet, J=8.6 Hz, 1H), 7.48-7.41 (m, 1H), 7.30 (br t, J=7.5 Hz, 1H), 7.18 (br t, J=8.0 Hz, 1H), 5.18-5.10 (m, 1H), 4.57 (d, J=13.3 Hz, 1H), 4.29-4.18 (m, 1H), 4.11 (d, J=13.3 Hz, 1H), 3.94 (dd, J=10.2, 3.2 Hz, 1H), 3.89-3.80 (m, 2H), 3.63 (td, J=11.3, 2.8 Hz, 1H), 3.44 (dd, J=10.7, 10.7 Hz, 1H), 3.04 (ddd, component of ABXY system, J=12, 11, 3.3 Hz, 1H), 2.96 (br d, half of AB quartet, J=12.5 Hz, 1H), 1.91 (s, 3H). Retention time of a sample of 16 [from C79 (DIAST-1)], prepared using the same method: 4.52 minutes [Analytical conditions. Column: Chiral Technologies Chiralcel OD-H, 4.6×250 mm, 5 μm; Mobile phase A: carbon dioxide; Mobile phase B: methanol containing 0.2% (7 M ammonia in methanol); Gradient: 25% B for 10.0 minutes, then 25% to 100% B over 1.0 minute; Flow rate: 1.5 mL/minute; Back pressure: 120 bar].

Step 7. Synthesis of (4R)-4-(3-chloro-2-fluorophenyl)-5-fluoro-4-methyl-2-{5-[(3R)-morpholin-3-yl]pyridin-2-yl}-6-{[1-(pyridazine-3-carbonyl)azetidin-3-yl]amino}-3,4-dihydro-2,7-naphthyridin-1(2H)-one, from C80 (DIAST-2) (17)

Methanesulfonic acid (18.3 mg, 0.190 mmol) was added to a 15° C. solution of C80 (DIAST-2) (28.4 mg, 38.0 μmol) in 1,1,1,3,3,3-hexafluoropropan-2-ol (0.5 mL), and the reaction mixture was stirred at 15° C. for 15 minutes. After the reaction mixture had been cooled to 0° C., triethylamine (52.8 μL, 0.379 mmol) was added, and the resulting mixture was concentrated in vacuo. Purification via reversed-phase HPLC (Column: Phenomenex C18, 30×80 mm, 5 μm; Mobile phase A: water containing 0.05% ammonium hydroxide; Mobile phase B: acetonitrile; Gradient: 33% to 53% B; Flow rate: 35 mL/minute) afforded (4R)-4-(3-chloro-2-fluorophenyl)-5-fluoro-4-methyl-2-{5-[(3R)-morpholin-3-yl]pyridin-2-yl}-6-{[1-(pyridazine-3-carbonyl)azetidin-3-yl]amino}-3,4-dihydro-2,7-naphthyridin-1(2H)-one, from C80 (DIAST-2) (17) as a white solid. Yield: 2.7 mg, 4.2 μmol, 11%. LCMS m/z 647.4 (chlorine isotope pattern observed) $[M+H]^+$. $^1$H NMR (400 MHz, methanol-$d_4$), characteristic peaks: δ 9.31-9.25 (m, 1H), 8.69 (s, 1H), 8.43 (d, J=2.4 Hz, 1H), 8.24 (dd, J=8.4, 1.7 Hz, 1H), 7.88 (dd, J=8.5, 5.1 Hz, 1H), 7.83 (dd, component of ABX system, J=8.6, 2.4 Hz, 1H), 7.73 (d, half of AB quartet, J=8.6 Hz, 1H), 7.44 (br t, J=7.4 Hz, 1H), 7.29 (t, J=7.5 Hz, 1H), 7.17 (t, J=8.0 Hz, 1H), 5.18-5.09 (m, 1H), 5.05-4.96 (m, 1H), 4.80-4.69 (m, 1H), 4.57 (d, J=13.2 Hz, 1H), 4.29-4.17 (m, 1H), 4.11 (d, J=13.3 Hz, 1H), 3.94 (dd, J=10.2, 3.2 Hz, 1H), 3.89-3.79 (m, 2H), 3.63 (td, J=11.3, 2.9 Hz, 1H), 3.44 (t, J=10.7 Hz, 1H), 3.09-3.00 (m, 1H), 2.96 (br d, half of AB quartet, J=12.3 Hz, 1H), 1.91 (s, 3H). Retention time of a sample of 17 [from C80 (DIAST-2)], prepared using the same method: 4.39 minutes {Analytical conditions identical to those used for 16 [from C79 (DIAST-1)]}.

Comparison of the retention times of 16 [from C79 (DIAST-1)] and 17 [from C80 (DIAST-2)] with those of samples of 16 and 17 prepared, respectively, from C81 and its enantiomer C82 (see Alternate Synthesis of Example 17 below), allowed for assignment of the absolute configuration of the morpholine, via the single-crystal X-ray structure determination of C81 described below.

Alternate Synthesis of Example 17

(4R)-4-(3-Chloro-2-fluorophenyl)-5-fluoro-4-methyl-2-{5-[(3R)-morpholin-3-yl]pyridin-2-yl}-6-{[1-(pyridazine-3-carbonyl)azetidin-3-yl]amino}-3,4-dihydro-2,7-naphthyridin-1(2H)-one, from C82 (17)

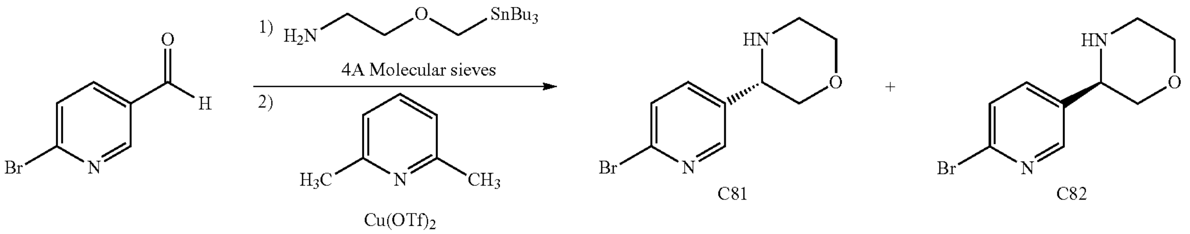

C81

C82

-continued

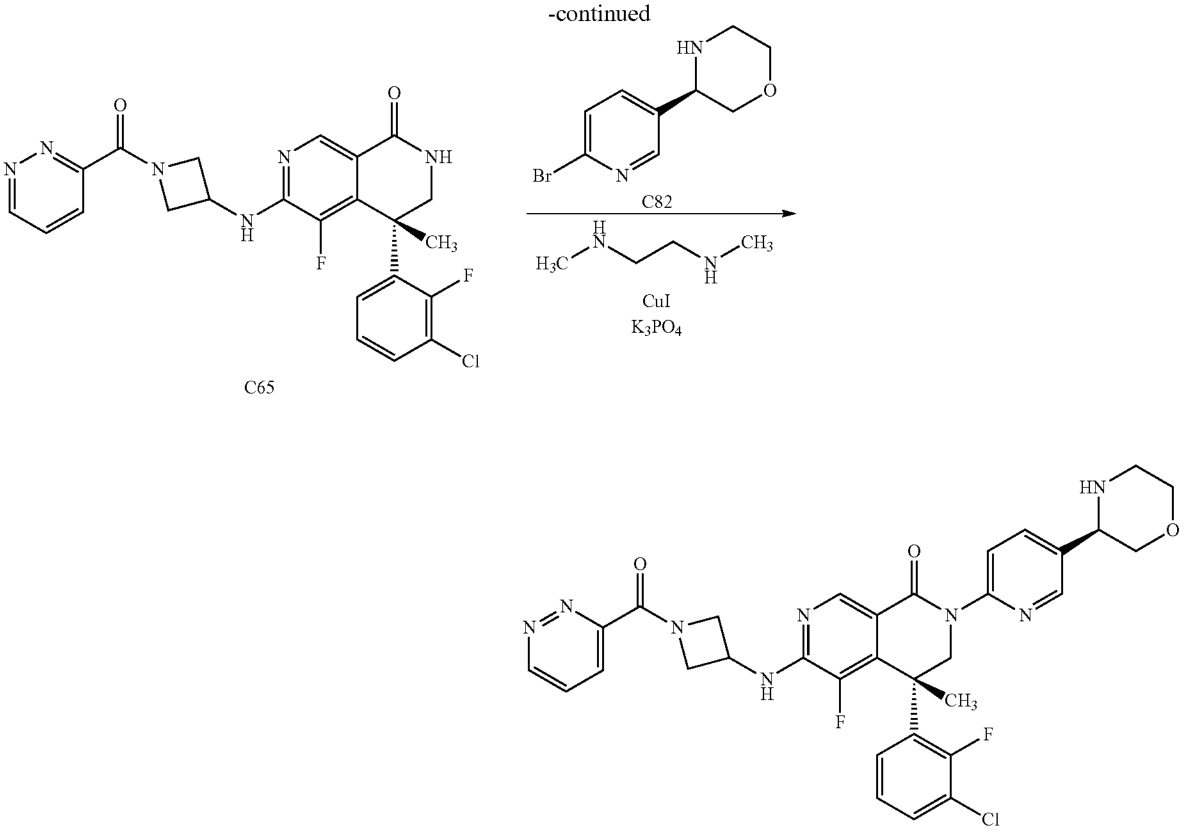

C65

C82

17 (from C82)

Step 1. Synthesis of 3-(6-bromopyridin-3-yl)morpholine, ENANT-1 (C81) and 3-(6-bromopyridin-3-yl)morpholine, ENANT-2 (C82)

Copper(II) trifluoromethanesulfonate (3.89 g, 10.8 mmol) was dried, with stirring, under high vacuum at 110° C. for 2.5 hours, whereupon the solid was allowed to cool to room temperature. Addition of 1,1,1,3,3,3-hexafluoropropan-2-ol (60 mL) followed by 2,6-dimethylpyridine (1.25 mL, 10.7 mmol) provided a blue suspension, which was stirred at room temperature.

In a separate flask, 2-[(tributylstannyl)methoxy]ethan-1-amine (3.92 g, 10.8 mmol) and activated, powdered 4 Å molecular sieves (1 g) were added to a solution of 6-bromopyridine-3-carbaldehyde (2.00 g, 10.8 mmol) in dichloromethane (50 mL), and this reaction mixture was stirred at room temperature. After 4.25 hours, this was filtered through diatomaceous earth; the filtrate was added to the copper slurry prepared above, and the reaction mixture was stirred at room temperature overnight. The reaction mixture was then treated sequentially with dichloromethane (80 L), saturated aqueous sodium chloride solution (60 mL), and a mixture of water and concentrated ammonium hydroxide solution (1:1, 60 mL). After the resulting solution had been vigorously stirred for 15 minutes, the aqueous layer was extracted twice with dichloromethane; the combined organic layers were washed sequentially with water and with saturated aqueous sodium chloride solution, dried over magnesium sulfate, filtered, and concentrated in vacuo. The residue was treated with toluene and concentrated again, whereupon silica gel chromatography (Gradient: 0% to 10% methanol in dichloromethane) afforded a racemic mixture of C81 and C82 as a pale-yellow solid. Yield: 1.69 g, 6.95 mmol, 64%. LCMS m/z 245.1 (bromine isotope pattern observed) $[M+H]^+$. $^1H$ NMR (400 MHz, chloroform-d) δ 8.39 (br s, 1H), 7.62 (br d, J=8.2 Hz, 1H), 7.45 (d, J=8.2 Hz, 1H), 3.94 (dd, J=10.1, 3.1 Hz, 1H), 3.88 (br d, J=11 Hz, 1H), 3.78 (dd, J=11.2, 3.2 Hz, 1H), 3.64 (br t, J=11.3 Hz, 1H), 3.34 (t, J=10.5 Hz, 1H), 3.11 (td, component of ABXY system, J=11.5, 3.2 Hz, 1H), 2.99 (br d, half of AB quartet, J=11.6 Hz, 1H), 2.04 (br s, 1H).

Separation of the enantiomers was carried out using supercritical fluid chromatography {Column: Chiral Technologies Chiralpak AD-H, 30×250 mm, 5 μm; Mobile phase: 55:45 carbon dioxide/[ethanol containing 0.2% (7 M ammonia in methanol)]; Back pressure: 100 bar; Flow rate: 80 mL/minute}. The first-eluting enantiomer was designated as C81 and the second-eluting enantiomer as C82. Both were obtained as tan solids.

C81—Yield: 751 mg, 3.09 mmol, 44% for the separation. Retention time: 4.94 minutes [Analytical conditions. Column: Chiral Technologies Chiralpak AD-H, 4.6×250 mm, 5 μm; Mobile phase A: carbon dioxide; Mobile phase B: ethanol containing 0.2% (7 M ammonia in methanol); Gradient: 5% B for 0.50 minutes, then 5% to 80% B over 4.50 minutes, then 80% B; Back pressure: 120 bar; Flow rate: 3.0 mL/minute]. A sample of C81 (50 mg) was dissolved in toluene (0.75 mL) and allowed to evaporate over 5 days, producing a crystal appropriate for single crystal X-ray crystallographic analysis (see below).

C82—Yield: 780 mg, 3.21 mmol, 46% for the separation. Retention time: 6.33 minutes (Analytical conditions identical to those used for C81).

Single-Crystal X-Ray Structural Determination of C81

Single Crystal X-Ray Analysis

Data collection was performed on a Bruker D8 Quest diffractometer at 298 K. Data collection consisted of omega and phi scans.

The structure was solved by intrinsic phasing using SHELX software suite in the monoclinic space group C2. The structure was subsequently refined by the full-matrix least squares method. All non-hydrogen atoms were found and refined using anisotropic displacement parameters.

The hydrogen atoms located on nitrogen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek). The results indicate that the absolute structure has been correctly assigned. The method calculates that the probability that the structure is correctly assigned is 1.0. The Hooft parameter is reported as 0.032 with an esd (estimated standard deviation) of 0.010 and the Parson's parameter is reported as −0.026 with an esd of 0.006.

The final R-index was 3.4%. A final difference Fourier revealed no missing or misplaced electron density.

Figure 4:
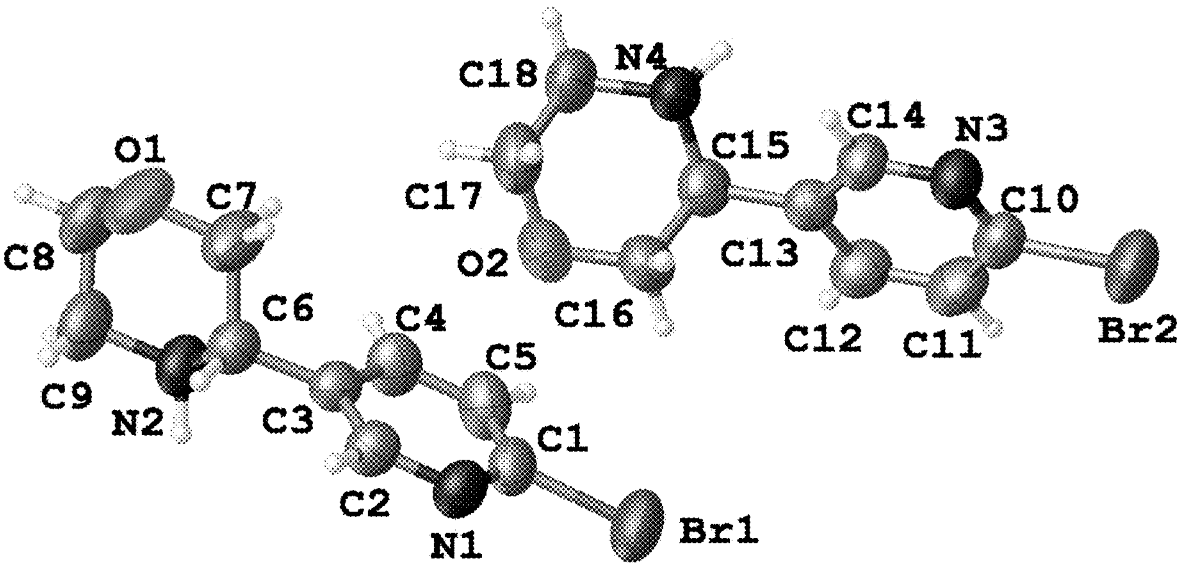
FIG. 4 is an illustration of a small molecule crystal structure of the compound of C81 of Example 17.

Pertinent crystal, data collection, and refinement information is summarized in Table F. Atomic coordinates, bond lengths, bond angles, and displacement parameters are listed in Tables G-K. FIG. 4 is an illustration of the crystal structure of C81.

Software and References

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE F

Crystal data and structure refinement for C81.

| | |
|---|---|
| Empirical formula | $C_9H_{11}BrN_2O$ |
| Formula weight | 243.10 |
| Temperature | 298.00K |
| Wavelength | 1.54178 Å |
| Crystal system | Monoclinic |
| Space group | C2 |
| Unit cell dimensions | a = 22.564(4) Å α = 90° |
| | b = 5.2319(10) Å β = 120.290(6)° |
| | c = 19.839(4) Å γ = 90° |
| Volume | 2022.3(7) $Å^3$ |
| Z | 8 |
| $\rho_{calc}$ | 1.597 $g/cm^3$ |
| μ | 5.248 $mm^{-1}$ |
| F(000) | 976.0 |
| Crystal size | 0.299 × 0.241 × 0.144 $mm^3$ |
| Radiation | CuKα |
| 2Θ range for data collection | 5.158 to 144.646° |
| Index ranges | −27 ≤ h ≤ 27, −6 ≤ k ≤ 6, −23≤ l ≤24 |

TABLE F-continued

Crystal data and structure refinement for C81.

| | |
|---|---|
| Reflections collected | 26953 |
| Independent reflections | 3949 [$R_{int}$ = 0.0432, $R_{sigma}$ = 0.0278] |
| Data/restraints/parameters | 3949/3/243 |
| Goodness-of-fit on $F^2$ | 1.053 |
| Final R indices [I ≥ 2σ(I)] | $R_1$ = 0.0342, $wR_2$ = 0.0975 |
| Final R indices (all data) | $R_1$ = 0.0361, $wR_2$ = 0.0990 |
| Largest diff. peak and hole | 0.38 and −0.27 e $Å^{-3}$ |
| Flack parameter | −0.028(15) |

TABLE G

Fractional Atomic coordinates (×$10^4$) and equivalent isotropic displacement parameters ($Å^2$ × $10^3$) for C81. U(eq) is defined as one-third of the trace of the orthogonalized $U^{ij}$ tensor.

| | x | y | z | U(eq) |
|---|---|---|---|---|
| Br1 | 8776.0(3) | 3149.8(16) | 9068.2(4) | 105.6(2) |
| O1 | 4783(2) | 5653(11) | 8006(3) | 116.9(15) |
| N1 | 7823.6(17) | 5598(7) | 9314(2) | 70.7(8) |
| N2 | 5809.5(19) | 2336(8) | 9083(2) | 76.4(10) |
| C1 | 7894(2) | 3588(9) | 8966(2) | 67.4(10) |
| C2 | 7208(2) | 5886(8) | 9251(2) | 64.3(8) |
| C3 | 6661.6(19) | 4239(8) | 8853(2) | 58.7(8) |
| C4 | 6763(2) | 2164(9) | 8491(2) | 71.8(10) |
| C5 | 7396(3) | 1802(10) | 8550(3) | 76.7(10) |
| C6 | 5991(2) | 4653(9) | 8838(2) | 65.3(9) |
| C7 | 5428(3) | 5421(15) | 8044(3) | 99.9(17) |
| C8 | 4613(2) | 3328(16) | 8248(4) | 101.0(16) |
| C9 | 5150(3) | 2625(14) | 9051(3) | 97.1(18) |
| Br2 | 9688.9(3) | 7007.7(18) | 5795.0(4) | 113.7(3) |
| O2 | 6927.0(19) | 6848(10) | 7279.9(18) | 95.2(10) |
| N3 | 8436.3(18) | 8127(9) | 5631(2) | 73.5(8) |
| N4 | 6659.0(18) | 6810(11) | 5733(2) | 81.1(10) |
| C10 | 8931(2) | 6415(10) | 5952(2) | 72.2(11) |
| C11 | 8945(2) | 4364(11) | 6385(3) | 81.4(12) |
| C12 | 8406(2) | 4080(9) | 6511(3) | 75.0(11) |
| C13 | 7865(2) | 5824(8) | 6193(2) | 61.1(8) |
| C14 | 7909(2) | 7792(8) | 5755(2) | 66.4(9) |
| C15 | 7280(2) | 5622(9) | 6348(2) | 67.1(9) |
| C16 | 7462(2) | 6968(13) | 7104(2) | 80.1(11) |
| C17 | 6323(3) | 7936(16) | 6675(3) | 96.6(16) |
| C18 | 6109(3) | 6567(17) | 5914(3) | 95.6(17) |

TABLE H

Bond lengths [Å] for C81.

| Atom | Atom | Length | Atom | Atom | Length |
|---|---|---|---|---|---|
| Br1 | C1 | 1.911(4) | Br2 | C10 | 1.912(4) |
| O1 | C7 | 1.423(7) | O2 | C16 | 1.417(6) |
| O1 | C8 | 1.429(9) | O2 | C17 | 1.405(7) |
| N1 | C1 | 1.310(6) | N3 | C10 | 1.317(6) |
| N1 | C2 | 1.339(5) | N3 | C14 | 1.342(5) |
| N2 | C6 | 1.441(6) | N4 | C15 | 1.454(6) |
| N2 | C9 | 1.464(6) | N4 | C18 | 1.462(6) |
| C1 | C5 | 1.371(7) | C10 | C11 | 1.364(7) |
| C2 | C3 | 1.381(6) | C11 | C12 | 1.370(7) |
| C3 | C4 | 1.382(6) | C12 | C13 | 1.393(6) |
| C3 | C6 | 1.514(6) | C13 | C14 | 1.383(6) |
| C4 | C5 | 1.387(6) | C13 | C15 | 1.503(6) |
| C6 | C7 | 1.497(6) | C15 | C16 | 1.514(7) |
| C8 | C9 | 1.480(8) | C17 | C18 | 1.513(9) |

TABLE J

| Bond angles [°] for C81. | | | | | | | |
|---|---|---|---|---|---|---|---|
| Atom | Atom | Atom | Angle | Atom | Atom | Atom | Angle |
| C7 | O1 | C8 | 110.5(5) | C17 | O2 | C16 | 110.6(3) |
| C1 | N1 | C2 | 115.9(4) | C10 | N3 | C14 | 115.8(4) |
| C6 | N2 | C9 | 110.7(4) | C15 | N4 | C18 | 109.5(4) |
| N1 | C1 | Br1 | 115.9(3) | N3 | C10 | Br2 | 114.9(3) |
| N1 | C1 | C5 | 125.8(4) | N3 | C10 | C11 | 125.8(4) |
| C5 | C1 | Br1 | 118.3(3) | C11 | C10 | Br2 | 119.3(3) |
| N1 | C2 | C3 | 124.6(4) | C10 | C11 | C12 | 117.3(4) |
| C2 | C3 | C4 | 117.0(4) | C11 | C12 | C13 | 120.1(4) |
| C2 | C3 | C6 | 121.1(4) | C12 | C13 | C15 | 121.3(4) |
| C4 | C3 | C6 | 121.8(4) | C14 | C13 | C12 | 116.6(4) |

TABLE J-continued

| Bond angles [°] for C81. | | | | | | | |
|---|---|---|---|---|---|---|---|
| Atom | Atom | Atom | Angle | Atom | Atom | Atom | Angle |
| C3 | C4 | C5 | 119.8(4) | C14 | C13 | C15 | 122.0(4) |
| C1 | C5 | C4 | 116.9(4) | N3 | C14 | C13 | 124.3(4) |
| N2 | C6 | C3 | 109.0(4) | N4 | C15 | C13 | 111.9(3) |
| N2 | C6 | C7 | 110.2(4) | N4 | C15 | C16 | 107.3(4) |
| C7 | C6 | C3 | 111.6(4) | C13 | C15 | C16 | 110.0(3) |
| O1 | C7 | C6 | 112.4(5) | O2 | C16 | C15 | 112.6(4) |
| O1 | C8 | C9 | 111.1(5) | O2 | C17 | C18 | 110.1(5) |
| N2 | C9 | C8 | 109.6(4) | N4 | C18 | C17 | 108.7(5) |

TABLE K

Anisotropic displacement parameters ($Å^2 \times 10^3$) for C81. The anisotropic displacement factor exponent takes the form: $-2\pi^2[h^2 a^{*2} U^{11} + 2 h k a^* b^* U^{12} + \ldots]$.

| | $U^{11}$ | $U^{22}$ | $U^{33}$ | $U^{23}$ | $U^{13}$ | $U^{12}$ |
|---|---|---|---|---|---|---|
| Br1 | 72.9(3) | 144.5(5) | 118.6(4) | 20.6(4) | 62.6(3) | 16.2(3) |
| O1 | 58.2(18) | 150(4) | 125(3) | 38(3) | 33.1(19) | 18(2) |
| N1 | 55.8(18) | 79(2) | 77.1(19) | −0.3(17) | 33.3(16) | −5.6(17) |
| N2 | 60.4(18) | 88(3) | 87(2) | 13.3(18) | 41.3(17) | −2.6(17) |
| C1 | 62(2) | 80(3) | 73(2) | 15.4(19) | 43.0(18) | 5.1(19) |
| C2 | 59(2) | 63.7(19) | 68(2) | −2.0(16) | 30.9(17) | −4.0(16) |
| C3 | 54.8(19) | 62.7(18) | 57.0(17) | 3.9(15) | 27.0(15) | −3.6(15) |
| C4 | 74(2) | 69(2) | 81(2) | −13.4(19) | 45(2) | −16(2) |
| C5 | 87(3) | 72(2) | 92(3) | −6(2) | 61(2) | −1(2) |
| C6 | 54(2) | 73(2) | 67(2) | −1.4(18) | 29.9(17) | −3.4(17) |
| C7 | 64(3) | 133(5) | 97(3) | 38(3) | 36(2) | 12(3) |
| C8 | 55(2) | 134(4) | 112(4) | −11(4) | 40(2) | −16(3) |
| C9 | 67(2) | 124(5) | 115(4) | 12(3) | 56(3) | −8(3) |
| Br2 | 66.7(3) | 165.3(7) | 125.1(5) | 3.9(4) | 60.3(3) | 4.4(3) |
| O2 | 91(2) | 136(3) | 75.0(17) | 12(2) | 54.5(17) | 3(2) |
| N3 | 63.4(18) | 88(2) | 77.2(19) | 7.2(19) | 41.3(15) | 1(2) |
| N4 | 54.7(17) | 128(3) | 64.4(17) | 1(2) | 32.4(14) | −5(2) |
| C10 | 55.6(19) | 91(3) | 71(2) | −6(2) | 33.0(17) | 0.9(19) |
| C11 | 61(2) | 86(3) | 87(3) | 5(2) | 31(2) | 13(2) |
| C12 | 68(2) | 73(2) | 78(2) | 8.8(19) | 33(2) | 4.7(19) |
| C13 | 58.2(19) | 66(2) | 57.6(18) | −3.3(15) | 28.3(15) | −4.9(16) |
| C14 | 56.9(19) | 74(2) | 73(2) | 7.9(18) | 35.8(17) | 7.3(17) |
| C15 | 66(2) | 70(2) | 71(2) | 6.4(17) | 38.4(18) | −4.6(18) |
| C16 | 75(3) | 107(3) | 62(2) | 7(2) | 38.0(19) | 1(3) |
| C17 | 85(3) | 130(4) | 102(3) | 11(3) | 67(3) | 8(3) |
| C18 | 63(2) | 147(5) | 87(3) | −1(3) | 46(2) | −9(3) |

Step 2. Synthesis of (4R)-4-(3-chloro-2-fluorophenyl)-5-fluoro-4-methyl-2-{5-[(3R)-morpholin-3-yl]pyridin-2-yl}-6-{[1-(pyridazine-3-carbonyl)azetidin-3-yl]amino}-3,4-dihydro-2,7-naphthyridin-1(2H)-one, from C82 (17)

A mixture of C65 (558 mg, 1.15 mmol), C82 (350 mg, 1.44 mmol), tripotassium phosphate (672 mg, 3.16 mmol), copper(I) iodide (219 mg, 1.15 mmol), butan-2-ol (0.55 mL), and $N^1$,$N^2$-dimethylethane-1,2-diamine (0.40 mL, 3.7 mmol) in toluene (11 mL; pre-sparged with nitrogen for 30 minutes), was sparged with nitrogen for 1 minute, whereupon the reaction mixture was heated at 88° C. for 16 hours. After it had cooled, the reaction mixture was partitioned between ethyl acetate (30 mL) and a mixture of water and saturated aqueous ammonium chloride solution (1:1, 20 mL). The aqueous layer was extracted with ethyl acetate (30 mL), and the combined organic layers were dried over sodium sulfate, filtered, and concentrated in vacuo. Chromatography on silica gel (Gradient: 0% to 14% methanol in dichloromethane) afforded (4R)-4-(3-chloro-2-fluorophenyl)-5-fluoro-4-methyl-2-{5-[(3R)-morpholin-3-yl]pyridin-2-yl}-6-{[1-(pyridazine-3-carbonyl)azetidin-3-yl]amino}-3,4-dihydro-2,7-naphthyridin-1(2H)-one, from C82 (17) as a white solid. Yield: 611 mg, 0.944 mmol, 82%. LCMS m/z 647.5 (chlorine isotope pattern observed) $[M+H]^+$. $^1H$ NMR (400 MHz, DMSO-$d_6$) δ 9.38-9.32 (m, 1H), 8.61 (s, 1H), 8.38 (br s, 1H), 8.13 (br d, J=8.6 Hz, 1H), 8.05 (br d, J=5.6 Hz, 1H), 7.92-7.84 (m, 1H), 7.84-7.76 (m, 2H), 7.61-7.53 (m, 1H), 7.45-7.35 (m, 1H), 7.30-7.22 (m, 1H), 4.99-4.90 (m, 1H), 4.90-4.80 (m, 1H), 4.67-4.52 (m, 1H), 4.52-4.37 (m, 2H), 4.21-4.05 (m, 2H), 3.86-3.78 (m, 1H), 3.78-3.66 (m, 2H), 3.51-3.40 (m, 1H), 3.23-3.13 (m, 1H), 2.99-2.79 (m, 3H), 1.83 (br s, 3H). Retention time of a sample of 17 prepared from C82 using the same method: 4.38 minutes [Analytical conditions. Column: Chiral Technologies Chiralcel OD-H, 4.6×250 mm, 5 μm; Mobile phase A: carbon dioxide; Mobile phase B: methanol containing 0.2% (7 M ammonia in methanol); Gradient: 25% B for 10.0 minutes, then 25% to 100% B over 1.0 minute; Flow rate: 1.5 mL/minute; Back pressure: 120 bar].

A sample of 16 was prepared in the same manner from the enantiomeric morpholine reactant C81. Retention time: 4.49 minutes (Analytical conditions identical to those used for 17 prepared from C82).

Example 18

(4R)-4-(3-Chloro-2-fluorophenyl)-5-fluoro-6-({1-[(1S,2S)-2-fluorocyclopropane-1-carbonyl]azetidin-3-yl}amino)-2-{5-[(1R)-1-hydroxyethyl]pyridin-2-yl}-4-methyl-3,4-dihydro-2,7-naphthyridin-1(2H)-one (18)

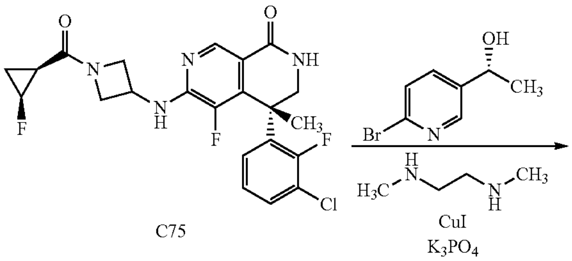

C75

-continued

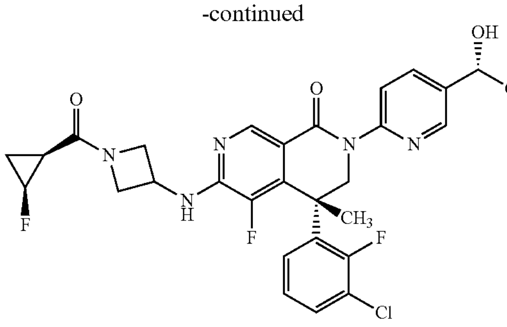

18

A mixture of C75 (90%, 500 mg, 0.968 mmol), (1R)-1-(6-bromopyridin-3-yl)ethan-1-ol (313 mg, 1.55 mmol), tripotassium phosphate (616 mg, 2.90 mmol), and copper(I) iodide (184 mg, 0.966 mmol) was treated with 1-methylpyrrolidin-2-one (9.7 mL) and $N^1$,$N^2$-dimethylethane-1,2-diamine (0.30 mL, 2.8 mmol), whereupon the reaction mixture was heated at 100° C. After 18 hours, it was allowed to cool to 25° C. and diluted with saturated aqueous ammonium chloride solution (10 mL). The aqueous layer was extracted with dichloromethane (4×10 mL), and the combined organic layers were washed with water (3×40 mL) and with saturated aqueous sodium chloride solution (40 mL), dried over magnesium sulfate, filtered, and concentrated in vacuo. Silica gel chromatography (Gradient: 0% to 20% methanol in dichloromethane) afforded a solid, which was combined with the product of a similar reaction carried out using C75 (90%, 500 mg, 0.968 mmol). The mixture was treated with 2-methyltetrahydrofuran (3 mL), heated to 40° C. for 8 hours, and allowed to cool to 25° C.; after 8 hours, the resulting solid was collected via filtration and rinsed with a mixture of heptane and 2-methyltetrahydrofuran (1:1, 10 mL), affording (4R)-4-(3-chloro-2-fluorophenyl)-5-fluoro-6-({1-[(1 S,2S)-2-fluorocyclopropane-1-carbonyl]azetidin-3-yl}amino)-2-{5-[(1R)-1-hydroxyethyl]pyridin-2-yl}-4-methyl-3,4-dihydro-2,7-naphthyridin-1(2H)-one (18) as a white solid. Combined yield: 530 mg, 0.904 mmol, 47%. LCMS m/z 586.3 (chlorine isotope pattern observed) $[M+H]^+$. $^1H$ NMR (400 MHz, DMSO-$d_6$) δ 8.60 (s, 1H), 8.34 (s, 1H), 8.06-7.98 (m, 1H), 7.81-7.72 (m, 2H), 7.58 (t, J=7.3 Hz, 1H), 7.45-7.36 (m, 1H), 7.27 (t, J=8.0 Hz, 1H), 5.29 (d, J=4.3 Hz, 1H), [4.97-4.90 (m) and 4.84-4.72 (m), total 3H], 4.64-4.48 (m, 1H), 4.43 (br d, J=13.3 Hz, 1H), 4.24-4.10 (m, 3H), 3.98-3.84 (m, 1H), 1.87-1.74 (m, 1H), 1.83 (s, 3H), 1.57-1.42 (m, 1H), 1.35 (d, J=6.4 Hz, 3H), 1.07-0.95 (m, 1H).

Example 19

3-{[(5R)-5-(3-Chloro-2-fluorophenyl)-4-fluoro-7-(3-fluoropyridin-2-yl)-5-methyl-8-oxo-5,6,7,8-tetrahydro-2,7-naphthyridin-3-yl]amino}azetidine-1-carboxamide (19)

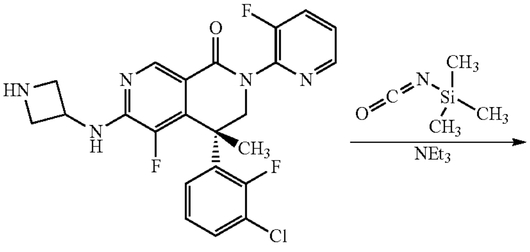

C57

-continued

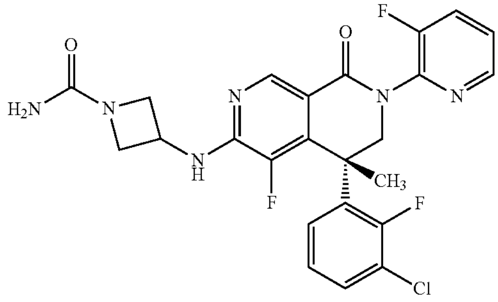

19

Isocyanato(trimethyl)silane (85%, 6.9 mg, 51 μmol) was added to a solution of C57 (20 mg, 42 μmol) and triethylamine (12 μL, 86 μmol) in acetonitrile (0.42 mL), whereupon the reaction mixture was heated at 50° C. After 16 hours, it was diluted with saturated aqueous sodium bicarbonate solution (1 mL) and the aqueous layer was extracted with ethyl acetate (3×2 mL). The combined organic layers were concentrated in vacuo; silica gel chromatography (Eluent: 10% methanol in dichloromethane) afforded 3-{[(5R)-5-(3-chloro-2-fluorophenyl)-4-fluoro-7-(3-fluoropyridin-2-yl)-5-methyl-8-oxo-5,6,7,8-tetrahydro-2,7-naphthyridin-3-yl]amino}azetidine-1-carboxamide (19) as a white solid. Yield: 5.0 mg, 9.7 μmol, 23%. LCMS m/z 517.2 (chlorine isotope pattern observed) $[M+H]^+$. $^1H$ NMR (400 MHz, chloroform-d) δ 8.82 (s, 1H), 8.25 (br d, J=4.7 Hz, 1H), 7.47 (ddd, J=9.6, 8.1, 1.5 Hz, 1H), 7.42-7.36 (m, 1H), 7.26-7.20 (m, 2H, assumed; partially obscured by solvent peak), 7.11 (dd, J=8.5, 7.4 Hz, 1H), 5.27 (br d, J=6 Hz, 1H), 4.94-4.84 (m, 1H), 4.57 (d, J=12.9 Hz, 1H), 4.44-4.36 (m, 2H), 4.31 (br s, 2H), 3.89 (dd, J=8.7, 5.2 Hz, 1H), 3.85 (dd, J=8.6, 5.1 Hz, 1H), 3.73 (d, J=12.9 Hz, 1H), 1.94 (s, 3H).

Example 20

3-{[(5R)-5-(3-Chloro-2-fluorophenyl)-4-fluoro-7-(3-fluoropyridin-2-yl)-5-methyl-8-oxo-5,6,7,8-tetrahydro-2,7-naphthyridin-3-yl]amino}-N-methylazetidine-1-carboxamide (20)

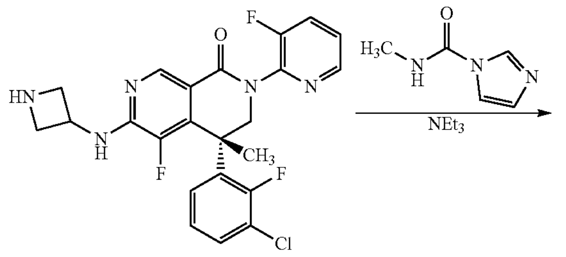

C57

-continued

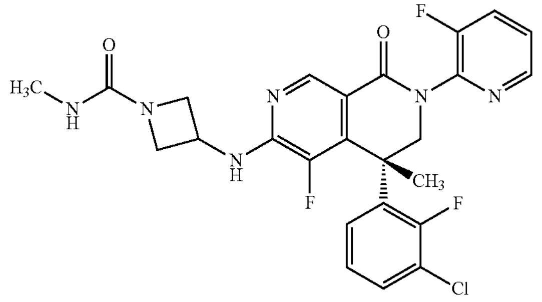

20

N-Methyl-1H-imidazole-1-carboxamide (11.6 mg, 92.7 μmol) was added to a solution of C57 (40 mg, 84 μmol) and triethylamine (23 μL, 0.16 mmol) in dichloromethane (0.84 mL). After 16 hours, the reaction mixture was diluted with water (1 mL) and the aqueous layer was extracted with ethyl acetate (3×2 mL). The combined organic layers were concentrated in vacuo; silica gel chromatography (Eluent: 8% methanol in dichloromethane) afforded a solid, which was treated with dichloromethane (2 mL) and a solution of dimethylamine in tetrahydrofuran (2 M; 0.15 mL, 0.30 mmol). After 16 hours, the mixture was diluted with water (4 mL) and the aqueous layer was extracted with dichloromethane (2×3 mL). The combined organic layers were concentrated in vacuo and purified using silica gel chromatography (Eluent: 5% methanol in dichloromethane), affording 3-{[(5R)-5-(3-chloro-2-fluorophenyl)-4-fluoro-7-(3-fluoropyridin-2-yl)-5-methyl-8-oxo-5,6,7,8-tetrahydro-2,7-naphthyridin-3-yl]amino}-N-methylazetidine-1-carboxamide (20) as a white solid. Yield: 11 mg, 21 μmol, 25%. LCMS m/z 531.2 (chlorine isotope pattern observed) $[M+H]^+$. $^1H$ NMR (400 MHz, chloroform-d) δ 8.81 (s, 1H), 8.24 (d, J=4.6 Hz, 1H), 7.47 (ddd, J=9.6, 8.1, 1.5 Hz, 1H), 7.39 (ddd, J=8.2, 6.8, 1.6 Hz, 1H), 7.26-7.20 (m, 2H), 7.11 (br t, J=8.0 Hz, 1H), 4.92-4.82 (m, 1H), 4.56 (d, J=12.9 Hz, 1H), 4.34 (t, J=7.9 Hz, 2H), 4.14-4.06 (m, 1H), 3.85-3.76 (m, 2H), 3.73 (d, J=12.9 Hz, 1H), 2.79 (d, J=4.8 Hz, 3H), 1.94 (s, 3H).

Example 21
(4R)-4-(3-Chloro-2-fluorophenyl)-5-fluoro-2-(4-fluoro-1-methyl-1H-pyrazol-3-yl)-4-methyl-6-({1-[(1 S,4S)-2-oxa-5-azabicyclo[2.2.1]heptane-5-carbonyl]azetidin-3-yl}amino)-3,4-dihydro-2,7-naphthyridin-1(2H)-one (21)
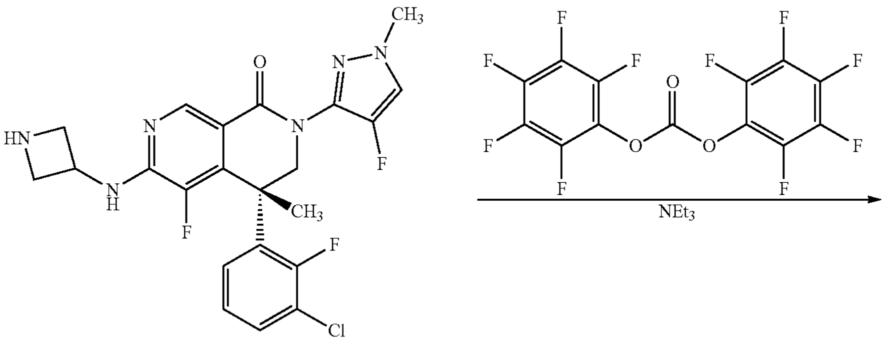
C59
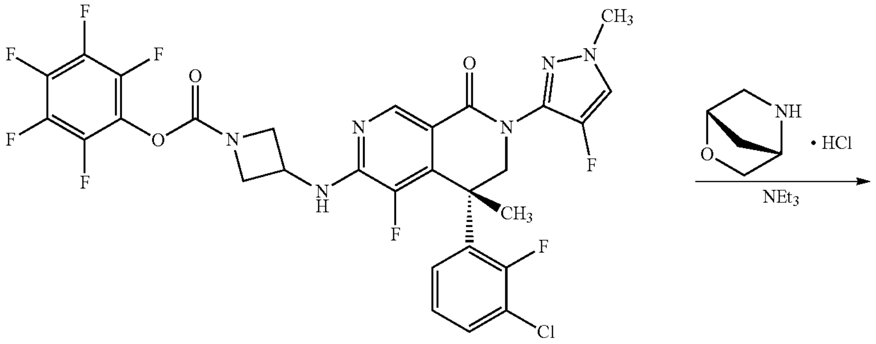
C83
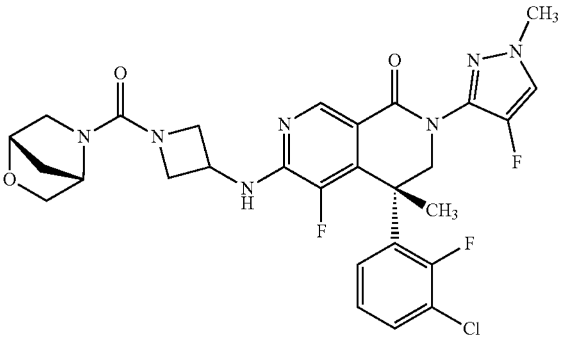
21

Step 1. Synthesis of 3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidine-1-carboxylate (C83)

Bis(pentafluorophenyl) carbonate (97.3 mg, 0.247 mmol) was added to a 25° C. solution of triethylamine (0.103 mL, 0.739 mmol) and C59 (118 mg, 0.247 mmol) in tetrahydrofuran (2 mL). After 3 hours, the reaction mixture was diluted with water (12 mL) and the aqueous layer was extracted with dichloromethane (2×20 mL). The combined organic layers were dried over sodium sulfate, filtered, and concentrated in vacuo; silica gel chromatography (Gradient: 20% to 100% ethyl acetate in heptane) afforded C83 as a white solid. Yield: 129 mg, 0.188 mmol, 76%. LCMS m/z 685.1 (chlorine isotope pattern observed) $[M-H]^-$. $^1H$ NMR (400 MHz, chloroform-d) δ 8.81 (s, 1H), 7.40 (br t, J=7.6 Hz, 1H), 7.30-7.20 (m, 2H, assumed; partially obscured by solvent peak), 7.12 (t, J=8.0 Hz, 1H), 5.50-5.20 (br s, 1H), 5.10-4.90 (m, 1H), 4.76-4.62 (m, 1H), 4.62-4.50 (m, 1H), 4.46 (d, J=12.8 Hz, 1H), 4.29-3.93 (m, 2H), 3.77 (s, 3H), 3.64 (d, J=12.8 Hz, 1H), 1.94 (s, 3H).

Step 2. Synthesis of (4R)-4-(3-chloro-2-fluorophenyl)-5-fluoro-2-(4-fluoro-1-methyl-1H-pyrazol-3-yl)-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one (21)

(1S,4S)-2-Oxa-5-azabicyclo[2.2.1]heptane, hydrochloride salt (74.0 mg, 0.546 mmol) was added to a solution of triethylamine (0.152 mL, 1.09 mmol) and C83 (125 mg, 0.182 mmol) in dimethyl sulfoxide (2 mL). The reaction mixture was heated at 60° C. for 2 hours, whereupon the mixture was allowed to cool to 25° C. and diluted with water (15 mL). The aqueous layer was extracted with ethyl acetate (2×20 mL), and the combined organic layers were washed with saturated aqueous sodium chloride solution (10 mL), dried over sodium sulfate, filtered, and concentrated in vacuo. Silica gel chromatography (Gradient: 0% to 7% methanol in dichloromethane) afforded a solid, which was partitioned between 10% pentane in ethyl acetate (15 mL) and water (15 mL); the organic layer was washed with saturated aqueous sodium chloride solution (10 mL), dried over sodium sulfate, filtered, and concentrated under reduced pressure to provide (4R)-4-(3-chloro-2-fluorophenyl)-5-fluoro-2-(4-fluoro-1-methyl-1H-pyrazol-3-yl)-4-methyl-6-({1-[(1 S,4S)-2-oxa-5-azabicyclo[2.2.1]heptane-5-carbonyl]azetidin-3-yl}amino)-3,4-dihydro-2,7-naphthyridin-1(2H)-one (21) as a white solid. Yield: 87.0 mg, 0.145 mmol, 80%. LCMS m/z 602.2 (chlorine isotope pattern observed) $[M+H]^+$. $^1H$ NMR (400 MHz, chloroform-d) δ 8.78 (s, 1H), 7.38 (ddd, J=8.2, 6.7, 1.6 Hz, 1H), 7.26-7.19 (m, 2H), 7.10 (t, J=7.9 Hz, 1H), 5.24 (br s, 1H), 4.90-4.75 (m, 1H), 4.59-4.52 (m, 2H), 4.48-4.39 (m, 2H), 4.31 (t, J=8.2 Hz, 1H), 3.96-3.89 (m, 2H), 3.82-3.72 (m, 2H), 3.76 (s, 3H), 3.63 (d, J=12.8 Hz, 1H), 3.32-3.25 (m, 2H), 1.92 (s, 3H), 1.84 (br d, half of AB quartet, J=10.0 Hz, 1H), 1.77 (dd, component of ABX system, J=10.0, 2.3 Hz, 1H).

Example 22

(4R)-4-(3-Chloro-2-fluorophenyl)-5-fluoro-2-[5-(hydroxymethyl)pyridin-2-yl]-4-methyl-6-({1-[(1 S,4S)-2-oxa-5-azabicyclo[2.2.1]heptane-5-carbonyl]azetidin-3-yl}amino)-3,4-dihydro-2,7-naphthyridin-1(2H)-one (22)

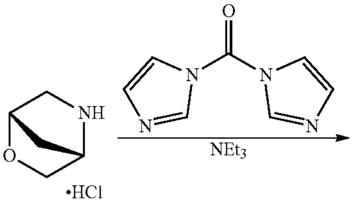

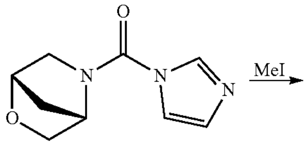

C84

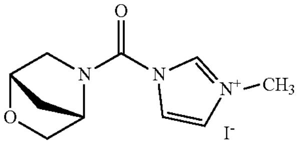

C85

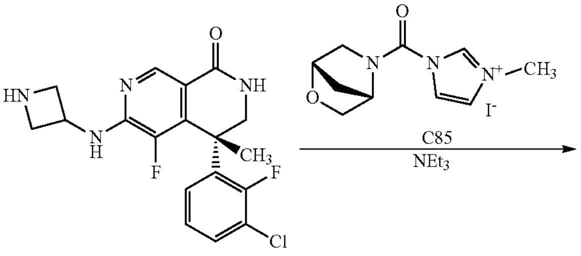

C64

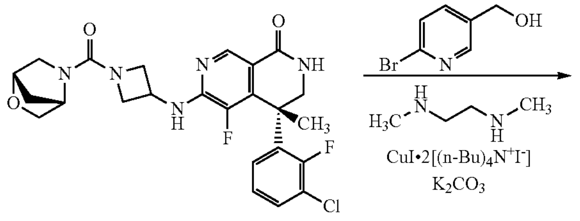

C86

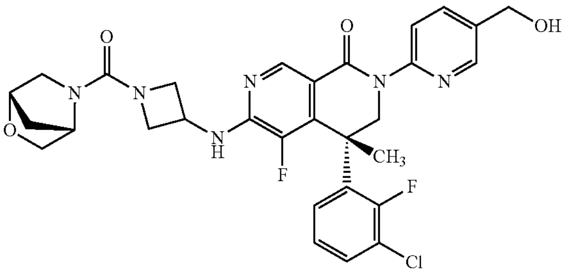

22

Step 1. Synthesis of (1H-imidazol-1-γ1)[(1S,4S)-2-oxa-5-azabicyclo[2.2.1]heptan-5-yl]methanone (C84)

1,1'-Carbonyldiimidazole (12.0 g, 74.0 mmol) was added to a solution of (1S,4S)-2-oxa-5-azabicyclo[2.2.1]heptane, hydrochloride salt (4.00 g, 29.5 mmol) in tetrahydrofuran (200 mL). After 5 minutes, triethylamine (14.4 mL, 103 mmol) was added, and stirring was continued for 16 hours, whereupon LCMS analysis indicated conversion to C84: LCMS m/z 194.3 $[M+H]^+$. The reaction mixture was concentrated in vacuo; silica gel chromatography (Gradient: 0% to 3% methanol in dichloromethane) afforded C84 as a colorless oil. Yield: 5.07 g, 26.2 mmol, 89%. $^1$H NMR (400 MHz, chloroform-d) δ 7.95 (br s, 1H), 7.27 (br s, 1H), 7.05 (br s, 1H), 4.76 (br s, 1H), 4.66 (br s, 1H), 4.05 (d, J=8.0 Hz, 1H), 3.86 (dd, J=8.0, 1.6 Hz, 1H), 3.62 (dd, component of ABX system, J=10.1, 1.5 Hz, 1H), 3.57 (br d, half of AB quartet, J=10.2 Hz, 1H), 2.01-1.91 (m, 2H).

Step 2. Synthesis of 3-methyl-1-[(1S,4S)-2-oxa-5-azabicyclo[2.2.1]heptane-5-carbonyl]-1H-imidazol-3-ium iodide (C85)

Iodomethane (3.0 mL, 48 mmol) was added to a solution of C84 (2.50 g, 12.9 mmol) in acetonitrile (120 mL). After 16 hours, iodomethane (1.5 mL, 24 mmol) was again added, and stirring was continued for 3 hours. The reaction mixture was then concentrated in vacuo to afford C85 as a white solid (3.93 g), which was used directly in the following step. LCMS m/z 208.2 $[M+H]^+$.

Step 3. Synthesis of (4R)-4-(3-chloro-2-fluorophenyl)-5-fluoro-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one (C86)

A solution of C64 (51%, 1.90 g, 2.56 mmol) and triethylamine (1.25 mL, 8.97 mmol) in dichloromethane (25 mL) was treated with C85 (from the previous step; 87%, 2.96 g, 7.68 mmol). After 30 minutes, the reaction mixture was diluted with water (25 mL) and extracted with dichloromethane (3×25 mL); the combined organic layers were washed with saturated aqueous sodium chloride solution (75 mL), dried over magnesium sulfate, filtered, and concentrated in vacuo. Silica gel chromatography (Gradient: 0% to 8% methanol in dichloromethane) provided C86 as a white solid. Yield: 1.10 g, 2.18 mmol, 85%. LCMS m/z 504.4 (chlorine isotope pattern observed) $[M+H]^+$. $^1$H NMR (400 MHz, DMSO-$d_6$), characteristic peaks: δ 8.40 (s, 1H), 7.89 (br s, 1H), 7.73 (br d, J=6.0 Hz, 1H), 7.59-7.53 (m, 1H), 7.38-7.31 (m, 1H), 7.25 (t, J=8.0 Hz, 1H), 4.71-4.61 (m, 1H), 4.51 (s, 1H), 4.35 (s, 1H), 4.20 (t, J=8.0 Hz, 1H), 4.09 (t, J=8.1 Hz, 1H), 3.91 (dd, J=8.6, 5.6 Hz, 1H), 3.75 (dd, J=8.4, 5.5 Hz, 1H), 3.23 (dd, component of ABX system, J=9.7, 1.6 Hz, 1H), 3.09 (d, half of AB quartet, J=9.6 Hz, 1H), 1.76 (s, 3H), 1.69 (s, 2H).

Step 4. Synthesis of (4R)-4-(3-chloro-2-fluorophenyl)-5-fluoro-2-[5-(hydroxymethyl)pyridin-2-yl]-4-methyl-6-({1-[(1 S,4S)-2-oxa-5-azabicyclo[2.2.1]heptane-5-carbonyl]azetidin-3-yl}amino)-3,4-dihydro-2,7-naphthyridin-1(2H)-one (22)

A mixture of C86 (1.10 g, 2.18 mmol), (6-bromopyridin-3-γ1)methanol (90%, 547 mg, 2.62 mmol), potassium carbonate (905 mg, 655 mmol), and bis[(tetrabutylammonium iodide)copper(I) iodide] (489 mg, 0.437 mmol) was treated with 2-methyltetrahydrofuran (25 mL) and $N^1$,$N^2$-dimethylethane-1,2-diamine (0.1 mL, 0.9 mmol). After the reaction mixture had been heated at 80° C. for 18 hours, it was allowed to cool to 25° C. and diluted with saturated aqueous ammonium chloride solution (25 mL). The aqueous layer was extracted with dichloromethane (4×25 mL), and the combined organic layers were washed with saturated aqueous sodium chloride solution (100 mL), dried over magnesium sulfate, filtered, and concentrated in vacuo. Silica gel chromatography (Gradient: 0% to 8% methanol in dichloromethane) provided a solid, which was treated with ethanol (2.8 mL), heated to 45° C. for 8 hours, and then allowed to cool to 25° C. After 64 hours, the resultant solid was collected via filtration and rinsed with cold ethanol (2×1 mL) to afford (4R)-4-(3-chloro-2-fluorophenyl)-5-fluoro-2-[5-(hydroxymethyl)pyridin-2-yl]-4-methyl-6-({1-[(1 S,4S)-2-oxa-5-azabicyclo[2.2.1]heptane-5-carbonyl]azetidin-3-yl}amino)-3,4-dihydro-2,7-naphthyridin-1(2H)-one (22) as a white solid. Yield: 650 mg, 1.06 mmol, 49%. LCMS m/z 611.4 (chlorine isotope pattern observed) $[M+H]^+$. $^1$H NMR (400 MHz, chloroform-d) δ 8.78 (s, 1H), 8.33 (d, J=2.3 Hz, 1H), 7.91 (d, J=8.5 Hz, 1H), 7.70 (dd, J=8.5, 2.4 Hz, 1H), 7.40-7.33 (m, 1H), 7.22-7.16 (m, 1H), 7.08 (t, J=8.0 Hz, 1H), 5.41-5.34 (m, 1H), 4.88-4.77 (m, 1H), 4.68 (br s, 2H), 4.60-4.50 (m, 3H), 4.41 (t, J=8.2 Hz, 1H), 4.31 (t, J=8.2 Hz, 1H), 4.19 (d, J=13.4 Hz, 1H), 3.98-3.87 (m, 2H), 3.81-3.71 (m, 2H), 3.32-3.23 (m, 2H), 2.33-2.23 (m, 1H), 1.86 (s, 3H), 1.83-1.73 (m, 2H).

Example 23

4-(3-Chloro-2,4-difluorophenyl)-5-fluoro-6-({1-[(1 S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one, from P3 (ENANT-2) (23)

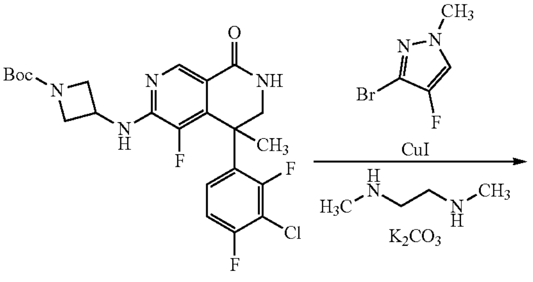

P3 (ENANT-2)

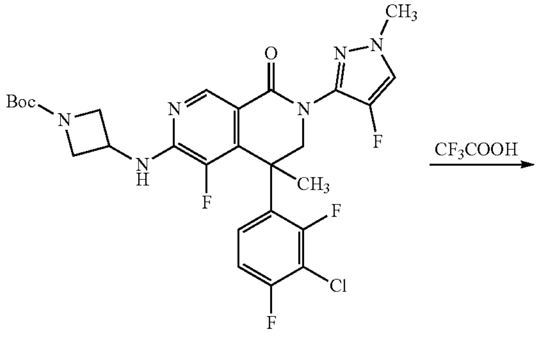

C87 [from P3 (ENANT-2)]

-continued

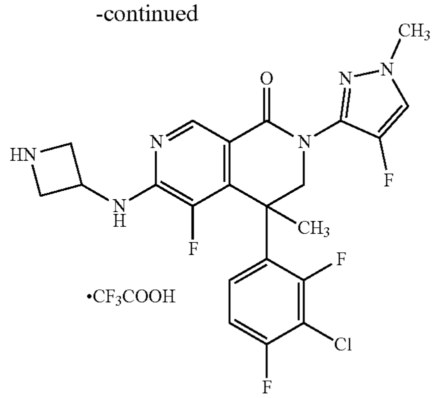

C88 [from P3 (ENANT-2)]

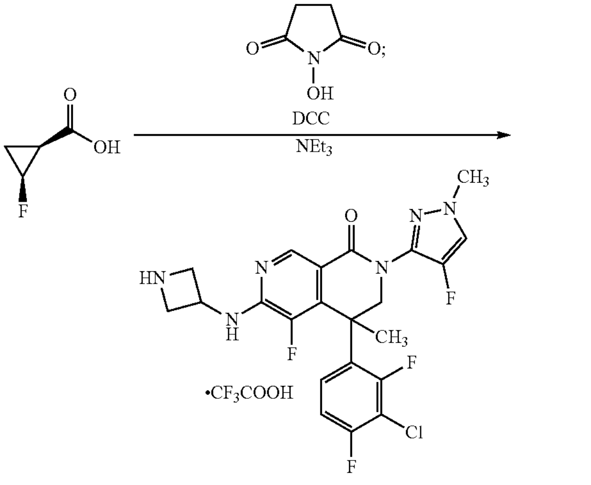

C88 [from P3 (ENANT-2)]

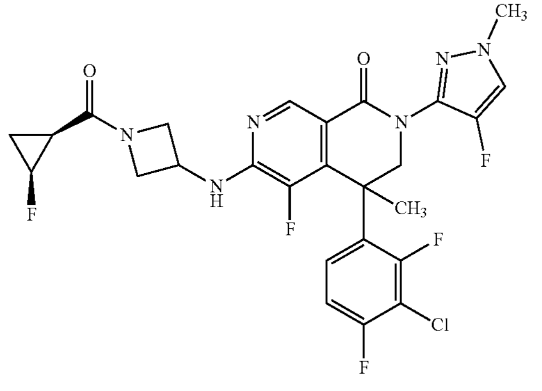

23 [from P3 (ENANT-2)]

Step 1. Synthesis of tert-butyl 3-{[5-(3-chloro-2,4-difluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidine-1-carboxylate, from P3 (ENANT-2) (C87)

A solution of P3 (ENANT-2) (170 mg, 0.342 mmol) in 1,4-dioxane (4 mL) was treated with potassium carbonate (142 mg, 1.03 mmol), copper(I) iodide (130 mg, 0.683 mmol), 3-bromo-4-fluoro-1-methyl-1H-pyrazole (200 mg, 1.12 mmol), and N',NM-dimethylethane-1,2-diamine (60.3 mg, 0.684 mmol), whereupon the reaction mixture was heated at 100° C. After 104 hours, the mixture was allowed to cool to 25° C., combined with a similar reaction carried out using P3 (ENANT-2) (20.0 mg, 40.2 μmol), and concentrated in vacuo. The residue was diluted with water (10 mL) and extracted with a mixture of ethyl acetate and tetrahydrofuran (1:1, 3×10 mL). The combined organic layers were dried over sodium sulfate, filtered, and concentrated under reduced pressure; silica gel chromatography (Gradient: 0% to 60% ethyl acetate in petroleum ether) afforded C87 [from P3 (ENANT-2)] as a yellow solid. Combined yield: 140 mg, 0.235 mmol, 62%. LCMS m/z 595.2 (chlorine isotope pattern observed) $[M+H]^+$.

Step 2. Synthesis of 6-[(azetidin-3-γl)amino]-4-(3-chloro-2,4-difluorophenyl)-5-fluoro-2-(4-fluoro-1-methyl-1H-pyrazol-3-yl)-4-methyl-3,4-dihydro-2,7-naphthyridin-1(2H)-one, trifluoroacetic acid salt, from P3 (ENANT-2) (C88)

Trifluoroacetic acid (1.5 mL) was added to a 15° C. solution of C87 [from P3 (ENANT-2)](0.140 g, 0.235 mmol) in dichloromethane (6 mL). After 1 hour, LCMS analysis indicated conversion to C88: LCMS m/z 495.1 (chlorine isotope pattern observed) $[M+H]^+$. The reaction mixture was concentrated in vacuo to provide C88 [from P3 (ENANT-2)], one-half of which was directly used in the following step.

Step 3. Synthesis of 4-(3-chloro-2,4-difluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one, from P3 (ENANT-2) (23)

1,3-Dicyclohexylcarbodiimide (DCC; 59.5 mg, 0.288 mmol) was added to a solution of 1-hydroxypyrrolidine-2,5-dione (33.2 mg, 0.288 mmol) and (1S,2S)-2-fluorocyclopropane-1-carboxylic acid (30.0 mg, 0.288 mmol) in tetrahydrofuran (1.5 mL). After 3 hours at room temperature, the mixture was filtered; to this filtrate was added a solution of C88 [from P3 (ENANT-2)] (one-half of the material from the previous step; 50.118 mmol) and triethylamine (59.5 mg, 0.588 mmol) in acetonitrile (1.5 mL). After 16 hours at room temperature, the reaction mixture was concentrated in vacuo and purified using reversed-phase HPLC (Column: Boston Prime C18, 25×150 mm, 5 μm; Mobile phase A: water containing 0.05% ammonium hydroxide; Mobile phase B: acetonitrile; Gradient: 37% to 62% B; Flow rate: 25 mL/minute), affording 4-(3-chloro-2,4-difluorophenyl)-5-fluoro-6-({1-[(1 S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one, from P3 (ENANT-2) (23) as a white solid. Yield: 16.0 mg, 27.5 μmol, 23% over 2 steps. LCMS m/z 581.1 (chlorine isotope pattern observed) $[M+H^+]$. $^1H$ NMR (400 MHz, methanol-$d_4$), δ 8.63 (d, J=1.6 Hz, 1H), 7.59 (d, J=4.5 Hz, 1H), 7.43-7.34 (m, 1H), 7.16 (br t, J=8.7 Hz, 1H), [4.97-4.80 (m) and 4.76-4.64 (m), total 3H, assumed; partially obscured by water peak], 4.44-4.30 (m, 2H), 4.30-4.21 (m, 1H), 4.06-3.97 (m, 1H), 3.78 (s, 3H), 3.71 (d, J=12.8 Hz, 1H), 1.94 (s, 3H), 1.87-1.76 (m, 1H), 1.73-1.59 (m, 1H), 1.16-1.03 (m, 1H).

Example 24

4-(3-Chloro-2-fluorophenyl)-5-fluoro-2-(3-fluoropyridin-2-yl)-4-methyl-6-{[(3R)-1-(1-methylpiperidine-4-carbonyl)pyrrolidin-3-yl]amino}-3,4-dihydro-2,7-naphthyridin-1(2H)-one, from P9 (DIAST-2) (24)

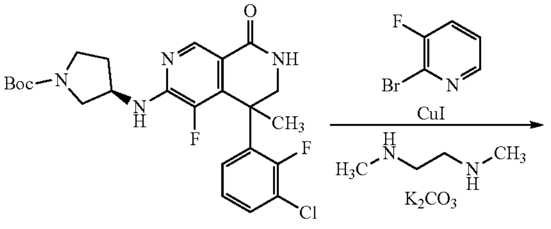

P9 (DIAST-2)]

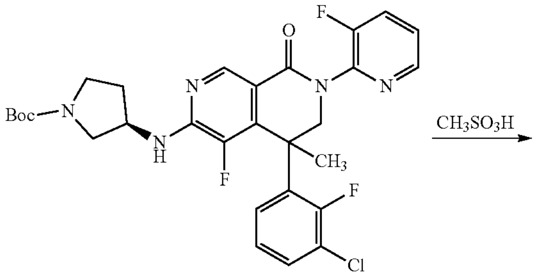

C89 [from P9 (DIAST-2)]

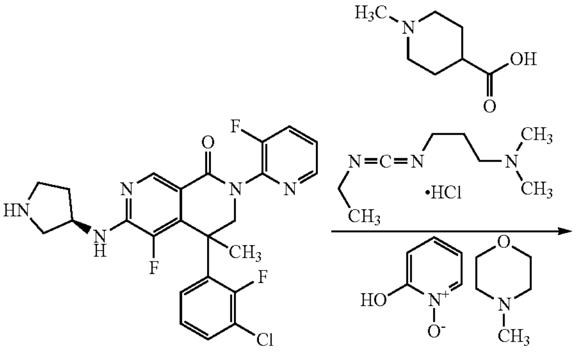

C90 [from P9 (DIAST-2)]

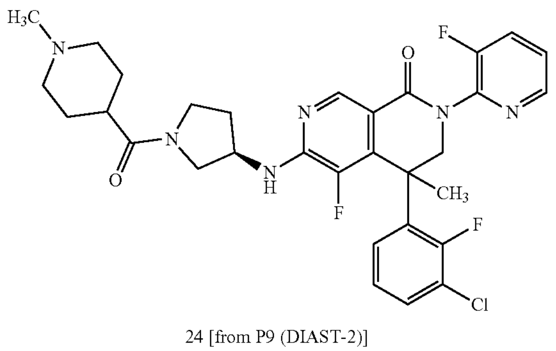

24 [from P9 (DIAST-2)]

Step 1. Synthesis of tert-butyl (3R)-3-{[5-(3-chloro-2-fluorophenyl)-4-fluoro-7-(3-fluoropyridin-2-yl)-5-methyl-8-oxo-5,6,7,8-tetrahydro-2,7-naphthyridin-3-yl]amino}pyrrolidine-1-carboxylate, from P9 (DIAST-2) (C89)

A mixture of P9 (DIAST-2) (850 mg, 1.72 mmol), potassium carbonate (715 mg, 5.17 mmol), and copper(I) iodide (328 mg, 1.72 mmol) was treated with 1,4-dioxane (20 mL), 2-bromo-3-fluoropyridine (455 mg, 2.59 mmol), and $N^1$,$N^2$-dimethylethane-1,2-diamine (152 mg, 1.72 mmol). After the reaction mixture had been heated at 100° C. for 32 hours, additional copper(I) iodide (328 mg, 1.72 mmol), 2-bromo-3-fluoropyridine (303 mg, 1.72 mmol), and $N^1$,$N^2$-dimethylethane-1,2-diamine (152 mg, 1.72 mmol) were added, and the reaction temperature was increased to 110° C. for 48 hours. It was then cooled to 25° C. and diluted with water (10 mL); the aqueous layer was extracted with ethyl acetate (3×10 mL), and the combined organic layers were washed with saturated aqueous sodium chloride solution (15 mL), dried over sodium sulfate, filtered, and concentrated in vacuo. Silica gel chromatography (Gradient: 0% to 100% ethyl acetate in petroleum ether) afforded C89 [from P9 (DIAST-2)] as a colorless gum. Yield: 720 mg, 1.22 mmol, 71%. LCMS m/z 588.2 (chlorine isotope pattern observed) $[M+H]^+$.

Step 2. Synthesis of 4-(3-chloro-2-fluorophenyl)-5-fluoro-2-(3-fluoropyridin-2-yl)-4-methyl-6-{[(3R)-pyrrolidin-3-yl]amino}-3,4-dihydro-2,7-naphthyridin-1(2H)-one, from P9 (DIAST-2) (C90)

Methanesulfonic acid (319 mg, 0.332 mmol) was added to a solution of C89 [from P9 (DIAST-2)] (195 mg, 0.332 mmol) in 1,1,1,3,3,3-hexafluoropropan-2-ol (3 mL). After 15 minutes, the pH was adjusted to >7 by addition of aqueous sodium hydroxide solution (1 M; 3.3 mL, 3.3 mmol), and 75% to 90% of the 1,1,1,3,3,3-hexafluoropropan-2-ol was removed in vacuo. The residue was partitioned between ethyl acetate (30 mL) and aqueous sodium hydroxide solution (1 M; 10 mL), whereupon the organic layer was washed sequentially with water (15 mL) and saturated aqueous sodium chloride solution (15 mL), dried over magnesium sulfate, filtered, and concentrated in vacuo to provide C90 [from P9 (DIAST-2)] as an oil, which was used directly in the following step. LCMS m/z 486.1 (chlorine isotope pattern observed) $[M-H]^-$.

Step 3. Synthesis of 4-(3-chloro-2-fluorophenyl)-5-fluoro-2-(3-fluoropyridin-2-yl)-4-methyl-6-{[(3R)-1-(1-methylpiperidine-4-carbonyl)pyrrolidin-3-yl]amino}-3,4-dihydro-2,7-naphthyridin-1(2H)-one, from P9 (DIAST-2) (24)

1-[3-(Dimethylamino)propyl]-3-ethylcarbodiimide hydrochloride (76.4 mg, 0.398 mmol) and 2-hydroxypyridine 1-oxide (36.9 mg, 0.332 mmol) were added to a 25° C. solution of C90 [from P9 (DIAST-2)] (from the previous step; 50.332 mmol) and 1-methylpiperidine-4-carboxylic acid (57.0 mg, 0.398 mmol) in N,N-dimethylacetamide (3.3 mL). 4-Methylmorpholine (0.110 mL 1.00 mmol) was added, and the reaction mixture was stirred for 22 hours, whereupon the reaction mixture was diluted with water (20 mL). The aqueous layer was extracted with ethyl acetate (2×25 mL), and the combined organic layers were washed with saturated aqueous sodium chloride solution (20 mL), dried over magnesium sulfate, filtered, and concentrated in vacuo. Purification via supercritical fluid chromatography (Column: Princeton HA-Morpholine, 30×250 mm, 5 μm; Mobile phase: 4:1 carbon dioxide/methanol; Back pressure: 120 bar; Flow rate: 10 mL/minute) afforded 4-(3-chloro-2-fluorophenyl)-5-fluoro-2-(3-fluoropyridin-2-yl)-4-methyl-6-{[(3R)-1-(1-methylpiperidine-4-carbonyl)pyrrolidin-3-yl]amino}-3,4-dihydro-2,7-naphthyridin-1(2H)-one, from P9 (DIAST-2) (24) as an off-white solid. $^1$H NMR analysis suggested that this material exists as a mixture of rotamers. Yield: 85 mg, 0.14 mmol, 42% over 2 steps. LCMS m/z 613.3 (chlorine isotope pattern observed) $[M+H]^+$. $^1$H NMR (400 MHz, DMSO-$d_6$), characteristic peaks: δ [8.59 (s) and 8.58 (s), total 1H], 8.30 (br d, J=4.8 Hz, 1H), 7.85-7.76 (m, 1H), 7.62-7.54 (m, 2H), 7.50-7.39 (m, 2H), 7.32-7.25 (m, 1H), 4.70-4.50 (m, 1H), 4.34 (d, J=12.8 Hz, 1H), [3.88-3.77 (m) and 3.59-3.51 (m), total 2H], 3.70-3.59 (m, 1H), 3.51-3.41 (m, 1H), 2.83-2.70 (m, 2H), 2.37-2.02 (m, 2H), [2.13 (s) and 2.12 (s), total 3H], 1.98-1.77 (m, 3H), 1.87 (s, 3H), 1.66-1.47 (m, 4H).

Example 25

4-(3-Chloro-2-fluorophenyl)-5-fluoro-2-(4-fluoro-1-methyl-1H-pyrazol-3-yl)-4-methyl-6-({(3R)-1-[(1S,4S)-2-oxa-5-azabicyclo[2.2.1]heptane-5-carbonyl]pyrrolidin-3-yl}amino)-3,4-dihydro-2,7-naphthyridin-1(2H)-one, from P9 (DIAST-2) (25)

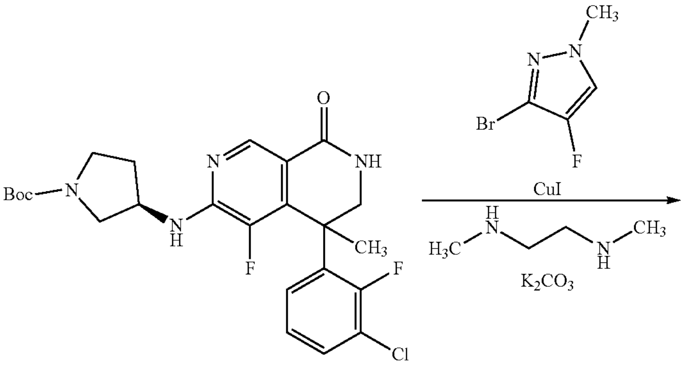

P9 (DIAST-2)

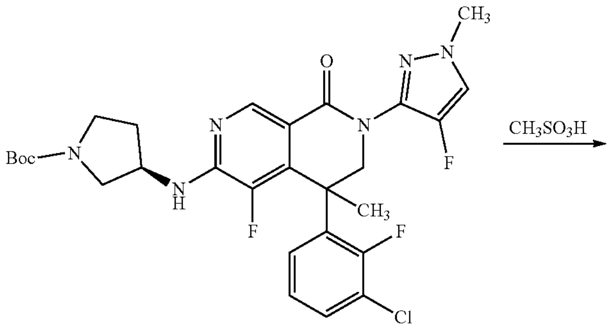

C91 [from P9 (DIAST-2)]

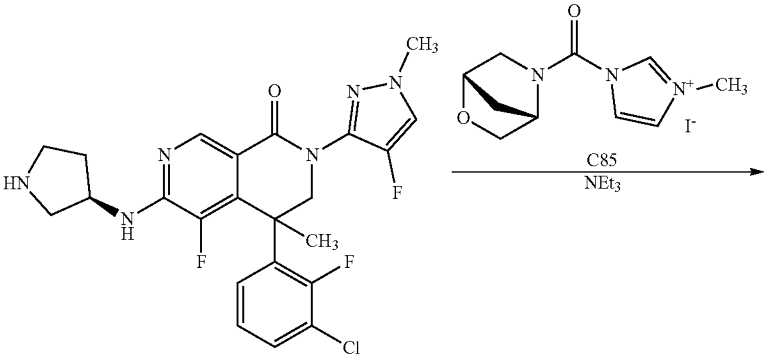

C92 [from P9 (DIAST-2)]

-continued

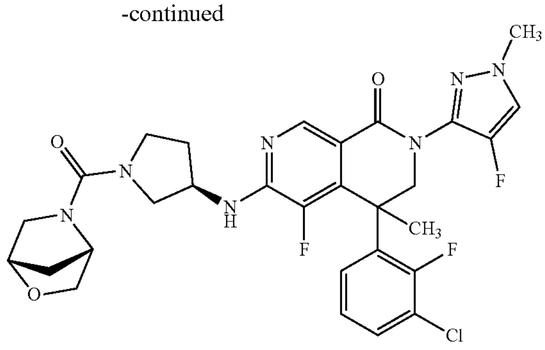

25 [from P9 (DIAST-2)]

Step 1. Synthesis of tert-butyl (3R)-3-{[5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}pyrrolidine-1-carboxylate, from P9 (DIAST-2) (C91)

A mixture of P9 (DIAST-2) (200 mg, 0.406 mmol), potassium carbonate (168 mg, 1.22 mmol), and copper(I) iodide (77.3 mg, 0.406 mmol) was treated with 1,4-dioxane (15 mL), 3-bromo-4-fluoro-1-methyl-1H-pyrazole (109 mg, 0.609 mmol), and $N^1$,$N^2$-dimethylethane-1,2-diamine (35.8 mg, 0.406 mmol), whereupon the reaction mixture was heated at 100° C. After 16 hours, additional copper(I) iodide (38.6 mg, 0.203 mmol) and $N^1$,$N^2$-dimethylethane-1,2-diamine (17.9 mg, 0.203 mmol) were added and heating was continued at 100° C. for 16 hours. The reaction mixture was then filtered, concentrated in vacuo, and purified via silica gel chromatography (Gradient: 0% to 100% ethyl acetate in petroleum ether) to provide C91 [from P9 (DIAST-2)] as a colorless gum. Yield: 200 mg, 0.338 mmol, 83%. LCMS m/z 591.3 (chlorine isotope pattern observed) $[M+H]^+$.

Step 2. Synthesis of 4-(3-chloro-2-fluorophenyl)-5-fluoro-2-(4-fluoro-1-methyl-1H-pyrazol-3-γ1)-4-methyl-6-{[(3R)-pyrrolidin-3-yl]amino}-3,4-dihydro-2,7-naphthyridin-1(2H)-one, from P9 (DIAST-2) (C92)

Methanesulfonic acid (50 uL, 0.8 mmol) was added to a 0° C. solution of C91 [from P9 (DIAST-2)] (38.0 mg, 64.3 μmol) in 1,1,1,3,3,3-hexafluoropropan-2-ol (1 mL), whereupon the reaction mixture was warmed to room temperature. After 10 minutes, it was cooled to 0° C., and the pH was adjusted to >7 by addition of aqueous sodium hydroxide solution (1 M; 3 mL). The aqueous layer was extracted with dichloromethane (4×5 mL), and the combined organic layers were washed with saturated aqueous sodium chloride solution (20 mL), dried over magnesium sulfate, filtered, and concentrated in vacuo to provide C92 [from P9 (DIAST-2)], which was used directly in the following step. LCMS m/z 491.4 (chlorine isotope pattern observed) $[M+H]^+$.

Step 3. Synthesis of 4-(3-chloro-2-fluorophenyl)-5-fluoro-2-(4-fluoro-1-methyl-1H-pyrazol-3-γ1)-4-methyl-6-({(3R)-1-[(1S,4S)-2-oxa-5-azabicyclo[2.2.1]heptane-5-carbonyl]pyrrolidin-3-yl}amino)-3,4-dihydro-2,7-naphthyridin-1(2H)-one, from P9 (DIAST-2) (25)

A solution of C92 [from P9 (DIAST-2)] (from the previous step; ≤64.3 μmol) and triethylamine (44.8 μL, 0.321 mmol) in dichloromethane (2 mL) was treated with C85 (85%, 76.1 mg, 0.193 mmol). After 30 minutes, the reaction mixture was diluted with water (3 mL) and extracted with dichloromethane (4×3 mL); the combined organic layers were washed with saturated aqueous sodium chloride solution (12 mL), dried over magnesium sulfate, filtered, and concentrated in vacuo. Purification was carried out via silica gel chromatography (Eluent: 2% methanol in dichloromethane), followed by reversed-phase HPLC (Column: Waters XBridge C18, 19×100 mm, 5 μm; Mobile phase A: water containing 0.03% ammonium hydroxide; Mobile phase B: acetonitrile containing 0.03% ammonium hydroxide; Gradient: 15% to 55% B; Flow rate: 25 mL/minute), to provide 4-(3-chloro-2-fluorophenyl)-5-fluoro-2-(4-fluoro-1-methyl-1H-pyrazol-3-yl)-4-methyl-6-({(3R)-1-[(1 S,4S)-2-oxa-5-azabicyclo[2.2.1]heptane-5-carbonyl]pyrrolidin-3-yl}amino)-3,4-dihydro-2,7-naphthyridin-1(2H)-one, from P9 (DIAST-2) (25) as a white solid. Yield: 17.1 mg, 27.8 μmol, 43% over 2 steps. LCMS m/z 616.5 (chlorine isotope pattern observed) $[M+H]^+$. Retention time: 2.51 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Example 26

8-(3-Chloro-2-fluorophenyl)-6-(3-fluoropyridin-2-yl)-2-{[1-(hydroxyacetyl)azetidin-3-yl]amino}-8-methyl-7,8-dihydropyrido[4,3-d]pyrimidin-5(6H)-one, from P13 (ENANT-2) (26)

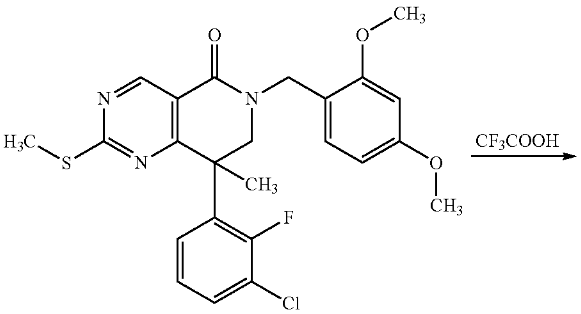

P13, ENANT-2

-continued

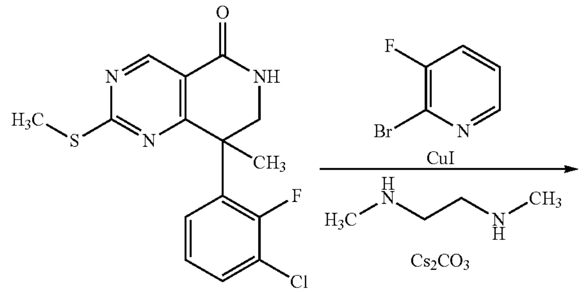

C93 [from P13 (ENANT-2)]

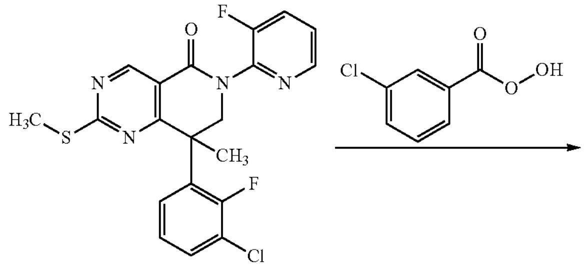

C94 [from P13 (ENANT-2)]

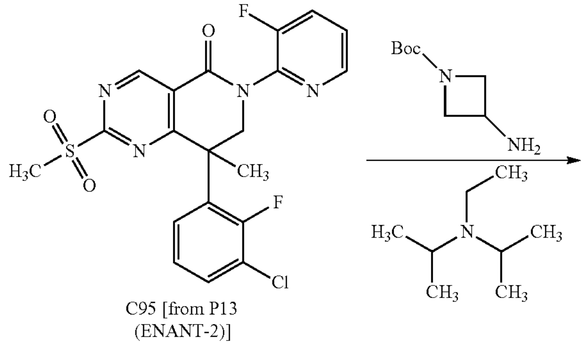

C95 [from P13 (ENANT-2)]

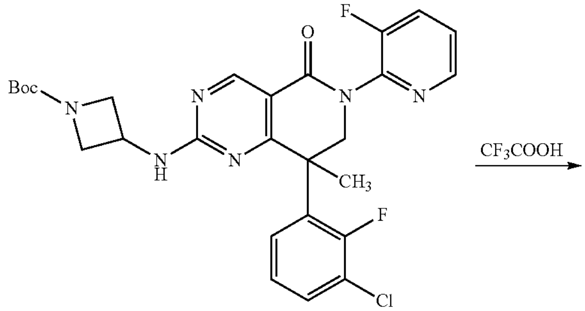

C96 [from P13 (ENANT-2)]

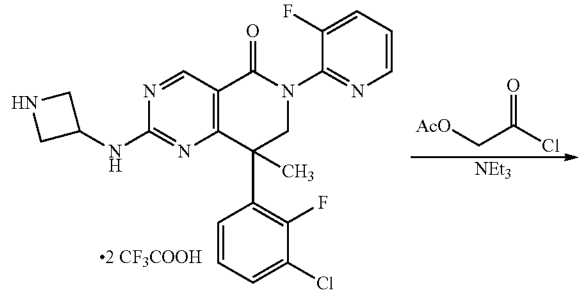

C97 [from P13 (ENANT-2)]

-continued

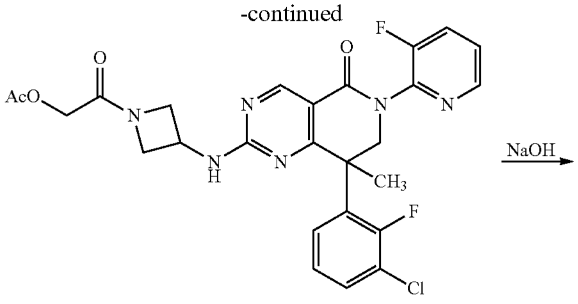

C98 [from P13 (ENANT-2)]

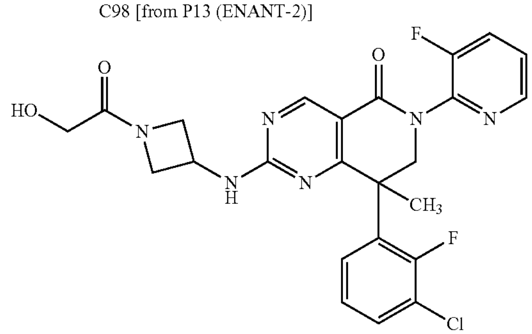

26 [from P13 (ENANT-2)]

Step 1. Synthesis of 8-(3-chloro-2-fluorophenyl)-8-methyl-2-(methylsulfanyl)-7,8-dihydropyrido[4,3-d]pyrimidin-5(6H)-one, from P13 (ENANT-2) (C93)

A mixture of P13, ENANT-2 (5.0 g, 10.2 mmol) and trifluoroacetic acid (25 mL, 324 mmol) was heated at 70° C. for 16 hours, whereupon the reaction mixture was allowed to cool to 25° C., concentrated in vacuo, treated with toluene (20 mL), and concentrated once more. The residue was diluted with ethyl acetate (120 mL), washed sequentially with aqueous sodium hydroxide solution (1 M; 100 mL) and saturated aqueous sodium chloride solution (50 mL), dried over magnesium sulfate, filtered, and concentrated under reduced pressure. The resulting material was taken up in a mixture of ethyl acetate and heptane (1:1, 10 mL), filtered through silica gel (25 g) using a mixture of ethyl acetate and heptane (3:1, 70 mL) and concentrated in vacuo to provide C93 [from P13 (ENANT-2)] as a light-yellow solid (4.19 g). A portion of this material was used directly in the next step without further purification. LCMS m/z 338.1 (chlorine isotope pattern observed) $[M+H]^+$. $^1H$ NMR (400 MHz, DMSO-$d_6$), product peaks only: δ 8.95 (s, 1H), 8.28 (br s, 1H), 7.57 (br t, J=7.5 Hz, 1H), 7.22 (t, J=8.0 Hz, 1H), 7.11 (br t, J=7.6 Hz, 1H), 3.83 (dd, J=13.4, 3.1 Hz, 1H), 3.42 (dd, J=13.4, 3.3 Hz, 1H), 2.44 (s, 3H), 1.72 (s, 3H).

Step 2. Synthesis of 8-(3-chloro-2-fluorophenyl)-6-(3-fluoropyridin-2-yl)-8-methyl-2-(methylsulfanyl)-7,8-dihydropyrido[4,3-d]pyrimidin-5(6H)-one, from P13 (ENANT-2) (C94)

A mixture of C93 [from P13 (ENANT-2)] (from the previous step; 2.50 g, 56.1 mmol) and 2-bromo-3-fluoropyridine (1.62 g, 9.21 mmol) in 1,4-dioxane (31 mL) was sparged with nitrogen for 20 minutes, whereupon cesium carbonate (6.00 g, 18.4 mmol), copper(I) iodide (1.17 g, 6.14 mmol), and $N^1$,$N^2$-dimethylethane-1,2-diamine (1.32 mL, 12.4 mmol) were added. After the reaction mixture had been heated at 100° C. for 4 hours, it was allowed to cool to 25°

C. and filtered through a plug of silica gel (5 g) with ethyl acetate (60 mL). The eluent was concentrated in vacuo and purified via silica gel chromatography (Gradient: 0% to 75% ethyl acetate in heptane), affording C94 [from P13 (ENANT-2)] as a white solid. Yield: 1.85 g, 4.27 mmol, 70% over 2 steps. LCMS m/z 433.1 (chlorine isotope pattern observed) $[M+H]^+$. $^1H$ NMR (400 MHz, chloroform-d) δ 9.20 (s, 1H), 8.28 (br d, J=4.8 Hz, 1H), 7.49 (ddd, J=9.6, 8.2, 1.5 Hz, 1H), 7.40-7.35 (m, 1H), 7.31-7.26 (m, 1H, assumed; partially obscured by solvent peak), 7.11-6.99 (m, 2H), 4.69 (d, J=13.1 Hz, 1H), 3.91 (d, J=13.1 Hz, 1H), 2.46 (s, 3H), 1.91 (s, 3H).

Step 3. Synthesis of 8-(3-chloro-2-fluorophenyl)-6-(3-fluoropyridin-2-yl)-2-(methanesulfonyl)-8-methyl-7,8-dihydropyrido[4,3-d]pyrimidin-5(6H)-one, from P13 (ENANT-2) (C95)

3-Chloroperoxybenzoic acid (77%, 1.53 g, 6.83 mmol) was added to a 0° C. solution of C94 [from P13 (ENANT-2)] (985 mg, 2.28 mmol) in dichloromethane (25 mL). The reaction mixture was stirred at 25° C. for 2.5 hours, whereupon LCMS analysis indicated conversion to C95: LCMS m/z 465.1 (chlorine isotope pattern observed) $[M+H]^+$. Saturated aqueous sodium thiosulfate solution (15 mL) and saturated aqueous sodium bicarbonate solution (15 mL) were added, and the resulting mixture was extracted with dichloromethane (4×40 mL); the combined organic layers were dried over sodium sulfate, filtered, and concentrated in vacuo, providing C95 [from P13 (ENANT-2)] as a white solid (1.10 g). Most of this material was progressed directly to the following step. $^1H$ NMR (400 MHz, chloroform-d) δ 9.60 (s, 1H), 8.32 (br d, J=4.7 Hz, 1H), 7.56 (ddd, J=9.5, 8.2, 1.5 Hz, 1H), 7.46-7.40 (m, 1H), 7.36-7.31 (m, 1H), 7.20-7.11 (m, 2H), 4.74 (d, J=13.2 Hz, 1H), 3.98 (d, J=13.3 Hz, 1H), 3.23 (s, 3H), 2.00 (s, 3H).

Step 4. Synthesis of tert-butyl 3-{[8-(3-chloro-2-fluorophenyl)-6-(3-fluoropyridin-2-yl)-8-methyl-5-oxo-5,6,7,8-tetrahydropyrido[4,3-d]pyrimidin-2-yl]amino}azetidine-1-carboxylate, from P13 (ENANT-2) (C96)

To a solution of C95 [from P13 (ENANT-2)] (from the previous step; 875 mg, ≤1.81 mmol) in toluene (10 mL) were added N,N-diisopropylethylamine (1.31 mL, 7.52 mmol) and tert-butyl 3-aminoazetidine-1-carboxylate (648 mg, 3.76 mmol). After the reaction mixture had been heated at 50° C. for 1 hour, LCMS analysis indicated conversion to C96: LCMS m/z 557.2 (chlorine isotope pattern observed) $[M+H]^+$. The reaction mixture was allowed to cool to 25° C. before being diluted with water (20 mL) and saturated aqueous sodium bicarbonate solution (10 mL). The aqueous layer was extracted with ethyl acetate (3×35 mL) and the combined organic layers were dried over sodium sulfate, filtered, and concentrated in vacuo. Silica gel chromatography (Gradient: 25% to 100% ethyl acetate in heptane) afforded C96 [from P13 (ENANT-2)] as a white solid. Yield: 927 mg, 1.66 mmol, 91% over 2 steps. $^1H$ NMR (400 MHz, chloroform-d), integrations are approximate for the azetidine moiety: δ 9.06 (br s, 1H), 8.29 (br d, J=4.8 Hz, 1H), 7.51 (br t, J=8.7 Hz, 1H), 7.39 (br t, J=7.2 Hz, 1H), 7.28-7.21 (m, 1H, assumed; partially obscured by solvent peak), 7.20-7.06 (m, 2H), [6.01 (br s) and 5.77 (br s), total 1H], [4.86-4.70 (m) and 4.32 (br s), total 2H], 4.64 (d, J=13.0 Hz, 1H), 3.90-3.55 (m, 3H), 3.79 (d, J=13.0 Hz, 1H), 1.85 (s, 3H), 1.43 (s, 9H).

Step 5. Synthesis of 2-[(azetidin-3-γ1)amino]-8-(3-chloro-2-fluorophenyl)-6-(3-fluoropyridin-2-γ1)-8-methyl-7,8-dihydropyrido[4,3-d]pyrimidin-5(6H)-one, bis(trifluoroacetate) salt, from P13 (ENANT-2) (C97)

Trifluoroacetic acid (5.0 mL, 65 mmol) was added to a 0° C. solution of C96 [from P13 (ENANT-2)] (925 mg, 1.66 mmol) in dichloromethane (5 mL). After 1 hour at room temperature, LCMS analysis indicated conversion to C97: LCMS m/z 457.2 (chlorine isotope pattern observed) $[M+H]^+$. The reaction mixture was diluted with a mixture of ethyl acetate and heptane (1:1, 10 mL) and concentrated under reduced pressure; this process was carried out twice. The resultant foam was diluted with toluene (10 mL) and concentrated, followed by dilution with chloroform (10 mL); concentration in vacuo afforded C97 [from P13 (ENANT-2)] as a brown foam (1.38 g), which was used directly in the following step.

Step 6. Synthesis of 2-(3-{[8-(3-chloro-2-fluorophenyl)-6-(3-fluoropyridin-2-yl)-8-methyl-5-oxo-5,6,7,8-tetrahydropyrido[4,3-d]pyrimidin-2-yl]amino}azetidin-1-yl)-2-oxoethyl acetate, from P13 (ENANT-2) (C98)

2-Chloro-2-oxoethyl acetate (0.206 mL, 1.92 mmol) was added drop-wise over 5 minutes to a 0° C. solution of C97 [from P13 (ENANT-2)] (from the previous step; ≤1.66 mmol) and triethylamine (1.62 mL, 11.6 mmol) in dichloromethane (25 mL). After 45 minutes, the reaction mixture was concentrated in vacuo; silica gel chromatography (Gradient: 0% to 4% methanol in dichloromethane) afforded C98 [from P13 (ENANT-2)] as a white solid. Yield: 759 mg, 1.36 mmol, 82% over 2 steps. LCMS m/z 557.2 (chlorine isotope pattern observed) $[M+H]^+$. $^1H$ NMR (400 MHz, chloroform-d) δ 9.05 (s, 1H), 8.26 (d, J=4.7 Hz, 1H), 7.55-7.45 (m, 1H), 7.45-7.36 (m, 1H), 7.31-7.22 (m, 1H, assumed; partially obscured by solvent peak), 7.20-7.06 (m, 2H), [6.34 (br s) and 5.88 (br s), total 1H], 4.71-4.19 (m, 5H), 4.18-4.02 (m, 1H), 4.00-3.71 (m, 3H), 2.15 (s, 3H), 1.86 (br s, 3H).

Step 7. Synthesis of 8-(3-chloro-2-fluorophenyl)-6-(3-fluoropyridin-2-yl)-2-{[1-(hydroxyacetyl)azetidin-3-yl]amino}-8-methyl-7,8-dihydropyrido[4,3-d]pyrimidin-5(6H)-one, from P13 (ENANT-2) (26)

An aqueous solution of sodium hydroxide (1 M; 2.7 mL, 2.7 mmol) was added to a 0° C. solution of C98 [from P13 (ENANT-2)] (760 mg, 1.36 mmol) in tetrahydrofuran (20 mL), and the reaction mixture was allowed to warm to 25° C. After 4 hours, it was concentrated in vacuo and diluted with water (30 mL); the resulting mixture was adjusted to a pH of 5 by addition of 1 M hydrochloric acid, then extracted with dichloromethane (3×30 mL). The combined organic layers were dried over sodium sulfate, filtered, and concentrated under reduced pressure. Purification via silica gel chromatography (Gradient: 0% to 10% methanol in dichloromethane) afforded 8-(3-chloro-2-fluorophenyl)-6-(3-fluoropyridin-2-yl)-2-{[1-(hydroxyacetyl)azetidin-3-yl]amino}-8-methyl-7,8-dihydropyrido[4,3-d]pyrimidin-5(6H)-one, from P13 (ENANT-2) (26) as a white solid. Yield: 583 mg, 1.13 mmol, 83%. LCMS m/z 515.1 (chlorine isotope pattern observed) $[M+H]^+$. $^1H$ NMR (400 MHz, chloroform-d) δ 9.06 (s, 1H), 8.27 (d, J=4.7 Hz, 1H), 7.56-7.37 (m, 2H), 7.35-7.07 (m, 3H, assumed; partially obscured by solvent peak), [6.15 (br s) and 5.84 (br s), total 1H], 4.64 (d, J=12.9 Hz, 1H), 4.58-4.07 (m, 2H), 4.07-3.58 (m, 6H), 1.86 (br s, 3H).

Example 27

8-(3-Chloro-2-fluorophenyl)-6-(3-fluoropyridin-2-yl)-2-{[1-(1-hydroxycyclopropane-1-carbonyl)azetidin-3-yl]amino}-8-methyl-7,8-dihydropyrido[4,3-d]pyrimidin-5(6H)-one, from P13 (ENANT-2) (27)

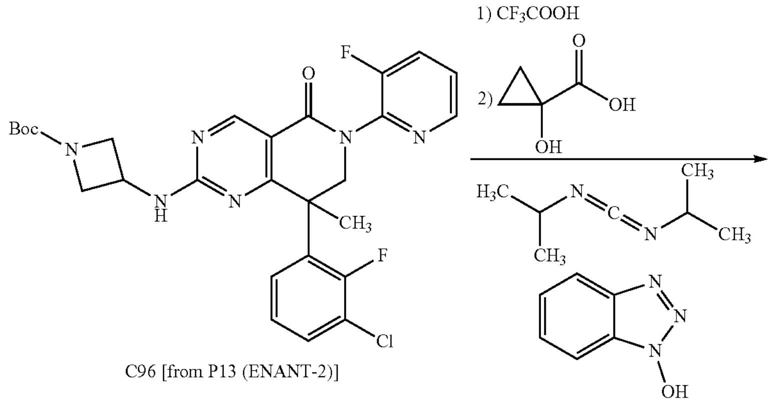

C96 [from P13 (ENANT-2)]

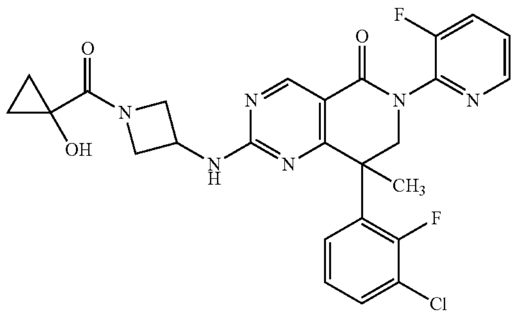

27 [from P13 (ENANT-2)]

A solution of C96 [from P13 (ENANT-2)] (145 mg, 0.260 mmol) and trifluoroacetic acid (99.6 μL, 1.29 mmol) in 1,1,1,3,3,3-hexafluoropropan-2-ol (2.6 mL) was stirred at room temperature for 1 hour, whereupon LCMS analysis indicated that the protecting group had been removed: LCMS m/z 457.3 (chlorine isotope pattern observed) $[M+H]^+$. The reaction mixture was diluted with dichloromethane (20 mL), followed by aqueous sodium hydroxide solution (1 M; 20 mL); the aqueous layer was extracted with dichloromethane and the combined organic layers were washed with 1 M aqueous sodium hydroxide solution, dried over sodium sulfate, and concentrated in vacuo to provide the secondary amine.

N,N'-Diisopropylcarbodiimide (32.9 mg, 0.261 mmol) was added to a 25° C. solution of 1H-benzotriazol-1-ol (39.9 mg, 0.295 mmol) and 1-hydroxycyclopropane-1-carboxylic acid (26.6 mg 0.261 mmol) in N,N-dimethylformamide (2.6 mL). After 2 hours, the secondary amine from above (50.260 mmol) was added, and stirring was continued for 2 hours, whereupon LCMS analysis indicated conversion to 27: LCMS m/z 541.2 (chlorine isotope pattern observed) $[M+H]^+$. The reaction mixture was diluted with saturated aqueous sodium chloride solution (10 mL) and extracted with ethyl acetate (3×25 mL); the combined organic layers were washed with saturated aqueous sodium chloride solution (4×20 mL), dried over sodium sulfate, filtered, concentrated in vacuo, and purified via silica gel chromatography (Gradient: 0.5% to 5% methanol in dichloromethane), affording 8-(3-chloro-2-fluorophenyl)-6-(3-fluoropyridin-2-yl)-2-{[1-(1-hydroxycyclopropane-1-carbonyl)azetidin-3-yl]amino}-8-methyl-7,8-dihydropyrido[4,3-d]pyrimidin-5(6H)-one, from P13 (ENANT-2) (27) as a white solid. Yield: 79.0 mg, 0.146 mmol, 56%. $^1H$ NMR (400 MHz, chloroform-d), integrations are approximate: δ 9.05 (s, 1H), 8.34-8.20 (m, 1H), 7.55-7.45 (m, 1H), 7.45-7.36 (m, 1H), 7.33-7.05 (m, 3H, assumed; partially obscured by solvent peak), 4.96-3.68 (m, 6H), 4.64 (br d, J=12.7 Hz, 1H), 1.87 (s, 3H), 0.98 (br s, 2H), 0.93-0.84 (m, 2H).

Examples 28 and 29

8-(3-Chloro-2-fluorophenyl)-6-(3-fluoropyridin-2-yl)-2-{[1-(1-hydroxy-2,2-dimethylcyclopropane-1-carbonyl)azetidin-3-yl]amino}-8-methyl-7,8-dihydropyrido[4,3-d]pyrimidin-5(6H)-one, from P13 (ENANT-2), DIAST-1 (28) and 8-(3-Chloro-2-fluorophenyl)-6-(3-fluoropyridin-2-yl)-2-{[1-(1-hydroxy-2,2-dimethylcyclopropane-1-carbonyl)azetidin-3-yl]amino}-8-methyl-7,8-dihydropyrido[4,3-d]pyrimidin-5(6H)-one, from P13 (ENANT-2), DIAST-2 (29)

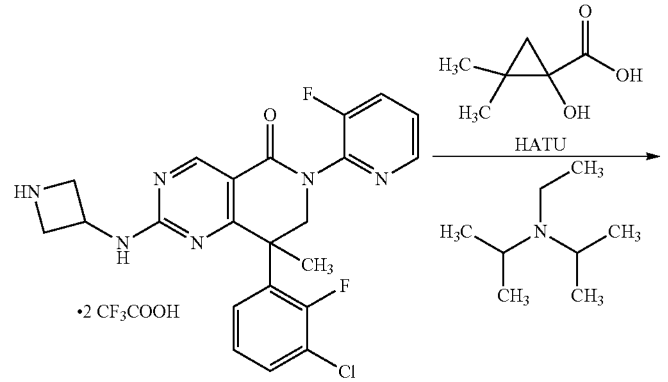

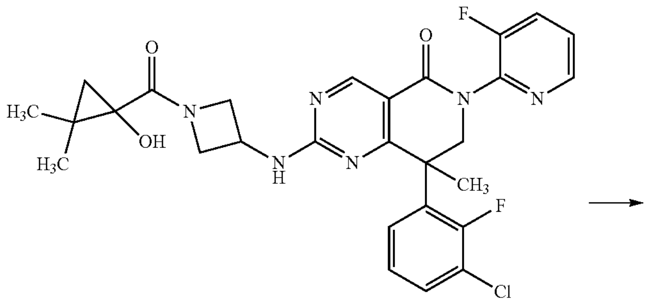

C99 [from P13 (ENANT-2)]

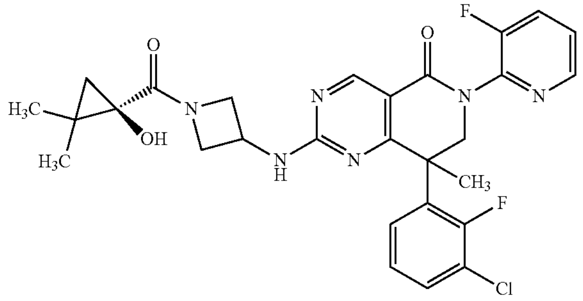

+

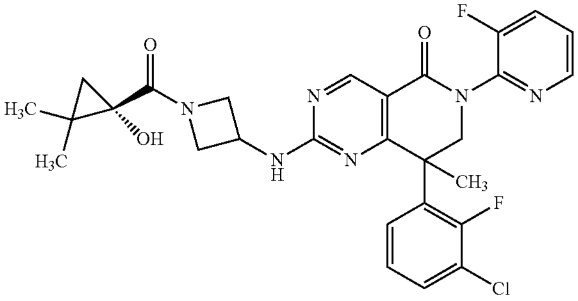

28 [from P13 (ENANT-2)] (DIAST-1) and
29 [from P13 (ENANT-2)] (DIAST-2)

Step 1. Synthesis of 8-(3-chloro-2-fluorophenyl)-6-(3-fluoropyridin-2-yl)-2-({1-[(1RS)-1-hydroxy-2,2-dimethylcyclopropane-1-carbonyl]azetidin-3-yl}amino)-8-methyl-7,8-dihydropyrido[4,3-d]pyrimidin-5(6H)-one, from P13 (ENANT-2) (C99)

O-(7-Azabenzotriazol-1-yl)-N,N,N'N'-tetramethyluronium hexafluorophosphate (HATU; 0.120 g, 0.316 mmol) was added to a 25° C. solution of C97 [from P13 (ENANT-2)] (144 mg, 0.210 mmol, 4.31 mmol) and N,N-diisopropylethylamine (55.0 μL, 0.316 mmol) in N,N-dimethylformamide (0.75 mL). After 30 minutes, a solution of 1-hydroxy-2,2-dimethylcyclopropane-1-carboxylic acid (41.0 mg, 0.315 mmol) and N,N-diisopropylethylamine (55.0 μL, 0.316 mmol) in N,N-dimethylformamide (0.75 mL) was added, and stirring was continued for 16 hours, whereupon LCMS analysis indicated the presence of C99: LCMS m/z 569.3 (chlorine isotope pattern observed) $[M+H]^+$. The reaction mixture was diluted with saturated aqueous sodium bicarbonate solution (15 mL) and extracted with ethyl acetate (4×20 mL); the combined organic layers were dried over sodium sulfate, filtered, and concentrated in vacuo. The residue was diluted with dichloromethane (20 mL) and washed with a mixture of aqueous sodium hydroxide solution (0.25 M; 15 mL) and saturated aqueous sodium chloride solution (10 mL). The aqueous layer was extracted with dichloromethane (25 mL), and the combined organic layers were dried over sodium sulfate, filtered, concentrated under reduced pressure, and purified via silica gel chromatography (Gradient: 0% to 10% methanol in dichloromethane), affording C99 [from P13 (ENANT-2)] as an off-white solid. Yield: 37.0 mg, 65.0 μmol, 31%. $^1H$ NMR (400 MHz, chloroform-d), characteristic peaks: δ 9.07 (s, 1H), 8.27 (d, J=4.7 Hz, 1H), 7.48 (t, J=8.7 Hz, 1H), 7.39 (br t, J=7.4 Hz, 1H), 7.27-7.21 (m, 1H, assumed; partially obscured by solvent peak), 7.21-7.05 (br m, 2H), 4.64 (d, J=13.0 Hz, 1H), 4.56-4.09 (br m, 2H), 4.08-3.71 (br m, 2H), 1.86 (s, 3H), 1.35 (d, J=5.4 Hz, 1H), 1.25 (s, 3H), 1.06 (br s, 3H), 0.61 (d, J=5.4 Hz, 1H).

Step 2. Isolation of 8-(3-chloro-2-fluorophenyl)-6-(3-fluoropyridin-2-yl)-2-{[1-(1-hydroxy-2,2-dimethylcyclopropane-1-carbonyl)azetidin-3-yl]amino}-8-methyl-7,8-dihydropyrido[4,3-d]pyrimidin-5(6H)-one, from P13 (ENANT-2), DIAST-1 (28) and 8-(3-chloro-2-fluorophenyl)-6-(3-fluoropyridin-2-yl)-2-{[1-(1-hydroxy-2,2-dimethylcyclopropane-1-carbonyl)azetidin-3-yl]amino}-8-methyl-7,8-dihydropyrido[4,3-d]pyrimidin-5(6H)-one, from P13 (ENANT-2), DIAST-2 (29)

Separation of C99 [from P13 (ENANT-2)] (37.0 mg, 65.0 mmol) into its component diastereomers was carried out via supercritical fluid chromatography [Column: Chiral Technologies Chiralpak IC, 21×250 mm, 5 μm; Mobile phase: 1:1 carbon dioxide/(methanol containing 0.2% ammonium hydroxide); Flow rate: 75 mL/minute; Back pressure: 100 bar]. The first-eluting diastereomer was designated as 28, and the second-eluting diastereomer as 29.

28 [from P13 (ENANT-2)], (DIAST-1)—Yield: 13.3 mg, 23.4 μmol, 36%. LCMS m/z 569.6 (chlorine isotope pattern observed) $[M+H]^+$. Retention time: 2.37 minutes (Analytical conditions. Column: Chiral Technologies Chiralpak IC, 4.6×100 mm, 5 μm; 3:2 carbon dioxide/(methanol containing 0.2% ammonium hydroxide); Flow rate: 1.5 mL/minute; Back pressure: 120 bar).

29 [from P13 (ENANT-2)], (DIAST-2)—Yield: 10.3 mg, 18.1 μmol, 28%. LCMS m/z 569.6 (chlorine isotope pattern observed) $[M+H]^+$. Retention time: 5.17 minutes. (Analytical conditions identical to those used for 28).

Example 30

8-(3-Chloro-2-fluorophenyl)-2-({1-[(1S,2S)-2-fluorocyclopropane-1-carbonyl]azetidin-3-yl}amino)-6-(4-fluoro-1-methyl-1H-pyrazol-3-yl)-8-methyl-7,8-dihydropyrido[4,3-d]pyrimidin-5(6H)-one, from P13 (ENANT-2) (30)

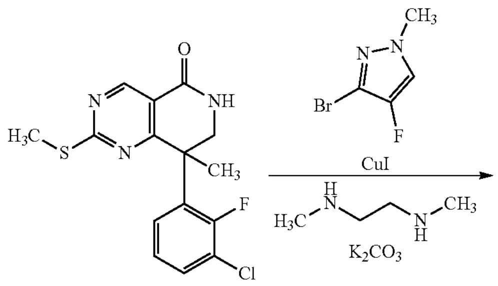

C93 [from P13 (ENANT-2)]

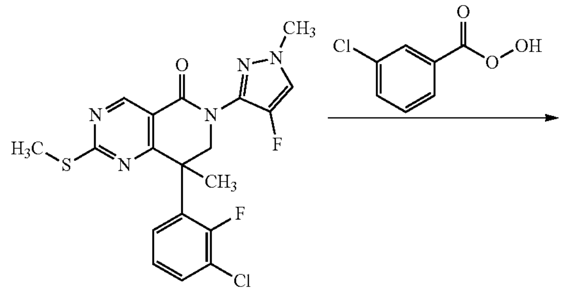

C100 [from P13 (ENANT-2)]

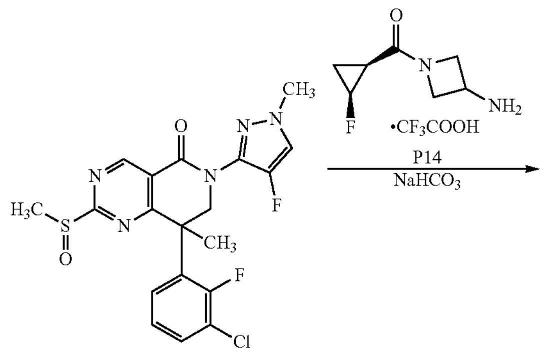

C101 [from P13 (ENANT-2)]

-continued

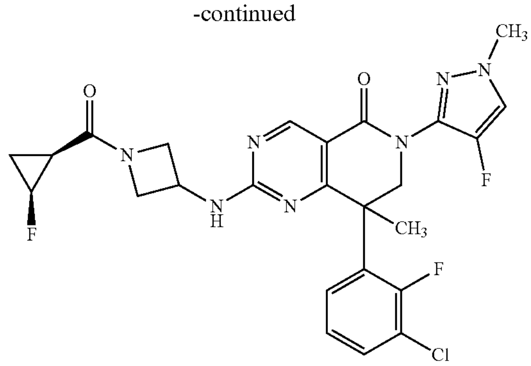

30 [from P13 (ENANT-2)]

Step 1. Synthesis of 8-(3-chloro-2-fluorophenyl)-6-(4-fluoro-1-methyl-1H-pyrazol-3-yl)-8-methyl-2-(methylsulfanyl)-7,8-dihydropyrido[4,3-d]pyrimidin-5(6H)-one, from P13 (ENANT-2) (C100)

3-Bromo-4-fluoro-1-methyl-1H-pyrazole (911 mg, 5.09 mmol), copper(I) iodide (646 mg, 3.39 mmol), potassium carbonate (1.41 g, 10.2 mmol), and $N^1$,$N^2$-dimethylethane-1,2-diamine (359 mg, 4.07 mmol) were added to a solution of C93 [from P13 (ENANT-2)] (1.15 g, 3.40 mmol) in 1,4-dioxane (30 mL). After the reaction mixture had been heated at 100° C. for 20 hours, additional 3-bromo-4-fluoro-1-methyl-1H-pyrazole (350 mg, 1.96 mmol) was added, and stirring was continued for 24 hours. The reaction mixture was then allowed to cool to 25° C., combined with a similar reaction carried out using C93 (100 mg, 0.296 mmol), diluted with water (50 mL), and extracted with ethyl acetate (3×50 mL). The combined organic layers were washed with saturated aqueous sodium chloride solution (50 mL), dried over sodium sulfate, filtered, and concentrated in vacuo; silica gel chromatography (Gradient: 0% to 50% ethyl acetate in petroleum ether) provided C100 [from P13 (ENANT-2)] as a white solid. Combined yield: 1.20 g, 2.75 mmol, 74%. LCMS m/z 436.2 (chlorine isotope pattern observed) $[M+H]^+$. $^1$H NMR (400 MHz, methanol-$d_4$) δ 9.07 (s, 1H), 7.60 (d, J=4.5 Hz, 1H), 7.50-7.45 (m, 1H), 7.21-7.15 (m, 2H), 4.50 (d, J=13.1 Hz, 1H), 3.91 (dd, J=13.1, 1.3 Hz, 1H), 3.79 (s, 3H), 2.45 (s, 3H), 1.89 (s, 3H).

Step 2. Synthesis of 8-(3-chloro-2-fluorophenyl)-6-(4-fluoro-1-methyl-1H-pyrazol-3-yl)-2-(methanesulfinyl)-8-methyl-7,8-dihydropyrido[4,3-d]pyrimidin-5(6H)-one, from P13 (ENANT-2) (C101)

3-Chloroperoxybenzoic acid (80%, 92.5 mg, 0.429 mmol) was added to a 0° C. solution of C100 [from P13 (ENANT-2)] (170 mg, 0.390 mmol) in dichloromethane (5 mL). After the reaction mixture had been stirred at 25° C. for 4 hours, LCMS analysis indicated conversion to C101: LCMS m/z 452.2 (chlorine isotope pattern observed) $[M+H]^+$. This reaction mixture was used directly in the following step.

Step 3. Synthesis of 8-(3-chloro-2-fluorophenyl)-2-({1-[(1S,2S)-2-fluorocyclopropane-1-carbonyl]azetidin-3-yl}amino)-6-(4-fluoro-1-methyl-1H-pyrazol-3-yl)-8-methyl-7,8-dihydropyrido[4,3-d]pyrimidin-5 (6H)-one, from P13 (ENANT-2) (30)

Sodium bicarbonate (159 mg, 1.89 mmol) was added to a 20° C. solution of P14 (from Preparation P14; 50.774 mmol) in dimethyl sulfoxide (2 mL). After 20 minutes, this mixture was added to a solution of C101 [from P13 (ENANT-2)] in dichloromethane (5 mL) (from the previous step; contained 50.390 mmol of C101). The reaction mixture was heated at 45° C. for 16 hours, whereupon it was allowed to cool to 20° C. and diluted with saturated aqueous sodium bicarbonate solution (10 mL). After 10 minutes, the mixture was extracted with dichloromethane (2×10 mL), and the combined organic layers were washed sequentially with saturated aqueous sodium bicarbonate solution (10 mL) and saturated aqueous sodium chloride solution (10 mL), dried over sodium sulfate, filtered, and concentrated in vacuo. Silica gel chromatography (Gradient: 0% to 10% methanol in dichloromethane) was followed by reversed-phase HPLC (Column: Phenomenex Gemini NX-C18, 30×150 mm, 5 μm; Mobile phase A: water containing 0.225% formic acid; Mobile phase B: acetonitrile; Gradient: 35% to 55% B; Flow rate: 35 mL/minute), affording 8-(3-chloro-2-fluorophenyl)-2-({1-[(1 S,2S)-2-fluorocyclopropane-1-carbonyl]azetidin-3-yl}amino)-6-(4-fluoro-1-methyl-1H-pyrazol-3-yl)-8-methyl-7,8-dihydropyrido[4,3-d]pyrimidin-5(6H)-one, from P13 (ENANT-2) (30) as a white solid. Yield: 0.119 g, 0.218 mmol, 56% over 2 steps. LCMS m/z 546.2 (chlorine isotope pattern observed) $[M+H]^+$. $^1$H NMR (400 MHz, methanol-$d_4$), characteristic peaks, integrations are approximate: δ 8.89 (s, 1H), 7.63-7.57 (m, 1H), 7.56-7.13 (m, 3H), 4.77-4.61 (m, 1H), 4.54-4.27 (m, 2H), 4.27-4.14 (m, 1H), 4.00-3.89 (m, 1H), 3.79 (s, 3H), 3.75 (d, J=12.8 Hz, 1H), 1.84 (s, 3H), 1.82-1.56 (m, 2H), 1.16-1.01 (m, 1H).

Example 31

6-(5-Aminopyridin-2-yl)-8-(3-chloro-2-fluorophenyl)-2-({1-[(1 S,2S)-2-fluorocyclopropane-1-carbonyl]azetidin-3-yl}amino)-8-methyl-7,8-dihydropyrido[4,3-d]pyrimidin-5(6H)-one, from P11 (ENANT-2) (31)

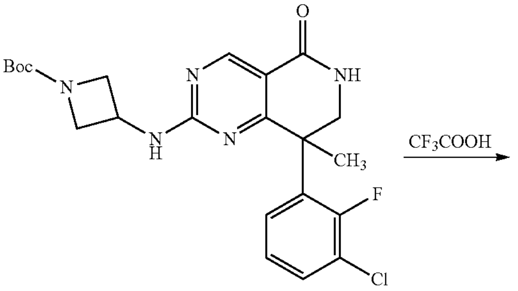

P11 (ENANT-2)

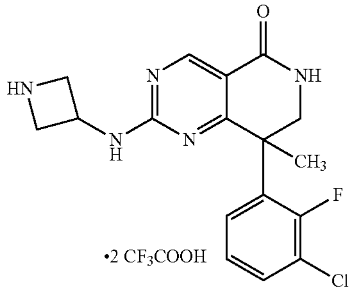

C102 [from P11 (ENANT-2)]

-continued

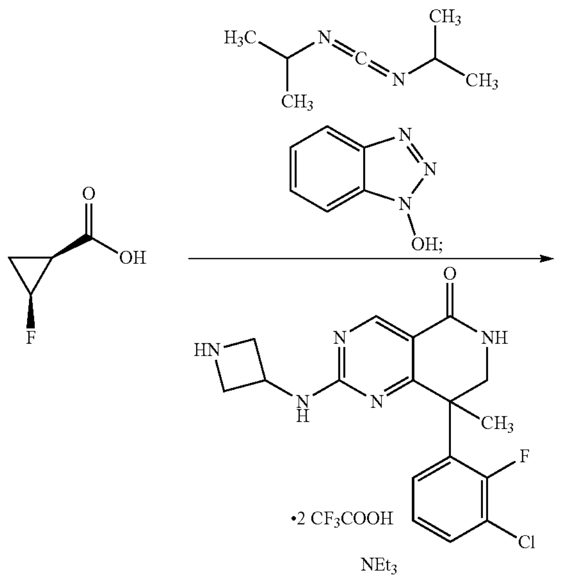

C102 [from P11 (ENANT-2)]

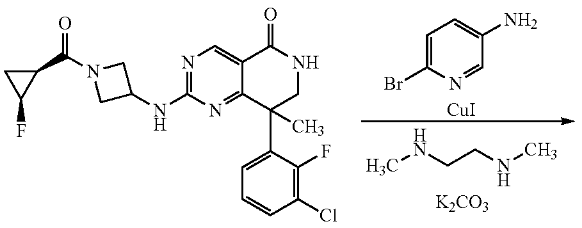

C103 [from P11 (ENANT-2)]

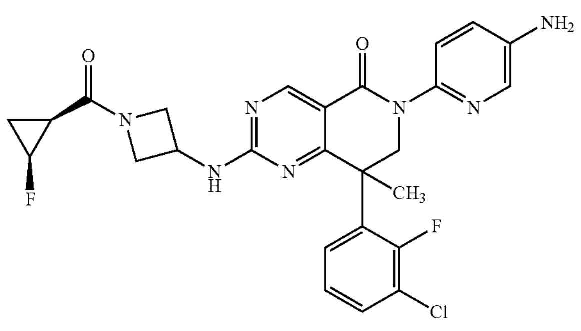

31 [from P11 (ENANT-2)]

Step 1. Synthesis of 2-[(azetidin-3-γl)amino]-8-(3-chloro-2-fluorophenyl)-8-methyl-7,8-dihydropyrido[4,3-d]pyrimidin-5(6H)-one, (bis)trifluoroacetate salt, from P11 (ENANT-2) (C102)

Trifluoroacetic acid (4.0 mL, 52 mmol) was added to a 15° C. solution of P11 (ENANT-2) (800 mg, 1.73 mmol) in dichloromethane (16 mL). After 3 hours, the reaction mixture was concentrated in vacuo, treated with acetonitrile (15 mL), and concentrated again, providing C102 [from P11 (ENANT-2)] as a brown gum. This material was used directly in the following step.

Step 2. Synthesis of 8-(3-chloro-2-fluorophenyl)-2-({1-[(1S,2S)-2-fluorocyclopropane-1-carbonyl]azetidin-3-yl}amino)-8-methyl-7,8-dihydropyrido[4,3-d]pyrimidin-5(6H)-one, from P11 (ENANT-2) (C103)

N,N'-Diisopropylcarbodiimide (262 mg, 2.08 mmol) was added to a 30° C. solution of 1H-benzotriazol-1-ol (280 mg, 2.07 mmol) and (1S,2S)-2-fluorocyclopropane-1-carboxylic acid (216 mg, 2.08 mmol) in N,N-dimethylformamide (10 mL). After 30 minutes, the reaction mixture was cooled to 15° C. and added drop-wise to a 15° C. solution of triethylamine (2.41 mL, 17.3 mmol) and C102 [from P11 (ENANT-2)] (from the previous step; 51.73 mmol) in acetonitrile (10 mL). After 16 hours, the reaction mixture was concentrated in vacuo; silica gel chromatography (Gradient: 0% to 6% methanol in dichloromethane) afforded C103 [from P11 (ENANT-2)] as a white solid. Yield: 640 mg, 1.43 mmol, 83% over 2 steps. LCMS m/z 448.0 (chlorine isotope pattern observed) $[M+H]^+$.

Step 3. Synthesis of 6-(5-aminopyridin-2-yl)-8-(3-chloro-2-fluorophenyl)-2-({1-[(1 S,2S)-2-fluorocyclopropane-1-carbonyl]azetidin-3-yl}amino)-8-methyl-7,8-dihydropyrido[4,3-d]pyrimidin-5(6H)-one, from P11 (ENANT-2) (31)

A mixture of C103 [from P11 (ENANT-2)] (40.0 mg, 89.3 μmol), potassium carbonate (37.0 mg, 0.268 mmol), and copper(I) iodide (17.0 mg, 89.3 μmol) was treated with 1,4-dioxane (2 mL), 6-bromopyridin-3-amine (20.1 mg, 0.116 mmol), and $N^1,N^2$-dimethylethane-1,2-diamine (15.7 mg, 0.178 mmol). The reaction mixture was heated at 85° C. for 24 hours, whereupon it was allowed to cool to 25° C. and diluted with saturated aqueous sodium chloride solution (5 mL). The aqueous layer was extracted with a mixture of ethyl acetate and tetrahydrofuran (1:1, 3×4 mL); the combined organic layers were dried over sodium sulfate, filtered, and concentrated in vacuo. Purification was carried out using reversed-phase HPLC (Column: Phenomenex Gemini C18, 50×250 mm, 10 μm; Mobile phase A: water containing 0.05% ammonium hydroxide; Mobile phase B: acetonitrile; Gradient: 35% to 55% B; Flow rate: 35 mL/minute), affording 6-(5-aminopyridin-2-yl)-8-(3-chloro-2-fluorophenyl)-2-({1-[(1S,2S)-2-fluorocyclopropane-1-carbonyl]azetidin-3-yl}amino)-8-methyl-7,8-dihydropyrido[4,3-d]pyrimidin-5(6H)-one, from P11 (ENANT-2) (31) as a solid. Yield: 4.83 mg, 8.94 μmol, 10%. LCMS m/z 540.3 (chlorine isotope pattern observed) $[M+H]^+$. $^1H$ NMR (400 MHz, methanol-$d_4$), characteristic peaks, integrations are approximate: δ 8.89 (s, 1H), 7.85 (s, 1H), 7.57-7.05 (m, 5H), 4.76-4.62 (m, 1H), 4.51 (d, J=12.9 Hz, 1H), 4.42-4.28 (m, 1H), 4.27-4.13 (m, 1H), 4.04-3.82 (m, 3H), 1.89-1.79 (m, 3H), 1.78-1.55 (m, 2H), 1.16-1.01 (m, 1H).

Example 32

8-(3-Chloro-2-fluorophenyl)-6-(3-fluoropyridin-2-yl)-2-({1-[(1R,4S,6S)-6-hydroxy-2-azabicyclo[2.2.1]heptane-2-carbonyl]azetidin-3-yl}amino)-8-methyl-7,8-dihydropyrido[4,3-d]pyrimidin-5(6H)-one, from P13 (ENANT-2) (32)

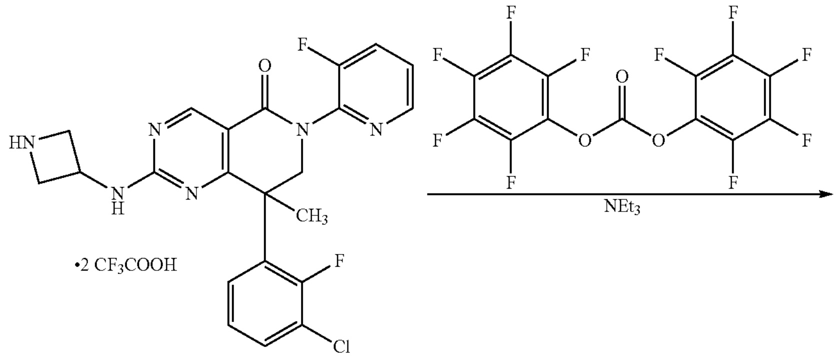

C97 [from P13 (ENANT-2)]

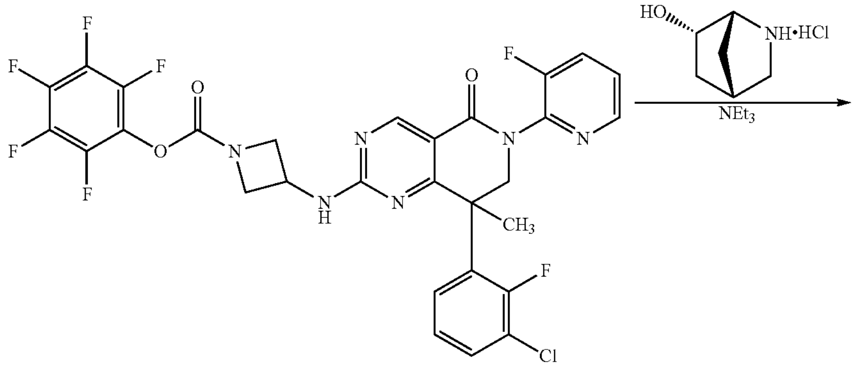

C104 [from P13 (ENANT-2)]

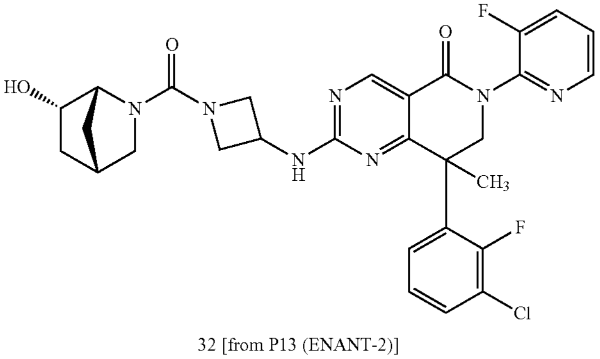

32 [from P13 (ENANT-2)]

Step 1. Synthesis of pentafluorophenyl 3-{[8-(3-chloro-2-fluorophenyl)-6-(3-fluoropyridin-2-yl)-8-methyl-5-oxo-5,6,7,8-tetrahydropyrido[4,3-d]pyrimidin-2-yl]amino}azetidine-1-carboxylate, from P13 (ENANT-2) (C104)

To a 25° C. mixture of C97 [from P13 (ENANT-2)] (4.06 g, 5.93 mmol) in tetrahydrofuran (50 mL) was added triethylamine (3.30 mL, 23.7 mmol). After the reaction mixture had been stirred at 25° C. for 30 minutes, bis(pentafluorophenyl) carbonate (2.80 g, 7.10 mmol) was added, and stirring was continued for 16 hours. The reaction mixture was then diluted with ethyl acetate (30 mL) and washed with water (50 mL); the organic layer was washed sequentially with saturated aqueous sodium bicarbonate solution (50 mL) and saturated aqueous sodium chloride solution (50 mL), filtered, and concentrated in vacuo. Silica gel chromatography (Gradient: 0% to 30% ethyl acetate in petroleum ether, followed by 10% methanol in dichloromethane) provided material that was then treated with methyl tert-butyl ether (20 mL) and petroleum ether (80 mL). The resulting suspension was stirred at 25° C. for 1 hour, whereupon the solid was collected via filtration to provide C104 [from P13 (ENANT-2)] as a white solid. Yield: 3.30 g, 4.95 mmol, 83%. LCMS m/z 667.2 (chlorine isotope pattern observed) $[M+H]^+$. $^1$H NMR (400 MHz, chloroform-d), integrations are approximate: δ 9.08 (s, 1H), 8.27 (d, J=4.4 Hz, 1H), 7.50 (t, J=8.8 Hz, 1H), 7.45-7.35 (m, 1H), 7.30-7.23 (m, 1H, assumed; partially obscured by solvent peak), 7.22-7.07 (m, 2H), [5.99 (br s) and 5.83 (br s), total 1H], [5.05-4.86 (m) and 4.59-3.87 (m), total 5H], 4.65 (d, J=12.9 Hz, 1H), 3.79 (d, J=12.9 Hz, 1H), 1.87 (s, 3H).

Step 2. Synthesis of 8-(3-chloro-2-fluorophenyl)-6-(3-fluoropyridin-2-yl)-2-({1-[(1R,4S,6S)-6-hydroxy-2-azabicyclo[2.2.1]heptane-2-carbonyl]azetidin-3-yl}amino)-8-methyl-7,8-dihydropyrido[4,3-d]pyrimidin-5(6H)-one, from P13 (ENANT-2) (32)

To a mixture of C104 [from P13 (ENANT-2)] (30.0 mg, 45.0 μmol) and (1R,4S,6S)-2-azabicyclo[2.2.1]heptan-6-ol (45.0 mg, 0.301 mmol) in dimethyl sulfoxide (1.0 mL) was added triethylamine (62.5 μL, 0.448 mmol). The reaction mixture was stirred at 70° C. for 16 hours, and then directly subjected to reversed-phase HPLC (Column: Phenomenex Gemini NX-C18, 30×75 mm, 3 μm; Mobile phase A: water containing 0.225% formic acid; Mobile phase B: acetonitrile; Gradient: 24% to 64% B; Flow rate: 25 mL/minute), providing 8-(3-chloro-2-fluorophenyl)-6-(3-fluoropyridin-2-yl)-2-({1-[(1R,4S,6S)-6-hydroxy-2-azabicyclo[2.2.1]heptane-2-carbonyl]azetidin-3-yl}amino)-8-methyl-7,8-dihydropyrido[4,3-d]pyrimidin-5(6H)-one, from P13 (ENANT-2) (32) as a white solid. Yield: 5.79 mg, 9.71 μmol, 22%. LCMS m/z 596.3 (chlorine isotope pattern observed) $[M+H]^+$. $^1$H NMR (400 MHz, methanol-$d_4$), integrations are approximate: δ [8.91 (s) and 8.88 (s), total 1H], 8.31 (d, J=4.9 Hz, 1H), 7.68 (ddd, J=9.8, 8.3, 1.5 Hz, 1H), 7.52-7.38 (m, 2H), 7.36-7.25 (m, 1H), 7.25-7.12 (m, 1H), 4.67-4.51 (m, 2H), [4.46-4.28 (m) and 4.26-4.11 (m), total 4H], 4.05-3.90 (m, 2H), [3.90-3.74 (m) and 3.45-3.36 (m), total 2H], 3.13-2.99 (m, 1H), 2.54-2.46 (m, 1H), 2.14-2.02 (m, 1H), 1.87 (s, 3H), 1.61-1.48 (m, 2H), 1.09-0.98 (m, 1H).

Example 33

8-(2,3-Difluorophenyl)-8-methyl-6-phenyl-2-({1-[(pyrrolidin-1-yl)acetyl]azetidin-3-yl}amino)-7,8-dihydropyrido[4,3-d]pyrimidin-5(6H)-one, from P16 (ENANT-2) (33)

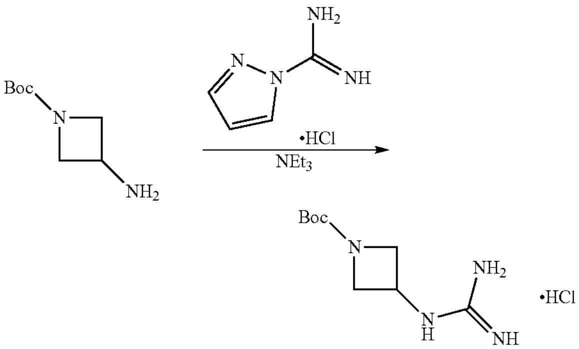

C105

-continued

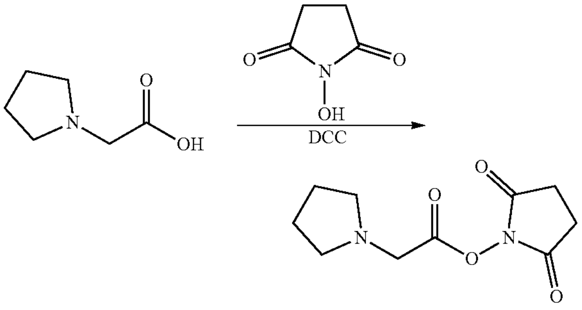

C106

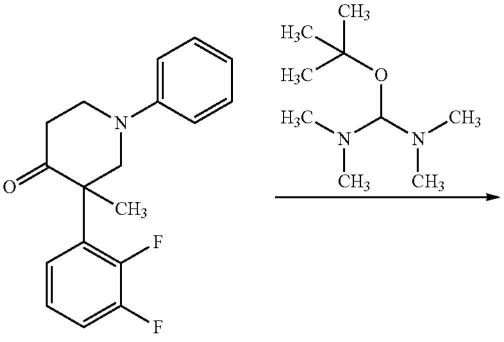

P16 (ENANT-2)

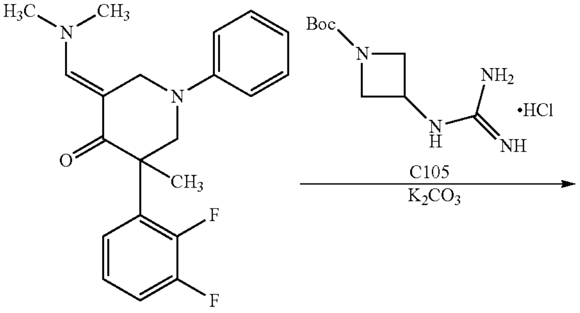

C107 [from P16 (ENANT-2)]

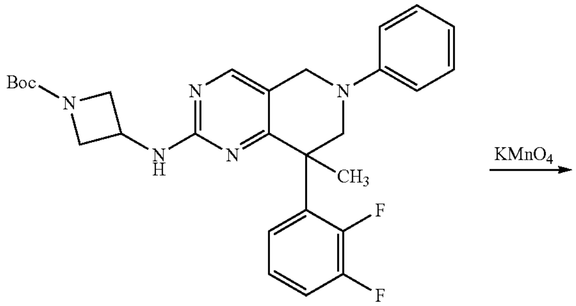

C108 [from P16 (ENANT-2)]

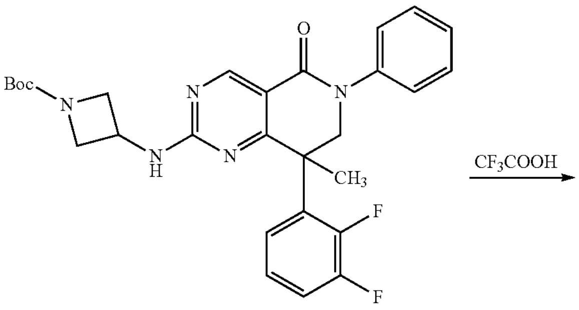

C109 [from P16 (ENANT-2)]

-continued

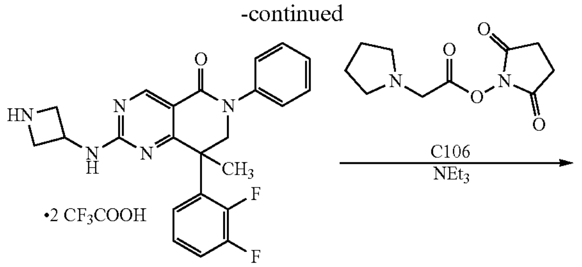

C110 [from P16 (ENANT-2)]

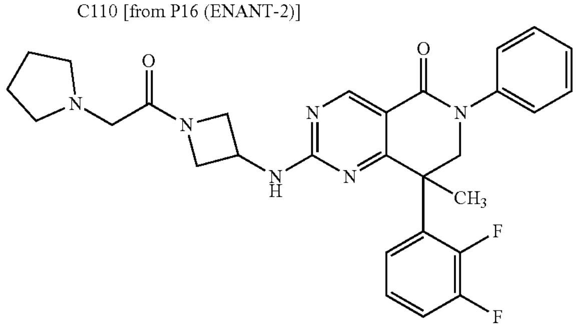

33 [from P16 (ENANT-2)]

Step 1. Synthesis of tert-butyl 3-carbamimidamidoazetidine-1-carboxylate, hydrochloride salt (C105)

A solution of tert-butyl 3-aminoazetidine-1-carboxylate (9.14 g, 53.1 mmol) in ethanol (150 mL) was treated with 1H-pyrazole-1-carboximidamide, hydrochloride salt (7.78 g, 53.1 mmol), followed by triethylamine (7.4 mL, 53.1 mmol), and stirred at reflux overnight. After the reaction mixture had cooled to room temperature, it was concentrated under reduced pressure to a volume of approximately 30 mL; this was slowly treated with diethyl ether (50 mL) and the turbid mixture was allowed to stir vigorously at room temperature for 30 minutes. Diethyl ether (50 mL) was again added and the slurry was stirred vigorously for 6 hours, whereupon it was filtered. The filter cake was washed with diethyl ether (3×50 mL) to afford C105 as an off-white solid. Yield: 11.16 g, 44.5 mmol, 84%. LCMS m/z 215.1 $[M+H]^+$. $^1H$ NMR (400 MHz, DMSO-$d_6$) δ 8.56 (d, J=7.3 Hz, 1H), 7.31 (br s, 4H), 4.35-4.24 (m, 1H), 4.13 (t, J=8.2 Hz, 2H), 3.76-3.65 (m, 2H), 1.38 (s, 9H).

Step 2. Synthesis of 1-{[(pyrrolidin-1-yl)acetyl]oxy}pyrrolidine-2,5-dione (C106)

To a mixture of (pyrrolidin-1-yl)acetic acid (548 mg, 4.24 mmol) and 1-hydroxypyrrolidine-2,5-dione (537 mg, 4.66 mmol) in N,N-dimethylformamide (5.0 mL) and dimethyl sulfoxide (0.5 mL) was added 1,3-dicyclohexylcarbodiimide (DCC; 875 mg, 4.24 mmol), whereupon the reaction mixture was stirred at room temperature (25° C. to 30° C.) for 6 hours. The resulting suspension was filtered, and the filtrate, containing C106, was used directly in Step 7 below, without further purification.

Step 3. Synthesis of 3-(2,3-difluorophenyl)-5-[(dimethylamino)methylidene]-3-methyl-1-phenylpiperidin-4-one, from P16 (ENANT-2) (C107)

A solution of P16 (ENANT-2) (2.87 g, 9.52 mmol) in toluene (40 mL) was treated with 1-tert-butoxy-N,N,N',N'-tetramethylmethanediamine (Bredereck's reagent; 3.95 mL, 19.1 mmol). After the reaction mixture had been stirred at 110° C. for 2.5 hours, it was cooled to room temperature and concentrated in vacuo to provide C107 [from P16 (ENANT-2)] (4.48 g) as a golden oil. This material was used directly in the following step. $^1H$ NMR (400 MHz, chloroform-d), characteristic peaks: δ 4.54 (br d, J=12.3 Hz, 1H), 4.22 (d, J=12.3 Hz, 1H), 3.74 (br d, J=12.8 Hz, 1H), 3.45 (br d, J=12.7 Hz, 1H), 3.18 (s, 6H).

Step 4. Synthesis of tert-butyl 3-{[8-(2,3-difluorophenyl)-8-methyl-6-phenyl-5,6,7,8-tetrahydropyrido[4,3-d]pyrimidin-2-yl]amino}azetidine-1-carboxylate, from P16 (ENANT-2) (C108)

A solution of C107 [from P16 (ENANT-2)] (from the previous step; 59.52 mmol) and C105 (3.47 g, 13.8 mmol) in ethanol (100 mL) was treated with potassium carbonate (5.27 g, 38.1 mmol), whereupon the reaction mixture was heated at 75° C. overnight. After cooling to room temperature, the reaction mixture was concentrated under reduced pressure, and the residue was partitioned between ethyl acetate and water. The organic layer was washed with saturated aqueous sodium chloride solution, dried over magnesium sulfate, filtered, and concentrated in vacuo; the resulting material was purified using silica gel chromatography (Gradient: 25% to 35.5% ethyl acetate in heptane) to provide C108 [from P16 (ENANT-2)] as an off-white solid. Yield: 4.15 g, 8.18 mmol, 86% over 2 steps. LCMS m/z 508.4 $[M+H]^+$. $^1H$ NMR (400 MHz, chloroform-d) δ 8.20 (s, 1H), 7.30-7.23 (m, 2H, assumed; partially obscured by solvent peak), 7.14-6.98 (m, 3H), 6.91 (br d, J=8.2 Hz, 2H), 6.86 (br t, J=7.3 Hz, 1H), 5.27 (br d, J=6.0 Hz, 1H), 4.49-4.36 (m, 1H), 4.28 (AB quartet, $J_{AB}$=14.4 Hz, $\Delta\nu_{AB}$=62.1 Hz, 2H), 4.21-4.13 (m, 1H), 4.08-3.92 (m, 1H), 3.80 (d, J=12.8 Hz, 1H), 3.73 (dd, J=9.1, 5.3 Hz, 1H), 3.68-3.58 (m, 1H), 3.51 (d, J=12.8 Hz, 1H), 1.82 (s, 3H), 1.43 (s, 9H).

Step 5. Synthesis of tert-butyl 3-{[8-(2,3-difluorophenyl)-8-methyl-5-oxo-6-phenyl-5,6,7,8-tetrahydropyrido[4,3-d]pyrimidin-2-yl]amino}azetidine-1-carboxylate, from P16 (ENANT-2) (C109)

Potassium permanganate (1.56 g, 9.87 mmol) was added to a 0° C. solution of C108 [from P16 (ENANT-2)] (2.50 g, 4.92 mmol) in acetonitrile (40 mL), and the reaction mixture was stirred rapidly for 1 hour at 20° C. It was then quenched by addition of saturated aqueous sodium thiosulfate solution (600 mL) and extracted with ethyl acetate (3×200 mL); the combined organic layers were dried over sodium sulfate, filtered, and concentrated in vacuo. The resulting material was dissolved in methyl tert-butyl ether (10 mL); after 2 hours at 20° C., the precipitate was collected via filtration and washed with petroleum ether (3×10 mL). This solid was again dissolved in methyl tert-butyl ether (8 mL) and allowed to stand at 20° C. for 3 hours, whereupon filtration and washing of the filter cake with petroleum ether (3×10 mL) provided C109 [from P16 (ENANT-2)] as a white solid. Yield: 1.50 g, 2.88 mmol, 58%. LCMS m/z 544.1 $[M+Na^+]$. $^1H$ NMR (400 MHz, methanol-$d_4$), characteristic peaks: δ 8.86 (br s, 1H), 7.40 (br t, J=7.7 Hz, 2H), 7.33-7.11 (m, 5H), 7.06-6.93 (m, 1H), 4.49 (d, J=12.9 Hz, 1H), 3.98-3.61 (m, 4H), 1.86 (s, 3H), 1.44 (s, 9H).

Step 6. Synthesis of 2-[(azetidin-3-yl)amino]-8-(2,3-difluorophenyl)-8-methyl-6-phenyl-7,8-dihydropyrido[4,3-d]pyrimidin-5(6H)-one, bis(trifluoroacetate) salt, from P16 (ENANT-2) (C110)

Trifluoroacetic acid (7 mL) was added to a solution of C109 [from P16 (ENANT-2)] (1.70 g, 3.26 mmol) in dichloromethane (21 mL). After the reaction mixture had been stirred at room temperature (25° C. to 30° C.) for 4 hours, it was concentrated in vacuo; acetonitrile (15 mL) was added to the residue, and the mixture was concentrated under reduced pressure, affording C110 [from P16 (ENANT-2)] as a brown gum. This material was used directly in the following step.

Step 7. Synthesis of 8-(2,3-difluorophenyl)-8-methyl-6-phenyl-2-({1-[(pyrrolidin-1-yl)acetyl]azetidin-3-yl}amino)-7,8-dihydropyrido[4,3-d]pyrimidin-5(6H)-one, from P16 (ENANT-2) (33)

Triethylamine (3.63 mL, 26.0 mmol) was added dropwise to a room temperature mixture of C110 [from P16 (ENANT-2)] (from the previous step; 53.26 mmol) in tetrahydrofuran (20 mL). A solution of C106 (from Step 2 above; 54.24 mmol) in a mixture of N,N-dimethylformamide (5 mL) and dimethyl sulfoxide (0.5 mL) was then added, and the reaction mixture was stirred at room temperature for 3 days. After removal of solvents in vacuo, the residue was purified using silica gel chromatography [Gradient: 0% to 10% (5% ammonia in methanol) in ethyl acetate], followed by further silica gel chromatography [Gradient: 0% to 15% (5% ammonia in methanol) in dichloromethane] to provide 8-(2,3-difluorophenyl)-8-methyl-6-phenyl-2-({1-[(pyrrolidin-1-yl)acetyl]azetidin-3-yl}amino)-7,8-dihydropyrido[4,3-d]pyrimidin-5(6H)-one, from P16 (ENANT-2) (33) as a white solid. Yield: 1.04 g, 1.95 mmol, 60% over 2 steps. LCMS m/z 533.3 $[M+H]^+$. $^1H$ NMR (400 MHz, methanol-$d_4$), characteristic peaks: δ 8.88 (br s, 1H), 7.46-7.36 (m, 2H), 7.34-7.11 (m, 5H), 7.10-6.86 (m, 1H), 4.27-3.76 (m, 4H), 3.29-3.10 (m, 2H), 2.75-2.55 (m, 4H), 1.94-1.73 (m, 7H).

Example 34

2-(3-{[4-(3-Chloro-2-fluorophenyl)-5-fluoro-2-(4-fluoro-1-methyl-1H-pyrazol-3-yl)-4-methyl-1-oxo-1,2,3,4-tetrahydroisoquinolin-6-yl]amino}azetidin-1-yl)-N-cyclopropyl-N-methylacetamide, formate salt, from P18 (ENANT-2) (34)

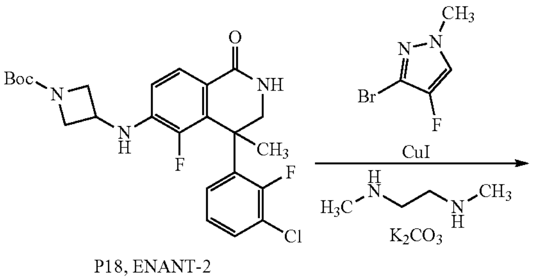

P18, ENANT-2

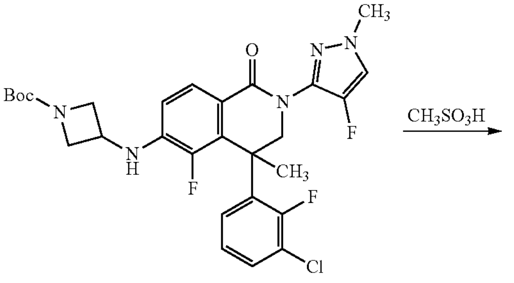

C111 [from P18 (ENANT-2)]

-continued

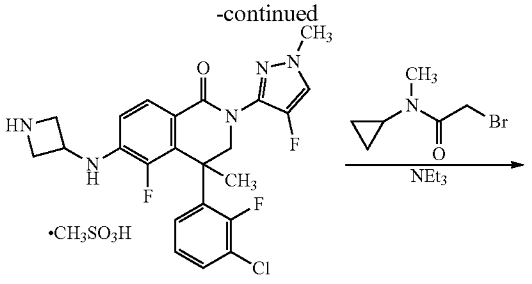

C112 [from P18 (ENANT-2)]

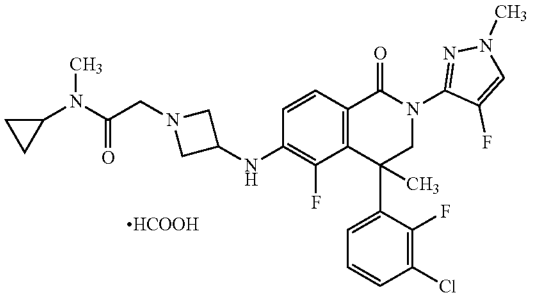

34 [from P18 (ENANT-2)]

Step 1. Synthesis of tert-butyl 3-{[4-(3-chloro-2-fluorophenyl)-5-fluoro-2-(4-fluoro-1-methyl-1H-pyrazol-3-yl)-4-methyl-1-oxo-1,2,3,4-tetrahydroisoquinolin-6-yl]amino}azetidine-1-carboxylate, from P18 (ENANT-2) (C111)

To a solution of P18, ENANT-2 (50.0 mg, 0.105 mmol) in 1,4-dioxane (1.2 mL) were added potassium carbonate (43.4 mg, 0.314 mmol), 3-bromo-4-fluoro-1-methyl-1H-pyrazole (28.1 mg, 0.157 mmol), copper(I) iodide (29.9 mg, 0.157 mmol), and $N^1$,$N^2$-dimethylethane-1,2-diamine (13.8 mg, 0.157 mmol), whereupon the reaction mixture was stirred at 100° C. for 16 hours. 3-Bromo-4-fluoro-1-methyl-1H-pyrazole (18.7 mg, 0.104 mmol) was again added, and stirring was continued at 100° C. for 16 hours. The reaction mixture was then concentrated in vacuo and purified via silica gel chromatography (Gradient: 0% to 100% ethyl acetate in petroleum ether) to provide C111 [from P18 (ENANT-2)] as a white gum. Yield: 40.0 mg, 69.4 μmol, 66%. LCMS m/z 576.1 (chlorine isotope pattern observed) $[M+H]^+$.

Step 2. Synthesis of 6-[(azetidin-3-yl)amino]-4-(3-chloro-2-fluorophenyl)-5-fluoro-2-(4-fluoro-1-methyl-1H-pyrazol-3-yl)-4-methyl-3,4-dihydroisoquinolin-1(2H)-one, methanesulfonate salt, from P18 (ENANT-2) (C112)

To a solution of C111 [from P18 (ENANT-2)] (40.0 mg, 69.4 μmol) in 1,1,1,3,3,3-hexafluoropropan-2-ol (2.0 mL) was added methanesulfonic acid (33.4 mg, 0.348 mmol). After the reaction mixture had been stirred at 25° C. for 15 minutes, it was concentrated in vacuo, affording C112 [from P18 (ENANT-2)] as a pale-yellow gum; this material was used directly in the following step.

Step 3. Synthesis of 2-(3-{[4-(3-chloro-2-fluorophenyl)-5-fluoro-2-(4-fluoro-1-methyl-1H-pyrazol-3-yl)-4-methyl-1-oxo-1,2,3,4-tetrahydroisoquinolin-6-yl]amino}azetidin-1-yl)-N-cyclopropyl-N-methylacetamide, formate salt, from P18 (ENANT-2) (34)

To a mixture of C112 [from P18 (ENANT-2)] (from the previous step; ≤69.4 μmol) and triethylamine (42.5 mg, 0.420 mmol) in chloroform (2.0 mL) was added 2-bromo-N-cyclopropyl-N-methylacetamide (20.1 mg, 0.105 mmol). After the reaction mixture had been stirred at 25° C. for 40 hours, it was concentrated in vacuo and purified twice via reversed-phase HPLC (Column: Phenomenex C18, 30×80 mm, 5 μm; Mobile phase A: water containing 0.05% ammonium hydroxide; Mobile phase B: acetonitrile; Gradient: 45% to 65% B; Flow rate: 35 mL/minute); followed by Column: Phenomenex C18, 30×80 mm, 5 μm; Mobile phase A: water containing 0.225% formic acid; Mobile phase B: acetonitrile; Gradient: 25% to 45% B; Flow rate: 35 mL/minute), affording 2-(3-{[4-(3-chloro-2-fluorophenyl)-5-fluoro-2-(4-fluoro-1-methyl-1H-pyrazol-3-yl)-4-methyl-1-oxo-1,2,3,4-tetrahydroisoquinolin-6-yl]amino}azetidin-1-yl)-N-cyclopropyl-N-methylacetamide, formate salt, from P18 (ENANT-2) (34) as a white solid. Yield: 3.15 mg, 4.98 μmol, 7% over 2 steps. LCMS m/z 587.3 (chlorine isotope pattern observed) $[M+H]^+$. $^1H$ NMR (400 MHz, methanol-$d_4$), characteristic peaks: δ 8.41 (br s, 1H), 7.89 (d, J=8.5 Hz, 1H), 7.58 (d, J=4.5 Hz, 1H), 7.44 (br t, J=7.4 Hz, 1H), 7.30 (br t, J=7.5 Hz, 1H), 7.17 (t, J=8.0 Hz, 1H), 6.71 (t, J=8.2 Hz, 1H), 4.7-4.42 (m, 2H; assumed; partially obscured by water peak), 4.40-4.32 (m, 3H), 4.05-3.95 (m, 2H), 3.78 (s, 3H), 3.67 (d, J=12.8 Hz, 1H), 2.93 (s, 3H), 2.79-2.71 (m, 1H), 1.93 (s, 3H), 0.97-0.88 (m, 2H), 0.88-0.79 (m, 2H).

Examples 35 and 36

4-(3-Chloro-2-fluorophenyl)-5-fluoro-2-(4-fluoro-1-methyl-1H-pyrazol-3-yl)-4-methyl-6-{[1-(2-oxopiperidin-3-yl)azetidin-3-yl]amino}-3,4-dihydroisoquinolin-1(2H)-one, from P18 (ENANT-2), DIAST-1 (35) and 4-(3-Chloro-2-fluorophenyl)-5-fluoro-2-(4-fluoro-1-methyl-1H-pyrazol-3-yl)-4-methyl-6-{[1-(2-oxopiperidin-3-yl)azetidin-3-yl]amino}-3,4-dihydroisoquinolin-1(2H)-one, from P18 (ENANT-2), DIAST-2 (36)

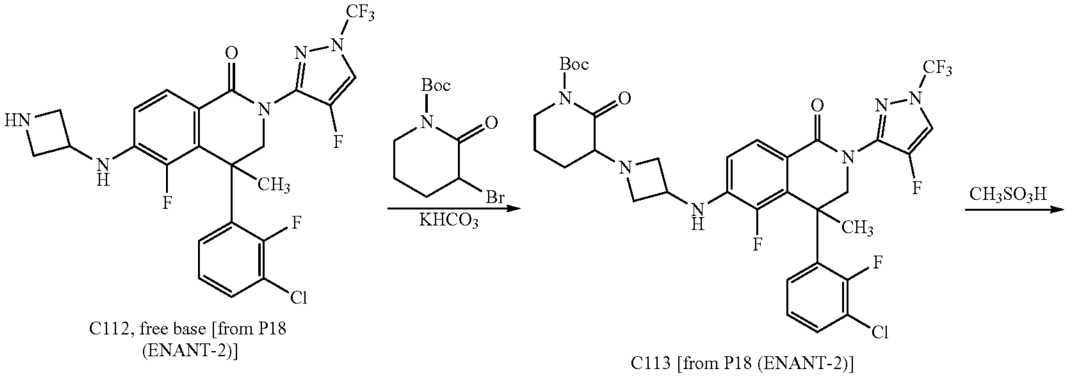

C112, free base [from P18 (ENANT-2)]

C113 [from P18 (ENANT-2)]

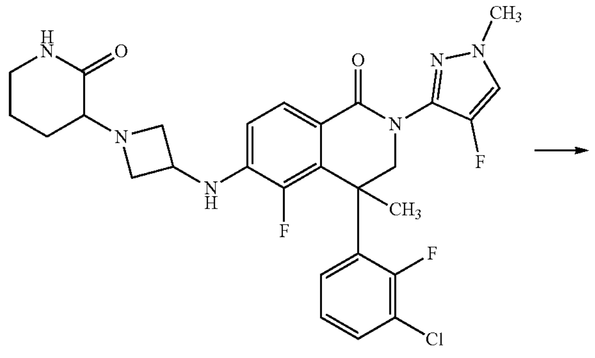

C114 [from P18 (ENANT-2)]

-continued

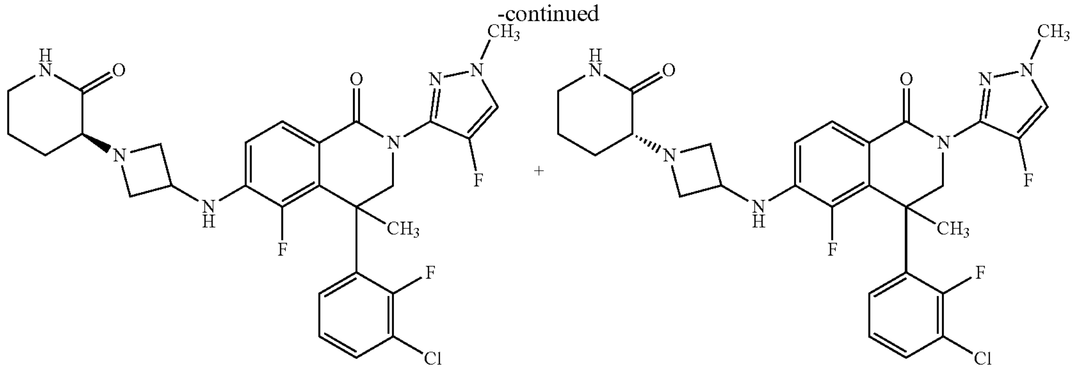

35 [from P18 (ENANT-2)] (DIAST-1) and
36 [from P18 (ENANT-2)] (DIAST-2)

Step 1. Synthesis of tert-butyl (3RS)-3-(3-{[4-(3-chloro-2-fluorophenyl)-5-fluoro-2-(4-fluoro-1-methyl-1H-pyrazol-3-yl)-4-methyl-1-oxo-1,2,3,4-tetrahydroisoquinolin-6-yl]amino}azetidin-1-yl)-2-oxopiperidine-1-carboxylate, from P18 (ENANT-2) (C113)

A mixture of C112, free base [from P18 (ENANT-2)] (70%, 47.8 mg, 70 μmol), potassium bicarbonate (35.2 mg, 0.352 mmol), and tert-butyl 3-bromo-2-oxopiperidine-1-carboxylate (39.1 mg, 0.141 mmol) in N,N-dimethylformamide (1 mL) was stirred at room temperature for 19 hours, whereupon the reaction mixture was partitioned between water and ethyl acetate. The organic layer was washed with saturated aqueous sodium chloride solution, dried over magnesium sulfate, filtered, concentrated in vacuo, and azeotroped with heptane, providing C113 [from P18 (ENANT-2)] (69 mg) as a white solid. This material was progressed directly to the following step. LCMS m/z 673.6 (chlorine isotope pattern observed) $[M+H]^+$.

Step 2. Synthesis of 4-(3-chloro-2-fluorophenyl)-5-fluoro-2-(4-fluoro-1-methyl-1H-pyrazol-3-yl)-4-methyl-6-({1-[(3RS)-2-oxopiperidin-3-yl]azetidin-3-yl}amino)-3,4-dihydroisoquinolin-1(2H)-one, from P18 (ENANT-2) (C114)

A solution of C113 [from P18 (ENANT-2)] (from the previous step; 570 μmol) in 1,1,1,3,3,3-hexafluoropropan-2-ol (1 mL) was treated with methanesulfonic acid (50 μL, 0.77 mmol) and stirred at room temperature for 35 minutes, whereupon the reaction mixture was concentrated under reduced pressure at 50° C. The resulting oil was partitioned between ethyl acetate (45 mL) and aqueous sodium hydroxide solution (1 M; 15 mL). The aqueous layer, which exhibited a pH of 10 to 11, was extracted with ethyl acetate (45 mL); the combined organic layers were dried over magnesium sulfate, filtered, and concentrated in vacuo to afford C114 [from P18 (ENANT-2)] as a pale-yellow oil (43 mg). LCMS m/z 573.5 (chlorine isotope pattern observed) $[M+H]^+$. $^1H$ NMR (600 MHz, DMSO-$d_6$) δ 7.75 (d, J=4.5 Hz, 1H), 7.68 (d, J=8.6 Hz, 1H), 7.50 (t, J=7.4 Hz, 1H), 7.35-7.26 (m, 2H), 7.20 (t, J=8.0 Hz, 1H), 6.60 (t, J=8.3 Hz, 1H), 6.57-6.53 (m, 1H), 4.16 (d, J=12.6 Hz, 1H), 4.01-3.93 (m, 1H), 3.74-3.67 (m, 1H), 3.66 (s, 3H), 3.65-3.63 (m, 1H), 3.61 (d, J=12.8 Hz, 1H), 3.25-3.14 (m, 1H), 3.07-2.92 (m, 3H), 2.72-2.63 (m, 1H), 1.80 (s, 3H), 1.77-1.69 (m, 2H), 1.54-1.45 (m, 1H), 1.45-1.37 (m, 1H).

Step 3. Isolation of 4-(3-chloro-2-fluorophenyl)-5-fluoro-2-(4-fluoro-1-methyl-1H-pyrazol-3-yl)-4-methyl-6-{[1-(2-oxopiperidin-3-yl)azetidin-3-yl]amino}-3,4-dihydroisoquinolin-1(2H)-one, from P18 (ENANT-2), DIAST-1 (35) and 4-(3-chloro-2-fluorophenyl)-5-fluoro-2-(4-fluoro-1-methyl-1H-pyrazol-3-yl)-4-methyl-6-{[1-(2-oxopiperidin-3-yl)azetidin-3-yl]amino}-3,4-dihydroisoquinolin-1(2H)-one, from P18 (ENANT-2), DIAST-2 (36)

Further purification of C114 [from P18 (ENANT-2)] (from the previous step; 43 mg, 570 μmol) was effected using reversed-phase chromatography (Column: Waters XBridge C18, 19×100 mm, 5 μm; Mobile phase A: water containing 0.03% ammonium hydroxide; Mobile phase B: acetonitrile containing 0.03% ammonium hydroxide; Gradient: 15% to 55% B; Flow rate: 25 mL/minute), affording C114 (18.8 mg). LCMS m/z 573.4 (chlorine isotope pattern observed) $[M+H]^+$. Retention time: 2.17 minutes (Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute).

Separation of this material (18.8 mg) into the component diastereomers of C114 [from P18 (ENANT-2)] was carried out using supercritical fluid chromatography [Column: Chiral Technologies Chiralpak AS-H, 21×250 mm, 5 μm; Mobile phase: 7:3 carbon dioxide (methanol containing 0.2% ammonium hydroxide); Back pressure: 120 bar; Flow rate: 75 mL/minute]. The first-eluting diastereomer was designated as 35 and the second-eluting diastereomer as 36.

35 [from P18 (ENANT-2)] (DIAST-1)—Yield: 3.4 mg, 5.9 μmol, 8% over 3 steps. LCMS m/z 573.4 (chlorine isotope pattern observed) $[M+H]^+$. Retention time: 2.55 minutes [Analytical conditions. Column: Chiral Technologies Chiralpak AS-H, 4.6×100 mm, 5 μm; Mobile phase: 65:35 carbon dioxide/(methanol containing 0.2% ammonium hydroxide); Back pressure: 120 bar; Flow rate: 1.5 mL/minute].

36 [from P18 (ENANT-2)] (DIAST-2)—Yield: 6.1 mg, 11 μmol, 16% over 3 steps. LCMS m/z 573.4 (chlorine isotope pattern observed) $[M+H]^+$. Retention time: 3.38 minutes (Analytical conditions identical to those used for 35).

Example 37
4-(3-Chloro-2-fluorophenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydroisoquinolin-1(2H)-one, from P18 (ENANT-2) (37)
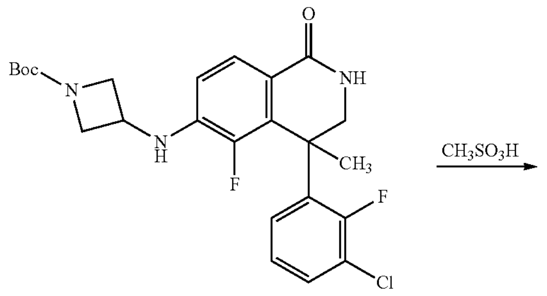
P18 (ENANT-2)
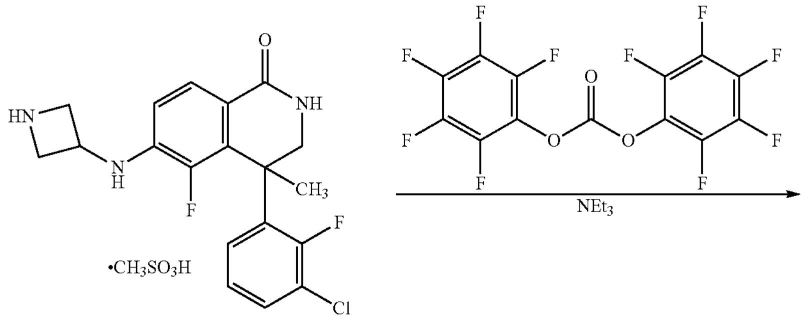
C115 [from P18 (ENANT-2)]
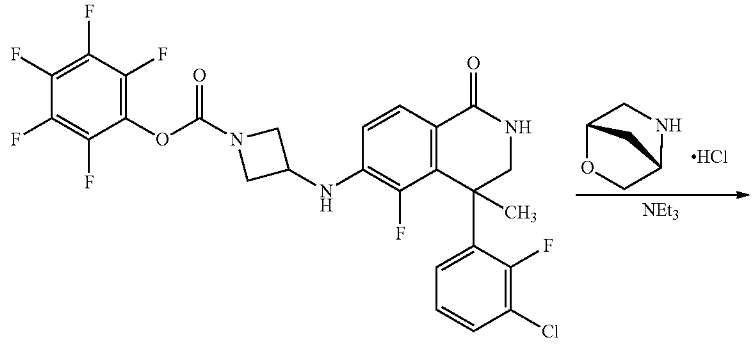
C116 [from P18 (ENANT-2)]
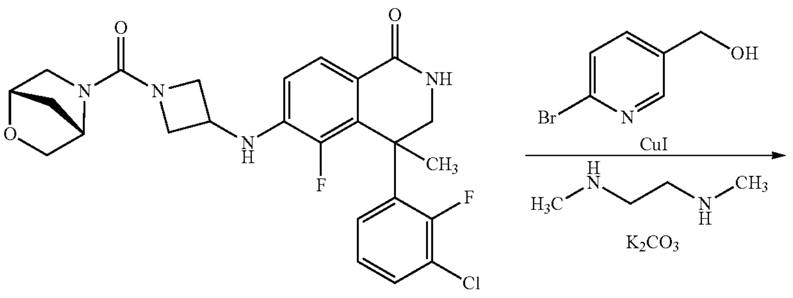
C117 [from P18 (ENANT-2)]

-continued

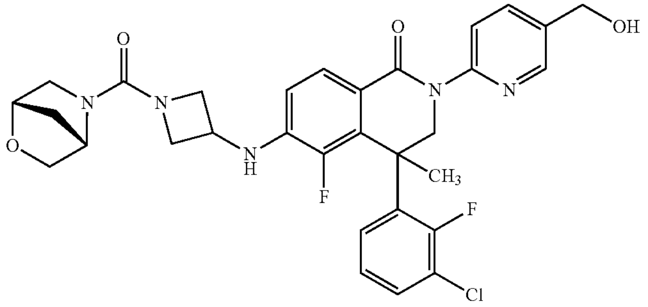

37 [from P18 (ENANT-2)]

Step 1. Synthesis of 6-[(azetidin-3-yl)amino]-4-(3-chloro-2-fluorophenyl)-5-fluoro-4-methyl-3,4-dihydroisoquinolin-1(2H)-one, methanesulfonate salt, from P18 (ENANT-2) (C115)

To a 30° C. mixture of P18 (ENANT-2) (100 mg, 0.209 mmol) in 1,1,1,3,3,3-hexafluoropropan-2-ol (1 mL) was added methanesulfonic acid (101 mg, 1.05 mmol) in one portion. After the reaction mixture had been stirred at 30° C. for 15 minutes, it was concentrated in vacuo to afford C115 [from P18 (ENANT-2)] as a yellow gum, which was used directly in the following step.

Step 2. Synthesis of pentafluorophenyl 3-{[4-(3-chloro-2-fluorophenyl)-5-fluoro-4-methyl-1-oxo-1,2,3,4-tetrahydroisoquinolin-6-yl]amino}azetidine-1-carboxylate, from P18 (ENANT-2) (C116)

To a 0° C. mixture of C115 [from P18 (ENANT-2)] (from the previous step; 50.209 mmol) in tetrahydrofuran (2 mL) was added triethylamine (0.292 mL, 2.09 mmol). After the mixture had been stirred at 30° C. for 10 minutes, bis(pentafluorophenyl) carbonate (98.9 mg, 0.251 mmol) was added and stirring was continued at 30° C. for 16 hours. The reaction mixture was then concentrated in vacuo and subjected to chromatography on silica gel (Gradient: 0% to 70% ethyl acetate in petroleum ether), providing C116 [from P18 (ENANT-2)] as a white solid. Yield: 85.0 mg, 0.145 mmol, 69% over 2 steps. LCMS m/z 588.3 (chlorine isotope pattern observed) $[M+H]^+$.

Step 3. Synthesis of 4-(3-chloro-2-fluorophenyl)-5-fluoro-4-methyl-6-({1-[(1 S,4S)-2-oxa-5-azabicyclo[2.2.1]heptane-5-carbonyl]azetidin-3-yl}amino)-3,4-dihydroisoquinolin-1(2H)-one, from P18 (ENANT-2) (C117)

To a 30° C. mixture of C116 [from P18 (ENANT-2)] (85 mg, 0.14 mmol) and triethylamine (146 mg, 1.44 mmol) in dimethyl sulfoxide (1 mL) was added (1S,4S)-2-oxa-5-azabicyclo[2.2.1]heptane, hydrochloride salt (29.4 mg, 0.217 mmol) in one portion, whereupon the reaction mixture was stirred at 80° C. for 16 hours. It was then cooled to 30° C., diluted with water (10 mL), and stirred at 30° C. for 1 hour. Collection of the resulting solid via filtration afforded C117 [from P18 (ENANT-2)] as a yellow solid. Yield: 55 mg, 0.11 mmol, 79%. LCMS m/z 525.2 (chlorine isotope pattern observed) $[M+Na^+]$.

Step 4. Synthesis of 4-(3-chloro-2-fluorophenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydroisoquinolin-1(2H)-one, from P18 (ENANT-2) (37)

To a solution of C117 [from P18 (ENANT-2)] (55 mg, 0.11 mmol) in 1,4-dioxane (2 mL) were added potassium carbonate (45.3 mg, 0.328 mmol), (6-bromopyridin-3-yl)methanol (24.7 mg, 0.131 mmol), copper(I) iodide (20.8 mg, 0.109 mmol), and $N^1$,$N^2$-dimethylethane-1,2-diamine (9.64 mg, 0.109 mmol). After the reaction mixture had been stirred at 100° C. for 16 hours, water (1 mL) was added, and the resulting mixture was extracted with a mixture of ethyl acetate and tetrahydrofuran (1:1, 3×10 mL). The combined organic layers were dried over sodium sulfate, filtered, and concentrated in vacuo; reversed-phase HPLC (Column: Boston Prime C18, 30×150 mm, 5 μm; Mobile phase A: water containing 0.05% ammonium hydroxide (v/v); Mobile phase B: acetonitrile; Gradient: 20% to 50% B; Flow rate: 25 mL/minute) provided 4-(3-chloro-2-fluorophenyl)-5-fluoro-2-[5-(hydroxymethyl)pyridin-2-yl]-4-methyl-6-({1-[(1 S,4S)-2-oxa-5-azabicyclo[2.2.1]heptane-5-carbonyl]azetidin-3-yl}amino)-3,4-dihydroisoquinolin-1(2H)-one, from P18 (ENANT-2) (37) as a white solid. Yield: 15.9 mg, 26.1 μmol, 24%. LCMS m/z 610.3 (chlorine isotope pattern observed) $[M+H]^+$. $^1$H NMR (400 MHz, methanol-$d_4$) δ 8.37 (dd, J=2.4, 0.9 Hz, 1H), 7.92 (dd, J=8.6, 1.2 Hz, 1H), 7.75 (dd, J=8.5, 2.4 Hz, 1H), 7.63 (dd, J=8.5, 0.8 Hz, 1H), 7.40 (ddd, J=7.7, 6.8, 1.8 Hz, 1H), 7.18 (ddd, J=8.7, 7.0, 1.9 Hz, 1H), 7.12 (td, J=7.9, 0.9 Hz, 1H), 6.68 (t, J=8.3 Hz, 1H), 4.65-4.55 (m, 4H), 4.52-4.49 (m, 1H), 4.48-4.36 (m, 2H), 4.33 (t, J=7.6 Hz, 1H), 4.06 (d, J=13.2 Hz, 1H), 3.99 (dd, J=8.3, 4.6 Hz, 1H), 3.88-3.81 (m, 2H), 3.77 (dd, component of ABX system, J=7.5, 1.5 Hz, 1H), 3.38 (dd, component of ABX system, J=9.6, 1.6 Hz, 1H), 3.3-3.26 (m, 1H, assumed; partially obscured by solvent peak), 1.91 (br s, 3H), 1.85 (br s, 2H).

Example 38

8-(3-Chloro-2-fluorophenyl)-4-(dimethylamino)-6-(3-fluoropyridin-2-yl)-2-{[1-(1-hydroxycyclopropane-1-carbonyl)azetidin-3-yl]amino}-8-methyl-7,8-dihydropyrido[4,3-d]pyrimidin-5(6H)-one, from C52 (ENANT-1) (38)

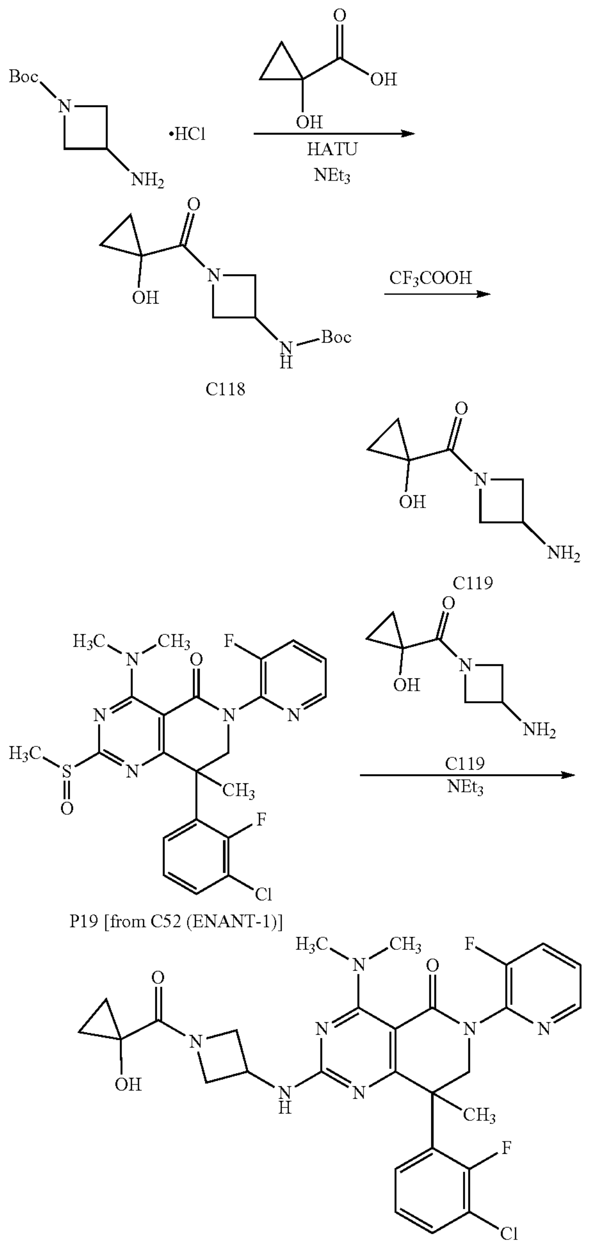

C118

C119

P19 [from C52 (ENANT-1)]

38 [from C52 (ENANT-1)]

Step 1. Synthesis of tert-butyl [1-(1-hydroxycyclopropane-1-carbonyl)azetidin-3-yl]carbamate (C118)

A slurry of 1-hydroxycyclopropane-1-carboxylic acid (1.10 g, 10.8 mmol) and tert-butyl azetidin-3-ylcarbamate, hydrochloride salt (2.25 g, 10.8 mmol) in acetonitrile (40 mL) was treated with triethylamine (4.51 mL, 32.4 mmol), followed by 0-(7-azabenzotriazol-1-γ1)-N,N,N',N'-tetramethyluronium hexafluorophosphate (HATU; 4.92 g, 12.9 mmol). After the reaction mixture had been stirred at room temperature for 18 hours, solids were collected via filtration, and the filter cake was washed with acetonitrile (5×10 mL). The resulting solid was partitioned between ethyl acetate (200 mL) and water (50 mL); the organic layer was washed once with saturated aqueous sodium chloride solution (50 mL). The combined aqueous layers, which contained solids, were extracted with ethyl acetate (200 mL), and the combined organic layers were dried over magnesium sulfate, filtered, and concentrated in vacuo to afford C118 as a white solid. Yield: 700 mg, 2.73 mmol, 25%. LCMS m/z 201.2 $[(M-2\text{-methylprop-1-ene})+H]^+$. $^1H$ NMR (400 MHz, DMSO-$d_6$) δ 7.56 (br d, J=6.5 Hz, 1H), 5.97 (s, 1H), 4.66-4.53 (m, 1H), 4.31-4.13 (m, 2H), 4.09-3.97 (m, 1H), 3.74-3.63 (m, 1H), 1.39 (s, 9H), 1.03-0.97 (m, 2H), 0.79-0.73 (m, 2H).

Step 2. Synthesis of (3-aminoazetidin-1-γ1)(1-hydroxycyclopropyl)methanone (C119)

Trifluoroacetic acid (3 mL) was added in one portion to a mixture of C118 (600 mg, 2.34 mmol) in dichloromethane (10 mL), whereupon the reaction mixture was stirred at 20° C. for 2 hours. After the reaction mixture had been concentrated under reduced pressure, the residue was dissolved in a mixture of methanol (20 mL) and dichloromethane (20 mL) and treated with Amberlyst™ A-21 ion exchange resin (3.0 g); this mixture was stirred at 20° C. for 1 hour, whereupon it was filtered, and the resin was rinsed with methanol (2×10 mL). The combined filtrates were concentrated in vacuo to afford C119 as a yellow gum. Yield: 330 mg, 2.11 mmol, 90%.

Step 3. Synthesis of (8-(3-chloro-2-fluorophenyl)-4-(dimethylamino)-6-(3-fluoropyridin-2-yl)-2-{[1-(1-hydroxycyclopropane-1-carbonyl)azetidin-3-yl]amino}-8-methyl-7,8-dihydropyrido[4,3-d]pyrimidin-5(6H)-one, from C52 (ENANT-1) (38)

To a solution of C119 (330 mg, 2.11 mmol) and triethylamine (309 mg, 3.05 mmol) in dimethyl sulfoxide (7 mL) was added a solution of P19 (500 mg, 1.02 mmol) in dimethyl sulfoxide (3 mL) in one portion, whereupon the reaction mixture was stirred at 60° C. for 3 hours. It was then combined with a similar reaction carried out using P19 (100 mg, 0.203 mmol) and poured into water (50 mL). The organic layer was extracted with ethyl acetate (3×50 mL), and the combined organic layers were washed with saturated aqueous sodium chloride solution (3×50 mL), dried over sodium sulfate, filtered, and concentrated in vacuo; silica gel chromatography (Gradient: 0% to 5% methanol in ethyl acetate) afforded 8-(3-chloro-2-fluorophenyl)-4-(dimethylamino)-6-(3-fluoropyridin-2-yl)-2-{[1-(1-hydroxycyclopropane-1-carbonyl)azetidin-3-yl]amino}-8-methyl-7,8-dihydropyrido[4,3-d]pyrimidin-5(6H)-one, from C52 (ENANT-1) (38) as a yellow solid. Combined yield: 480 mg, 0.822 mmol, 67%. LCMS m/z 584.3 (chlorine isotope pattern observed) $[M+H]^+$. $^1H$ NMR (400 MHz, methanol-$d_4$) δ 8.26 (d, J=4.6 Hz, 1H), 7.59 (t, J=9.0 Hz, 1H), 7.42-7.31 (m, 2H), [7.27-7.15 (br m) and 7.10 (t, J=7.9 Hz), total 2H], 4.95-4.82 (m, 1H, assumed; completely obscured by water peak), 4.72-4.57 (br m, 1H), [4.57-4.40 (br m) and 4.40-4.23 (br m), total 2H], 4.48 (d, J=13.0 Hz, 1H), 4.05-3.92 (br m, 1H), 3.86 (br d, J=13.1 Hz, 1H), 3.11 (s, 6H), 1.80 (s, 3H), 1.21-1.14 (m, 2H), 0.94-0.85 (m, 2H).

Example 112

(4R)-4-(3-Chloro-2-fluorophenyl)-5-fluoro-6-({1-[(1S,2S)-2-fluorocyclopropane-1-carbonyl]azetidin-3-yl}amino)-2-(4-fluoro-1H-pyrazol-3-yl)-4-methyl-3,4-dihydro-2,7-naphthyridin-1(2H)-one (112)

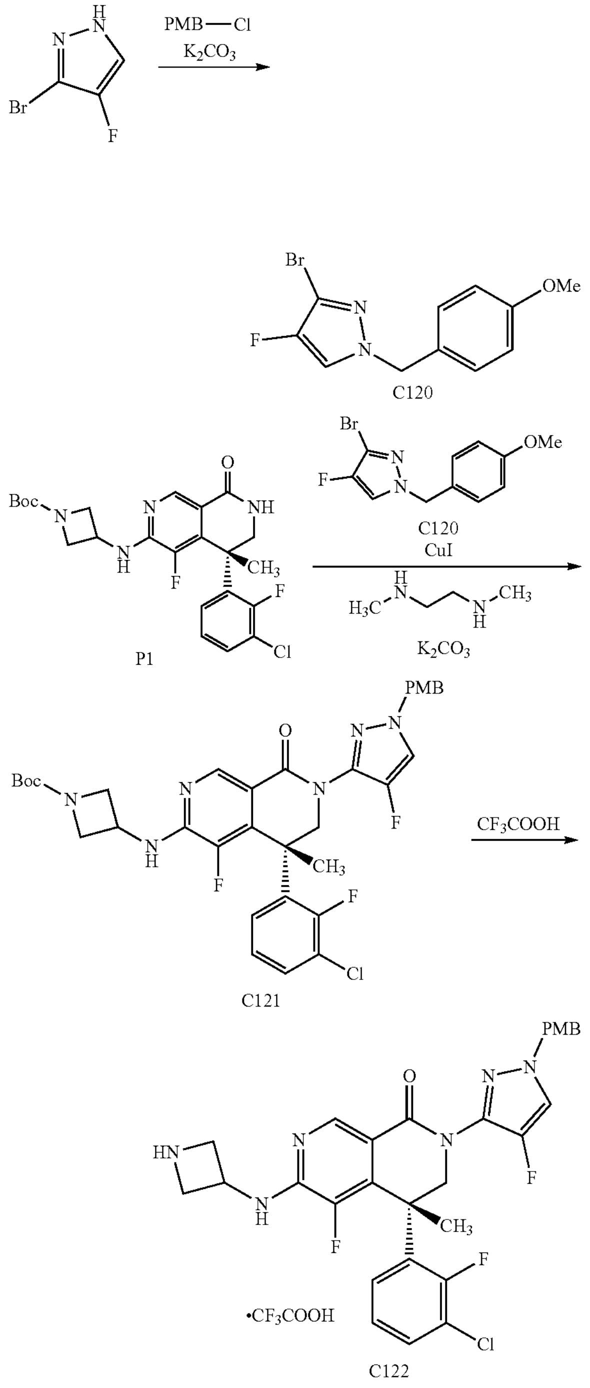

C120, P1, C121, C122

-continued

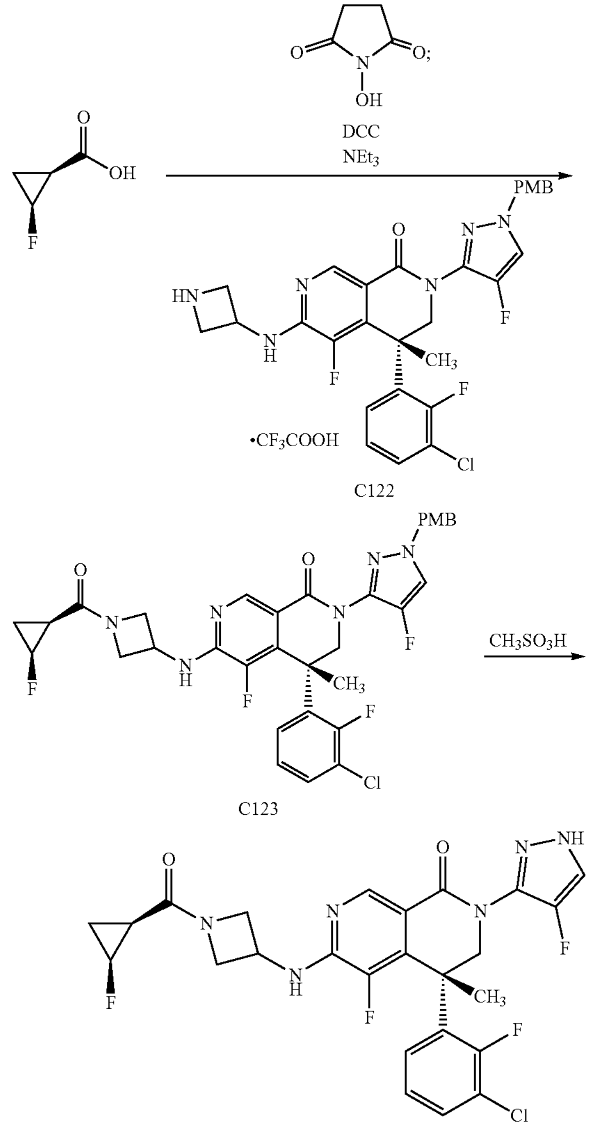

C122, C123, 112

Step 1. Synthesis of 3-bromo-4-fluoro-1-[(4-methoxyphenyl)methyl]-1H-pyrazole (C120)

p-Methoxybenzyl chloride (356 mg, 2.27 mmol) was added to a suspension of 3-bromo-4-fluoro-1H-pyrazole (250 mg, 1.52 mmol) and potassium carbonate (628 mg, 4.55 mmol) in acetone (10 mL). The reaction mixture was stirred at ambient temperature for 16 hours prior to concentration in vacuo. The residue was diluted with water (5 mL) and extracted with ethyl acetate (3x5 mL). The pooled ethyl acetate layers were washed with saturated aqueous sodium chloride solution (5 mL), dried over sodium sulfate, filtered, and concentrated in vacuo. The concentrate was purified by silica gel chromatography (Gradient: 0% to 10% ethyl acetate in petroleum ether) to afford C120 as a colorless oil. Yield: 280 mg, 0.98 mmol, 65%. $^1H$ NMR (400 MHz, chloroform-d) δ 7.20 (d, J=8.6 Hz, 2H), 7.11 (d, J=5.1 Hz, 1H), 6.89 (d, J=8.7 Hz, 2H), 5.11 (s, 2H), 3.81 (s, 3H).

Step 2. Synthesis of tert-butyl 3-{[(5R)-5-(3-chloro-2-fluorophenyl)-4-fluoro-7-{4-fluoro-1-[(4-methoxyphenyl)methyl]-1H-pyrazol-3-yl}-5-methyl-8-oxo-5,6,7,8-tetrahydro-2,7-naphthyridin-3-yl]amino}azetidine-1-carboxylate (C121)

To a solution of P1 (130 mg, 0.27 mmol) in 1,4-dioxane (6.0 mL) were added potassium carbonate (113 mg, 0.81 mmol), C120 (85.1 mg, 0.30 mmol), copper(I) iodide (51.7 mg, 0.27 mmol), and N,N-dimethylethylenediamine (23.9 mg, 0.27 mmol). The reaction mixture was stirred at 95° C. for 16 hours prior to addition of additional reagents: potassium carbonate (113 mg, 0.81 mmol), C120 (85.1 mg, 0.30 mmol), copper(I) iodide (51.7 mg, 0.27 mmol), and N,N-dimethylethylenediamine (23.9 mg, 0.27 mmol). The reaction mixture was stirred at 100° C. for another 16 hours. It was allowed to cool back to ambient temperature, then was combined with a similar reaction carried out using P1 (20 mg, 0.042 mmol), filtered, and the filtrate concentrated in vacuo. The residue was purified by silica gel chromatography (Gradient: 0% to 100% ethyl acetate in petroleum ether) to afford C121 as a white solid. Yield: 170 mg, 0.25 mmol, 80%. LCMS m/z 683.0 (chlorine isotope pattern observed) $[M+H]^+$.

Step 3. Synthesis of (4R)-6-[(azetidin-3-γl)amino]-4-(3-chloro-2-fluorophenyl)-5-fluoro-2-{4-fluoro-1-[(4-methoxyphenyl)methyl]-1H-pyrazol-3-yl}-4-methyl-3,4-dihydro-2,7-naphthyridin-1(2H)-one, trifluoroacetate salt (C122)

Trifluoroacetic acid (1.0 mL, 13.0 mmol) was added to a solution of C121 (170 mg, 0.25 mmol) in dichloromethane (4.0 mL). The reaction mixture was stirred at ambient temperature for 2 hours, then concentrated in vacuo to afford C122 as a yellow gum (173 mg), which was used directly in the following step. LCMS m/z 583.0 (chlorine isotope pattern observed) $[M+H]^+$.

Step 4. Synthesis of (4R)-4-(3-chloro-2-fluorophenyl)-5-fluoro-6-({1-[(1S,2S)-2-fluorocyclopropane-1-carbonyl]azetidin-3-yl}amino)-2-{4-fluoro-1-[(4-methoxyphenyl)methyl]-1H-pyrazol-3-yl}-4-methyl-3,4-dihydro-2,7-naphthyridin-1(2H)-one (C123)

1,3-Dicyclohexylcarbodiimide (DCC; 63.4 mg, 0.31 mmol) was added to a solution of 1-hydroxypyrrolidine-2,5-dione (38.9 mg, 0.34 mmol) and (1S,2S)-2-fluorocyclopropane-1-carboxylic acid (32 mg, 0.31 mmol) in tetrahydrofuran (1 mL). After 16 hours, the reaction mixture was added to a suspension of C122 (173 mg, 0.248 mmol) and triethylamine (176 mg, 1.74 mmol) in tetrahydrofuran (3.0 mL). The reaction mixture was stirred at ambient temperature for 16 hours, then filtered; the filtrate was concentrated in vacuo, then purified via silica gel chromatography (Gradient: 0% to 100% ethyl acetate in petroleum ether) to afford C123 as a white solid. Yield: 145 mg, 0.22 mmol, 87% over 2 steps. LCMS m/z 669.1 (chlorine isotope pattern observed) $[M+H]^+$.

Step 5. Synthesis of (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1H-pyrazol-3-yl)-4-methyl-3,4-dihydro-2,7-naphthyridin-1(2H)-one (112)

Methanesulfonic acid (50.0 mg, 0.52 mmol) was added to a mixture of C123 (115 mg, 0.17 mmol) in 1,1,1,3,3,3-hexafluoropropan-2-ol (3.0 mL) at ambient temperature. The reaction mixture was stirred at 50° C. for 5 hours, then to it was added triethylamine (104 mg, 1.03 mmol). The resulting mixture was concentrated in vacuo and then purified twice via reversed-phase HPLC (1st separation: Column: Phenomenex Gemini C18, 50×250 mm, 10 μm; Mobile phase A: water containing 0.05% ammonium hydroxide; Mobile phase B: acetonitrile; Gradient: 35% to 55% B; Flow rate: 35 mL/minute. 2nd separation: Column: Phenomenex Gemini C18, 50×250 mm, 10 μm; Mobile phase A: water containing 0.225% formic acid; Mobile phase B: acetonitrile; Gradient: 33% to 53% B; Flow rate: 35 mL/minute) to afford (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1H-pyrazol-3-yl)-4-methyl-3,4-dihydro-2,7-naphthyridin-1(2H)-one (112) as a white solid. Yield: 26.2 mg, 0.048 mmol, 28%. $^1H$ NMR (400 MHz, methanol-$d_4$) δ 8.66 (d, J=1.5 Hz, 1H), 7.63 (d, J=4.5 Hz, 1H), 7.49 (ddd, J=8.3, 6.9, 1.6 Hz, 1H), 7.39 (tt, J=7.7, 2.0 Hz, 1H), 7.29-7.14 (m, 1H), 5.00-4.90 (m, 1H, assumed; partially obscured by water peak), 4.81-4.67 (m, 2H), 4.46-4.34 (m, 2H), 4.27 (ddd, J=13.5, 9.1, 5.3 Hz, 1H), 4.03 (td, J=10.4, 5.5 Hz, 1H), 3.72 (dt, J=12.9, 1.4 Hz, 1H), 1.97 (s, 3H), 1.84 (dddt, J=11.7, 7.0, 4.3, 2.0 Hz, 1H), 1.67 (dtt, J=22.8, 6.8, 3.2 Hz, 1H), 1.11 (ddtd, J=12.5, 9.5, 6.3, 3.2 Hz, 1H). LCMS m/z 549.0 (chlorine isotope pattern observed) $[M+H]^+$.

Method A

N,N-Disubstituted 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-γl)acetamides, via alkylation of C59 with 2-chloro-N,N-dialkylacetamides

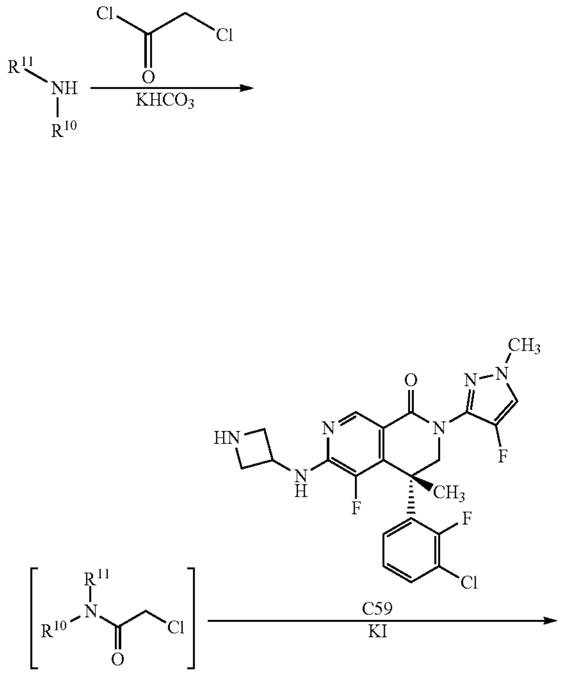

-continued

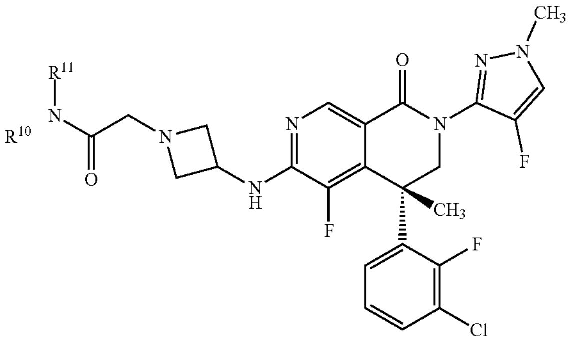

Chloroacetyl chloride (3.34 μL, 4.74 mg, 41.9 μmol) was added drop-wise to a 0° C. solution of secondary amine $R^AR^BNH$ (41.9 μmol) and potassium bicarbonate (21 mg, 0.21 mmol) in acetonitrile (1 mL). After 20 minutes, the reaction mixture was allowed to warm to 25° C. and stirred for 1.75 hours, whereupon a solution of C59 (20 mg, 42 μmol) in acetonitrile (0.5 mL) was added, followed by potassium iodide (1.4 mg, 8.4 μmol). The reaction mixture was heated at 55° C. for 1 hour, then allowed to cool to 25° C. and diluted with water (4 mL). The aqueous layer was extracted with ethyl acetate (3x4 mL); the combined organic layers were dried over sodium sulfate, filtered, and concentrated in vacuo. Purification via reversed-phase HPLC (Column: Waters XBridge C18, 19x100 mm, 5 μm; Mobile phase A: water containing 0.03% ammonium hydroxide; Mobile phase B: acetonitrile containing 0.03% ammonium hydroxide; Gradient: chosen for particular product; Flow rate: 25 mL/minute), afforded the N,N-disubstituted 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl) acetamide.

TABLE 3

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 39 | Ex. 7; C59 | 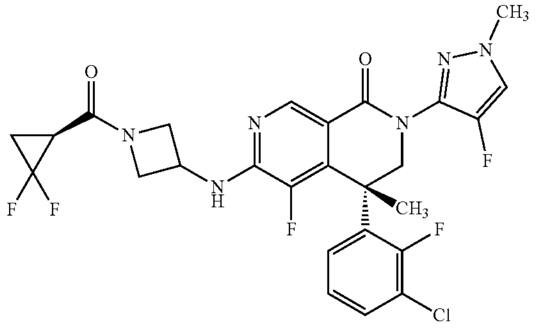 [SMILES: Cn1cc(F)c(N2C[C@](C)(c3cccc(Cl)c3F)c3c(cnc(NC4CN(C(=O)[C@@H]5CC5(F)F)C4)c3F)C2=O)n1] | 8.63 (d, J = 2.1 Hz, 1H), 7.58 (d, J = 4.4 Hz, 1H), 7.50 - 7.44 (m, 1H), 7.39 - 7.30 (m, 1H), 7.20 (t, J = 8.0 Hz, 1H), 5.00 - 4.86 (m, 1H), 4.75 - 4.61 (m, 1H), 4.44 - 4.32 (m, 2H), 4.30 - 4.22 (m, 1H), 4.06 - 3.96 (m, 1H), 3.78 (s, 3H), 3.74 - 3.66 (m, 1H), 2.66 - 2.52 (m, 1H), 2.05 - 1.93 (m, 1H), 1.94 (s, 3H), 1.85 - 1.72 (m, 1H); 581.3 (chlorine isotope pattern observed) |
| 40 | Example 7; C59 | 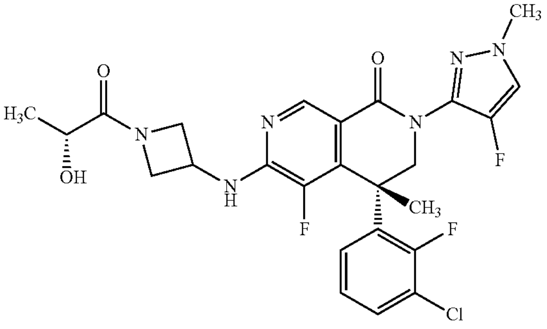 [SMILES: C[C@@H](O)C(=O)N1CC(Nc2ncc3c(c2F)[C@@](C)(c2cccc(Cl)c2F)CN(c2nn(C)cc2F)C3=O)C1] | 8.62 (s, 1H), 7.58 (d, J = 4.5 Hz, 1H), 7.47 (ddd, J = 8.3, 7.0, 1.6 Hz, 1H), 7.39 - 7.32 (m, 1H), 7.20 (t, J = 8.0 Hz, 1H), 4.95 - 4.86 (m, 1H, assumed; largely obscured by water peak), 4.77 - 4.67 (m, 1H), 4.43 - 4.33 (m, 1H), 4.36 (d, J = 13.0 Hz, 1H), 4.32 - 4.24 (m, 2H), 4.06 - 3.93 (m, 1H), 3.78 (s, 3H), 3.69 (d, J = 12.9 Hz, 1H), 1.94 (br s, 3H), 1.33 (d, J = 6.8 Hz, 3H); 549.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 41 | Example 7; C59 | 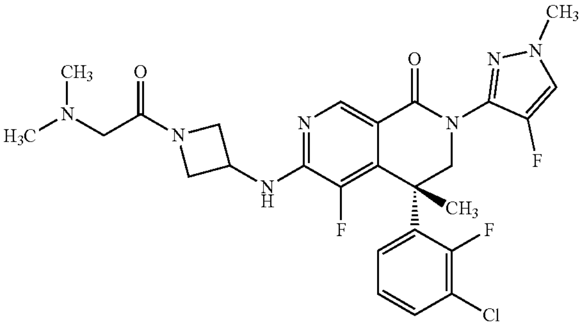 [SMILES: CN(C)CC(=O)N1CC(Nc2ncc3c(c2F)[C@@](C)(c2cccc(Cl)c2F)CN(c2nn(C)cc2F)C3=O)C1] | $^1$H NMR (400 MHz, methanol-$d_4$), characteristic peaks: δ 8.62 (s, 1H), 7.59 (d, J = 4.5 Hz, 1H), 7.47 (t, J = 7.3 Hz, 1H), 7.40 - 7.32 (m, 1H), 7.21 (t, J = 8.0 Hz, 1H), 4.41 - 4.34 (m, 1H), 4.36 (d, J = 12.6 Hz, 1H), 4.22 - 4.13 (m, 1H), 4.03 - 3.94 (m, 1H), 3.78 (s, 3H), 3.69 (d, J = 12.9 Hz, 1H), [3.05 (s) and 3.04 (s), total 2H], [2.30 (s) and 2.30 (s), total 6H], 1.94 (s, 3H); 562.3 (chlorine isotope pattern observed) |
| 42 | Example 7[1]; C59 | 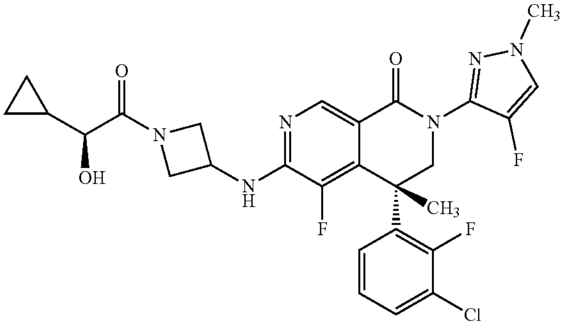 [SMILES: Cn1cc(F)c(N2C[C@](C)(c3cccc(Cl)c3F)c3c(cnc(NC4CN(C(=O)[C@@H](O)C5CC5)C4)c3F)C2=O)n1] or 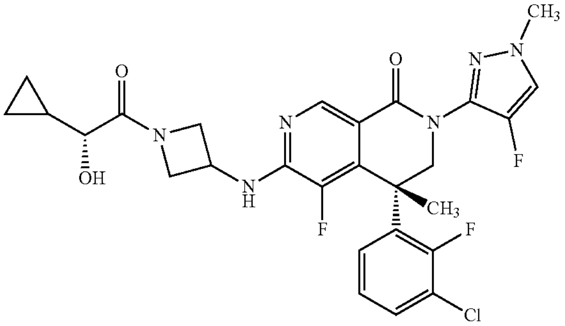 DIAST-1 | 8.62 (s, 1H), 7.58 (d, J = 4.5 Hz, 1H), 7.47 (ddd, J = 8.3, 6.9, 1.6 Hz, 1H), 7.39 - 7.31 (m, 1H), 7.21 (t, J = 8.0 Hz, 1H), 4.9 - 4.80 (m, 1H, assumed; partially obscured by water peak), 4.79 - 4.69 (m, 1H), 4.45 - 4.26 (m, 2H), 4.36 (d, J = 12.7 Hz, 1H), 4.02 (br dd, J = 10.7, 5.4 Hz, 1H), 3.78 (s, 3H), 3.70 (d, J = 12.9 Hz, 1H), 3.62 (d, J = 7.7 Hz, 1H), 1.94 (s, 3H), 1.19 - 1.09 (m, 1H), 0.58 - 0.49 (m, 2H), 0.48 - 0.38 (m, 2H); 575.3 (chlorine isotope pattern observed) |
| 43 | Example 7[1]; C59 | 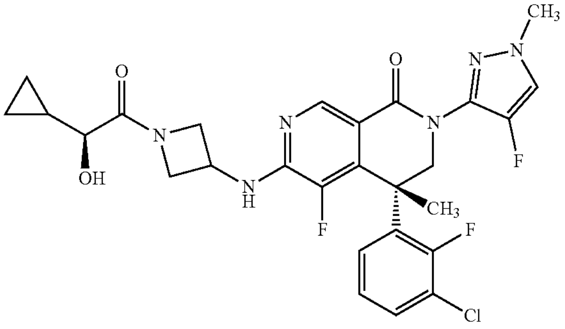 [SMILES: Cn1cc(F)c(N2C[C@](C)(c3cccc(Cl)c3F)c3c(cnc(NC4CN(C(=O)[C@@H](O)C5CC5)C4)c3F)C2=O)n1] | $^1$H NMR (400 MHz, methanol-$d_4$), characteristic peaks: δ 8.62 (s, 1H), 7.58 (d, J = 4.5 Hz, 1H), 7.50 - 7.44 (m, 1H), 7.39 - 7.32 (m, 1H), 7.20 (t, J = 8.0 Hz, 1H), 4.79 - 4.69 (m, 1H), 4.46 - 4.23 (m, 2H), 4.36 (d, J = 12.9 Hz, 1H), 4.08 - 3.95 (m, 1H), 3.78 (s, 3H), 3.70 (d, J = 12.9 Hz, 1H), [3.63 (d, J = 7.6 Hz) and 3.62 (d, J = 7.6 Hz), total 1H], 1.94 (br s, 3H), 1.20 - 1.09 (m, 1H), 0.57 - 0.50 (m, 2H), 0.48 - 0.39 (m, 2H); 575.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | or<br>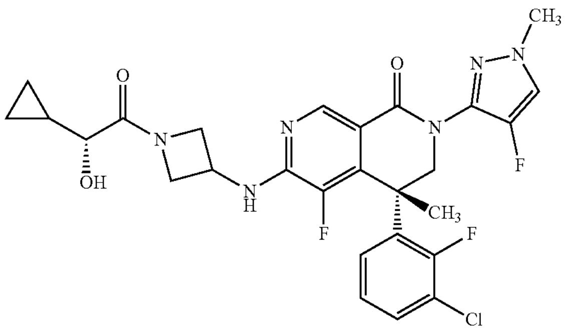<br>DIAST-2 | |
| 44 | Example 7[2]; C59 | 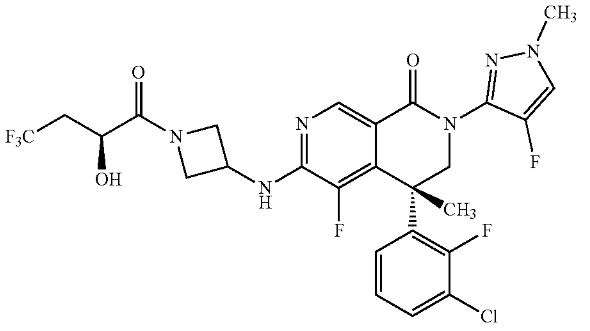<br>or<br>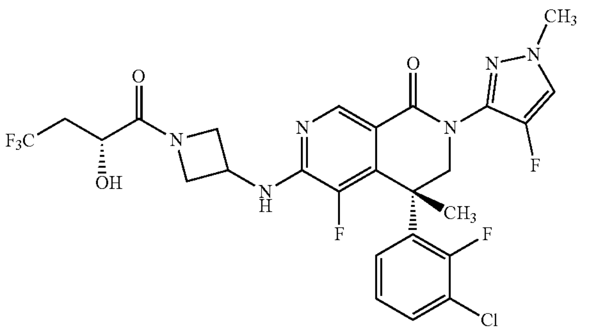<br>DIAST-1 | $^1$H NMR (400 MHz, methanol-$d_4$), characteristic peaks: δ 8.62 (s, 1H), 7.59 (d, J = 4.4 Hz, 1H), 7.50 - 7.44 (m, 1H), 7.38 - 7.32 (m, 1H), 7.20 (t, J = 8.0 Hz, 1H), 4.9 - 4.70 (m, 1H, assumed; partially obscured by water peak), 4.52 - 4.44 (m, 1H), [4.44 - 4.32 (m) and 4.32 - 4.26 (m), total 2H], 4.36 (d, J = 13.1 Hz, 1H), 4.05 - 3.97 (m, 1H), 3.78 (s, 3H), 3.70 (d, J = 13.0 Hz, 1H), 2.72 - 2.59 (m, 1H), 2.56 - 2.42 (m, 1H), 1.94 (br s, 3H); 617.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^{1}H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 45 | Example 7[2]; C59 | 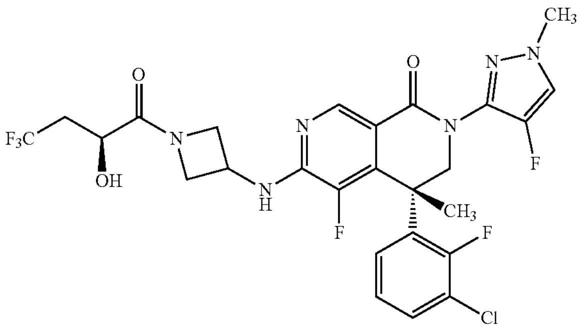<br>or<br>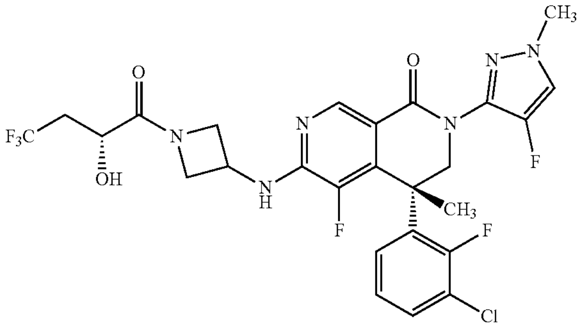<br>DIAST-2 | 8.62 (s, 1H), 7.58 (d, J = 4.5 Hz, 1H), 7.47 (ddd, J = 8.3, 6.9, 1.6 Hz, 1H), 7.39 - 7.32 (m, 1H), 7.20 (br t, J = 8.0 Hz, 1H), 4.9 - 4.69 (m, 2H, assumed; partially obscured by water peak), 4.51 - 4.44 (m, 1H), 4.43 - 4.29 (m, 2H), 4.36 (d, J = 13.2 Hz, 1H), 4.06 - 3.95 (m, 1H), 3.78 (s, 3H), 3.70 (d, J = 12.9 Hz, 1H), 2.74 - 2.57 (m, 1H), 2.56 - 2.40 (m, 1H), 1.94 (br s, 3H); 617.3 (chlorine isotope pattern observed) |
| 46 | Example 7[3]; C59 | 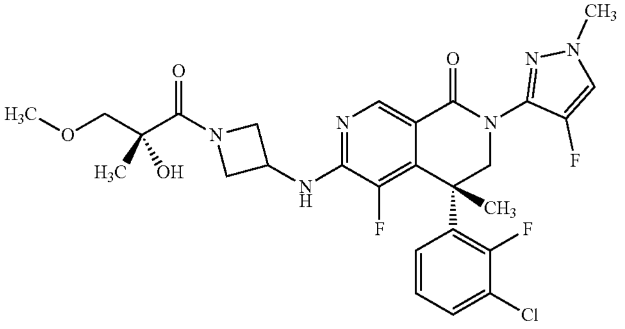<br>or | $^{1}H$ NMR (400 MHz, methanol-$d_4$), characteristic peaks: δ 8.62 (s, 1H), 7.58 (d, J = 4.5 Hz, 1H), 7.50 - 7.44 (m, 1H), 7.39 - 7.31 (m, 1H), 7.20 (t, J = 8.0 Hz, 1H), [4.52 - 4.44 (m) and 4.43 - 4.30 (m), total 2H], 4.36 (d, J = 12.9 Hz, 1H), 4.02 - 3.92 (m, 1H), 3.78 (s, 3H), 3.73 - 3.64 (m, 2H), [3.38 (s) and 3.35 (s), total 3H], 3.3 - 3.26 (m, 1H, assumed; partially obscured by solvent peak), 1.94 (s, 3H), [1.31 (s) and 1.29 (s), total 3H]; 593.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 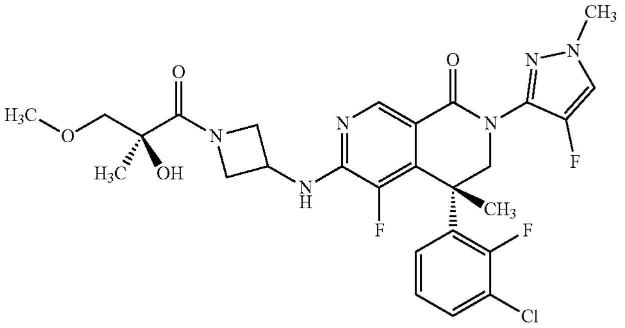 DIAST-1 | |
| 47 | Example 7[3]; C59 | 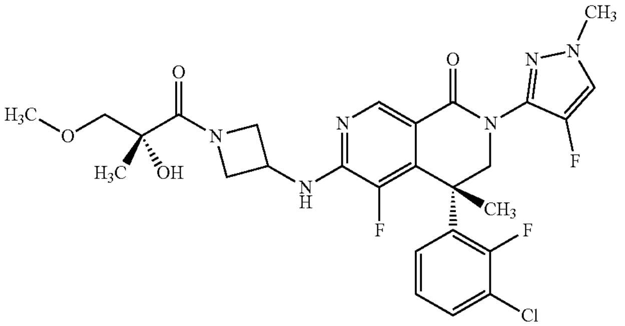 or 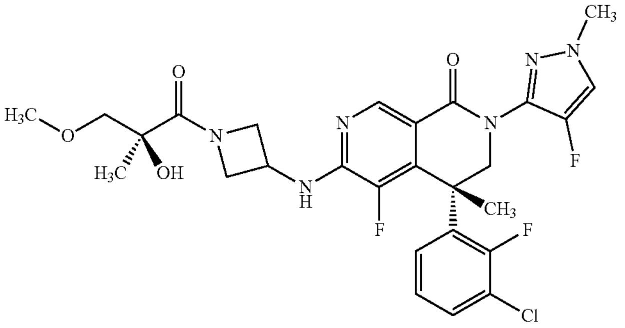 DIAST-2 | $^1H$ NMR (400 MHz, methanol-$d_4$), characteristic peaks: δ 8.62 (s, 1H), 7.58 (d, J = 4.5 Hz, 1H), 7.47 (ddd, J = 8.3, 6.9, 1.6 Hz, 1H), 7.35 (t, J = 7.5 Hz, 1H), 7.20 (br t, J = 8.0 Hz, 1H), 4.49 - 4.40 (m, 1H), 4.39 - 4.31 (m, 1H), 4.36 (d, J = 13.1 Hz, 1H), 4.02 - 3.91 (m, 1H), 3.78 (s, 3H), 3.73 - 3.63 (m, 2H), [3.38 (s) and 3.35 (s), total 3H], 3.3 - 3.25 (m, 1H, assumed; partially obscured by solvent peak), 1.94 (s, 3H), [1.31 (s) and 1.30 (s), total 3H]; 593.3 (chlorine isotope pattern observed) |
| 48 | Example 18; C75 | 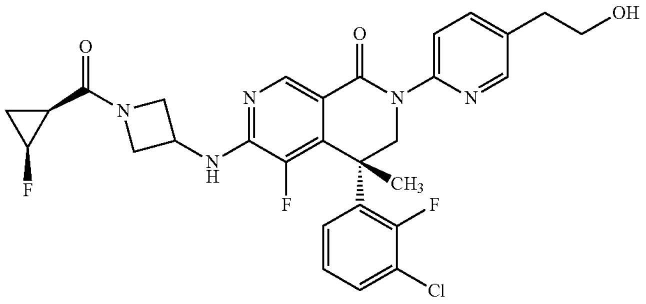 [SMILES: C[C@]1(c2cccc(Cl)c2F)CN(c2ccc(CCO)cn2)C(=O)c2cnc(NC3CN(C(=O)[C@@H]4C[C@@H]4F)C3)c(F)c21] | 2.31 minutes[4]; 586.4 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 49 | Example 18; C75 | 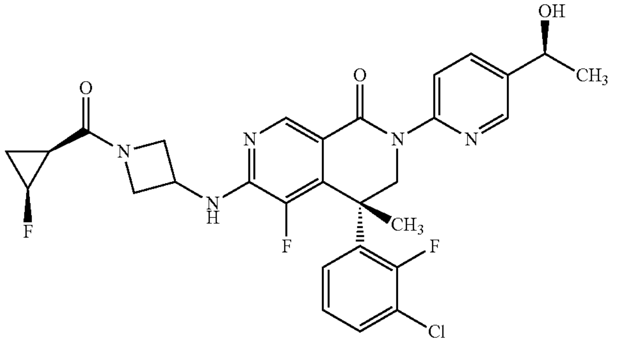 [SMILES: C[C@H](O)c1ccc(N2C[C@](C)(c3cccc(Cl)c3F)c3c(cnc(NC4CN(C(=O)[C@@H]5C[C@@H]5F)C4)c3F)C2=O)nc1] | 2.35 minutes[4]; 586.4 (chlorine isotope pattern observed) |
| 50 | Example 18; C75 | 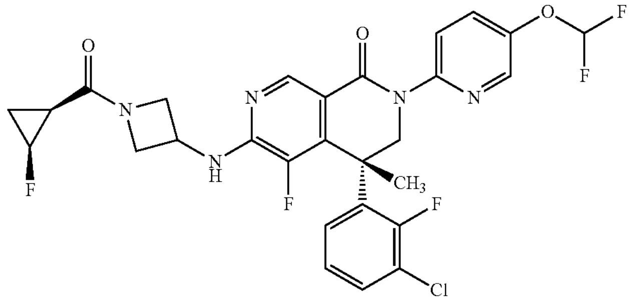 [SMILES: C[C@]1(c2cccc(Cl)c2F)CN(c2ccc(OC(F)F)cn2)C(=O)c2cnc(NC3CN(C(=O)[C@@H]4C[C@@H]4F)C3)c(F)c21] | 8.69 (d, J = 1.5 Hz, 1H), 8.27 (d, J = 2.9 Hz, 1H), 7.83 (d, half of AB quartet, J = 9.0 Hz, 1H), 7.62 (dd, component of ABX system, J = 9.0, 2.9 Hz, 1H), 7.46 (ddd, J = 8.3, 6.9, 1.6 Hz, 1H), 7.35 - 7.29 (m, 1H), 7.19 (t, J = 8.0 Hz, 1H), 6.89 (t, $J_{HF}$ = 73.2 Hz, 1H), 4.99 - 4.9 (m, 1H, assumed; partially obscured by water peak), 4.77 - 4.65 (m, 2H), 4.55 (d, J = 13.4 Hz, 1H), 4.44 - 4.34 (m, 1H), 4.31 - 4.22 (m, 1H), [4.13 (d, J = 13.4 Hz) and 4.12 (d, J = 13.4 Hz), total 1H], 4.06 - 3.97 (m, 1H), 1.91 (s, 3H), 1.89 - 1.76 (m, 1H), 1.73 - 1.59 (m, 1H), 1.15 - 1.04 (m, 1H); 608.3 (chlorine isotope pattern observed) |
| 51 | Example 18; C75 | 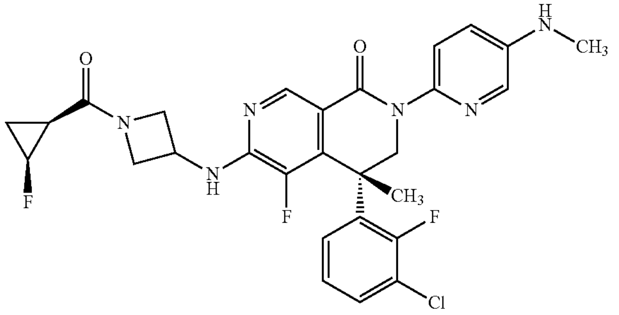 [SMILES: CNc1ccc(N2C[C@](C)(c3cccc(Cl)c3F)c3c(cnc(NC4CN(C(=O)[C@@H]5C[C@@H]5F)C4)c3F)C2=O)nc1] | $^1$H NMR (400 MHz, methanol-$d_4$), characteristic peaks δ 8.63 (d, J = 1.3 Hz, 1H), 7.79 - 7.73 (m, 1H), 7.49 - 7.43 (m, 1H), 7.37 - 7.31 (m, 1H), 7.25 - 7.16 (m, 2H), 7.02 (dd, J = 8.8, 3.0 Hz, 1H), 4.77 - 4.65 (m, 2H), 4.46 - 4.33 (m, 2H), 4.30 - 4.20 (m, 1H), 4.06 - 3.96 (m, 1H), 3.82 (d, J = 13.0 Hz, 1H), 2.80 (s, 3H), 1.93 (br s, 3H), 1.89 - 1.76 (m, 1H), 1.72 - 1.59 (m, 1H), 1.15 - 1.03 (m, 1H); 571.3 (chlorine isotope pattern observed) |
| 52 | Example 18; C75 | 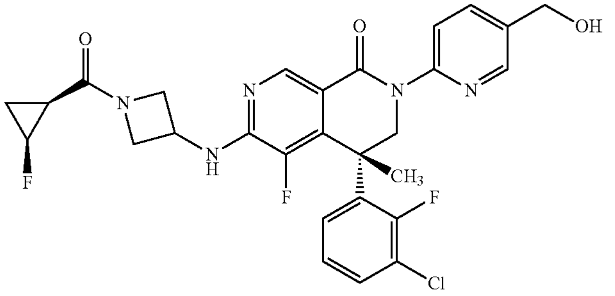 [SMILES: C[C@]1(c2cccc(Cl)c2F)CN(c2ccc(CO)cn2)C(=O)c2cnc(NC3CN(C(=O)[C@@H]4C[C@@H]4F)C3)c(F)c21] | $^1$H NMR (400 MHz, DMSO-$d_6$) δ [8.62 (s) and 8.61 (s), total 1H], 8.32 (br d, J = 2.3 Hz, 1H), 8.03 (br t, J = 7.4 Hz, 1H), 7.79 (br d, half of AB quartet, J = 8.5 Hz, 1H), 7.73 (dd, component of ABX system, J = 8.6, 2.3 Hz, 1H), 7.61 - 7.54 (m, 1H), 7.44 - 7.36 (m, 1H), 7.26 (t, J = 8.0 Hz, 1H), 5.30 (t, J = 5.7 Hz, 1H), [4.96 - 4.90 (m) and 4.85 - 4.73 (m), total 2H], [4.60 (t, J = 8.2 Hz) and 4.55 - 4.48 (m), total 1H], 4.51 (d, J = 5.8 Hz, 2H), [4.46 (d, J = 13.4 Hz) and 4.45 (d, J = 13.3 |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-d$_4$) δ; Mass spectrum, observed ion m/z [M + H]$^+$ or HPLC retention time; Mass spectrum m/z [M + H]$^+$ (unless otherwise indicated) |
|---|---|---|---|
| | | | Hz), total 1H], 4.24 - 4.11 (m, 3H), 3.98 - 3.85 (m, 1H), 1.83 (s, 3H), 1.83 - 1.72 (m, 1H), 1.57 - 1.43 (m, 1H), 1.07 - 0.95 (m, 1H); 572.4 (chlorine isotope pattern observed) |
| 53 | Example 18; C75, C82 | 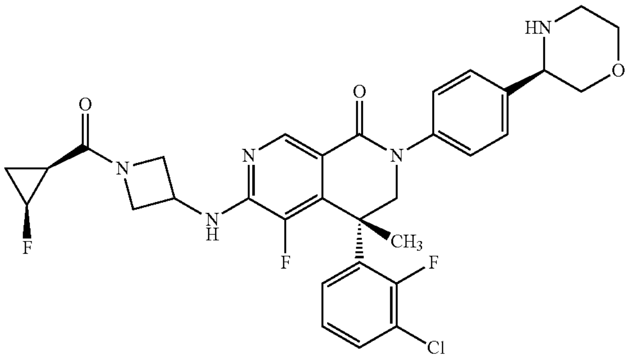 [SMILES: C[C@]1(c2cccc(Cl)c2F)CN(c2ccc([C@@H]3COCCN3)cc2)C(=O)c2cnc(NC3CN(C(=O)[C@@H]4C[C@@H]4F)C3)c(F)c21] | $^1$H NMR (500 MHz, methanol-d$_4$) δ 8.62 (d, J = 2.0 Hz, 1H), 7.48 (ddd, J = 8.3, 6.9, 1.6 Hz, 1H), 7.43 (d, J = 8.3 Hz, 2H), 7.31 - 7.24 (m, 1H), 7.23 - 7.16 (m, 3H), 4.97 - 4.9 (m, 1H, assumed; partially obscured by water peak), [4.78 - 4.72 (m) and 4.64 - 4.59 (m), total 1H], 4.73 - 4.66 (m, 1H), 4.43 - 4.34 (m, 2H), 4.30 - 4.22 (m, 1H), 4.05 - 3.97 (m, 1H), 3.91 (dd, J = 10.3, 3.2 Hz, 1H), 3.87 - 3.83 (m, 1H), 3.81 (dd, J = 11.2, 3.3 Hz, 1H), [3.76 (d, J = 12.9 Hz) and 3.74 (d, J = 12.9 Hz), total 1H], 3.62 (td, J = 11.4, 2.7 Hz, 1H), 3.40 (dd, J = 11.2, 10.3 Hz, 1H), 3.05 (td, J = 12.0, 3.4 Hz, 1H), 3.00 - 2.94 (m, 1H), 1.96 (s, 3H), 1.88 - 1.77 (m, 1H), 1.72 - 1.60 (m, 1H), 1.14 - 1.04 (m, 1H); 626.3 (chlorine isotope pattern observed) |
| 54 | Example 18; C75 | 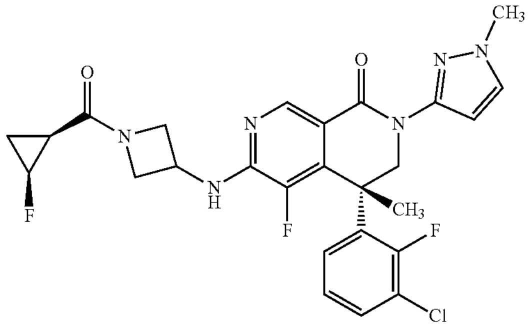 [SMILES: Cn1ccc(N2C[C@](C)(c3cccc(Cl)c3F)c3c(cnc(NC4CN(C(=O)[C@@H]5C[C@@H]5F)C4)c3F)C2=O)n1] | 8.64 (d, J = 1.6 Hz, 1H), 7.49 (d, J = 2.4 Hz, 1H), 7.49 - 7.43 (m, 1H), 7.38 - 7.31 (m, 1H), 7.20 (br t, J = 8.0 Hz, 1H), 6.59 (d, J = 2.4 Hz, 1H), 4.98 - 4.85 (m, 1H, assumed; partially obscured by water peak), 4.77 - 4.64 (m, 2H), 4.44 (d, J = 13.4 Hz, 1H), 4.43 - 4.33 (m, 1H), 4.30 - 4.20 (m, 1H), 4.08 (d, J = 13.2 Hz, 1H), 4.05 - 3.96 (m, 1H), 3.81 (s, 3H), 1.89 (br s, 3H), 1.88 - 1.75 (m, 1H), 1.72 - 1.59 (m, 1H), 1.15 - 1.03 (m, 1H); 545.1 (chlorine isotope pattern observed) |
| 55 | Example 18; C75 | 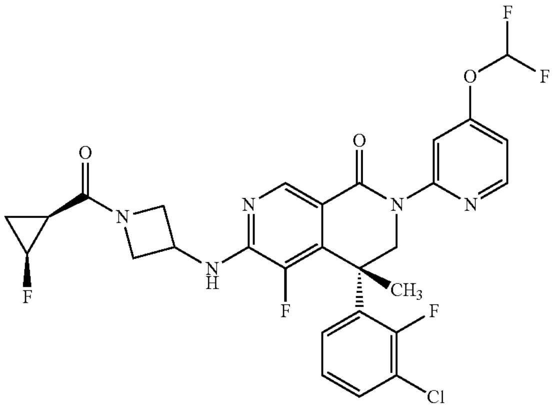 [SMILES: C[C@]1(c2cccc(Cl)c2F)CN(c2cc(OC(F)F)ccn2)C(=O)c2cnc(NC3CN(C(=O)[C@@H]4C[C@@H]4F)C3)c(F)c21] | $^1$H NMR (400 MHz, methanol-d$_4$), characteristic peaks: δ 8.70 (d, J = 1.6 Hz, 1H), 8.36 (d, J = 5.7 Hz, 1H), 7.63 (d, J = 2.2 Hz, 1H), 7.49 - 7.42 (m, 1H), 7.31 (t, J = 7.5 Hz, 1H), 7.19 (t, J = 8.0 Hz, 1H), 7.08 (t, $J_{HF}$ = 72.6 Hz, 1H), 6.97 (dd, J = 5.8, 2.2 Hz, 1H), 4.76 - 4.63 (m, 1H, assumed; partially obscured by water peak), 4.44 - 4.34 (m, 1H), 4.31 - 4.23 (m, 1H), 4.23 - 4.16 (m, 1H), 4.06 - 3.97 (m, 1H), 1.91 (s, 3H), 1.89 - 1.76 (m, 1H), 1.73 - 1.59 (m, 1H), 1.16 - 1.03 (m, 1H); 608.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 56 | Example 18; C75 | 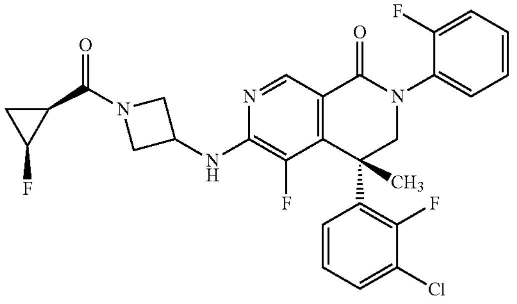 [SMILES: C[C@]1(c2cccc(Cl)c2F)CN(c2ccccc2F)C(=O)c2cnc(NC3CN(C(=O)[C@@H]4C[C@@H]4F)C3)c(F)c21] | 2.71 minutes[4]; 559.3 (chlorine isotope pattern observed) |
| 57 | Example 4; C63 | 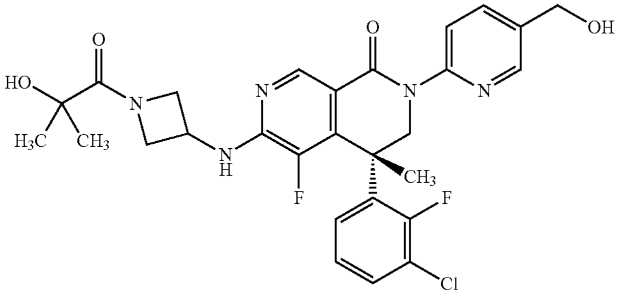 [SMILES: CC(C)(O)C(=O)N1CC(Nc2ncc3c(c2F)[C@@](C)(c2cccc(Cl)c2F)CN(c2ccc(CO)cn2)C3=O)C1] | 8.67 (s, 1H), 8.41 - 8.35 (m, 1H), 7.78 (dd, component of ABX system, J = 8.5, 2.4 Hz, 1H), 7.70 (d, half of AB quartet, J = 8.4 Hz, 1H), 7.45 (ddd, J = 8.2, 6.8, 1.6 Hz, 1H), 7.34 - 7.27 (m, 1H), 7.18 (t, J = 8.0 Hz, 1H), 4.93 - 4.78 (m, 2H, assumed; partially obscured by water peak), 4.62 (s, 2H), 4.57 (d, J = 13.3 Hz, 1H), 4.48 - 4.39 (m, 1H), 4.39 - 4.32 (m, 1H), 4.10 (d, J = 13.3 Hz, 1H), 4.02 - 3.93 (m, 1H), 1.92 (br s, 3H), 1.39 (s, 3H), [1.38 (s) and 1.37 (s), total 3H]; 572.1 (chlorine isotope pattern observed) |
| 58 | Example 4; C63 | 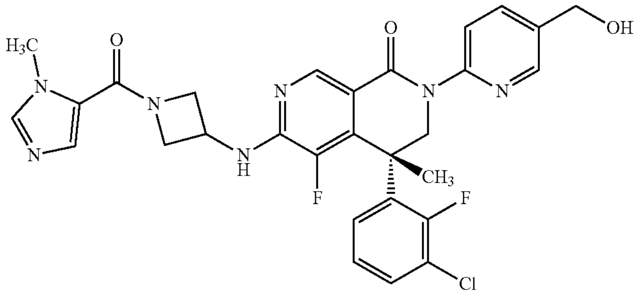 [SMILES: Cn1cncc1C(=O)N1CC(Nc2ncc3c(c2F)[C@@](C)(c2cccc(Cl)c2F)CN(c2ccc(CO)cn2)C3=O)C1] | $^1$H NMR (400 MHz, methanol-$d_4$), characteristic peaks: δ 8.69 (s, 1H), 8.39 - 8.36 (m, 1H), 7.80 - 7.75 (m, 2H), 7.70 (d, half of AB quartet, J = 8.5 Hz, 1H), 7.45 (ddd, J = 8.4, 6.9, 1.6 Hz, 1H), 7.41 (br s, 1H), 7.34 - 7.28 (m, 1H), 7.18 (t, J = 8.0 Hz, 1H), 4.70 - 4.60 (m, 1H), 4.62 (s, 2H), 4.57 (d, J = 13.3 Hz, 1H), 4.46 - 4.32 (br m, 1H), 4.20 - 4.05 (br m, 1H), 4.10 (d, J = 13.3 Hz, 1H), 3.91 (s, 3H), 1.92 (br s, 3H); 594.3 (chlorine isotope pattern observed) |
| 59 | Example 4; C63 | 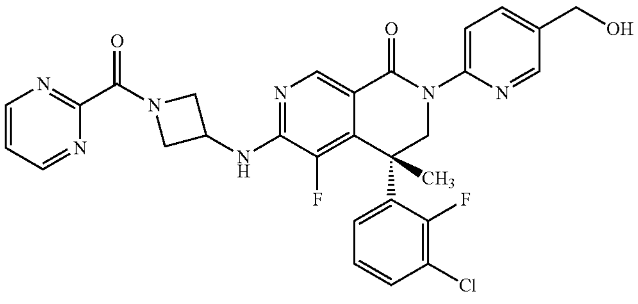 [SMILES: C[C@]1(c2cccc(Cl)c2F)CN(c2ccc(CO)cn2)C(=O)c2cnc(NC3CN(C(=O)c4ncccn4)C3)c(F)c21] | $^1$H NMR (400 MHz, methanol-$d_4$), characteristic peaks, integrations are approximate: δ 8.95 - 8.90 (m, 2H), 8.69 (s, 1H), 8.38 (br d, J = 2.3 Hz, 1H), 7.78 (br dd, component of ABX system, J = 8.5, 2.4 Hz, 1H), 7.72 - 7.67 (m, 1H), 7.61 - 7.56 (m, 1H), 7.48 - 7.41 (m, 1H), 7.35 - 7.27 (m, 1H), 7.18 (t, J = 8.0 Hz, 1H), 5.13 - 4.9 (m, 1H, assumed; partially obscured by water peak), 4.70 - 4.53 (m, 3H), 4.63 (s, 2H), 4.28 - 4.16 (m, 1H), |

TABLE 3-continued

| Method of synthesis, structure, and physicochemical data for Examples 39-111. The examples below were made from analogous processes to the Example(s) identified and from appropriate analogous starting materials. Ex. stands for Example. | | | |
|---|---|---|---|
| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| | | | 4.10 (d, J = 13.3 Hz, 1H), 1.92 (s, 3H); 592.2 (chlorine isotope pattern observed) |
| 60 | Example 4; C63 | 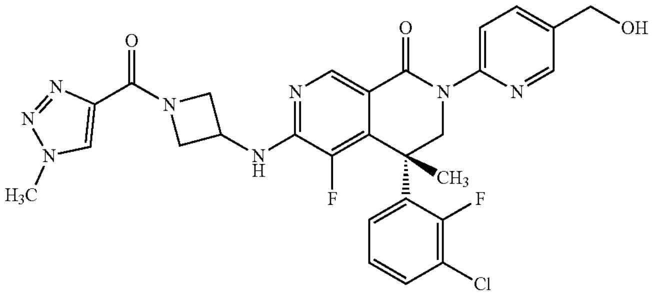 [SMILES: Cn1cc(C(=O)N2CC(Nc3ncc4c(c3F)[C@@](C)(c3cccc(Cl)c3F)CN(c3ccc(CO)cn3)C4=O)C2)nn1] | $^1H$ NMR (400 MHz, methanol-$d_4$), characteristic peaks, integrations are approximate: 8 8.69 (s, 1H), 8.38 (br d, J = 2.2 Hz, 1H), 8.34 (s, 1H), 7.78 (dd, component of ABX system, J = 8.5, 2.4 Hz, 1H), 7.70 (d, half of AB quartet, J = 8.5 Hz, 1H), 7.48 – 7.41 (m, 1H), 7.30 (t, J = 7.4 Hz, 1H), 7.18 (t, J = 8.0 Hz, 1H), 5.11 – 4.9 (m, 1H, assumed; partially obscured by solvent peak), 4.68 – 4.52 (m, 3H), 4.62 (s, 2H), 4.20 – 4.10 (m, 1H), 4.14 (s, 3H), 4.10 (d, J = 13.4 Hz, 1H), 1.92 (s, 3H); 595.3 (chlorine isotope pattern observed) |
| 61 | Examples 9 and 10; C59 | 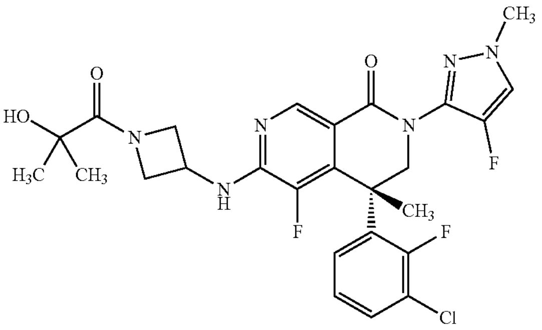 [SMILES: Cn1cc(F)c(N2C[C@](C)(c3cccc(Cl)c3F)c3c(cnc(NC4CN(C(=O)C(C)(C)O)C4)c3F)C2=O)n1] | 8.62 (s, 1H), 7.58 (d, J = 4.5 Hz, 1H), 7.50 – 7.44 (m, 1H), 7.35 (br t, J = 7.5 Hz, 1H), 7.20 (t, J = 8.0 Hz, 1H), 4.9 – 4.76 (m, 2H, assumed; partially obscured by water peak), 4.48 – 4.30 (m, 2H), 4.36 (d, J = 12.7 Hz, 1H), 4.02 – 3.91 (m, 1H), 3.78 (s, 3H), 3.70 (d, J = 12.9 Hz, 1H), 1.94 (br s, 3H), 1.38 (s, 3H), 1.37 (br s, 3H); 563.2 (chlorine isotope pattern observed) |
| 62 | Examples 9 and 10; C59 | 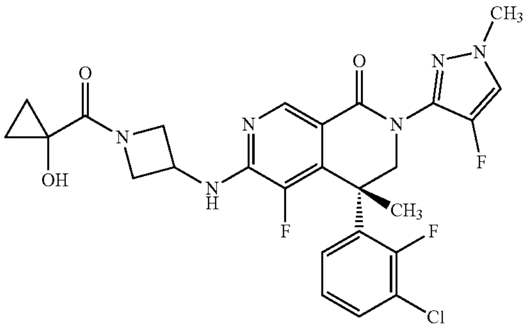 [SMILES: Cn1cc(F)c(N2C[C@](C)(c3cccc(Cl)c3F)c3c(cnc(NC4CN(C(=O)C5(O)CC5)C4)c3F)C2=O)n1] | 2.34 minutes[4]; 561.4 (chlorine isotope pattern observed) |

TABLE 3-continued

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | Method of synthesis, structure, and physicochemical data for Examples 39-111. The examples below were made from analogous processes to the Example(s) identified and from appropriate analogous starting materials. Ex. stands for Example. | | |
| 63 | Examples 9 and 10; C59 | 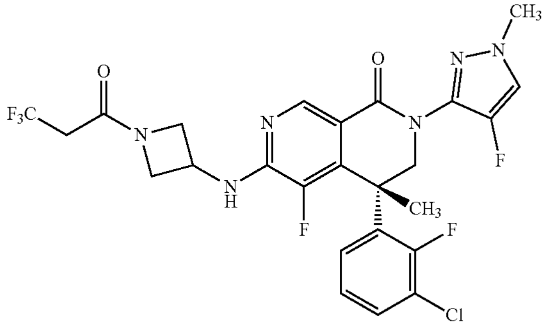 [SMILES: Cn1cc(F)c(N2C[C@](C)(c3cccc(Cl)c3F)c3c(cnc(NC4CN(C(=O)CC(F)(F)F)C4)c3F)C2=O)n1] | 2.66 minutes[4]; 587.4 (chlorine isotope pattern observed) |
| 64 | Examples 9 and 10; C59 | 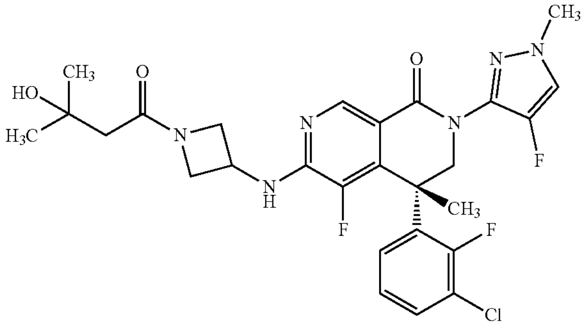 [SMILES: Cn1cc(F)c(N2C[C@](C)(c3cccc(Cl)c3F)c3c(cnc(NC4CN(C(=O)CC(C)(C)O)C4)c3F)C2=O)n1] | 2.42 minutes[4]; 577.5 (chlorine isotope pattern observed) |
| 65 | Example 11; C59 | 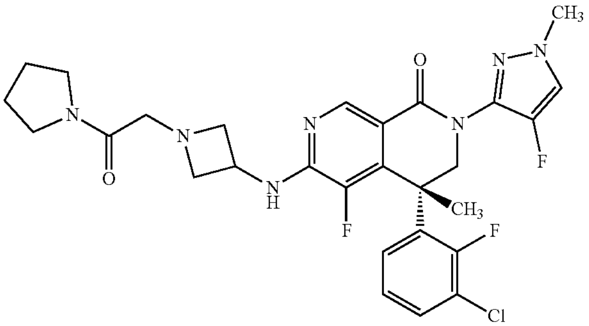 [SMILES: Cn1cc(F)c(N2C[C@](C)(c3cccc(Cl)c3F)c3c(cnc(NC4CN(CC(=O)N5CCCC5)C4)c3F)C2=O)n1] | $^1$H NMR (400 MHz, methanol-$d_4$), characteristic peaks: δ 8.61 (s, 1H), 7.58 (d, J = 4.5 Hz, 1H), 7.47 (br t, J = 7.3 Hz, 1H), 7.35 (br t, J = 7.4 Hz, 1H), 7.20 (t, J = 7.9 Hz, 1H), 4.81 - 4.71 (m, 1H), 4.35 (d, J = 12.9 Hz, 1H), 3.96 - 3.87 (m, 2H), 3.78 (s, 3H), 3.68 (d, J = 12.9 Hz, 1H), 3.47 - 3.37 (m, 6H), 2.02 - 1.82 (m, 4H), 1.93 (br s, 3H); 588.2 (chlorine isotope pattern observed) |
| 66 | Example 115; C59 | 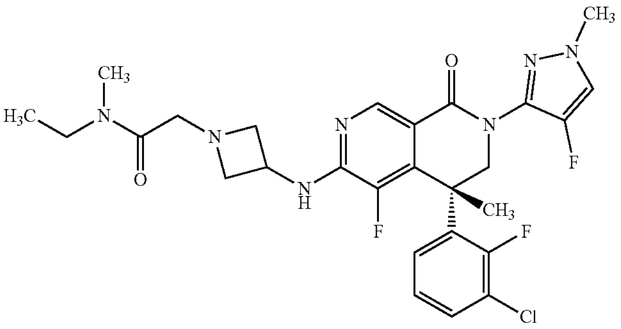 [SMILES: CCN(C)C(=O)CN1CC(Nc2ncc3c(c2F)[C@@](C)(c2cccc(Cl)c2F)CN(c2nn(C)cc2F)C3=O)C1] | 8.60 (s, 1H), 7.58 (d, J = 4.5 Hz, 1H), 7.47 (ddd, J = 8.3, 7.0, 1.6 Hz, 1H), 7.38 - 7.31 (m, 1H), 7.20 (br t, J = 8.0 Hz, 1H), 4.81 - 4.71 (m, 1H), 4.35 (d, J = 12.9 Hz, 1H), 3.92 - 3.84 (m, 2H), 3.78 (s, 3H), 3.68 (d, J = 12.9 Hz, 1H), [3.48 (s) and 3.45 (s), total 2H], 3.42 - 3.3 (m, 2H, assumed; partially obscured by solvent peak), 3.27 - 3.19 (m, 2H), [2.97 (s) and 2.88 (s), total 3H], 1.93 (br s, 3H), [1.18 (t, J = 7.1 Hz) and 1.09 (t, J = 7.1 Hz), total 3H]; 576.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^{1}H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| --- | --- | --- | --- |
| 67 | Example 11; C59 | 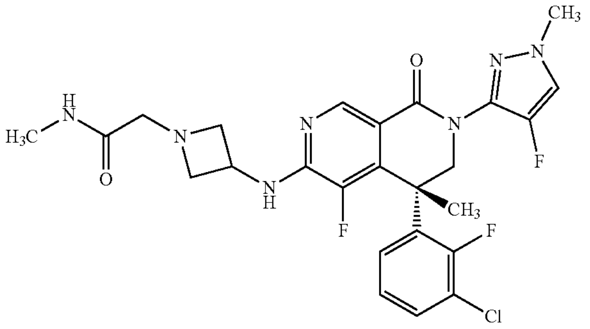 [SMILES: CNC(=O)CN1CC(Nc2ncc3c(c2F)[C@@](C)(c2cccc(Cl)c2F)CN(c2nn(C)cc2F)C3=O)C1] | 8.59 (s, 1H), 7.57 (d, J = 4.5 Hz, 1H), 7.46 (br t, J = 7.4 Hz, 1H), 7.38 - 7.31 (m, 1H), 7.19 (t, J= 8.0 Hz, 1H), 4.80 - 4.70 (m, 1H), 4.35 (d, J = 12.9 Hz, 1H), 3.86 - 3.78 (m, 2H), 3.77 (s, 3H), 3.68 (d, J = 12.9 Hz, 1H), 3.23 - 3.14 (m, 1H), 3.17 (s, 3H), 2.74 (s, 3H), 1.93 (br s, 3H); LCMS m/z 546.2 $[M - H]^-$ (chlorine isotope pattern observed) |
| 68 | Example 11; C59 | 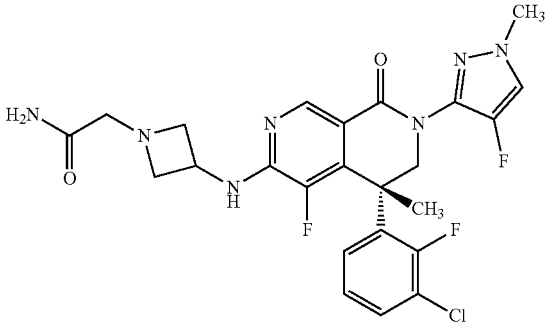 [SMILES: Cn1cc(F)c(N2C[C@](C)(c3cccc(Cl)c3F)c3c(cnc(NC4CN(CC(N)=O)C4)c3F)C2=O)n1] | 8.60 (s, 1H), 7.58 (d, J = 4.4 Hz, 1H), 7.47 (t, J = 7.5 Hz, 1H), 7.34 (t, J = 7.4 Hz, 1H), 7.20 (t, J = 8.0 Hz, 1H), 4.80 - 4.71 (m, 1H), 4.35 (d, J = 12.9 Hz, 1H), 3.89 - 3.80 (m, 2H), 3.78 (s, 3H), 3.68 (d, J = 12.8 Hz, 1H), 3.25 - 3.15 (m, 2H), 3.19 (s, 2H), 1.93 (br s, 3H); 534.2 (chlorine isotope pattern observed) |
| 69 | Example 11[6,7]; C59 | 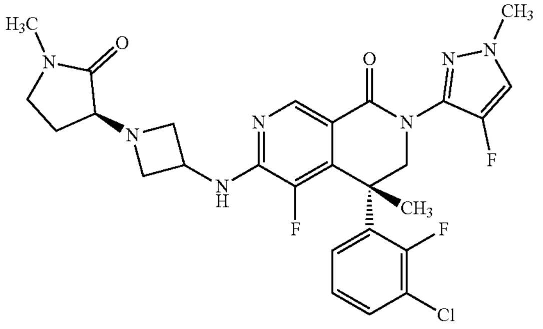 [SMILES: CN1CC[C@H](N2CC(Nc3ncc4c(c3F)[C@@](C)(c3cccc(Cl)c3F)CN(c3nn(C)cc3F)C4=O)C2)C1=O]<br>or<br>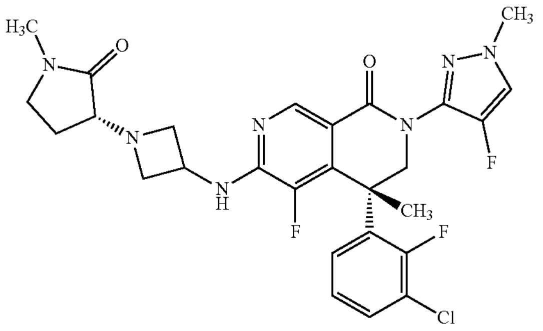<br>DIAST-1 | 2.53 minutes[8]; 574.4 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 70 | 11[6,7]; C59 | 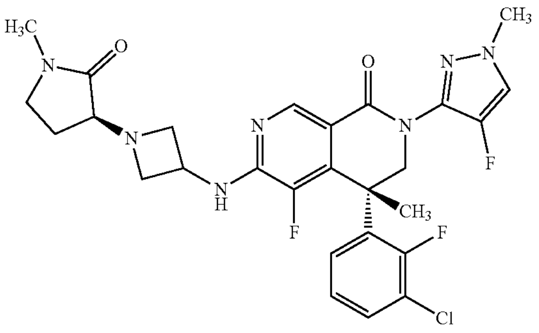 [SMILES: CN1CC[C@H](N2CC(Nc3ncc4c(c3F)[C@@](C)(c3cccc(Cl)c3F)CN(c3nn(C)cc3F)C4=O)C2)C1=O] or 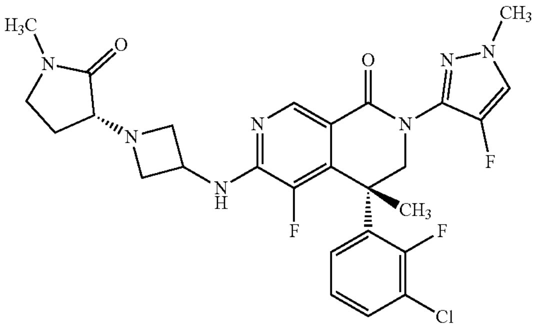 DIAST-2 | 3.09 minutes[8]; 574.4 (chlorine isotope pattern observed) |
| 71 | Example 11[6,9]; C59 | 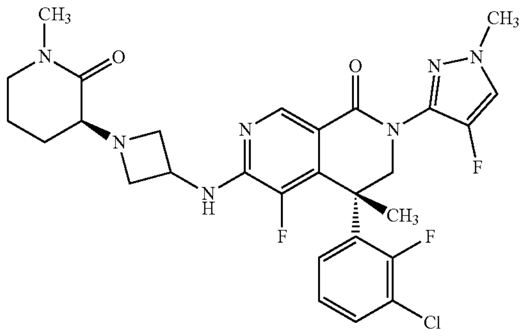 [SMILES: CN1CCC[C@H](N2CC(Nc3ncc4c(c3F)[C@@](C)(c3cccc(Cl)c3F)CN(c3nn(C)cc3F)C4=O)C2)C1=O] | 2.66 minutes[8]; 588.5 (chlorine isotope pattern observed) |

TABLE 3-continued

| Ex. | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| | | or 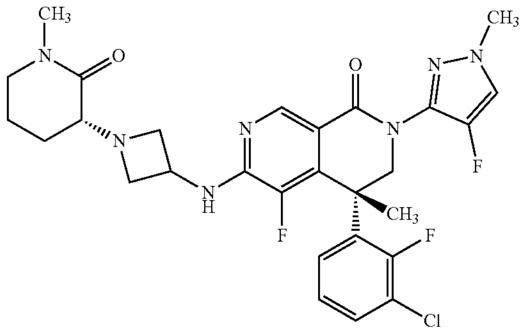 DIAST-1 | |
| 72 | Example 116,9; C59 | 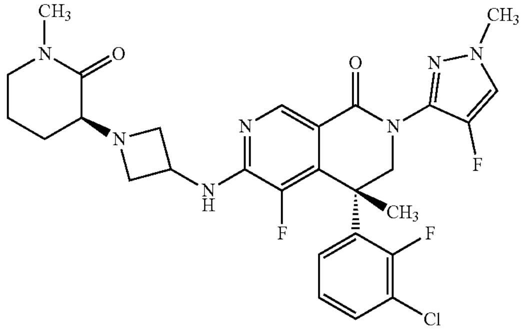 [SMILES: CN1CCC[C@H](N2CC(Nc3ncc4c(c3F)[C@@](C)(c3cccc(Cl)c3F)CN(c3nn(C)cc3F)C4=O)C2)C1=O] or 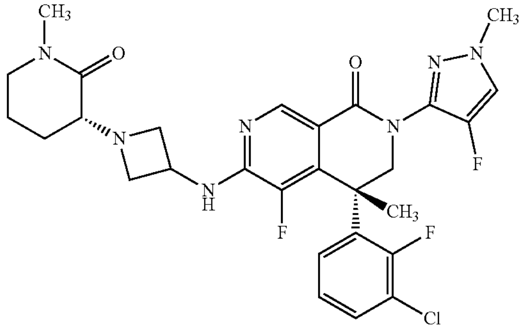 DIAST-2 | 3.04 minutes[8]; 588.5 (chlorine isotope pattern observed) |

Method of synthesis, structure, and physicochemical data for Examples 39-111. The examples below were made from analogous processes to the Example(s) identified and from appropriate analogous starting materials. Ex. stands for Example.

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 73 | Method A; C59 | 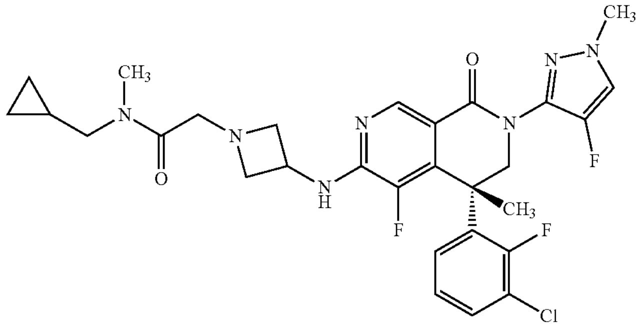 [SMILES: CN(CC1CC1)C(=O)CN1CC(Nc2ncc3c(c2F)[C@@](C)(c2cccc(Cl)c2F)CN(c2nn(C)cc2F)C3=O)C1] | 2.38 minutes[4]; 602.4 (chlorine isotope pattern observed) |
| 74 | Method A; C59 | 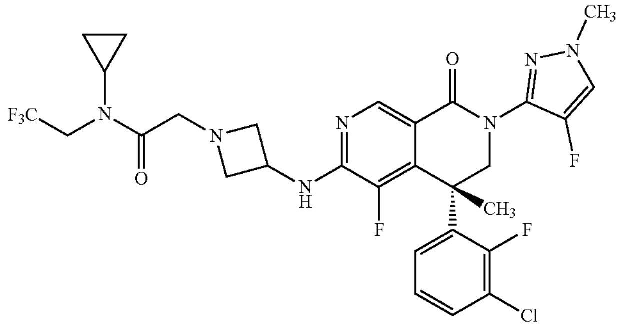 [SMILES: Cn1cc(F)c(N2C[C@](C)(c3cccc(Cl)c3F)c3c(cnc(NC4CN(CC(=O)N(CC(F)(F)F)C5CC5)C4)c3F)C2=O)n1] | 2.51 minutes[4]; 656.4 (chlorine isotope pattern observed) |
| 75 | Method A; C59 | 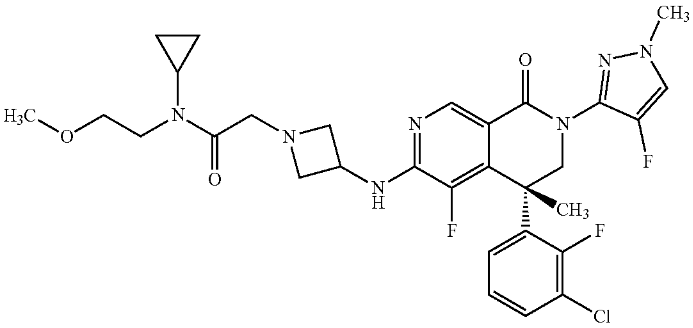 [SMILES: COCCN(C(=O)CN1CC(Nc2ncc3c(c2F)[C@@](C)(c2cccc(Cl)c2F)CN(c2nn(C)cc2F)C3=O)C1)C1CC1] | 2.33 minutes[4]; 632.4 (chlorine isotope pattern observed) |
| 76 | Example 12; C70 | 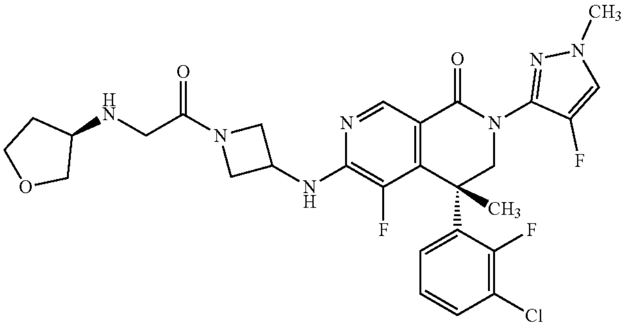 [SMILES: Cn1cc(F)c(N2C[C@](C)(c3cccc(Cl)c3F)c3c(cnc(NC4CN(C(=O)CN[C@@H]5CCOC5)C4)c3F)C2=O)n1] | $^1$H NMR (400 MHz, DMSO-$d_6$) δ 8.51 (s, 1H), 8.00 - 7.94 (m, 1H), 7.82 (d, J = 4.5 Hz, 1H), 7.59 (t, J = 7.5 Hz, 1H), 7.41 (t, J = 7.8 Hz, 1H), 7.27 (t, J = 8.0 Hz, 1H), 4.81 - 4.70 (m, 1H), 4.45 (t, J= 8.3 Hz, 1H), 4.26 - 4.12 (m, 2H), [4.12 - 4.04 (m) and 4.04 - 3.97 (m), total 1H], 3.96 - 3.82 (m, 1H), 3.77 - 3.58 (m, 7H), 3.44 - 3.37 (m, 1H), 3.28 - 3.20 (m, 1H), 3.15 - 3.08 (m, 2H), 1.98 - 1.81 (m, 2H), 1.85 (s, 3H), 1.70 - 1.58 (m, 1H); 604.5 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 77 | Example 15[10]; C75 | 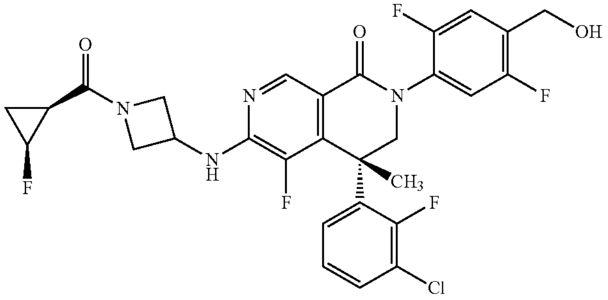 [SMILES: C[C@]1(c2cccc(Cl)c2F)CN(c2cc(F)c(CO)cc2F)C(=O)c2cnc(NC3CN(C(=O)[C@@H]4C[C@@H]4F)C3)c(F)c21] | 8.63 (d, J = 1.5 Hz, 1H), 7.52 - 7.45 (m, 1H), 7.39 - 7.28 (m, 2H), 7.21 (t, J = 8.0 Hz, 1H), 7.10 - 7.02 (m, 1H), 4.97 - 4.81 (m, 2H, assumed; partially obscured by water peak), 4.76 - 4.66 (m, 1H), 4.65 (s, 2H), 4.44 - 4.33 (m, 2H), 4.31 - 4.21 (m, 1H), 4.06 - 3.96 (m, 1H), 3.69 - 3.61 (m, 1H), 1.97 (s, 3H), 1.89 - 1.76 (m, 1H), 1.73 - 1.59 (m, 1H), 1.15 - 1.03 (m, 1H); 607.2 (chlorine isotope pattern observed) |
| 78 | Example 2; C59 | 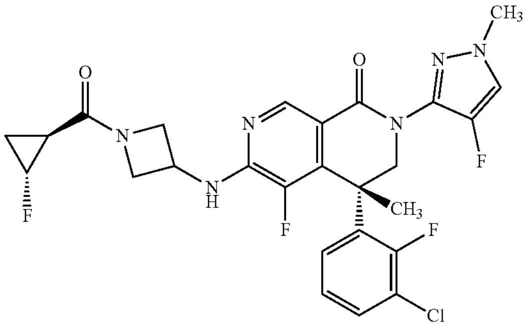 [SMILES: Cn1cc(F)c(N2C[C@](C)(c3cccc(Cl)c3F)c3c(cnc(NC4CN(C(=O)[C@@H]5C[C@H]5F)C4)c3F)C2=O)n1] | $^1$H NMR (600 MHz, DMSO-$d_6$) δ 8.52 (s, 1H), 7.99 (t, J = 7.2 Hz, 1H), 7.82 (d, J = 4.4 Hz, 1H), 7.61 - 7.56 (m, 1H), 7.43 - 7.37 (m, 1H), 7.27 (t, J = 8.0 Hz, 1H), [4.84 - 4.76 (m) and 4.72 - 4.66 (m), total 2H], 4.60 (t, J = 7.9 Hz, 1H), 4.26 - 4.11 (m, 2H), 4.21 (d, J = 13.1 Hz, 1H), 3.90 - 3.81 (m, 1H), 3.74 - 3.68 (m, 1H), 3.71 (s, 3H), 2.16 - 2.06 (m, 1H), 1.85 (br s, 3H), 1.45 - 1.35 (m, 1H), 1.15 - 1.04 (m, 1H); 563.2 (chlorine isotope pattern observed) |
| 79 | Example 31; C103 [from P11 (ENANT-2)] | 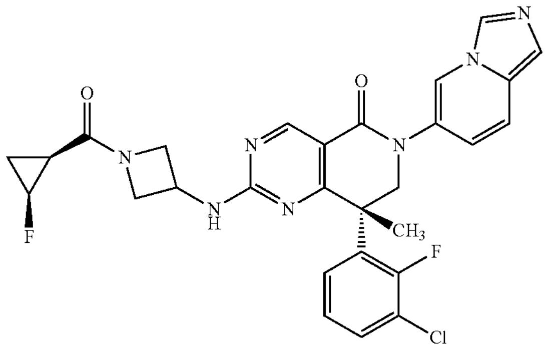 [SMILES: C[C@]1(c2cccc(Cl)c2F)CN(c2ccc3cncn3c2)C(=O)c2cnc(NC3CN(C(=O)[C@@H]4C[C@@H]4F)C3)nc21] or 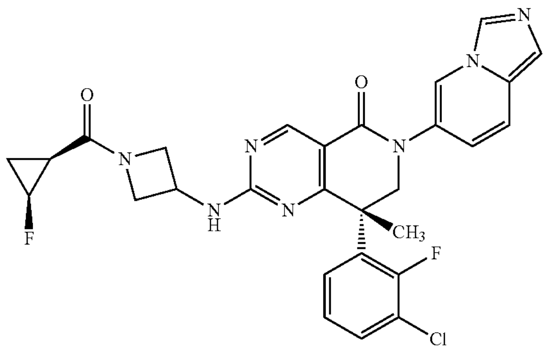 from P11 (ENANT-2) | 8.90 (br s, 1H), 8.39 - 8.27 (m, 2H), [7.60 - 7.36 (m) and 7.34 - 7.16 (m), total 5H], 6.82 - 6.63 (m, 1H), 4.9 - 4.79 (m, 1H, assumed; partially obscured by water peak), 4.77 - 4.63 (m, 1H), [4.60 - 4.43 (m) and 4.43 - 4.28 (m), total 2H], 4.27 - 4.14 (m, 1H), [4.04 - 3.83 (m) and 3.78 (d, J = 12.8 Hz), total 3H], [1.93 (s) and 1.90 (s), total 3H], 1.85 - 1.56 (m, 2H), 1.16 - 1.02 (m, 1H); 564.0 (chlorine isotope pattern observed) |

TABLE 3-continued

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | Method of synthesis, structure, and physicochemical data for Examples 39-111. The examples below were made from analogous processes to the Example(s) identified and from appropriate analogous starting materials. Ex. stands for Example. | |
| 80 | Example 31; C103 [from P11 (ENANT-2)] | 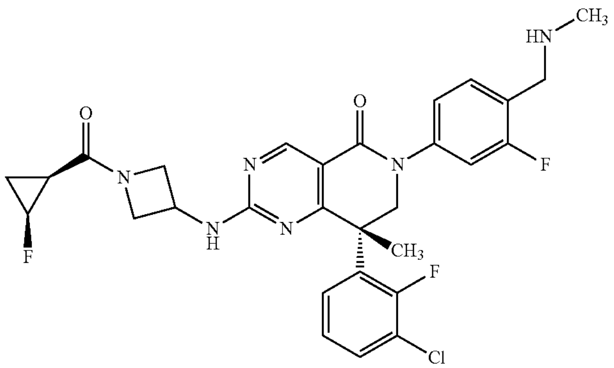 [SMILES: CNCc1ccc(N2C[C@](C)(c3cccc(Cl)c3F)c3nc(NC4CN(C(=O)[C@@H]5C[C@@H]5F)C4)ncc3C2=O)cc1F] or 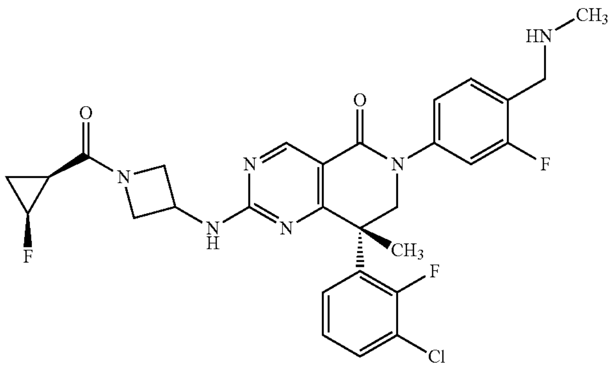 from P11 (ENANT-2) | $^1H$ NMR (400 MHz, methanol-$d_4$), integrations are approximate: δ 8.89 (s, 1H), 7.58 - 7.37 (m, 2H), [7.37 - 7.28 (m) and 7.28 - 6.98 (m), total 4H], 4.94 - 4.80 (m, 1H, assumed; almost completely obscured by water peak), 4.76 - 4.62 (m, 1H), [4.58 - 4.45 (m) and 4.43 - 4.31 (m), total 2H], 4.28 - 4.15 (m, 1H), 4.09 - 3.87 (m, 2H), 3.81 (d, J = 13.4 Hz, 1H), 3.78 (s, 2H), 2.39 (s, 3H), [1.88 (s) and 1.85 (s), total 3H], 1.83 - 1.56 (m, 2H), 1.15 - 1.03 (m, 1H); 585.2 (chlorine isotope pattern observed) |
| 81 | Example 4; C97 [from P13 (ENANT-2)] | 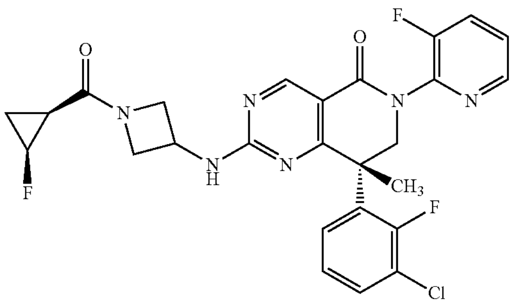 or | $^1H$ NMR (400 MHz, methanol-$d_4$), integrations are approximate: δ 8.91 (br s, 1H), 8.36 - 8.28 (m, 1H), 7.75 - 7.63 (m, 1H), [7.58 - 7.35 (m) and 7.34 - 7.13 (m), total 4H], 4.77 - 4.63 (m, 1H), 4.63 - 4.43 (m, 2H), 4.43 - 4.29 (m, 1H), 4.28 - 4.14 (m, 1H), 4.05 - 3.88 (m, 2H), 3.85 (d, J = 12.8 Hz, 1H), [1.89 (s) and 1.86 (s), total 3H], 1.83 - 1.56 (m, 2H), 1.17 - 1.01 (m, 1H); 543.2 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 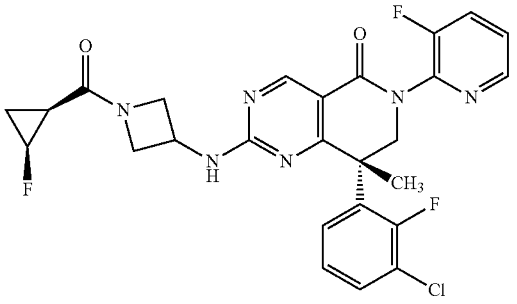 from P13 (ENANT-2) | |
| 82 | Example 4; C97 [from P13 ENANT-2)] | 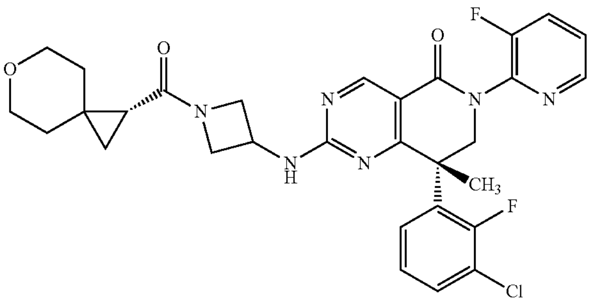 or 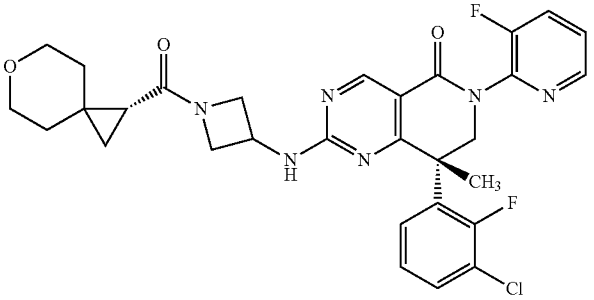 from P13 (ENANT-2) | $^1$H NMR (400 MHz, methanol-$d_4$), characteristic peaks, integrations are approximate: δ 8.93 (br s, 1H), 8.33 (br d, J = 4.7 Hz, 1H), 7.77 - 7.65 (m, 1H), [7.54 - 7.40 (m) and 7.35 - 7.15 (m), total 4H], 4.41 - 4.12 (m, 2H), 4.03 - 3.46 (m, 7H), [1.92 (s) and 1.89 (s), total 3H], [1.76 - 1.61 (m), 1.61 - 1.44 (m), and 1.43 - 1.36 (m), total 5H], 1.17 (t, J = 4.8 Hz, 1H), 0.99 - 0.86 (m, 1H); 595.2 (chlorine isotope pattern observed) |
| 83 | Examples 28 and 29[11,12]; C97 [from P13 (ENANT-2)] | 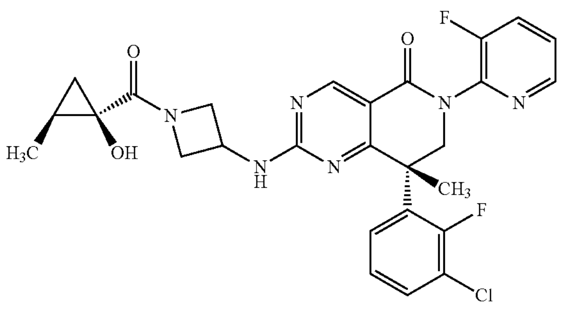 or | 3.01 minutes[13]; 555.6 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 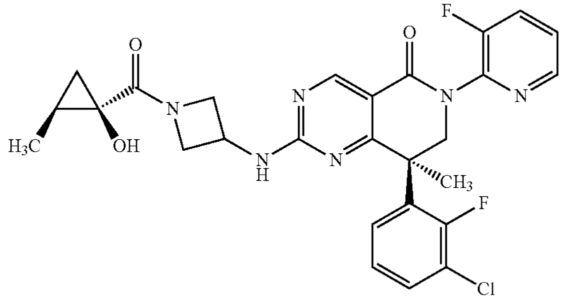<br>or<br>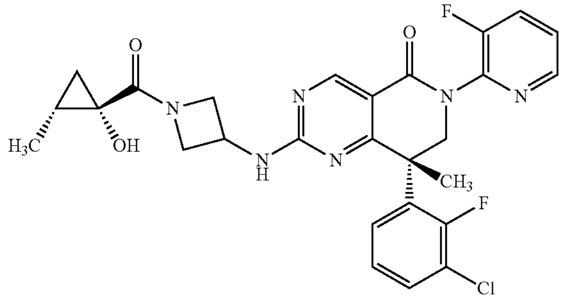<br>or<br>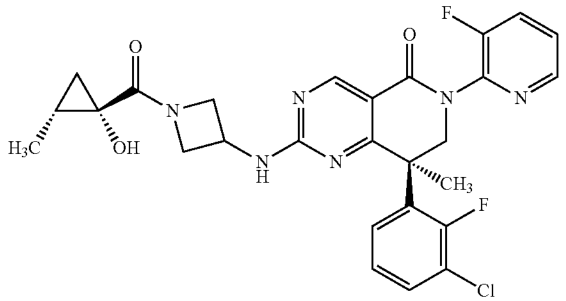<br>from P13 (ENANT-2), DIAST-1 | |
| 84 | Examples 28 and 29[11,12]; C97 [from P13 (ENANT-2)] | 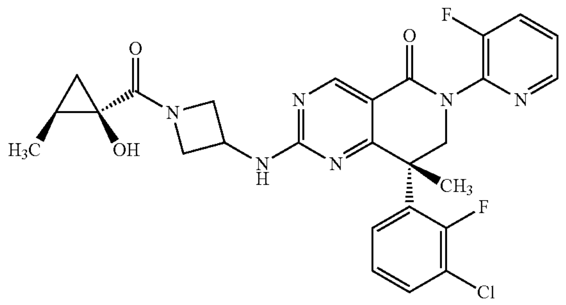<br>or | 3.37 minutes[13]; 555.6 (chlorine isotope pattern observed) |

TABLE 3-continued

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 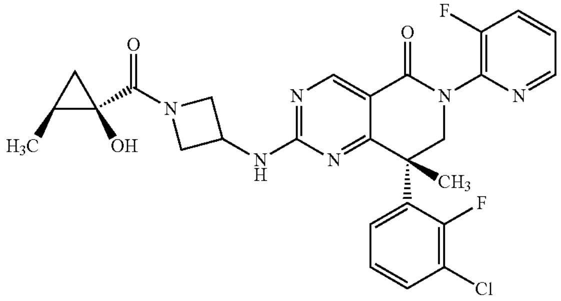 or 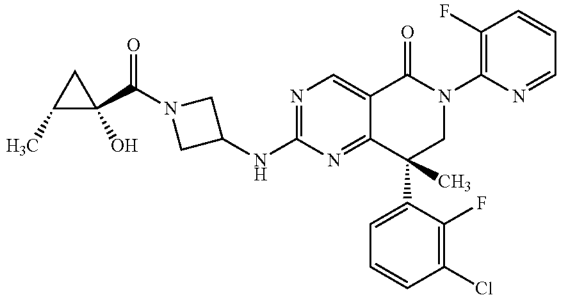 or 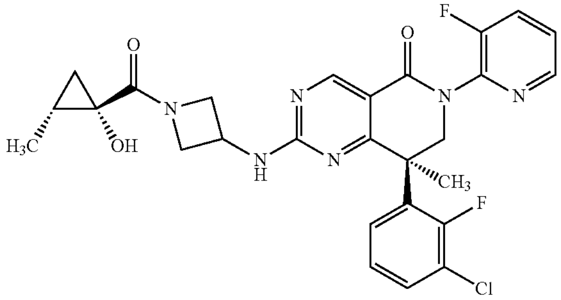 from P13 (ENANT-2), DIAST-2 | |
| 85 | Example 32; C104 [from P13 (ENANT-2)] | 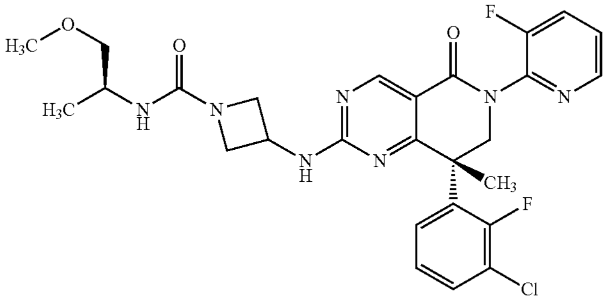 or | 2.63 minutes[4]; 572.4 (chlorine isotope pattern observed) |

Method of synthesis, structure, and physicochemical data for Examples 39-111. The examples below were made from analogous processes to the Example(s) identified and from appropriate analogous starting materials. Ex. stands for Example.

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 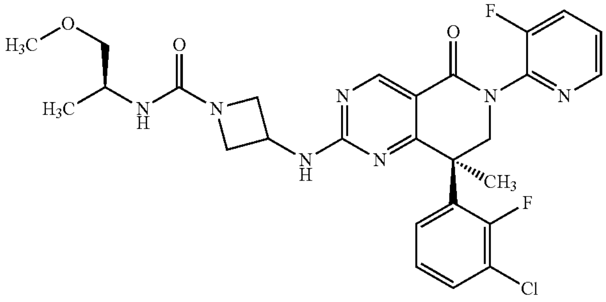 from P13 (ENANT-2) | |
| 86 | Example 32; C104 [from P13 (ENANT-2)] | 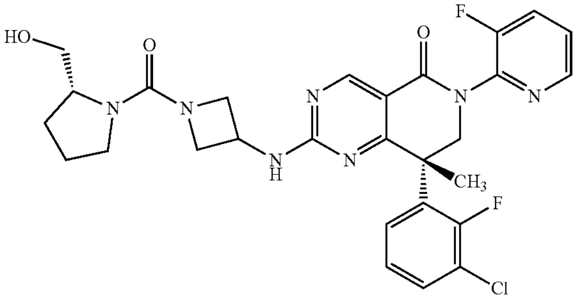 or 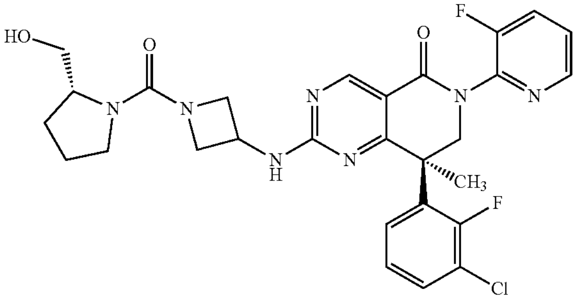 from P13 (ENANT-2) | 2.59 minutes[4]; 584.4 (chlorine isotope pattern observed) |
| 87 | Example 32; C104 [from P13 (ENANT-2)] | 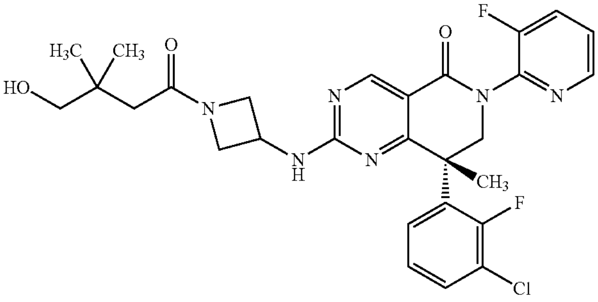 or | 2.56 minutes[4]; 572.4 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 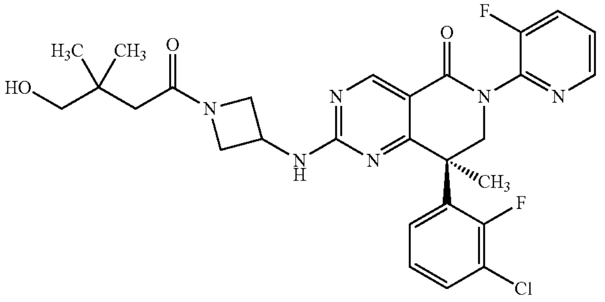<br>from P13 (ENANT-2) | |
| 88 | Example 32; C104 [from P13 (ENANT-2)] | 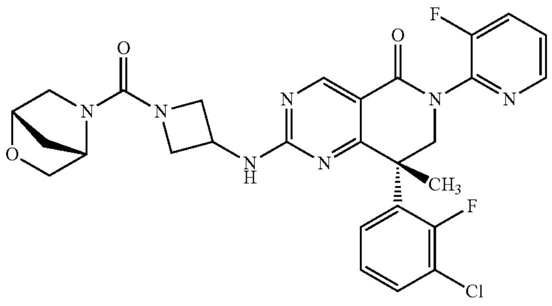<br>or<br>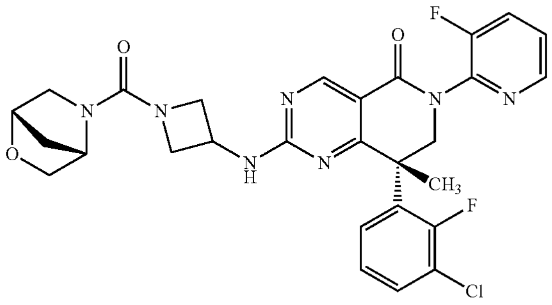<br>from P13 (ENANT-2) | 2.53 minutes[4]; 582.4 (chlorine isotope pattern observed) |
| 89 | Example 32; C104 [from P13 (ENANT-2)] | 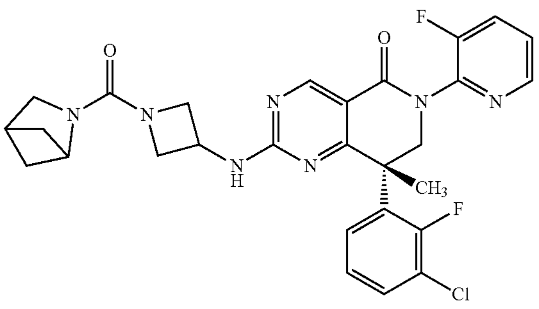<br>or | 2.88 minutes[4]; 566.4 (chlorine isotope pattern observed) |

TABLE 3-continued

| | | | |
|---|---|---|---|
| Method of synthesis, structure, and physicochemical data for Examples 39-111. The examples below were made from analogous processes to the Example(s) identified and from appropriate analogous starting materials. Ex. stands for Example. | | | |
| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| | | 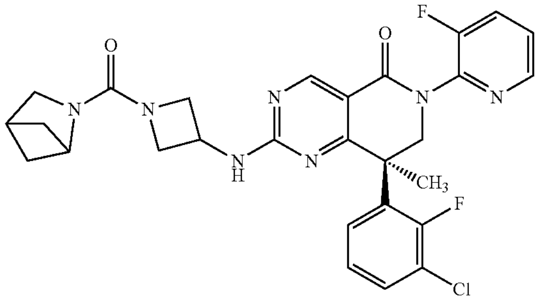 from P13 (ENANT-2) | |
| 90 | Example 34; C112 [from P18 (ENANT-2)] | 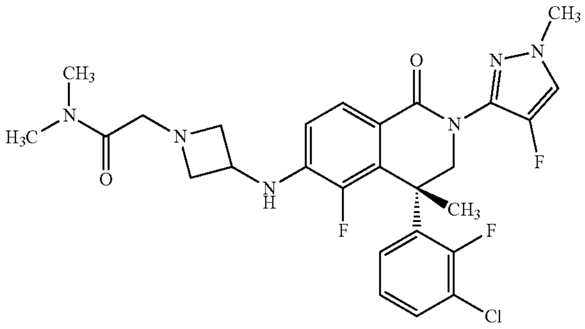 or 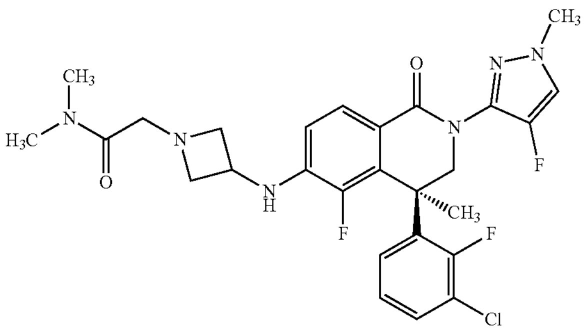 from P18 (ENANT-2) | 2.19 minutes[4]; 561.4 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| --- | --- | --- | --- |
| 91 | Example 34; C112 [from P18 (ENANT-2)] | 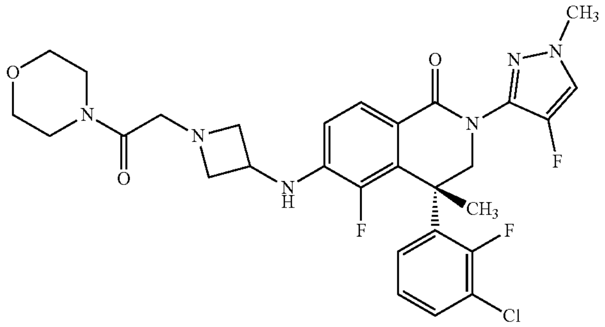 or 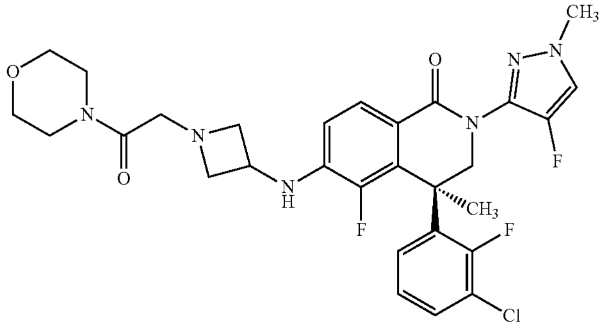 from P18 (ENANT-2) | 2.18 minutes[4]; 603.4 (chlorine isotope pattern observed) |
| 92 | Example 34[14]; C112 [from P18 (ENANT-2)] | 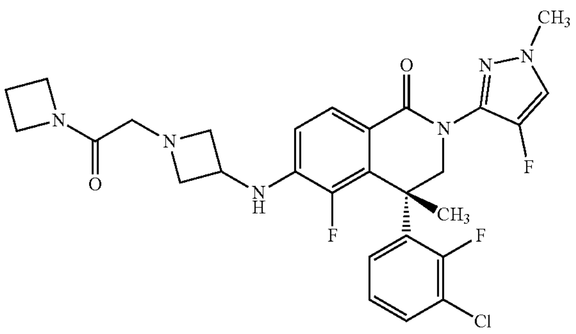 or | 2.20 minutes[4]; 573.4 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 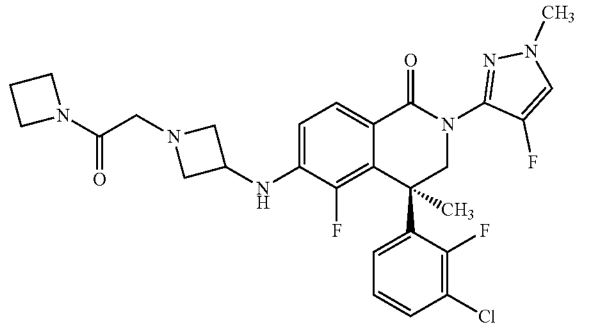 from P18 (ENANT-2) | |
| 93 | Example 4; P1 | 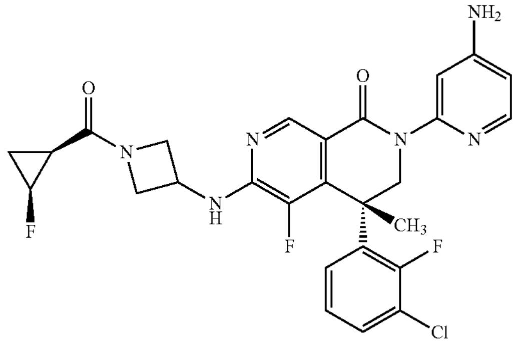 [SMILES: C[C@]1(c2cccc(Cl)c2F)CN(c2cc(N)ccn2)C(=O)c2cnc(NC3CN(C(=O)[C@@H]4C[C@@H]4F)C3)c(F)c21] | 8.65 (br s, 1H), 7.86 (d, J = 5.8 Hz, 1H), 7.50 - 7.42 (m, 1H), 7.39 - 7.30 (m, 1H), 7.20 (t, J= 8.0 Hz, 1H), 6.66 - 6.61 (m, 1H), 6.46 (dd, J = 5.8, 2.2 Hz, 1H), 4.98 - 4.79 (m, 1H, assumed; largely obscured by water peak), 4.78 - 4.62 (m, 2H), 4.47 - 4.33 (m, 2H), 4.31 - 4.20 (m, 1H), 4.07 - 3.96 (m, 1H), [3.82 (d, J = 13.1 Hz) and 3.82 (d, J = 13.1 Hz), total 1H], 1.91 (s, 3H), 1.88 - 1.76 (m, 1H), 1.73 - 1.59 (m, 1H), 1.16 - 1.03 (m, 1H); 557.4 (chlorine isotope pattern observed) |
| 94 | Example 4; C61, trifluoroacetate salt | 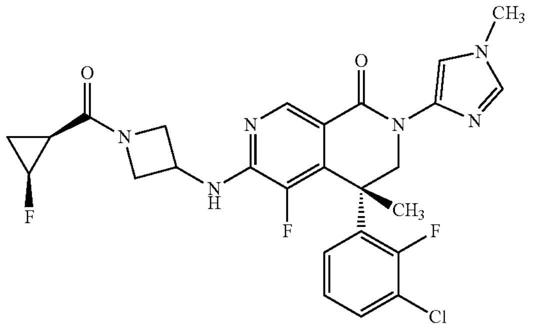 [SMILES: Cn1cnc(N2C[C@](C)(c3cccc(Cl)c3F)c3c(cnc(NC4CN(C(=O)[C@@H]5C[C@@H]5F)C4)c3F)C2=O)c1] | 8.63 (s, 1H), 7.64 - 7.54 (m, 1H), 7.50 - 7.35 (m, 3H), 7.21 (t, J= 8.0 Hz, 1H), 4.97 - 4.85 (m, 1H, assumed; largely obscured by water peak), 4.77 - 4.64 (m, 2H), 4.42 (d, J = 13.1 Hz, 1H), 4.42 - 4.33 (m, 1H), 4.30 - 4.20 (m, 1H), 4.09 (br d, J = 13.2 Hz, 1H), 4.05 - 3.96 (m, 1H), 3.74 (s, 3H), 1.90 (br s, 3H), 1.88 - 1.76 (m, 1H), 1.73 - 1.59 (m, 1H), 1.15 - 1.03 (m, 1H); 545.2 (chlorine isotope pattern observed) |
| 95 | Example 4[15], C59 | 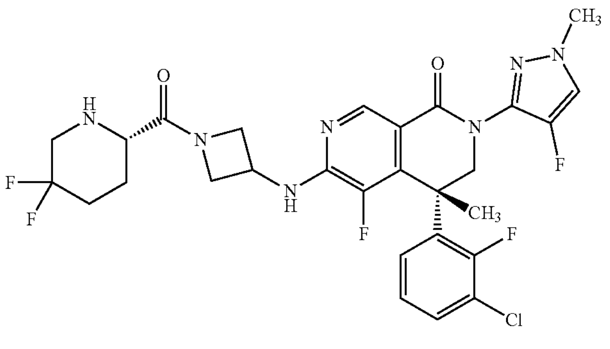 or | 8.62 (s, 1H), 7.59 (d, J = 4.5 Hz, 1H), 7.47 (t, J = 7.4 Hz, 1H), 7.41 - 7.32 (m, 1H), 7.21 (t, J = 8.0 Hz, 1H), 4.9 - 4.57 (m, 2H, assumed; partially obscured by water peak), 4.43 - 4.30 (m, 1H), 4.36 (d, J = 12.9 Hz, 1H), 4.27 - 4.17 (m, 1H), 4.06 - 3.93 (m, 1H), 3.78 (s, 3H), 3.69 (d, J = 12.9 Hz, 1H), 3.49 - 3.39 (m, 1H), 3.22 - 3.09 (m, 1H), 2.98 - 2.81 (m, 1H), 2.26 - 2.12 (m, 1H), 2.10 - 1.87 (m, 2H), 1.94 (s, 3H), 1.84 - 1.67 (m, 1H); 624.5 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| | | 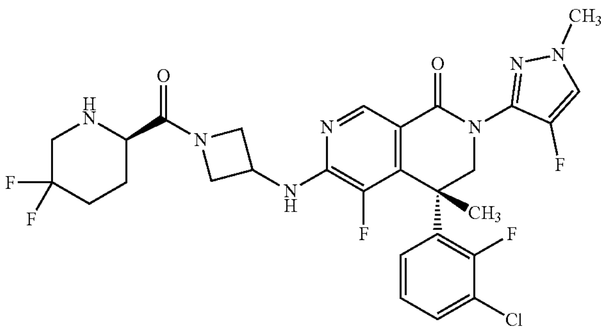 DIAST-1 | |
| 96 | Example 4[15], C59 | 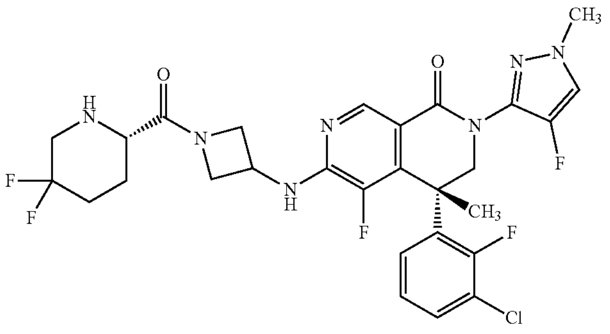 or 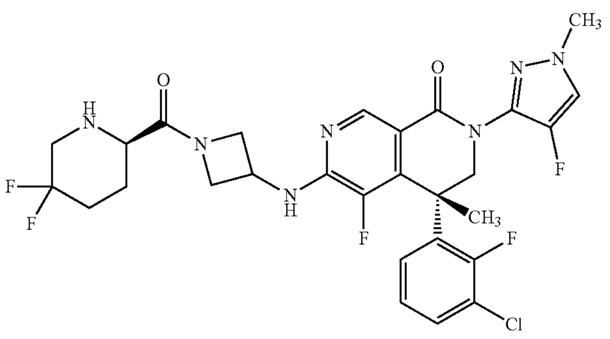 DIAST-2 | 8.62 (s, 1H), 7.59 (d, J = 4.5 Hz, 1H), 7.51 - 7.44 (m, 1H), 7.40 - 7.32 (m, 1H), 7.20 (br t, J = 8.0 Hz, 1H), 4.9 - 4.58 (m, 2H, assumed; partially obscured by water peak), 4.43 - 4.30 (m, 1H), 4.36 (d, J = 13.1 Hz, 1H), [4.26 (dd, J = 9.3, 5.3 Hz) and 4.18 (dd, J = 9.3, 5.1 Hz), total 1H], 4.04 - 3.96 (m, 1H), 3.78 (s, 3H), 3.69 (d, J = 12.9 Hz, 1H), 3.50 - 3.41 (m, 1H), 3.22 - 3.10 (m, 1H), 2.98 - 2.82 (m, 1H), 2.26 - 2.12 (m, 1H), 2.10 - 1.88 (m, 2H), 1.94 (s, 3H), 1.84 - 1.70 (m, 1H); 624.1 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z [M + H]$^+$ or HPLC retention time; Mass spectrum m/z [M + H]$^+$ (unless otherwise indicated) |
|---|---|---|---|
| 97 | Examples 9 and 10[16]; C61 | 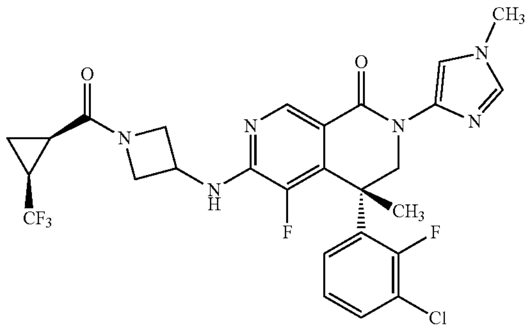<br>or<br>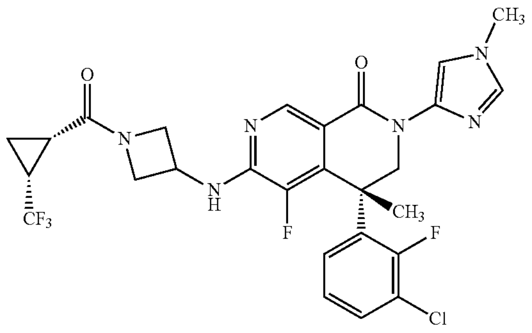<br>DIAST-1 | 3.78 minutes[17]; 595.3 (chlorine isotope pattern observed) |
| 98 | Examples 9 and 10[16]; C61 | 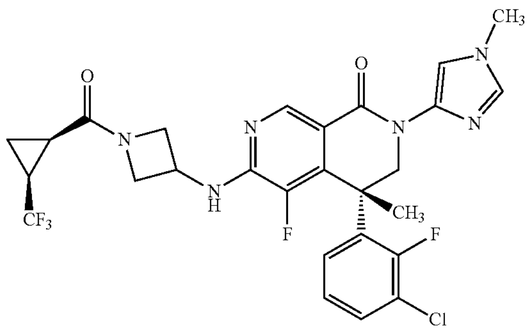<br>or | 4.73 minutes[17]; 595.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 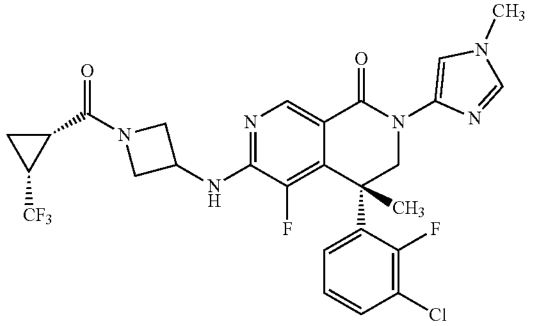 DIAST-2 | |
| 99 | Example 15[10]; C64 | 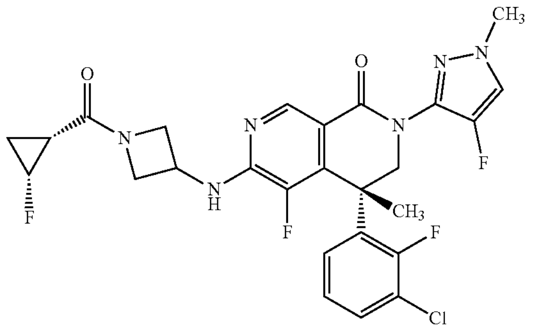 [SMILES: Cn1cc(F)c(N2C[C@](C)(c3cccc(Cl)c3F)c3c(cnc(NC4CN(C(=O)[C@H]5C[C@H]5F)C4)c3F)C2=O)n1] | $^1H$ NMR (400 MHz, DMSO-$d_6$) δ 8.53 (s, 1H), 8.06 - 7.97 (m, 1H), 7.82 (d, J = 4.5 Hz, 1H), 7.58 (t, J = 7.6 Hz, 1H), 7.41 (t, J = 7.5 Hz, 1H), 7.27 (t, J = 8.0 Hz, 1H), [4.97 - 4.88 (m) and 4.85 - 4.71 (m), total 2H], [4.59 (t, J = 8.2 Hz) and 4.51 (t, J = 8.2 Hz), total 1H], [4.28 - 4.12 (m) and 4.08 (dd, J = 8.7, 5.3 Hz), total 3H], 3.98 - 3.85 (m, 1H), 3.76 - 3.68 (m, 4H), 1.86 (s, 3H), 1.85 - 1.73 (m, 1H), 1.57 - 1.43 (m, 1H), 1.08 - 0.94 (m, 1H); 563.4 (chlorine isotope pattern observed) |
| 100 | Example 21; C57 | 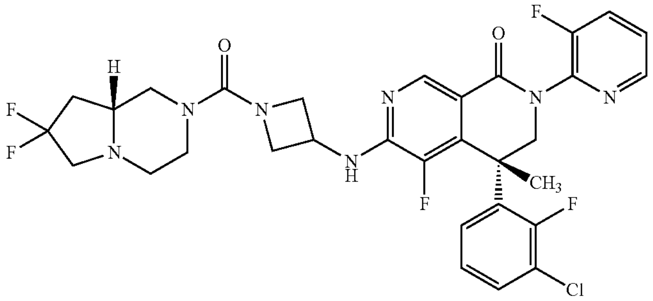 [SMILES: C[C@]1(c2cccc(Cl)c2F)CN(c2ncccc2F)C(=O)c2cnc(NC3CN(C(=O)N4CCN5CC(F)(F)C[C@@H]5C4)C3)c(F)c21] | 8.64 (s, 1H), 8.29 (dt, J = 4.7, 1.2 Hz, 1H), 7.67 (ddd, J = 9.7, 8.3, 1.5 Hz, 1H), 7.47 (ddd, J = 8.3, 6.9, 1.6 Hz, 1H), 7.41 (ddd, J = 8.3, 4.8, 3.7 Hz, 1H), 7.39 - 7.35 (m, 1H), 7.21 (br t, J = 8.0 Hz, 1H), 4.85 - 4.77 (m, 1H), 4.48 (d, J = 12.9 Hz, 1H), 4.42 - 4.33 (m, 2H), 4.04 - 3.94 (m, 3H), 3.88 - 3.81 (m, 1H), 3.78 (d, J = 12.9 Hz, 1H), 3.38 (ddd, J = 13.9, 10.7, 3.5 Hz, 1H), 3.02 (ddd, J = 13.1, 11.6, 3.2 Hz, 1H), 2.95 (ddd, J = 11.1, 3.2, 1.9 Hz, 1H), 2.69 (dd, J = 12.8, 10.1 Hz, 1H), 2.64 - 2.51 (m, 1H), 2.42 - 2.27 (m, 2H), 2.23 (td, J = 11.3, 3.2 Hz, 1H), 1.99 - 1.84 (m, 1H), 1.95 (s, 3H); 662.4 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 101 | Example 4; C87 [from P3 (ENANT-2)] | 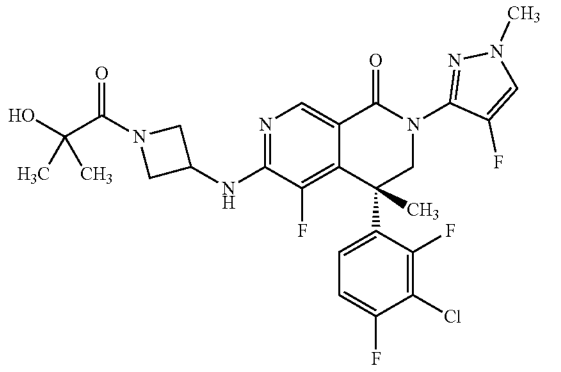 or 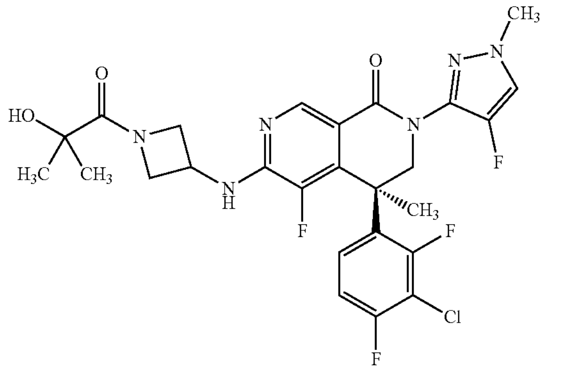 from P3 (ENANT-2) | 8.62 (s, 1H), 7.59 (d, J = 4.5 Hz, 1H), 7.43 - 7.34 (m, 1H), 7.19 - 7.12 (m, 1H), 4.93 - 4.77 (m, 2H, assumed; partially obscured by water peak), 4.48 - 4.38 (m, 1H), 4.38 - 4.29 (m, 1H), 4.33 (d, J = 13.0 Hz, 1H), 4.01 - 3.92 (m, 1H), 3.78 (s, 3H), 3.71 (d, J = 13.0 Hz, 1H), 1.94 (s, 3H), 1.39 (s, 3H), [1.37 (s) and 1.37 (s), total 3H]; 581.3 (chlorine isotope pattern observed) |
| 102 | Example 4; P3 (ENANT-2) | 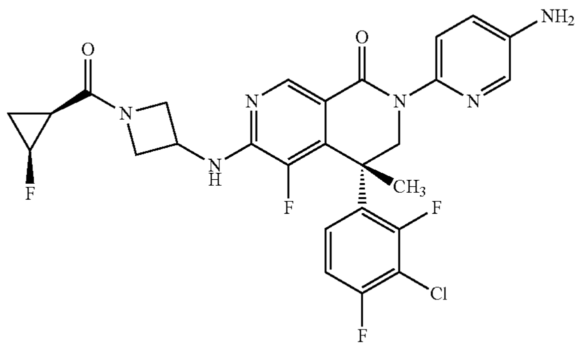 or | [8.63 (s) and 8.63 (s), total 1H], 7.83 (d, J = 2.9 Hz, 1H), 7.39 (td, J = 8.8, 5.8 Hz, 1H), 7.23 (d, half of AB quartet, J = 8.7 Hz, 1H), 7.18 - 7.12 (m, 1H), 7.10 (dd, component of ABX system, J = 8.7, 2.9 Hz, 1H), [4.98 - 4.78 (m) and 4.77 - 4.64 (m), total 3H, assumed; partially obscured by water peak], 4.41 (d, J = 12.9 Hz, 1H), 4.41 - 4.33 (m, 1H), 4.30 - 4.20 (m, 1H), 4.06 - 3.96 (m, 1H), 3.83 (d, J = 13.1 Hz, 1H), 1.92 (s, 3H), 1.88 - 1.76 (m, 1H), 1.73 - 1.59 (m, 1H), 1.15 - 1.03 (m, 1H); 575.3 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| --- | --- | --- | --- |
| | | 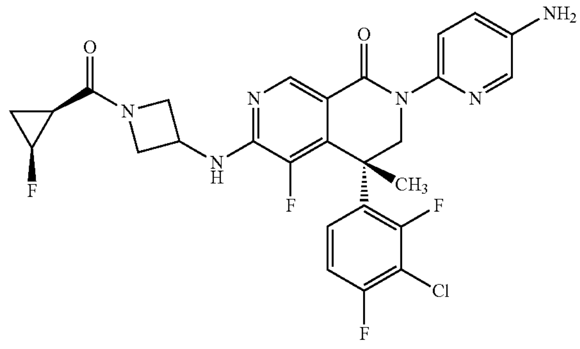 from P3 (ENANT-2) | |
| 103 | Example 22[18]; P3 (ENANT-2), C85 | 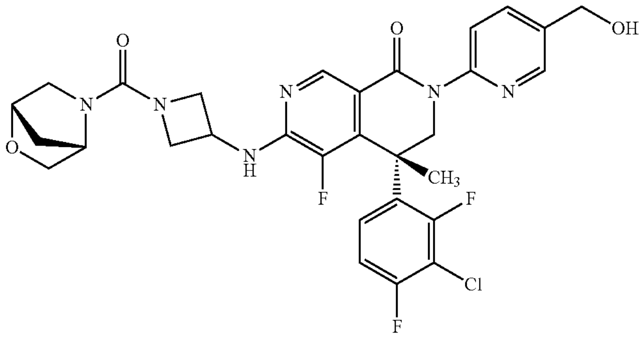 or 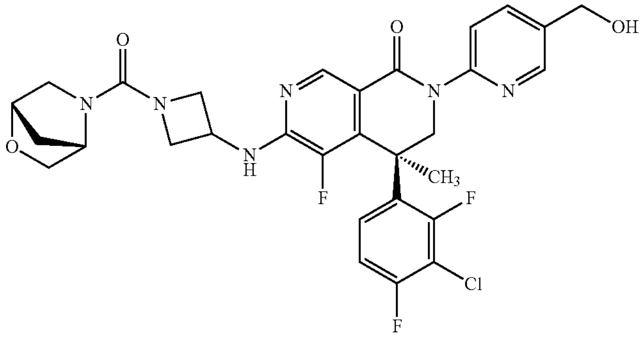 from P3 (ENANT-2) | 8.75 (s, 1H), 8.31 (d, J = 2.2 Hz, 1H), 7.85 (d, J = 8.5 Hz, half of AB quartet, 1H), 7.68 (dd, component of ABX system, J = 8.5, 2.4 Hz, 1H), 7.19 - 7.11 (m, 1H), 6.95 (ddd, J = 9.1, 7.7, 1.6 Hz, 1H), 5.65 - 5.57 (m, 1H), 4.86 - 4.76 (m, 1H), 4.65 (s, 2H), 4.57 - 4.47 (m, 3H), 4.39 (t, J = 8.2 Hz, 1H), 4.28 (t, J = 8.2 Hz, 1H), 4.14 (d, J = 13.4 Hz, 1H), 3.96 - 3.86 (m, 2H), 3.78 - 3.71 (m, 2H), 3.30 - 3.22 (m, 2H), 1.86 - 1.78 (m, 1H), 1.84 (s, 3H), 1.74 (dd, component of ABX system, J = 9.9, 2.3 Hz, 1H); 629.4 (chlorine isotope pattern observed) |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 104 | Example 4; P5 (ENANT-2) | 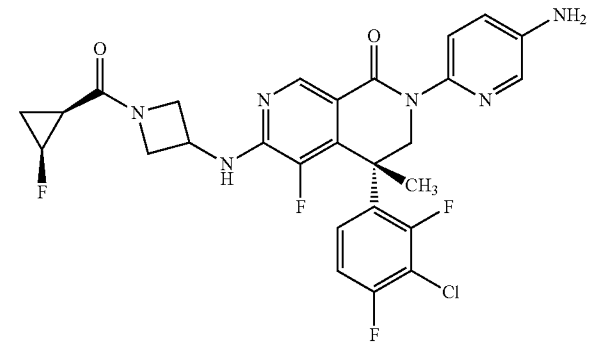 or 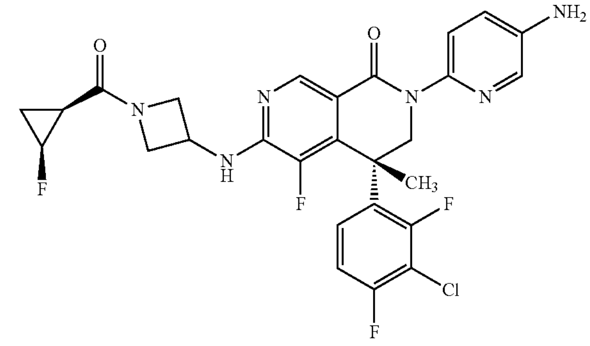 from P5 (ENANT-2) | [8.61 (s) and 8.61 (s), total 1H], 7.83 (d, J = 2.9 Hz, 1H), 7.25 - 7.16 (m, 1H), 7.18 (d, half of AB quartet, J = 8.8 Hz, 1H), 7.10 (dd, component of ABX system, J = 8.7, 2.9 Hz, 1H), 6.93 (t, J = 8.7 Hz, 1H), 4.98 - 4.78 (m, 2H, assumed; largely obscured by water peak), 4.77 - 4.64 (m, 1H), 4.45 - 4.33 (m, 2H), 4.29 - 4.20 (m, 1H), 4.05 - 3.96 (m, 1H), 3.77 (d, J = 13.0 Hz, 1H), 2.13 (s, 3H), 1.89 (s, 3H), 1.88 - 1.75 (m, 1H), 1.73 - 1.59 (m, 1H), 1.16 - 1.02 (m, 1H); 555.5 [8.67 (s) and 8.67 (s), total 1H], |
| 105 | Example 4; P5 (ENANT-2) | 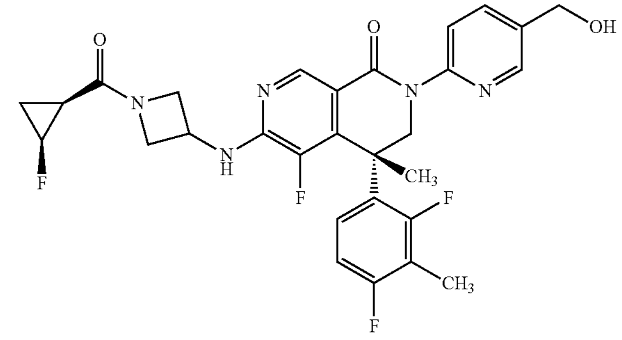 or | 8.38 (d, J = 2.3 Hz, 1H), 7.78 (dd, component of ABX system, J = 8.5, 2.4 Hz, 1H), 7.69 (d, half of AB quartet, J = 8.4 Hz, 1H), 7.24 - 7.14 (m, 1H), 6.92 (t, J = 8.7 Hz, 1H), [4.98 - 4.80 (m) and 4.76 - 4.65 (m), total 3H, assumed; partially obscured by water peak], 4.62 (s, 2H), 4.56 (d, J = 13.2 Hz, 1H), 4.44 - 4.34 (m, 1H), 4.30 - 4.22 (m, 1H), 4.09 - 3.97 (m, 2H), 2.12 (s, 3H), 1.88 (s, 3H), 1.88 - 1.76 (m, 1H), 1.73 - 1.59 (m, 1H), 1.15 - 1.03 (m, 1H); 570.3 |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
| --- | --- | --- | --- |
| | | 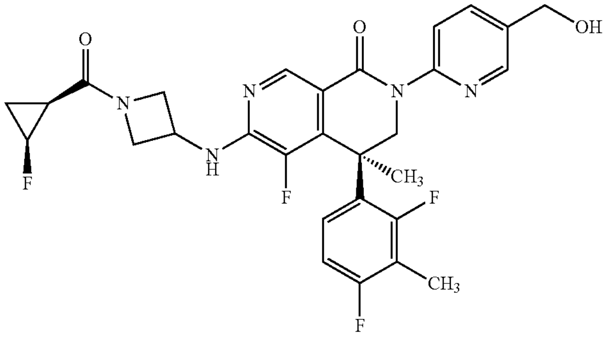 from P5 (ENANT-2) | |
| 106 | Example 24; P5 (ENANT-2) | 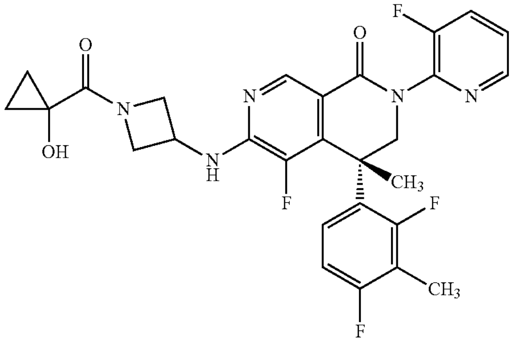 or 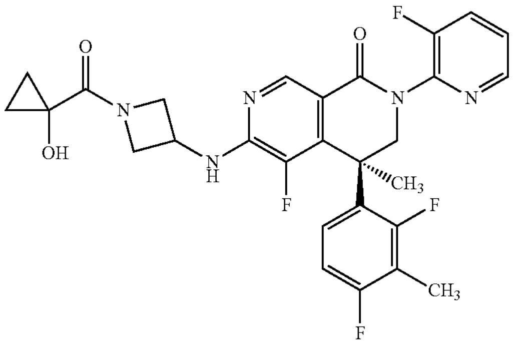 from P5 (ENANT-2) | 8.64 (s, 1H), 8.29 (d, J = 4.7 Hz, 1H), 7.67 (ddd, J = 9.7, 8.2, 1.4 Hz, 1H), 7.41 (dt, J = 8.4, 4.2 Hz, 1H), 7.31 - 7.21 (m, 1H), 6.99 - 6.191 (m, 1H), 5.01 - 4.72 (m, 2H, assumed; largely obscured by water peak), 4.54 - 4.43 (m, 1H), 4.49 (d, J = 12.9 Hz, 1H), 4.42 - 4.33 (m, 1H), 4.05 - 3.93 (m, 1H), 3.73 (d, J = 12.8 Hz, 1H), 2.14 (s, 3H), 1.93 (s, 3H), 1.24 - 1.15 (m, 2H), 0.95 - 0.87 (m, 2H); 556.2 |

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| 107 | Example 21[19]; P5 (ENANT-2) | 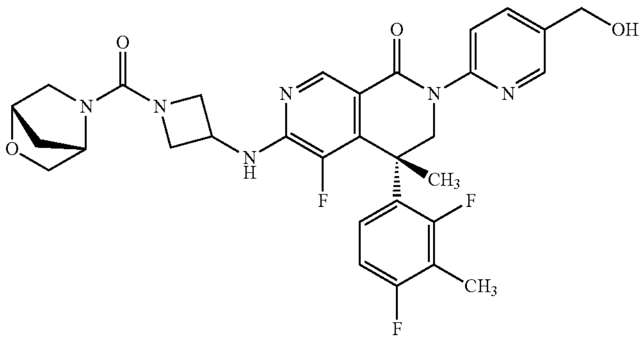 [SMILES: Cc1c(F)ccc([C@@]2(C)CN(c3ccc(CO)cn3)C(=O)c3cnc(NC4CN(C(=O)N5C[C@@H]6C[C@H]5CO6)C4)c(F)c32)c1F]<br>or<br>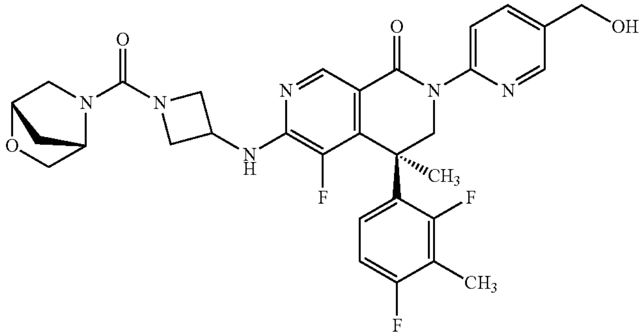<br>from P5 (ENANT-2) | $^1$H NMR (400 MHz, methanol-$d_4$), characteristic peaks: δ 8.65 (s, 1H), 8.38 (d, J = 2.2 Hz, 1H), 7.78 (dd, component of ABX system, J = 8.5, 2.4 Hz, 1H), 7.68 (d, half of AB quartet, J = 8.4 Hz, 1H), 7.23 - 7.14 (m, 1H), 6.92 (t, J = 8.7 Hz, 1H), 4.62 (s, 2H), 4.55 (d, J = 13.2 Hz, 1H), 4.52 - 4.49 (m, 1H), 4.42 (t, J= 8.2 Hz, 1H), 4.31 (t, J = 8.2 Hz, 1H), 4.07 - 4.01 (m, 2H), 3.89 (dd, J = 8.7, 5.5 Hz, 1H), 3.85 (d, half of AB quartet, J = 7.5 Hz, 1H), 3.77 (dd, c omponent of ABX system, J = 7.5, 1.6 Hz, 1H), 3.38 (dd, J = 9.7, 1.6 Hz, 1H), 2.14 - 2.10 (m, 3H), 1.88 (s, 3H), 1.86 - 1.84 (m, 2H); 608.9 |
| 108 | Example 4; P7 (ENANT-2) | 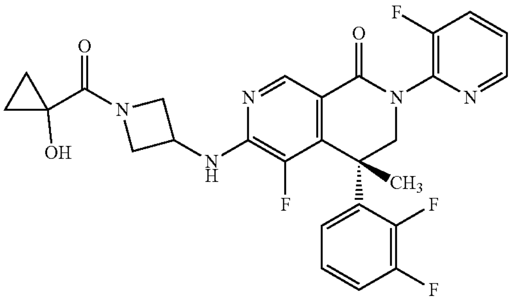<br>or | 8.65 (s, 1H), 8.30 (d, J = 4.8 Hz, 1H), 7.67 (ddd, J = 9.7, 8.2, 1.4 Hz, 1H), 7.44 - 7.38 (m, 1H), 7.31 - 7.15 (m, 3H), 5.00 - 4.78 (m, 2H, assumed; largely obscured by water peak), 4.53 - 4.43 (m, 1H), 4.50 (d, J = 12.9 Hz, 1H), 4.38 (t, J = 9.1 Hz, 1H), 4.06 - 3.95 (m, 1H), 3.82 (d, J = 13.0 Hz, 1H), 1.96 (s, 3H), 1.25 - 1.15 (m, 2H), 0.96 - 0.87 (m, 2H); 542.1 |

TABLE 3-continued

| Ex. | Method of synthesis; Non-commercial starting materials | Structure | $^1H$ NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | 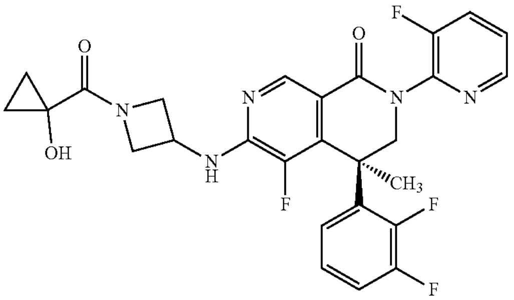 from P7 (ENANT-2) | |
| 109 | Examples 28 and 29; C90 [from P9 (DIAST-2)] | 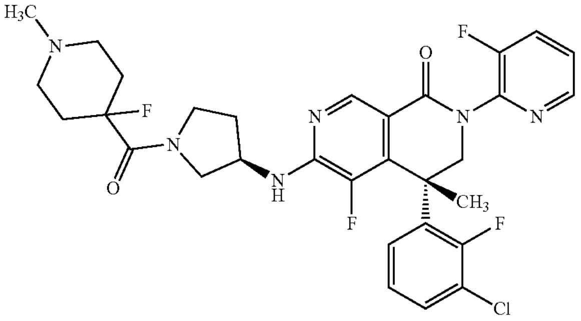 or 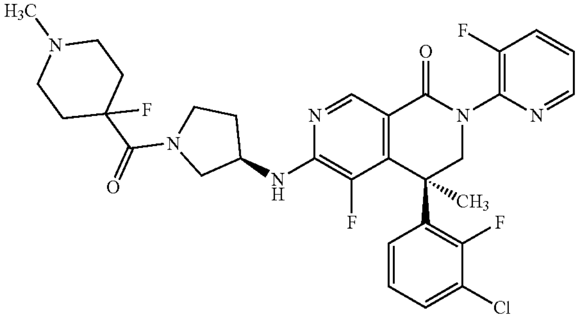 from P9 (DIAST-2) | 2.33 minutes[4]; 631.6 (chlorine isotope pattern observed) |
| 110 | Example 34; C92 [from P9 (DIAST-2)] | 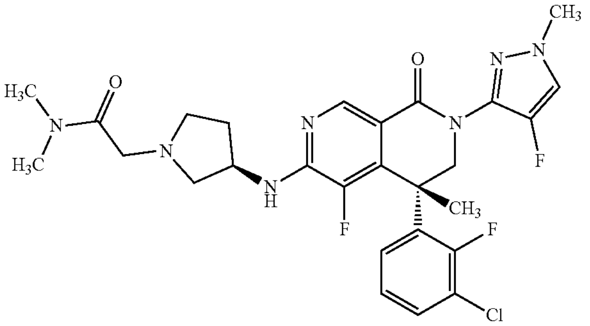 [SMILES: CN(C)C(=O)CN1CC[C@@H](Nc2ncc3c(c2F)[C@@](C)(c2cccc(Cl)c2F)CN(c2nn(C)cc2F)C3=O)C1] | 8.60 (s, 1H), 7.58 (d, J = 4.5 Hz, 1H), 7.46 (ddd, J = 8.3, 7.0, 1.6 Hz, 1H), 7.35 (ddd, J = 7.7, 7.0, 1.6 Hz, 1H), 7.20 (t, J = 8.0 Hz, 1H), 4.73 - 4.64 (m, 1H), 4.35 (d, J = 12.9 Hz, 1H), 3.78 (s, 3H), 3.68 (d, J = 12.9 Hz, 1H), 3.43 (AB quartet, JAB = 15.6 Hz, ΔVAB = 12.9 Hz, 2H), 3.05 (s, 3H), 3.02 - 2.95 (m, 1H), 2.93 (s, 3H), 2.89 - 2.79 (m, 2H), 2.56 - 2.47 (m, 1H), 2.40 - 2.29 (m, 1H), 1.93 (br s, 3H), 1.83 - 1.73 (m, 1H); 576.5 (chlorine isotope pattern observed) |

Method of synthesis, structure, and physicochemical data for Examples 39-111. The examples below were made from analogous processes to the Example(s) identified and from appropriate analogous starting materials. Ex. stands for Example.

TABLE 3-continued

Method of synthesis, structure, and physicochemical data for Examples 39-111. The examples below were made from analogous processes to the Example(s) identified and from appropriate analogous starting materials. Ex. stands for Example.

| Ex. | Method of synthesis; Non-commercial starting materials | Structure | $^1$H NMR (400 MHz, methanol-$d_4$) δ; Mass spectrum, observed ion m/z $[M + H]^+$ or HPLC retention time; Mass spectrum m/z $[M + H]^+$ (unless otherwise indicated) |
|---|---|---|---|
| | | or<br>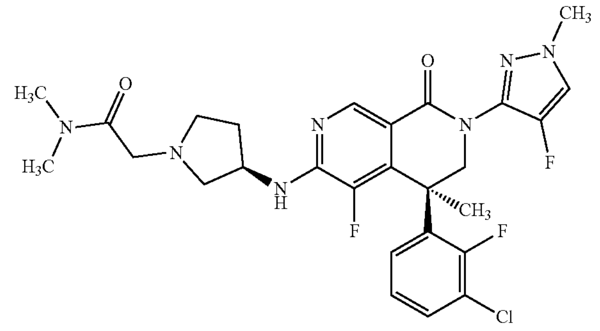<br>from P9 (DIAST-2) | |
| 111 | Example 4; C97 [from P13 (ENANT-2)] | 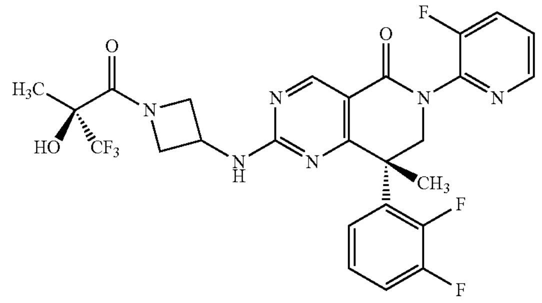 [SMILES: C[C@]1(c2cccc(F)c2F)CN(c2ncccc2F)C(=O)c2cnc(NC3CN(C(=O)[C@](C)(O)C(F)(F)F)C3)nc21]<br>or<br>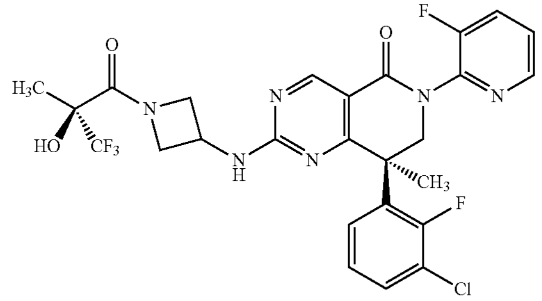<br>from P13 (ENANT-2) | $^1$H NMR (400 MHz, methanol-$d_4$), characteristic peaks; integrations are approximate: δ [8.92 (br s) and 8.89 (s), total 1H], 8.31 (d, J = 4.8 Hz, 1H), 7.69 (br t, J = 9.1 Hz, 1H), 7.53 - 7.38 (m, 2H), 7.34 - 7.22 (m, 1H), 7.22 - 7.13 (m, 1H), 4.48 - 4.31 (m, 2H), [4.23 - 4.10 (m) and 4.02 - 3.73 (m), total 3H], 1.86 (s, 3H), [1.55 (br s) and 1.51 (s), total 3H]; 597.2 (chlorine isotope pattern observed) |

1. A mixture of Examples 42 and 43 was separated into its component diastereomers using supercritical fluid chromatography [Column: Chiral Technologies Chiralcel OD, 30×250 mm, 10 μm; Mobile phase: 65:35 carbon dioxide/(ethanol containing 0.1% ammonium hydroxide); Flow rate: 80 mL/minute]. The first-eluting diastereomer was designated as Example 42, and the second-eluting diastereomer as Example 43. On analytical supercritical fluid chromatography (Column: Chiral Technologies Chiralcel OD-3, 4.6×100 mm, 3 μm; Mobile phase A: carbon dioxide; Mobile phase B: ethanol containing 0.05% diethylamine; Gradient: 5% to 40% B over 4.0 minutes, then 40% B for 2.5 minutes; Flow rate: 2.8 mL/minute; Back pressure: 1500 psi), Example 42 exhibited a retention time of 4.65 minutes. Example 43 had a retention time of 4.97 minutes under the same conditions.
2. A mixture of Examples 44 and 45 was separated into its component diastereomers using supercritical fluid chromatography [Column: Phenomenex Lux Cellulose-2, 30×250 mm, 10 μm; Mobile phase: 3:2 carbon dioxide/(ethanol containing 0.1% ammonium hydroxide); Flow rate: 80 mL/minute]. The first-eluting diastereomer was designated as Example 44, and the second-eluting diastereomer as Example 45. On analytical supercritical fluid chromatography [Column: Phenomenex Lux Cellulose-2, 4.6×100 mm, 3 μm; 1:1 carbon dioxide/(ethanol containing 0.05% diethylamine); Flow rate: 2.8 mL/minute; Back pressure: 1500 psi], Example 44 exhibited a retention time of 1.00 minutes. Example 45 had a retention time of 1.52 minutes under the same conditions.

3. A mixture of Examples 46 and 47 was separated into its component diastereomers using supercritical fluid chromatography [Column: Chiral Technologies Chiralpak AD, 30×250 mm, 10 μm; Mobile phase: 3:2 carbon dioxide/(propan-2-ol containing 0.1% ammonium hydroxide); Flow rate: 80 mL/minute]. The first-eluting diastereomer was designated as Example 46, and the second-eluting diastereomer as Example 47. On analytical supercritical fluid chromatography (Column: Chiral Technologies Chiralpak AD-3, 4.6×150 mm, 3 μm; Mobile phase A: carbon dioxide; Mobile phase B: propan-2-ol containing 0.05% diethylamine; Gradient: 5% to 40% B over 5.0 minutes, then 40% B for 2.5 minutes; Flow rate: 2.5 mL/minute; Back pressure: 1500 psi), Example 46 exhibited a retention time of 6.26 minutes. Example 47 had a retention time of 6.78 minutes under the same conditions.
4. Analytical conditions. Column: Waters Atlantis dC18, 4.6×50 mm, 5 μm; Mobile phase A: water containing 0.05% trifluoroacetic acid (v/v); Mobile phase B: acetonitrile containing 0.05% trifluoroacetic acid (v/v); Gradient: 5.0% to 95% B over 4.0 minutes, then 95% B for 1.0 minute; Flow rate: 2 mL/minute
5. In this case, potassium carbonate was used for the alkylation in place of N,N-diisopropylethylamine; the reaction was carried out in acetonitrile.
6. In this case, potassium bicarbonate was used for the alkylation in place of N,N-diisopropylethylamine; the reaction was carried out in N,N-dimethylformamide.
7. A mixture of Examples 69 and 70 was separated into its component diastereomers using supercritical fluid chromatography [Column: Chiral Technologies Chiralcel OD-H, 21×250 mm, 5 μm; Mobile phase: 3:1 carbon dioxide/(methanol containing 0.2% ammonium hydroxide); Flow rate: 75 mL/minute; Back pressure: 120 bar]. The first-eluting diastereomer was designated as Example 69, and the second-eluting diastereomer as Example 70.
8. Analytical conditions. Column: Phenomenex Lux Cellulose-1, 4.6×100 mm, 5 μm; 3:2 carbon dioxide/(methanol containing 0.2% ammonium hydroxide); Flow rate: 1.5 mL/minute; Back pressure: 120 bar.
9. A mixture of Examples 71 and 72 was separated into its component diastereomers using supercritical fluid chromatography [Column: Chiral Technologies Chiralcel OD-H, 21×250 mm, 5 μm; Mobile phase: 3:1 carbon dioxide/(methanol containing 0.2% ammonium hydroxide); Flow rate: 75 mL/minute; Back pressure: 120 bar]. The first-eluting diastereomer was designated as Example 71, and the second-eluting diastereomer as Example 72.
10. In this case, butan-1-ol was not employed as a co-solvent in the final step.
11. The requisite rac-(1R,2S)-1-hydroxy-2-methylcyclopropane-1-carboxylic acid was prepared using chemistry described by J. Salaun et al., *Tetrahedron* 1989, 45, 3151-3162.
12. A mixture of Examples 83 and 84 was separated into its component diastereomers using supercritical fluid chromatography [Column: Chiral Technologies Chiralpak IC, 21×250 mm, 5 μm; Mobile phase: 65:35 carbon dioxide/(methanol containing 0.2% ammonium hydroxide); Flow rate: 75 mL/minute; Back pressure: 150 bar)]. The first-eluting diastereomer was designated as Example 83, and the second-eluting diastereomer as Example 84.
13. Analytical conditions. Column: Chiral Technologies Chiralpak IC, 4.6×100 mm, 5 μm; Mobile phase: 1:1 carbon dioxide/(methanol containing 0.2% ammonium hydroxide); Flow rate: 1.5 mL/minute; Back pressure: 200 bar).
14. In this case, the reactant was the chloro derivative 1-(azetidin-1-yl)-2-chloroethan-1-one.
15. A mixture of Examples 95 and 96 was separated into its component diastereomers using supercritical fluid chromatography [Column: Chiral Technologies Chiralpak AD, 30×250 mm, 10 μm; Mobile phase: 55:45 carbon dioxide/(ethanol containing 0.1% ammonium hydroxide); Flow rate: 70 mL/minute]. The first-eluting diastereomer was designated as Example 95 and the second-eluting diastereomer as Example 96. Example 96 was further purified via reversed-phase HPLC (Column: Phenomenex C18, 30×80 mm, 5 μm; Mobile phase A: water containing 0.05% ammonium hydroxide; Mobile phase B: acetonitrile; Gradient: 35% to 55% B; Flow rate: 35 mL/minute). On analytical supercritical fluid chromatography [Column: Chiral Technologies Chiralpak AD-3, 4.6×150 mm, 3 μm; Mobile phase: 3:2 carbon dioxide/(ethanol containing 0.05% diethylamine); Flow rate: 2.5 mL/minute; Back pressure: 100 bar], Example 95 exhibited a retention time of 2.40 minutes. Example 96 had a retention time of 3.81 minutes under the same conditions.
16. A mixture of Examples 97 and 98 was separated into its component diastereomers using supercritical fluid chromatography [Column: Chiral Technologies Chiralpak AS-H, 21×250 mm, 5 μm; Mobile phase: 4:1 carbon dioxide/(methanol containing 0.2% ammonium hydroxide); Flow rate: 75 mL/minute; Back pressure: 150 bar]. The first-eluting diastereomer was designated as Example 97, and the second-eluting diastereomer as Example 98.
17. Analytical conditions. Column: Chiral Technologies Chiralpak AS-H, 4.6×100 mm, 5 μm; Mobile phase: 3:1 carbon dioxide/(methanol containing 0.2% ammonium hydroxide); Flow rate: 1.5 mL/minute; Back pressure: 120 bar.
18. Reaction of P3 (ENANT-2) with methanesulfonic acid produced the requisite (4R)-6-[(azetidin-3-γ1)amino]-4-(3-chloro-2,4-difluorophenyl)-5-fluoro-4-methyl-3,4-dihydro-2,7-naphthyridin-1(2H)-one.
19. The requisite 6-[(azetidin-3-γ1)amino]-4-(2,4-difluoro-3-methylphenyl)-5-fluoro-2-[5-(hydroxymethyl)pyridin-2-yl]-4-methyl-3,4-dihydro-2,7-naphthyridin-1(2H)-one was synthesized from P5 (ENANT-2) using the method described for conversion of P1 to C63 in Example 4.

In Vitro Pharmacology Assays

Primary Cellular Assay—γ3 Associated Phospho-Thr172 AMPK Detection in α2β2γ3 Bulk Transiently Transfected HEK293 Cells The cellular potencies of the compounds were evaluated using a custom pAMPK Surefire AlphaLISA designed to assess γ3 associated phospho-Thr172 AMPK and modulation by small molecules in AMPK α2β2γ3 transiently transfected HEK293 cells.

A pAMPK Surefire AlphaLISA (PE-ASLU-PAMPK) assay available through Perkin Elmer was modified to selectively assess γ3 pThr172 AMPK content (as opposed to total pThr172 AMPK) by labeling a γ3 antibody with a CaptSure™ tag and substituting it for the total α1c/α2 AMPK labeled antibodies in the kit. In the modified assay, the overall abundance of γ3 AMPK is recognized by the CaptSure γ3 antibody and the phosphorylated AMPK is recognized by biotinylated pThr172 antibody. Subsequent reactivity with streptavitin donor beads and anti CaptSure conjugated acceptor beads brings the molecules into close proximity. Upon excitation at 680 nm, the donor bead converts ambient oxygen to a more excited singlet state which reacts with the acceptor bead and emits light at 520 to 620 nm. The intensity of the signal is proportional to the level of γ3 associated pThr172 AMPK phosphorylation.

In short, AMPK-α2+β2+γ3 MaxCyte bulk-transfected HEK293AD cells were thawed in growth media (DMEM High glucose+10% FBS) in a collagen-coated T150 flask and the cells were allowed to adhere and grow overnight in a 37° C. incubator. The following day, the cells were harvested and resuspended in plating medium (DMEM Low glucose+10% FBS) at a concentration of 100,000 cells per mL and 50 μL of this cell suspension was added to all wells of a 384-well plate using a Multidrop Combi. The cells were allowed to adhere and grow for 2 days in a 37° C. incubator. On assay day, compounds were diluted in 100% dimethyl sulfoxide (DMSO) in a 11 dose, half log dilution scheme and spotted in the cell plates at 1000× the final concentration. Compound incubations were performed in plating media for 20 minutes. Cells were washed with PBS, lysed and the signal was generated by subsequent additions of RB1 reagent from the kit, 1:1000 CaptSure γ3 labeled antibody in 1× immunoassay buffer, Anti-CaptSure acceptor beads and Streptavitin donor beads at final concentration of 10 mg/mL. The γ3 pThr172 AMPK signal was developed using EnVision™ multilabel reader (Perkin Elmer) using Alphascreen settings. The fluorescence emission was used to calculate the % effect relative to the HPE (30 μM) and ZPE (DMSO). EC50 curves were generated with the ActivityBase software using the XLfit model 205 to determine EC50 and Emax values.

For screening purposes, bulk AMPK-α2+β2+γ3 MaxCyte bulk transfection into HEK293AD cells were generated to support SAR screening as follows.

HEK293AD cells were seeded into 10 flasks at $2.7\times10^{7}$ cells per flask. The following day 12 mL of Trypl E dissociation reagent were added to each flask to lift the cells and the cells were then spun at 300×g for 5 minutes. Cells were washed once in MaxCyte EP buffer and then resuspended in MaxCyte EP buffer at $1\times10^{8}$ cells per mL. For transfection, $500\times10^{6}$ cells in 500 μl MaxCyte EP buffer were placed in a CL1.1 Processing Assembly (electroporation cell) with 1 mg/mL (500 mg total) of each of the plasmids pcDNA3.1(+)-human AMPK alpha 2, pcDNA3.1 (+)-human AMPK beta 2 and pcDNA3.1(+)-human AMPK gamma 3 and the electroporation was carried out on the MaxCyte STX using the HEK293 electroporation protocol. Following electroporation, cells were transferred to a T175 flask containing growth medium (DMEM High glucose+10% FBS) and allowed to recover for 25 minutes, then the cells were resuspended to final volume of 900 mL and distributed into 6XT175 flasks and allowed to adhere and grow overnight in a 37° C. incubator. The following day the cells were lifted with Trypl E, brought to 400 mL with growth medium and spun at 300×g for 8 minutes, then the cell pellets were resuspended in 100 mL freezing medium and 1.2 mL were distributed into cryovials. The vials were placed in a freezing chamber at −80° C. for 48 hours until being transferred to liquid nitrogen for long term storage.

The $EC_{50}$ values of the compounds of Examples 1-111 for activation of human AMPK α2β2γ3 in transiently transfected HEK293 cells was generated using ActivityBase software. The results are shown in Table 4, where the assay data (IC50s) are presented for the Examples below in accordance with the above-described assay using the geometric mean (GMean) of the asymptotic max in percent, based on the number of replicates ($N^{\%}$) tested and the GMean of the $EC_{50}$ data in nM, based on the number of replicates ($N^{50}$) tested.

TABLE 4

Biological activity and IUPAC name for Examples 1-111.

| Ex. | Assay GMean Asy. Max (%) | $N^{\%}$ | Assay GMean $EC_{50}$ (nM) | $N^{50}$ | IUPAC Name |
|---|---|---|---|---|---|
| 1 | 112 | 18 | 33.6 | 18 | (4R)-4-(3-chloro-2-fluorophenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one |
| 2 | 81.7 | 32 | 29.9 | 32 | (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one |
| 3 | 56.0 | 8 | 112 | 8 | (4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one |
| 4 | 96.3 | 5 | 66.3 | 5 | (4R)-4-(3-chloro-2-fluorophenyl)-5-fluoro-2-[5-(hydroxymethyl)pyridin-2-yl]-4-methyl-6-{[1-(pyridazine-3-carbonyl)azetidin-3-yl]amino}-3,4-dihydro-2,7-naphthyridin-1(2H)-one |
| 5 | 64.9 | 6 | 27.7 | 6 | (4R)-4-(3-chloro-2-fluorophenyl)-5-fluoro-6-({1-[(1S,2S)-2-fluorocyclopropane-1- |

TABLE 4-continued

Biological activity and IUPAC name for Examples 1-111.

| Ex. | Assay GMean Asy. Max (%) | N% | Assay GMean $EC_{50}$ (nM) | $N^{50}$ | IUPAC Name |
|---|---|---|---|---|---|
| | | | | | carbonyl]azetidin-3-yl}amino)-4-methyl-2-(pyridin-2-yl)-3,4-dihydro-2,7-naphthyridin-1(2H)-one |
| 6 | 58.0 | 9 | 22.2 | 9 | (4R)-4-(3-chloro-2-fluorophenyl)-5-fluoro-6-({1-[(1S,2S)-2-fluorocyclopropane-1-carbonyl]azetidin-3-yl}amino)-2-(3-fluoropyridin-2-yl)-4-methyl-3,4-dihydro-2,7-naphthyridin-1(2H)-one |
| 7 | 123 | 6 | 144 | 6 | (4R)-4-(3-chloro-2-fluorophenyl)-5-fluoro-2-(4-fluoro-1-methyl-1H-pyrazol-3-yl)-6-{[1-(1-hydroxycyclobutane-1-carbonyl)azetidin-3-yl]amino}-4-methyl-3,4-dihydro-2,7-naphthyridin-1(2H)-one |
| 8 | 58.2 | 4 | 63.8 | 4 | (4R)-4-(3-chloro-2-fluorophenyl)-5-fluoro-6-({1-[(1R,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one |
| 9 | 118.8 | 8 | >55.7 | 9 | (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-1 |
| 10 | 89.6 | 3 | 21.3 | 3 | (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-2 |
| 11 | 160 | 4 | 22.7 | 4 | 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-cyclopropyl-N-methylacetamide |
| 12 | 77.9 | 5 | 43.5 | 5 | (4R)-4-(3-chloro-2-fluorophenyl)-5-fluoro-2-(4-fluoro-1-methyl-1H-pyrazol-3-yl)-4-methyl-6-({1-[(pyrrolidin-1-yl)acetyl]azetidin-3-yl}amino)-3,4-dihydro-2,7-naphthyridin-1(2H)-one |
| 13 | 46.2 | 8 | 108 | 8 | (4R)-4-(3-chloro-2-fluorophenyl)-5-fluoro-2-(4-fluoro-1-methyl-1H-pyrazol-3-yl)-4-methyl-6-[(1-{[(propan-2-yl)amino]acetyl}azetidin-3-yl)amino]-3,4-dihydro-2,7-naphthyridin-1(2H)-one |
| 14 | 69.4 | 4 | 33.7 | 4 | (4R)-2-[4-(aminomethyl)-2,5-difluorophenyl]-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one, partial formate salt (0.5 equivalents) |
| 15 | 61.5 | 30 | 31.5 | 30 | (4R)-2-(5-aminopyridin-2-yl)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one |
| 16 | 75.4 | 5 | 759 | 5 | (4R)-4-(3-chloro-2-fluorophenyl)-5-fluoro-4-methyl-2-{5-[(3S)-morpholin-3-yl]pyridin-2-yl}-6-{[1-(pyridazine-3-carbonyl)azetidin-3-yl]amino}-3,4-dihydro-2,7-naphthyridin-1(2H)-one |
| 17 | 120 | 10 | 144 | 10 | (4R)-4-(3-chloro-2-fluorophenyl)-5-fluoro-4-methyl-2-{5-[(3R)-morpholin-3-yl]pyridin-2-yl}-6-{[1-(pyridazine-3-carbonyl)azetidin-3-yllamino}-3,4-dihydro-2,7-naphthyridin-1(2H)-one |
| 18 | 79.2 | 5 | 165 | 5 | (4R)-4-(3-chloro-2-fluorophenyl)-5-fluoro-6-({1-[(1S,2S)-2-fluorocyclopropane-1-carbonyl]azetidin-3-yl}amino)-2-{5-[(1R)-1-hydroxyethyl]pyridin-2-yl}-4-methyl-3,4-dihydro-2,7-naphthyridin-1(2H)-one |
| 19 | 31.3 | 3 | 87.2 | 3 | 3-{[(5R)-5-(3-chloro-2-fluorophenyl)-4-fluoro-7-(3-fluoropyridin-2-yl)-5-methyl-8-oxo-5,6,7,8-tetrahydro-2,7-naphthyridin-3-yl]amino}azetidine-1-carboxamide |

TABLE 4-continued

| Ex. | Assay GMean Asy. Max (%) | N% | Assay GMean $EC_{50}$ (nM) | $N^{50}$ | IUPAC Name |
|---|---|---|---|---|---|
| | | | | | Biological activity and IUPAC name for Examples 1-111. |
| 20 | 43.1 | 3 | 23.9 | 3 | 3-{[(5R)-5-(3-chloro-2-fluorophenyl)-4-fluoro-7-(3-fluoropyridin-2-yl)-5-methyl-8-oxo-5,6,7,8-tetrahydro-2,7-naphthyridin-3-yl]amino}-N-methylazetidine-1-carboxamide |
| 21 | 142 | 5 | 39.8 | 5 | (4R)-4-(3-chloro-2-fluorophenyl)-5-fluoro-2-(4-fluoro-1-methyl-1H-pyrazol-3-yl)-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one |
| 22 | 136 | 8 | 44.7 | 8 | (4R)-4-(3-chloro-2-fluorophenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one |
| 23 | 91.4 | 8 | 28.1 | 8 | 4-(3-chloro-2,4-difluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one, from P3 (ENANT-2) |
| 24 | 139 | 5 | 79.5 | 5 | 4-(3-chloro-2-fluorophenyl)-5-fluoro-2-(3-fluoropyridin-2-yl)-4-methyl-6-{[(3R)-1-(1-methylpiperidine-4-carbonyl)pyrrolidin-3-yl]amino}-3,4-dihydro-2,7-naphthyridin-1(2H)-one, from P9 (DIAST-2) |
| 25 | 52.2 | 3 | 160 | 3 | 4-(3-chloro-2-fluorophenyl)-5-fluoro-2-(4-fluoro-1-methyl-1H-pyrazol-3-yl)-4-methyl-6-({(3R)-1-[(1S,4S)-2-oxa-5-azabicyclo[2.2.1]heptane-5-carbonyl]pyrrolidin-3-yl}amino)-3,4-dihydro-2,7-naphthyridin-1(2H)-one, from P9 (DIAST-2) |
| 26 | 47.6 | 104 | 182.6 | 105 | 8-(3-chloro-2-fluorophenyl)-6-(3-fluoropyridin-2-yl)-2-{[1-(hydroxyacetyl)azetidin-3-yl]amino}-8-methyl-7,8-dihydropyrido[4,3-d]pyrimidin-5(6H)-one, from P13 (ENANT-2) |
| 27 | 173.9 | 100 | 176.9 | 102 | 8-(3-chloro-2-fluorophenyl)-6-(3-fluoropyridin-2-yl)-2-{[1-(1-hydroxycyclopropane-1-carbonyl)azetidin-3-yl]amino}-8-methyl-7,8-dihydropyrido[4,3-d]pyrimidin-5(6H)-one, from P13 (ENANT-2) |
| 28 | 98.9 | 4 | 571 | 4 | 8-(3-chloro-2-fluorophenyl)-6-(3-fluoropyridin-2-yl)-2-{[1-(1-hydroxy-2,2-dimethylcyclopropane-1-carbonyl)azetidin-3-yl]amino}-8-methyl-7,8-dihydropyrido[4,3-d]pyrimidin-5(6H)-one, from P13 (ENANT-2), DIAST-1 |
| 29 | 216 | 6 | 181 | 6 | 8-(3-chloro-2-fluorophenyl)-6-(3-fluoropyridin-2-yl)-2-{[1-(1-hydroxy-2,2-dimethylcyclopropane-1-carbonyl)azetidin-3-yl]amino}-8-methyl-7,8-dihydropyrido[4,3-d]pyrimidin-5(6H)-one, from P13 (ENANT-2), DIAST-2 |
| 30 | 178 | 4 | 740 | 4 | 8-(3-chloro-2-fluorophenyl)-2-({1-[(1S,2S)-2-fluorocyclopropane-1-carbonyl]azetidin-3-yl}amino)-6-(4-fluoro-1-methyl-1H-pyrazol-3-yl)-8-methyl-7,8-dihydropyrido[4,3-d]pyrimidin-5(6H)-one, from P13 (ENANT-2) |
| 31 | 110 | 2 | 221 | 2 | 6-(5-aminopyridin-2-yl)-8-(3-chloro-2-fluorophenyl)-2-({1-[(1S,2S)-2-fluorocyclopropane-1-carbonyl]azetidin-3-yl}amino)-8-methyl-7,8-dihydropyrido[4,3-d]pyrimidin-5(6H)-one, from P11 (ENANT-2) |
| 32 | 173 | 3 | 219 | 3 | 8-(3-chloro-2-fluorophenyl)-6-(3-fluoropyridin-2-yl)-2-({1-[(1R,4S,6S)-6-hydroxy-2-azabicyclo[2.2.1]heptane-2-carbonyl]azetidin-3-yl}amino)-8-methyl-7,8-dihydropyrido[4,3-d]pyrimidin-5(6H)-one, from P13 (ENANT-2) |
| 33 | 104.3 | 181 | 906.1 | 185 | 8-(2,3-difluorophenyl)-8-methyl-6-phenyl-2-({1-[(pyrrolidin-1-yl)acetyl]azetidin-3-yl}amino)-7,8-dihydropyrido[4,3-d]pyrimidin-5(6H)-one, from P16 (ENANT-2) |

TABLE 4-continued

Biological activity and IUPAC name for Examples 1-111.

| Ex. | Assay GMean Asy. Max (%) | $N^{\%}$ | Assay GMean $EC_{50}$ (nM) | $N^{50}$ | IUPAC Name |
|---|---|---|---|---|---|
| 34 | 208 | 2 | 31.7 | 2 | 2-(3-{[4-(3-chloro-2-fluorophenyl)-5-fluoro-2-(4-fluoro-1-methyl-1H-pyrazol-3-yl)-4-methyl-1-oxo-1,2,3,4-tetrahydroisoquinolin-6-yl]amino}azetidin-1-yl)-N-cyclopropyl-N-methylacetamide, formate salt, from P18 (ENANT-2) |
| 35 | 119 | 2 | 27.2 | 2 | 4-(3-chloro-2-fluorophenyl)-5-fluoro-2-(4-fluoro-1-methyl-1H-pyrazol-3-yl)-4-methyl-6-{[1-(2-oxopiperidin-3-yl)azetidin-3-yl]amino}-3,4-dihydroisoquinolin-1(2H)-one, from P18 (ENANT-2), DIAST-1 |
| 36 | 96.5 | 4 | 149 | 4 | 4-(3-chloro-2-fluorophenyl)-5-fluoro-2-(4-fluoro-1-methyl-1H-pyrazol-3-yl)-4-methyl-6-{[1-(2-oxopiperidin-3-yl)azetidin-3-yl]amino}-3,4-dihydroisoquinolin-1(2H)-one, from P18 (ENANT-2), DIAST-2 |
| 37 | 163 | 2 | 19.1 | 2 | 4-(3-chloro-2-fluorophenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydroisoquinolin-1(2H)-one, from P18 (ENANT-2) |
| 38 | 217 | 7 | 146 | 7 | 8-(3-chloro-2-fluorophenyl)-4-(dimethylamino)-6-(3-fluoropyridin-2-yl)-2-{[1-(1-hydroxycyclopropane-1-carbonyl)azetidin-3-yl]amino}-8-methyl-7,8-dihydropyrido[4,3-d]pyrimidin-5(6H)-one, from C52 (ENANT-1) |
| 39 | 91.2 | 5 | 68.7 | 5 | (4R)-4-(3-chloro-2-fluorophenyl)-6-({1-[(1S)-2,2-difluorocyclopropane-1-carbonyl]azetidin-3-yl}amino)-5-fluoro-2-(4-fluoro-1-methyl-1H-pyrazol-3-yl)-4-methyl-3,4-dihydro-2,7-naphthyridin-1(2H)-one |
| 40 | 58.8 | 5 | 113 | 5 | (4R)-4-(3-chloro-2-fluorophenyl)-5-fluoro-2-(4-fluoro-1-methyl-1H-pyrazol-3-yl)-6-({1-[(2R)-2-hydroxypropanoyl]azetidin-3-yl}amino)-4-methyl-3,4-dihydro-2,7-naphthyridin-1(2H)-one |
| 41 | 80.2 | 4 | 120 | 4 | (4R)-4-(3-chloro-2-fluorophenyl)-6-({1-[(dimethylamino) acetyl]azetidin-3-yl}amino)-5-fluoro-2-(4-fluoro-1-methyl-1H-pyrazol-3-yl)-4-methyl-3,4-dihydro-2,7-naphthyridin-1(2H)-one |
| 42 | 76.2 | 3 | 59.1 | 3 | (4R)-4-(3-chloro-2-fluorophenyl)-6-({1-[cyclopropyl(hydroxy)acetyl]azetidin-3-yl}amino)-5-fluoro-2-(4-fluoro-1-methyl-1H-pyrazol-3-yl)-4-methyl-3,4-dihydro-2,7-naphthyridin-1(2H)-one, DIAST-1 |
| 43 | 77.4 | 4 | 172 | 4 | (4R)-4-(3-chloro-2-fluorophenyl)-6-({1-[cyclopropyl(hydroxy)acetyl]azetidin-3-yl}amino)-5-fluoro-2-(4-fluoro-1-methyl-1H-pyrazol-3-yl)-4-methyl-3,4-dihydro-2,7-naphthyridin-1(2H)-one, DIAST-2 |
| 44 | 77.9 | 2 | 78.1 | 2 | (4R)-4-(3-chloro-2-fluorophenyl)-5-fluoro-2-(4-fluoro-1-methyl-1H-pyrazol-3-yl)-4-methyl-6-{[1-(4,4,4-trifluoro-2-hydroxybutanoyl)azetidin-3-yl]amino}-3,4-dihydro-2,7-naphthyridin-1(2H)-one, DIAST-1 |
| 45 | 100 | 2 | 66.4 | 2 | (4R)-4-(3-chloro-2-fluorophenyl)-5-fluoro-2-(4-fluoro-1-methyl-1H-pyrazol-3-yl)-4-methyl-6-{[1-(4,4,4-trifluoro-2-hydroxybutanoyl)azetidin-3-yl]amino}-3,4-dihydro-2,7-naphthyridin-1(2H)-one, DIAST-2 |
| 46 | 111 | 3 | 86.1 | 3 | (4R)-4-(3-chloro-2-fluorophenyl)-5-fluoro-2-(4-fluoro-1-methyl-1H-pyrazol-3-yl)-6-{[1-(2-hydroxy-3-methoxy-2-methylpropanoyl)azetidin-3-yl]amino}-4-methyl-3,4-dihydro-2,7-naphthyridin-1(2H)-one, DIAST-1 |
| 47 | 105 | 3 | 264 | 3 | (4R)-4-(3-chloro-2-fluorophenyl)-5-fluoro-2-(4-fluoro-1-methyl-1H-pyrazol-3-yl)-6-{[1-(2-hydroxy-3-methoxy-2-methylpropanoyl)azetidin-3-yl]amino}-4-methyl-3,4-dihydro-2,7-naphthyridin-1(2H)-one, DIAST-2 |

TABLE 4-continued

| Biological activity and IUPAC name for Examples 1-111. | | | | | |
|---|---|---|---|---|---|
| Ex. | Assay GMean Asy. Max (%) | N% | Assay GMean $EC_{50}$ (nM) | $N^{50}$ | IUPAC Name |
| 48 | 71.4 | 6 | 110 | 6 | (4R)-4-(3-chloro-2-fluorophenyl)-5-fluoro-6-({1-[(1S,2S)-2-fluorocyclopropane-1-carbonyl]azetidin-3-yl}amino)-2-[5-(2-hydroxyethyl)pyridin-2-yl]-4-methyl-3,4-dihydro-2,7-naphthyridin-1(2H)-one |
| 49 | 77.3 | 3 | 63.9 | 3 | (4R)-4-(3-chloro-2-fluorophenyl)-5-fluoro-6-({1-[(1S,2S)-2-fluorocyclopropane-1-carbonyl]azetidin-3-yl}amino)-2-{5-[(1S)-1-hydroxyethyl]pyridin-2-yl}-4-methyl-3,4-dihydro-2,7-naphthyridin-1(2H)-one |
| 50 | 63.7 | 2 | 233 | 2 | (4R)-4-(3-chloro-2-fluorophenyl)-2-[5-(difluoromethoxy)pyridin-2-yl]-5-fluoro-6-({1-[(1S,2S)-2-fluorocyclopropane-1-carbonyl]azetidin-3-yl}amino)-4-methyl-3,4-dihydro-2,7-naphthyridin-1(2H)-one |
| 51 | 63.2 | 3 | 49.1 | 3 | (4R)-4-(3-chloro-2-fluorophenyl)-5-fluoro-6-({1-[(1S,2S)-2-fluorocyclopropane-1-carbonyl]azetidin-3-yl}amino)-4-methyl-2-[5-(methylamino)pyridin-2-yl]-3,4-dihydro-2,7-naphthyridin-1(2H)-one |
| 52 | 65.4 | 6 | 47.4 | 6 | (4R)-4-(3-chloro-2-fluorophenyl)-5-fluoro-6-({1-[(1S,2S)-2-fluorocyclopropane-1-carbonyl]azetidin-3-yl}amino)-2-[5-(hydroxymethyl)pyridin-2-yl]-4-methyl-3,4-dihydro-2,7-naphthyridin-1(2H)-one |
| 53 | 91.0 | 7 | 131 | 7 | (4R)-4-(3-chloro-2-fluorophenyl)-5-fluoro-6-({1-[(1S,2S)-2-fluorocyclopropane-1-carbonyl]azetidin-3-yl}amino)-4-methyl-2-{4-[(3R)-morpholin-3-yl]phenyl}-3,4-dihydro-2,7-naphthyridin-1(2H)-one |
| 54 | 79.5 | 6 | 58.1 | 6 | (4R)-4-(3-chloro-2-fluorophenyl)-5-fluoro-6-({1-[(1S,2S)-2-fluorocyclopropane-1-carbonyl]azetidin-3-yl}amino)-4-methyl-2-(1-methyl-1H-pyrazol-3-yl)-3,4-dihydro-2,7-naphthyridin-1(2H)-one |
| 55 | 30.9 | 2 | 24.0 | 2 | (4R)-4-(3-chloro-2-fluorophenyl)-2-[4-(difluoromethoxy)pyridin-2-yl]-5-fluoro-6-({1-[(1S,2S)-2-fluorocyclopropane-1-carbonyl]azetidin-3-yl}amino)-4-methyl-3,4-dihydro-2,7-naphthyridin-1(2H)-one |
| 56 | 92.9 | 3 | 256 | 3 | (4R)-4-(3-chloro-2-fluorophenyl)-5-fluoro-6-({1-[(1S,2S)-2-fluorocyclopropane-1-carbonyl]azetidin-3-yl}amino)-2-(2-fluorophenyl)-4-methyl-3,4-dihydro-2,7-naphthyridin-1(2H)-one |
| 57 | 84.9 | 3 | 75.0 | 3 | (4R)-4-(3-chloro-2-fluorophenyl)-5-fluoro-6-{[1-(2-hydroxy-2-methylpropanoyl)azetidin-3-yl]amino}-2-[5-(hydroxymethyl)pyridin-2-yl]-4-methyl-3,4-dihydro-2,7-naphthyridin-1(2H)-one |
| 58 | 74.6 | 3 | 113 | 3 | (4R)-4-(3-chloro-2-fluorophenyl)-5-fluoro-2-[5-(hydroxymethyl)pyridin-2-yl]-4-methyl-6-{[1-(1-methyl-1H-imidazole-5-carbonyl)azetidin-3-yl]amino}-3,4-dihydro-2,7-naphthyridin-1(2H)-one |
| 59 | 62.4 | 4 | 157 | 4 | (4R)-4-(3-chloro-2-fluorophenyl)-5-fluoro-2-[5-(hydroxymethyl)pyridin-2-yl]-4-methyl-6-{[1-(pyrimidine-2-carbonyl)azetidin-3-yl]amino}-3,4-dihydro-2,7-naphthyridin-1(2H)-one |
| 60 | 48.6 | 6 | 53.5 | 6 | (4R)-4-(3-chloro-2-fluorophenyl)-5-fluoro-2-[5-(hydroxymethyl)pyridin-2-yl]-4-methyl-6-{[1-(1-methyl-1H-1,2,3-triazole-4-carbonyl)azetidin-3-yl]amino}-3,4-dihydro-2,7-naphthyridin-1(2H)-one |
| 61 | 100 | 4 | 92.2 | 4 | (4R)-4-(3-chloro-2-fluorophenyl)-5-fluoro-2-(4-fluoro-1-methyl-1H-pyrazol-3-yl)-6-{[1-(2-hydroxy-2-methylpropanoyl)azetidin-3-yl]amino}-4-methyl-3,4-dihydro-2,7-naphthyridin-1(2H)-one |
| 62 | 138 | 5 | 98.1 | 5 | (4R)-4-(3-chloro-2-fluorophenyl)-5-fluoro-2-(4-fluoro-1-methyl-1H-pyrazol-3-yl)-6-{[1-(1-hydroxycyclopropane-1-carbonyl)azetidin-3-yl]amino}-4-methyl-3,4-dihydro-2,7-naphthyridin-1(2H)-one |

TABLE 4-continued

| Ex. | Assay GMean Asy. Max (%) | N% | Assay GMean $EC_{50}$ (nM) | $N^{50}$ | IUPAC Name |
|---|---|---|---|---|---|
| Biological activity and IUPAC name for Examples 1-111. | | | | | |
| 63 | 90.0 | 5 | 55.1 | 5 | (4R)-4-(3-chloro-2-fluorophenyl)-5-fluoro-2-(4-fluoro-1-methyl-1H-pyrazol-3-yl)-4-methyl-6-{[1-(3,3,3-trifluoropropanoyl)azetidin-3-yl]amino}-3,4-dihydro-2,7-naphthyridin-1(2H)-one |
| 64 | 80.4 | 4 | 159.5 | 4 | (4R)-4-(3-chloro-2-fluorophenyl)-5-fluoro-2-(4-fluoro-1-methyl-1H-pyrazol-3-yl)-6-{[1-(3-hydroxy-3-methylbutanoyl)azetidin-3-yl]amino}-4-methyl-3,4-dihydro-2,7-naphthyridin-1(2H)-one |
| 65 | 83.4 | 2 | 55.1 | 2 | (4R)-4-(3-chloro-2-fluorophenyl)-5-fluoro-2-(4-fluoro-1-methyl-1H-pyrazol-3-yl)-4-methyl-6-({1-[2-oxo-2-(pyrrolidin-1-yl)ethyl]azetidin-3-yl}amino)-3,4-dihydro-2,7-naphthyridin-1(2H)-one |
| 66 | 88.8 | 2 | 29.8 | 2 | 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-ethyl-N-methylacetamide |
| 67 | 40.1 | 2 | 76.8 | 2 | 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-methylacetamide |
| 68 | 29.6 | 3 | 247 | 3 | 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)acetamide |
| 69 | 81.6 | 2 | 29.2 | 2 | (4R)-4-(3-chloro-2-fluorophenyl)-5-fluoro-2-(4-fluoro-1-methyl-1H-pyrazol-3-yl)-4-methyl-6-{[1-(1-methyl-2-oxopyrrolidin-3-yl)azetidin-3-yl]amino}-3,4-dihydro-2,7-naphthyridin-1(2H)-one, DIAST-1 |
| 70 | 80.4 | 2 | 47.6 | 2 | (4R)-4-(3-chloro-2-fluorophenyl)-5-fluoro-2-(4-fluoro-1-methyl-1H-pyrazol-3-yl)-4-methyl-6-{[1-(1-methyl-2-oxopyrrolidin-3-yl)azetidin-3-yl]amino}-3,4-dihydro-2,7-naphthyridin-1(2H)-one, DIAST-2 |
| 71 | 139 | 2 | 19.8 | 2 | (4R)-4-(3-chloro-2-fluorophenyl)-5-fluoro-2-(4-fluoro-1-methyl-1H-pyrazol-3-yl)-4-methyl-6-{[1-(1-methyl-2-oxopiperidin-3-yl)azetidin-3-yl]amino}-3,4-dihydro-2,7-naphthyridin-1(2H)-one, DIAST-1 |
| 72 | 121 | 3 | 42.3 | 3 | (4R)-4-(3-chloro-2-fluorophenyl)-5-fluoro-2-(4-fluoro-1-methyl-1H-pyrazol-3-yl)-4-methyl-6-{[1-(1-methyl-2-oxopiperidin-3-yl)azetidin-3-yl]amino}-3,4-dihydro-2,7-naphthyridin-1(2H)-one, DIAST-2 |
| 73 | 46.1 | 2 | 45.3 | 2 | 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-(cyclopropylmethyl)-N-methylacetamide |
| 74 | 129 | 2 | 39.9 | 2 | 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-cyclopropyl-N-(2,2,2-trifluoroethyl)acetamide |
| 75 | 134 | 2 | 52.1 | 2 | 2-(3-{[(5R)-5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}azetidin-1-yl)-N-cyclopropyl-N-(2-methoxyethyl)acetamide |
| 76 | 59.3 | 4 | 56.6 | 4 | (4R)-4-(3-chloro-2-fluorophenyl)-5-fluoro-2-(4-fluoro-1-methyl-1H-pyrazol-3-yl)-4-methyl-6-{[1-({[(3R)-oxolan-3-yl]amino}acetyl)azetidin-3-yl]amino}-3,4-dihydro-2,7-naphthyridin-1(2H)-one |

TABLE 4-continued

Biological activity and IUPAC name for Examples 1-111.

| Ex. | Assay GMean Asy. Max (%) | $N^{\%}$ | Assay GMean $EC_{50}$ (nM) | $N^{50}$ | IUPAC Name |
|---|---|---|---|---|---|
| 77 | 78.2 | 5 | 38.4 | 5 | (4R)-4-(3-chloro-2-fluorophenyl)-2-[2,5-difluoro-4-(hydroxymethyl)phenyl]-5-fluoro-6-({1-[(1S,2S)-2-fluorocyclopropane-1-carbonyl]azetidin-3-yl}amino)-4-methyl-3,4-dihydro-2,7-naphthyridin-1(2H)-one |
| 78 | 80.7 | 4 | 62.3 | 4 | (4R)-4-(3-chloro-2-fluorophenyl)-5-fluoro-6-({1-[(1S,2R)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one |
| 79 | 121 | 3 | 2830 | 3 | 8-(3-chloro-2-fluorophenyl)-2-({1-[(1S,2S)-2-fluorocyclopropane-1-carbonyl]azetidin-3-yl}amino)-6-(imidazo[1,5-a]pyridin-6-yl)-8-methyl-7,8-dihydropyrido[4,3-d]pyrimidin-5(6H)-one, from P11 (ENANT-2) |
| 80 | 154 | 3 | 2500 | 3 | 8-(3-chloro-2-fluorophenyl)-2-({1-[(1S,2S)-2-fluorocyclopropane-1-carbonyl]azetidin-3-yl}amino)-6-{3-fluoro-4-[(methylamino)methyl]phenyl}-8-methyl-7,8-dihydropyrido[4,3-d]pyrimidin-5(6H)-one, from P11 (ENANT-2) |
| 81 | 123 | 4 | >1060 | 6 | 8-(3-chloro-2-fluorophenyl)-2-({1-[(1S,2S)-2-fluorocyclopropane-1-carbonyl]azetidin-3-yl}amino)-6-(3-fluoropyridin-2-yl)-8-methyl-7,8-dihydropyrido[4,3-d]pyrimidin-5(6H)-one, from P13 (ENANT-2) |
| 82 | 218 | 6 | 107 | 6 | 8-(3-chloro-2-fluorophenyl)-6-(3-fluoropyridin-2-yl)-8-methyl-2-({1-[(1R)-6-oxaspiro[2.5]octane-1-carbonyl]azetidin-3-yl}amino)-7,8-dihydropyrido[4,3-d]pyrimidin-5(6H)-one, from P13 (ENANT-2) |
| 83 | 152 | 3 | 82.8 | 3 | 8-(3-chloro-2-fluorophenyl)-6-(3-fluoropyridin-2-yl)-2-({1-[(1R,2S)-1-hydroxy-2-methylcyclopropane-1-carbonyl]azetidin-3-yl}amino)-8-methyl-7,8-dihydropyrido[4,3-d]pyrimidin-5(6H)-one, from P13 (ENANT-2), DIAST-1 or 8-(3-chloro-2-fluorophenyl)-6-(3-fluoropyridin-2-yl)-2-({1-[(1S,2R)-1-hydroxy-2-methylcyclopropane-1-carbonyl]azetidin-3-yl}amino)-8-methyl-7,8-dihydropyrido[4,3-d]pyrimidin-5(6H)-one, from P13 (ENANT-2), DIAST-1 |
| 84 | 184 | 3 | 72.4 | 3 | 8-(3-chloro-2-fluorophenyl)-6-(3-fluoropyridin-2-yl)-2-({1-[(1R,2S)-1-hydroxy-2-methylcyclopropane-1-carbonyl]azetidin-3-yl}amino)-8-methyl-7,8-dihydropyrido[4,3-d]pyrimidin-5(6H)-one, from P13 (ENANT-2), DIAST-2 or 8-(3-chloro-2-fluorophenyl)-6-(3-fluoropyridin-2-yl)-2-({1-[(1S,2R)-1-hydroxy-2-methylcyclopropane-1-carbonyl]azetidin-3-yl}amino)-8-methyl-7,8-dihydropyrido[4,3-d]pyrimidin-5(6H)-one, from P13 (ENANT-2), DIAST-2 |
| 85 | 141 | 4 | 162 | 4 | 3-{[8-(3-chloro-2-fluorophenyl)-6-(3-fluoropyridin-2-yl)-8-methyl-5-oxo-5,6,7,8-tetrahydropyrido[4,3-d]pyrimidin-2-yl]amino}-N-[(2S)-1-methoxypropan-2-yl]azetidine-1-carboxamide, from P13 (ENANT-2) |
| 86 | 106 | 2 | 34.6 | 2 | 8-(3-chloro-2-fluorophenyl)-6-(3-fluoropyridin-2-yl)-2-({1-[(2R)-2-(hydroxymethyl)pyrrolidine-1-carbonyl]azetidin-3-yl}amino)-8-methyl-7,8-dihydropyrido[4,3-d]pyrimidin-5(6H)-one, from P13 (ENANT-2) |
| 87 | 175 | 5 | 152 | 5 | 3-{[8-(3-chloro-2-fluorophenyl)-6-(3-fluoropyridin-2-yl)-8-methyl-5-oxo-5,6,7,8-tetrahydropyrido[4,3-d]pyrimidin-2-yl]amino}-N-(1-hydroxy-2-methylpropan-2-yl)azetidine-1-carboxamide, from P13 (ENANT-2) |

TABLE 4-continued

| Ex. | Assay GMean Asy. Max (%) | N% | Assay GMean $EC_{50}$ (nM) | $N^{50}$ | IUPAC Name |
|---|---|---|---|---|---|
| Biological activity and IUPAC name for Examples 1-111. | | | | | |
| 88 | 213 | 4 | 71.6 | 4 | 8-(3-chloro-2-fluorophenyl)-6-(3-fluoropyridin-2-yl)-8-methyl-2-({1-[(1S,4S)-2-oxa-5-azabicyclo[2.2.1]heptane-5-carbonyl]azetidin-3-yl}amino)-7,8-dihydropyrido[4,3-d]pyrimidin-5(6H)-one, from P13 (ENANT-2) |
| 89 | 148 | 4 | 152 | 4 | 2-{[1-(2-azabicyclo[2.1.1]hexane-2-carbonyl)azetidin-3-yl]amino}-8-(3-chloro-2-fluorophenyl)-6-(3-fluoropyridin-2-yl)-8-methyl-7,8-dihydropyrido[4,3-d]pyrimidin-5(6H)-one, from P13 (ENANT-2) |
| 90 | 120.2 | 4 | 146.7 | 4 | 2-(3-{[4-(3-chloro-2-fluorophenyl)-5-fluoro-2-(4-fluoro-1-methyl-1H-pyrazol-3-yl)-4-methyl-1-oxo-1,2,3,4-tetrahydroisoquinolin-6-yl]amino}azetidin-1-yl)-N,N-dimethylacetamide, from P18 (ENANT-2) |
| 91 | 99.7 | 4 | 168.3 | 4 | 4-(3-chloro-2-fluorophenyl)-5-fluoro-2-(4-fluoro-1-methyl-1H-pyrazol-3-yl)-4-methyl-6-({1-[2-(morpholin-4-yl)-2-oxoethyl]azetidin-3-yl}amino)-3,4-dihydroisoquinolin-1(2H)-one, from P18 (ENANT-2) |
| 92 | 109 | 2 | 58.9 | 2 | 6-({1-[2-(azetidin-1-yl)-2-oxoethyl]azetidin-3-yl}amino)-4-(3-chloro-2-fluorophenyl)-5-fluoro-2-(4-fluoro-1-methyl-1H-pyrazol-3-yl)-4-methyl-3,4-dihydroisoquinolin-1(2H)-one, from P18 (ENANT-2) |
| 93 | 57.5 | 4 | 65.3 | 4 | (4R)-2-(4-aminopyridin-2-yl)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one |
| 94 | 50.3 | 4 | 212 | 4 | (4R)-4-(3-chloro-2-fluorophenyl)-5-fluoro-6-({1-[(1S,2S)-2-fluorocyclopropane-1-carbonyl]azetidin-3-yl}amino)-4-methyl-2-(1-methyl-1H-imidazol-4-yl)-3,4-dihydro-2,7-naphthyridin-1(2H)-one |
| 95 | 78.0 | 2 | 125 | 2 | (4R)-4-(3-chloro-2-fluorophenyl)-6-{[1-(5,5-difluoropiperidine-2-carbonyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-1 |
| 96 | 85.5 | 2 | 60.5 | 2 | (4R)-4-(3-chloro-2-fluorophenyl)-6-{[1-(5,5-difluoropiperidine-2-carbonyl)azetidin-3-yl]amino}-5-fluoro-2-(4-fluoro-1-methyl-1H-pyrazol-3-yl)-4-methyl-3,4-dihydro-2,7-naphthyridin-1(2H)-one, DIAST-2 |
| 97 | 25.8 | 2 | 150 | 2 | (4R)-4-(3-chloro-2-fluorophenyl)-5-fluoro-4-methyl-2-(1-methyl-1H-imidazol-4-yl)-6-({1-[cis-2-(trifluoromethyl)cyclopropane-1-carbonyl]azetidin-3-yl}amino)-3,4-dihydro-2,7-naphthyridin-1(2H)-one, DIAST-1 |
| 98 | 66.2 | 2 | 114 | 2 | (4R)-4-(3-chloro-2-fluorophenyl)-5-fluoro-4-methyl-2-(1-methyl-1H-imidazol-4-yl)-6-({1-[cis-2-(trifluoromethyl)cyclopropane-1-carbonyl]azetidin-3-yl}amino)-3,4-dihydro-2,7-naphthyridin-1(2H)-one, DIAST-2 |
| 99 | 49.7 | 5 | 70.2 | 5 | (4R)-4-(3-chloro-2-fluorophenyl)-5-fluoro-6-({1-[(1R,2R)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one |
| 100 | 22.8 | 3 | 11.6 | 3 | (4R)-4-(3-chloro-2-fluorophenyl)-6-({1-[(8aR)-7,7-difluorohexahydropyrrolo[1,2-a]pyrazine-2(1H)-carbonyl]azetidin-3-yl}amino)-5-fluoro-2-(3-fluoropyridin-2-yl)-4-methyl-3,4-dihydro-2,7-naphthyridin-1(2H)-one |
| 101 | 108.2 | 5 | 135.2 | 5 | 4-(3-chloro-2,4-difluorophenyl)-5-fluoro-2-(4-fluoro-1-methyl-1H-pyrazol-3-yl)-6-{[1-(2-hydroxy-2-methylpropanoyl)azetidin-3-yl]amino}-4-methyl-3,4-dihydro-2,7-naphthyridin-1(2H)-one, from P3 (ENANT-2) |

TABLE 4-continued

Biological activity and IUPAC name for Examples 1-111.

| Ex. | Assay GMean Asy. Max (%) | N% | Assay GMean $EC_{50}$ (nM) | $N^{50}$ | IUPAC Name |
|---|---|---|---|---|---|
| 102 | 51.4 | 5 | 25.9 | 5 | 2-(5-aminopyridin-2-yl)-4-(3-chloro-2,4-difluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one, from P3 (ENANT-2) |
| 103 | 113 | 2 | 27.5 | 2 | 4-(3-chloro-2,4-difluorophenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one, from P3 (ENANT-2) |
| 104 | 49.8 | 7 | 32.1 | 7 | 2-(5-aminopyridin-2-yl)-4-(2,4-difluoro-3-methylphenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one, from P5 (ENANT-2) |
| 105 | 38.4 | 1 | 19.8 | 1 | 4-(2,4-difluoro-3-methylphenyl)-5-fluoro-6-({1-[(1S,2S)-2-fluorocyclopropane-1-carbonyl]azetidin-3-yl}amino)-2-[5-(hydroxymethyl)pyridin-2-yl]-4-methyl-3,4-dihydro-2,7-naphthyridin-1(2H)-one, from P5 (ENANT-2) |
| 106 | 70.5 | 3 | 33.9 | 3 | 4-(2,4-difluoro-3-methylphenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one, from P5 (ENANT-2) |
| 107 | 119 | 2 | 32.7 | 2 | 4-(2,4-difluoro-3-methylphenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one, from P5 (ENANT-2) |
| 108 | 76.8 | 4 | 123 | 4 | 4-(2,3-difluorophenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one, from P7 (ENANT-2) |
| 109 | 81.7 | 2 | 76.2 | 2 | 4-(3-chloro-2-fluorophenyl)-5-fluoro-6-{[(3R)-1-(4-fluoro-1-methylpiperidine-4-carbonyl)pyrrolidin-3-yl]amino}-2-(3-fluoropyridin-2-yl)-4-methyl-3,4-dihydro-2,7-naphthyridin-1(2H)-one, from P9 (DIAST-2) |
| 110 | 63.2 | 4 | 266 | 4 | 2-[(3R)-3-{[5-(3-chloro-2-fluorophenyl)-4-fluoro-7-(4-fluoro-1-methyl-1H-pyrazol-3-yl)-5-methyl-8-oxo-5,6,7,8-tetrahydro-2,7-naphthyridin-3-yl]amino}pyrrolidin-1-yl]-N,N-dimethylacetamide, from P9 (DIAST-2) |
| 111 | 159 | 3 | 342 | 3 | 8-(3-chloro-2-fluorophenyl)-6-(3-fluoropyridin-2-yl)-8-methyl-2-({1-[(2S)-3,3,3-trifluoro-2-hydroxy-2-methylpropanoyl]azetidin-3-yl}amino)-7,8-dihydropyrido[4,3-d]pyrimidin-5(6H)-one, from P13 (ENANT-2) |
| 112 | 72.1 | 7 | 899.1 | 7 | (4R)-4-(3-Chloro-2-fluorophenyl)-5-fluoro-6-({1-[(1S,2S)-2-fluorocyclopropane-1-carbonyl]azetidin-3-yl}amino)-2-(4-fluoro-1H-pyrazol-3-yl)-4-methyl-3,4-dihydro-2,7-naphthyridin-1(2H)-one |

Prophetic Deuterated Analogs

General methods/reviews of obtaining metabolite profile and identifying metabolites of a compound are described in: Dalvie, et al., "Assessment of Three Human in Vitro Systems in the Generation of Major Human Excretory and Circulating Metabolites," Chemical Research in Toxicology, 2009, 22, 2, 357-368, tx8004357 (acs.orgi); King, R., "Biotransformations in Drug Metabolism," Ch.3, Drug Metabolism Handbook Introduction, https://doi.org/10.1002/9781119851042.ch3; Wu, Y., et al, "Metabolite Identification in the Preclinical and Clinical Phase of Drug Development," Current Drug Metabolism, 2021, 22, 11, 838-857, 10.2174/1389200222666211006104502; Godzien, J., et al, "Chapter Fifteen—Metabolite Annotation and Identification".

Numerous publicly available and commercially available software tools are available to aid in the predictions of metabolic pathways and metabolites of compounds. Examples of such tools include, BioTransofrmer 3.0 (biotransformer.ca/new), which predicts the metabolic biotransformations of small molecules using a database of known metabolic reactions; MetaSite (moldiscovery.com/software/metasite/), which predicts metabolic transformations related to cytochrome P450 and flavin-containing monooxygenase mediated reactions in phase I metabolism; and Lhasa Meteor Nexus (lhasalimited.orq/products/meteor-nexus.htm) offers prediction of metabolic pathways and metabolite structures using a range of machine learning models, which covers phase I and phase II biotransformations of small molecules.

Predicted deuterated analogs in the examples may afford certain therapeutic advantages resulting from greater metabolic stability, for example, increased in vivo half-life, reduced dosage requirements, increased AMPKγ3 activation (competitive or time dependent), or an improvement in therapeutic index or tolerability.

A person with ordinary skill may make additional deuterated analogs of the disclosed compounds with different combinations of deuterium replacing hydrogen. Such additional deuterated analogs may provide similar therapeutic advantages that may be achieved by the deuterated analogs as illustrated below.

In the examples, the "$Y_i$" is used to indicate the order of the sites most likely to be metabolized based on MetaSite predictions for the respective compound, where i=1 indicates the most likely, i=2 indicates the second most likely site and so on. It is noted that where $Y_i$ is indicated as being deuterated, D, each $Y_i$ independently can be D as long as at least one $Y_i$ is D. For example, if $Y_1$ is deuterated and there are two $Y_1$ groups in the compound, then one or both groups can be deuterated as long as at least one $Y_1$ group is deuterated.

These examples are not intended to be limited to the specific compounds or locations of deuteration.

Example 2D

Formula 2D is the generic formula of deuterated Example 2, wherein $Y_1$, $Y_2$, $Y_3$, $Y_4$, $Y_5$, $Y_6$, $Y_7$, $Y_8$, $Y_9$, and $Y_{10}$ are each independently H or D. Table 5 shows some examples of deuterated compounds based on the most likely metabolized sites that can be applied to the compounds predicted by MetaSite.

2D

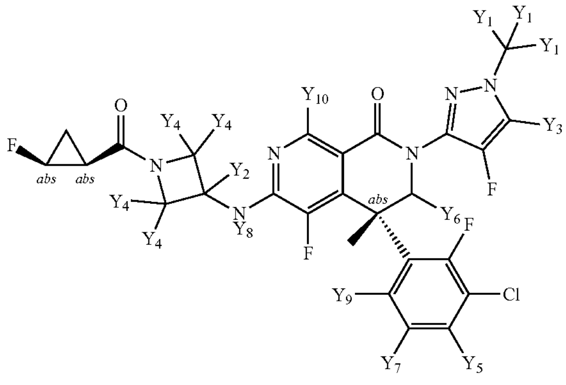

TABLE 5

| Deuteration Example | $Y_1$ | $Y_2$ | $Y_3$ | $Y_4$ | $Y_5$ | $Y_6$ | $Y_7$ | $Y_8$ | $Y_9$ | $Y_{10}$ |
|---|---|---|---|---|---|---|---|---|---|---|
| 2DA | D | H | H | H | H | H | H | H | H | H |
| 2DB | D | D | H | H | H | H | H | H | H | H |

TABLE 5-continued

| Deuteration Example | $Y_1$ | $Y_2$ | $Y_3$ | $Y_4$ | $Y_5$ | $Y_6$ | $Y_7$ | $Y_8$ | $Y_9$ | $Y_{10}$ |
|---|---|---|---|---|---|---|---|---|---|---|
| 2DC | D | D | D | H | H | H | H | H | H | H |
| 2DD | D | H | D | H | H | H | H | H | H | H |
| 2DE | D | H | H | D | H | H | H | H | H | H |
| 2DF | D | H | H | H | D | H | H | H | H | H |
| 2DG | D | H | H | H | H | D | H | H | H | H |
| 2DH | D | H | H | H | H | H | D | H | H | H |
| 2DI | D | H | H | H | H | H | H | D | H | H |
| 2DJ | D | H | H | H | H | H | H | H | D | H |
| 2DK | D | H | H | H | H | H | H | H | H | D |
| 2DL | D | D | D | D | H | H | H | H | H | H |
| 2DM | H | D | D | H | H | H | H | H | H | H |
| 2DN | H | D | H | D | H | H | H | H | H | H |
| 2DO | H | D | H | H | D | H | H | H | H | H |
| 2DP | H | D | H | H | H | D | H | H | H | H |
| 2DQ | H | D | H | H | H | H | D | H | H | H |
| 2DR | H | D | H | H | H | H | H | D | H | H |
| 2DS | H | D | H | H | H | H | H | H | D | H |
| 2DT | H | D | H | H | H | H | H | H | H | D |
| 2DU | D | H | D | D | H | H | H | H | H | H |
| 2DV | D | D | H | D | H | H | H | H | H | H |

Example 3D

Formula 3D is the generic formula of deuterated Example 3, wherein $Y_1$, $Y_2$, $Y_3$, and $Y_4$ are each independently H or D.

3D

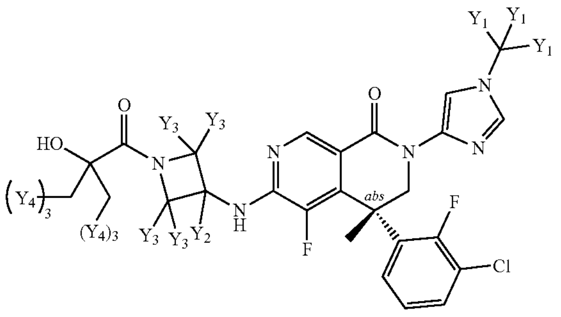

Example 6D

Formula 6D is the generic formula of deuterated Example 6, wherein $Y_1$, $Y_2$, $Y_3$, and $Y_4$ are each independently H or D.

6D

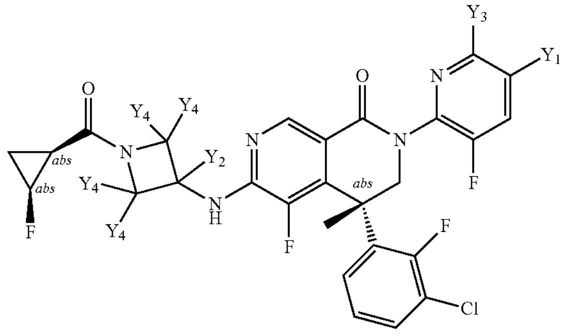

Example 22D

Formula 22D is the generic formula of deuterated Example 22, wherein $Y_1$, $Y_2$, $Y_3$, $Y_4$, $Y_5$, $Y_6$, and $Y_7$ are each independently H or D.

22D

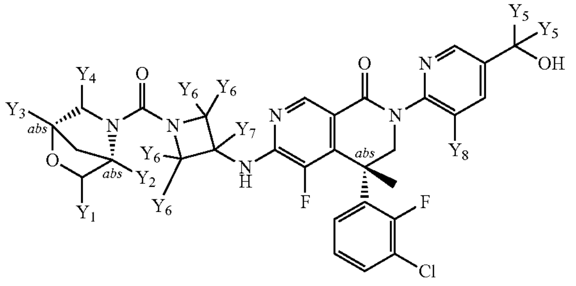

Example 23D

Formula 23D is the generic formula of deuterated Example 23, wherein $Y_1$, $Y_2$, $Y_3$, and $Y_4$ are each independently H or D.

23D

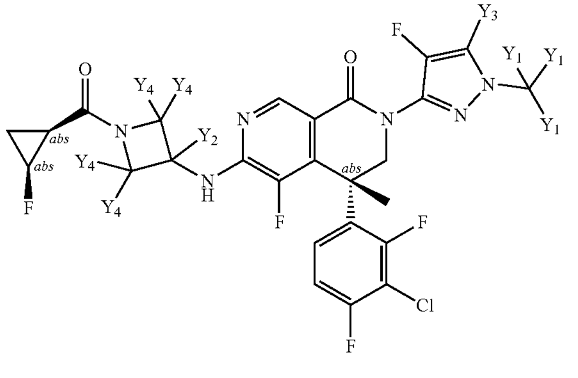

All references cited herein, including patents, patent applications, papers, textbooks, and the like, and the references cited therein, to the extent that they are not already, are hereby incorporated by reference in their entireties for all purposes. In the event that one or more of the incorporated literature and similar materials differs from or contradicts this disclosure, including but not limited to defined terms, term usage, described techniques, or the like, this disclosure controls.

We claim:

1. A compound of Formula I:

Formula I

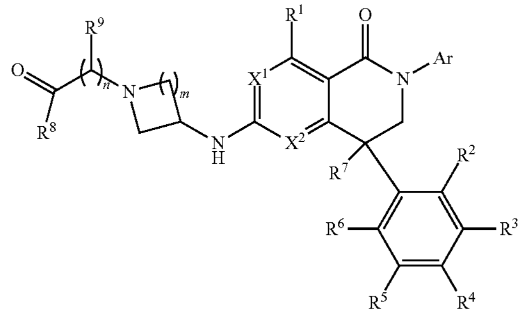

wherein:

Ar is ($C_2$-$C_9$)heteroaryl or phenyl; wherein Ar is optionally substituted with 1, 2, or 3 substituents selected from the group consisting of halogen, —N($R^{10}$)($R^{11}$), —$CH_2$—($NR^{10}R^{11}$), —($C_1$-$C_6$)alkyl, —($C_1$-$C_6$)hydroxyalkyl, —($C_1$-$C_6$)haloalkyl, —($C_1$-$C_6$)haloalkoxy, —($C_1$-$C_6$)alkoxy, —$OR^{10}$, —($C_3$-$C_6$)cycloalkyl, and —($C_3$-$C_6$)heterocycloalkyl;

$X^1$ is CH or nitrogen;

$X^2$ is $CR^{12}$ or nitrogen;

$R^1$ is hydrogen, —O—($C_1$-$C_6$)alkyl, —O—($C_1$-$C_6$)cycloalkyl, or —N($R^{10}$)($R^{11}$);

$R^2$, $R^3$, $R^4$, $R^5$ and $R^6$ are each independently hydrogen, halogen, —($C_1$-$C_3$)alkyl, or —N($R^{10}$)($R^{11}$);

$R^7$ is —H, —($C_1$-$C_6$)alkyl, —($C_3$-$C_6$)cycloalkyl, —OH, or —$CH_2OH$;

$R^8$ is —($C_1$-$C_6$)alkyl, —($C_0$-$C_2$)alkyl-($C_3$-$C_8$)cycloalkyl, —($C_0$-$C_2$)alkyl-N($R^{10}R^{11}$), —($C_0$-$C_2$)alkyl-($C_3$-$C_9$)heterocycloalkyl, —($C_1$-$C_6$)haloalkoxy, —($C_1$-$C_6$)alkyl-($C_1$-$C_6$)alkoxy, or —($C_0$-$C_2$)alkyl-($C_2$-$C_6$)heteroaryl; wherein $R^8$ is optionally substituted with 1, 2, 3, or 4 substituents selected from the group consisting of halogen, hydroxy, —($C_1$-$C_6$)alkyl, —($C_1$-$C_6$)haloalkyl, —($C_1$-$C_6$)alkoxy, —($C_1$-$C_6$)hydroxyalkyl, —($C_1$-$C_6$)haloalkoxy, —($C_1$-$C_6$) hydroxyalkoxy, and —($C_3$-$C_6$)cycloalkyl;

$R^9$ is hydrogen or —($C_1$-$C_3$)alkyl; or $R^8$ and $R^9$ taken together form a ($C_4$-$C_9$)heterocycloalkyl, wherein the ($C_4$-$C_9$)heterocycloalkyl is optionally substituted with 1 or 2 substituents selected from the group consisting of oxo, halogen, and —($C_1$-$C_6$)alkyl; and $R^{10}$ and $R^{11}$ are each independently hydrogen, —($C_1$-$C_6$) alkyl, —($C_1$-$C_6$) haloalkyl, —($C_0$-$C_2$)alkyl-($C_3$-$C_6$)cycloalkyl, —($C_1$-$C_6$)alkyl-($C_1$-$C_6$)alkoxy, or —($C_3$-$C_5$) heterocycloalkyl; or wherein $R^{10}$ and $R^{11}$ form ($C_3$-$C_5$) heterocycloalkyl; wherein $R^{10}$ and $R^{11}$ independently are optionally substituted with 1 or 2 substituents selected from the group consisting of hydroxy, oxo, halogen, and cyclopropyl;

$R^{12}$ is hydrogen, methyl, —$CH_2OH$, or halogen;

m is 1, 2, or 3;

n is 0 or 1, wherein, when n is 0 $R^9$ is absent;

or a pharmaceutically acceptable salt of said compound.

2. The compound of claim 1, wherein the compound has the formula Ia:

Formula Ia

Ia

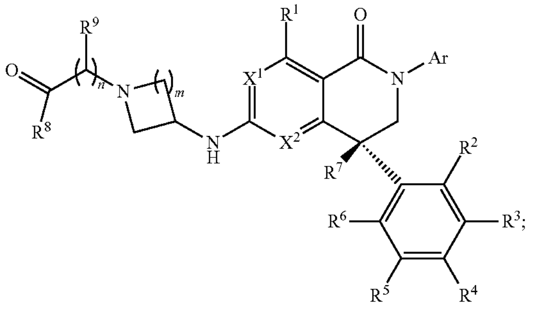

or a pharmaceutically acceptable salt of said compound.

3. The compound of claim 1, wherein Ar is $(C_2-C_6)$ heteroaryl that is substituted with 1 or 2 substituents selected from the group consisting of F, —$(C_1-C_3)$alkyl, —$(C_1-C_3)$ hydroxyalkyl, —$NH_2$, and morpholino; or a pharmaceutically acceptable salt thereof.

4. The compound of claim 1, wherein Ar is pyrazolyl, imidazolyl, pyridinyl, or imidazopyridinyl and wherein Ar is optionally substituted with 1 or 2 substituents selected from the group consisting of F, —$(C_1-C_3)$alkyl, —$(C_1-C_2)$hydroxyalkyl, —$NH_2$, and

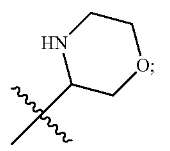 [SMILES: *C1COCCN1]

or a pharmaceutically acceptable salt thereof.

5. The compound of claim 1, wherein at least one of m is 1 or n is 0; or a pharmaceutically acceptable salt thereof.

6. The compound of claim 1, wherein $R^8$ is —$(C_0-C_2)$ alkyl-cyclopropyl substituted with 1 or 2 substituents selected from the group consisting of F, hydroxy, or —$(C_1-C_3)$alkyl; or a pharmaceutically acceptable salt thereof.

7. The compound of claim 1, wherein at least one of $R^1$ is hydrogen, $R^7$ is methyl, or $R^8$ is —$(C_1-C_3)$alkyl, —$(C_0-C_2)$alkyl-cyclopropyl, —$(C_0-C_2)$alkyl-$NH(R^{11})$, $(C_3-C_6)$ heterocycloalkyl, or —$(C_0-C_2)$alkyl-$(C_2-C_6)$heteroaryl; wherein $R^8$ is optionally substituted with 1 or 2 substituents selected from the group consisting of F, hydroxy, —$(C_1-C_3)$ alkyl, —$(C_1-C_2)$fluoroalkyl, —$(C_1-C_3)$alkoxy, —$(C_1-C_3)$ hydroxyalkyl, and cyclopropyl; or a pharmaceutically acceptable salt thereof.

8. The compound of claim 1, wherein $R^2$ is F; $R^3$ is $C_1$, methyl, or F; $R^4$ is hydrogen or F; and $R^5$ and $R^6$ are H; or a pharmaceutically acceptable salt thereof.

9. The compound of claim 1, wherein the compound is:

(4R)-4-(3-chloro-2-fluorophenyl)-5-fluoro-6-({1-[(1S, 2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one;

(4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one;

(4R)-4-(3-chloro-2-fluorophenyl)-5-fluoro-6-({1-[(1S, 2S)-2-fluorocyclopropane-1-carbonyl]azetidin-3-yl}amino)-2-(3-fluoropyridin-2-yl)-4-methyl-3,4-dihydro-2,7-naphthyridin-1(2H)-one;

(4R)-4-(3-chloro-2-fluorophenyl)-5-fluoro-2-(3-fluoropyridin-2-yl)-6-{[1-(1-hydroxycyclopropane-1-carbonyl)azetidin-3-yl]amino}-4-methyl-3,4-dihydro-2,7-naphthyridin-1(2H)-one;

(4R)-4-(3-chloro-2-fluorophenyl)-5-fluoro-2-[5-(hydroxymethyl)pyridin-2-yl]-4-methyl-6-({1-[(1S,4S)-2-oxa-5-azabicyclo[2.2.1]heptane-5-carbonyl]azetidin-3-yl}amino)-3,4-dihydro-2,7-naphthyridin-1(2H)-one;

(4R)-2-(5-aminopyridin-2-yl)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one; or (4R)-4-(3-chloro-2-fluorophenyl)-6-{[1-(2-cyclopropyl-2-hydroxypropanoyl)azetidin-3-yl]amino}-5-fluoro-2-(4-fluoro-1-methyl-1H-pyrazol-3-yl)-4-methyl-3,4-dihydro-2,7-naphthyridin-1(2H)-one;

or a pharmaceutically acceptable salt thereof.

10. The compound of claim 1, wherein the compound is (4R)-4-(3-chloro-2-fluorophenyl)-5-fluoro-6-({1-[(1S, 2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1(2H)-one;

(4R)-4-(3-chloro-2-fluorophenyl)-5-fluoro-6-{[1-(2-hydroxy-2-methylpropanoyl)azetidin-3-yl]amino}-4-methyl-2-(1-methyl-1H-imidazol-4-yl)-3,4-dihydro-2,7-naphthyridin-1(2H)-one;

(4R)-2-(5-aminopyridin-2-yl)-4-(3-chloro-2-fluorophenyl)-5-fluoro-6-({1-[(1S,2S)-2-fluorocyclopropane-1-carbonyl]azetidin-3-yl}amino)-4-methyl-3,4-dihydro-2,7-naphthyridin-1(2H)-one;

or a pharmaceutically acceptable salt thereof.

11. The compound of claim 1, wherein Ar is $(C_2-C_9)$ heteroaryl or phenyl; wherein Ar is optionally substituted with 1, 2, or 3 substituents selected from the group consisting of halogen, —$N(R^{10})(R^{11})$, —$CH_2$—$(NR^{10}R^{11})$, —$(C_1-C_6)$alkyl, —$(C_1-C_6)$hydroxyalkyl, —$(C_1-C_6)$haloalkyl, —$(C_1-C_6)$haloalkoxy, —$OR^{10}$, —$(C_3-C_6)$cycloalkyl, and —$(C_3-C_6)$heterocycloalkyl.

12. The compound of claim 1, wherein at least one hydrogen is deuterium.

13. The compound of claim 12, wherein the compound has the formula 3D, 6D, 22D, or 23D:

3D

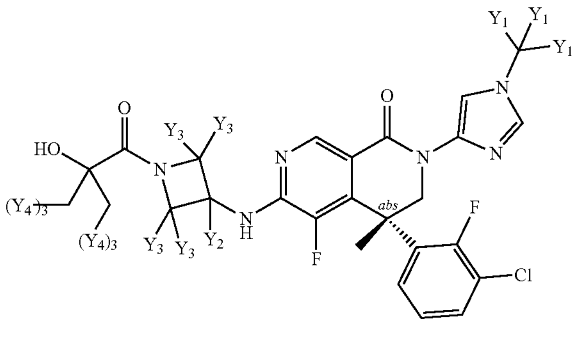

-continued

6D

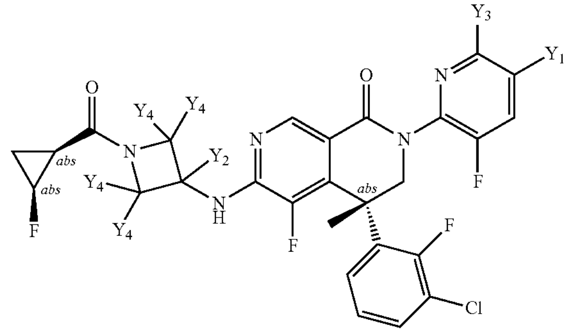

22D

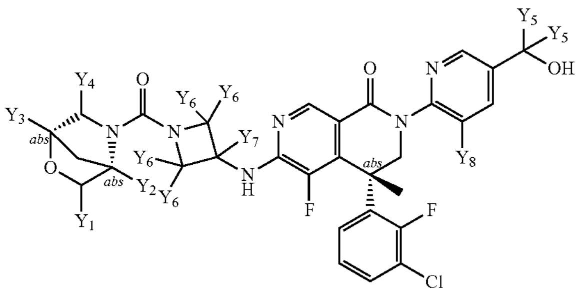

23D

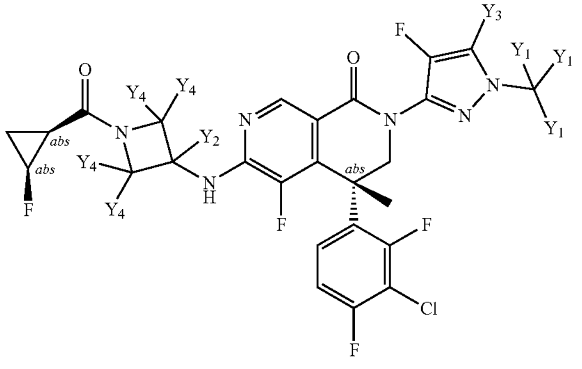

or a pharmaceutically acceptable salt thereof;

wherein $Y_1$, $Y_2$, $Y_3$, $Y_4$, $Y_5$, $Y_6$, and $Y_7$ are each independently H or D; wherein when the compound is of the formula 3D, at least one of $Y_1$, $Y_2$, $Y_3$, and $Y_4$ in formula 3D is D; when the compound is of the formula 6D, at least one of $Y_1$, $Y_2$, $Y_3$, and $Y_4$ in formula 6D is D; when the compound is of the formula 22D, at least one of $Y_1$, $Y_2$, $Y_3$, $Y_4$, $Y_5$, $Y_6$, and $Y_7$ in formula 22D is D; and when the compound is of the formula 23D, at least one of $Y_1$, $Y_2$, $Y_3$, and $Y_4$ in formula 23D is D.

14. The compound of claim 12, wherein the compound is of the formula 2D-I or 2D-II:

2D-I

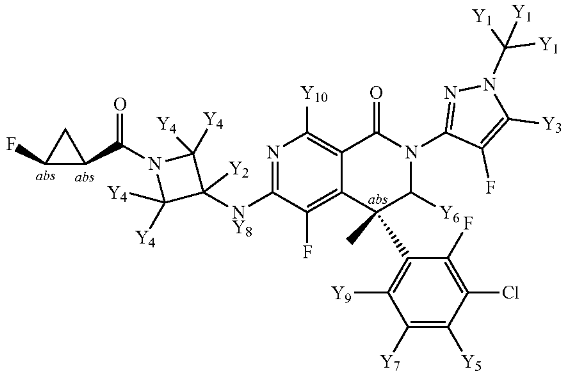

2D-II

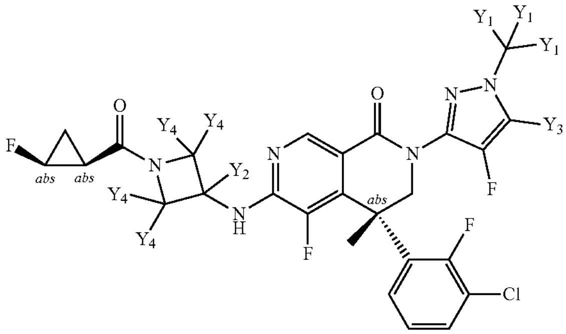

or a pharmaceutically acceptable salt thereof;

wherein $Y_1$, $Y_2$, $Y_3$, $Y_4$, $Y_5$, $Y_6$, $Y_7$, $Y_8$, $Y_9$, and $Y_{10}$ are each independently H or D; wherein when the compound is of the formula 2D-I, at least one of $Y_1$, $Y_2$, $Y_3$, $Y_4$, $Y_5$, $Y_6$, $Y_7$, $Y_8$, $Y_9$, and $Y_{10}$ in formula 2D-I is D; and when the compound is of the formula 2D-II, then at least one of $Y_1$, $Y_2$, $Y_3$, or $Y_4$ in formula 2D-II is D.

15. A compound, wherein the compound is (4R)-4-(3-chloro-2-fluorophenyl)-5-fluoro-6-({1-[(1S,2S)-2-fluorocyclopropane-1-carbonyl]azetidin-3-yl}amino)-2-(4-fluoro-1-methyl-1H-pyrazol-3-yl)-4-methyl-3,4-dihydro-2,7-naphthyridin-1 (2H)-one; or a pharmaceutically acceptable salt thereof.

16. A compound, where in the compound is

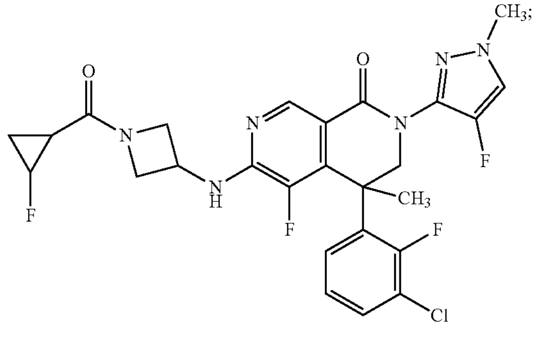 [SMILES: Cn1cc(F)c(N2CC(C)(c3cccc(Cl)c3F)c3c(cnc(NC4CN(C(=O)C5CC5F)C4)c3F)C2=O)n1]

or a pharmaceutically acceptable salt thereof.

17. A compound, where in the compound is

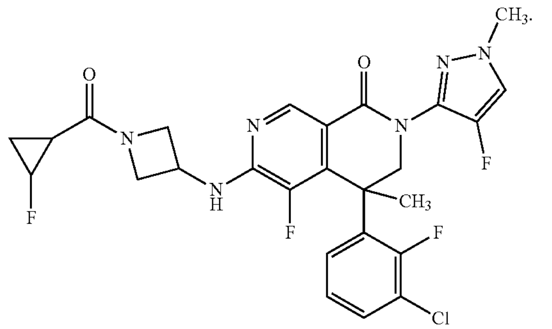 [SMILES: Cn1cc(F)c(N2CC(C)(c3cccc(Cl)c3F)c3c(cnc(NC4CN(C(=O)C5CC5F)C4)c3F)C2=O)n1]

18. A crystal comprising a compound having the structure:

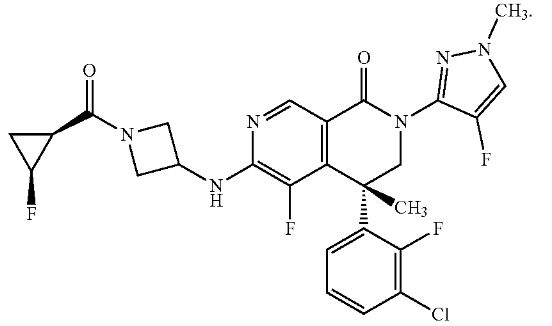 [SMILES: Cn1cc(F)c(N2C[C@](C)(c3cccc(Cl)c3F)c3c(cnc(NC4CN(C(=O)[C@@H]5C[C@@H]5F)C4)c3F)C2=O)n1]

19. The crystal of claim 18, having a powder x-ray diffraction pattern comprising 2-theta values of (CuKα radiation, wavelength of 1.54056 Å) 9.8±0.2, 17±0.2, and 19.8±0.2; or 6.1±0.2, 7.2±0.2, 12.2±0.2, and 13.2±0.2.

20. A pharmaceutical composition comprising:

the compound of claim 1 or a pharmaceutically acceptable salt of said compound; and a pharmaceutically acceptable carrier, vehicle, or diluent.

21. A pharmaceutical combination composition comprising:

a first compound, the first compound being the compound of claim 1 or a pharmaceutically acceptable salt of said compound;

a second compound, said second compound being an anti-heart failure treatment agent; wherein said anti-heart failure treatment agent is optionally an ACE inhibitor, an SGLT-2 inhibitor, an angiotensin receptor blocker, an angiotensin-receptor neprilysin inhibitor, a beta-adrenergic receptor blocker, a calcium channel blocker, or a vasodilator; and a pharmaceutical carrier, vehicle, or diluent.

22. A method of treating or reducing the risk of hospitalization for heart failure, cardiovascular death, congestive heart failure, heart failure with New York Heart Association Class I-IV symptoms, heart failure with reduced left ventricular function (HF-rEF), heart failure with preserved left ventricular function (HF-pEF), heart failure with midrange ejection fraction (HF-mrEF), heart failure in patients with Type II diabetes mellitus, coronary heart disease, unstable angina, peripheral vascular disease, renovascular disease, pulmonary hypertension, vasculitis, acute coronary syndromes and modification of cardiovascular risk comprising administering to a human in need of such treatment the compound of claim 1 or a pharmaceutically acceptable salt of said compound.

23. The method of claim 22, wherein heart failure or peripheral artery disease is treated.

* * * * *